US012187756B2

(12) United States Patent
Emmadi et al.

(10) Patent No.: US 12,187,756 B2
(45) Date of Patent: Jan. 7, 2025

(54) **STABLE VACCINE AGAINST *CLOSTRIDIUM DIFFICILE***

(71) Applicant: IDORSIA PHARMACEUTICALS LTD, Allschwil (CH)

(72) Inventors: Madhu Emmadi, Berlin (DE); Marilda P. Lisboa, Berlin (DE); Daniel Knopp, Berlin (DE); Bopanna Monnanda, Berlin (DE); Arne Von Bonin, Allschwil (CH); Claney Lebev Pereira, Berlin (DE)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 763 days.

(21) Appl. No.: 17/296,194

(22) PCT Filed: Nov. 22, 2019

(86) PCT No.: PCT/EP2019/082331
§ 371 (c)(1),
(2) Date: May 21, 2021

(87) PCT Pub. No.: WO2020/104697
PCT Pub. Date: May 28, 2020

(65) Prior Publication Data
US 2023/0045939 A1 Feb. 16, 2023

(30) Foreign Application Priority Data

Nov. 22, 2018 (EP) .................................. 18207920

(51) Int. Cl.
*C07H 17/04* (2006.01)
*A61K 47/64* (2017.01)

(52) U.S. Cl.
CPC ........... *C07H 17/04* (2013.01); *A61K 47/646* (2017.08)

(58) Field of Classification Search
CPC ............................. C07H 17/04; A61K 47/646
USPC ........................................................ 514/27
See application file for complete search history.

(56) References Cited

U.S. PATENT DOCUMENTS

| 11,479,574 | B2 | 10/2022 | Parameswarappa et al. |
| 11,891,413 | B2 | 2/2024 | Naini et al. |
| 2016/0137724 | A1 | 5/2016 | Seeberger et al. |
| 2023/0122752 | A1 | 4/2023 | Parameswarappa et al. |

FOREIGN PATENT DOCUMENTS

| DE | 19648681 A1 | 5/1998 |
| WO | WO 96/27379 * | 9/1996 |
| WO | WO 2006/120576 A2 | 11/2006 |
| WO | WO 2009/033268 A1 | 3/2009 |
| WO | WO 2012/085668 A2 | 6/2012 |
| WO | WO 2012/119769 A1 | 9/2012 |
| WO | WO 2014/080251 A1 | 5/2014 |
| WO | WO 2014/130613 A2 | 8/2014 |
| WO | WO 2017/021549 A1 | 2/2017 |

OTHER PUBLICATIONS

Bernlind, C. et al., "Synthesis of a D,D- and L,D-Heptose-containing Hexasaccharide Corresponding to a Structure from *Haemophilus ducreyi* Lipopolysaccharides," Tetrahedron: *Asymmetry*, 2000, 22, 481-492.
Sanapala, S. et al., "Chemical Synthesis of Asparagine-Linked Archaeal N-Glycan from *Methanothermus fervidus*," Chemistry A European Journal, 2014, 20, 3578-3583.
Adamo, R. et al., "Phosphorylation of the Synthetic Hexasaccharide Repeating Unit Is Essential for the Induction of Antibodies to *Clostridium difficile* PSII Cell Wall Polysaccharide," ACS Chemical Biology, 2012, 7, 1420-1428.
Adamo, R., "Advancing Homogeneous Antimicrobial Glycoconjugate Vaccines," Accounts of Chemical Research, 2017, 50, 1270-1279.
Arcuri, M. et al., "The Influence of Conjugation Variables on the Design and Immunogenicity of a Glycoconjugate Vaccine against *Salmonella* Typhi," PLoS One, 2017, 12(12): e0189100, 19 pages, https://doi.org/10.1371/journal.pone.0189100.
Berti, F. et al., "Antimicrobial Glycoconjugate Vaccines: An Overview of Classic and Modern Approaches for Protein Modification," Chemical Society Reviews, 2018, 47, 9015-9025.
Boeckler, C. et al., "Immunogenicity of New Heterobifunctional Cross-linking Reagents Used in the Conjugation of Synthetic Peptides to Liposomes," Journal of Immunological Methods, 1996, 191, 1-10.
Borodkin, V. et al., "Synthesis of β-D-Galp-(1-→4)-α-D-Manp Methanephosphonate, a Substrate Analogue for the Elongating α-D-Mannosyl Phosphate Transferase in the *Leishmania*," Tetrahedron Letters, 2001, 42, 5305-5308.
Boulineau, F. et al., "Conversion of D-Gucals into L-Glycals and Mirror-Image Carbohydrates," Organic Letters, 2004, 6 (1), 119-121.
Brooks, G. et al., "Synthesis of Derivatives of Muramic Acid and C-1 Homologated α-D-Glucose as Potential Inhibitors of Bacterial Transglycosylase," Tetrahedron, 1995, 51 (29), 7999-8014.
Chalopin, T. et al., "Second Generation of Thiazolylmannosides, FimH Antagonists for *E. coli*-Induced Crohn's Disease," Organic and Biomolecular Chemistry, 2016, 14, 3913-3925.
Chatani, N. et al., "Catalytic Siloxymethylation of Glycosides by the $HSiR_3/CO/Co_2(CO)_8$ Reaction. A New Entry to C-Glycosyl Compounds," Journal of Organic Chemistry, 1988, 53 (14), 3387-3389.
Dai, X. et al., "Formal Synthesis of Anticoagulant Drug Fondaparinux Sodium," Journal of Organic Chemistry, 2016, 81, 162-184.

(Continued)

*Primary Examiner* — Yih-Horng Shiao
(74) *Attorney, Agent, or Firm* — Hoxie & Associates LLC

(57) ABSTRACT

The present invention relates to a synthetic saccharide of general formulate (I) that is related to *Clostridium difficile* PS-II cell-surface polysaccharide and conjugate thereof. Said synthetic saccharide, said conjugate and pharmaceutical composition containing said synthetic saccharide or said conjugate are useful for prevention and/or treatment of diseases associated with *Clostridium difficile*. Furthermore, the synthetic saccharide of general formula (I) is useful as marker in immunological assays for detection of antibodies against *Clostridium difficile* bacteria.

33 Claims, 24 Drawing Sheets

(56) References Cited

OTHER PUBLICATIONS

Danieli, E. et al., "First Synthesis of *C. difficile* PS-II Cell Wall Polysaccharide Repeating Unit," Organic Letters, 2011, 13 (3), 378-381.

Francisco, C. et al., "Intramolecular Hydrogen Abstraction Reaction Promoted by Alkoxy Radicals in Carbohydrates. Synthesis of Chiral 2,7-Dioxabicyclo[2.2.1]heptane and 6,8-Dioxabicyclo[3.2.1]octane Ring Systems," Journal of Organic Chemistry, 2002, 67, 7439-7445.

Gaurat, O. et al., "A Concise Synthesis of C-glycosyl Phosphate and Phosphonate Analogues of N-Acetyl-α-D-glucosamine 1-Phosphate," Tetrahedron Letters, 2000, 41, 1187-1189.

Giannis, A. et al., "Stereoselective Synthesis of α-C-Allyl-glycopyranosides," Tetrahedron Letters, 1985, 26 (12), 1479-1482.

Grandjean, C. et al., "On the Preparation of Carbohydrate-Protein Conjugates Using the Traceless Staudinger Ligation," Journal of Organic Chemistry, 2005, 70, 7123-7132.

Huang, Q. et al., "PEG as a Spacer Arm Markedly Increases the Immunogenicity of Meningococcal Group Y Polysaccharide Conjugate Vaccine," Journal of Controlled Release, 2013, 172, 382-389.

International Search Report for International Application No. PCT/EP2019/082331, mailed Feb. 25, 2020, 5 pages.

Kawano, T. et al., "Natural Killer-like Nonspecific Tumor Cell Lysis Mediated by Specific Ligand-activate Vα14 NKT Cells," Proceedings of the National Academy of Sciences, 1998, 95, 5690-5693.

Lewis, M. et al., "Highly Stereoselective Approaches to α- and βC-Glycopyranosides," Journal of the American Chemical Society, 1982, 104, 4976-4978.

Lin, C-K. et al., "Synthesis of 1-C-Glycoside-Linked Lipid II Analogues Toward Bacterial Transglycosylase Inhibition," Chemistry A European Journal, 2015, 21, 7511-7519.

Monteiro, M. et al., "Carbohydrate-based Clostridium difficile Vaccines," Expert Review of Vaccines, 2013, 12 (4), 421-431.

Monteiro, "The Design of a *Clostridium difficile* Carbohydrate-Based Vaccine," Methods in Molecular Biology, 2016, 1403, 397-408.

Oberli, M. et al., "A Possible Oligosaccharide-Conjugate Vaccine Candidate for *Clostridium difficile* is Antigenic and Immunogenic," Chemistry & Biology, 2011, 18, 580-588.

Peeters, C. et al., "Preparation of Polysaccharide-Conjugate Vaccines," in Vaccine Protocols. Methods in Molecular Medicine, 2003, 87, 153-173, abstract.

Price, N. et al., "Functionalized C-Glycoside Ketohydrazones: Carbohydrate Derivatives that Retain the Ring Integrity of the Terminal Reducing Sugar," Analytical Chemistry, 2010, 82 (7), 2893-2899.

Sanapala, S. et al., Supporting Information for "Chemical Synthesis of Asparagine-Linked Archaeal N-Glycan from *Methanothermus fervidus*," Chemistry A European Journal, copyright 2014, 84 pages, retrieved on Mar. 23, 2022, from: https://chemistry-europe.onlinelibrary.wiley.com/action/downloadSupplement?doi=10.1002%2Fchem.201304950&file=chem_201304950_sm_miscellaneous_information.pdf.

Smoot, J. et al., "Development of an Arming Participating Group for Stereoselective Glycosylation and Chemoselective Oligosaccharide Synthesis," Angewandte Chemie International Edition, 2005, 44, 7123-7126.

Teodorović, P. et al., "Synthesis of Stable C-phosphonate analogues of *Neisseria meningitidis* Group A Capsular Polysaccharide Structures Using Modified Mitsunobu Reaction Conditions," Organic & Biomolecular Chemistry, 2006, 4, 4485-4490.

Torres-Sánchez, M. et al., "Synthesis of the Phosphono Analogue of the Dimeric Subunit of *Neisseria meningitidis* Type A Capsular Polysaccharide," Synlett, 2005, 7, 1147-1151.

Written Opinion of the International Searching Authority for International Application No. PCT/EP2019/082331, mailed Feb. 25, 2020, 8 pages.

Broecker, F. et al., "Synthetic Oligosaccharide-Based Vaccines Protect Mice from *Clostridioides difficile* Infections," ACS Chemical Biology, 2019, 14, 2720-2728.

Supplementary Information for Broecker, F. et al., "Synthetic Oligosaccharide-Based Vaccines Protect Mice from *Clostridioides difficile* Infections," ACS Chemical Biology, 2019, 14, 2720-2728, pp. S1-S14.

\* cited by examiner

Figure 2

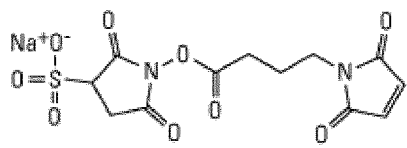

Sulfo-GMBS
N-(γ-Maleimidobutyryloxy) sulfosuccinimide ester
MW 382.28
Spacer Arm 7.3 Å

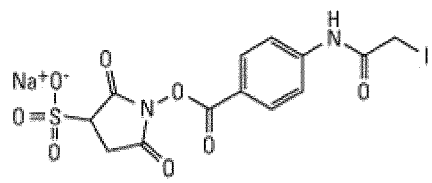

Sulfo-SIAB
Sulfosuccinimidyl (4-iodoacetyl) aminobenzoate
MW 504.19
Spacer Arm 10.6 Å

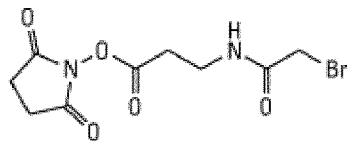

SBAP
Succinimidyl-3-(bromoacetamido)propionate
MW 307.10
Spacer Arm 6.2 Å

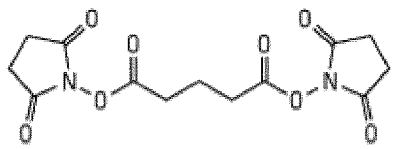

DSG
Disuccinimidyl glutarate
MW 326.26
Spacer Arm 7.7 Å

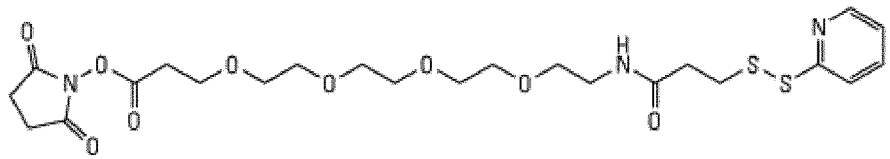

PEG4-SPDP
2-Pyridyldithiol-tetraoxatetradecane-N-hydroxysuccinimide
MW 559.17
Spacer Arm 25.7 Å

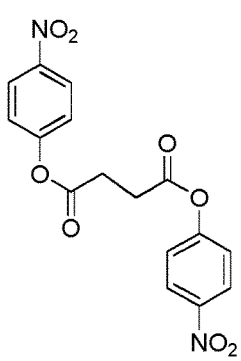

Bis-(4-nitrophenyl)succinate

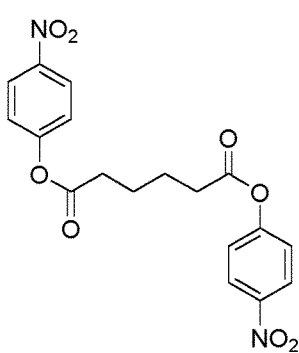

Bis-(4-nitrophenyl) adipate

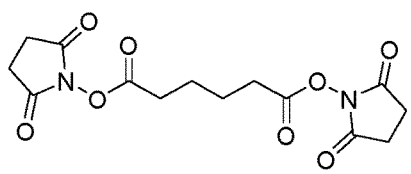

DSA
Disuccinimidyl adipate

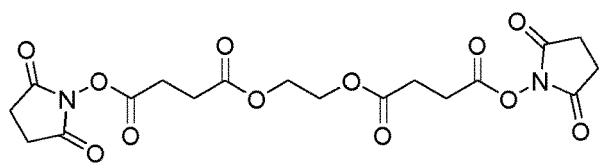

Ethylene glycol-bis(succinic acid
N-hydroxysuccinimide ester)

(V-2)

STABLE VACCINE AGAINST *CLOSTRIDIUM DIFFICILE*

CROSS REFERENCE TO RELATED APPLICATIONS

This application is a United States Application under 35 U.S.C. § 371 of International Application No. PCT/EP2019/082331, filed on Nov. 22, 2019, which claims priority to and the benefit of European Patent Application No. 18207920.2, filed on Nov. 22, 2018, the contents of each of which are incorporated herein by reference in their entireties.

FIELD OF THE INVENTION

The present invention relates to a synthetic saccharide of general formula (I) that is related to *Clostridium difficile* PS-II cell-surface polysaccharide and conjugate thereof. Said synthetic saccharide, said conjugate and pharmaceutical composition containing said synthetic saccharide or said conjugate are hydrolysis-resistant, long-term stable, thermostable and useful for prevention and/or treatment of diseases associated with *Clostridium difficile*, now named *Clostridioides difficile*. Furthermore, the synthetic saccharide of general formula (I) is useful as marker in immunological assays for detection of antibodies against *Clostridium difficile* bacteria.

BACKGROUND OF THE INVENTION

*Clostridioides difficile*, in the past known as *Clostridium difficile* is a Gram-positive spore-forming anaerobic bacterium, which is considered the most important definable cause of nosocomial diarrhea. The term Clostridioides *difficile* and *Clostridium difficile* are used herein synonymously and are both abbreviated with *C. difficile*. It colonizes the intestinal tract of humans thus leading to *Clostridium difficile* infections (CDI). CDI has also become the most commonly diagnosed cause of hospital-acquired diarrhea, particularly in the risk groups including elderly and immunodeficient patients as well as those receiving antibiotic treatment. Infections caused by *C. difficile* are becoming an important challenge due to the rapid increase of CDI incidence over the last ten years, which is mainly attributed to the emergence of the hypervirulent, and now predominant strain ribotype 027, causing epidemic outbreaks with increased morbidity, mortality and high relapse rates. The treatment costs of greatly increased, particularly in the case of recurring CDI. Thus, prevention of infections caused by *Clostridium difficile* is highly desirable, and vaccination of risk groups is the most cost-efficient and the most powerful means. However, a vaccine against *Clostridium difficile* has not been developed yet.

Carbohydrates exposed on the cell-surface of bacteria are often immunogenic and constitute potential candidates for vaccine development. In comparison with proteins, carbohydrates are evolutionarily more stable and when covalently connected to a carrier protein, oligosaccharide antigens can elicit long lasting, T-cell-dependent protection.

Three different structures of the cell-wall polysaccharide expressed by *C. difficile* cells, named PS-I, PS-II and PS-III were identified (*Expert Rev. Vaccines* 2013, 12, 421). While the expression of PS-I saccharide may be more restricted e.g. expressed in ribotype 027, the PS-II saccharide was found in in all examined *C. difficile* ribotypes, indicating that the PS-II saccharide may be a conserved surface antigen.

The repeating unit of the *C. difficile* PS-II saccharide consists of:

$$\rightarrow 6)\text{-}\beta\text{-D-Glc-}(1,3)\text{-}\beta\text{-D-GalNAc-}(1,4)\text{-}\alpha\text{-D-Glc-}(1,4)\text{-}\beta\text{-D-GalNAc-}(1,3)\text{-}\alpha\text{-D-Man-}(1\rightarrow OPO_3\rightarrow$$
$$3$$
$$\uparrow$$
$$1$$
$$\beta\text{-D-Glc}$$

The *C. difficile* PS-II saccharide hydrolyzes in water due to the chemical lability of the (1→6) phosphodiester bond interconnecting the PS-II repeating units at the anomeric position of mannose, thereby complicating the extraction from cells by commonly used hot acetic acid or water/phenol. The cleavage of the O1-C1 phosphodiester bond is followed by removal of a phosphomonoester group, leading to PS-II hexasaccharide unit. The phosphodiester bond cleavage of the PS-II saccharide is increased in the presence of acids, bases or metal ions. Because of the instability of *C. difficile* PS-II saccharide in solution, the saccharide or its conjugate, when used as a vaccine, has to be suitably buffered in a liquid formulation or lyophilized as a solid formulation, which has to be reconstituted before use. However, lyophilization and cold storage of vaccines lead to an increase of the cost of production and the complexity of the vaccine delivery, as a working cold chain system ensuring optimal temperatures during transport, storage and handling is required. The instability of the *C. difficile* PS-II saccharide is well documented in art. Thus, new stable *C. difficile* vaccine in form of a liquid formulation is required.

The international patent application WO 2009/033268 A1 discloses the isolation of the PS-I and PS-II cell-surface saccharide of *C. difficile* from *C. difficile* bacteria of strains ribotype 027, MOH900 and MOH718. A synthetic approach to PS-II cell-surface saccharide of *C. difficile* was followed by Danieli et al. (Org. let. 2011, 13, 378-381), Costantino et al. (WO 2012/085668 A2), Seeberger (WO 2012/119769 A1) and Oberli et al. (Chemistry & Biology 2011, 18, 580). Monteiro (Meth Mol. Biol. 2016, 397-408) reports on the isolation of water-soluble PS-I and PS-II as well as water- and phenol soluble PS-III polysaccharide from *C. difficile* biomass by hot water-phenol treatment.

It is the objective of the present invention to provide a well-defined synthetic saccharide of general formula (I) that is metabolic stable, hydrolysis-resistant and shelf-stable in liquid formulations and that elicits antibodies which protect against diseases caused by *C. difficile*. Said saccharide can be conjugated to an immunogenic carrier to provide a conjugate and pharmaceutical composition thereof that are useful for prevention and/or treatment of diseases associated with *C. difficile*. Furthermore, the synthetic saccharide of general formula (I) is useful as marker in immunological assays for detection of antibodies against *C. difficile* bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. By keeping a certain distance between the saccharide and the immunogenic carrier the shielding of immunogenic saccharides epitopes by the structure of the immunogenic carrier (e.g. secondary structure of the carrier protein) is avoided. In addition, the linker provides greater efficiency of coupling with saccharides by reducing steric hindrance of reactive groups (Methods in Molecular Medicine 2003, 87, 153-174). More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

Any linker for saccharide conjugates (e.g. saccharide-carrier protein conjugate, antibody-drug conjugate) known in the art can be used within the present invention. From the large number of publications directed to saccharide carrier protein conjugates the person skilled in the art can readily envision suitable linkers for the herein discloses saccharides and conjugates (see "Antimicrobial glycoconjugate vaccines: an overview of classic and modern approaches for protein modification" in Chem Soc Rev 2018, Advance Article, DOI: 10.1039/C8CS00495A; as well as Acc Chem Res 2017, 50, 1270-1279) since the used linker, i.e. its length and linkage type, does not significantly influence the immunogenicity of a saccharide conjugate (see PLoS ONE 2017, 12(12): e0189100; J. Immun. Meth. 1996, 191, 1-10). Such suitable linkers are harmless (i.e. non-toxic) and non-immunogenic (i.e. do not lead to the formation of nonprotective antibodies on immunization with a conjugate) and include but are not restricted to commercially available bifunctional polyethylene glycol (Journal of Controlled Release 2013, 172, 382-389; J. Immun. Meth. 1996, 191, 1-10), glutaric acid derivatives (J. Org. Chem. 2005, 70(18), 7123-7132), adipic acid derivatives, squarate derivatives, alkynes, N-hydroxysuccinimides, such as the commercially available MFCO-NHS (monofluoro-substituted cyclooctyne N-hydroxysuccinimide ester), maleimides (as disclosed in Acc. Chem. Res. 2017, 50, 1270-1279), or hydrophilic alkyl phosphinates and sulfonyls (as described in WO2014080251A1).

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 3 displays examples of commercially available interconnecting molecules, but does not restrict the interconnecting molecules that can be used according to the present invention to the examples displayed herein. It is to be understood that an interconnecting molecule does not form part of the linker or immunogenic carrier or solid support.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminium salts (or mixtures thereof). Calcium salts include calcium phosphate. Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminium hydroxide and aluminium phosphate may be also used. The invention can use any of the "hydroxide" or "phosphate" adjuvants that are in general used as adjuvants. The adjuvants known as "aluminium hydroxide" are typically aluminium oxy-hydroxide salts, which are usually at least partially crystalline.

The adjuvants known as "aluminium phosphate" are typically aluminium hydroxyphosphates, often also containing a small amount of sulfate (i. e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from *Smilax ornata* (sarsaprilla), *Gypsophilla paniculata* (brides veil), and *Saponaria officinalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS 7, QS 17, QS 18, QS21, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 μm in diameter, more preferably 200 nm to 30 μm in diameter, or 500 nm to 10 μm in diameter) formed from materials that are biodegradable and non-toxic. Such non-toxic and biodegradable materials include, but are not restricted to poly(α-hydroxy acid), polyhydroxybutyric acid, polyorthoester, polyanhydride, polycaprolactone;

CD1d ligands, such as an α-glycosylceramide, phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-sulfo-galactosyl-ceramide;

immunostimulatory oligonucleotides, such CpG motif containing ones (a dinucleotide sequence containing an unmethylated cytosine residue linked by a phosphate bond to a guanosine residue), or CO motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as MPLA or the TLR4 antagonist E5564;

oil emulsions (e.g. Freund's adjuvant).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can:

direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and—blocking the rapid dispersal of the antigen challenge.

Saccharides are known by the person skilled in the art as TI-2 (T cell independent-2) antigens and poor immunogens. Therefore, to produce a saccharide-based vaccine, said saccharides are conjugated to an immunogenic carrier to provide a conjugate, which presents an increased immunogenicity in comparison with the saccharide. In this context the term "immunogenic carrier" is defined as a structure, which is conjugated to the saccharide to form a conjugate that presents an increased immunity in comparison with the saccharide per se. Thus, the conjugation of the saccharides to the immunogenic carrier, preferably protein carrier, has as effect the stimulation of the immune response against said saccharide, without inducing an immune response against the said immunogenic carrier.

Hence, the present invention is directed to a saccharide of general formula (I)

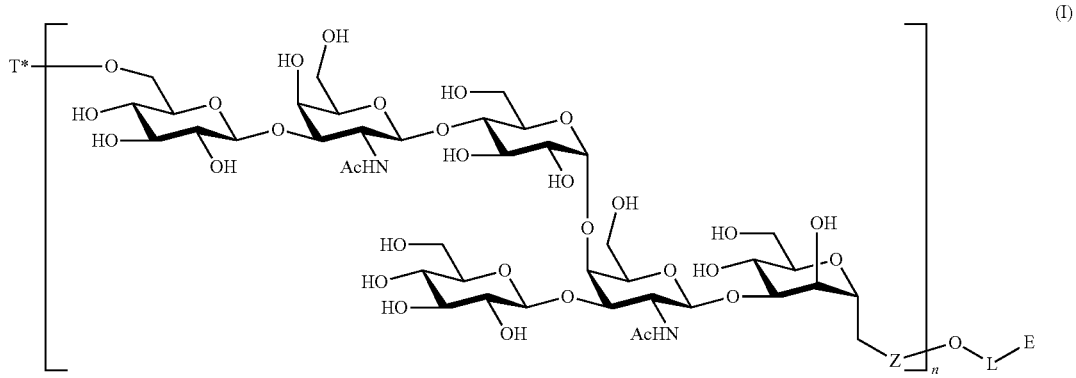

wherein n is an integer selected from 1, 2, 3, 4, 5, 6, 7, 8, 9 and 10;

T*- represents H— or a phosphate group;

Z represents

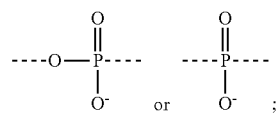

L represents a linker and;

E represents —NH$_2$, —N$_3$, —CN, —O—NH$_2$, —CH=CH$_2$, —C≡CH, —Br, —Cl, —I, —CO$_2$R', —CONH—NH$_2$, —SH, —OH or —SAc;

R' represents —H, -Me, -Et, 4-nitrophenyl, pentafluorophenyl, or N-succinimidyl;

or a diastereoisomer or a pharmaceutically acceptable salt thereof.

In all general formulae (I), (II), (III) and also all general subformula n is preferably an integer from 1 to 8, more preferably an integer from 1 to 6 and represents still more preferably 1, 2, 3, 4, or 5, still more preferably 1, 2, 3, or 4, still more preferably 1, 2, or 3, still more preferably 1 or 2, and still more preferably 1.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-L-NH$_2$) and the NH$_2$-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the NH$_2$-group) consists of 2 to 6 atoms, these are preferably carbon atoms. In case the shortest chain consists of 4 to 8 atoms, the chain may contain 1 or 2 heteroatoms selected from O, N and S. In case the shortest chain consists of 9 to 14 atoms, the chain may contain 1, 2, 3, or 4 heteroatoms selected from O, N and S.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L- may also contain amide (—NH—CO—, —CO—NH—) and/or urea (—NH—CO—NH—) residues and preferably only one amide or urea residue. The linker may also contain substituents and preferably two substituents such as R$^{10}$ and R$^{11}$ or four substituents such as R$^{10}$, R$^{11}$, R$^{15}$ and R$^{14}$, which have the meanings as defined herein and which are preferably selected from: —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$.

In case the linker -L- is fluorinated, more than two substituents —F are preferred.

Preferably the linker -L- is selected from: —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$—O—CH$_2$—, —CH$_2$—O—(CH$_2$)$_2$—, —(CH$_2$)$_2$—O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$-;

wherein

-L$^a$- is selected from: —(CH$_2$)$_o$—, —(CF$_2$)$_o$—, —(CH$_2$—CH$_2$—O)$_o$—C$_2$H$_4$—, —(CH$_2$—CH$_2$—O)$_o$—CH$_2$—, —(CR$^{10}$R$^{11}$)$_o$—,

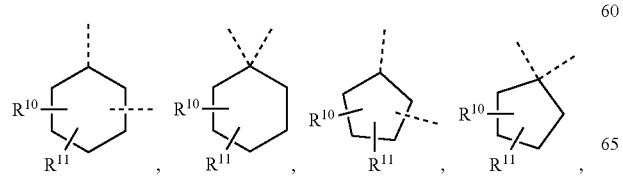

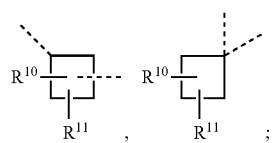

-L$^b$- and -L$^c$- are independently of each other selected from: —O—, —NH—C(O)—NH—, —NH—C(S)—NH—, —NH—C(O)—, —C(O)—NH—, —NH—C(O)—O—, —NR$^9$—, —NR$^{18}$—, —SO$_2$—,

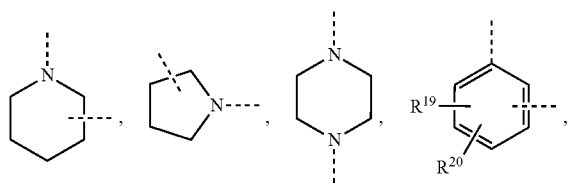

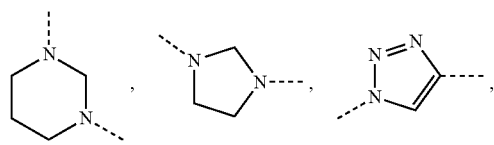

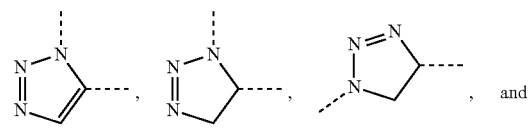

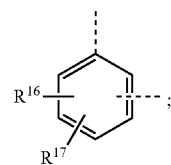

-L$^d$- represents —(CH$_2$)$_q$—, —(CF$_2$)$_q$—, —(CR$^{12}$R$^{13}$)$_q$—, —(CH$_2$—CH$_2$—O)$_q$—C$_2$H$_4$—, —(CH$_2$—CH$_2$—O)$_q$—CH$_2$—,

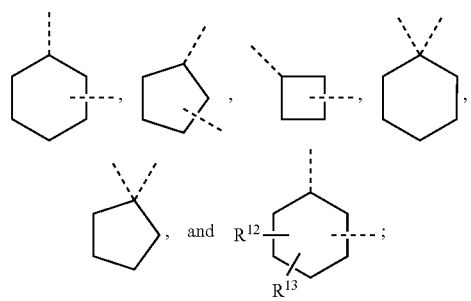

-L$^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

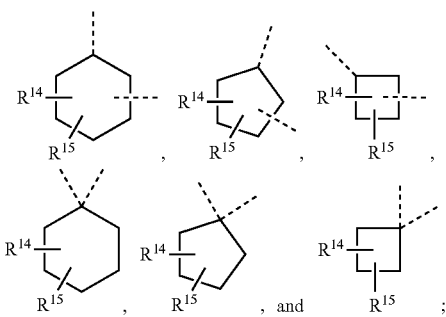

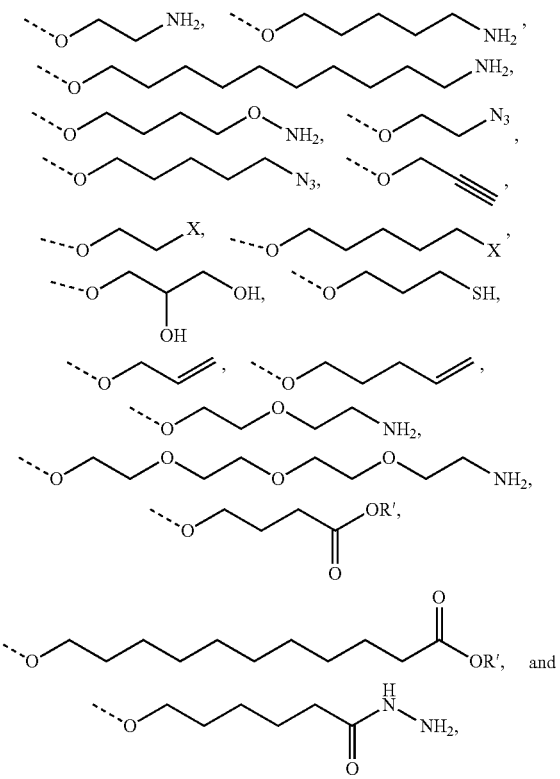

$R^9$ and $R^{18}$ are independently of each other selected from: —$CH_3$, —$C_2H_5$, —$C_3H_7$ and —$C(O)CH_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —C(O)—$NH_2$, —$SCH_3$, —$SC_2H_5$, —NHC(O)$CH_3$, —N($CH_3$)$_2$ and —N($C_2H_5$)$_2$;

o, q, p1 and p2 are independently of each other an integer selected from 1, 2, 3, 4, 5, 6, 7, 8, 9, and 10.

More preferred, -L- represents -$L^a$-, -$L^a$-$L^e$-, -$L^a$-$L^b$-$L^e$-, or -$L^a$-$L^d$-$L^e$-;

-$L^a$- represents —($CH_2$)$_o$—, —($CH_2$—$CH_2$—O)$_o$—$C_2H_4$—, or —($CH_2$—$CH_2$—O)$_o$—$CH_2$;

-$L^b$- represents —O—;

-$L^d$- represents —($CH_2$)$_q$—, —(CH(OH))$_q$—, —($CF_2$)$_q$—, —($CH_2$—$CH_2$—O)$_q$—$C_2H_4$—, or —($CH_2$—$CH_2$—O)$_q$—$CH_2$—;

-$L^e$- represents —($CH_2$)$_{p1}$—, —($CF_2$)$_{p1}$—, —$C_2H_4$—(O—$CH_2$—$CH_2$)$_{p1}$—, —$CH_2$—(O—$CH_2$—$CH_2$)$_{p1}$— or —($CH_2$)$_{p1}$—O—($CH_2$)$_{p2}$—; and o, q, p1 and p2 are independently of each other an integer selected from 1, 2, 3, 4, 5, and 6.

Most preferred, the saccharide of the formula (I) has the group —O-L-E selected from the group consisting of:

wherein R' represents —H, -Me, -Et, 4-nitrophenyl, pentafluorophenyl, or N-succinimidyl;

X represents —Br, —Cl, —I, —$CO_2H$, —CN, —$NO_2$ or —SAc.

The linker L may also comprise the repeating unit of the *C. difficile* PS-II saccharide or fragments thereof:

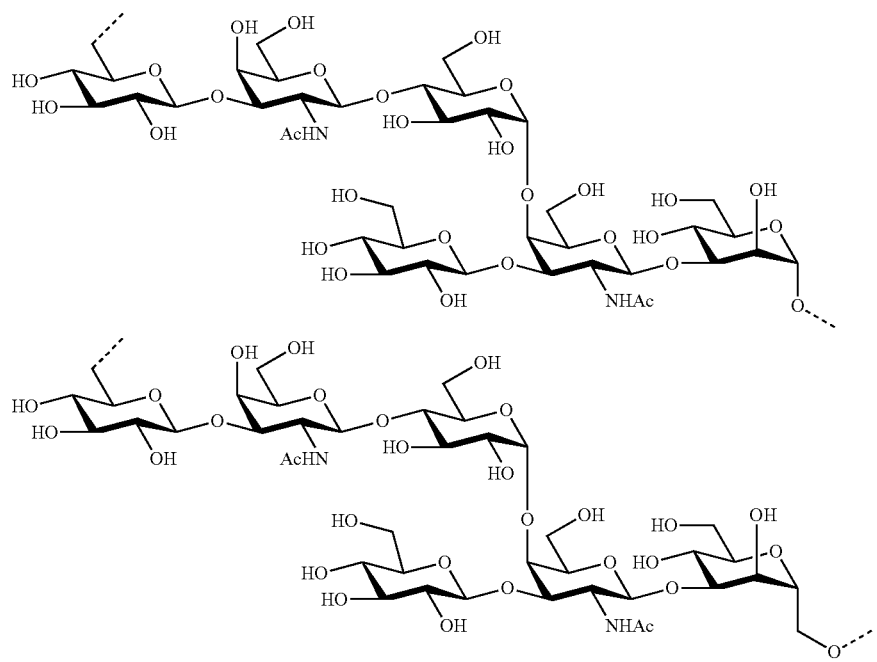

Thus, the linker L is preferably selected from one of the following structures:
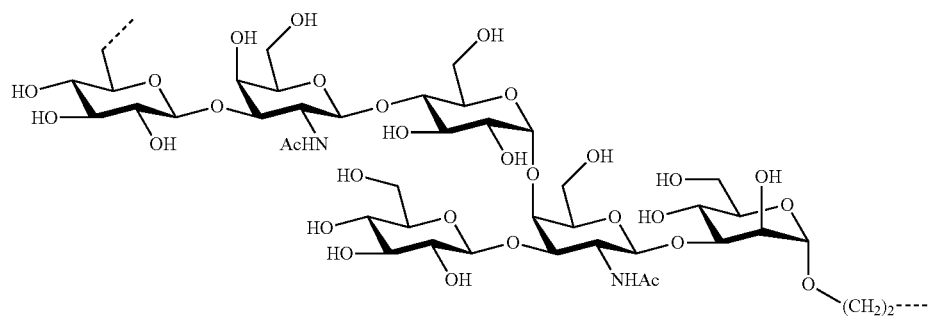
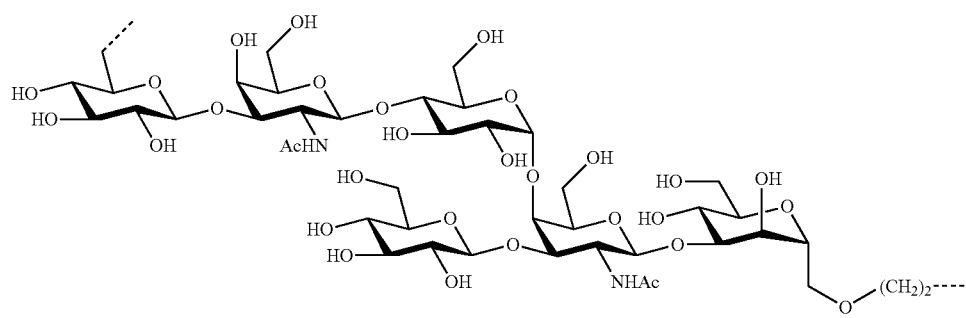
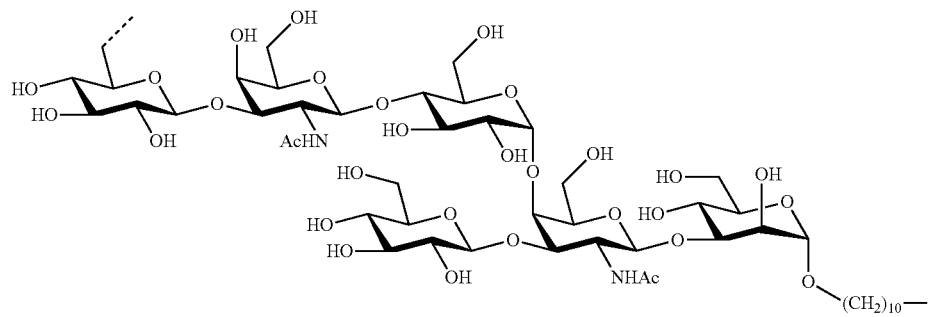
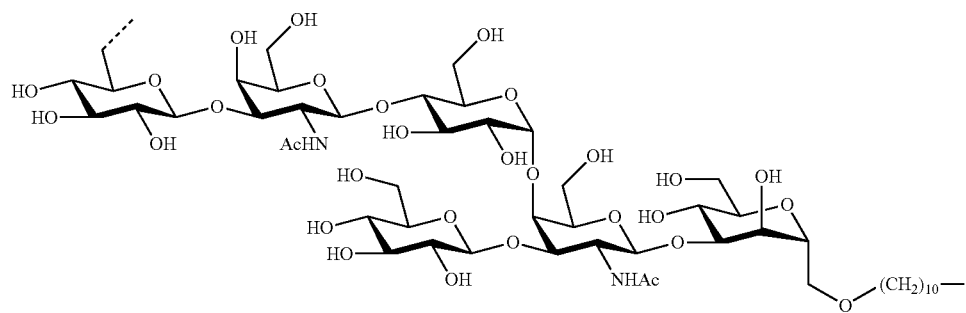
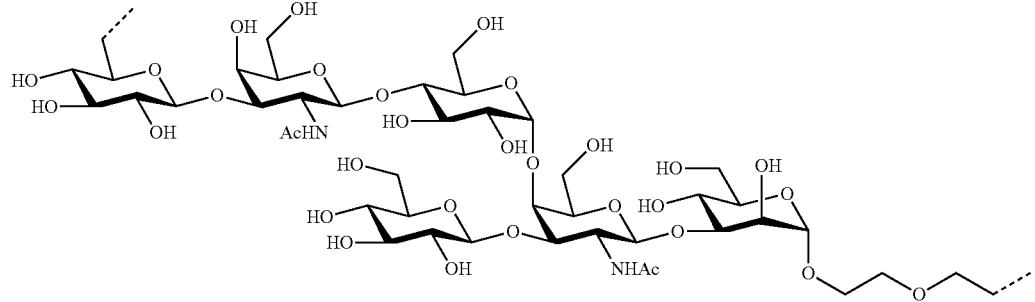

-continued
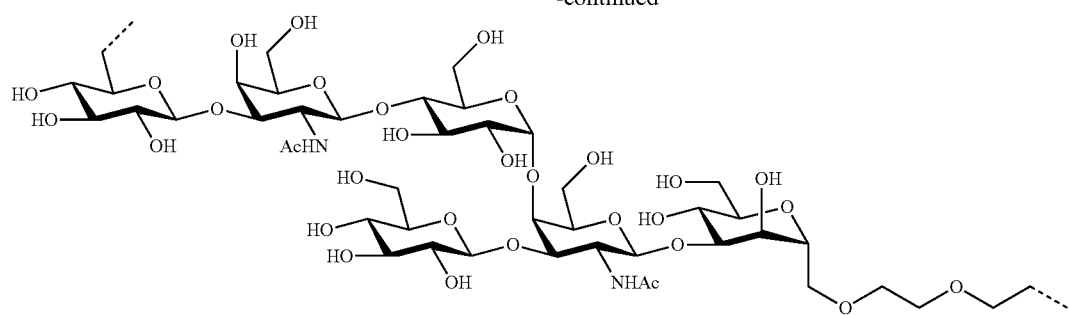
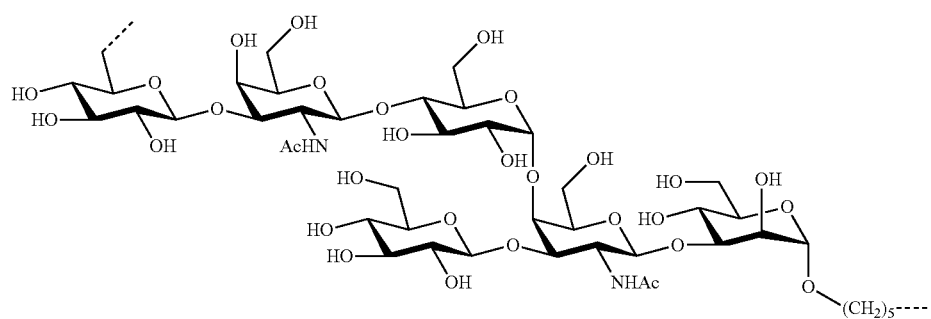
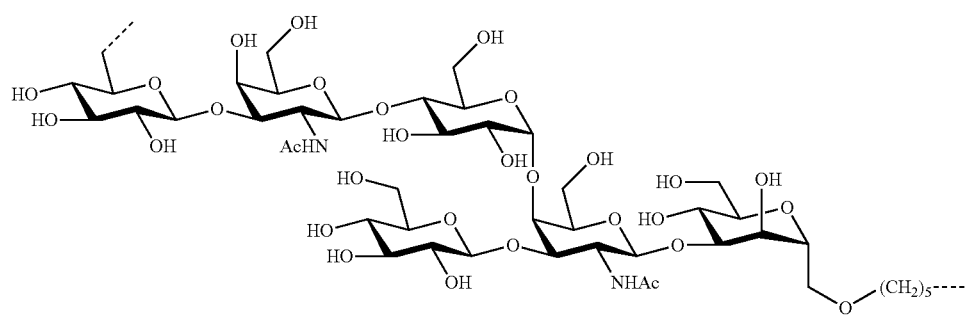
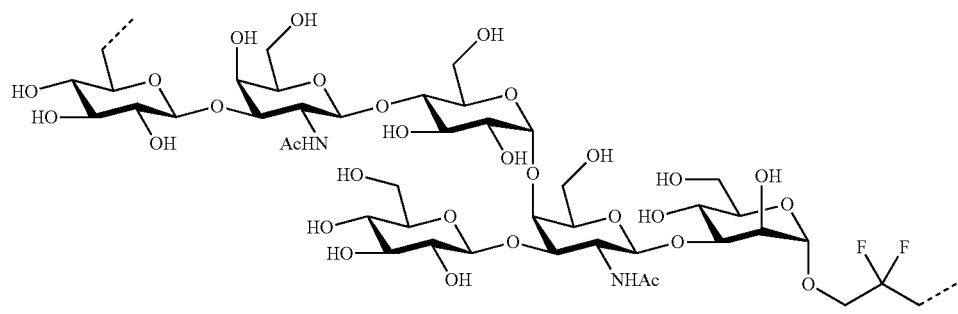
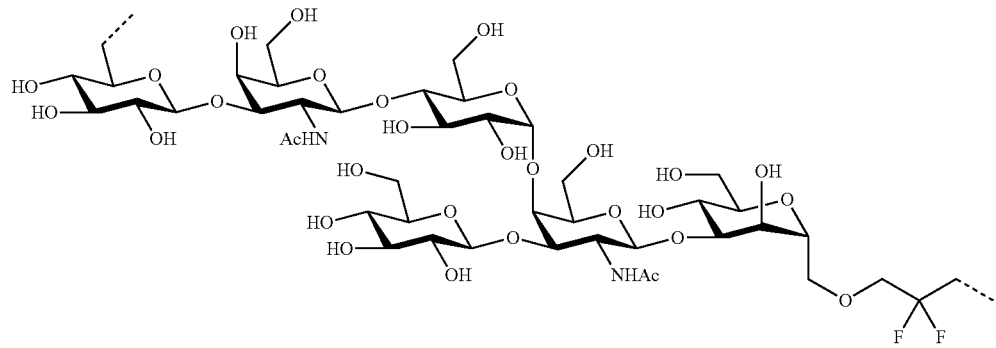

-continued
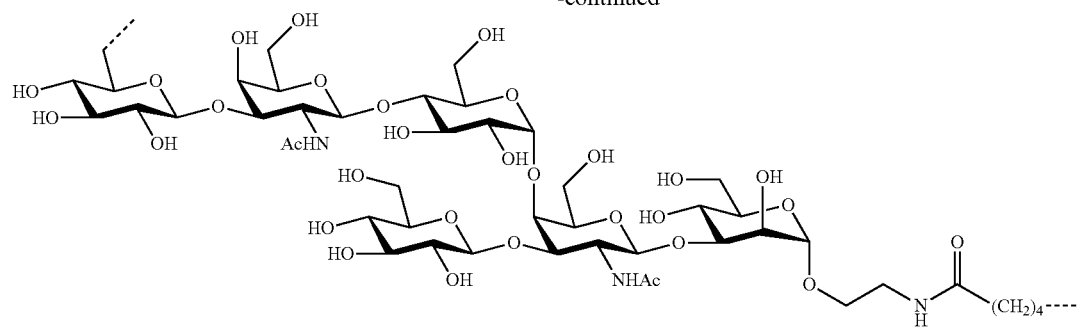
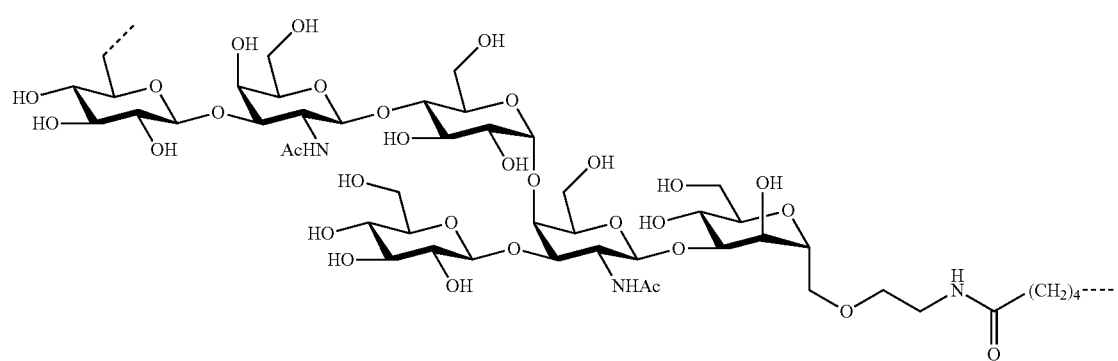
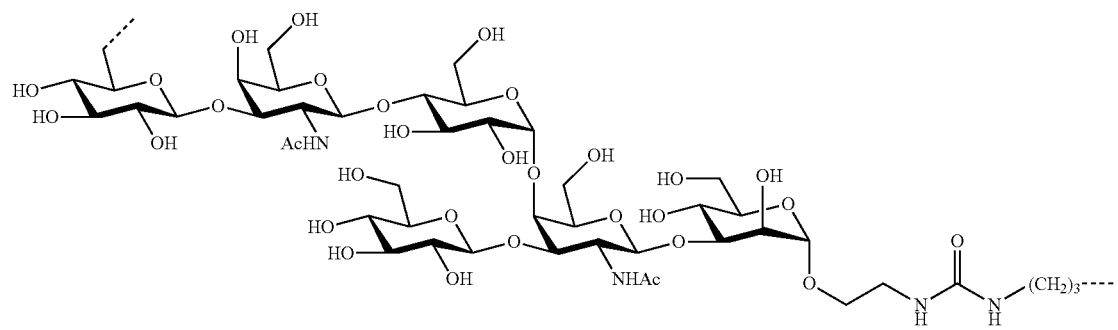
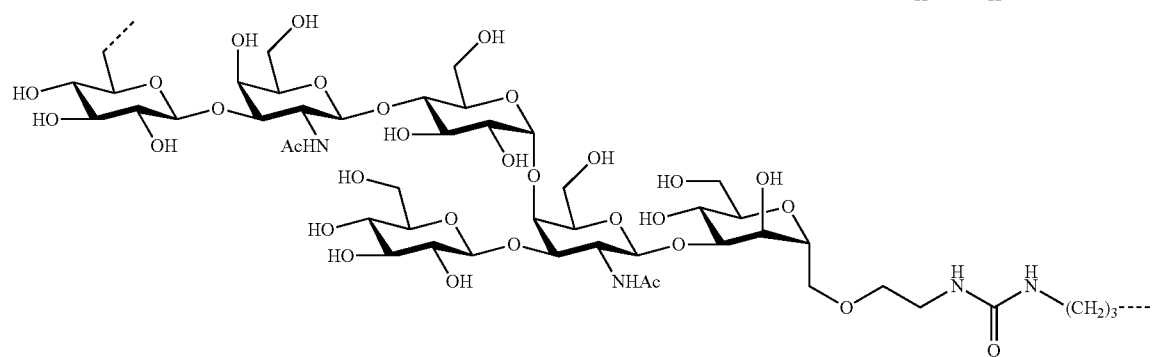
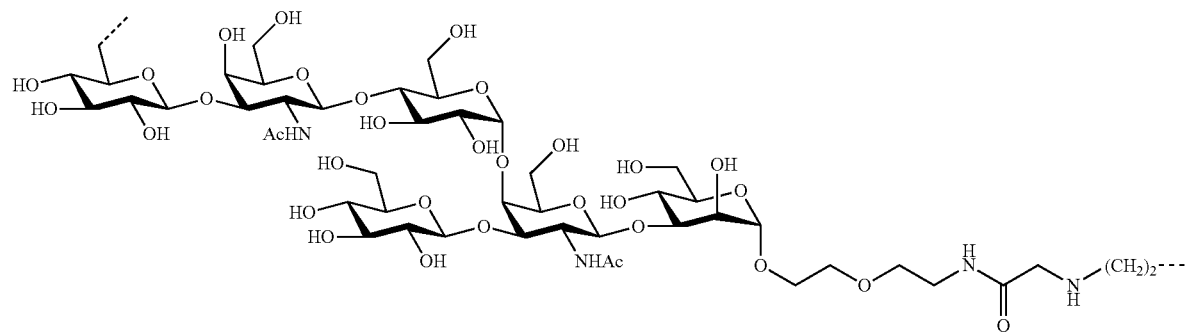

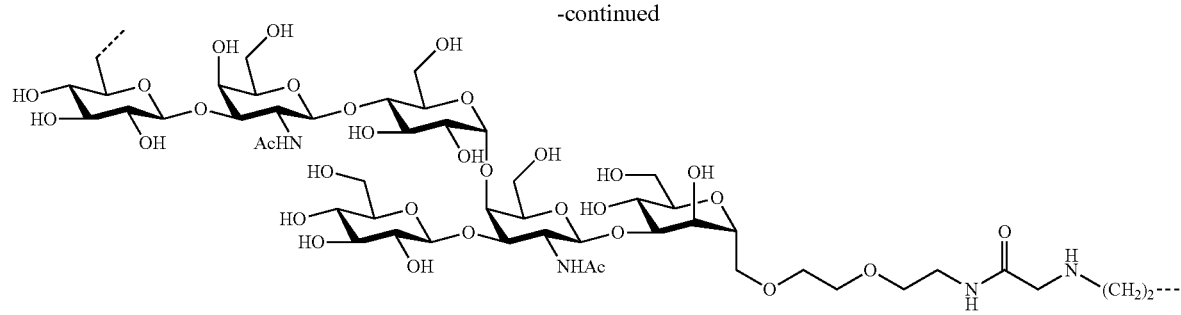
Therefore, preferred is also the saccharide of the formula (I) having the group —O-L-E selected from the group consisting of:
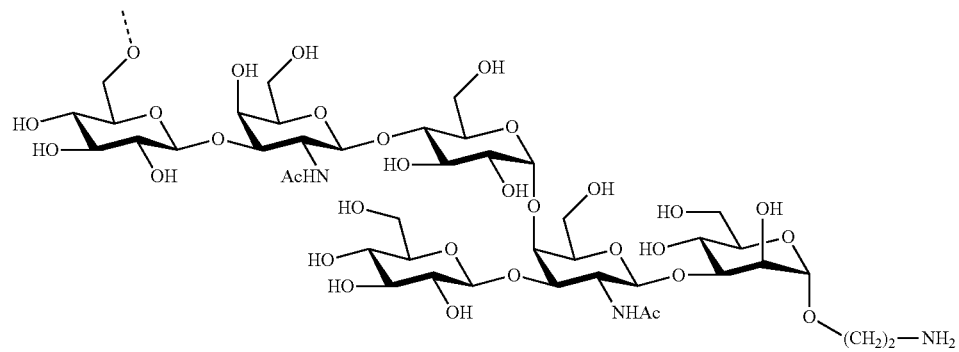
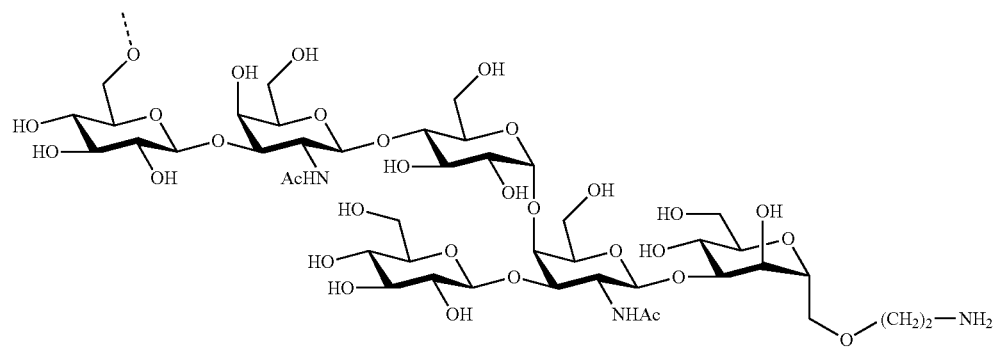
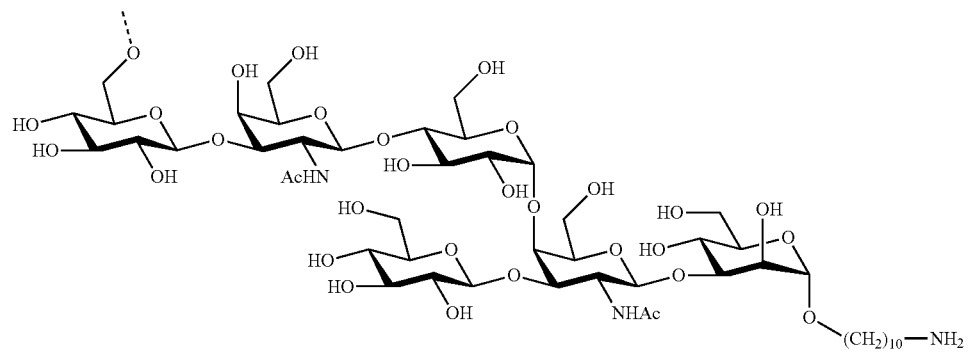

-continued
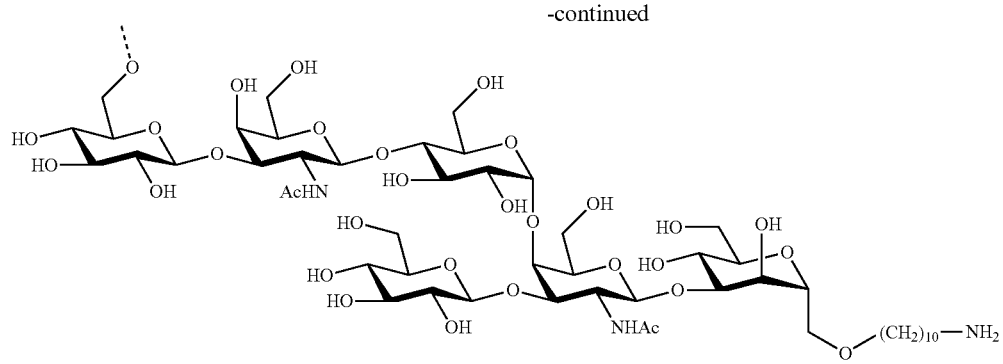
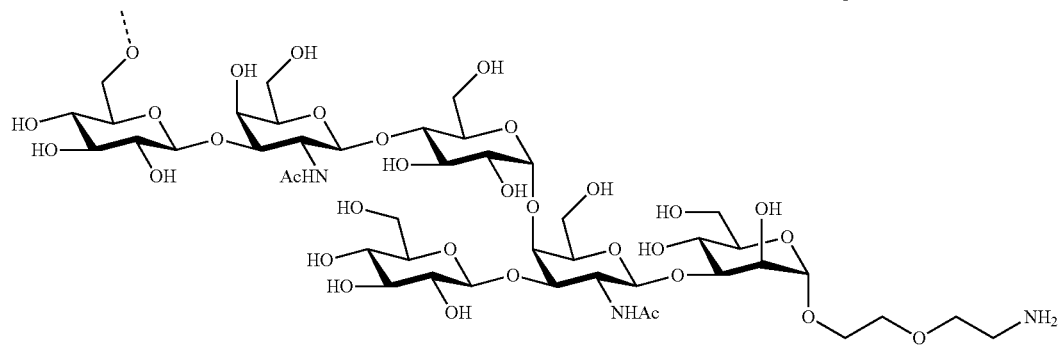
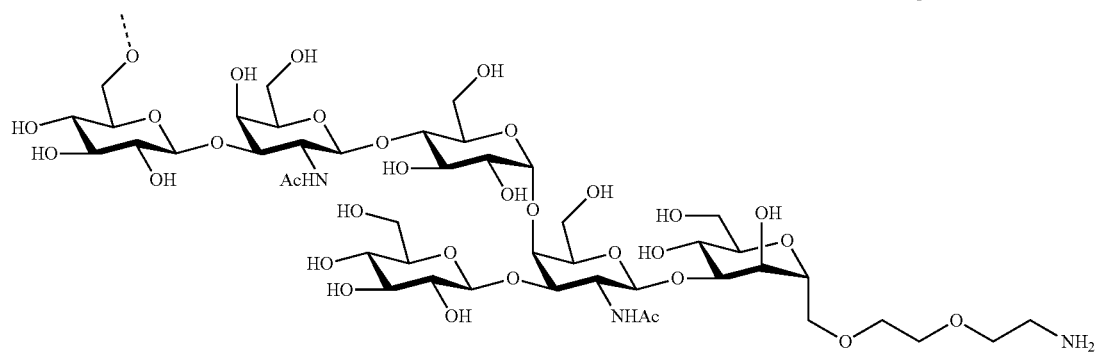
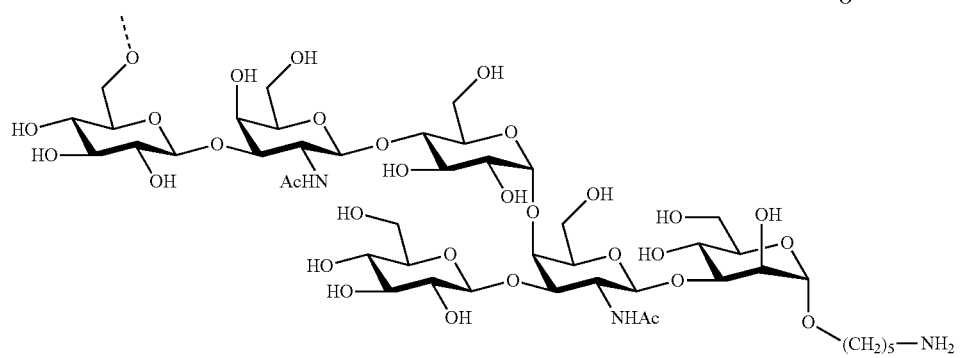
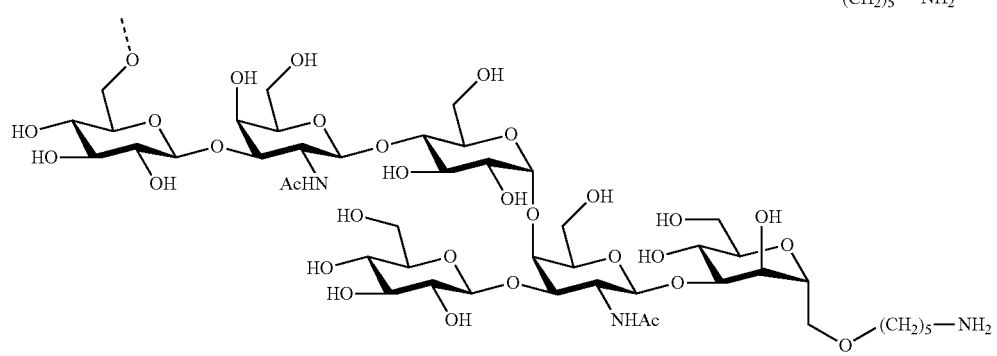

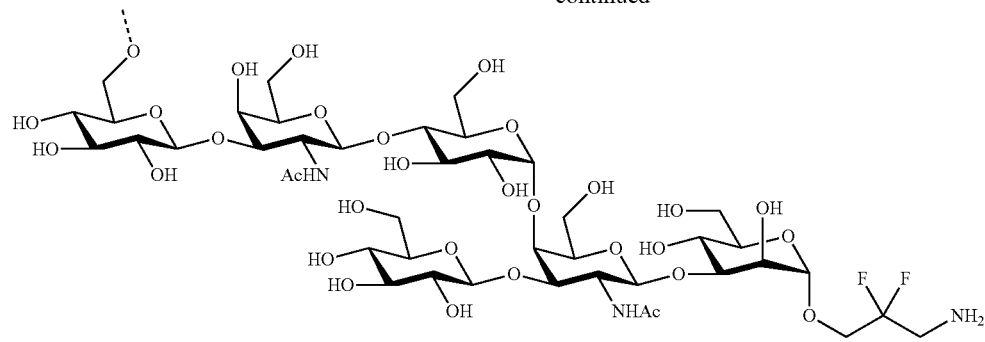
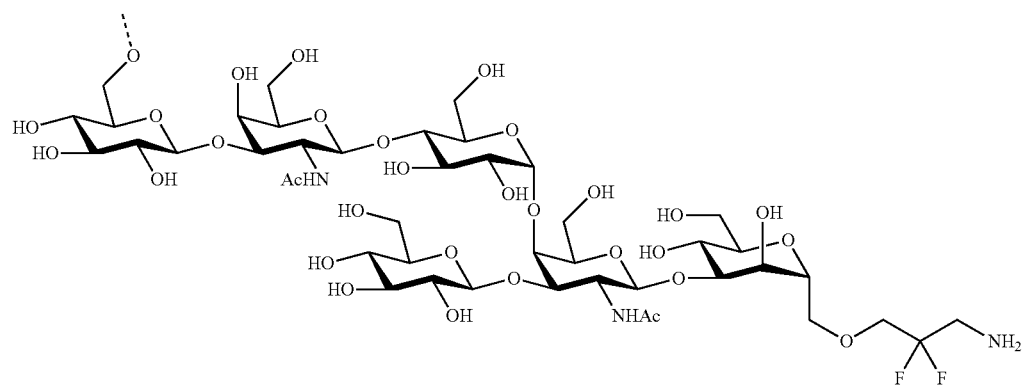
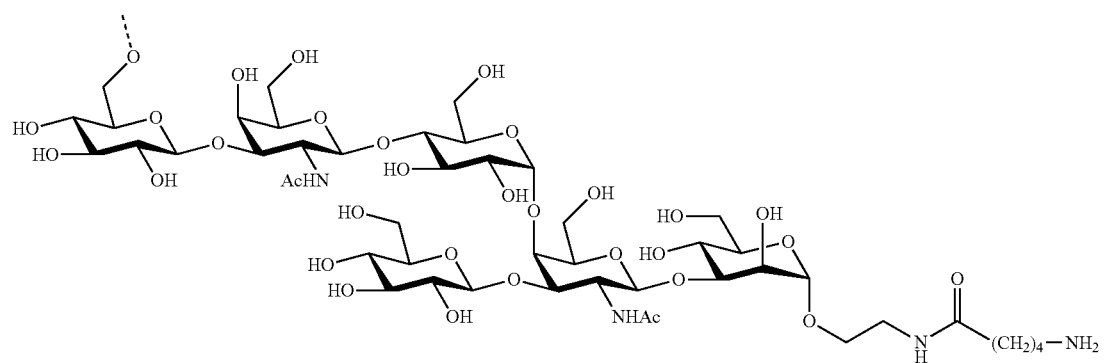
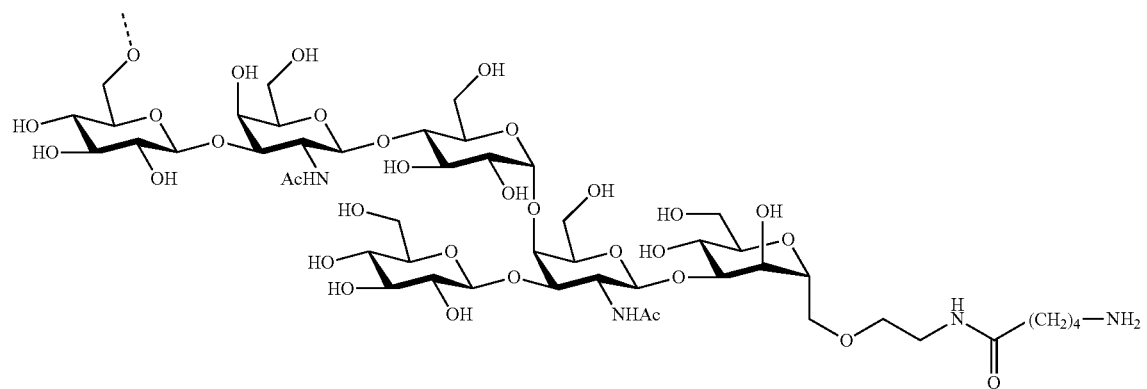

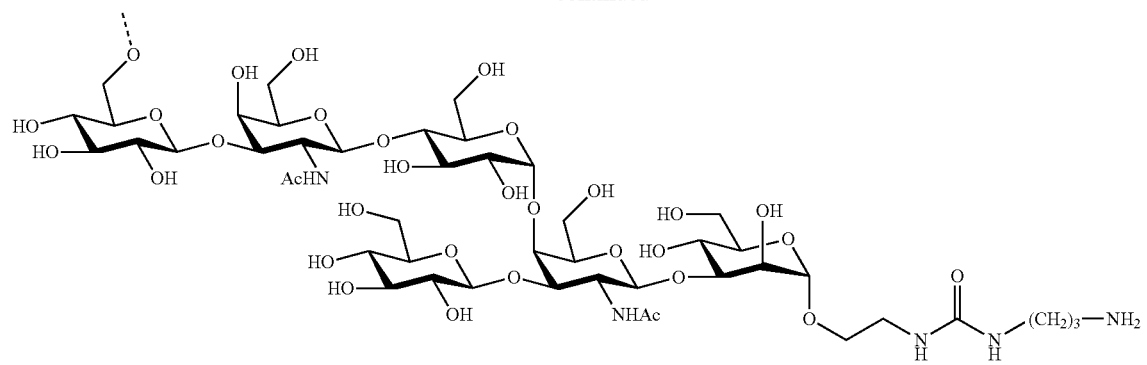
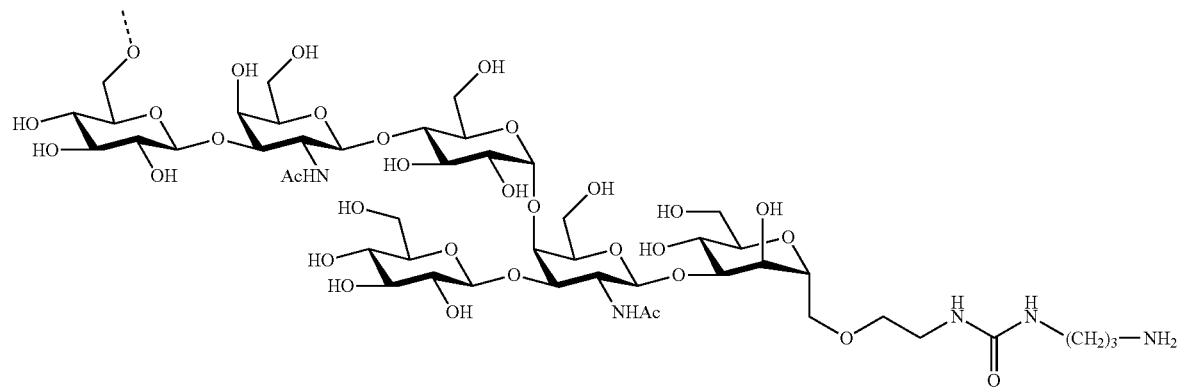
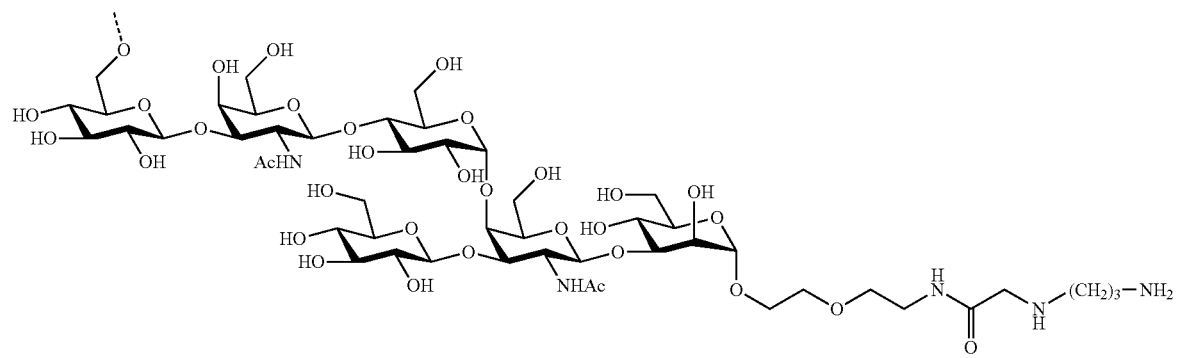
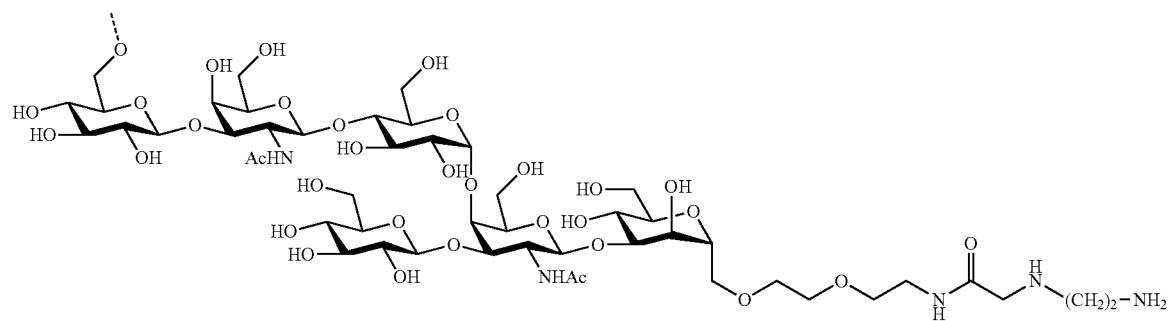

-continued
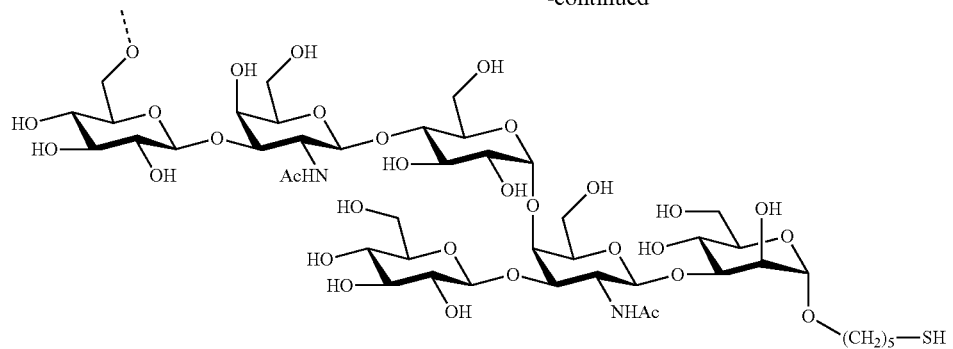
or preferably the disulfide of this moiety
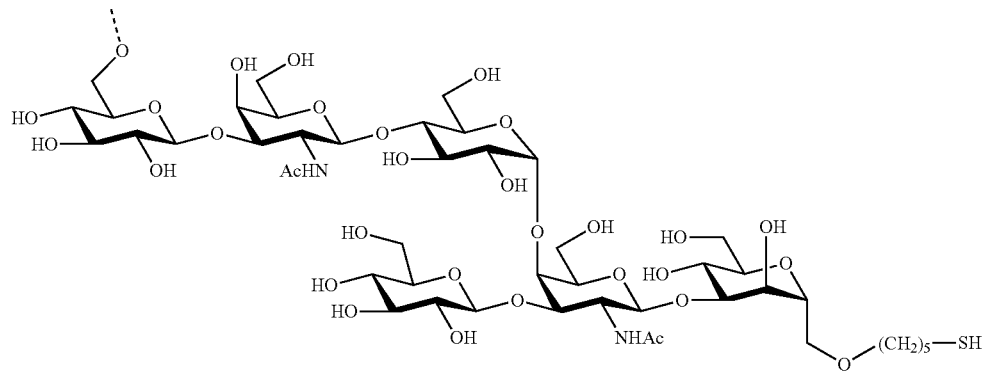
35
or preferably the disulfide of this moiety
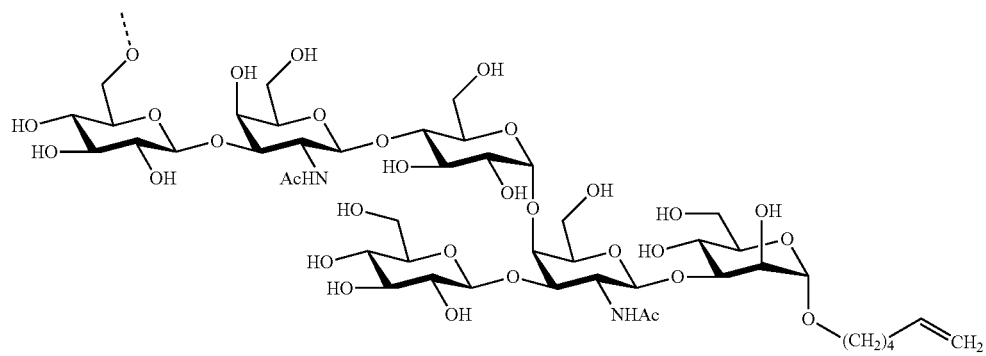
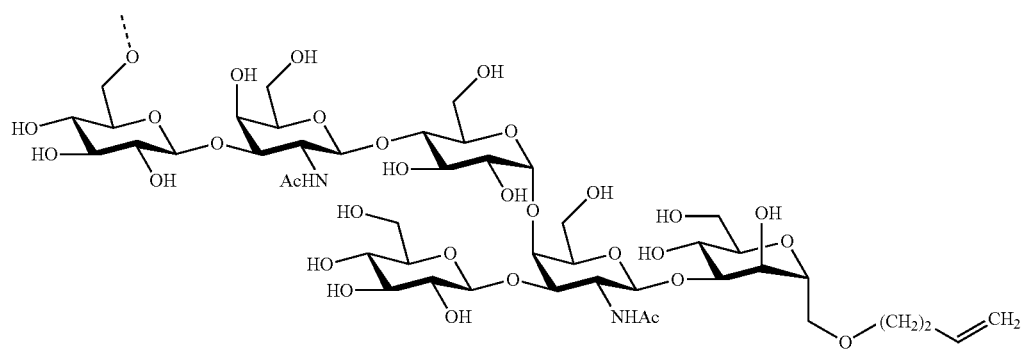

-continued

The saccharides of the present invention can be hygroscopic and thus can build various hydrates thereof. Preferred, molar ratio of water molecule to the saccharide is in the range of 1 to 20, more preferred, 1 to 10, most preferred, 5-10.

The saccharides of the present invention bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

It is clear for the skilled person in the art of carbohydrate chemistry that the saccharides of general (I) are not containing —O—O— bonds and or sugar fragments connected or bound to each other via their anomeric or C-1 carbons.

Surprisingly, it was found that a saccharide of general formula (I) contains an immunogenic protective epitope and is able to induce a protective immune response against *Clostridium difficile* bacteria in a human and/or animal host. The saccharide of general formula (I) elicits antibodies that are cross-reacting with the natural *Clostridium difficile* PS-II cell-surface saccharide, recognize specifically *Clostridium difficile* bacteria and opsonize them for killing by phagocytes, thus conferring protection against *Clostridium difficile* bacteria.

It was also surprisingly found that the saccharides of general formula (I) are stable in acidic aqueous media, basic aqueous media as well as suspensions containing aluminum phosphate or aluminum hydroxide, such as the commonly used adjuvant Alhydrogel. While natural *Clostridium difficile* PS-II saccharide hydrolyzes within one day in acidic aqueous media, in basic aqueous media, or in the presence of aluminum salts, the saccharides of general formula (I) as well as conjugates thereof are stable over several days even at elevated temperatures. The increased stability is particularly advantageous for their use in vaccines against *Clostridium difficile*. Thus the saccharides of general formula (I) as well as conjugates thereof are particularly useful for shelf-stable liquid vaccine formulations against *Clostridium difficile* which can be stored at ambient temperature.

The saccharides of the present invention overcome all the problems associated with the saccharides produced from bacterial sources and conjugates thereof in terms of purity and easiness of production. Firstly, the production of the cell wall saccharides requires optimization of the growth conditions. Secondly, depolymerization conditions under which the structural integrity of the constituting monosaccharides is maintained need to be found. Finally, purification conditions enabling the isolation of the pure saccharide of defined length and structure need to be determined. Besides usual contaminants, such as cellular polysaccharides, nucleic acids, lipids and proteins, also the undesired saccharides obtained through the depolymerization process, must be excluded. Thus, the production of pure saccharides of defined structure and length from bacterial sources is a tedious, almost impossible process.

Preferred are synthetic saccharides of formula (I) or (II) or (III), wherein T*- represents a phosphate group ($-P(=O)(OH)_2$ or $-P(=O)(O^-)(OH)$ or $-PO_3^{2-}$). Thus, the present invention is also directed to a saccharide of general formula (I) or (II) or (III), wherein n is an integer selected from 1, 2, 3, 4, 5, 6, 7, 8, 9 and 10;

T*- represents a phosphate group, i.e. T*- represents $-P(=O)(OH)_2$ or $-P(=O)(O^-)(OH)$ or $-PO_3^{2-}$;

Z represents $$\cdots\text{O}-\overset{\overset{\displaystyle O}{\|}}{\underset{\underset{\displaystyle O^-}{|}}{P}}\cdots \quad \text{or} \quad \cdots\overset{\overset{\displaystyle O}{\|}}{\underset{\underset{\displaystyle O^-}{|}}{P}}\cdots \quad ;$$

preferably Z represents $$\cdots\text{O}-\overset{\overset{\displaystyle O}{\|}}{\underset{\underset{\displaystyle O^-}{|}}{P}}\cdots \quad ;$$

L represents a linker and preferably the linker disclosed herein;

And the other substituents have the meanings as defined herein.

Preferred are synthetic saccharides of formula (I), wherein T*- represents hydrogen or a phosphate group ($-P(=O)(OH)_2$ or $-P(=O)(O^-)(OH)$ or $-PO_3^{2-}$). Thus, the present invention is also directed to a saccharide of general formula (I) or (II) or (III), wherein n is an integer selected from 1, 2, 3, 4, 5, 6, 7, 8, 9 and 10;

T*- represents —H or a phosphate group, i.e. T*- represents —H or $-P(=O)(OH)_2$ or $-P(=O)(O^-)(OH)$ or $-PO_3^{2-}$;

Z represents $$\cdots\text{O}-\overset{\overset{\displaystyle O}{\|}}{\underset{\underset{\displaystyle O^-}{|}}{P}}\cdots \quad \text{or} \quad \cdots\overset{\overset{\displaystyle O}{\|}}{\underset{\underset{\displaystyle O^-}{|}}{P}}\cdots \quad ;$$

preferably Z represents $$\cdots\text{O}-\overset{\overset{\displaystyle O}{\|}}{\underset{\underset{\displaystyle O^-}{|}}{P}}\cdots \quad ;$$

L represents a linker and;
E represents $-NH_2$, $-N_3$, $-CN$, $-O-NH_2$, $-CH=CH_2$, $-C\equiv CH$, $-Br$, $-Cl$, $-I$, $-CO_2R'$, $-CONH-NH_2$, $-SH$, $-OH$ or $-SAc$;
R' represents $-H$, -Me, -Et, 4-nitrophenyl, pentafluorophenyl, or N-succinimidyl.

Preferred are synthetic saccharides of general formula (II)

wherein n, L, E and T* have the meanings as defined herein.

Thus, a saccharide of general formula (II-a) or (II-b), wherein n, L, and E have the meanings defined herein is especially preferred.

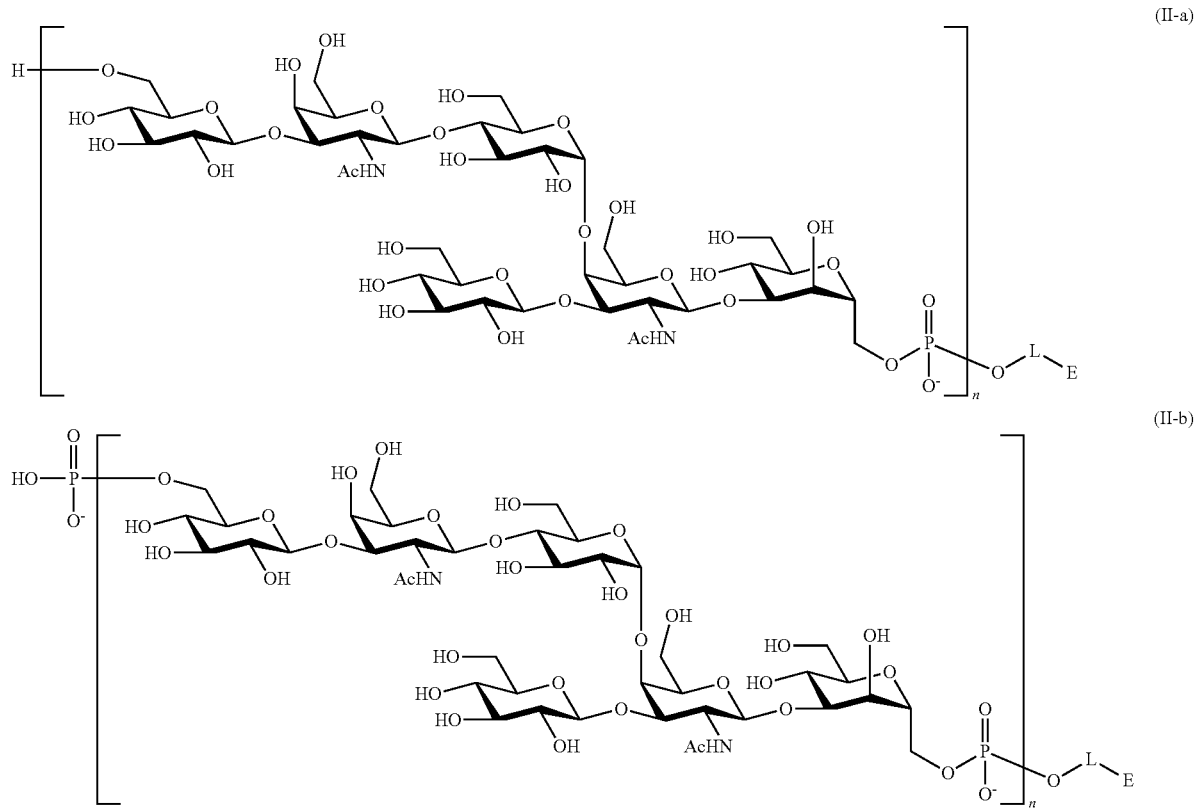

(II-a)

(II-b)

Also preferred are synthetic saccharides of general formula (III)

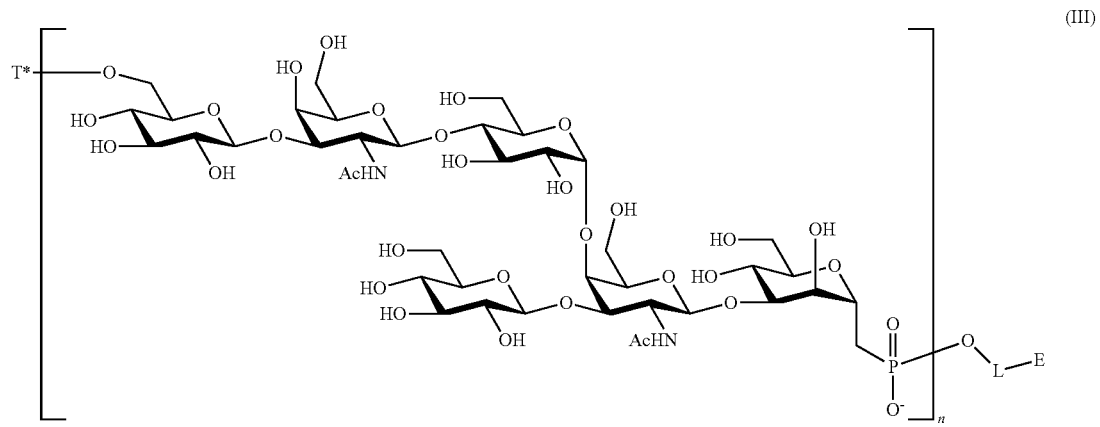

(III)

wherein n, L, E and T* have the meanings as defined herein.

Thus, a saccharide of general formula (III-a) or (III-b), wherein n, L, and E have the meanings defined herein is especially preferred.

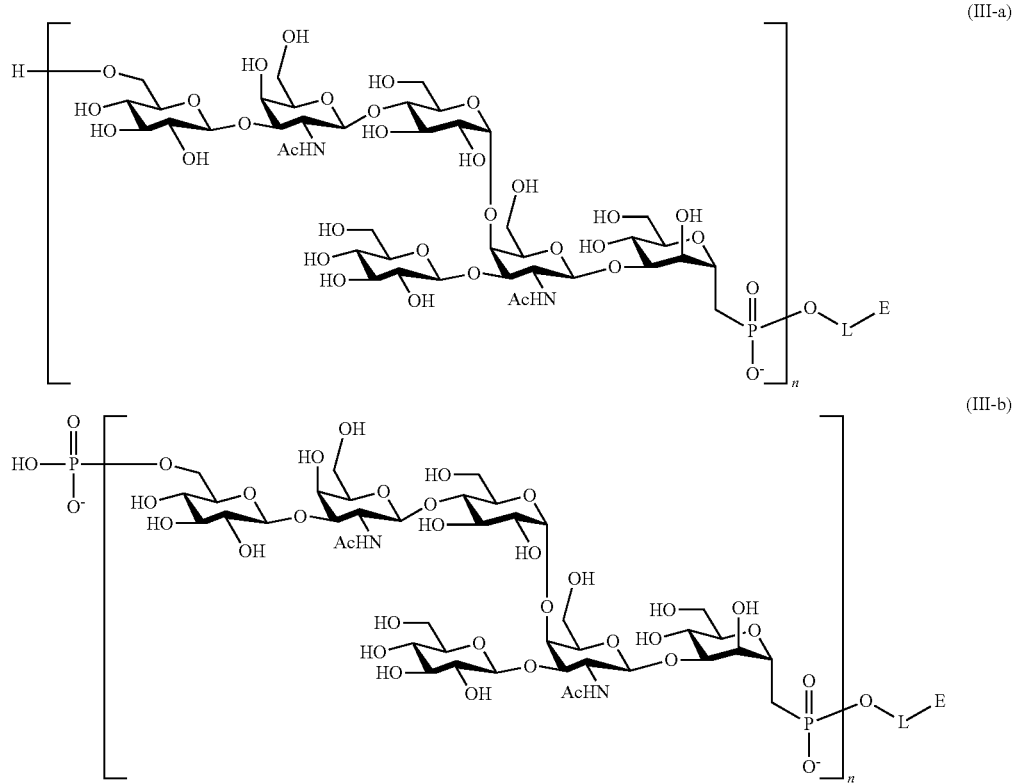

Preferably, n represents an integer selected from 1 to 10, more preferably from 1 to 6, more preferably from 1 to 3 and even more preferably from 1 to 2. Hence, a saccharide of general formula (I), (II), (II-a), (II-b), (III), (III-a) or (III-b), wherein n represents an integer selected from 1 to 2 is especially preferred.

Preferably the linker -L- represents -$L^a$-, -$L^a$-$L^e$-, -$L^a$-$L^b$-$L^e$-, or -$L^a$-$L^d$-$L^e$-;
- -$L^a$- represents —$(CH_2)_o$—, —$(CH_2—CH_2—O)_o$—$C_2H_4$—, or —$(CH_2—CH_2—O)_o$—$CH_2$;
- -$L^b$- represents —O—;
- -$L^d$- represents —$(CH_2)_q$—, —$(CH(OH))_q$—, —$(CF_2)_q$—, —$(CH_2—CH_2—O)_q$—$C_2H_4$—, or —$(CH_2—CH_2—O)_q$—$CH_2$—;
- -$L^e$- represents —$(CH_2)_{p1}$—, —$(CF_2)_{p1}$—, —$C_2H_4$—$(O—CH_2—CH_2)_{p1}$—, —$CH_2$—$(O—CH_2—CH_2)_{p1}$— or —$(CH_2)_{p1}$—O—$(CH_2)_{p2}$—; and
- o, q, p1 and p2 are independently of each other an integer selected from 1, 2, 3, 4, 5, and 6.

Therefore, a saccharide of any one of general formulae (I), (II), (II-a), (II-b), (III), (III-a) or (III-b), wherein
- -L- represents -$L^a$-, -$L^a$-$L^e$-, -$L^a$-$L^b$-$L^e$-, or -$L^a$-$L^d$-$L^e$-;
- -$L^a$- represents —$(CH_2)_o$—, —$(CH_2—CH_2—O)_o$—$C_2H_4$—, or —$(CH_2—CH_2—O)_o$—$CH_2$;
- -$L^b$- represents —O—;
- -$L^d$- represents —$(CH_2)_q$—, —$(CH(OH))_q$—, —$(CF_2)_q$—, —$(CH_2—CH_2—O)_q$—$C_2H_4$—, or —$(CH_2—CH_2—O)_q$—$CH_2$—;
- -$L^e$- represents —$(CH_2)_{p1}$—, —$(CF_2)_{p1}$—, —$C_2H_4$—$(O—CH_2—CH_2)_{p1}$—, —$CH_2$—$(O—CH_2—CH_2)_{p1}$— or —$(CH_2)_{p1}$—O—$(CH_2)_{p2}$—; and
- o, q, p1 and p2 are independently of each other an integer selected from 1, 2, 3, 4, 5, and 6 is especially preferred.

A saccharide of any one of general formulae (I), (II), (II-a), (II-b), (III), (III-a) or (III-b), wherein
- -L- is selected from: $L^a$, -$L^a$-$L^e$-, -$L^a$-$L^b$-$L^e$-, and -$L^a$-$L^d$-$L^e$-;
- -$L^a$- is selected from: —$(CH_2)_o$—, —$(CH_2—CH_2—O)_o$—$C_2H_4$—, —$(CH_2—CH_2—O)_o$—$CH_2$;
- -$L^b$- represents —O—;
- -$L^d$- is selected from: —$(CH_2)_q$—, —$(CF_2)_q$—, —$(CH_2—CH_2—O)_q$—$C_2H_4$—, and —$(CH_2—CH_2—O)_q$—$CH_2$—;
- -$L^e$- is selected from: —$(CH_2)_{p1}$—, —$(CF_2)_{p1}$—, —$C_2H_4$—$(O—CH_2—CH_2)_{p1}$—, —$CH_2$—$(O—CH_2—CH_2)_{p1}$— and —$(CH_2)_{p1}$—O—$(CH_2)_{p2}$—;
- o, q, p1 and p2 are independently of each other an integer selected from 1, 2, 3, 4, 5, and 6; and n represents 1 is also preferred.

Even more preferred is a saccharide of general formula (I), (II), (II-a), (II-b), (III), (III-a) or (III-b), wherein -L- represents —$(CH_2)_o$— and o is an integer selected from 1, 2, 3, 4, 5 and 6.

Also preferred is a saccharide of general (I), (II), (II-a), (II-b), (III), (III-a) or (III-b), wherein -L- represents —$(CH_2)_o$—, o is an integer selected from 1, 2, 3, 4, 5 and 6, and n represents an integer selected from 1 to 2.

In the most preferred embodiment, —O-L-E is selected from the group consisting of:

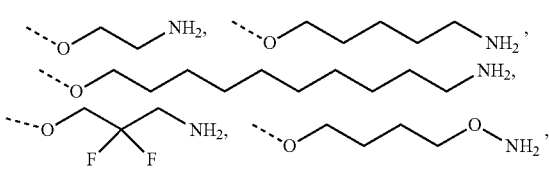

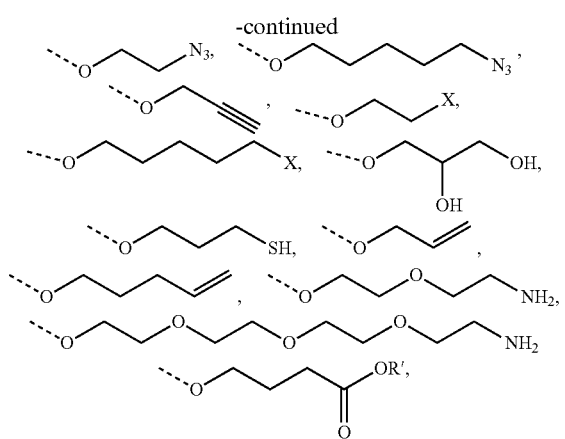
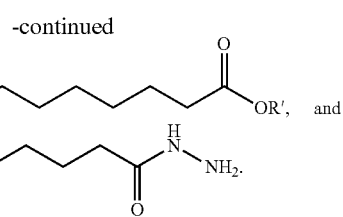
wherein R' represents —H, -Me, -Et, 4-nitrophenyl, pentafluorophenyl, or N-succinimidyl;
X represents —Br, —Cl, —I, —CO₂H, —CN, —NO₂ or —SAc.
Also preferred is a saccharide of general (I), (II), (II-a), (II-b), (III), (III-a) or (III-b), wherein the group —O-L-E is selected from the group consisting of:
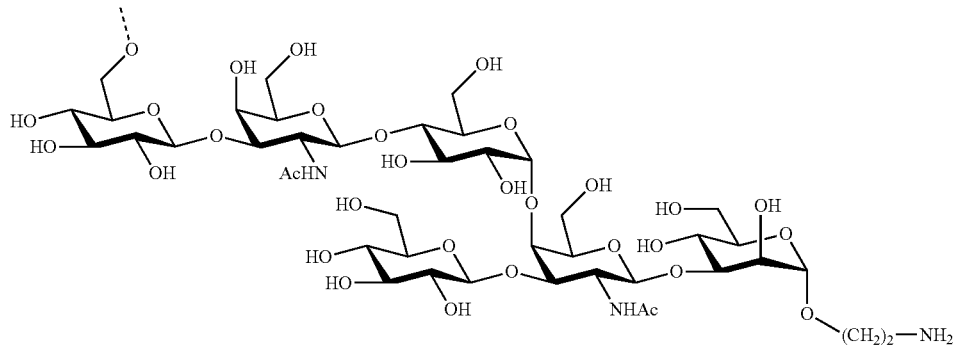
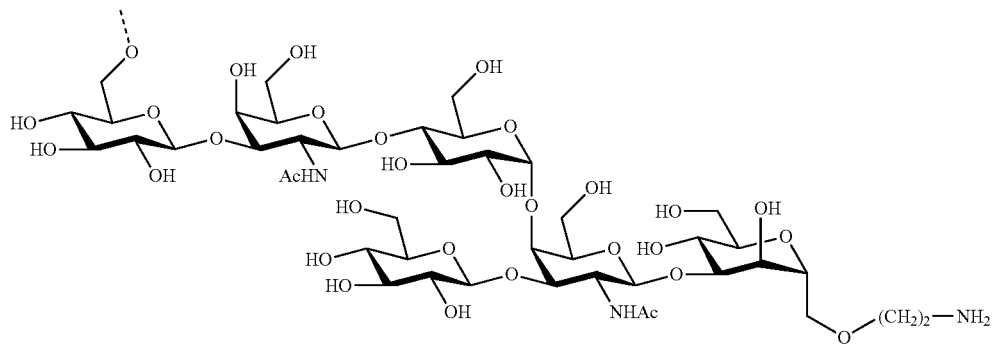
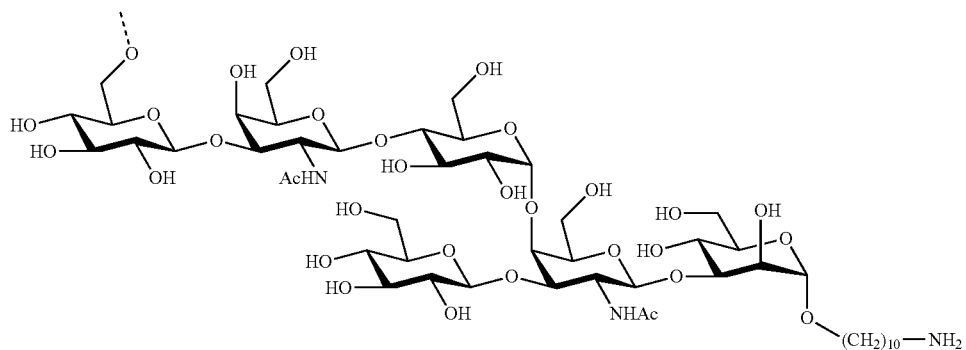

-continued
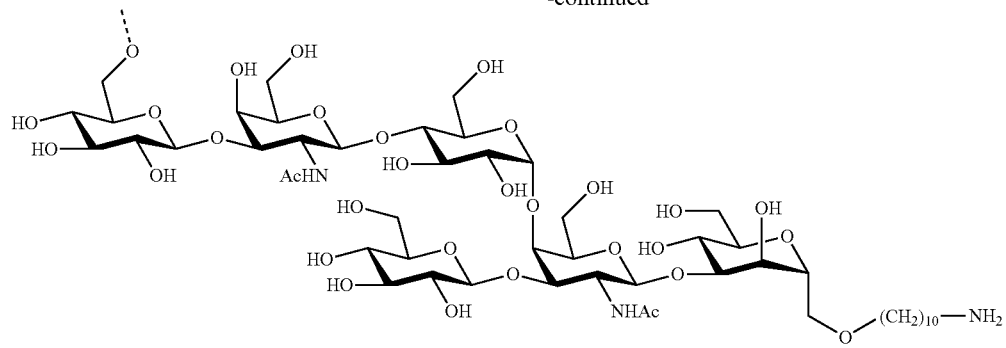
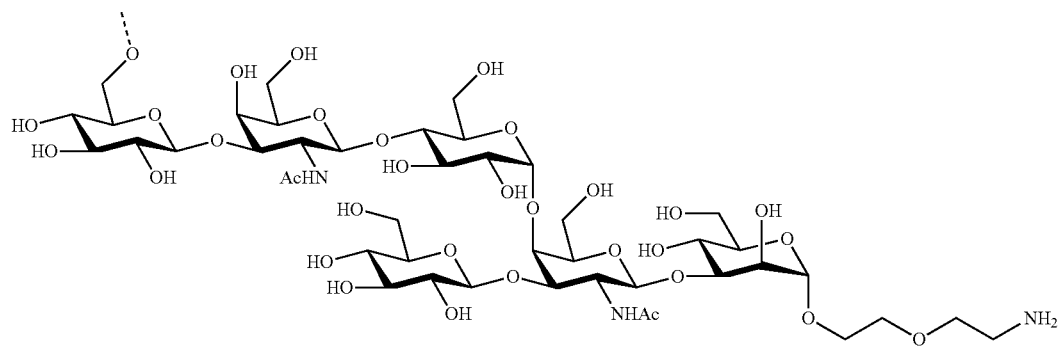
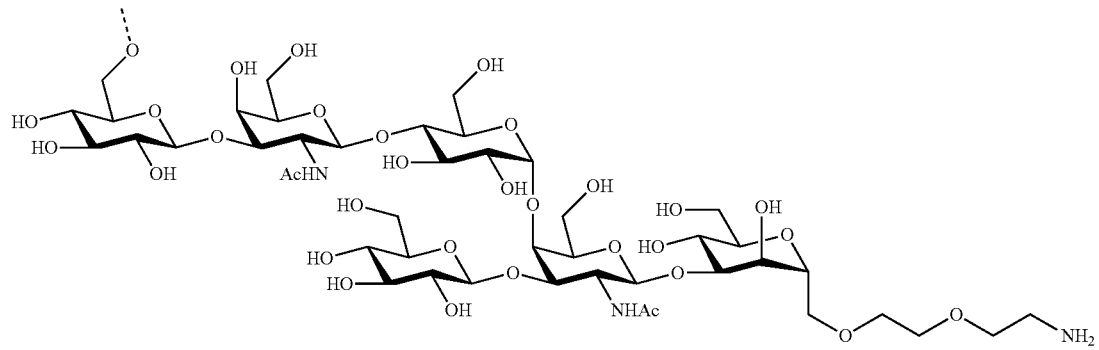
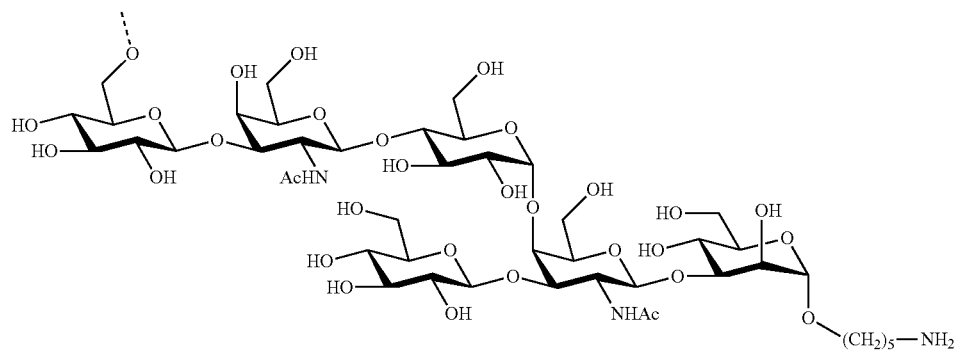
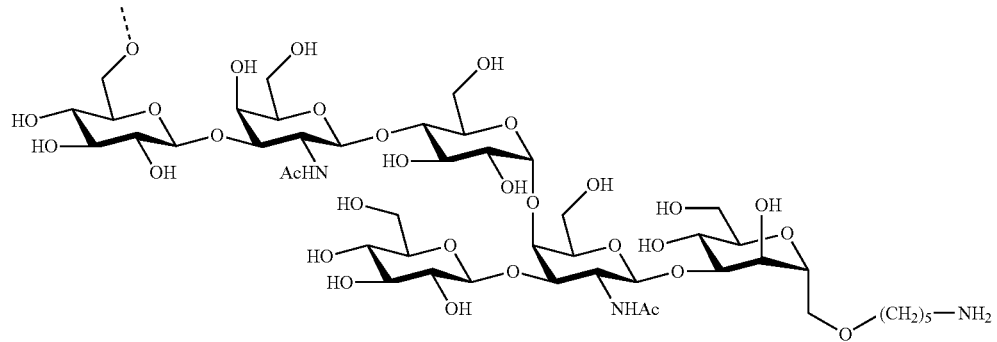

-continued
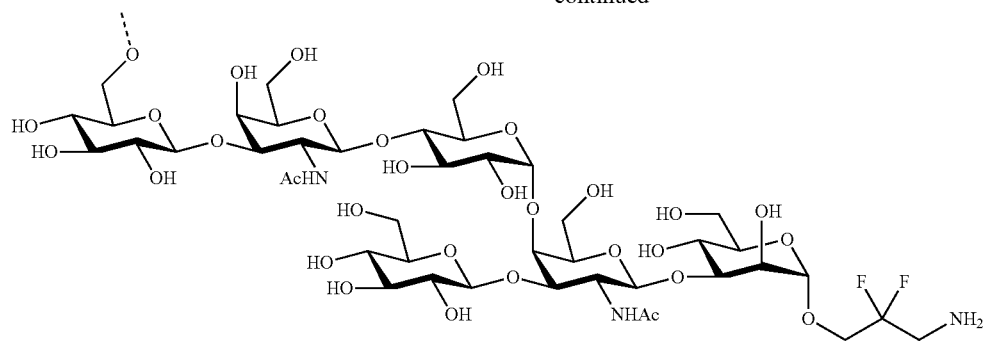
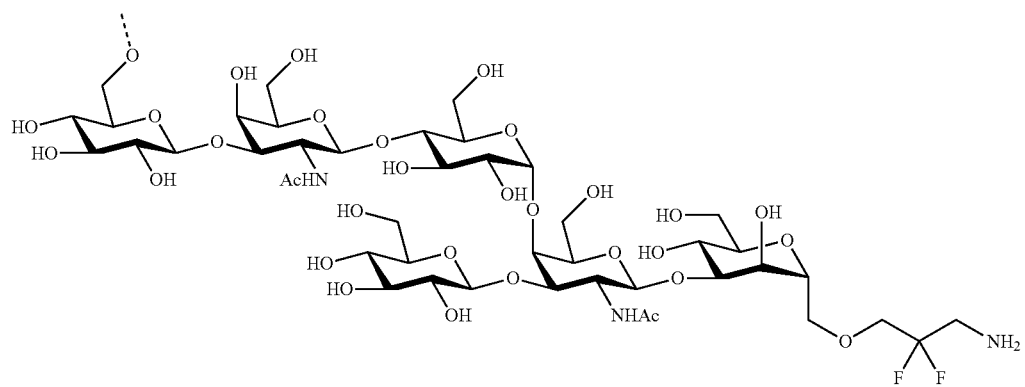
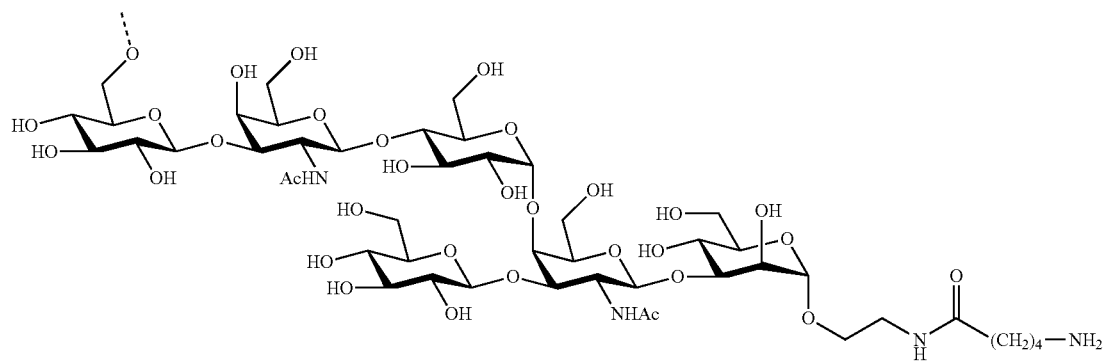
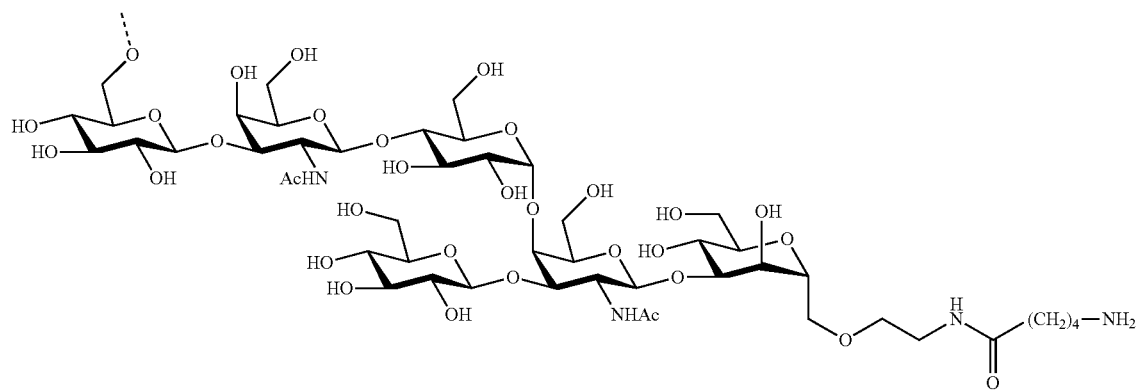

-continued
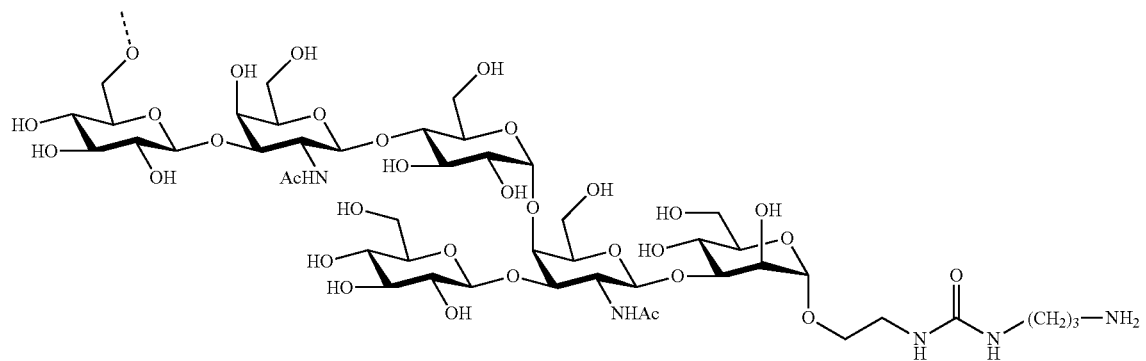
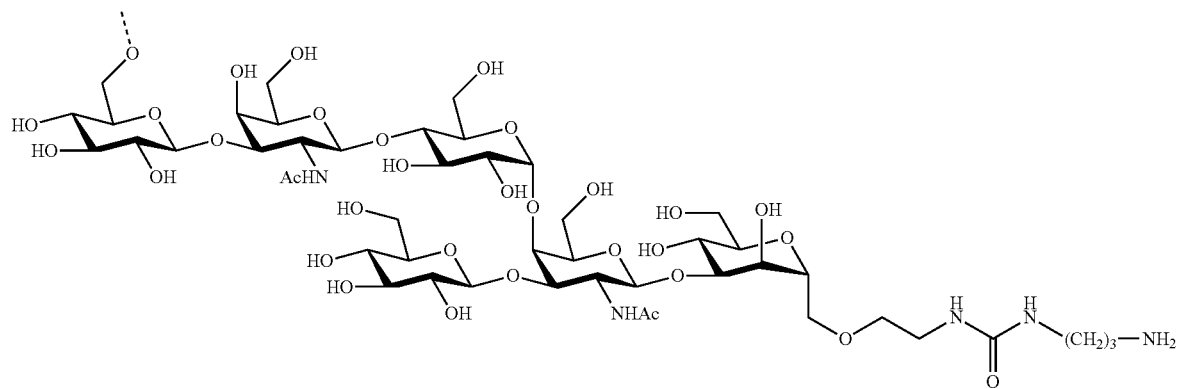
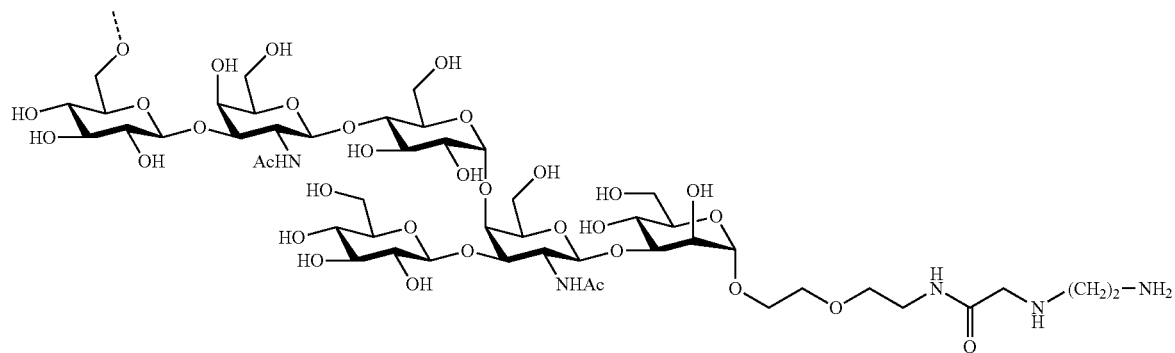
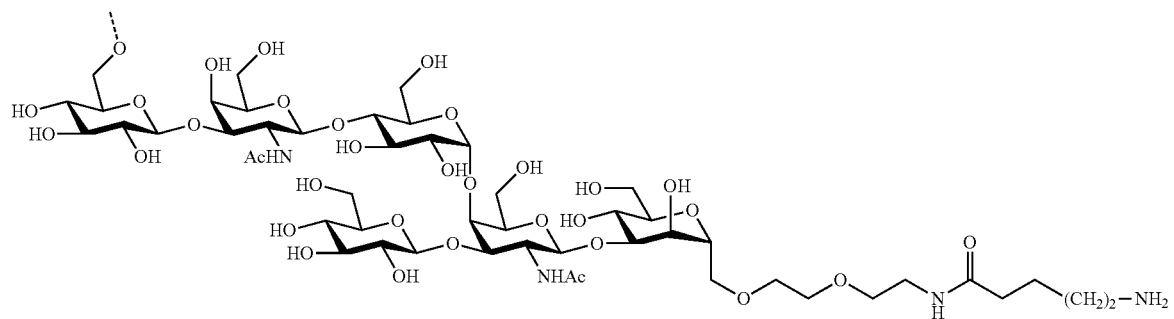

-continued
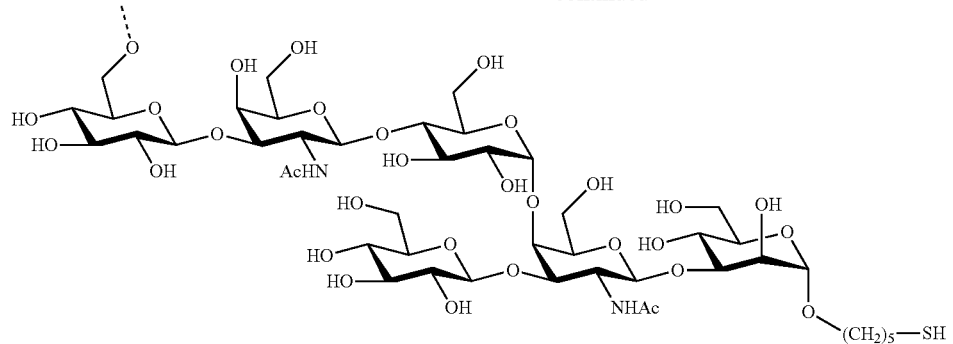
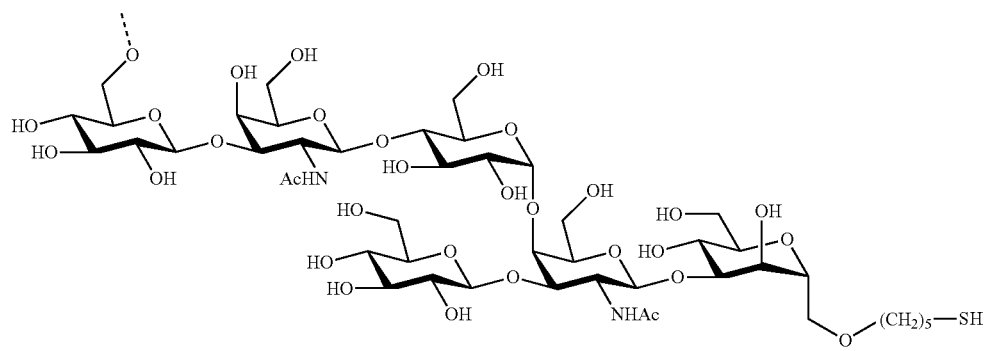
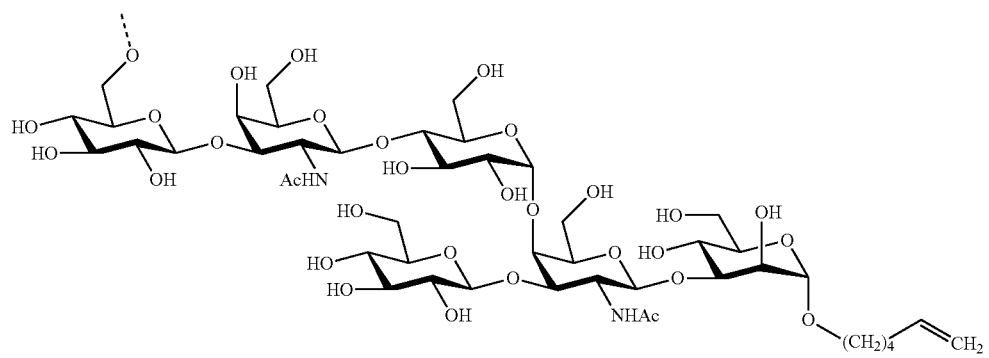
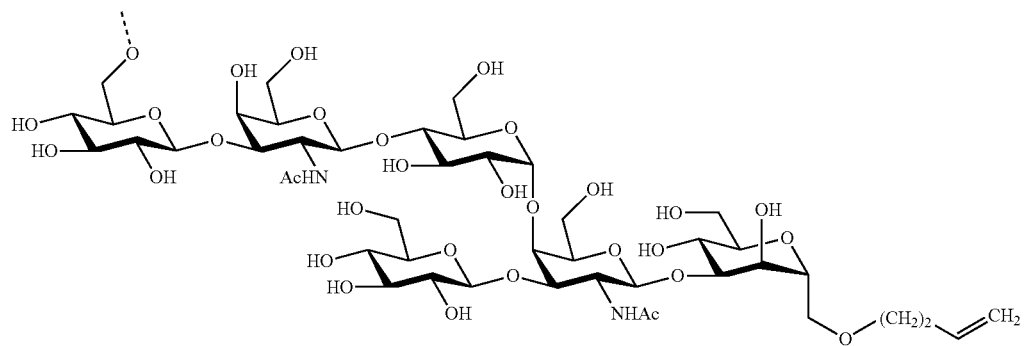

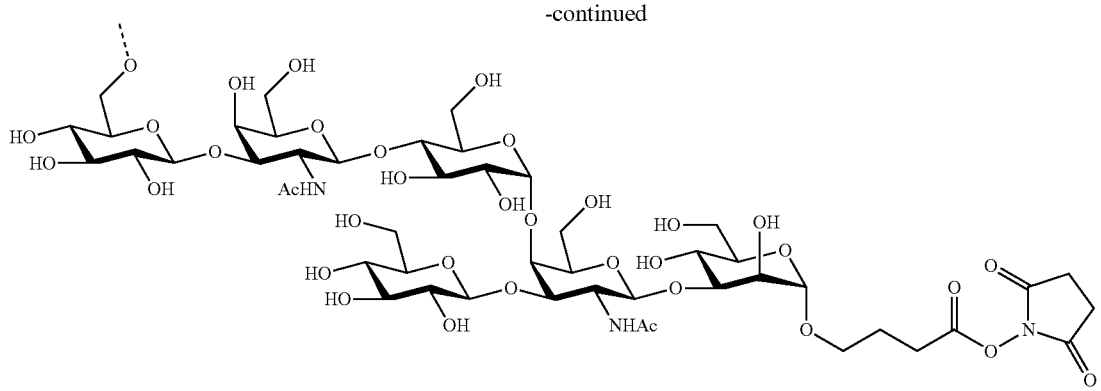

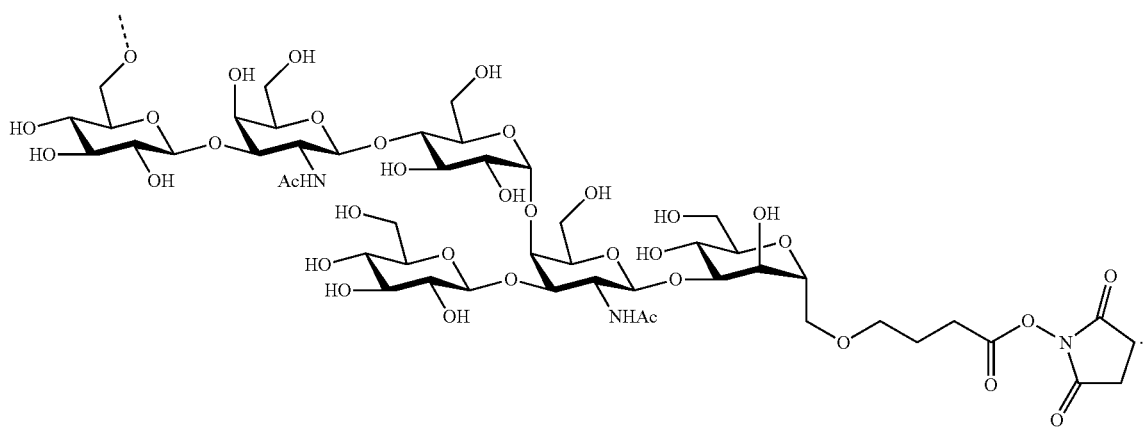

Also preferred is a saccharide of general formula (I), (II), (II-a), (II-b), (III), (III-a) or (III-b), wherein -L- represents —(CH$_2$)$_o$—, o is an integer selected from 2, 3, 4, 5 and 6, and E represents an amino group.

Preferred is a synthetic saccharide of formula (II-b), wherein n is 1 and E is an amino group. More preferred is a synthetic saccharide of formula (II-b), wherein n is 1, E is an amino group and the linker -L- represents -L$^a$-, -L$^a$-L$^e$-, -L$^a$-L$^b$-L$^e$-, or -L$^a$-L$^d$-L$^e$-;

-L$^a$- represents —(CH$_2$)$_o$—, —(CH$_2$—CH$_2$—O)$_o$—C$_2$H$_4$—, or —(CH$_2$—CH$_2$—O)$_o$—CH$_2$;

-L$^b$- represents —O—;

-L$^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—, -L$^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and o, q, p1 and p2 are independently of each other an integer selected from 1, 2, 3, 4, 5, and 6.

Particularly preferred is a synthetic saccharide of formula (II-b), wherein n is 1, E is an amino group, the linker -L- represents —(CH$_2$)$_o$— and o is an integer selected from 1, 2, 3, 4, 5, 6, 7, 8, 9 and 10. Even more preferred is a synthetic saccharide of formula (II-b), wherein n is 1, E is an amino group, the linker -L- represents —(CH$_2$)$_o$— and o is an integer selected from 1, 2, 3, 4, 5, and 6.

Preferred is a synthetic saccharide of formula (II-b), wherein n is 2 and E is an amino group. More preferred is a synthetic saccharide of formula (II-b), wherein n is 2, E is an amino group and the linker -L- represents -L$^a$-, -L$^a$-L$^e$-, -L$^a$-L$^b$-L$^e$-, or -L$^a$-L$^d$-L$^e$-;

-L$^a$- represents —(CH$_2$)$_o$—, —(CH$_2$—CH$_2$—O)$_o$—C$_2$H$_4$—, or —(CH$_2$—CH$_2$—O)$_o$—CH$_2$;

-L$^b$- represents —O—;

-L$^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;

-L$^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and o, q, p1 and p2 are independently of each other an integer selected from 1, 2, 3, 4, 5, and 6.

Particularly preferred is a synthetic saccharide of formula (II-b), wherein n is 2, E is an amino group, the linker -L- represents —(CH$_2$)$_o$— and o is an integer selected from 1, 2, 3, 4, 5, 6, 7, 8, 9 and 10. Even more preferred is a synthetic saccharide of formula (II-b), wherein n is 2, E is an amino group, the linker -L- represents —(CH$_2$)$_o$— and o is an integer selected from 1, 2, 3, 4, 5, and 6.

In yet another preferred embodiment, the saccharide according to the present invention is selected from the group consisting of:

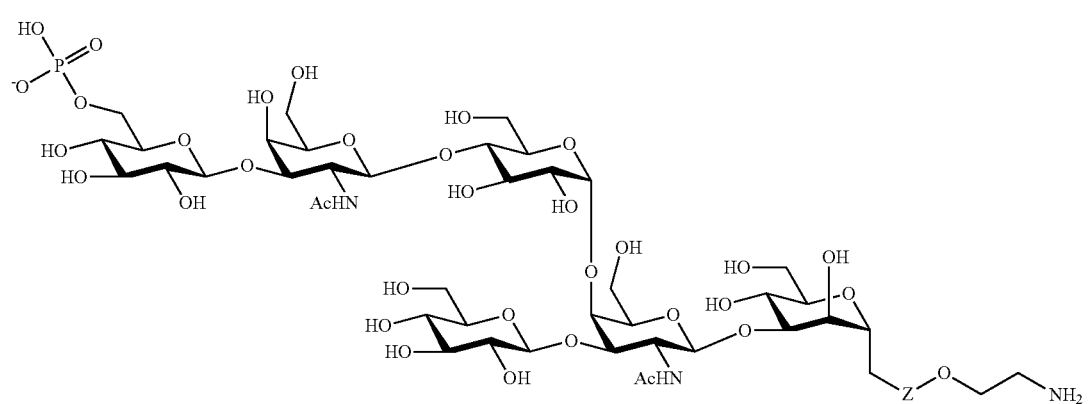
(I'a-1)
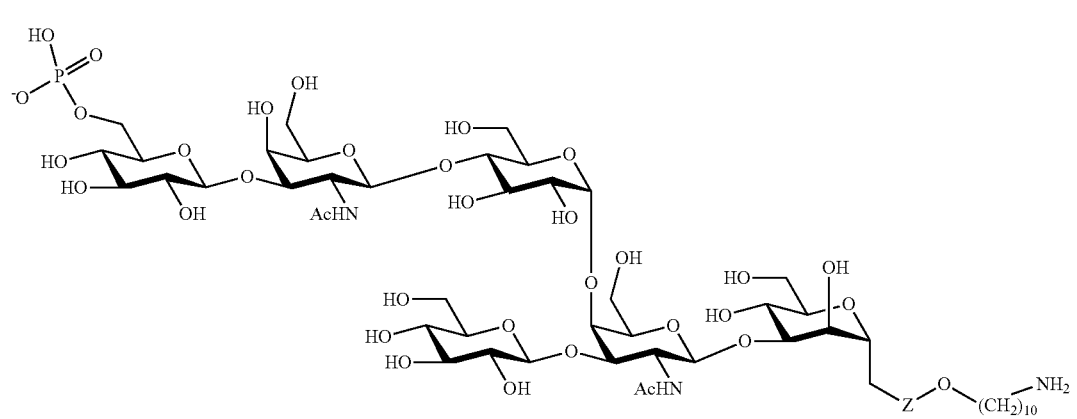
(I'a-2)
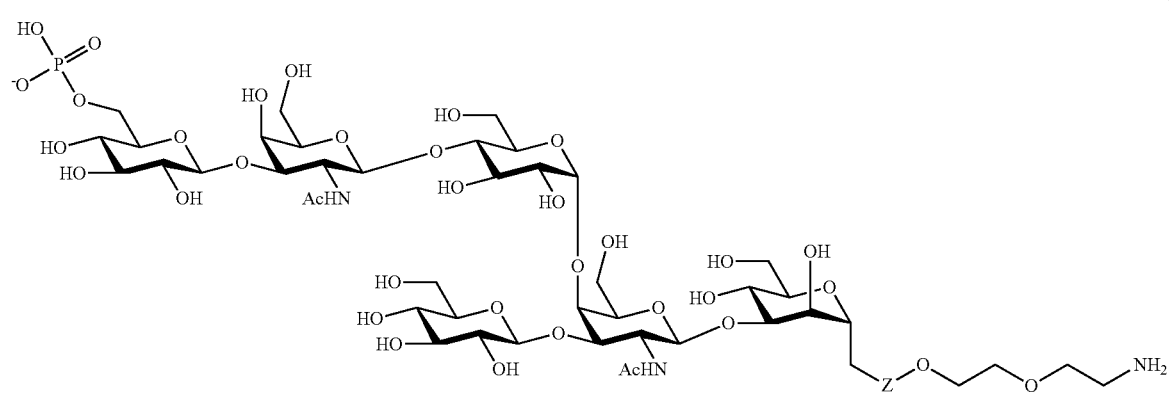
(I'a-3)
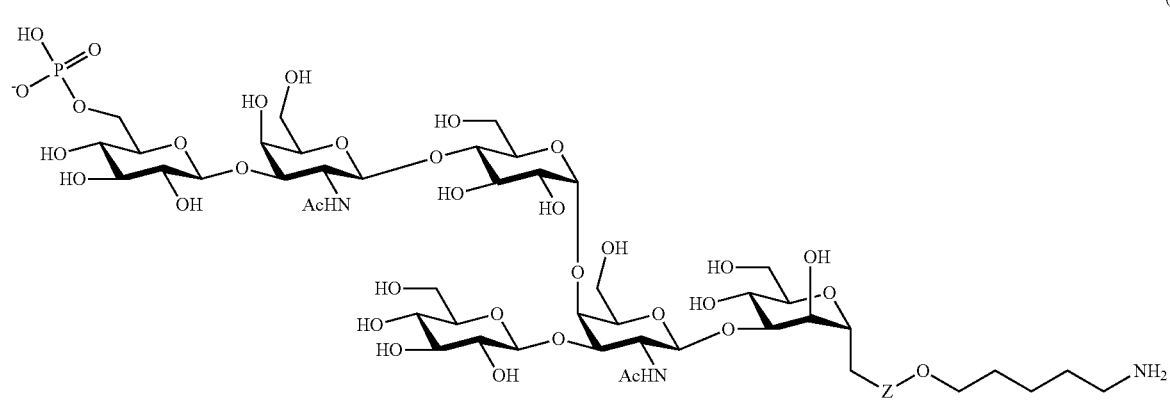
(I'a-4)

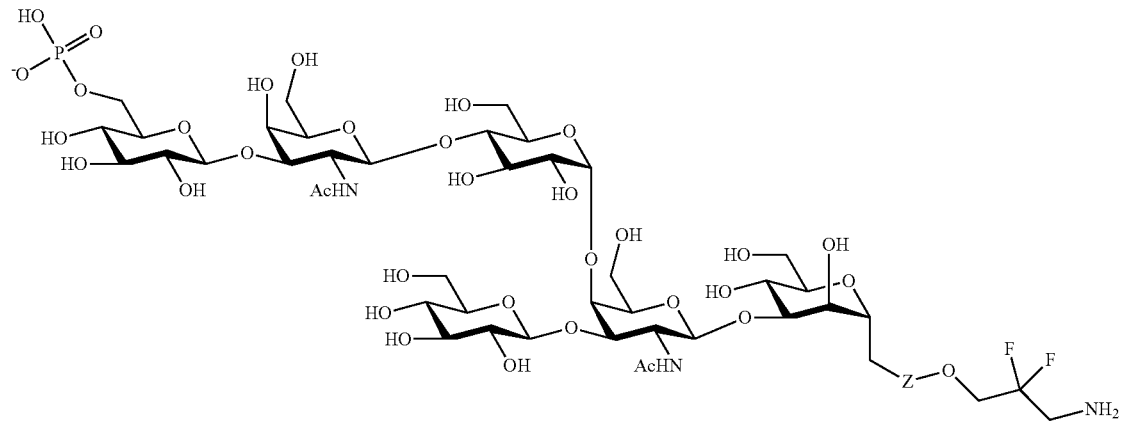
(I'a-5)
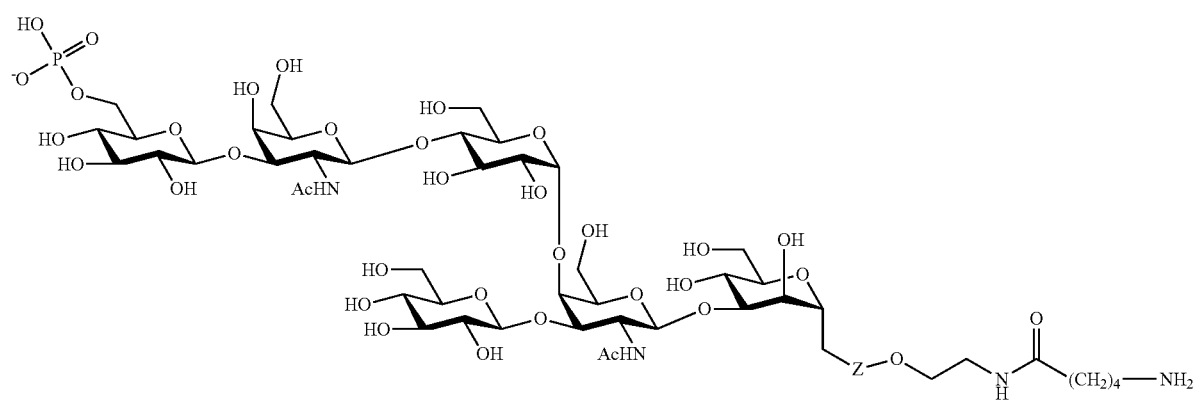
(I'a-6)
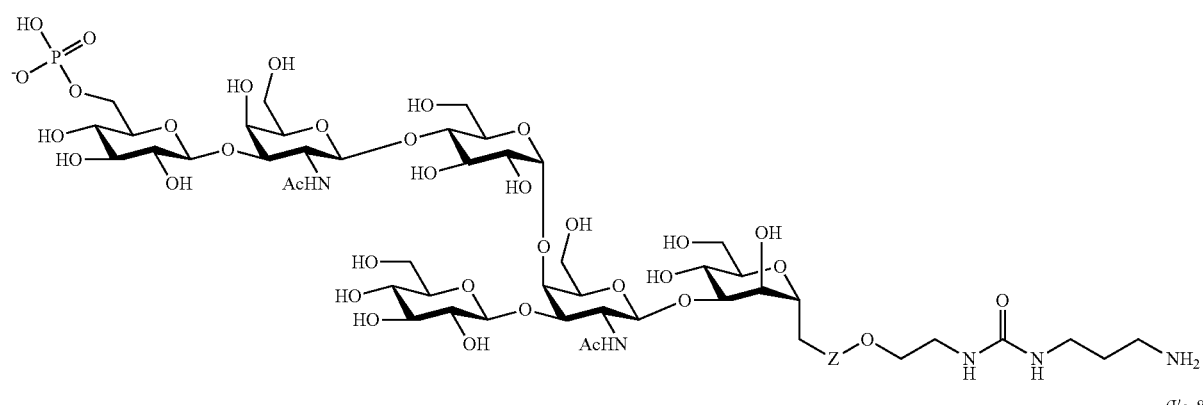
(I'a-7)
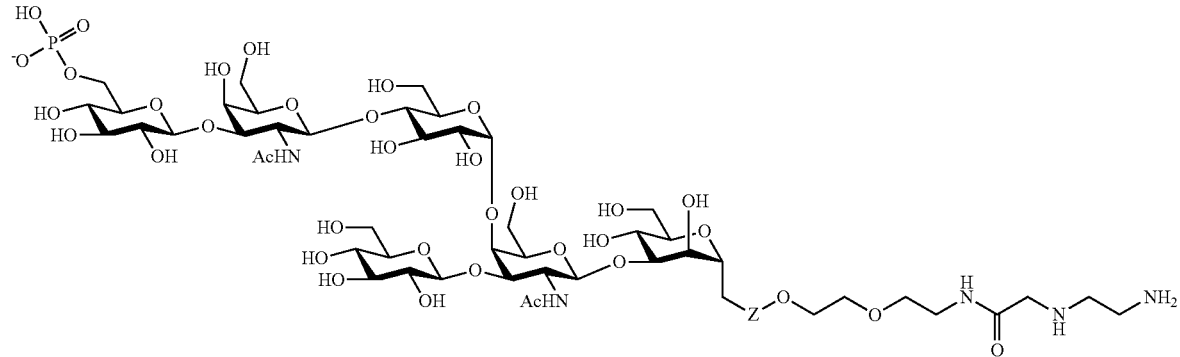
(I'a-8)

(I'a-9)
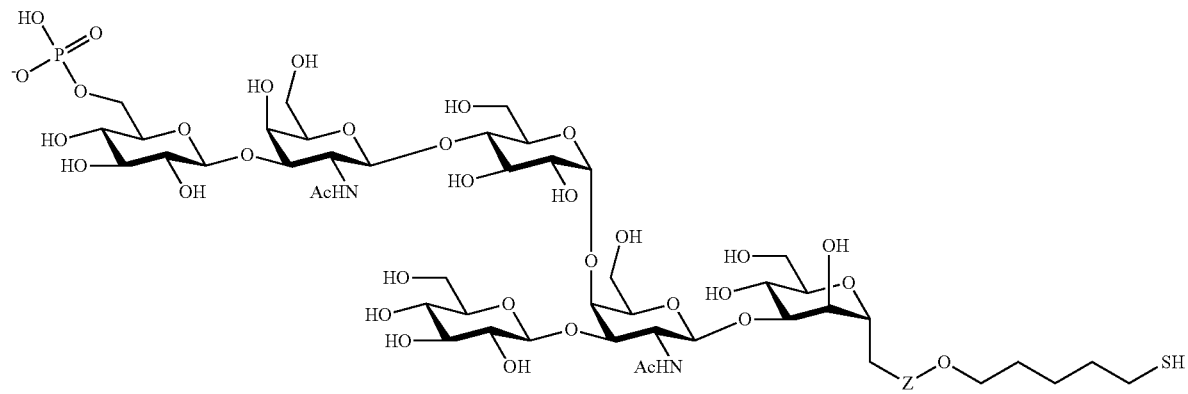
(I'a-10)
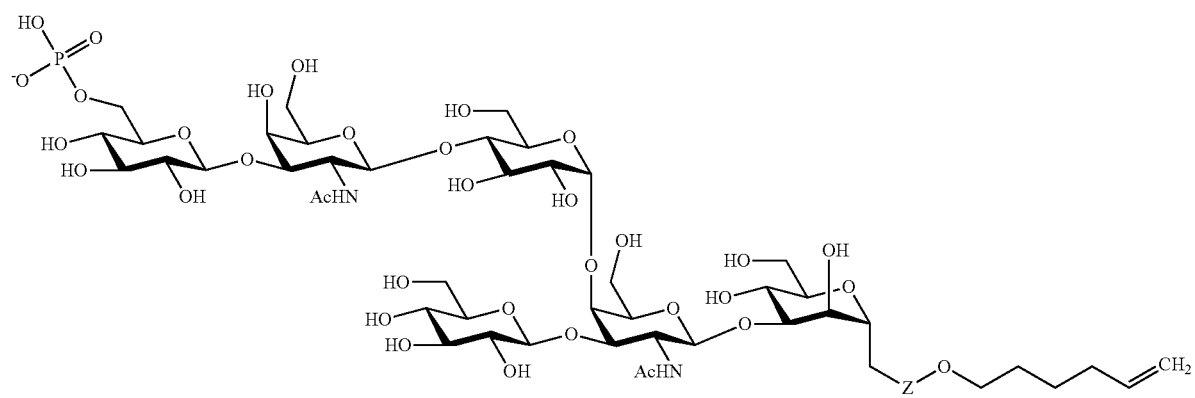
(I'a-11)
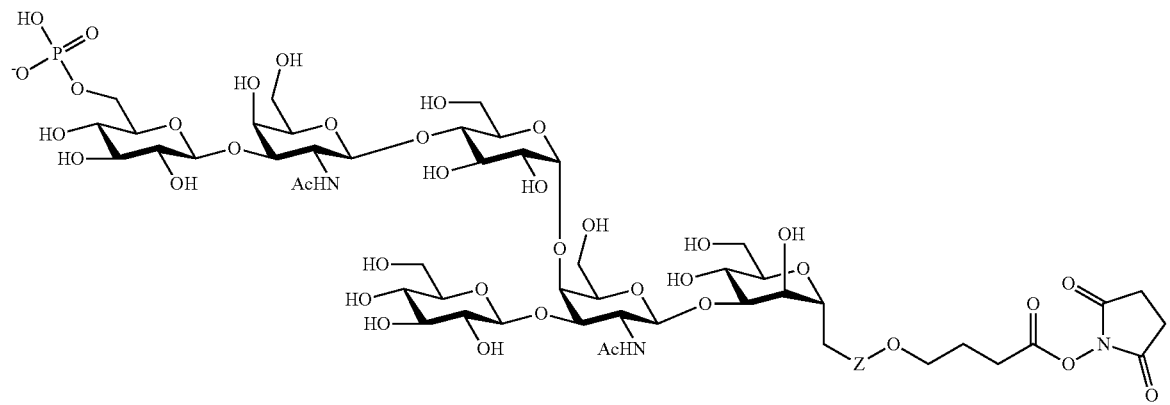

(I'a-12)
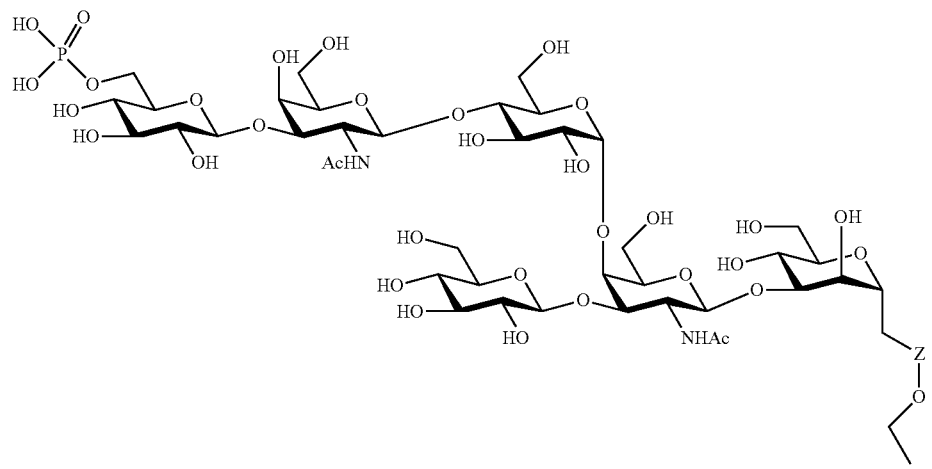
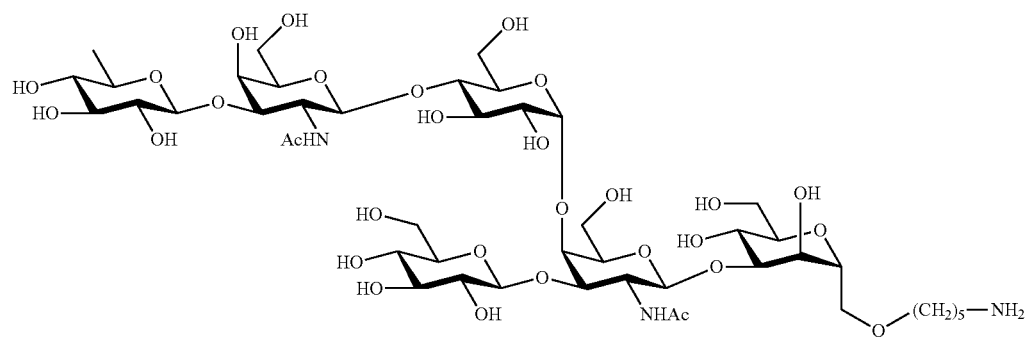
(I'a-13)
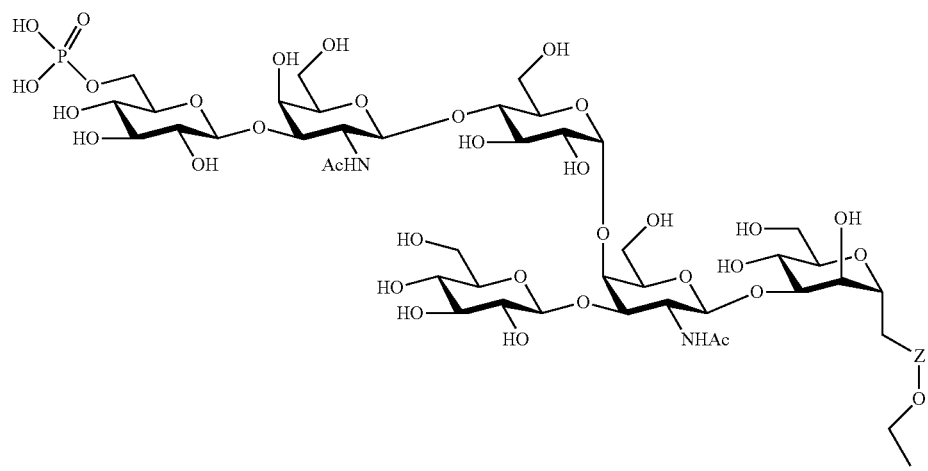
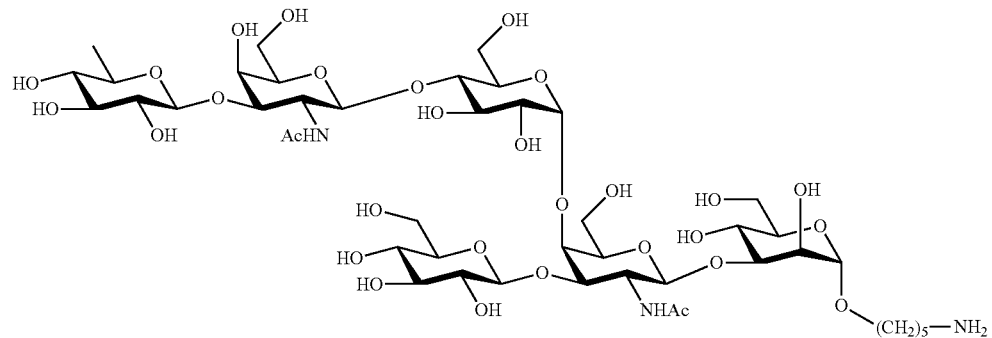

(I'b-1)
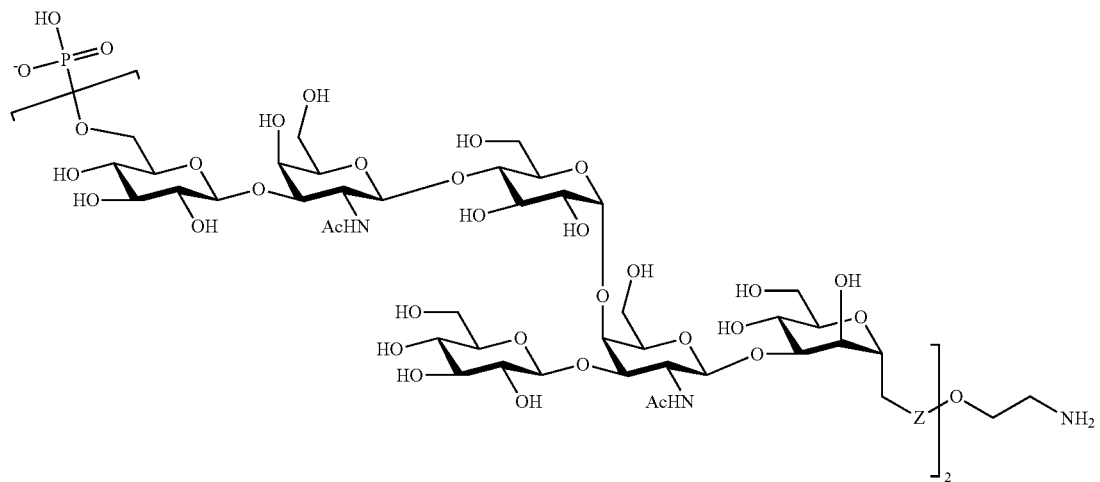
(I'b-2)
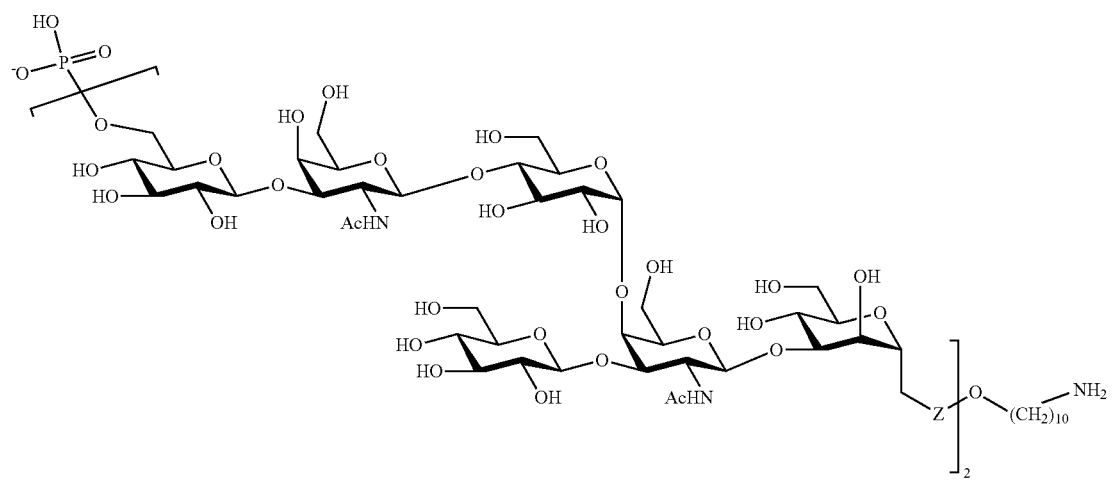
(I'b-3)
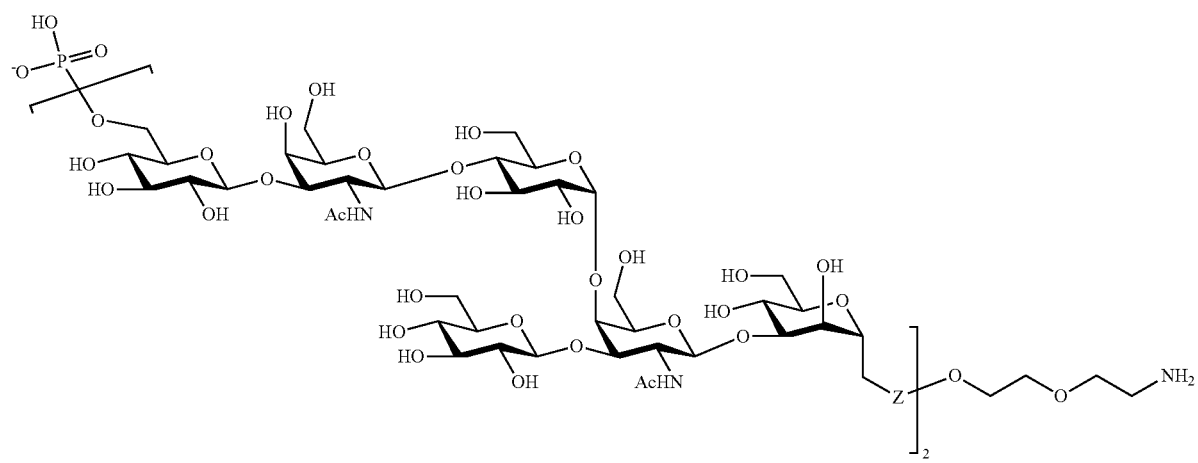

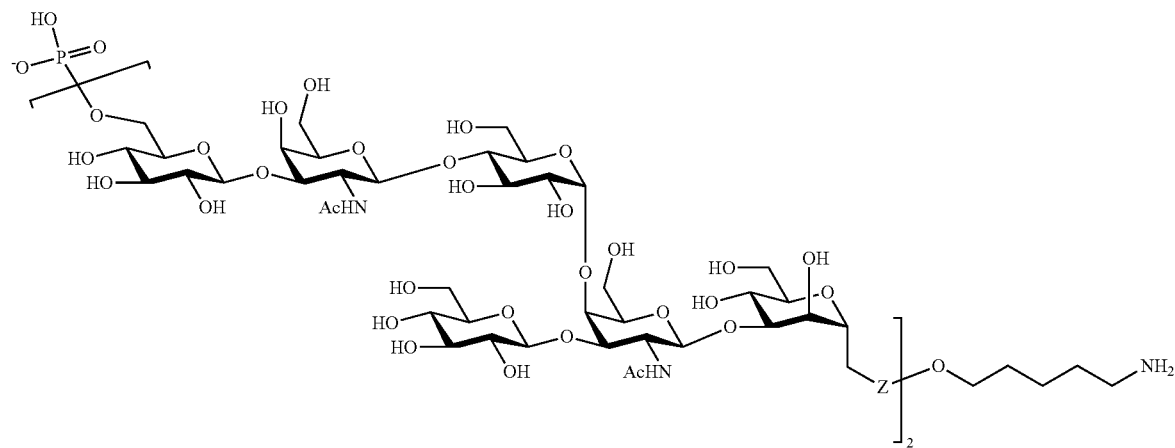
(I'b-4)
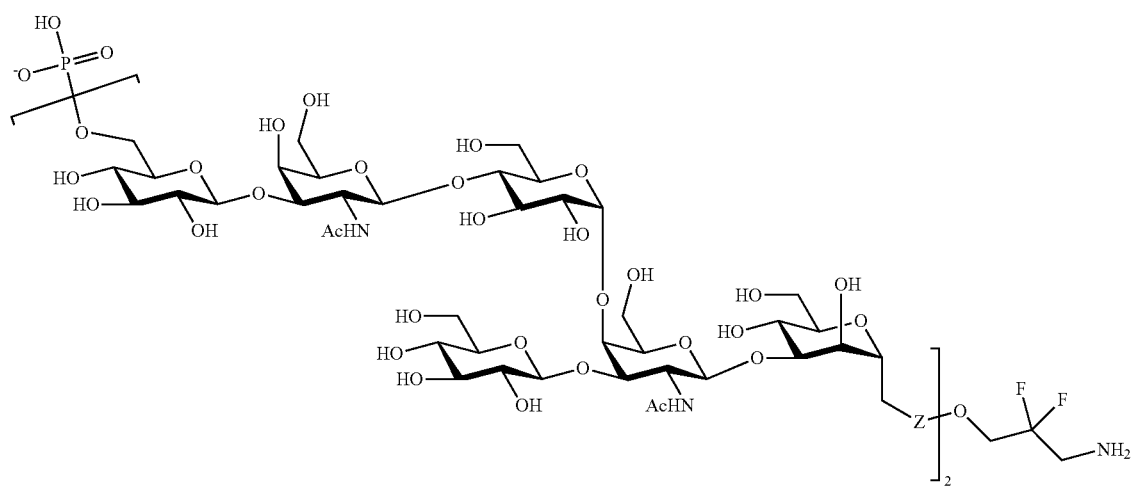
(I'b-5)
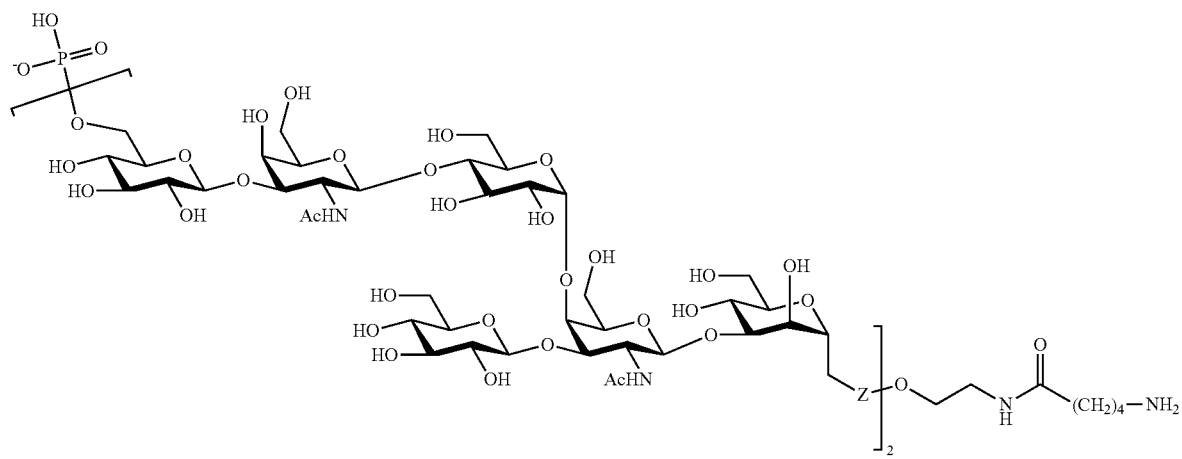
(I'b-6)

-continued
(I′b-7)
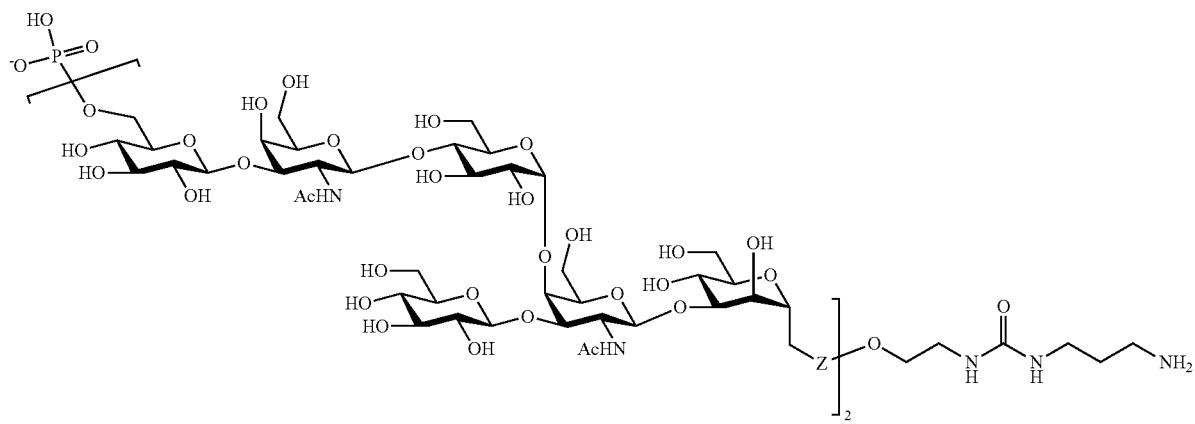
(I′b-8)
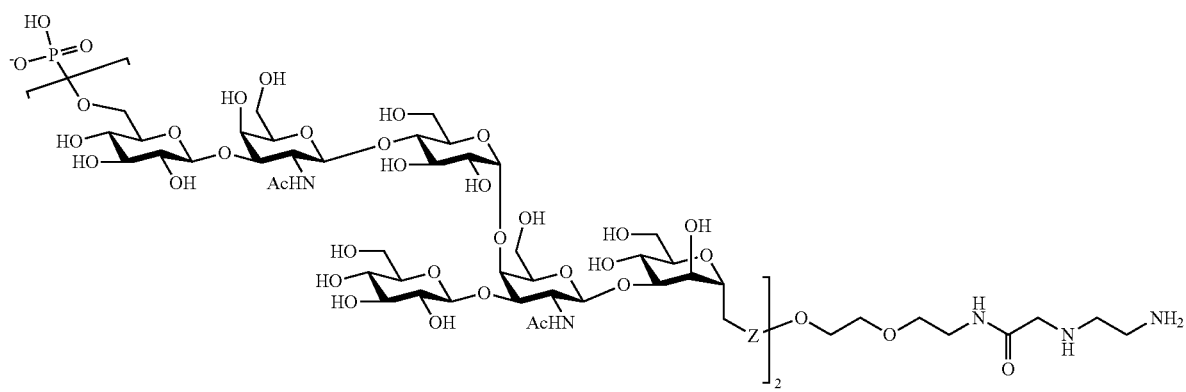
(I′b-9)
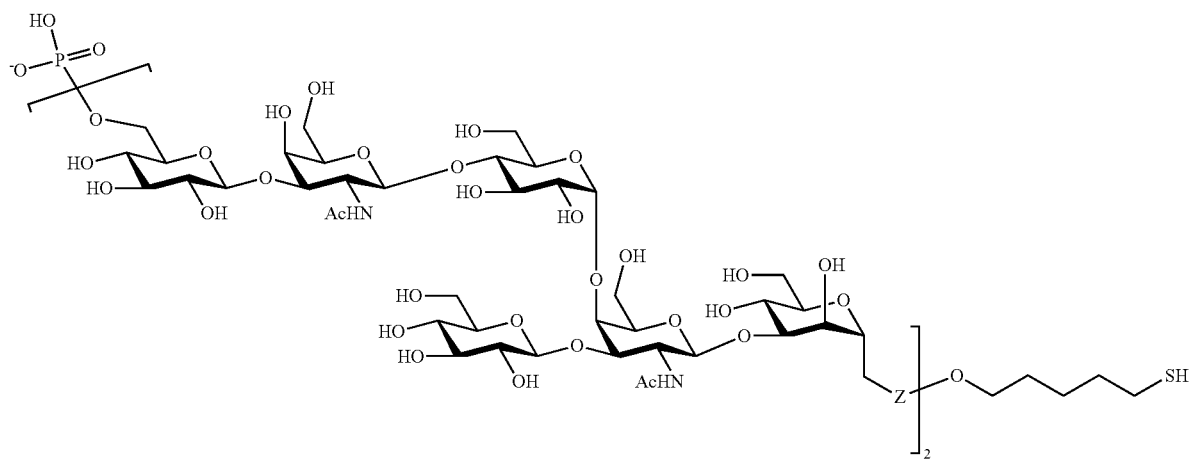

(I'b-10)
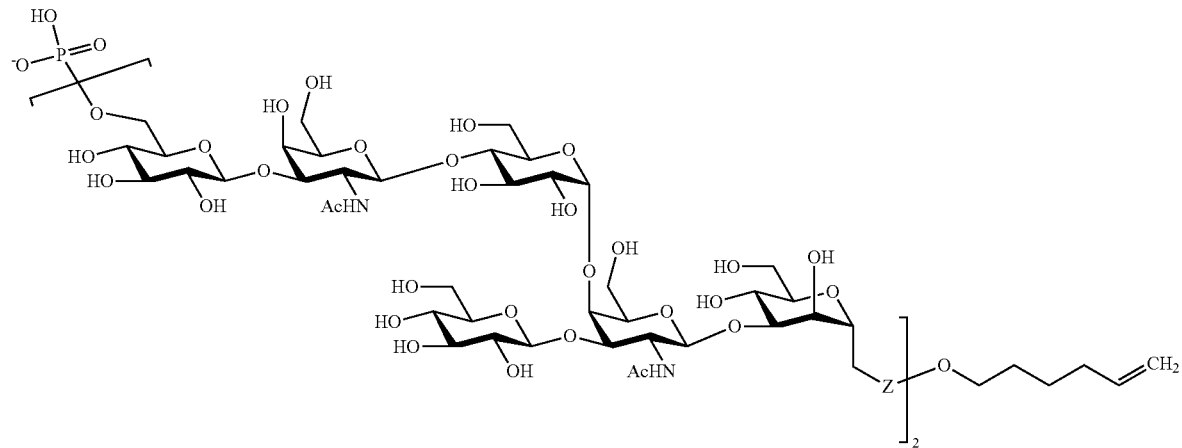
(I'b-11)
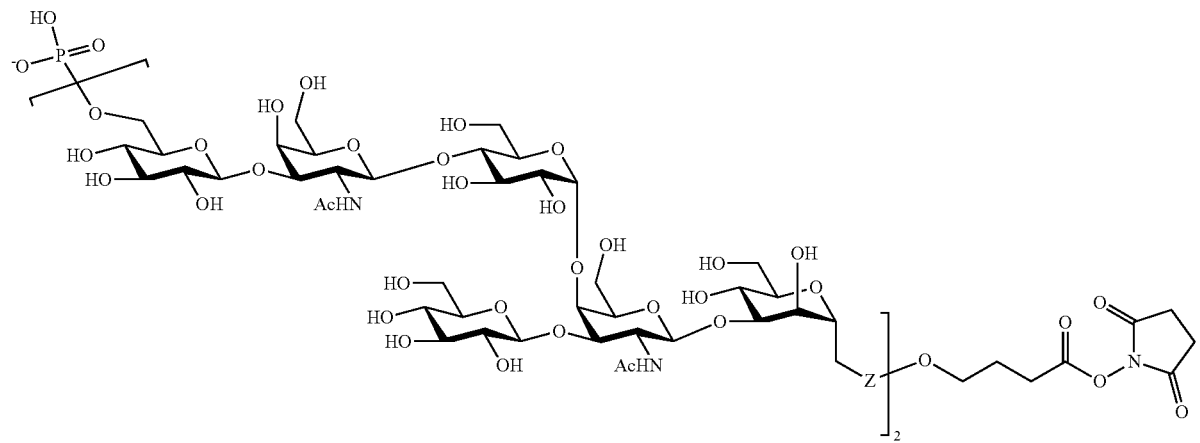
(I'b-12)
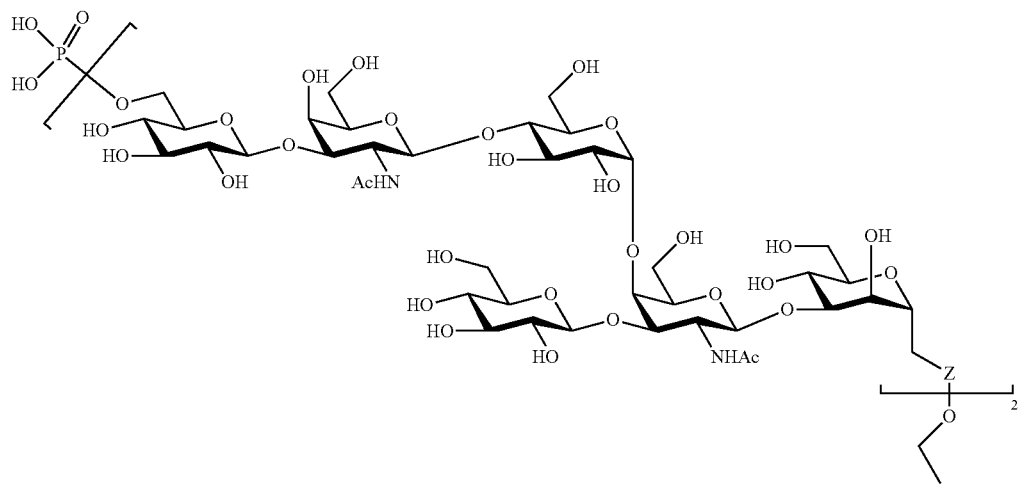

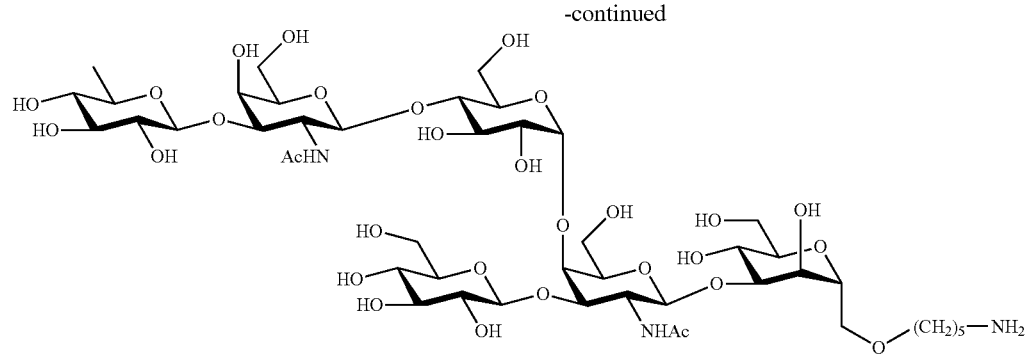
(I′b-13)
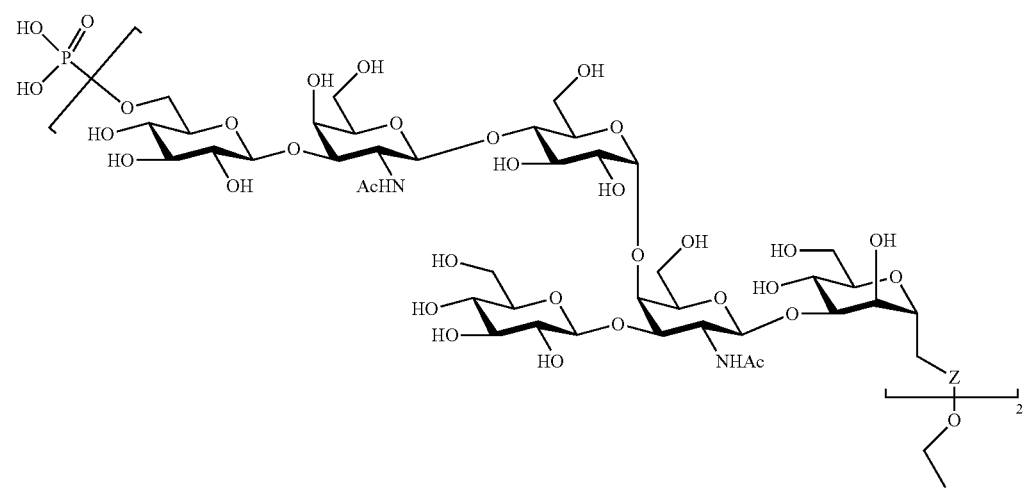
(I′c-1)
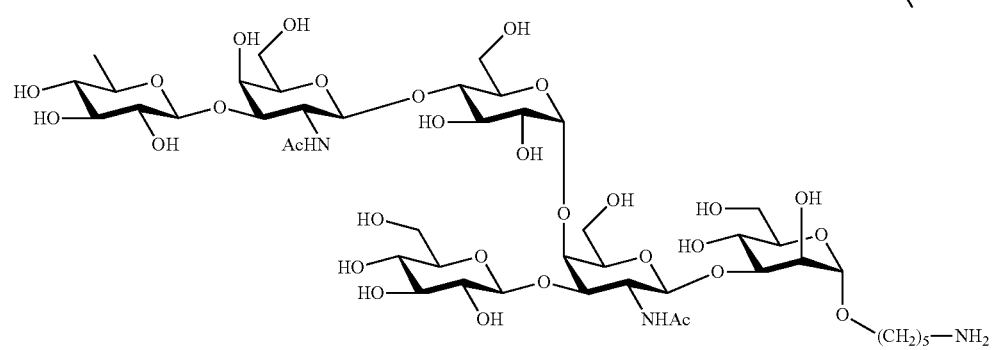
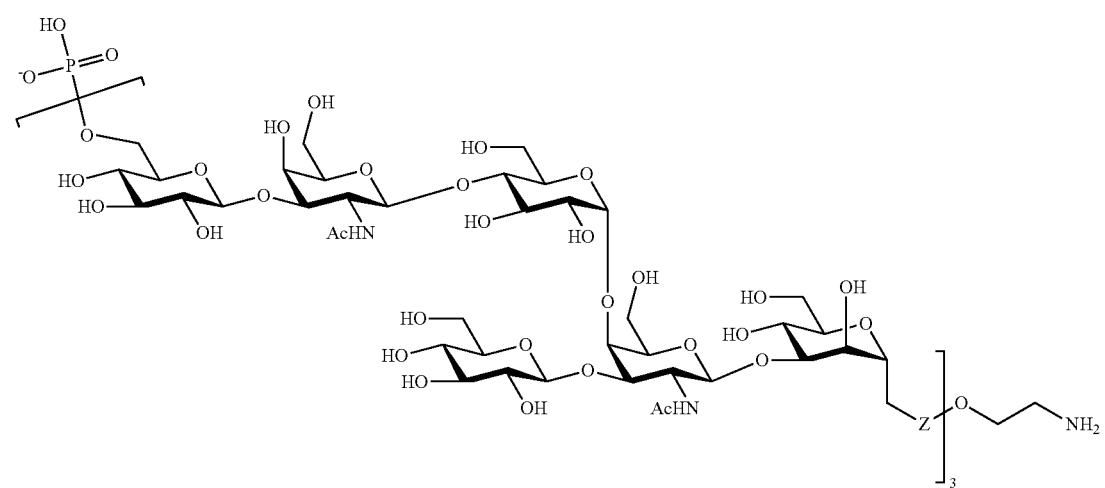

(I'c-2)
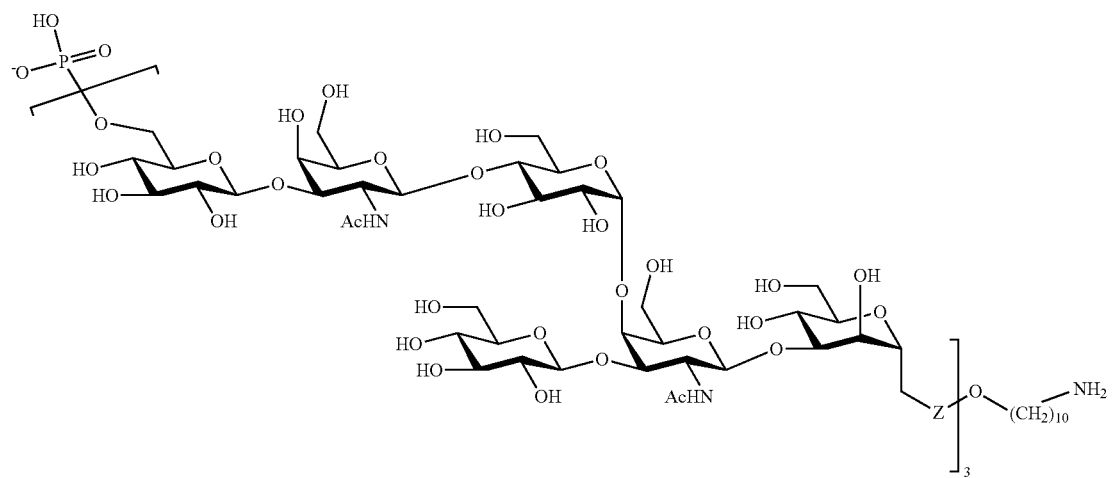
(I'c-3)
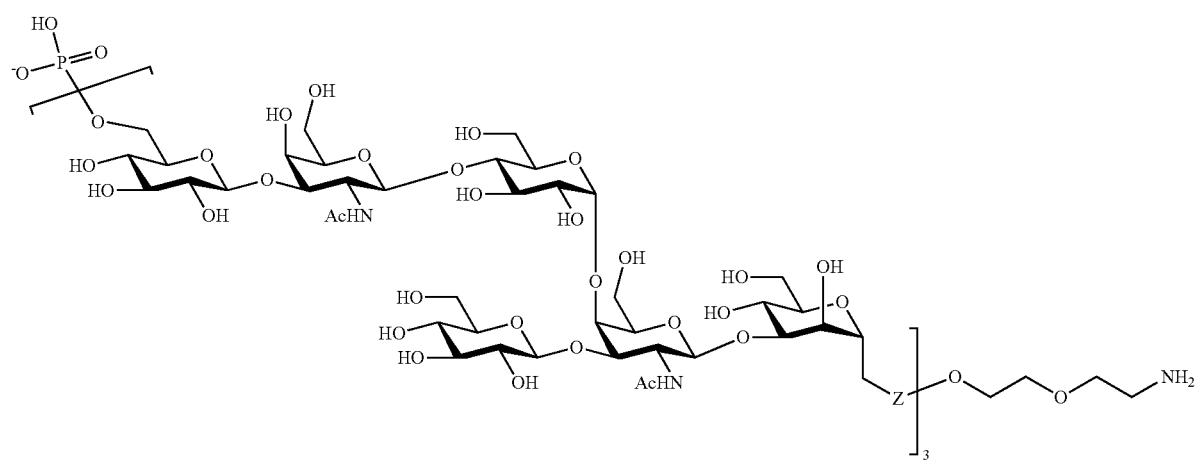
(I'c-4)
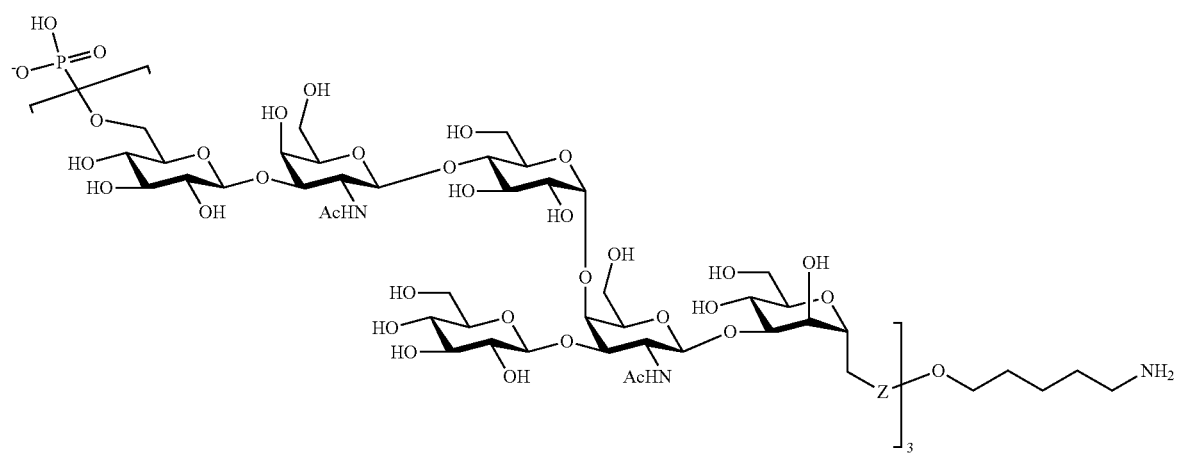

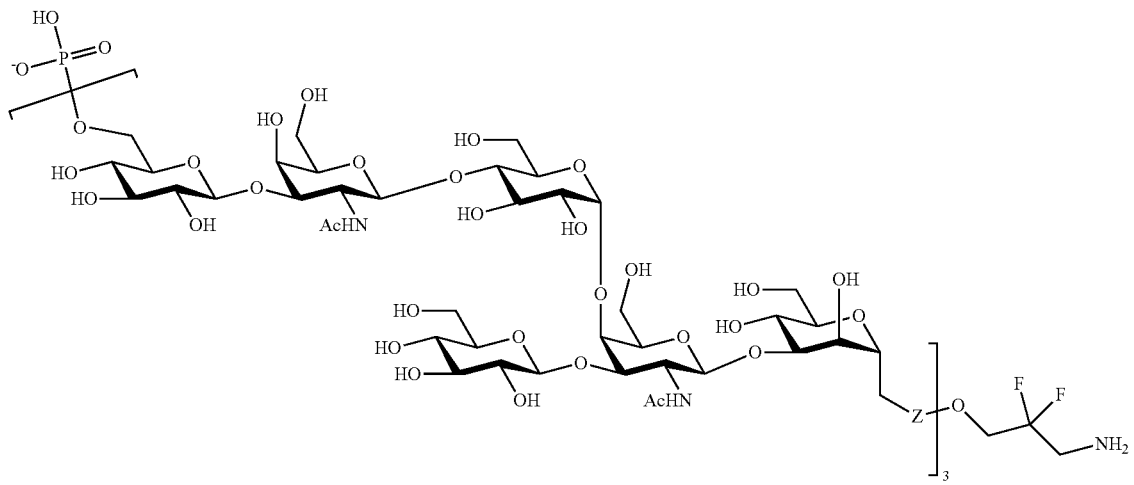
(I'c-5)
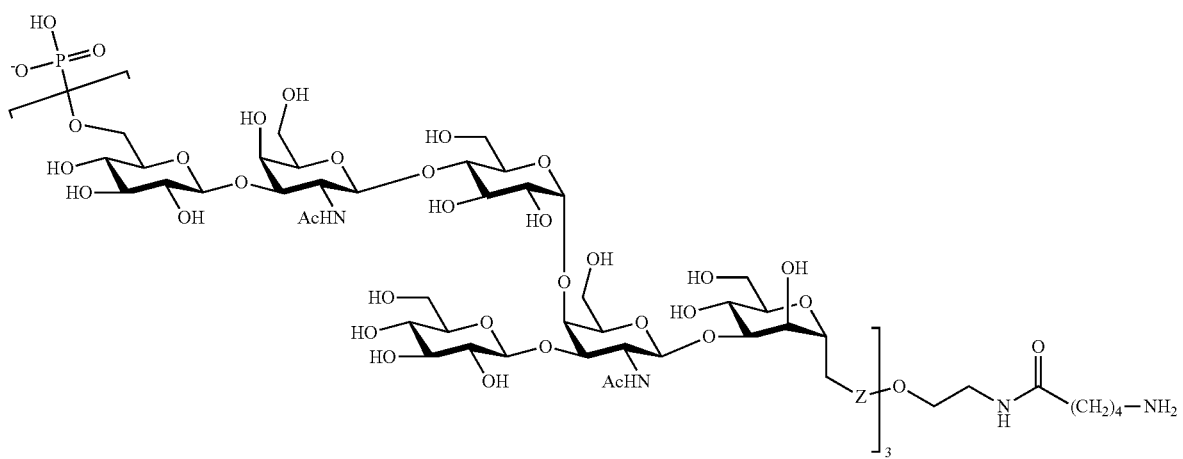
(I'c-6)
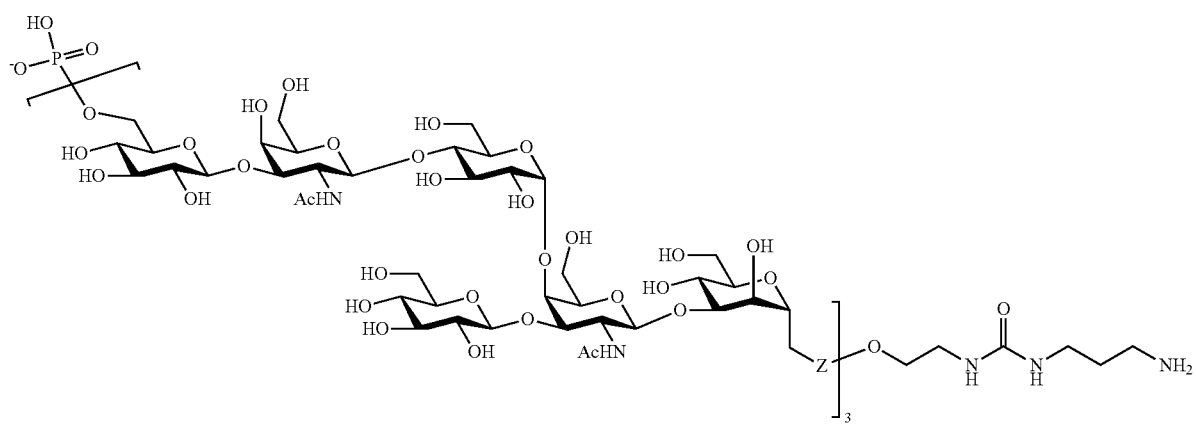
(I'c-7)

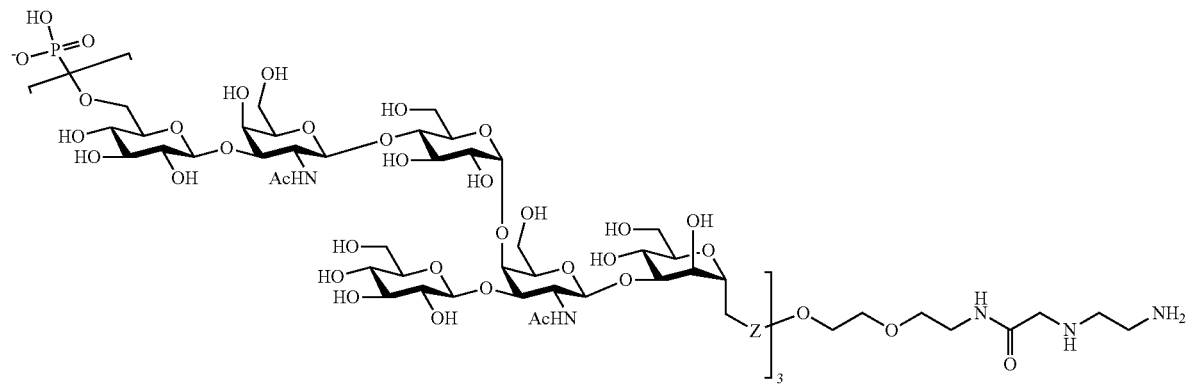
(I'c-8)
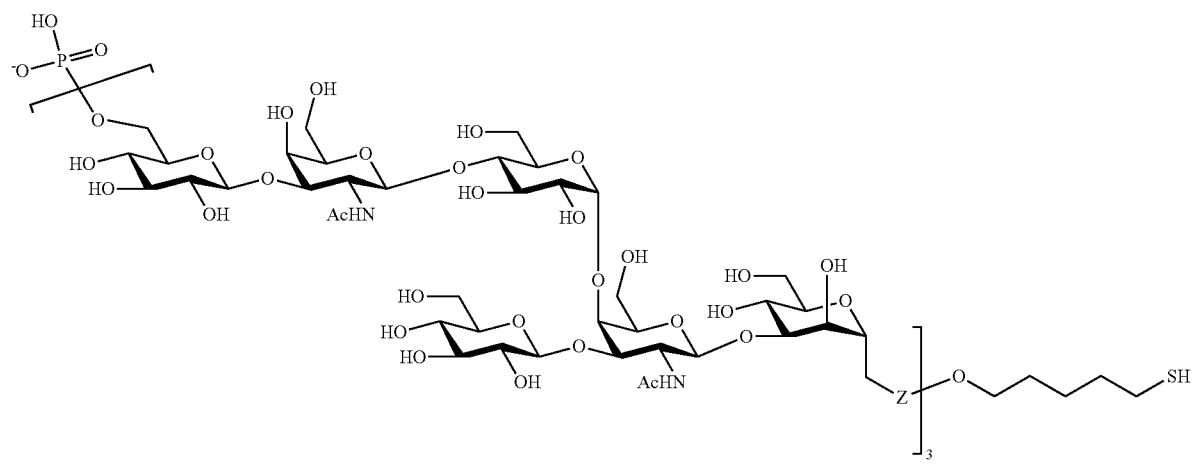
(I'c-9)
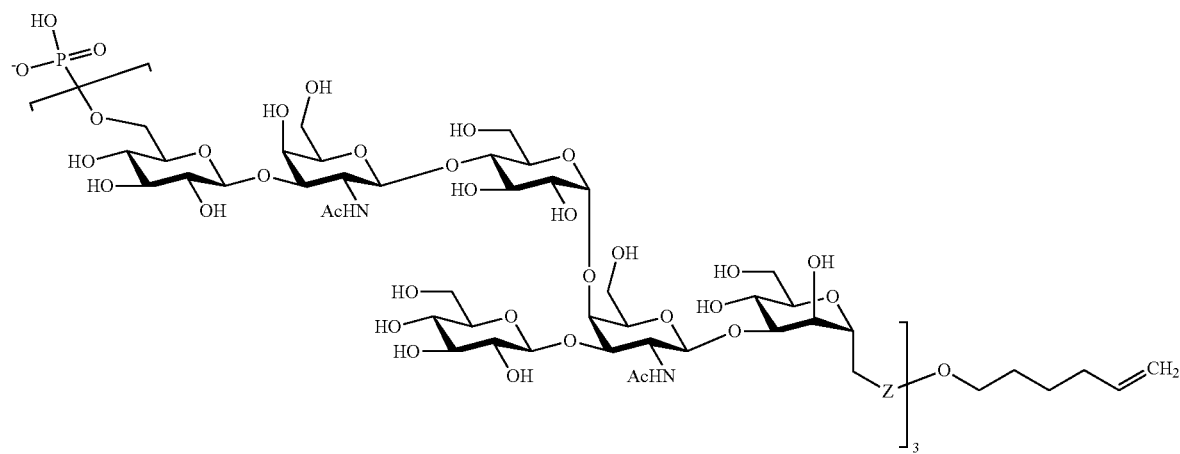
(I'c-10)

(I'c-11)
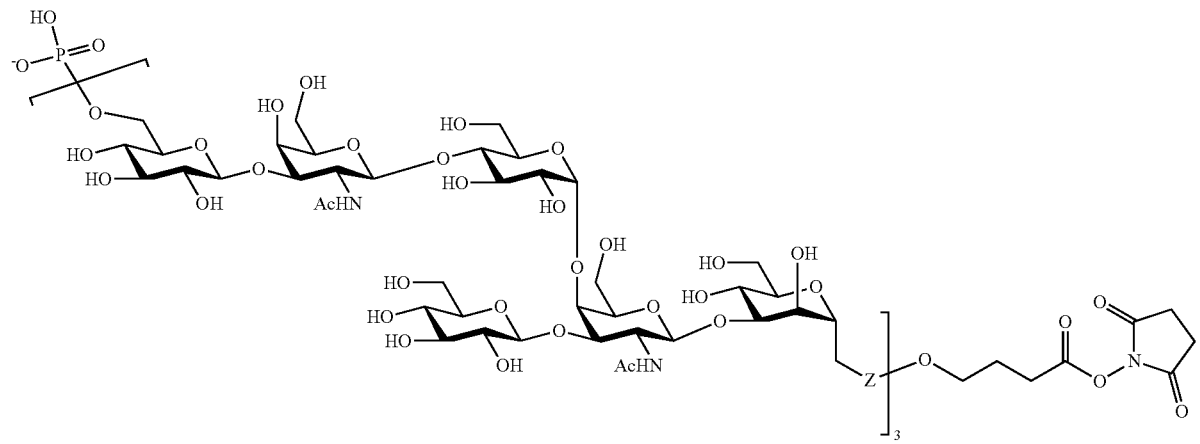
(I'c-12)
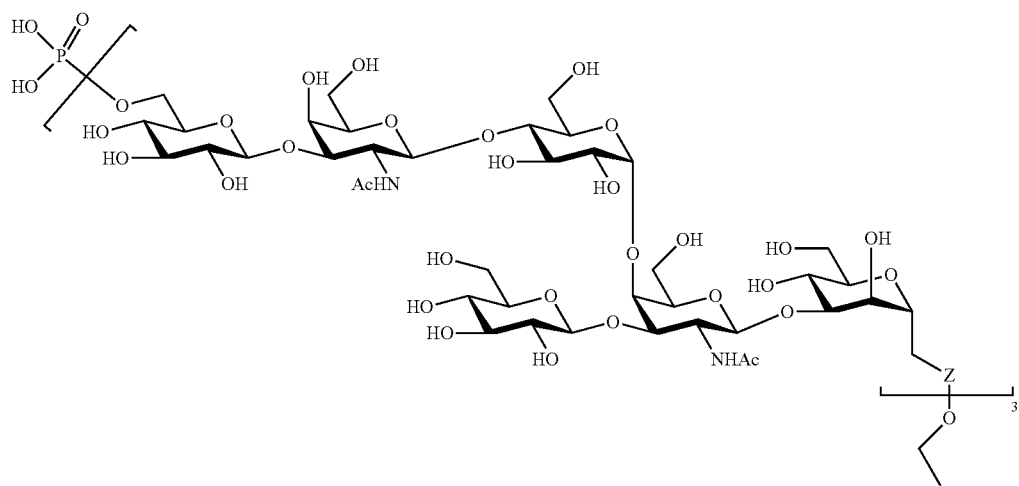
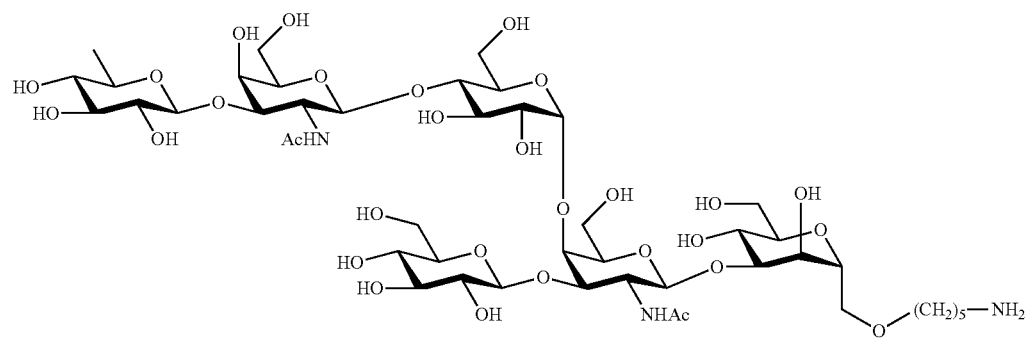

-continued
(I'c-13)
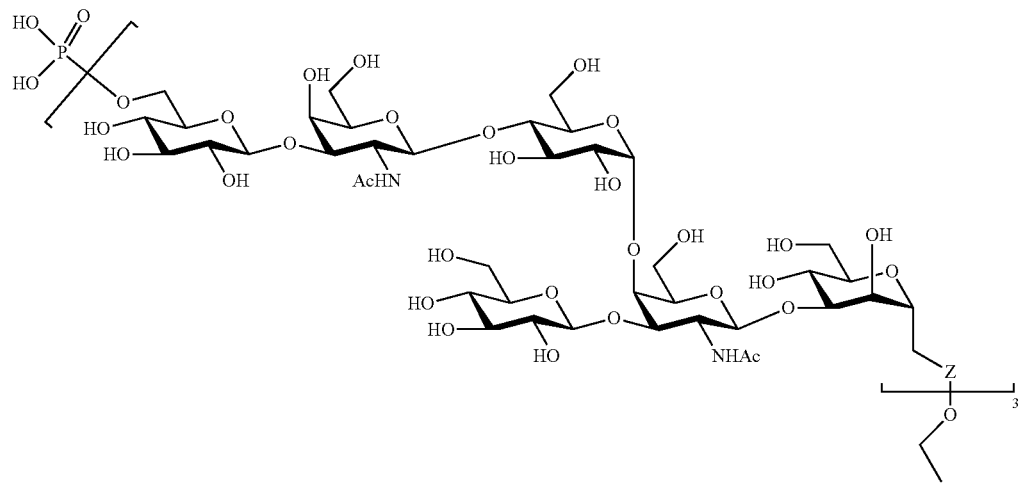
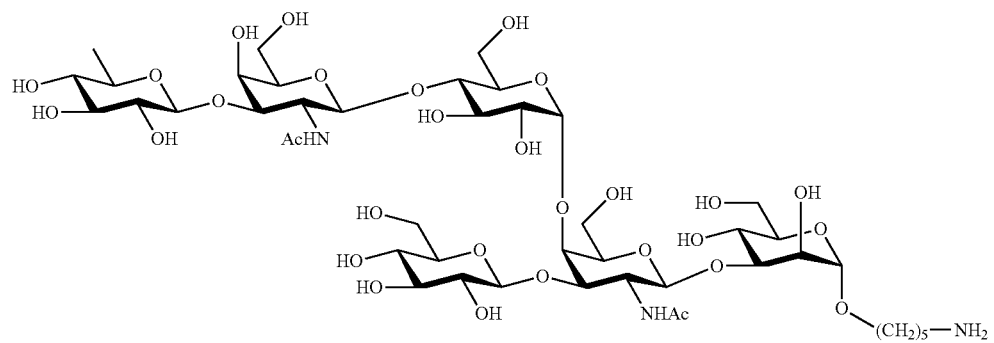
(I'd-1)
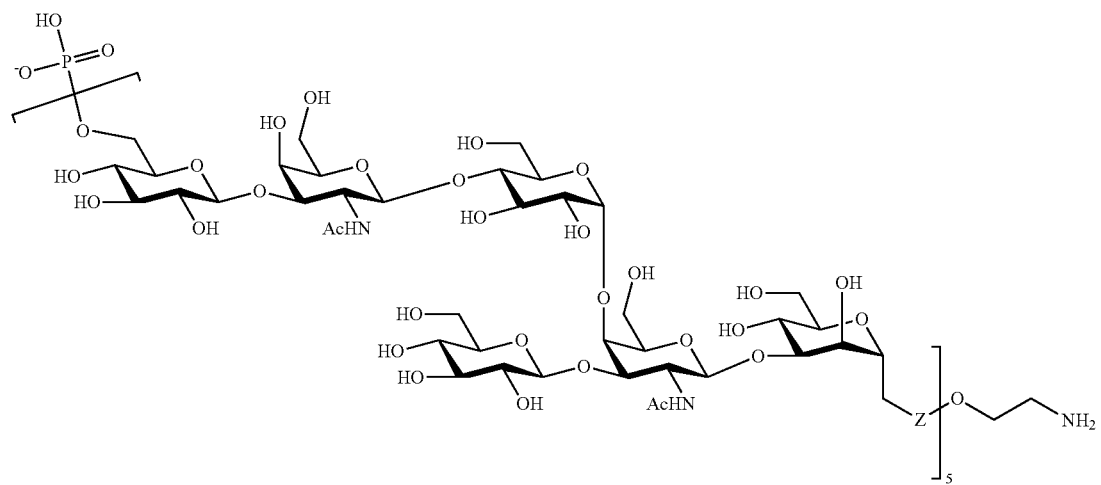

-continued
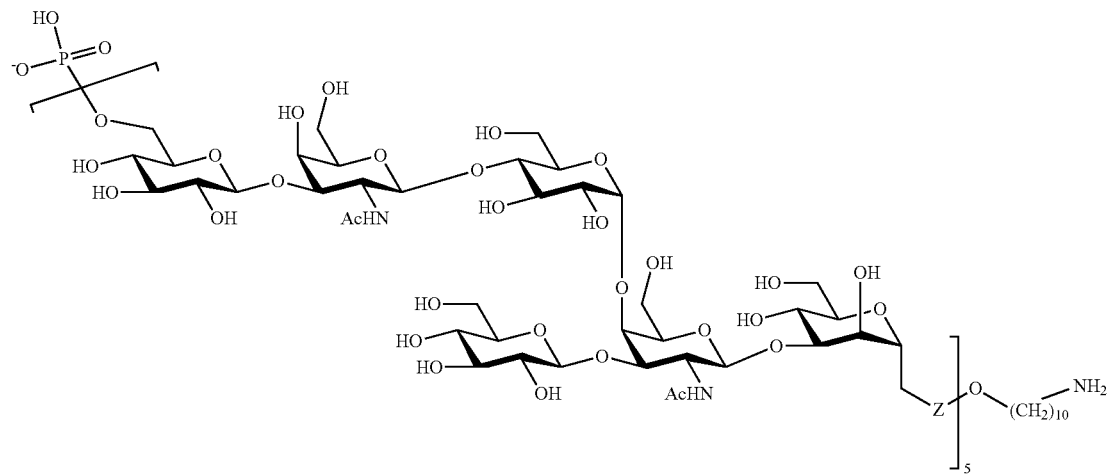
(I'd-2)
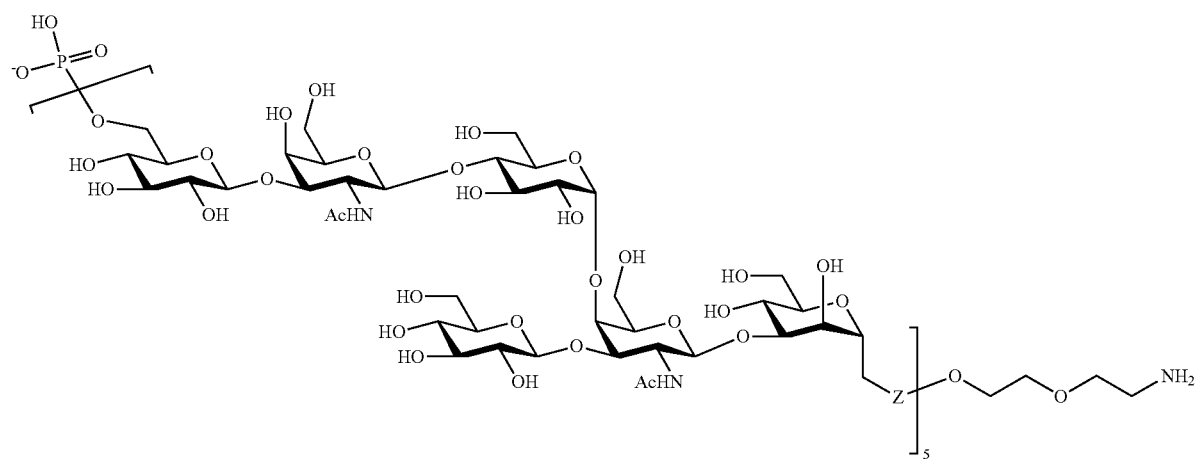
(I'd-3)
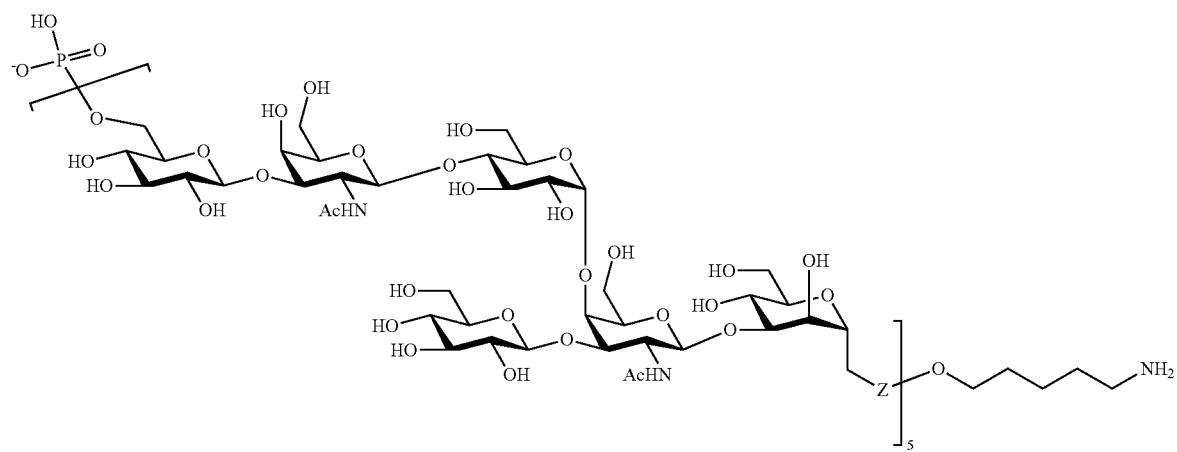
(I'd-4)

(I'd-5)
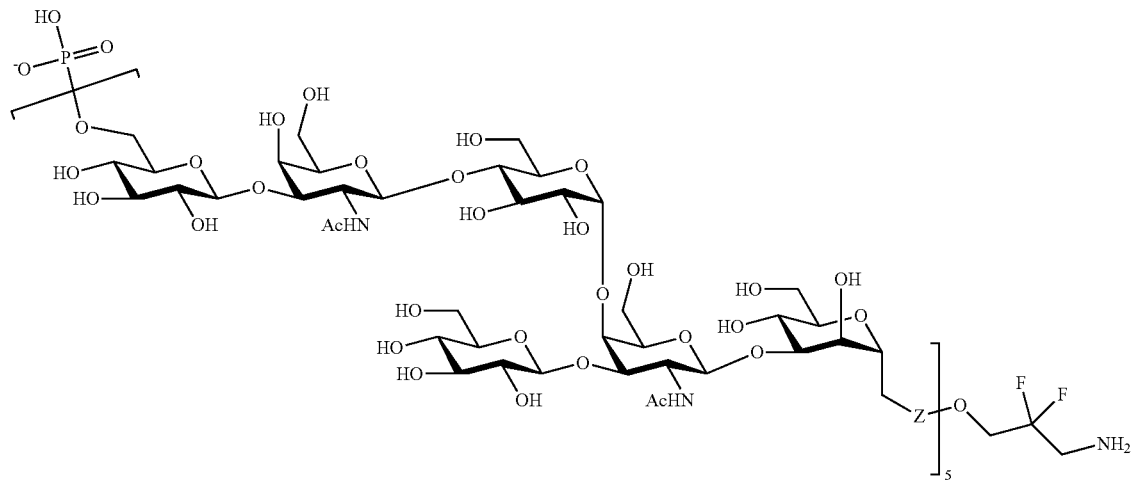
(I'd-6)
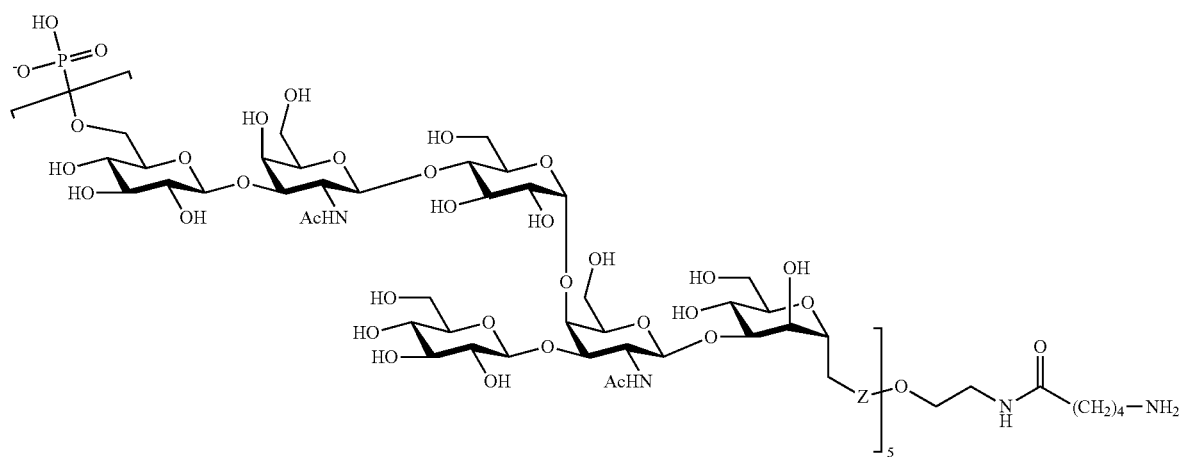
(I'd-7)
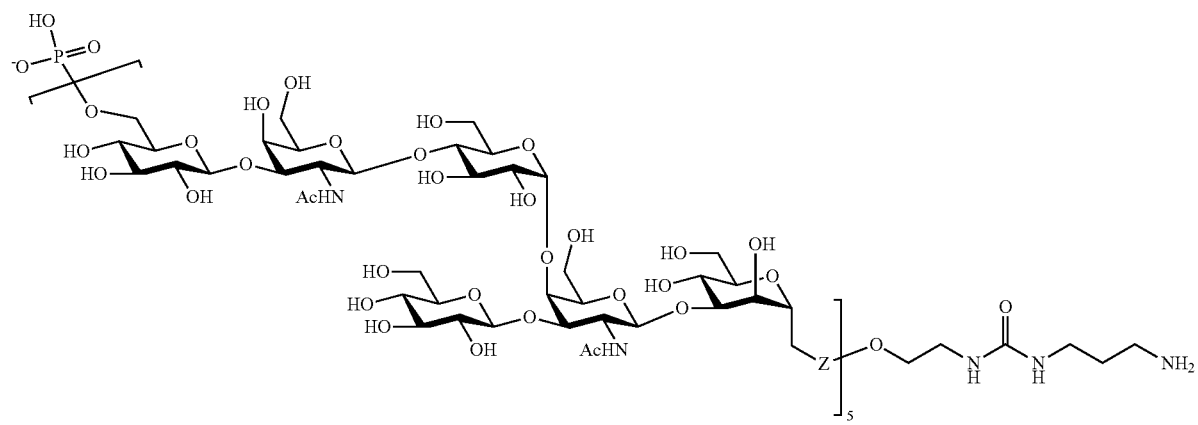

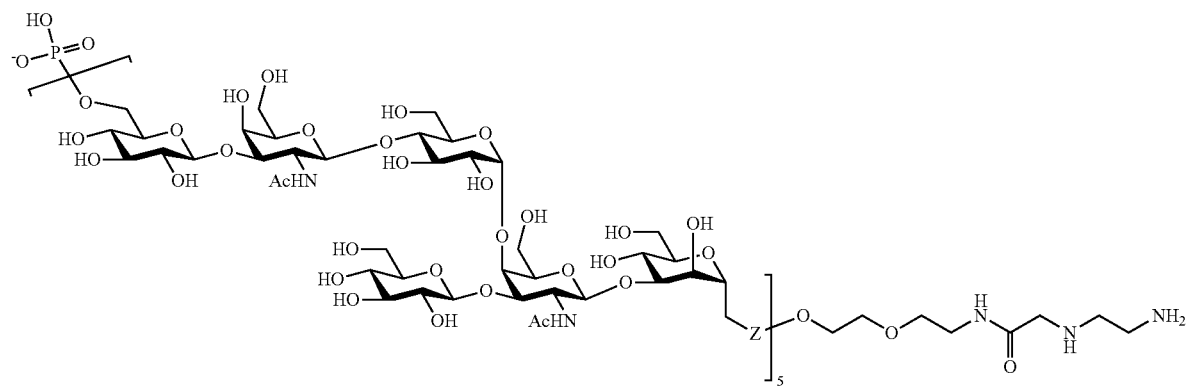
(I'd-8)
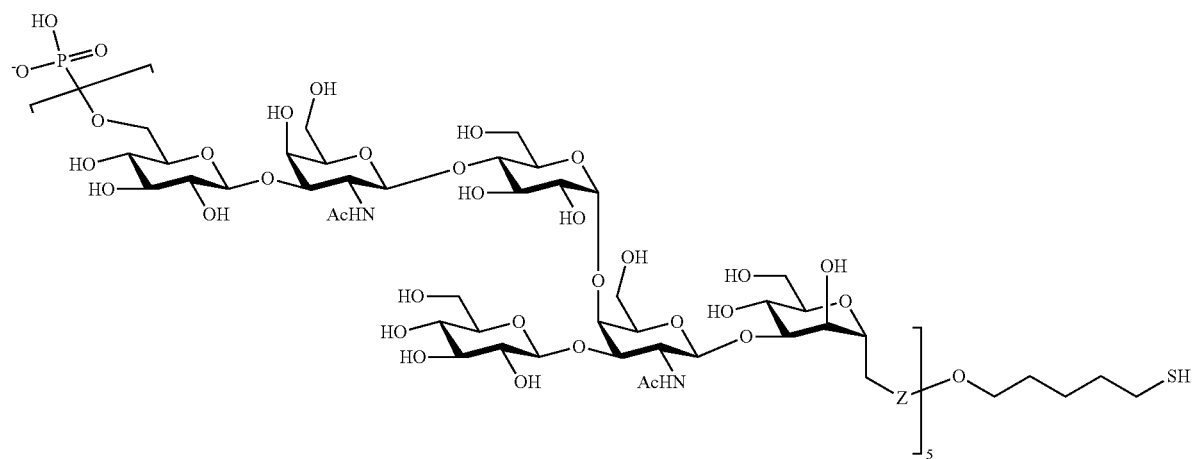
(I'd-9)
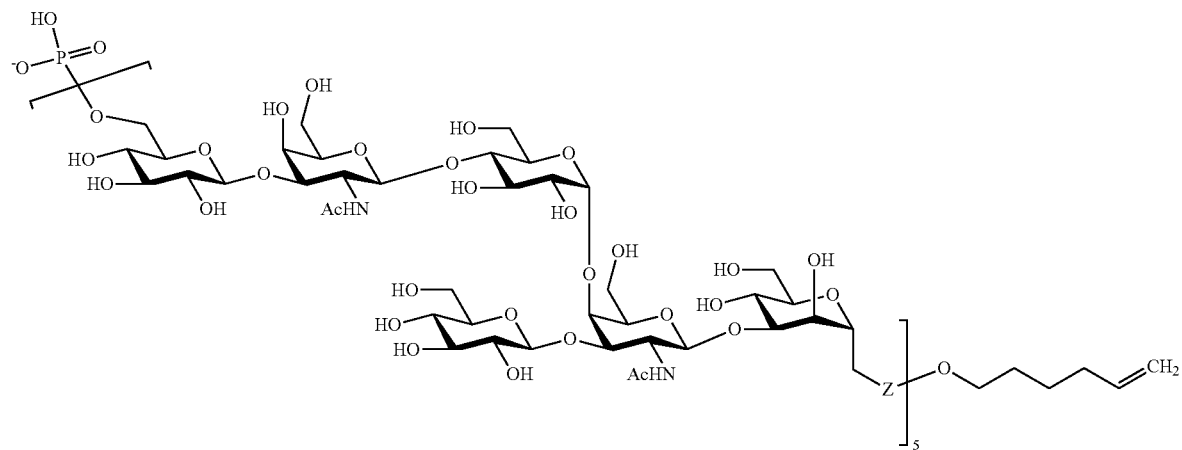
(I'd-10)

(I'd-11)
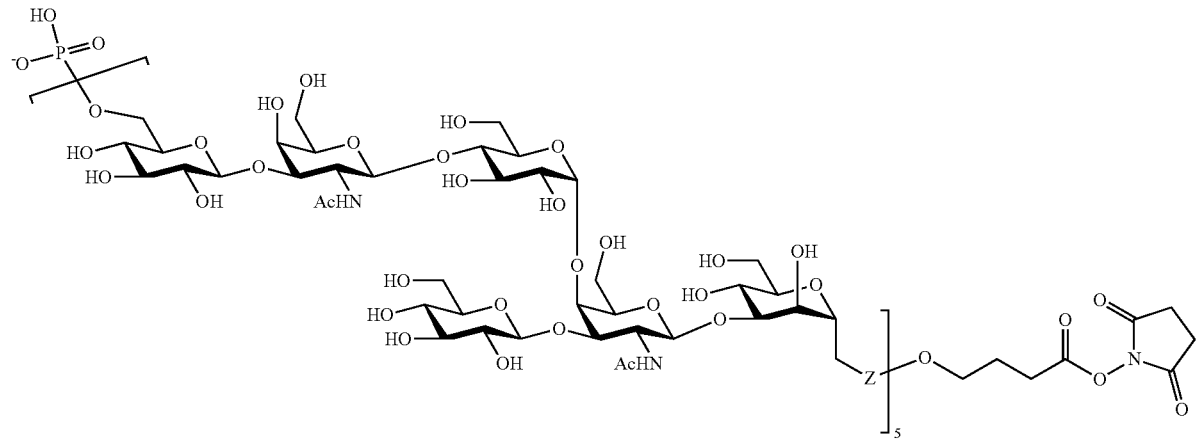
(I'd-12)
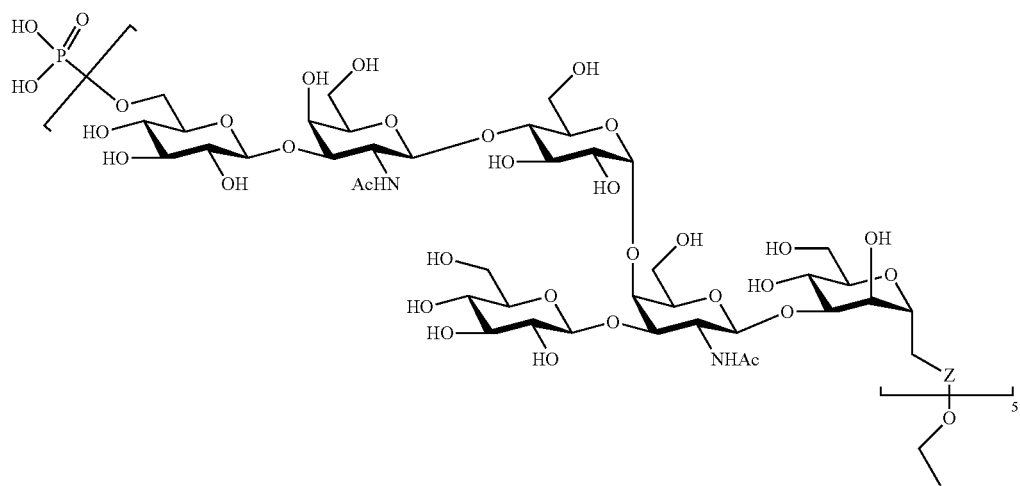
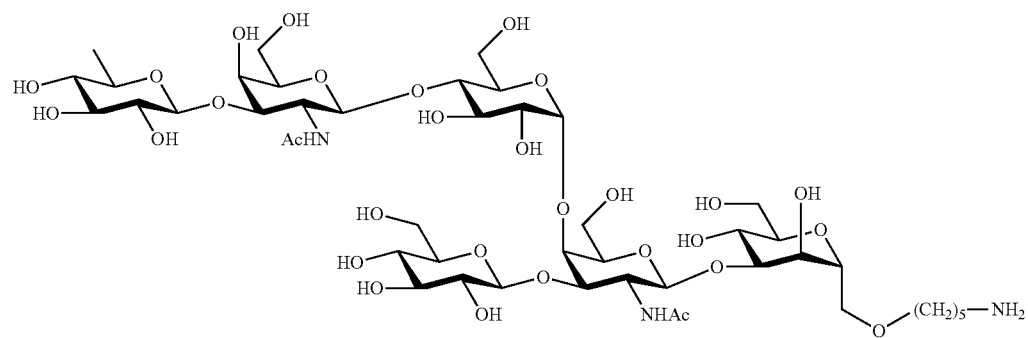

-continued
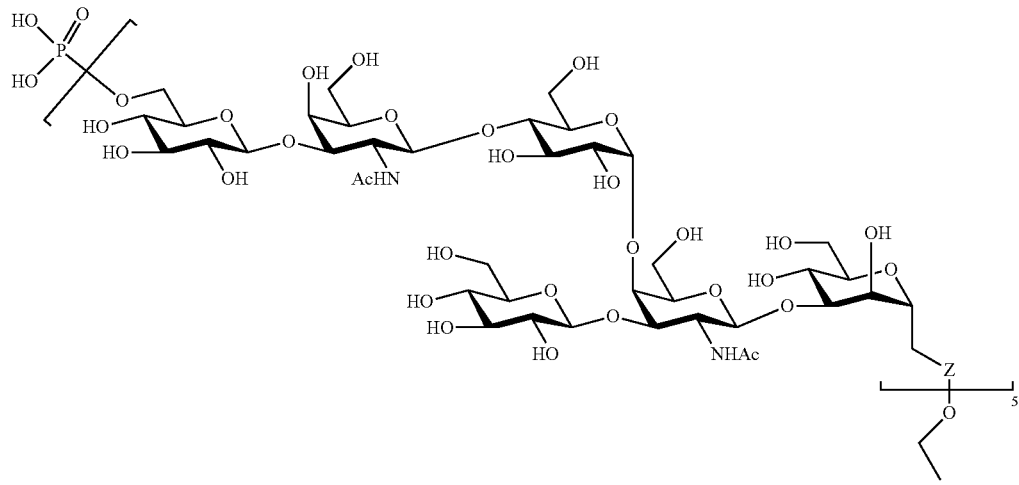
(I'd-13)
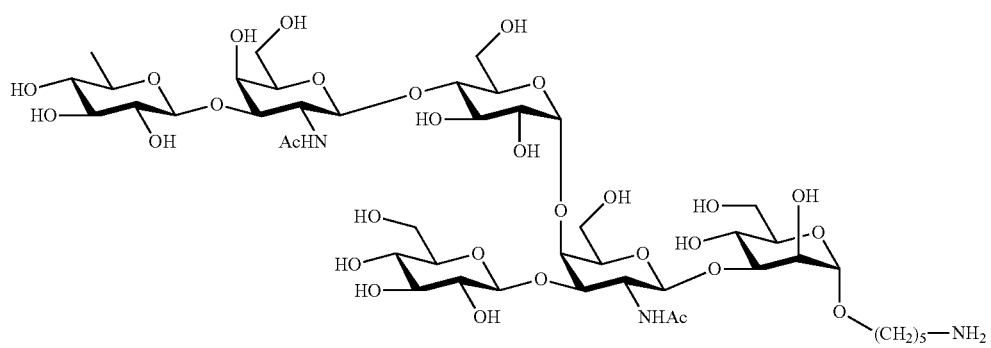
wherein Z represents
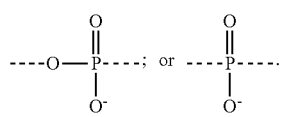
Particularly preferred is a saccharide formula (I'a-4), wherein Z represents
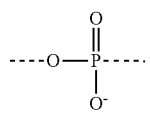
Particularly preferred is a saccharide formula (I'b-4), wherein Z represents
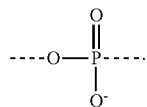
Chemical Synthesis
Another aspect of the present invention is directed to a method of synthesis of a saccharide of general formula (I)

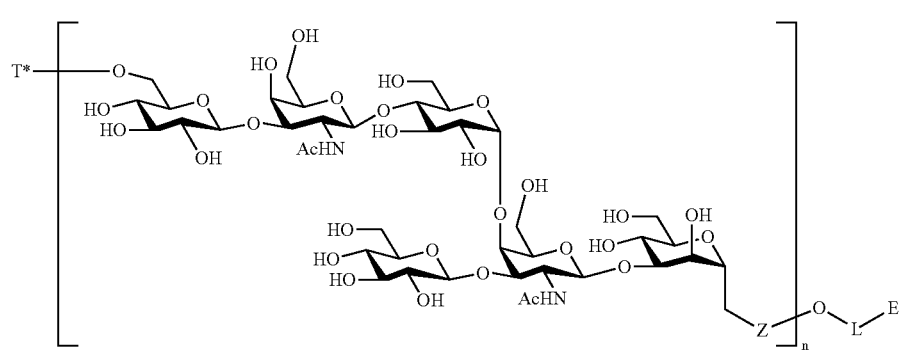
(I)

wherein n is 1;

T*- represents H— or a phosphate group;

Z represents

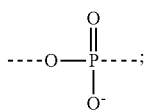

L represents a linker; and

E represents —NH$_2$, —N$_3$, —CN, —O—NH$_2$, —CH=CH$_2$, —C≡CH, —Br, —Cl, —I, —CO$_2$R', —CONH—NH$_2$, —SH, —OH or —SAc;

R' represents —H, -Me, -Et, 4-nitrophenyl, pentafluorophenyl, or N-succinimidyl;

comprising the following steps:

A1) Providing a monosaccharide of formula 1*:

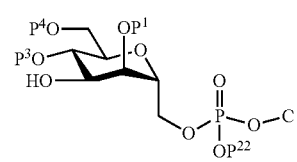
(1*)

wherein $P^1$, $P^3$, $P^4$ and $P^{22}$ represent protecting groups, C represents -L-E$_p$ with E$_p$ being a solid support or a protected end group; and A2) reacting monosaccharide of formula 1* with compound of formula 2* to obtain compound 3*:

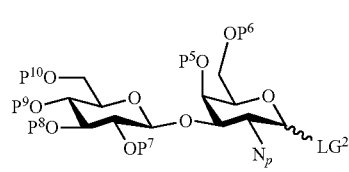
(2*)

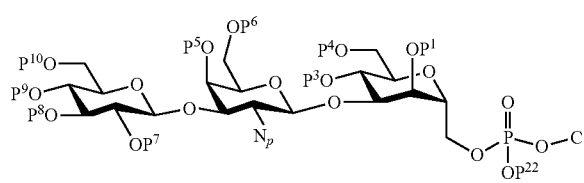
(3*)

wherein $P^1$, $P^3$, $P^4$-$P^{10}$ and $P^{22}$ represent protecting groups, C represents -L-E$_p$ with E$_p$ being a solid support or a protected end group E, LG$^2$ represents a leaving group and N$_p$ represents a protected amino group; and A3) Performing removal of protecting group $P^5$ of compound 3* to obtain compound 4*

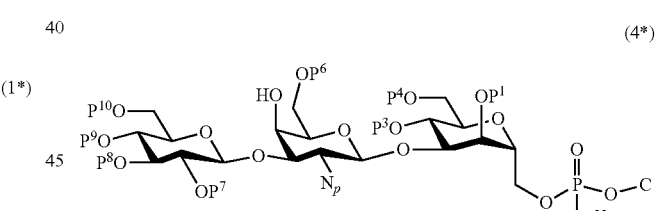
(4*)

wherein $P^1$, $P^3$, $P^4$, $P^6$-$P^{10}$ and $P^{22}$ represent protecting groups, C represents -L-E$_p$ with E$_p$ being a solid support or a protected end group E and N$_p$ represents a protected amino group; and A4) reacting compound 4* with monosaccharide 5* to obtain compound 6*

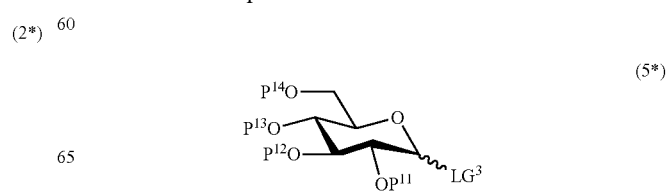
(5*)

(6*)

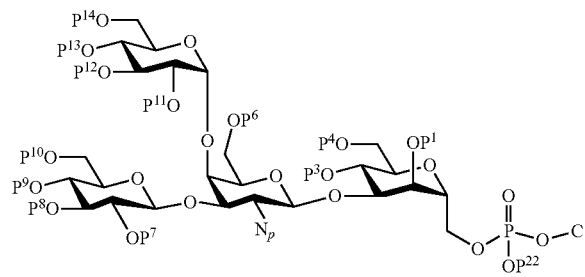

wherein $P^1$, $P^3$, $P^4$, $P^6$-$P^{14}$ and $P^{22}$ represent protecting groups, C represents -L-$E_p$ with $E_p$ being a solid support or a protected end group E, $LG^3$ represents a leaving group and $N_p$ represents a protected amino group; and A5) Performing removal of protecting group $P^{13}$ of compound 6* to obtain compound 7*

(7*)

wherein $P^1$, $P^3$, $P^4$, $P^6$-$P^{12}$, $P^{14}$ and $P^{22}$ represent protecting groups, C represents -L-$E_p$ with $E_p$ being a solid support or a protected end group E and $N_p$ represents a protected amino group; and A6) Reacting compound 7* with monosaccharide 8* to obtain compound 9*

(8*)

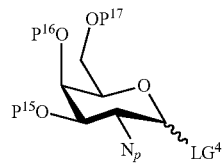

(9*)

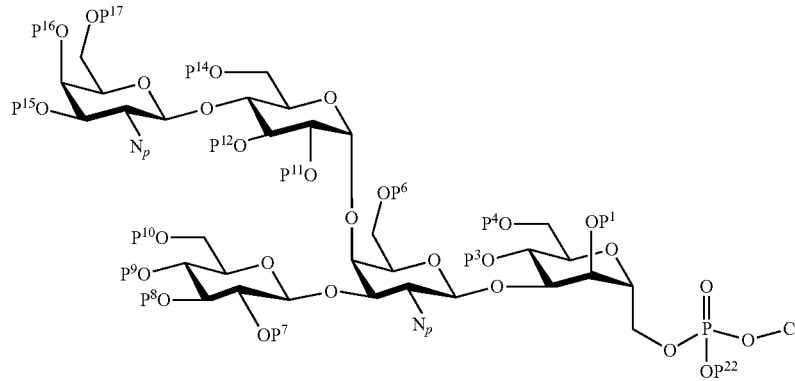

wherein $P^1$, $P^3$, $P^4$, $P^6$-$P^{12}$, $P^{14}$-$P^{17}$ and $P^{22}$ represent protecting groups, C represents -L-$E_p$ with $E_p$ being a solid support or a protected end group E, $LG^4$ represents a leaving group and $N_p$ represents a protected amino group; and A7) Performing removal of protecting group $P^{15}$ of compound 9* to obtain compound 10*

(10*)

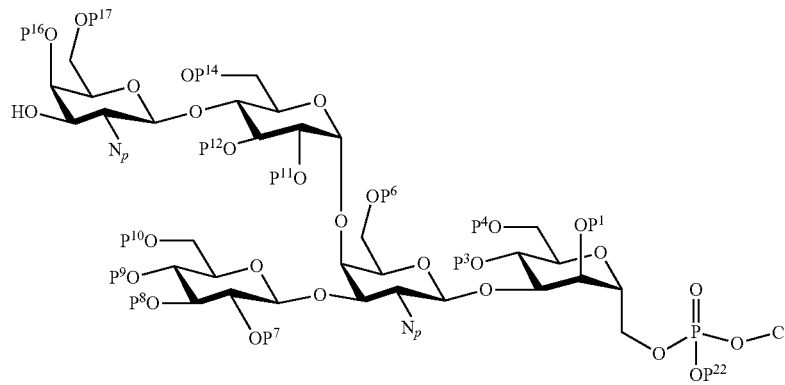

wherein $P^1$, $P^3$, $P^4$, $P^6$-$P^{12}$, $P^{14}$, $P^{16}$, $P^{17}$ and $P^{22}$ represent protecting groups, C represents -L-$E_p$ with $E_p$ being a solid support or a protected end group E and $N_p$ represents a protected amino group; and A8) reacting compound 10* with monosaccharide 11* to obtain compound 12*

(11*)

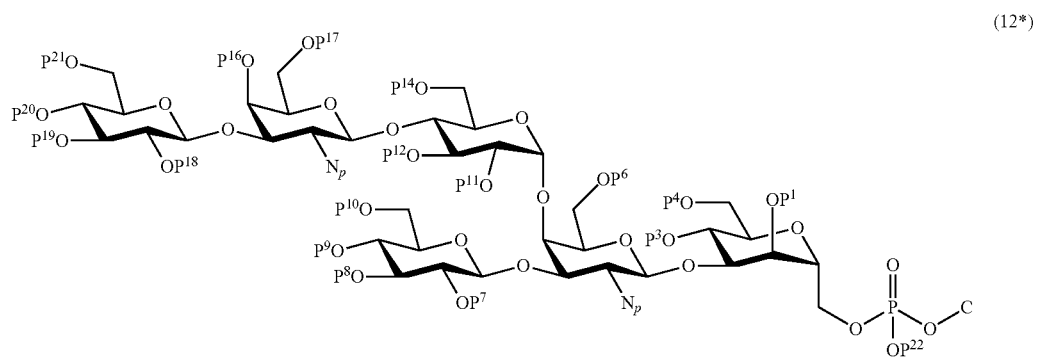

(12*)

wherein $P^1$, $P^3$, $P^4$, $P^6$-$P^{12}$, $P^{14}$ and $P^{16}$-$P^{22}$ represent protecting groups, C represents -L-$E_p$ with $E_p$ being a solid support or a protected end group E, $LG^5$ represents a leaving group and $N_p$ represents a protected amino group; and A9) Optionally performing removal of protecting group $P^{21}$ of compound 12* to obtain compound 13* and reacting compound 13* with a phosphorylating agent to obtain compound 14*

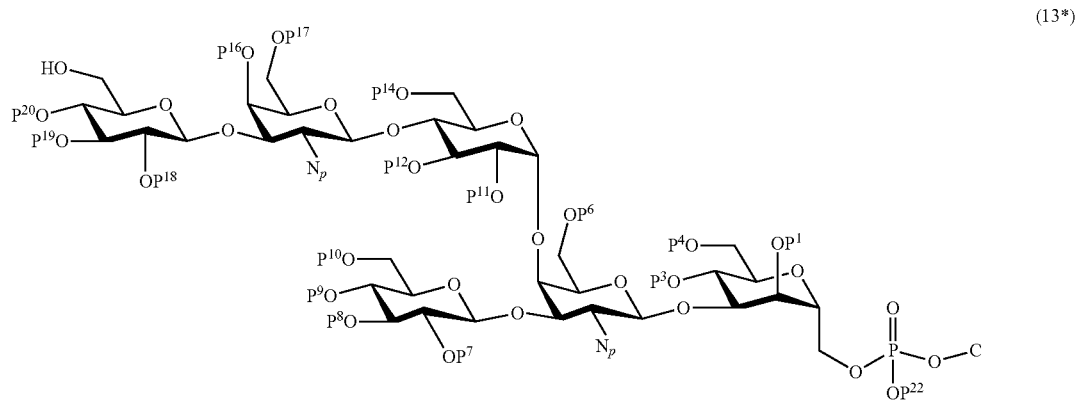

(13*)

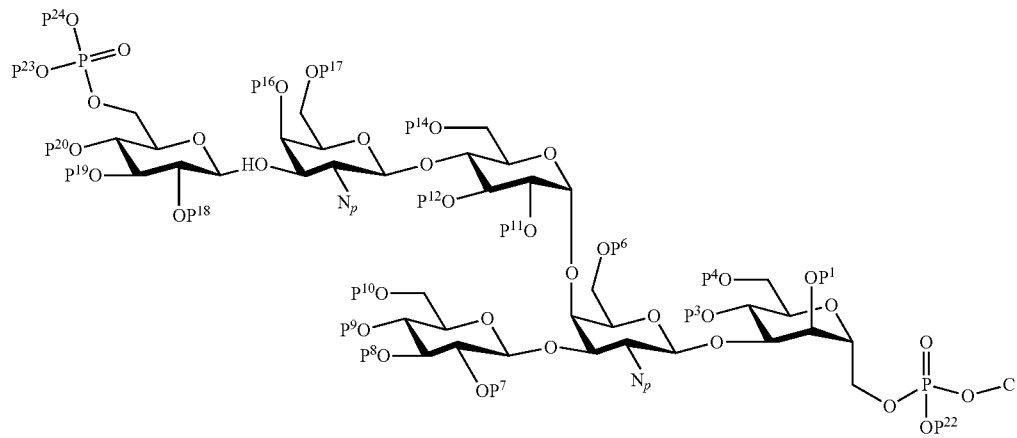

(14*)

wherein $P^1$, $P^3$, $P^4$, $P^6$-$P^{12}$, $P^{14}$, $P^{16}$-$P^{20}$ and $P^{22}$-$P^{24}$ represent protecting groups, C represents -L-$E_p$ with $E_p$ being a solid support or a protected end group E and $N_p$ represents a protected amino group; and A10) Converting the protected amino groups of compound 12* or 14* to the corresponding acetamido groups to obtain compound 15* or 16*

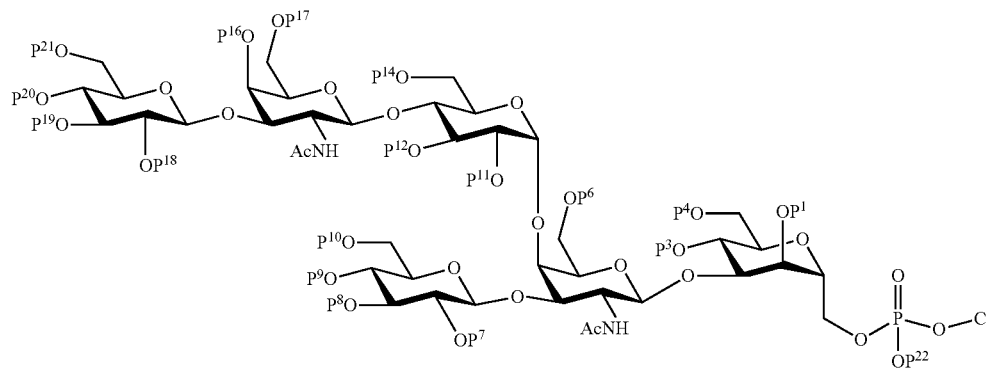

(15*)

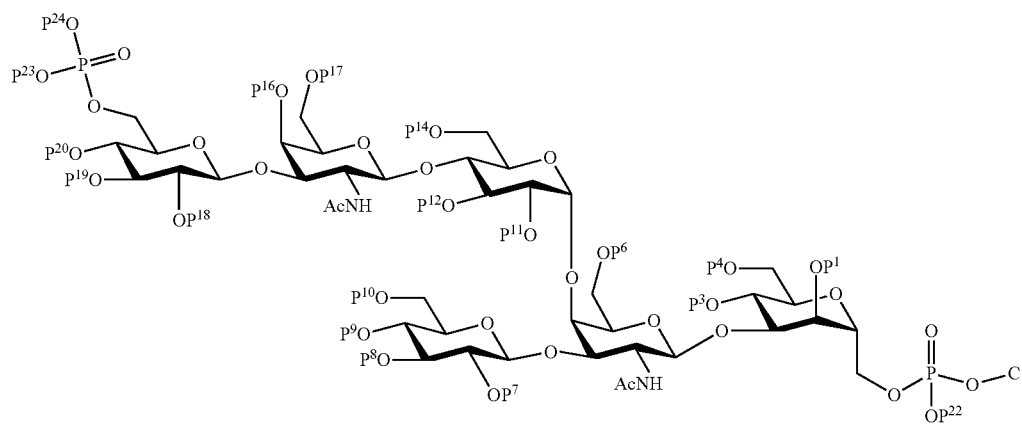

(16*)

wherein $P^1$, $P^3$, $P^4$, $P^6$-$P^{12}$, $P^{14}$ and $P^{16}$-$P^{24}$ represent protecting groups and C represents -L-$E_p$ with $E_p$ being a solid support or a protected end group; and A11) Performing removal of all remaining protecting groups from compound 15* or 16* to obtain compound 17* or 18* of general formula (I)

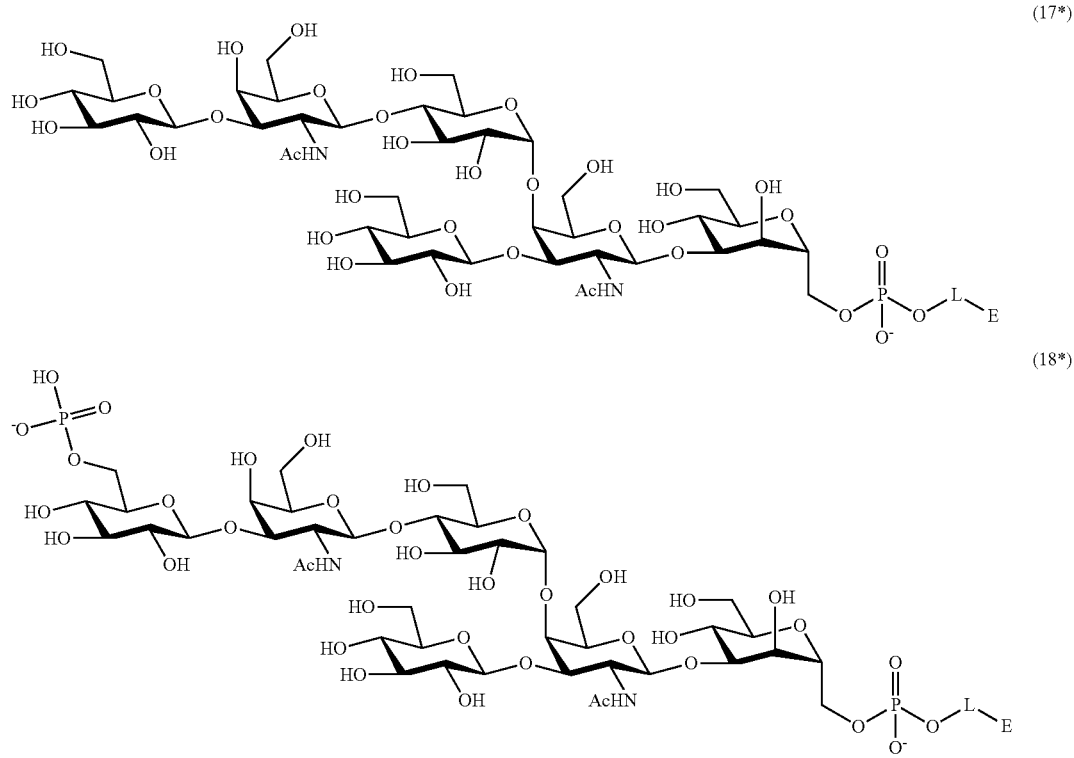

(17*)

(18*)

Another aspect of the present invention is directed to the synthesis of saccharide 17* or 18* of general formula (I), wherein hexasaccharide intermediate 12* is obtained directly from compound 7* by performing step A6'.

A6') Reacting compound 7* with the disaccharide 19* to obtain compound 12*

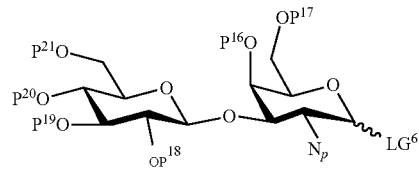

(19*)

wherein $P^{16}$-$P^{20}$ and $P^{21}$ represent protecting groups, $LG^6$ represents a leaving group and $N_p$ represents a protected amino group.

Thus, in one embodiment a method of synthesis of saccharide 17* or 18* of general formula (I) comprises the steps A1), A2), A3), A4), A5), A6'), A9), A10) and A11).

Another aspect of the present invention is directed to the synthesis of saccharide 17* or 18* of general formula (I), wherein hexasaccharide intermediate 12* is obtained directly from compound 1* by performing step A2'.

A2') Reacting compound 1 with the pentasaccharide 20* to obtain compound 12*

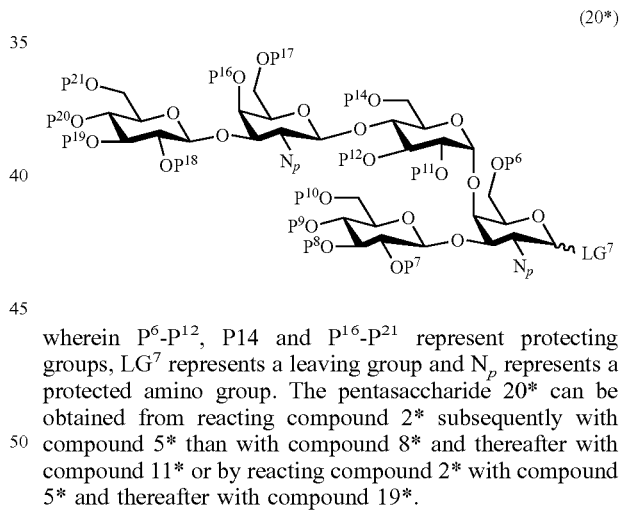

(20*)

wherein $P^6$-$P^{12}$, P14 and $P^{16}$-$P^{21}$ represent protecting groups, $LG^7$ represents a leaving group and $N_p$ represents a protected amino group. The pentasaccharide 20* can be obtained from reacting compound 2* subsequently with compound 5* than with compound 8* and thereafter with compound 11* or by reacting compound 2* with compound 5* and thereafter with compound 19*.

Thus, in one embodiment a method of synthesis of saccharide 17* or 18* of general formula (I) comprises the steps A1), A2'), A9), A10) and A11).

Compound 1* may be obtained from the corresponding protected mannose donor 21* by steps A1a), A1b) and A1c).

A1a) Providing compound 21*

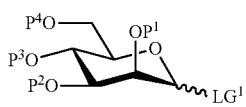

(21*)

wherein P¹-P⁴ represent protecting groups and LG' represents a leaving group; and converting compound of formula 21* to alcohol of formula 22*

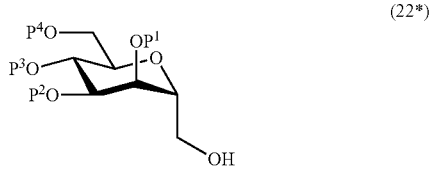
(22*)

wherein P¹-P⁴ represent protecting groups; and

A1b) Reacting a compound of formula 22* with alcohol HO-L-C in presence of a phosphorylating agent to obtain a compound 23*;

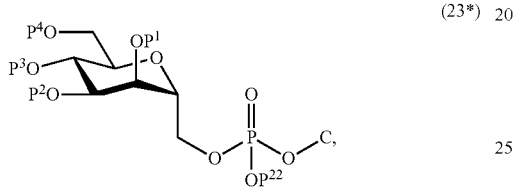
(23*)

wherein P¹-P⁴ and P²² represent protecting groups and C represents -L-$E_p$ with $E_p$ being a solid support or a protected end group E; and The alcohol 22* in step A1a) may be prepared according to Brooks et al. (Tetrahedron 1995, 51, 7999) by reacting compound 21* with allyltrimethylsilane in presence of a Lewis acid (J. Am. Chem Soc. 1982, 104, 4976; Tetrahedron Letters, 1985, 26, 1479), subsequent isomerization with bis(benzonitrile)palladium (II) chloride in refluxing toluene to propenyl C-mannoside, ozonolysis or Lemieux-Johnson oxidation with sodium periodate and osmium tetroxide, and reduction to alcohol 22* with sodium acetoxyborohydride (see also Org. Biomol. Chem 2016, 14, 3913).

Alternatively, the alcohol 22* in step A1a) may be prepared by reacting compound 21* with (iPrO)Me₂SiCH₂MgCl in the presence of copper(I) iodide (Org. Lett. 2004, 6, 119). Further, the alcohol 22* in step A1a) may be prepared by reacting compound 21* with a vinyl Grignard reagent that is afterwards oxidized with osmium tetroxide and sodium periodate and reduced to alcohol 22* by a sodium borohydride reagent, such as sodium acetoxyborohydride.

In another embodiment, the alcohol 22* is obtained from the corresponding glycoside by reacting with trimethylsulfoxonium iodide and sodium hydride (J. Org. Chem. 2002, 67, 7439) or by reacting with propargyl trimethylsilane and BF₃·OEt₂ with subsequent ozonolysis and sodium borohydride reduction (Synlett 2005, 7, 1147).

A1c) Performing removal of protecting group P² of compound 23* to obtain compound 1*

Another aspect of the present invention is directed to a method of synthesis of a saccharide of general formula (I), wherein n is an integer selected from 2, 3, 4, 5, 6, 7, 8, 9 or 10;

T*- represents H— or a phosphate group;

Z represents

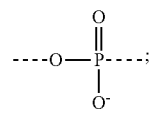

L represents a linker and;

E represents —NH₂, —N₃, —CN, —O—NH₂, —CH=CH₂, —C≡CH, —Br, —Cl, —I, —CO₂R', —CONH—NH₂, —SH, —OH or —SAc;

R' represents —H, -Me, -Et, 4-nitrophenyl, pentafluorophenyl, or N-succinimidyl;

comprising the following steps:

B1) Providing compound 13*

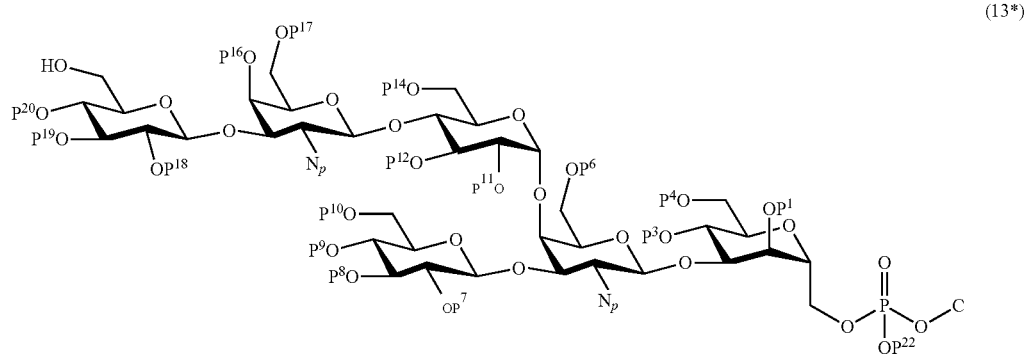
(13*)

wherein P¹, P³, P⁴, P⁶-P¹², P¹⁴, P¹⁶-P²⁰ and P²² represent protecting groups, C represents -L-$E_p$ with $E_p$ being a solid support or a protected end group E and $N_p$ represents a protected amino group;

and repeating the following steps n–1 times:

B1.1) Reacting with a compound of formula 22* in presence of a phosphorylating agent, B1.2) Performing removal of protecting group P²;

B1.3) Performing steps A2)-A8) or steps A2)-A5) and A6') or step A2');

B1.4) Performing removal of protecting group P²¹;

or

B2.1) Reacting compound 13* with a compound of the formula (13#)

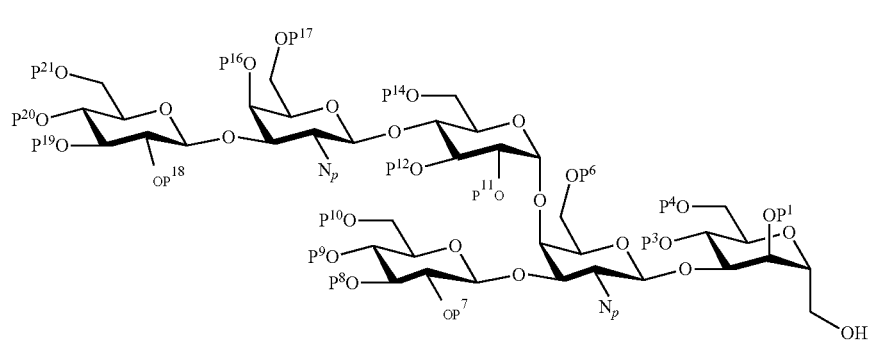

in presence of a phosphorylating agent,
B2.2) Performing removal of protecting group $P^{21}$;
B2.3) optionally repeating the steps B2.1 and B2.2 one to eight times in order to synthesize the corresponding trisaccharides (n=3) to decasaccharides (n=10);
to provide compound 24*:

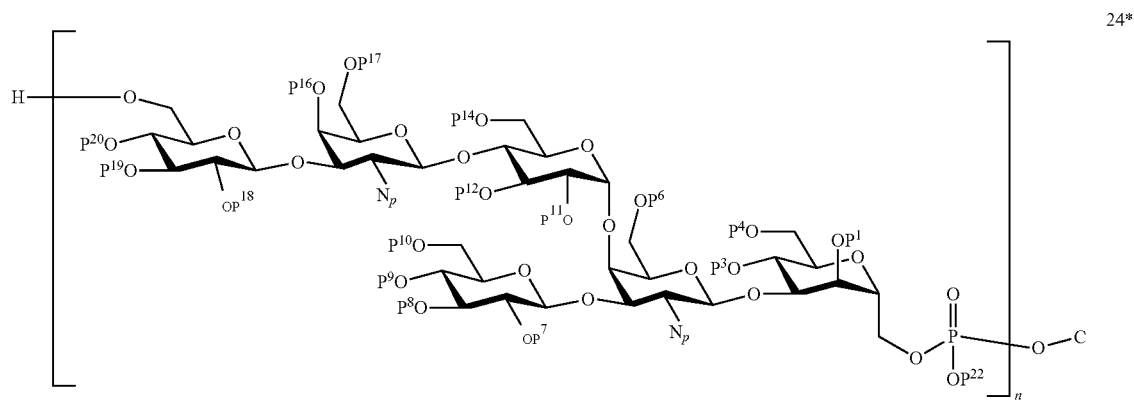

24* wherein $P^1$, $P^3$, $P^4$, $P^6$-$P^{14}$, $P^{16}$-$P^{20}$ and $P^{22}$ represent protecting groups, C represents -L-$E_p$ with $E_p$ being a solid support or a protected end group E, $N_p$ represents a protected amino group and n represents an integer from 2 to 10; and B2) Optionally reacting compound 24* with a phosphorylating agent to obtain compound 25*

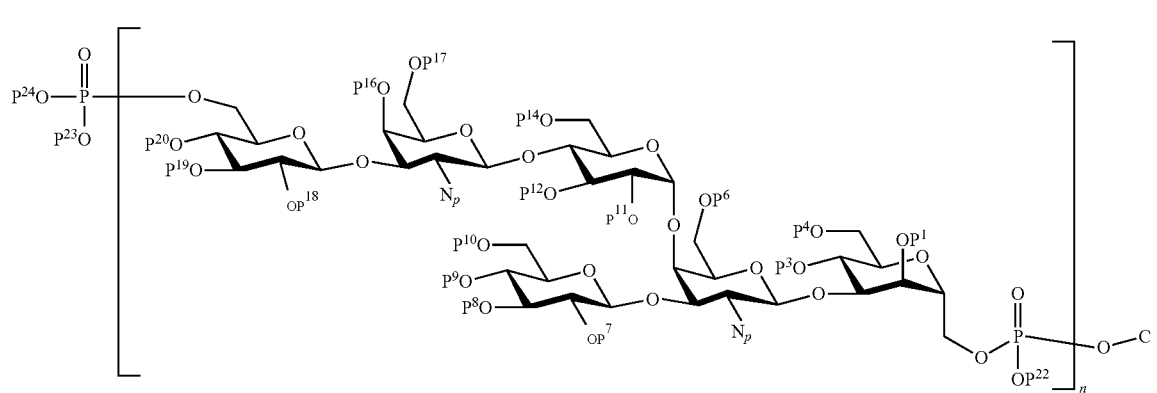

25* wherein $P^1$, $P^3$, $P^4$, $P^6$-P12, $P^{14}$, $P^{16}$-$P^{20}$ and $P^{22}$-$P^{24}$ represent protecting groups, C represents -L-$E_p$ with $E_p$ being a solid support or a protected end group E, $N_p$ represents a protected amino group and n represents an integer from 2 to 10; and B3) Converting the protected amino groups of compound 24* or 25* to the corresponding acetamido groups to obtain compound 26* or 27*

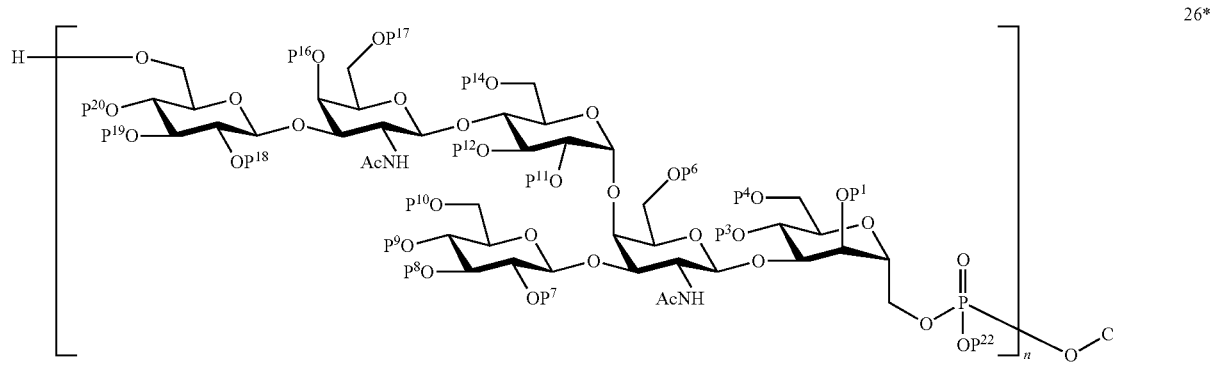

26*

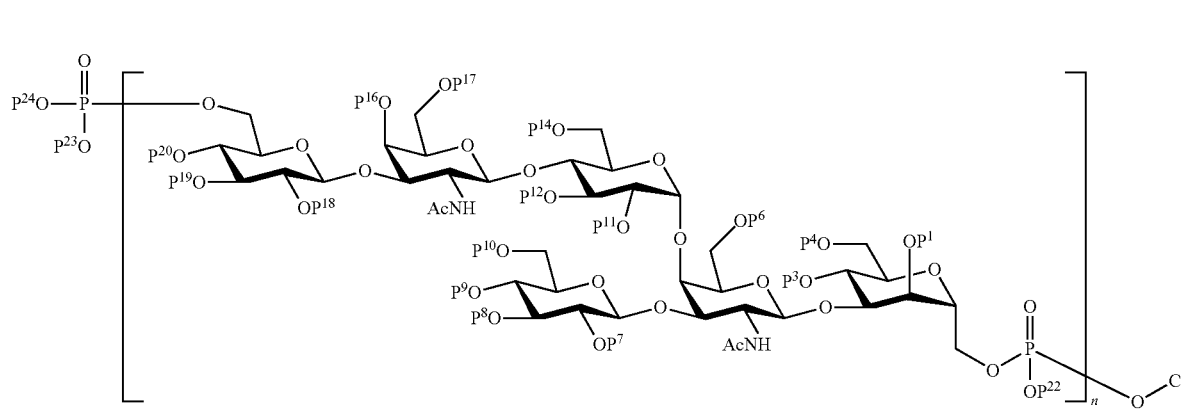

27* wherein $P^1$, $P^3$, $P^4$, $P^6$-$P^{12}$, $P^{14}$, $P^{16}$-$P^{20}$ and $P^{22}P^{24}$ represent protecting groups, C represents -L-$E_p$ with $E_p$ being a solid support or a protected end group E and n represents an integer from 2 to 10; and B4) Performing removal of all remaining protecting groups from compound 26* or 27* to obtain compound 28* or 29* of general formula (I)

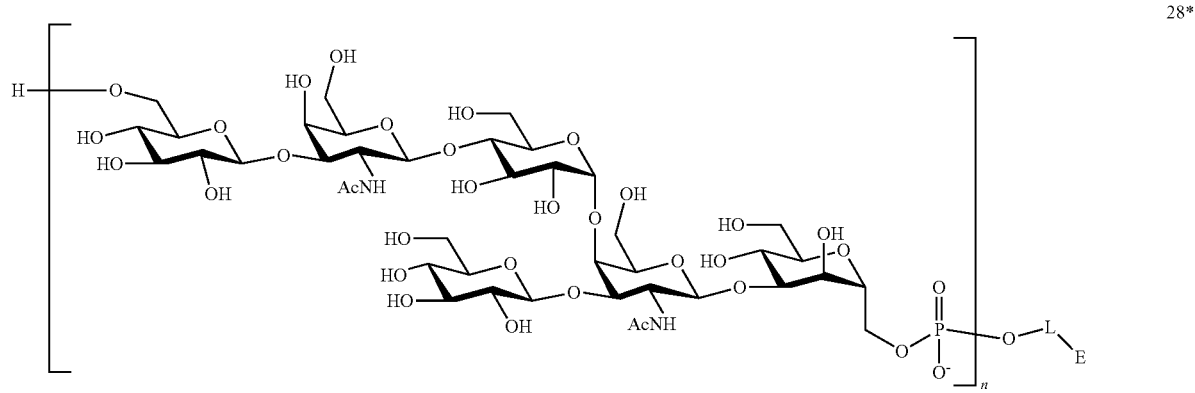

28*

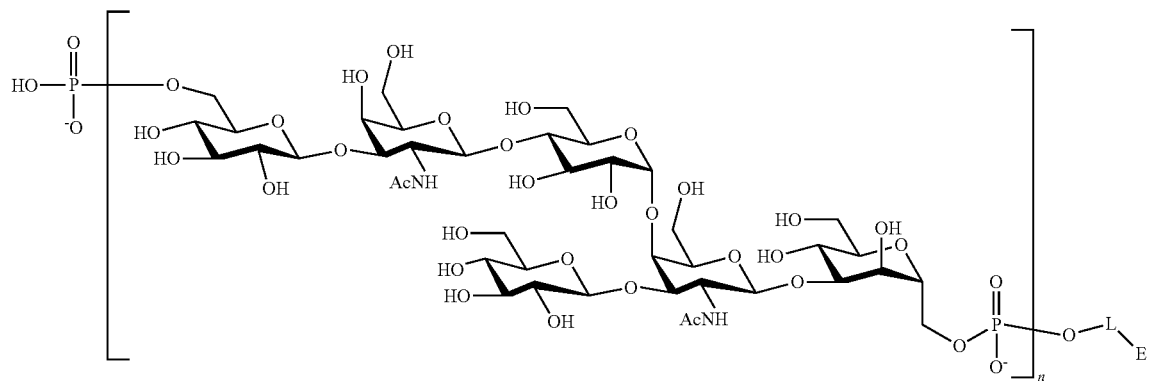
(29*)

wherein n represents an integer from 2 to 10 and L and E have the meanings as defined herein.

Another aspect of the present invention is directed to a method of synthesis of a saccharide of general formula (I)

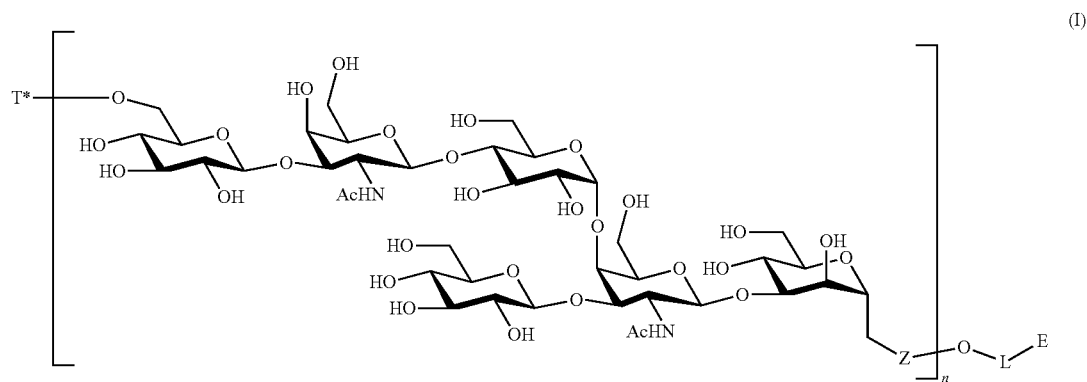
(I)

wherein n is 1;

T*- represents H— or a phosphate group;

Z represents

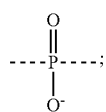

L represents a linker and;

E represents —NH$_2$, —N$_3$, —CN, —O—NH$_2$, —CH═CH$_2$, —C≡CH, —Br, —Cl, —I, —CO$_2$R', —CONH—NH$_2$, —SH, —OH or —SAc;

R' represents —H, -Me, -Et, 4-nitrophenyl, pentafluorophenyl, or N-succinimidyl;

comprising the following steps:

C1) Providing a monosaccharide of formula 30* which can be obtained according to the procedure disclosed in Chem. Eur. J. 2015, 21, 7511-7519 or Synlett, 2005, 7, 1147-1151:

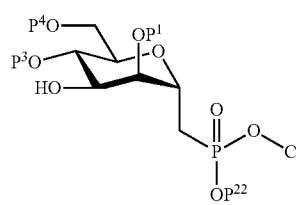
(30*)

wherein P$^1$, P$^3$, P$^4$ and P$^{22}$ represent protecting groups, C represents -L-E$_p$ with E$_p$ being a solid support or a protected end group; and C2) Reacting monosaccharide of formula 30* with compound of formula 2* to obtain compound 31*:

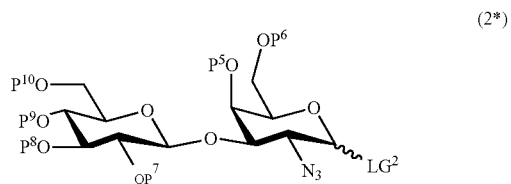
(2*)

(31*)

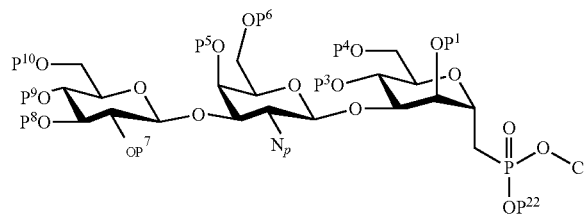

wherein $P^1$, $P^3$, $P^4$-$P^{10}$ and $P^{22}$ represent protecting groups, C represents -L-$E_p$ with $E_p$ being a solid support or a protected end group E, $LG^2$ represents a leaving group and $N_p$ represents a protected amino group; and C3) Performing removal of protecting group $P^5$ of compound 31* to obtain compound 32*

(32*)

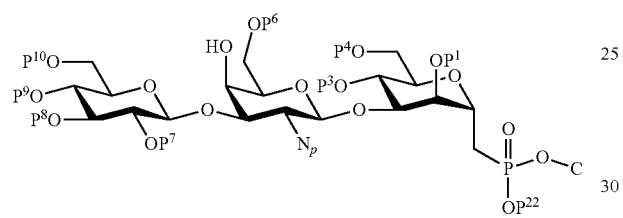

wherein $P^1$, $P^3$, $P^4$, $P^6$-$P^{10}$ and $P^{22}$ represent protecting groups, C represents -L-$E_p$ with $E_p$ being a solid support or a protected end group E and $N_p$ represents a protected amino group; and C4) Reacting compound 32* with monosaccharide 5* to obtain compound 33*

(5*)

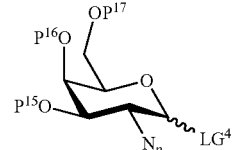

(33*)

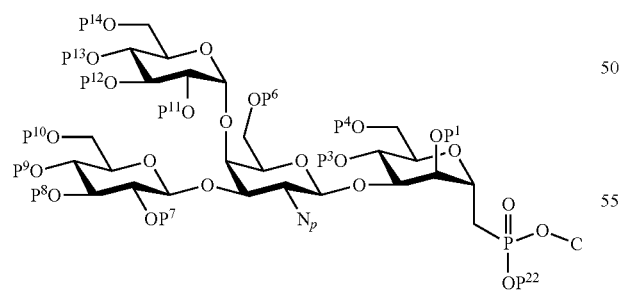

wherein $P^1$, $P^3$, $P^4$, $P^6$-$P^{14}$ and $P^{22}$ represent protecting groups, C represents -L-$E_p$ with $E_p$ being a solid support or a protected end group E, $LG^3$ represents a leaving group and $N_p$ represents a protected amino group; and C5) Performing removal of protecting group $P^{13}$ of compound 33* to obtain compound 7*

(34*)

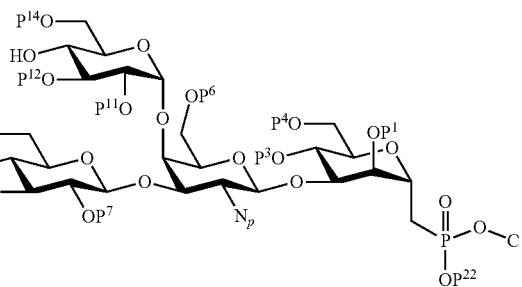

wherein $P^1$, $P^3$, $P^4$, $P^6$-$P^{12}$, $P^{14}$ and $P^{22}$ represent protecting groups, C represents -L-$E_p$ with $E_p$ being a solid support or a protected end group E and $N_p$ represents a protected amino group; and C6) Reacting compound 34* with monosaccharide 8* to obtain compound 35*

(8*)

(35*)

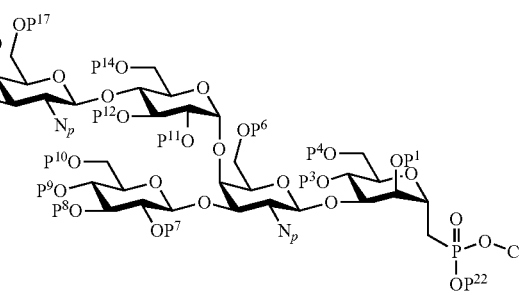

wherein $P^1$, $P^3$, $P^4$, $P^6$-$P^{12}$, $P^{14}$-$P^{17}$ and $P^{22}$ represent protecting groups, C represents -L-$E_p$ with $E_p$ being a solid support or a protected end group E, $LG^4$ represents a leaving group and $N_p$ represents a protected amino group; and C7) Performing removal of protecting group $P^{15}$ of compound 35* to obtain compound 36*

(36*)

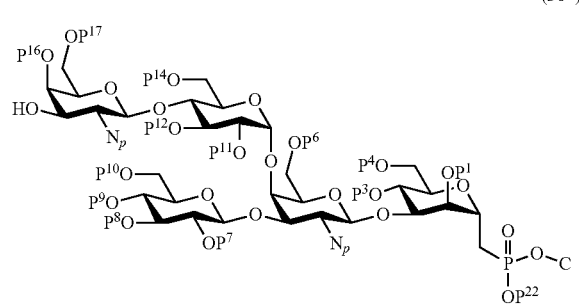

wherein $P^1$, $P^3$, $P^4$, $P^6$-$P^{12}$, $P^{14}$, $P^{16}$, $P^{17}$ and $P^{22}$ represent protecting groups, C represents -L-$E_p$ with $E_p$ being a solid support or a protected end group E and $N_p$ represents a protected amino group; and C8) Reacting compound 36* with monosaccharide 11* to obtain compound 37*

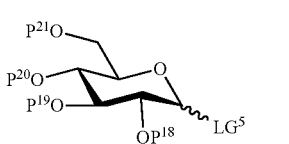

(11*)

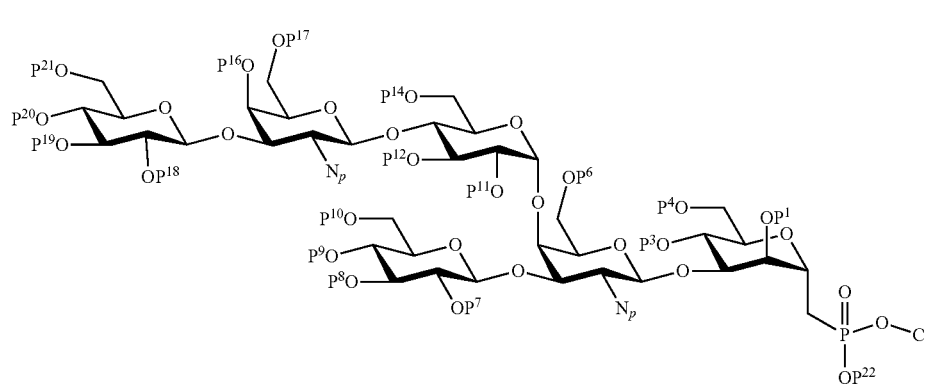

(37*)

wherein $P^1$, $P^3$, $P^4$, $P^6$-$P^{12}$, $P^{14}$ and $P^{16}$-$P^{22}$ represent protecting groups, C represents -L-$E_p$ with $E_p$ being a solid support or a protected end group E, $LG^5$ represents a leaving group and $N_p$ represents a protected amino group; and C9) Optionally performing removal of protecting group $P^{21}$ of compound 37* to obtain compound 38* and reacting compound 38* with a phosphorylating agent to obtain compound 39*

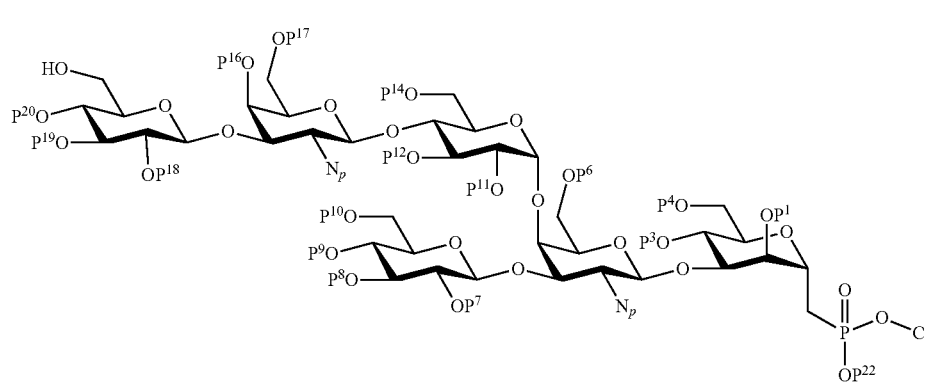

(38*)

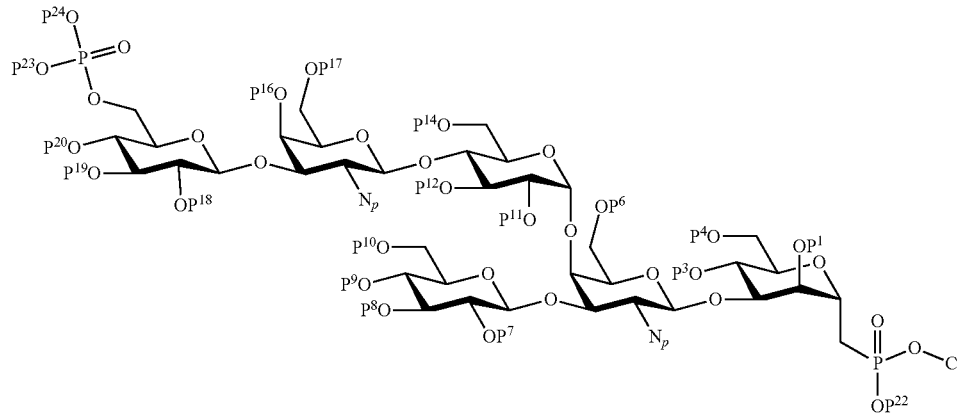

(39*)

wherein $P^1$, $P^3$, $P^4$, $P^6$-$P^{12}$, $P^{14}$, $P^{16}$-P20 and $P^{22}$-$P^{24}$ represent protecting groups, C represents -L-$E_p$ with $E_p$ being a solid support or a protected end group E and $N_p$ represents a protected amino group; and C10) Converting the protected amino groups of compound 37* or 39* to the corresponding acetamido groups to obtain compound 40* or 41*

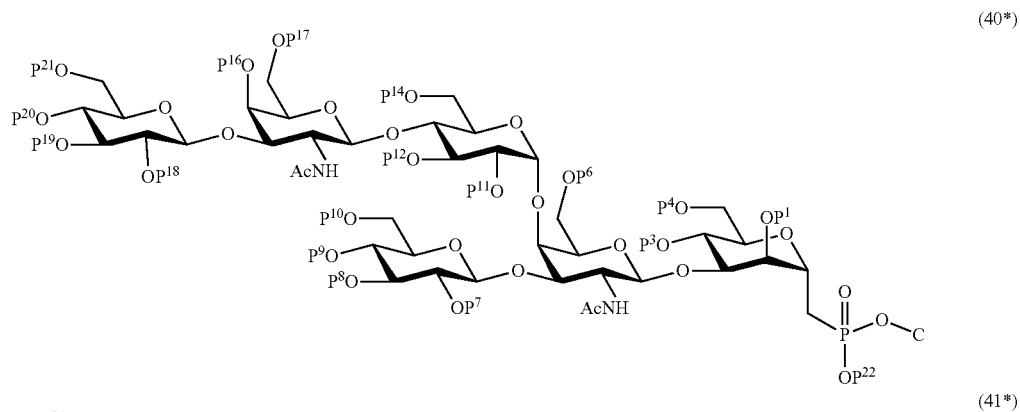

(40*)

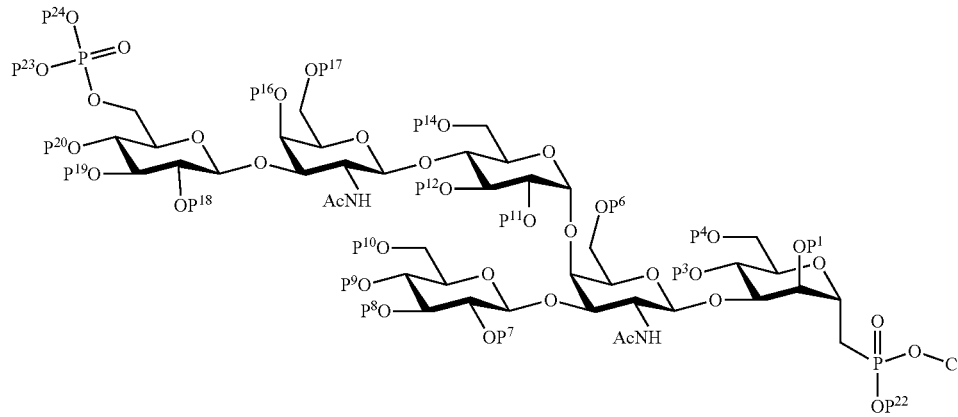

(41*)

wherein $P^1$, $P^3$, $P^4$, $P^6$-$P^{12}$, $P^{14}$ and $P^{16}$-$P^{24}$ represent protecting groups and C represents -L-$E_p$ with $E_p$ being a solid support or a protected end group; and C11) Performing removal of all remaining protecting groups from compound 40* or 41* to obtain compound 42* or 43* of general formula (I)

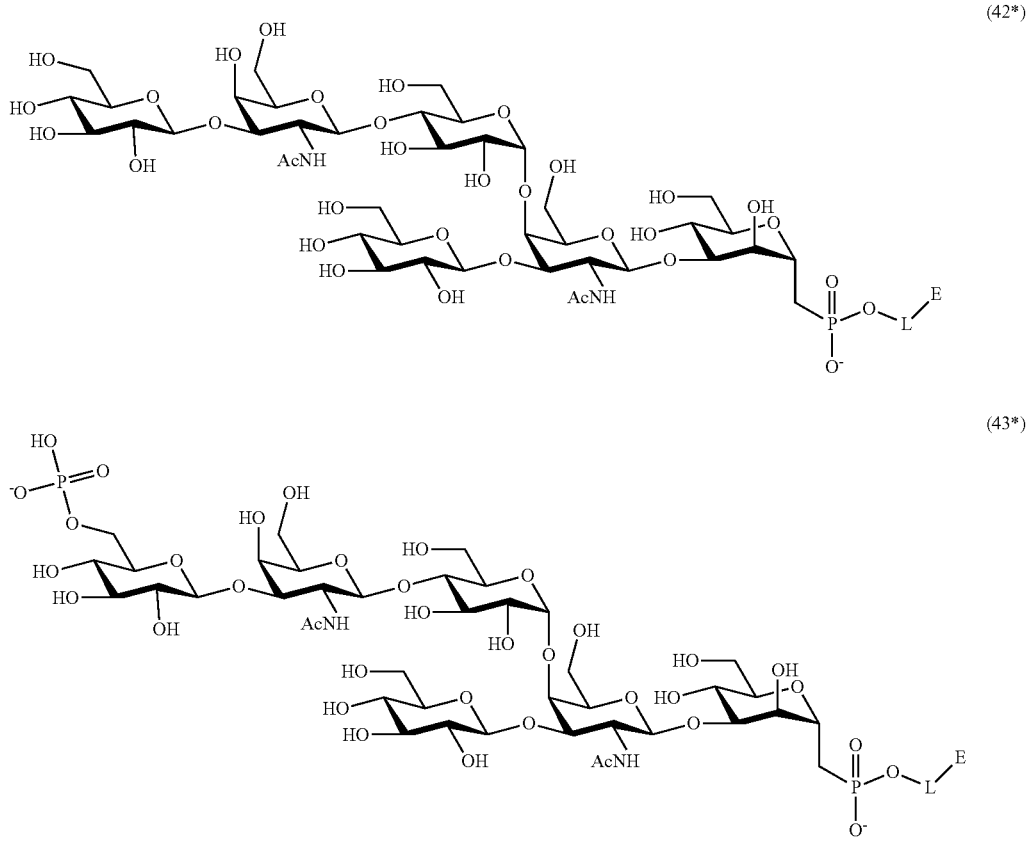

(42*)

(43*)

Another aspect of the present invention is directed to the synthesis of saccharide 42* or 43* of general formula (I), wherein hexasaccharide intermediate 37* is obtained directly from compound 34* by performing step A6'). Thus, in one embodiment a method of synthesis of saccharide 42* or 43* of general formula (I) comprises the steps C1), C2), C3), C4), C5), A6'), C9), C10) and C11).

Another aspect of the present invention is directed to the synthesis of saccharide 42* or 43* of general formula (I), wherein hexasaccharide intermediate 37* is obtained directly from compound 30* by performing step A2'. Thus, in one embodiment a method of synthesis of saccharide 42* or 43* of general formula (I) comprises the steps C1), A2'), C9), C10) and C11).

Thus, another method for synthesis of saccharide of general formula (I) comprises the following steps:

C1) Providing a monosaccharide of formula 30*:

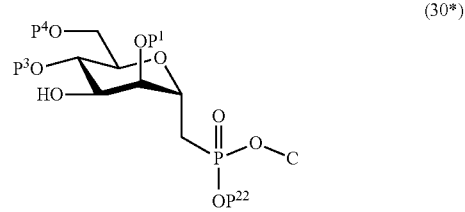

(30*)

wherein $P^1$, $P^3$, $P^4$ and $P^{22}$ represent protecting groups, C represents -L-$E_p$ with $E_p$ being a solid support or a protected end group; and C2') Reacting compound 30* with the pentasaccharide 20* to obtain compound 37*

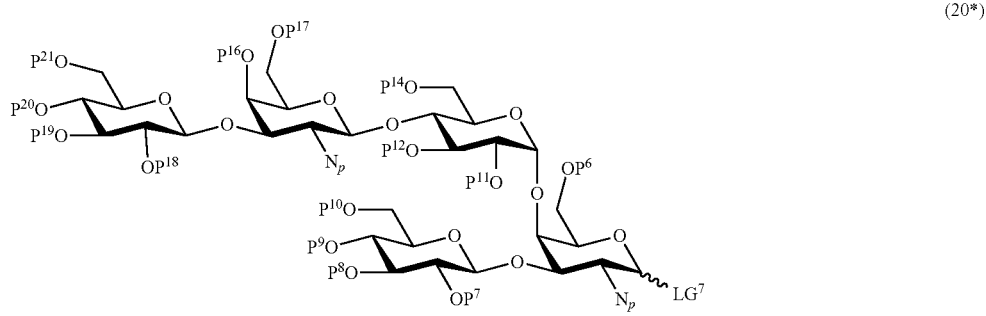

(20*)

(37*)

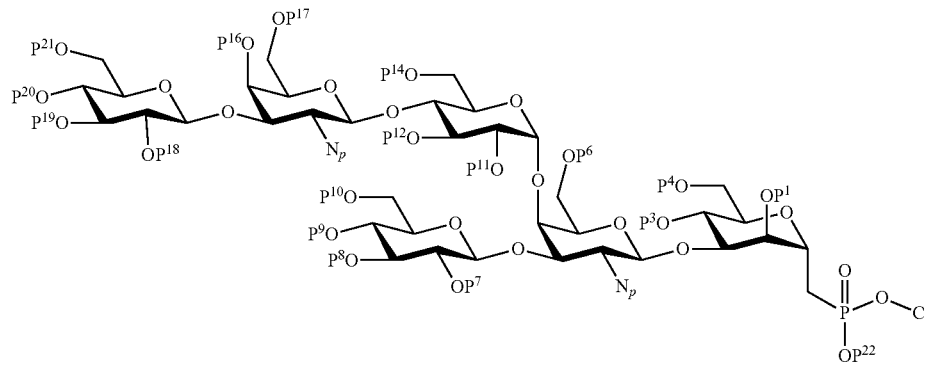

wherein $P^6$-$P^{12}$, $P^{14}$ and $P^{16}$-$P^{21}$ represent protecting groups, $LG^7$ represents a leaving group and $N_p$ represents a protected amino group.

C9) Optionally performing removal of protecting group $P^{21}$ of compound 37* to obtain compound 38* and reacting compound 38* with a phosphorylating agent to obtain compound 39*

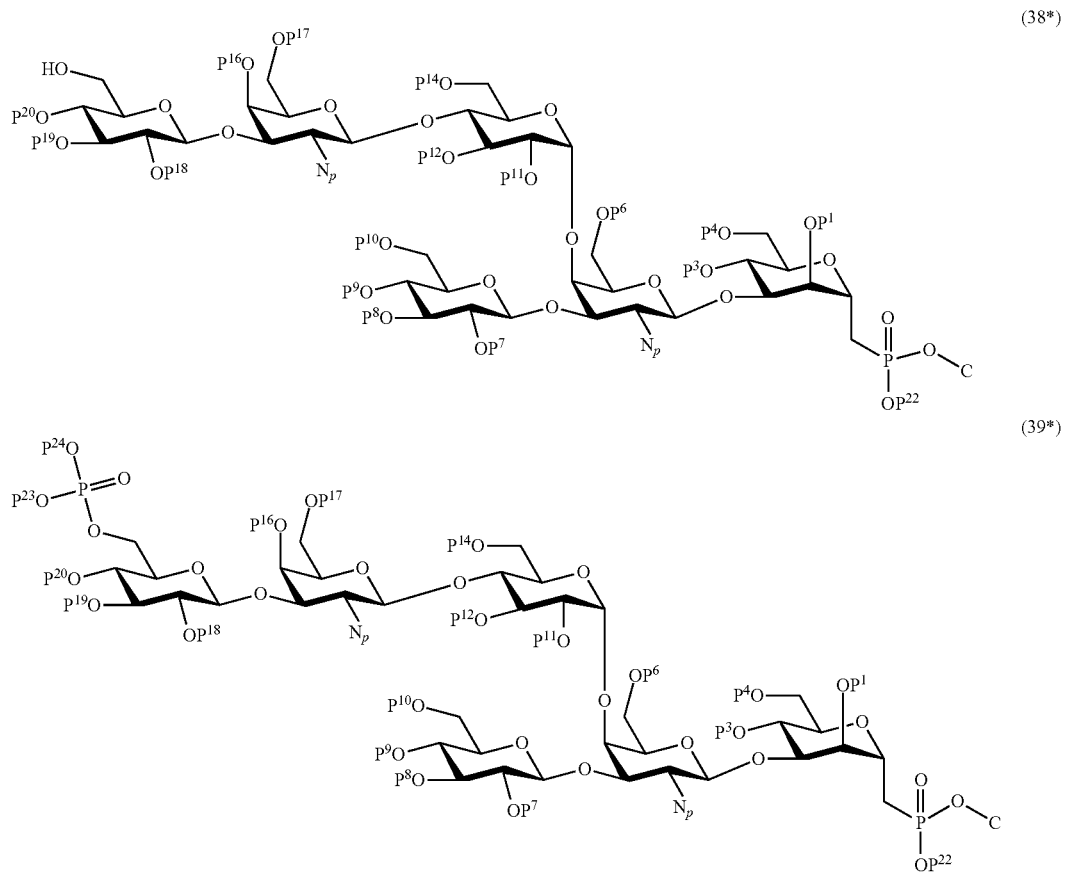

(38*)

(39*)

wherein $P^1$, $P^3$, $P^4$, $P^6$-$P^{12}$, $P^{14}$, $P^{16}$-$P20$ and $P^{22}$-$P^{24}$ represent protecting groups, C represents -L-$E_p$ with $E_p$ being a solid support or a protected end group E and $N_p$ represents a protected amino group; and C10) Converting the protected amino groups of compound 37* or 39* to the corresponding acetamido groups to obtain compound 40* or 41*

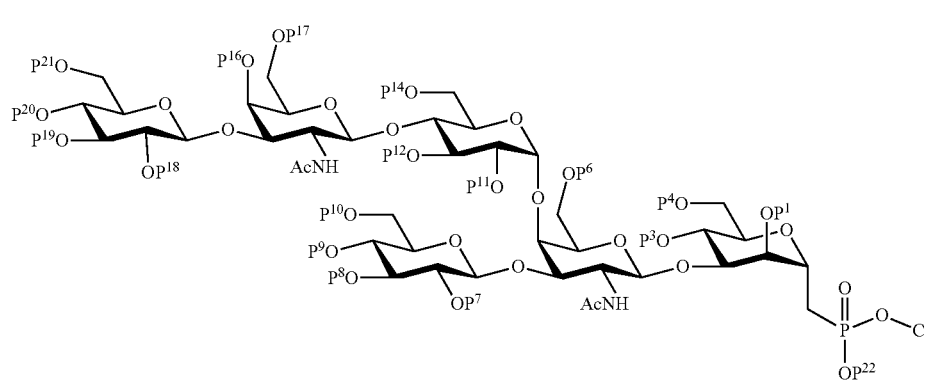
(40*)
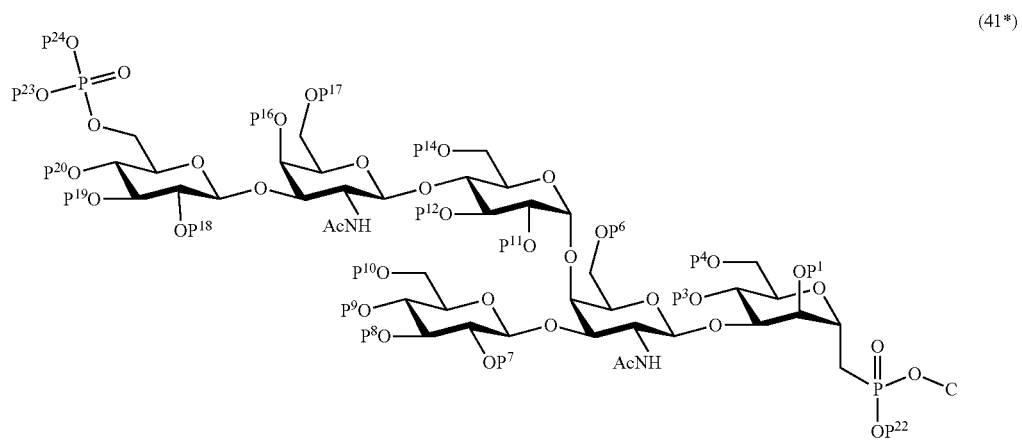
(41*)
wherein $P^1$, $P^3$, $P^4$, $P^6$-$P^{12}$, $P^{14}$ and $P^{16}$-$P^{24}$ represent protecting groups and C represents -L-$E_p$ with $E_p$ being a solid support or a protected end group; and
C11) Performing removal of all remaining protecting groups from compound 40* or 41* to obtain compound 42* or 43* of general formula (I)
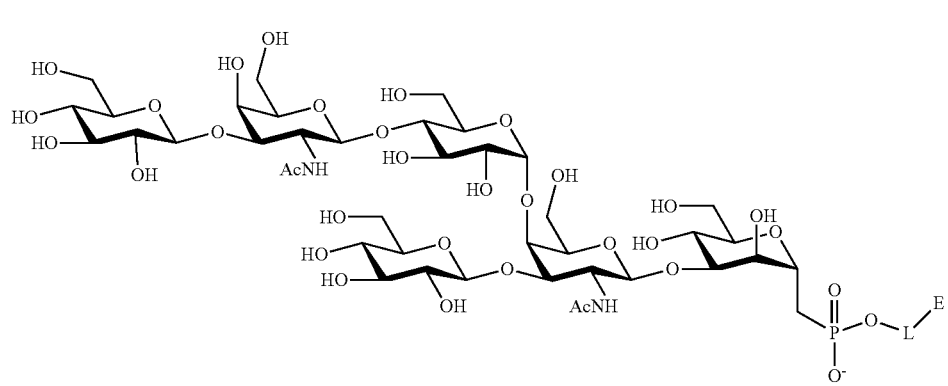
(42*)

(43*)

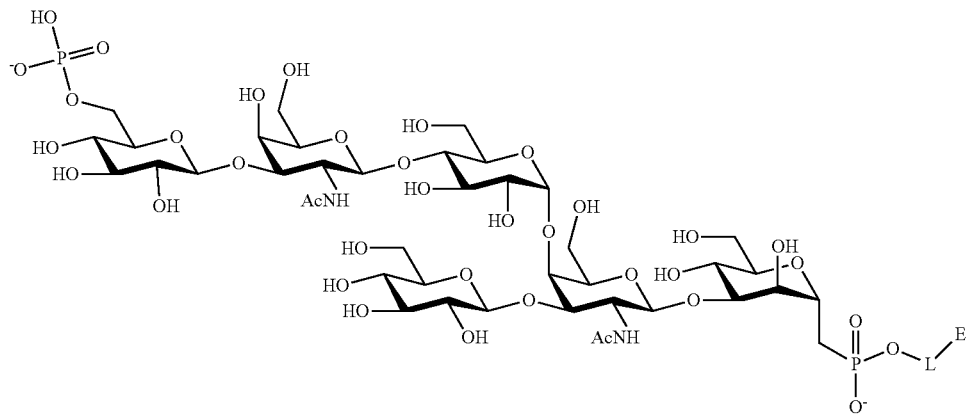

wherein L and E have the meanings as defined herein.

Compound 30* may be obtained from the corresponding protected mannose donor 21* by steps A1a), C1b), C1c) and C1 d).

C1b) Converting a compound of formula 22* to the corresponding halogenide 44*

(44*)

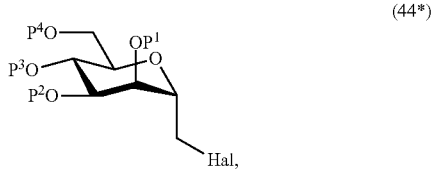

wherein $P^1$-$P^4$ represent protecting groups and Hal is selected from —Br or —I; and C1c) Reacting a compound of formula 44* with alcohol HO-L-C in presence of a phosphite to obtain a compound 45*;

(45*)

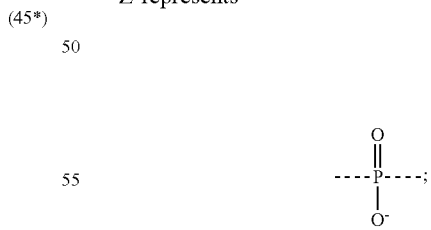

wherein $P^1$-$P^4$ and $P^{22}$ represent protecting groups and C represents -L-$E_p$ with $E_p$ being a solid support or a protected end group E; and C1d) Performing removal of protecting group $P^2$ of compound 45* to obtain compound 30*.

The conversion of alcohol 22* to the corresponding halogenide 44* in step C1b) can be achieved according to standard procedures, i.e. by reacting alcohol 22* with $CBr_4$ or $I_2$ in presence of $PPh_3$, or alternatively, converting alcohol 22* to methansulfonate or trifluoromethansulfonate and subsequent displacement with tetrabutylammonium bromide or tetrabutylammonium iodide.

The phosphite employed in step C1c) is preferably a trialkyl phosphite such as triethyl phosphite which is reacted with halogenide 44* to a phosphonate and subsequently hydrolyzed to a phosphonic acid with a Lewis acid, such as bromotrimethylsilane followed by water (Tetrahedron 1995, 51, 7999). The phosphonic acid is brought to reaction with alcohol HO-L-C in presence trichloroacetonitrile to obtain compound 45*.

Alternatively, the phosphite employed in step C1c) can be a phosphoroamidite, such as dialkyl or dibenzyl N,N-diethylphosphoroamidite, or bis(diisopropylamino)benzyloxyphosphine, that reacts with compound 44* in an Arbuzow reaction and with alcohol HO-L-C under release of diethylamine.

Another aspect of the present invention is directed to a method of synthesis of a saccharide of general formula (I), wherein n is an integer selected from 2, 3, 4, 5, 6, 7, 8, 9 or 10;

T*- represents H— or a phosphate group;

Z represents

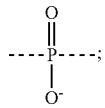

L represents a linker and;

E represents —$NH_2$, —$N_3$, —CN, —O—$NH_2$, —CH=$CH_2$, —C≡CH, —Br, —Cl, —I, —$CO_2R'$, —CONH—$NH_2$, —SH, —OH or —SAc;

R' represents —H, -Me, -Et, 4-nitrophenyl, pentafluorophenyl, or N-succinimidyl;

comprising the following steps:
D1) Providing compound 38*

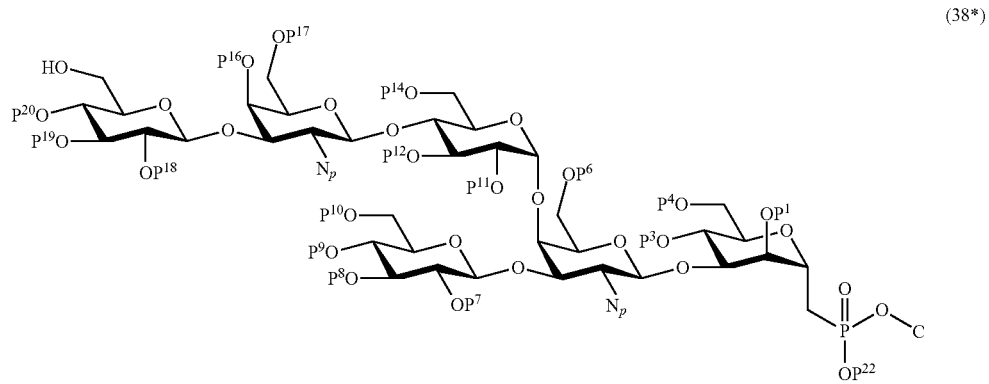

(38*)

wherein $P^1$, $P^3$, $P^4$, $P^6$-$P^{14}$, $P^{16}$-$P^{20}$ and $P^{22}$ represent protecting groups, C represents -L-$E_p$ with $E_p$ being a solid support or a protected end group E and $N_p$ represents a protected amino group;

and repeating the following steps n−1 times:

D1.1) Reacting with a compound of formula 44* in presence of a phosphite,

D1.2) Performing removal of protecting group $P^2$;

D1.3) Performing steps C2)-C8) or steps C2)-C5) and A6') or step A2');

D1.4) Performing removal of protecting group $P^{21}$;

or

D2.1) Reacting compound 38* with a compound of the formula

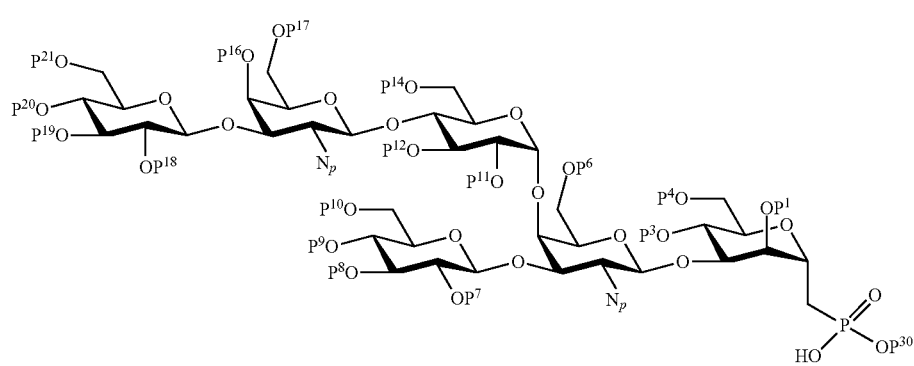

in presence of a coupling agent,

D2.2) Performing removal of protecting group $P^{21}$;

D2.3) optionally repeating the steps D2.1 and D2.2 one to eight times in order to synthesize the corresponding trisaccharides (n=3) to decasaccharides (n=10);

to provide compound 46*:

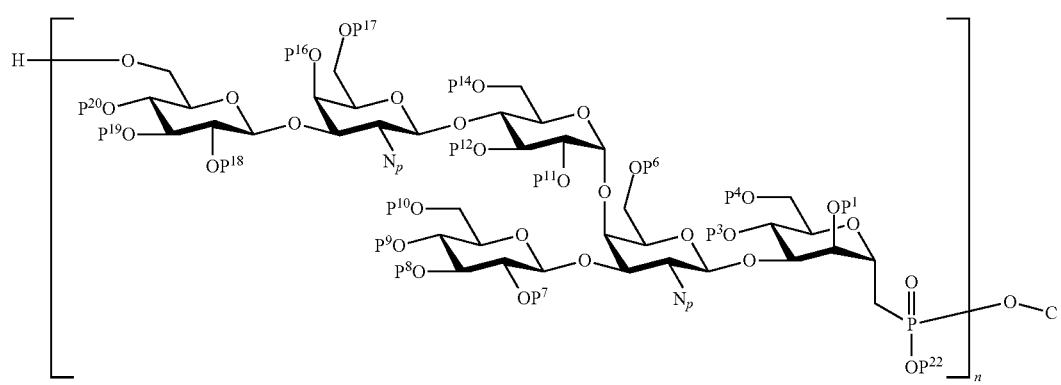

wherein $P^1$, $P^3$, $P^4$, $P^6$-$P^{14}$, $P^{16}$-$P^{20}$ and $P^{22}$ represent protecting groups, C represents -L-$E_p$ with $E_p$ being a solid support or a protected end group E, $N_p$ represents a protected amino group and n represents an integer from 2 to 10; and D2) Optionally reacting compound 46* with a phosphorylating agent to obtain compound 47*

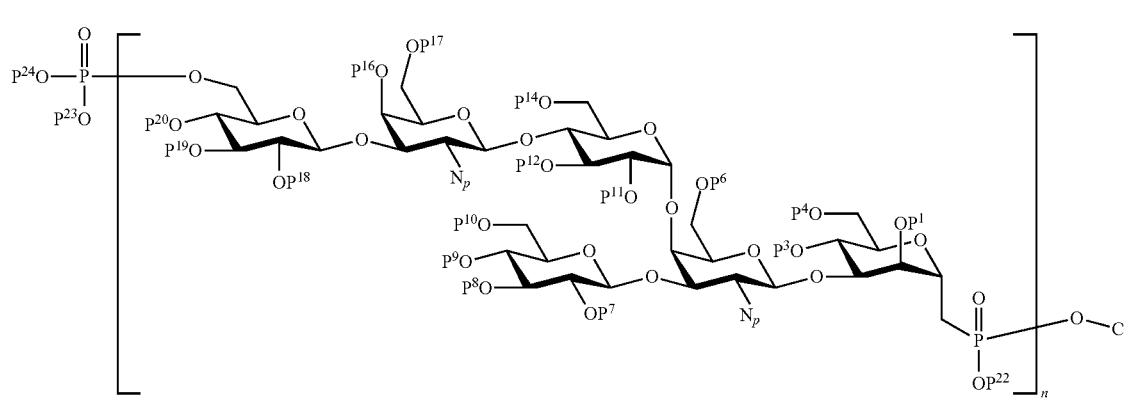

wherein $P^1$, $P^3$, $P^4$, $P^6$-$P^{14}$, $P^{16}$-$P^{20}$ and $P^{22}$-$P^{24}$ represent protecting groups, C represents -L-$E_p$ with $E_p$ being a solid support or a protected end group E, $N_p$ represents a protected amino group and n represents an integer from 2 to 10; and D3) Converting the protected amino groups of compound 46* or 47* to the corresponding acetamido groups to obtain compound 48* or 49*

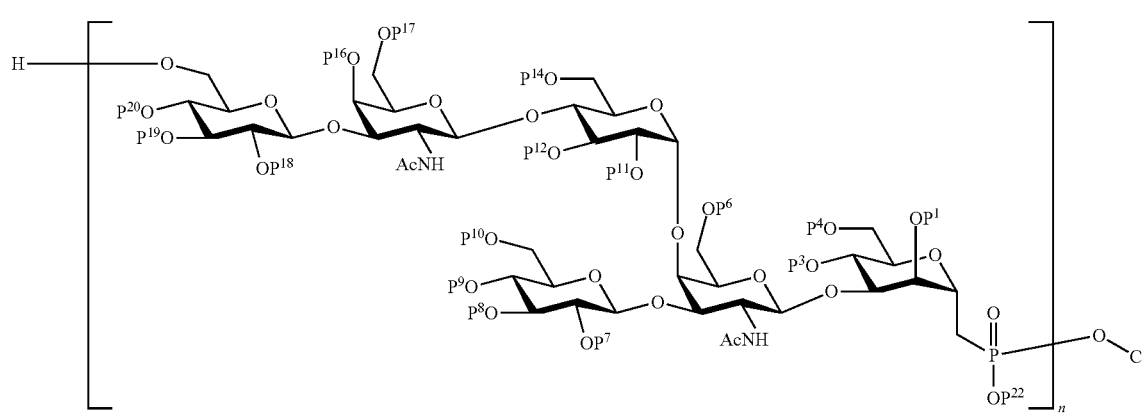

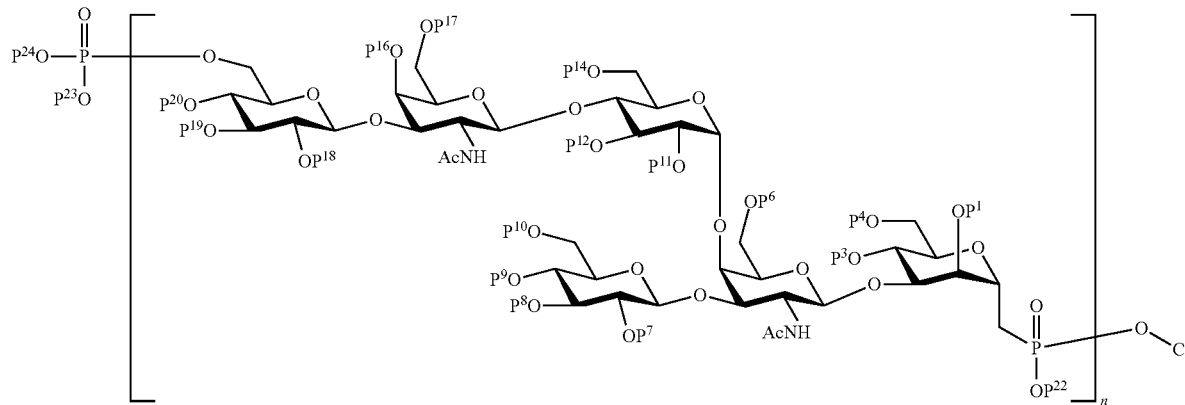

wherein $P^1$, $P^3$, $P^4$, $P^6$-$P^{12}$, $P^{14}$, $P^{16}$-P20 and $P^{22}$-$P^{24}$ represent protecting groups, C represents -L-$E_p$ with $E_p$ being a solid support or a protected end group E and n represents an integer from 2 to 10; and D4) Performing removal of all remaining protecting groups from compound 48* or 49* to obtain compound 50* or 51* of general formula (I)

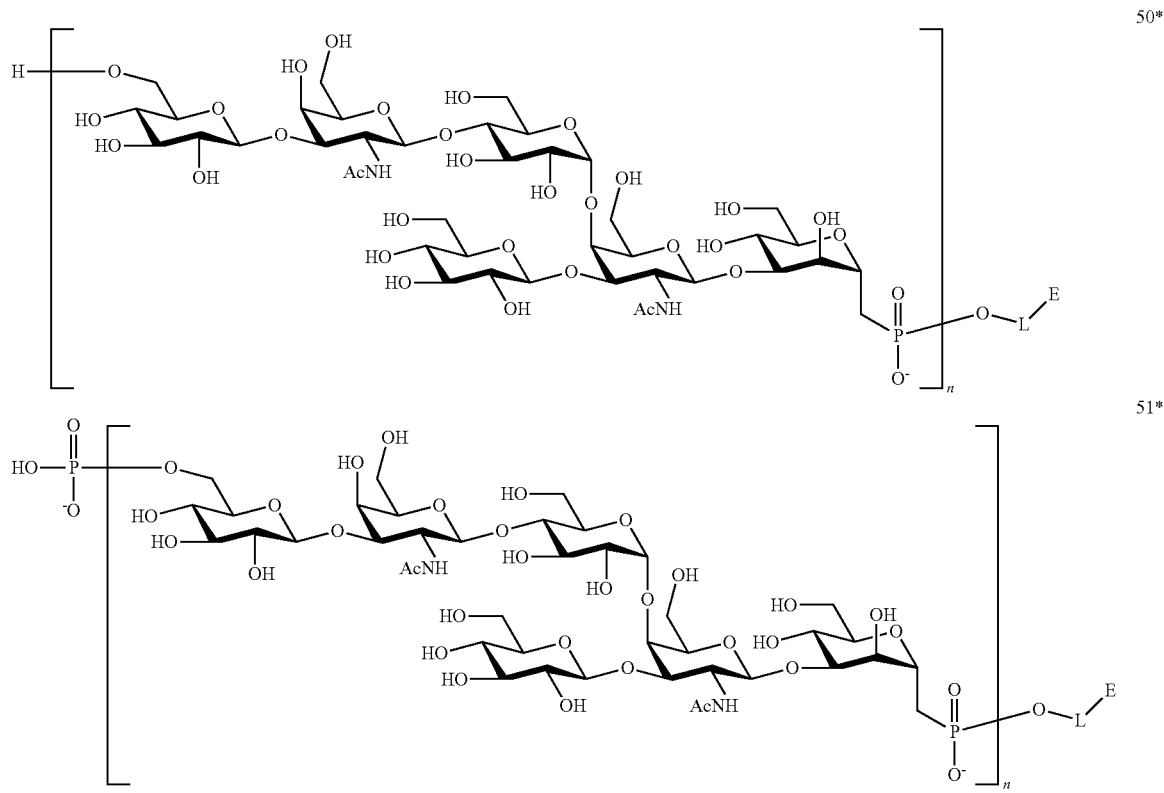

wherein n represents an integer from 2 to 10 and L and E have the meanings as defined herein.

Another aspect of the present invention is directed to a method of synthesis of a saccharide of general formula (I), wherein n is 1;

T*- represents H— or a phosphate group;

Z represents

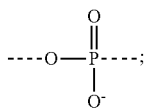

L represents a linker and;
E represents —NH$_2$, —N$_3$, —CN, —O—NH$_2$, —CH=CH$_2$, —C≡CH, —Br, —Cl, —I, —CO$_2$R', —CONH—NH$_2$, —SH, —OH or —SAc;
R' represents —H, -Me, -Et, 4-nitrophenyl, pentafluorophenyl, or N-succinimidyl;
comprising the following steps:
E1) Providing a monosaccharide of formula 52*:

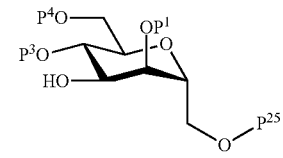
(52*)

wherein P$^1$, P$^3$, P$^4$ and P$^{25}$ represent protecting groups; and
E2) reacting monosaccharide of formula 52* with compound of formula 2* to obtain compound 53*:

(2*)

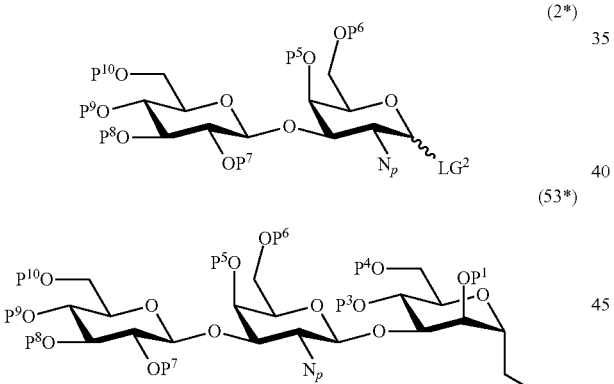
(53*)

wherein P$^1$, P$^3$, P$^4$-P$^{10}$ and P$^{25}$ represent protecting groups, LG$^2$ represents a leaving group and N$_p$ represents a protected amino group; and
E3) Performing removal of protecting group P$^5$ of compound 53* to obtain compound 54*

(54*)

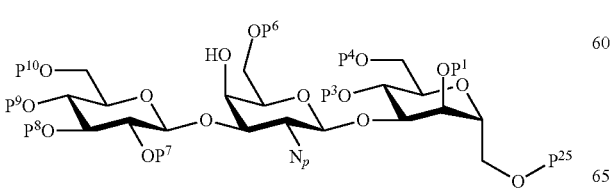

wherein P$^1$, P$^3$, P$^4$, P$^6$-P$^{10}$ and P$^{25}$ represent protecting groups, and N$_p$ represents a protected amino group; and
E4) reacting compound 54* with monosaccharide 5* to obtain compound 55*

(5*)

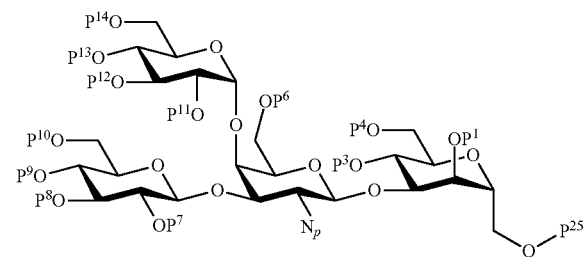
(55*)

wherein P$^1$, P$^3$, P$^4$, P$^6$-P$^{14}$ and P$^{25}$ represent protecting groups, LG$^3$ represents a leaving group and N$_p$ represents a protected amino group; and
E5) Performing removal of protecting group P$^{13}$ of compound 55* to obtain compound 56*

(56*)

wherein P$^1$, P$^3$, P$^4$, P$^6$-P$^{12}$, P$^{14}$ and P$^{25}$ represent protecting groups, and N$_p$ represents a protected amino group; and
E6) Reacting compound 56* with the disaccharide 19* to obtain compound 57*

(19*)

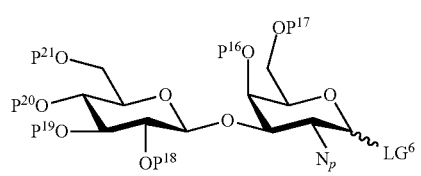

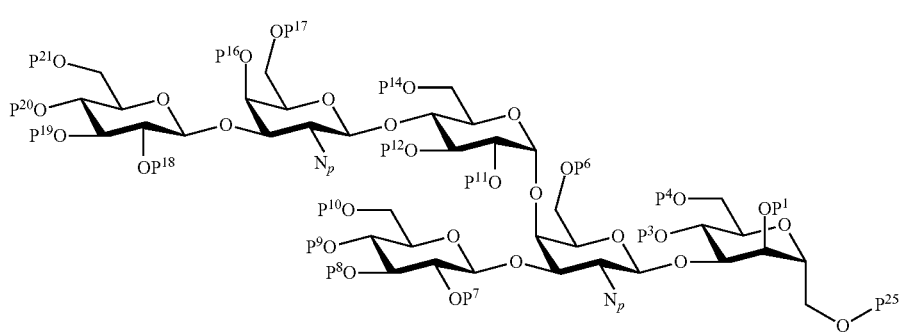

(57*)

wherein $P^1$, $P^3$, $P^4$, $P^6\text{-}P^{12}$, $P^{14}$ and $P^{16}\text{-}P^{25}$ represent protecting groups, $LG^6$ represents a leaving group and $N_p$ represents a protected amino group; and E7) Converting the protected amino groups of compound 57* to the corresponding acetamido groups to obtain compound 58*

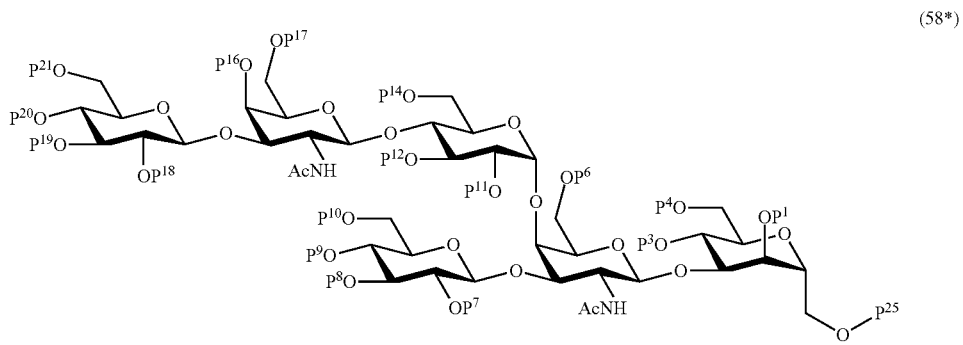

(58*)

wherein $P^1$, $P^3$, $P^4$, $P^6\text{-}P^{12}$, $P^{14}$, $P^{21}$ and $P^{25}$ represent protecting groups; and E8) Performing removal of protecting group $P^{25}$ of compound 58* to obtain compound 59* and reacting compound 59* with alcohol HO-L-C in presence of a phosphorylating agent to obtain compound 15*

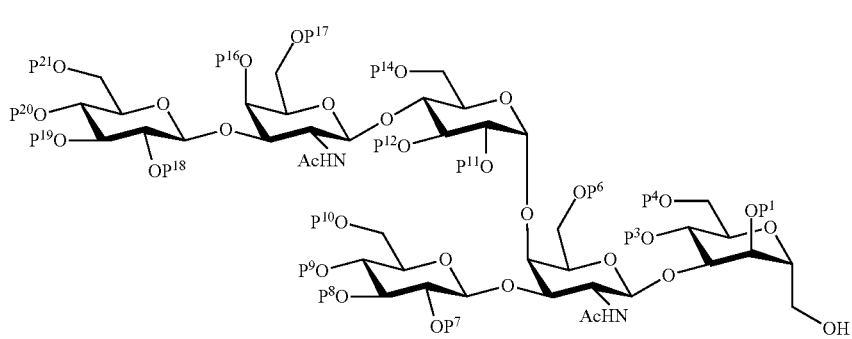

(59*)

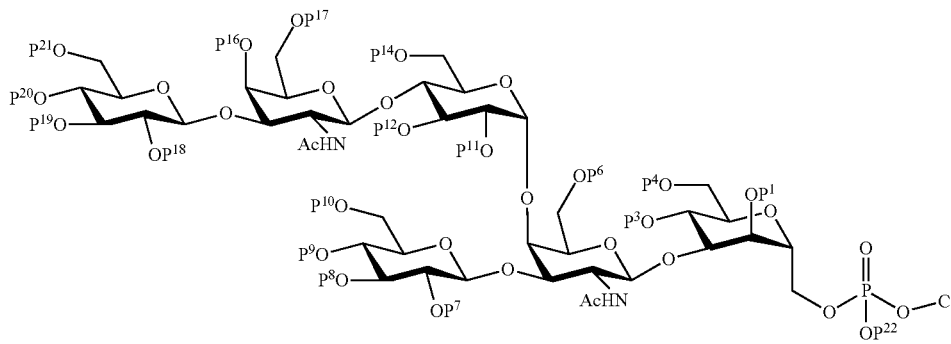

(15*)

wherein $P^1$, $P^3$, $P^4$, $P^6$-$P^{12}$, $P^{14}$, $P^{16}$-$P^{22}$ represent protecting groups, and E9) Optionally performing removal of protecting group $P^{21}$ of compound 15* to obtain compound 60* and reacting compound 60* with a phosphorylating agent to obtain compound 16*

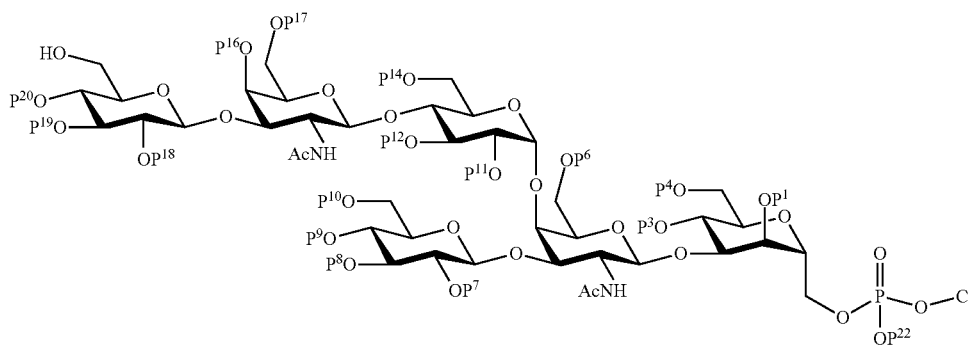

(60*)

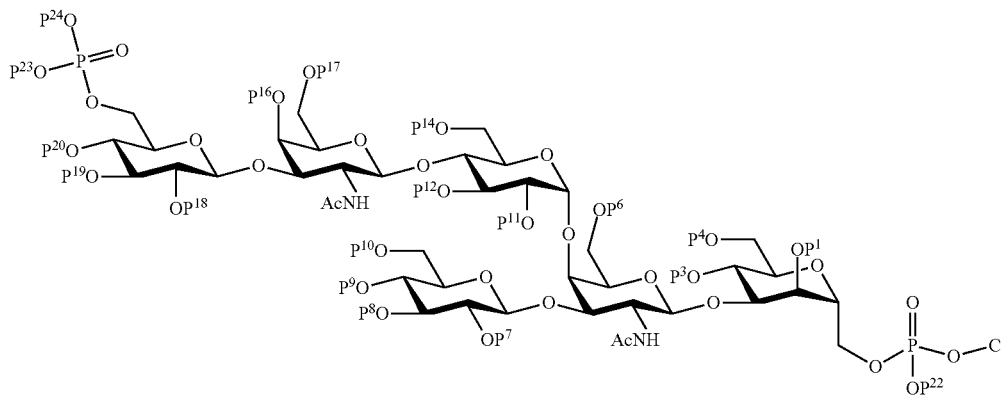

(16*)

wherein $P^1$, $P^3$, $P^4$, $P^6$-$P^{12}$, $P^{14}$, $P^{16}$-$P^{20}$ and $P^{22}$-$P^{24}$ represent protecting groups, C represents -L-$E_p$ with $E_p$ being a solid support or a protected end group E; and E10) Performing removal of all remaining protecting groups from compound 15* or 16* to obtain compound 17* or 18* of general formula (I)

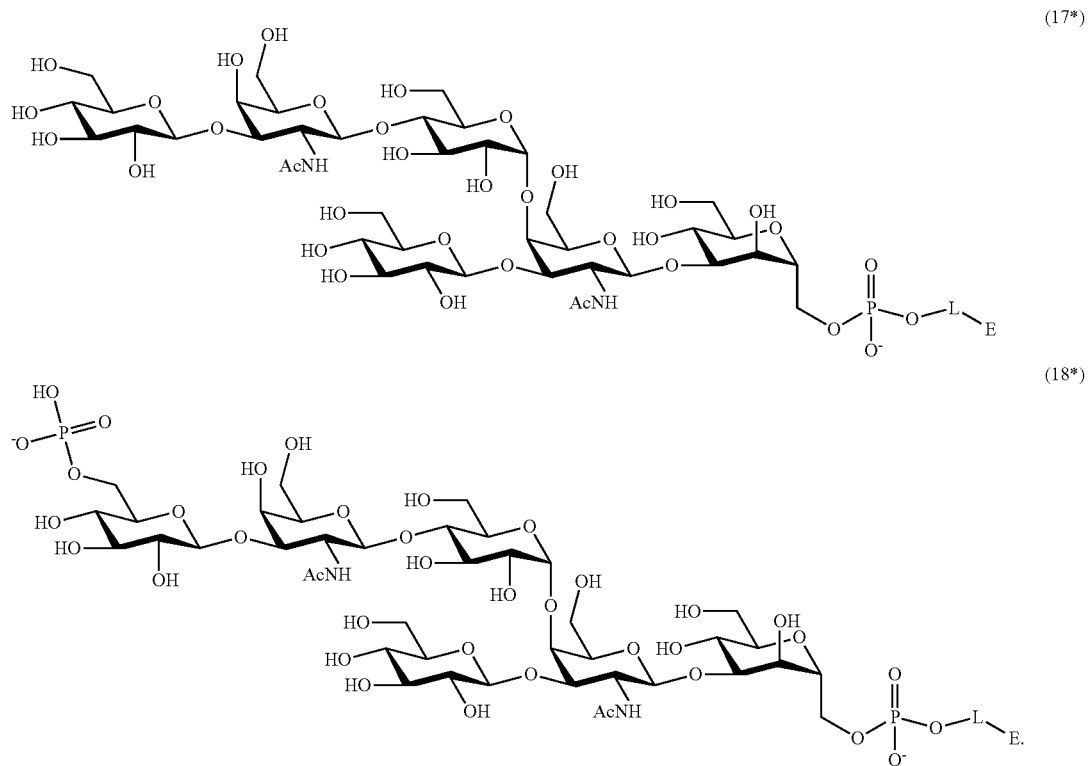

(17*)

(18*)

Another aspect of the present invention is directed to a method of synthesis of a saccharide of general formula (I), wherein n is an integer selected from 2, 3, 4, 5, 6, 7, 8, 9 or 10;
T*- represents H— or a phosphate group;
Z represents

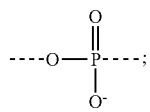

L represents a linker and;
E represents —$NH_2$, —$N_3$, —CN, —O—$NH_2$, —CH=$CH_2$, —C≡CH, —Br, —Cl, —I, —$CO_2R'$, —CONH—$NH_2$, —SH, —OH or —SAc;
R' represents —H, -Me, -Et, 4-nitrophenyl, pentafluorophenyl, or N-succinimidyl;
comprising the following steps:
F1) Providing compound 60*

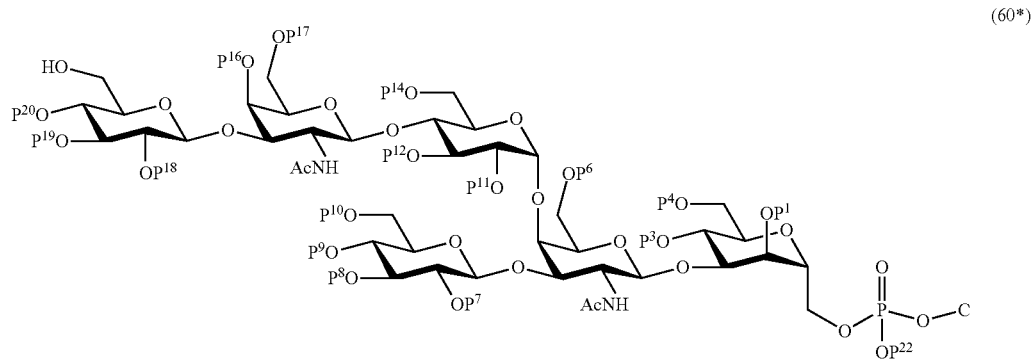

(60*)

wherein $P^1$, $P^3$, $P^4$, $P^6$-$P^{12}$, $P^{14}$, $P^{16}$-$P^{20}$ and $P^{22}$ represent protecting groups, C represents -L-$E_p$ with $E_p$ being a solid support or a protected end group;

F2.1) Reacting compound 60* with a compound of the formula

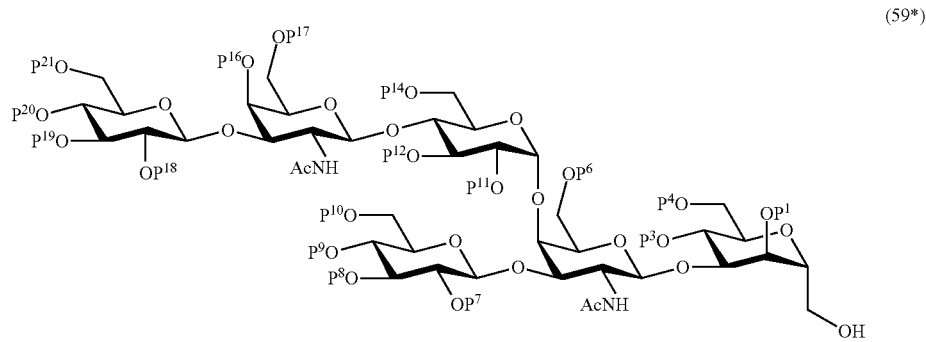

(59*)

in presence of a phosphorylating agent,

F2.2) Performing removal of protecting group $P^{21}$;

F3) optionally repeating the steps F2.1 and F2.2 n–2 times in order to synthesize the corresponding trimers (n=3) to decamers (n=10); to provide compound 26*:

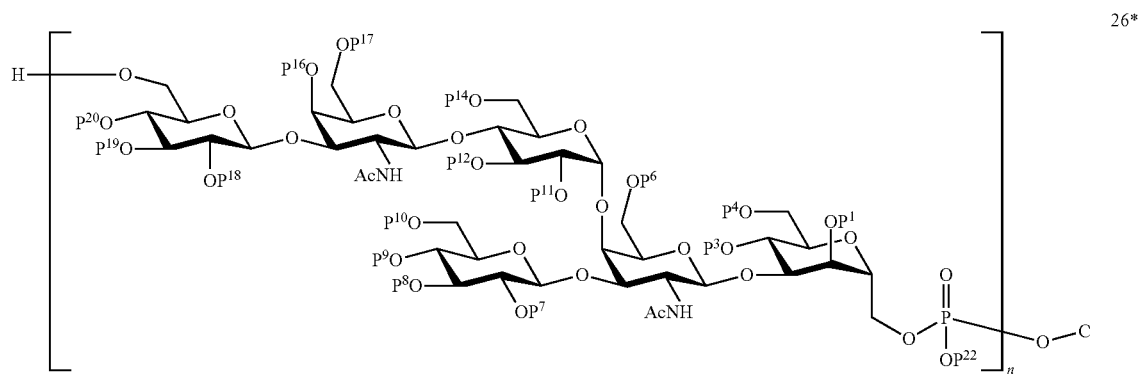

26* wherein $P^1$, $P^3$, $P^4$, $P^6$-$P^{14}$, $P^{16}$-$P^{20}$ and $P^{22}$ represent protecting groups, C represents -L-$E_p$ with $E_p$ being a solid support or a protected end group E, and n represents an integer from 2 to 10; and F4) Optionally reacting compound 26* with a phosphorylating agent to obtain compound 27*

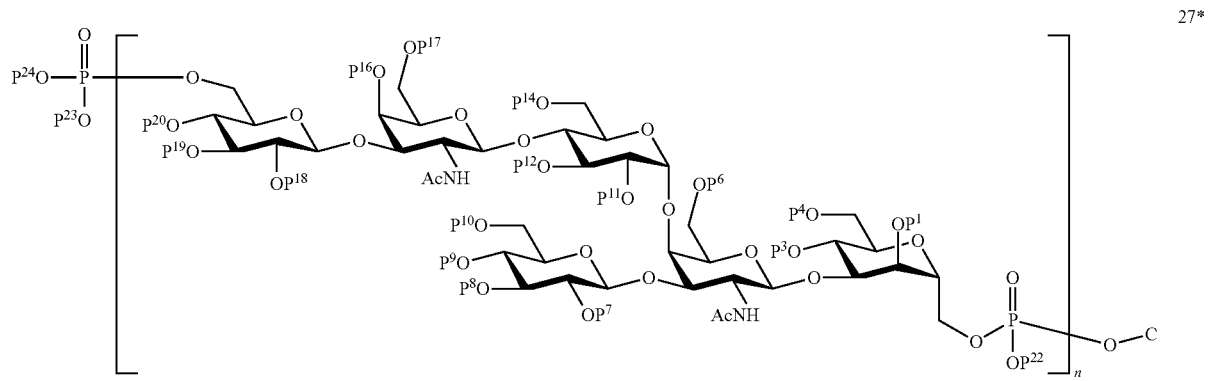

27* wherein $P^1$, $P^3$, $P^4$, $P^6$-$P^{12}$, $P^{14}$, $P^{16}$-P20 and $P^{22}$-$P^{24}$ represent protecting groups, C represents -L-$E_p$ with $E_p$ being a solid support or a protected end group E, and n represents an integer from 2 to 10; and F5) Performing removal of all remaining protecting groups from compound 26* or 27* to obtain compound 28* or 29* of general formula (I)

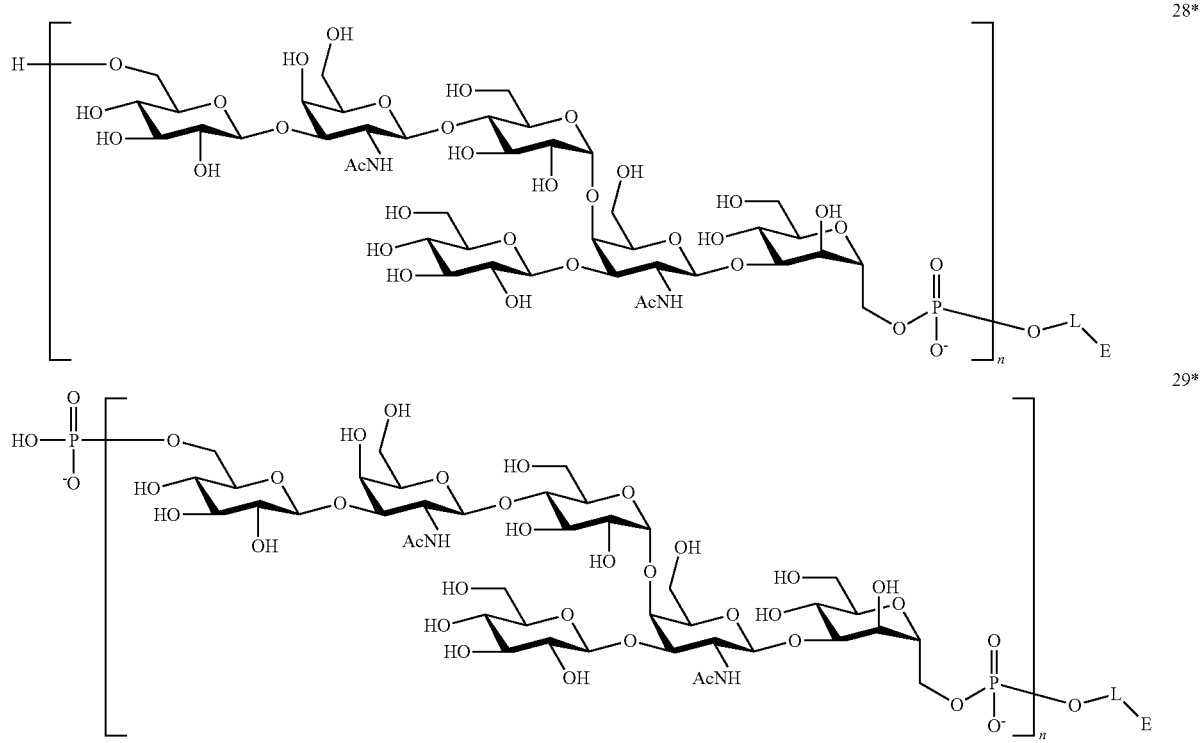

wherein n represents an integer from 2 to 10 and L and E have the meanings as defined herein.

Another aspect of the present invention is directed to a method of synthesis of a saccharide of general formula (I), wherein n is an integer selected from 1, 2, 3, 4, 5, 6, 7, 8, 9, 10;

T*- represents H— or a phosphate group;

Z represents

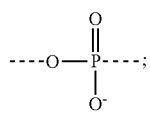

L represents a linker and;

E represents —NH$_2$, —N$_3$, —CN, —O—NH$_2$, —CH=CH$_2$, —C≡CH, —Br, —Cl, —I, —CO$_2$R', —CONH—NH$_2$, —SH, —OH or —SAc;

R' represents —H, -Me, -Et, 4-nitrophenyl, pentafluorophenyl, or N-succinimidyl;

comprising the following steps:

G1) Providing a monosaccharide of formula 52*:

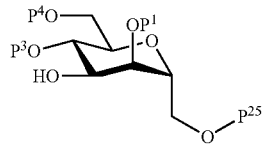

wherein $P^1$, $P^3$, $P^4$ and $P^{25}$ represent protecting groups; and

G2) reacting monosaccharide of formula 52* with compound of formula 2* to obtain compound 3*:

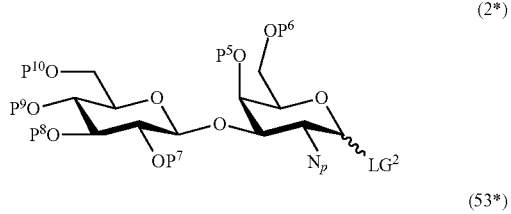

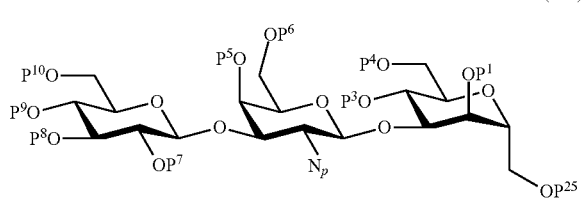

wherein $P^1$, $P^3$, $P^4$-$P^{10}$ and $P^{25}$ represent protecting groups, $LG^2$ represents a leaving group and $N_p$ represents a protected amino group; and G3) Performing removal of protecting group $P^5$ of compound 53* to obtain compound 54*

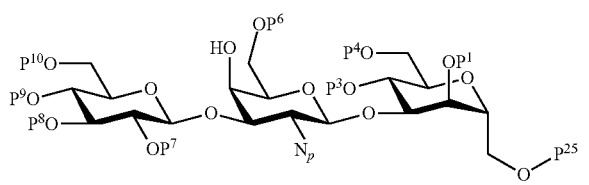

(54*)

wherein $P^1$, $P^3$, $P^4$, $P^6$-$P^{10}$ and $P^{25}$ represent protecting groups, and $N_p$ represents a protected amino group; and G4) reacting compound 54* with monosaccharide 5* to obtain compound 55*

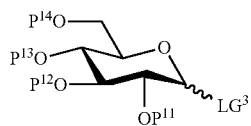

(5*)

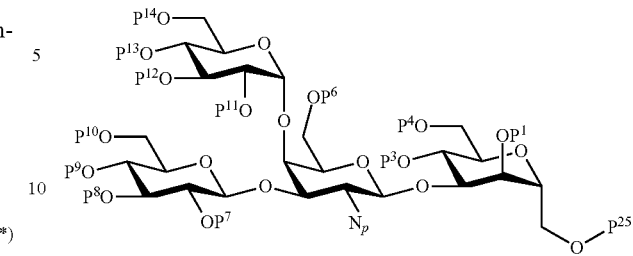

(55*)

wherein $P^1$, $P^3$, $P^4$, $P^6$-$P^{14}$ and $P^{25}$ represent protecting groups, $LG^3$ represents a leaving group and $N_p$ represents a protected amino group; and G5) Performing removal of protecting group $P^{13}$ of compound 55* to obtain compound 56*

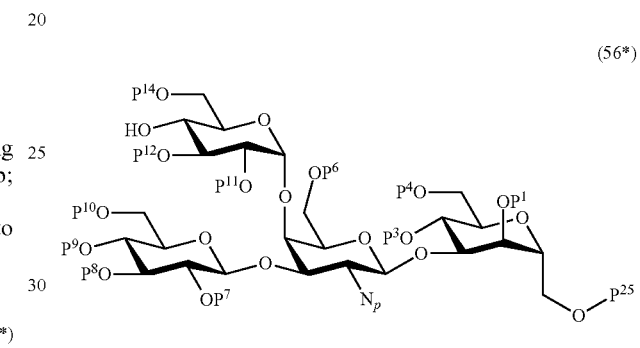

(56*)

wherein $P^1$, $P^3$, $P^4$, $P^6$-$P^{12}$, $P^{14}$ and $P^{25}$ represent protecting groups, and $N_p$ represents a protected amino group; and G6) Reacting compound 56* with the disaccharide 19* to obtain compound 57*

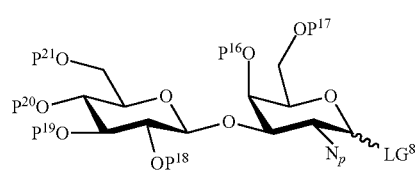

(19*)

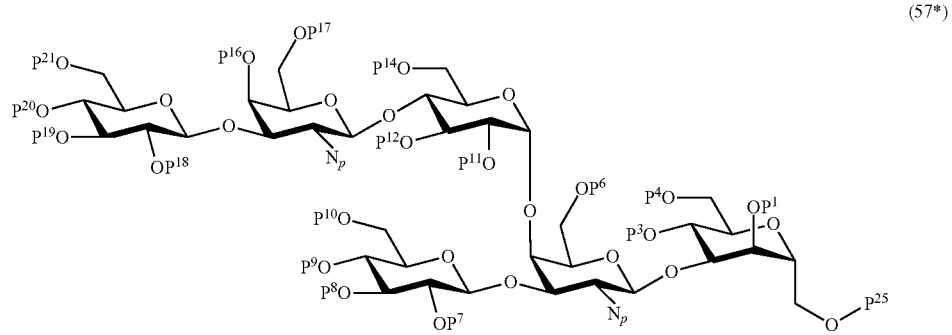

(57*)

wherein $P^1$, $P^3$, $P^4$, $P^6$-$P^{12}$, $P^{14}$ and $P^{16}$-$P^{25}$ represent protecting groups, $LG^6$ represents a leaving group and $N_p$ represents a protected amino group; and G7) Converting the protected amino groups of compound 57* to the corresponding acetamido groups to obtain compound 58*

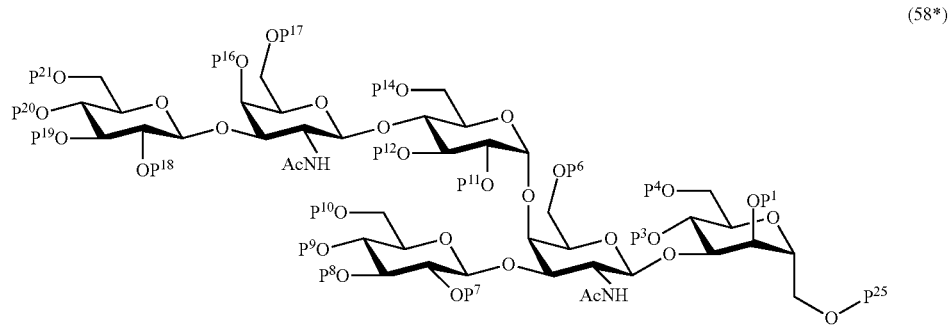

(58*)

wherein $P^1$, $P^3$, $P^4$, $P^6$-$P^{12}$, $P^{14}$, $P^{21}$ and $P^{25}$ represent protecting groups; and G8) Performing removal of protecting group $P^{25}$ of compound 58* to obtain compound 59* and reacting compound 59* with alcohol HO-L-C in presence of a phosphorylating agent to obtain compound 15*

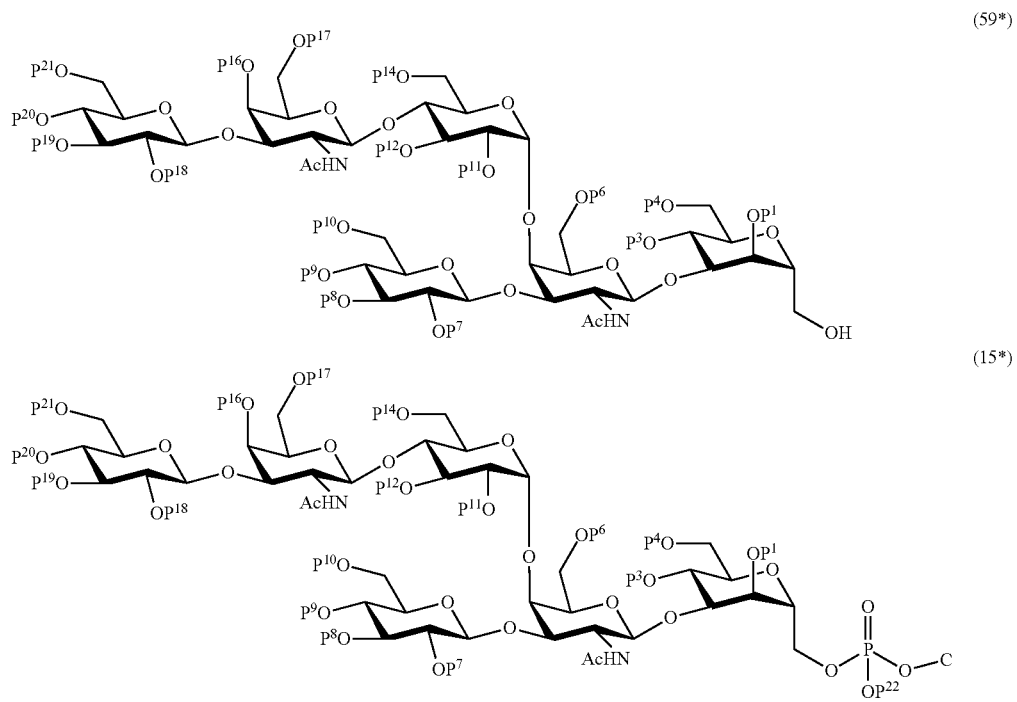

(59*)

(15*)

wherein $P^1$, $P^3$, $P^4$, $P^6$-$P^{12}$, $P^{14}$, $P^{16}$-$P^{22}$ represent protecting groups, and G9) Repeating the steps G9.1 and G9.2 n−1 times in order to synthesize the corresponding dimers (n=3) to decamers (n=10);

G9.1) Performing removal of protecting group $P^{21}$; and

G9.2) Reacting the product of step G9.1) with a compound of the formula (59*)

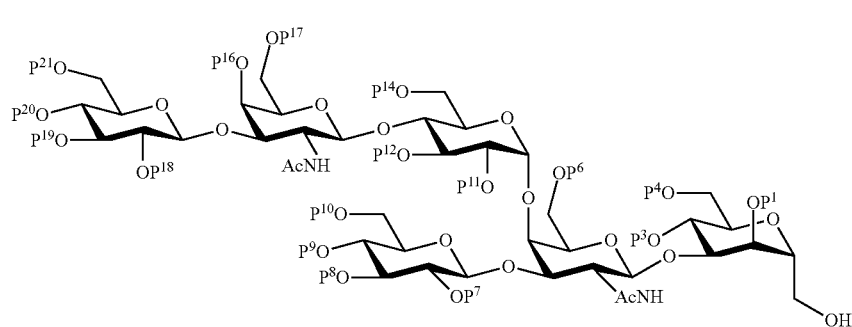

in presence of a phosphorylating agent, to provide compound 61*

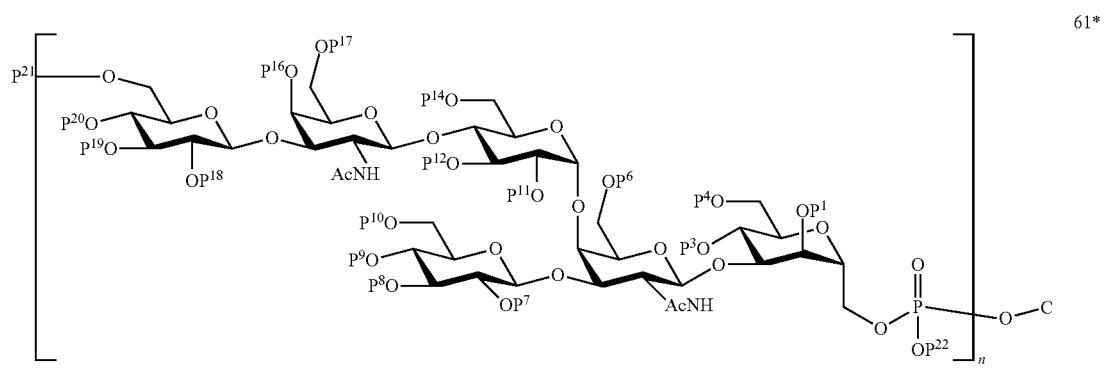

wherein $P^1$, $P^3$, $P^4$, $P^6$-$P^{12}$, $P^{14}$, $P^{16}$-$P^{22}$ represent protecting groups, C represents -L-$E_p$ with $E_p$ being a solid support or a protected end group;

G10) Optionally performing removal of protecting group $P^{21}$ of compound 61* or compound 15* to obtain compound 26* and reacting compound 26* with a phosphorylating agent to obtain compound 27* to provide compound 26*:

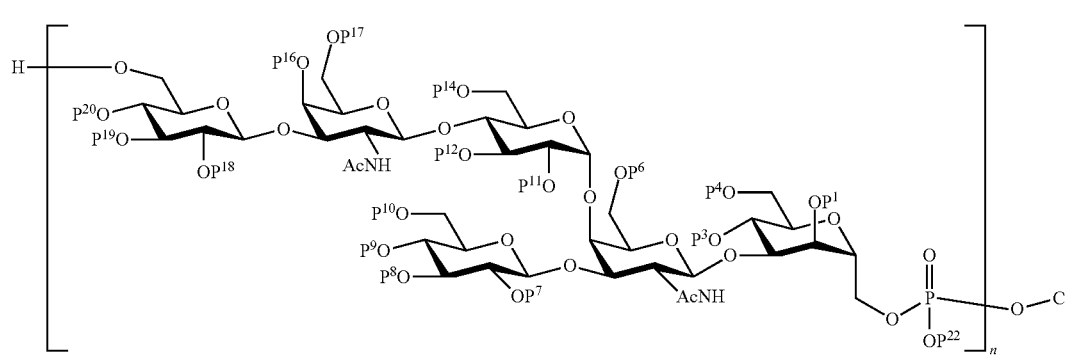

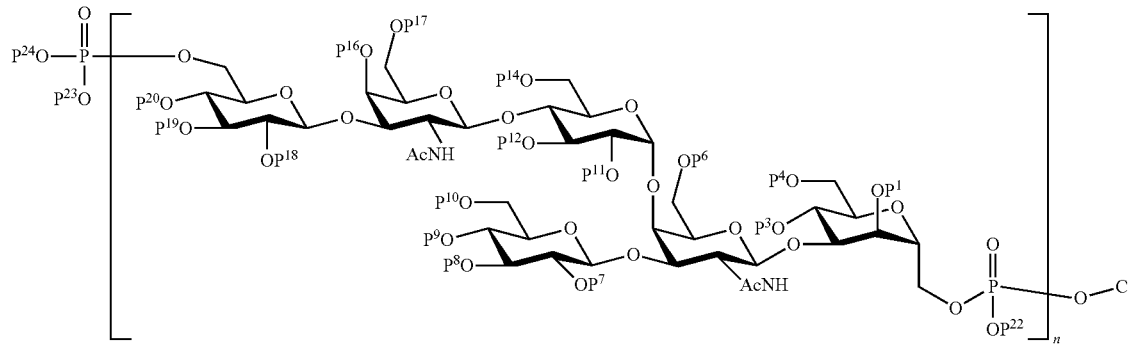

27* wherein $P^1$, $P^3$, $P^4$, $P^6$-$P^{12}$, $P^{14}$, $P^{16}$-$P^{20}$ and $P^{22}$-$P^{24}$ represent protecting groups, C represents -L-$E_p$ with $E_p$ being a solid support or a protected end group E, and n represents an integer from 1 to 10; and G11) Performing removal of all remaining protecting groups from compound 26* or 27* to obtain compound 28* or 29* of general formula (I)

$N_p$ is a protected amino group. Preferably, Np is selected from —$N_3$, —NH—CO—$CCl_3$ and —NH—COO—$CH_2$—$CCl_3$ (Troc).

$P^1$, $P^2$, $P^3$, $P^4$, $P^5$, $P^6$, $P^7$, $P^8$, $P^9$, $P^{10}$, $P^{11}$, $P^{12}$, $P^{13}$, $P^{14}$, $P^{15}$, $P^{16}$, $P^{17}$, $P^{18}$, $P^{19}$, $P^{20}$, $P^{21}$, $P^{22}$, $P^{23}$, $P^{24}$, $P^{25}$, $P^{26}$ and $P^{27}$ represent protecting groups. The term "protecting group" as used herein refers to commonly used groups in

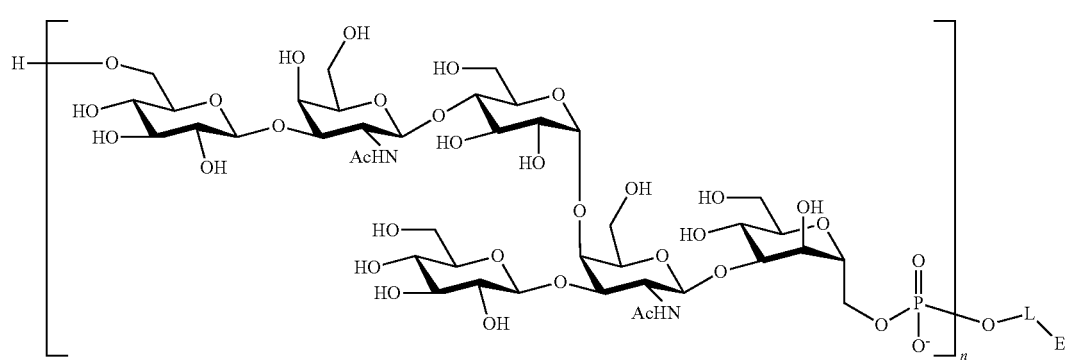

28*

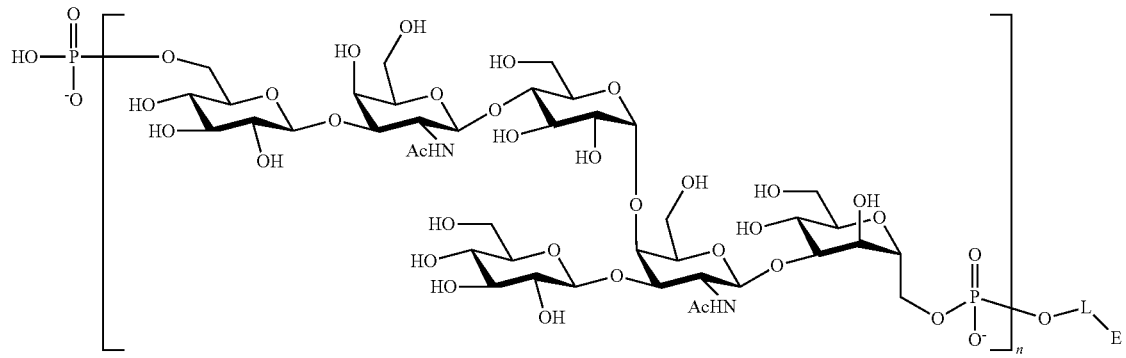

29* wherein n represents an integer from 1 to 10 and L and E have the meanings as defined herein.

$E_p$ represents a solid support or a protected end group. E represents —$NH_2$, —$N_3$, —ON, —O—$NH_2$, —CH=$CH_2$, —C≡CH, —Br, —Cl, —I, —$CO_2$R', —$CONHNH_2$, —SH, —OH or —SAc; and the corresponding protected end group $E_p$ represents —N($P^{26}$)($P^{27}$), —$N_3$, —ON, —O—N($P^{26}$)($P^{27}$), —CH=$CH_2$, —C≡CH, —Br, —Cl, —I, —$CO_2$R', —CONHN($P^{26}$)($P^{27}$), —$SP_s$, or —SAc organic synthesis, preferably used for protection of hydroxyl groups, amino groups and thiols.

It is preferred that the protecting group $P^{21}$ can be removed under conditions under which the other protecting groups present in the molecule are stable.

The amino protecting groups are preferably stable under the conditions applied to remove the hydroxyl protecting groups present in the molecule.

The hydroxyl protecting groups preferably except protecting group $P^{21}$ can preferably be removed through hydrogenation.

More preferably, $P^1$, $P^2$, $P^3$, $P^4$, $P^5$, $P^6$, $P^7$, $P^8$, $P^9$, $P^{10}$, $P^{11}$, $P^{12}$, $P^{13}$, $P^{14}$, $P^{15}$, $P^{16}$, $P^{17}$, $P^{18}$, $P^{19}$, $P^{20}$, $P^{21}$, $P^{22}$, $P^{23}$, $P^{24}$, and $P^{25}$ are suitable protecting groups for hydroxyl groups, more preferably different suitable protecting groups for hydroxyl groups capable of being removed subsequently one after another by a suitable sequence of deprotection reactions. Preferred protecting groups for hydroxyl groups are acetyl, phenyl, benzyl, isopropylidene, benzylidene, benzoyl, p-methoxybenzyl, p-methoxybenzylidene, p-methoxyphenyl, p-bromobenzyledene, p-nitrophenyl, allyl, acetyl, isopropyl, p-bromobenzyl, dimethoxytrityl, trityl, 2-naphthylmethyl, pivaloyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl, levulinoyl, naphthylidene, chloroacetyl, picoloyl, thexyldimethylsilyl (TDS), (2-nitrophenyl)acetyl (NPAc), 2-(azidomethyl)benzoyl (AzmB).

The protecting groups can be differentiated in permanent protecting groups and temporary protecting groups. Permanent protecting groups are protecting groups that are stable during the entire synthesis and that can be efficiently removed at the late stage of the synthesis. In this case, permanent protecting groups include $P^1$, $P^3$, $P^4$, $P^6$-$P^{12}$, $P^{14}$, $P^{16}$-$P^{20}$, $P^{22}$-$P^{26}$. $P^1$, $P^3$, $P^4$, $P^6$-$P^{12}$, $P^{14}$, $P^{16}$-$P^{20}$ and $P^{22}$-$P^{24}$ are masking the hydroxyl groups during the entire synthesis, while protecting groups $P^{26}$ and $P^{27}$ are masking the terminal amino group present in the end group $E_p$. Preferably protecting groups $P^3$, $P^4$, $P^8$-$P^{12}$, $P^{14}$, $P^{16}$-$P^{20}$ and $P^{22}$-$P^{24}$ are benzyl groups, protecting group $P^1$ is a benzoyl group, protecting groups $P^7$ and $P^{18}$ are acetyl groups, protecting group $P^{26}$ is a benzyl group and protecting group $P^{27}$ is a benzyloxycarbonyl group (Cbz).

The temporary protecting groups are generally orthogonal protecting groups that can be selectively removed at different levels of the synthesis to free hydroxyl groups for subsequent introduction of different substituents, including monosaccharides, other protecting groups or other residues present on the molecule. In this case, temporary protecting groups include $P^2$, $P^5$, $P^{13}$, $P^{15}$, $P^{21}$ and $P^{25}$.

Temporary protecting groups $P^2$, $P^5$, $P^{13}$, $P^{15}$, $P^{21}$ and $P^{25}$ are preferably selected from, but are not restricted to: allyl, p-methoxybenzyl, 2-naphthylmethyl, tri-isopropylsilyl, tert-butyldimethylsilyl, tert-butyl methoxyphenylsilyl, triethylsilyl, trimethylsilyl, 2-trimethylsilylethoxymethyl, 9-fluorenylmethoxycarbonyl, thexyldimethylsilyl, (2-nitrophenyl)acetyl, 2-(azidomethyl)benzoyl, and levulinoyl. Preferably, protecting groups $P^2$, $P^5$, $P^{13}$, $P^{15}$, $P^{21}$ and $P^{25}$ can be selectively removed in presence of protecting groups $P^1$, $P^3$, $P^4$, $P^6$-$P^{12}$, $P^{14}$, $P^{16}$-$P^{20}$, $P^{22}$-$P^{24}$. Preferably, $P^2$, $P^5$, $P^{13}$, $P^{15}$, $P^{21}$ and $P^{25}$ are 9-fluorenylmethoxycarbonyl or levulinoyl. In a preferred embodiment, protecting groups $P^{13}$ and $P^{21}$ represent 9-fluorenylmethoxycarbonyl and protecting groups $P^1$, $P^5$ and $P^{15}$ represent levulinoyl.

Preferably, $P^{21}$ is selected from tri-isopropylsilyl, tert-butyldimethylsilyl, tert-butylmethoxyphenylsilyl. Preferably, $P^{25}$ is 2-naphthylmethyl.

The ingenious choice of protecting groups allows expedient access to a library of saccharides of general formulae (I), (II), (II-a), (II-b), (III), (III-a) or (III-b), functionalized with a terminal group for subsequent conjugation to an immunogenic carrier or a solid support. Moreover, the choice of leaving groups affects the stereochemical outcome of the glycosylation reactions in steps A1a), A2), A2'), A4), A6), A6'), A8), B1.3), C2), C4), C6), C8), D1.3), E2), E4) and E6).

Building blocks 2*, 5*, 8*, 11*, 19*, 20* and 21* are glycosylating agents. As used herein, the term glycosylating agent refers to a monosaccharide functionalized at the anomeric position with a leaving group that upon activation with a suitable activating agent provide an oxocarbenium intermediate able to react with a nucleophile, such as a hydroxyl group. Hence, glycosylating agents 2*, 5*, 8*, 11*, 19*, 20* and 21* are functionalized at the anomeric position with leaving groups $LG^1$, $LG^2$, $LG^3$, $LG^4$, $LG^5$, $LG^6$ and $LG^7$. Examples of leaving groups suitable for the present synthesis are well known to the person skilled in carbohydrate chemistry and include halides, thioethers, imidates, acetate, and phosphate.

Preferably, leaving groups $LG^1$, $LG^2$, $LG^3$, $LG^4$, $LG^5$, $LG^6$ and $LG^7$ are selected from halogen (—Cl, —Br, —F, —I), —O—C(=NH)—CCl$_3$, —O—C(=NPh)-CF$_3$, —OAc, —SR$^L$, —SO—R$^L$, —SO-Ph, —SO—CH$_2$-Ph, —SO-Tol, —SO—C$_6$H$_4$-(para-OCH$_3$), —O—(CH$_2$)$_3$—CH=CH$_2$, —O—P(OR$^L$)$_2$, —O—PO(OR$^L$)$_2$, —O—CO—OR$^L$, —O—CO—SR$^L$, —O—CS—SR$^L$,

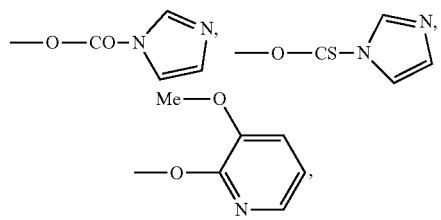

—O—CS—OR$^L$, wherein R$^L$ may be any alkyl or aryl group, preferably, methyl, ethyl, propyl, isopropyl, phenyl or toluyl.

Preferably, leaving groups $LG^1$, $LG^2$, $LG^3$, $LG^4$, $LG^5$, $LG^6$ and $LG^7$ are selected from the group of leaving groups consisting of: SBox, STaz,

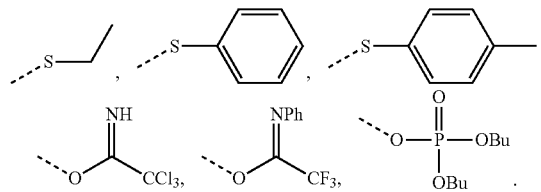

wherein the thioethers can also be substituted.

As mentioned, the provision of an oxocarbenium intermediate relies on the activation of the leaving group installed at the anomeric position of the glycosylating agent with an appropriate or suitable activating agent. It is common knowledge for the skilled person that suitable activating agents for phosphate (i.e. phosphate activating agents) and imidate (i.e. imidate activating agents) are Lewis acids, such as silyl triflate or silver triflate, while suitable activating agents for thioether i.e. thioether activating agents include, but are not restricted to: NIS/TfOH, NIS/TMSOTf, NIS/BF$_3$·Et$_2$O, NIS/AgOTf, DMTST/Tf$_2$O, IDPC, BSP/Tf$_2$O, Ph$_2$SO/Tf$_2$O. Examples of silyl triflate include, but are not restricted to trimethylsilyl trifluoromethanesulfonate, tert-butyl dimethyl trifluoromethanesulfonate, triiospropyl trifluoromethanesulfonate.

Preferably, $LG^1$, $LG^2$, $LG^3$, $LG^4$, $LG^5$, $LG^6$ and $LG^7$ are thioethers and even more preferred is when $LG^1$, $LG^2$, $LG^3$, $LG^4$, $LG^5$, $LG^6$ and $LG^7$ are selected from the group consisting of:

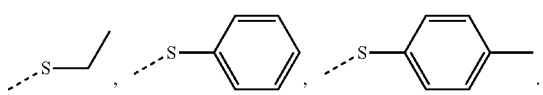

It is preferred that the coupling reaction between saccharides in the steps A1a), A2), A2'), A4), A6), A6'), A8), B1.3), C2), C4), C6), C8), D1.3), E2), E4) and E6) is performed by activation with NIS/TfOH or TMSOTf, in a mixture of apolar solvent and polar aprotic solvent at a temperature of between −10° C. and 10° C. Even more preferred is that said reaction is performed in a mixture of apolar solvent and polar aprotic solvent, by treatment with NIS/TfOH at a temperature of about 0° C.

Preferred polar aprotic solvents are tetrahydrofuran, diethyl ether and dioxane. Preferred apolar solvents are toluene, halogenated solvents such as chloroform and methylene chloride. Preferred mixtures of apolar and polar aprotic solvent are: methylene chloride/tetrahydrofuran, methylene chloride/diethyl ether, toluene/diethyl ether, toluene/tetrahydrofuran.

The removal of protecting groups $P^1$, $P^3$, $P^4$, $P^6$-$P^{12}$, $P^{14}$, $P^{16}$-$P^{20}$, $P^{22}$-$P^{24}$, $P^{26}$ and $P^{27}$ performed at steps A11), B4), C11), 04) and F5) involves:

first cleavage of the base-labile protecting groups by treatment with a base in presence of hydrogen peroxide in a mixture of solvents. Preferably, the base is NaOMe or LiOH; and second cleavage of the protecting groups sensitive to hydrogenation by subjecting the compound to hydrogen in presence of a palladium catalyst in a mixture of solvents.

The phosphorylating agent used in steps A9), B2), C9), D2), E9) and F2.1) is a compound capable of introducing the group $P(O)(OH)_2$ in its free form or as a monoester at a reactive position in a compound. Thus, a phosphate group is transferred to a hydroxyl group in steps A9), B2), C9), D2), E9) and F2.1). Preferred phosphorylating agents used in the present invention are diphenylphosphite, bis(diisopropylamino)benzyloxyphosphine, benzyl N,N-diisopropylphosphonamidate or N,N-diethyl-1,5-dihydro-3H-2,3,4-benzodioxaphosphepin-3-amine in combination with an activating agent such as 1H-tetrazole and subsequent oxidation with an oxidizing agent such as hydrogen peroxide or 3-chloroperbenzoic acid. In a preferred embodiment, in steps A9), B2), C9), D2), E9) and F2.1) the phosphorylating agent is bis(diisopropylamino)benzyloxyphosphine in combination with 1H-tetrazole and 3-chloroperbenzoic acid. In a preferred embodiment, in steps A9), B2), C9), D2), E9) and F2.1) the phosphorylating agent is diphenylphosphite.

The phosphorylating agent used in step A1b) is preferably bis(diisopropylamino)-benzyloxyphosphine, benzyl N,N-diisopropylphosphonamidate or N,N-diethyl-1,5-dihydro-3H-2,3,4-benzodioxaphosphepin-3-amine. Preferred activating agent used in step A1b), is 1H-tetrazole, 4,5-dicyanoimidazole, 2-benzylthiotetrazole, 5-ethylthio-tetrazole, benzimidazolium triflate or imidazolium triflate. Most preferred is 1H-tetrazole as activating agent. The oxidation reaction is preferably carried out in the presence of an oxidizing agent such as hydrogen peroxide or 3-chloroperbenzoic acid.

A further aspect according to the present invention refers to an intermediate compound for preparing a saccharide of the general formulae (I), (II), (II-a), (II-b), (III), (III-a) or (III-b), wherein the intermediate compound has any one of general formulae (I2a), (I2b), (I2c), (I2d), (I2e), (I2f), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i), (I5j), (I6a), (I6b), (I6c), (I6d), (I6e), (I6f), (I6g), (I6h), (I7a), (I7b), (I7c), (I7d), (I7e), (I7f), (I7g), (I7h), (I7i), (I7j), (I7k), (I7m), (I7n), (I7o) or (I7p):

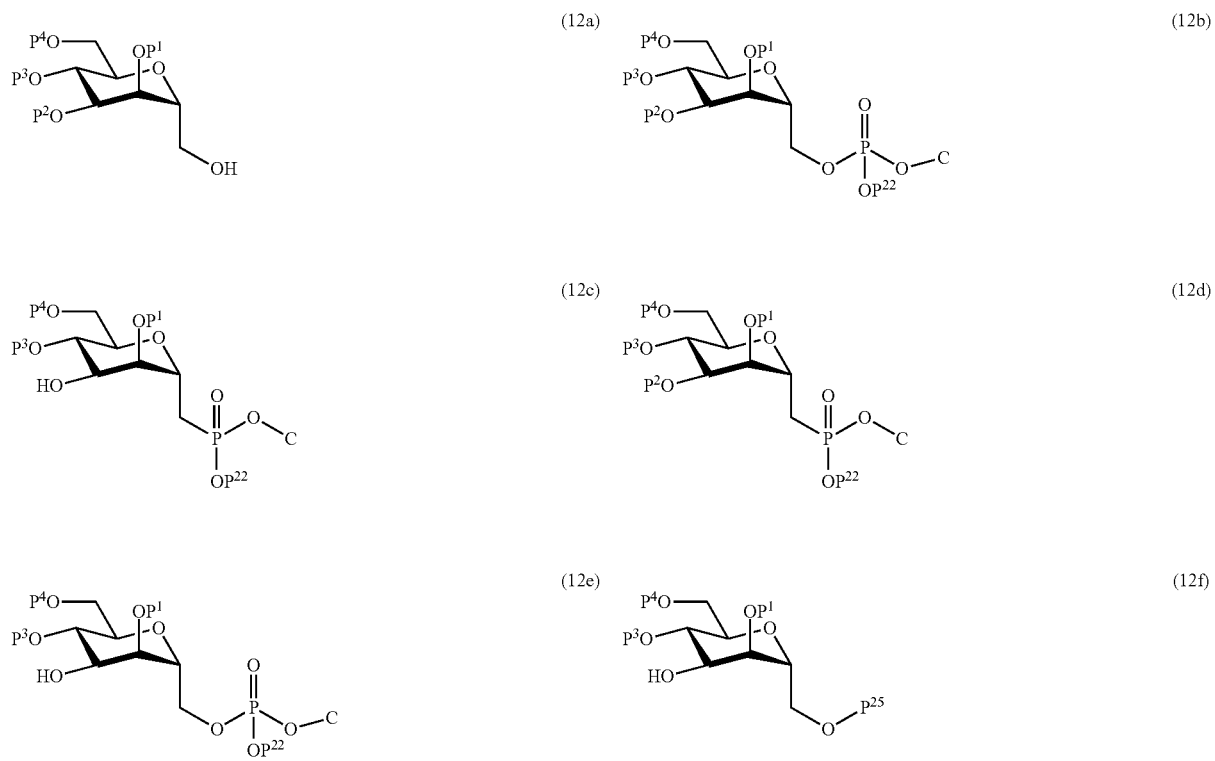

-continued
(14a)
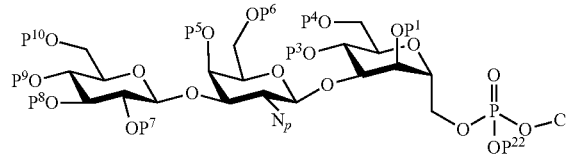
(14b)
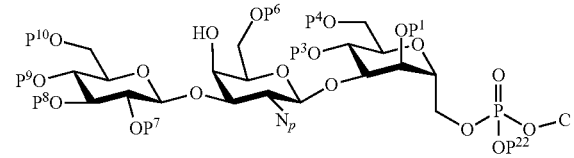
(14c)
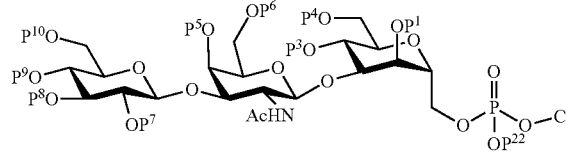
(14d)
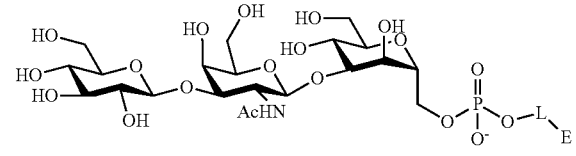
(14e)
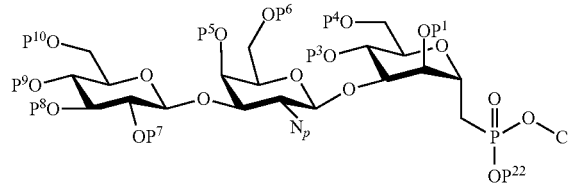
(14f)
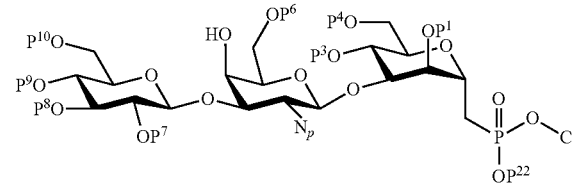
(14g)
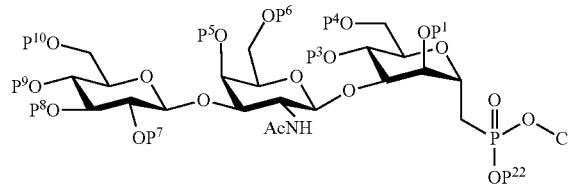
(14h)
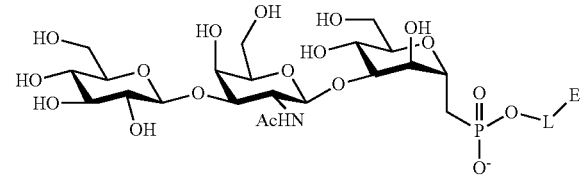
(14i)
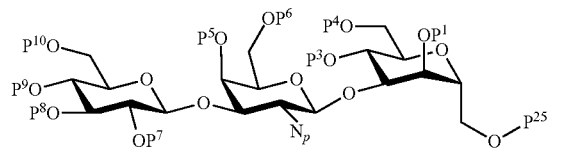
(14j)
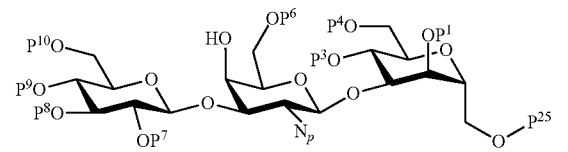
(15a)
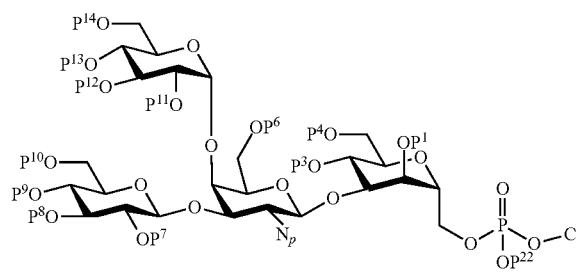
(15b)
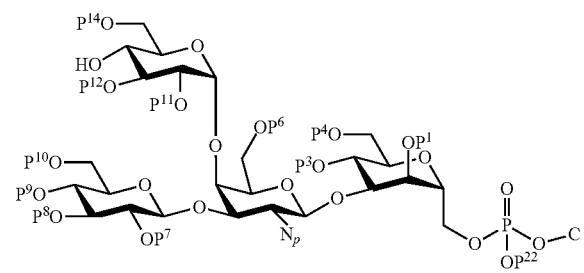
(15c)
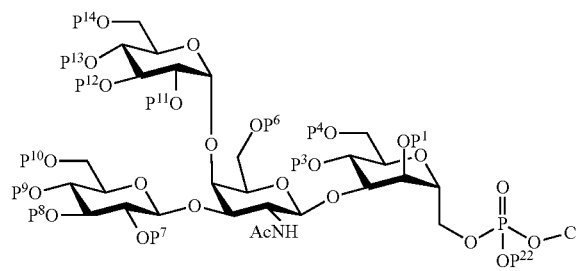
(15d)
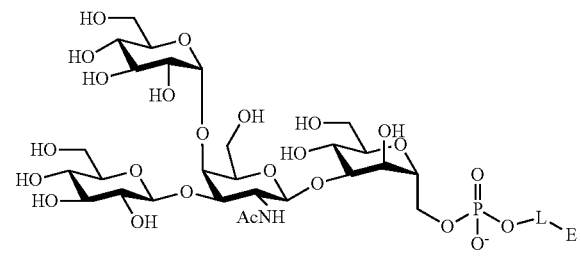

-continued
(15e)
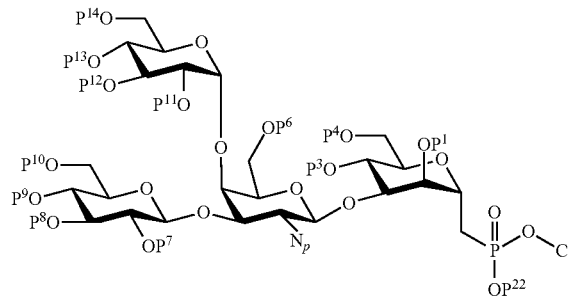
(15f)
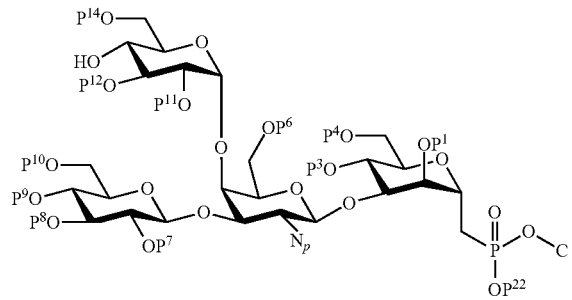
(15g)
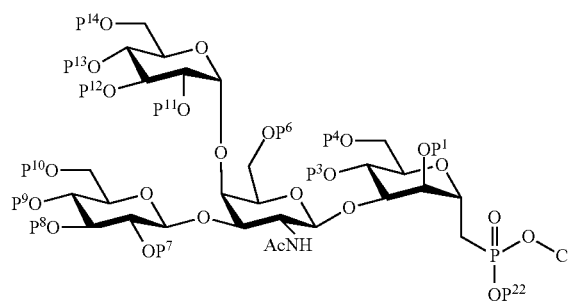
(15h)
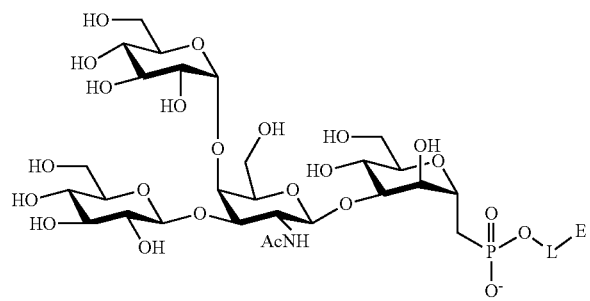
(15i)
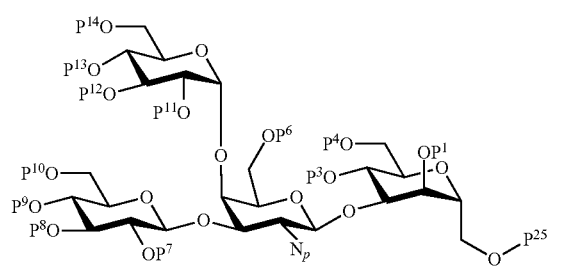
(15j)
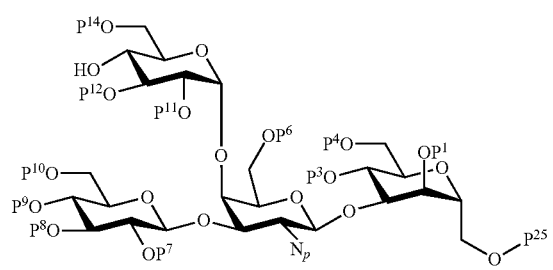
(16a)
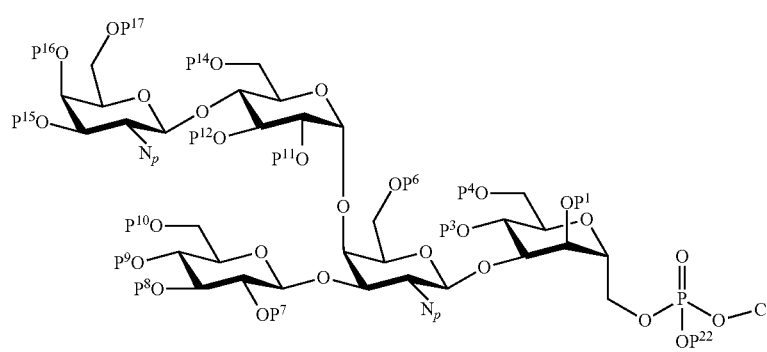
(16b)
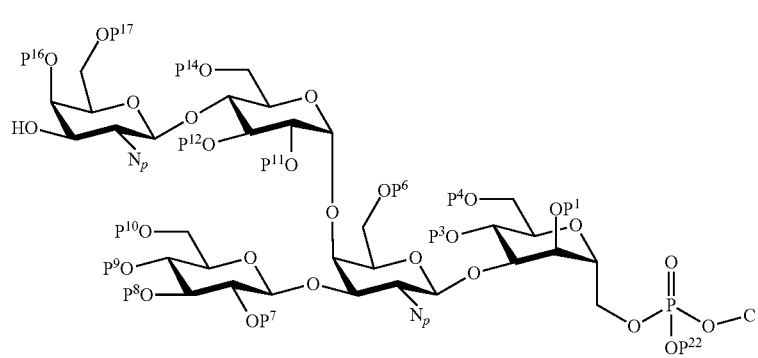

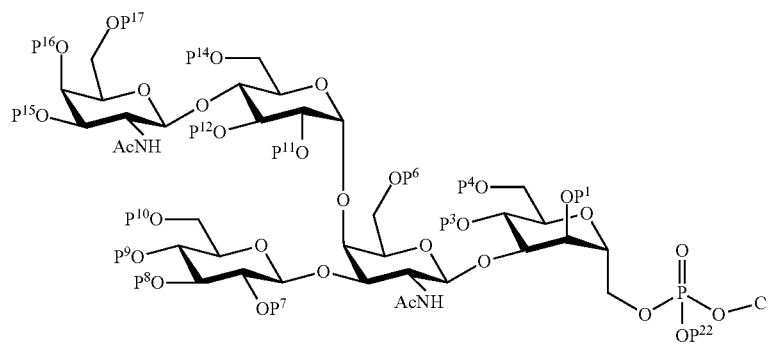
(16c)
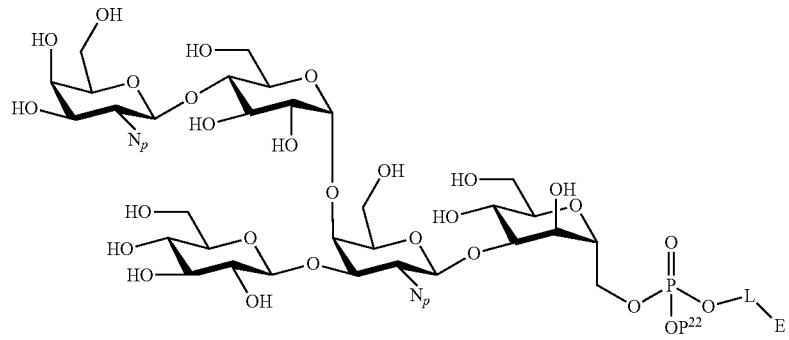
(16d)
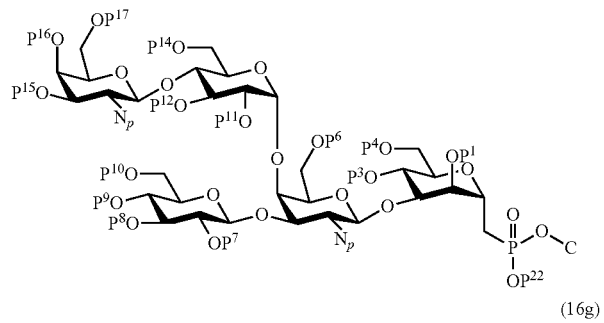
(16e)
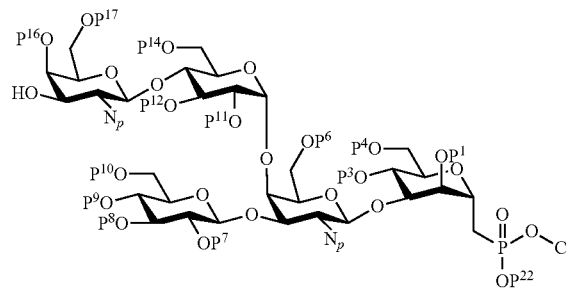
(16f)
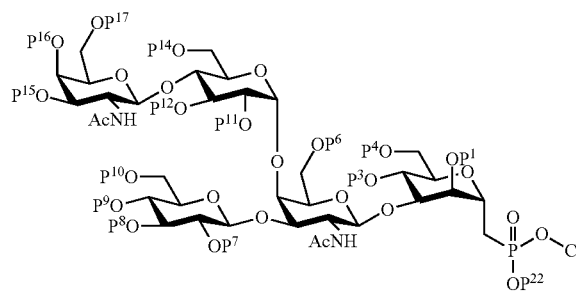
(16g)
(16h)
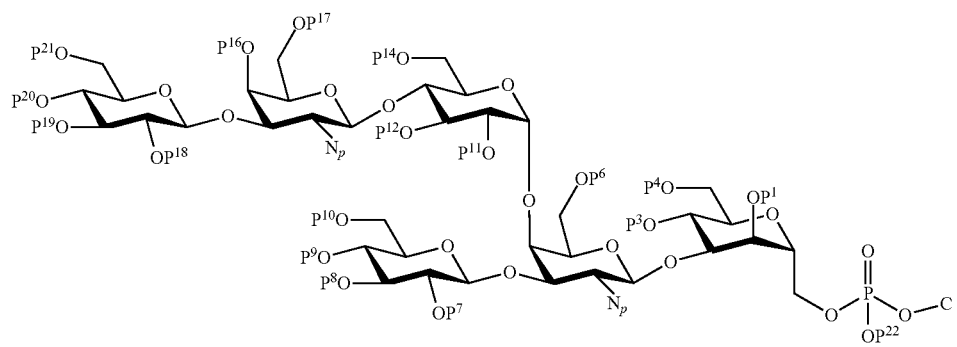
(17a)

-continued
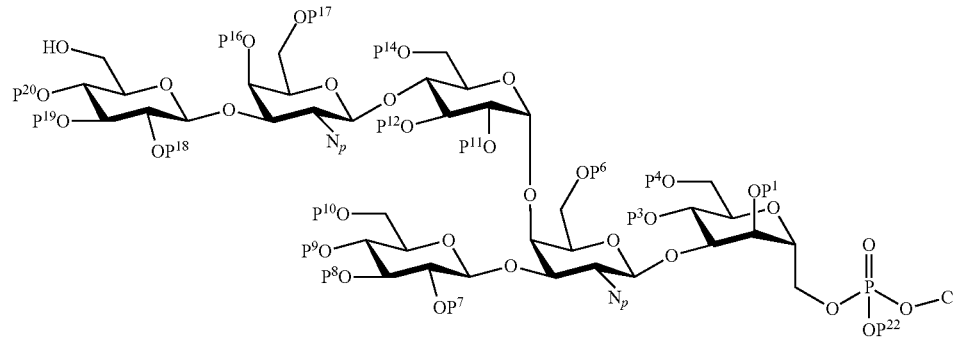
(17b)
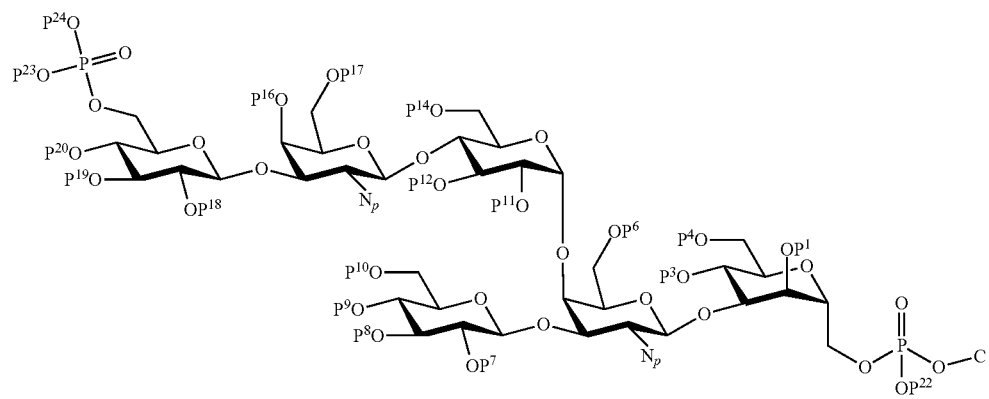
(17c)
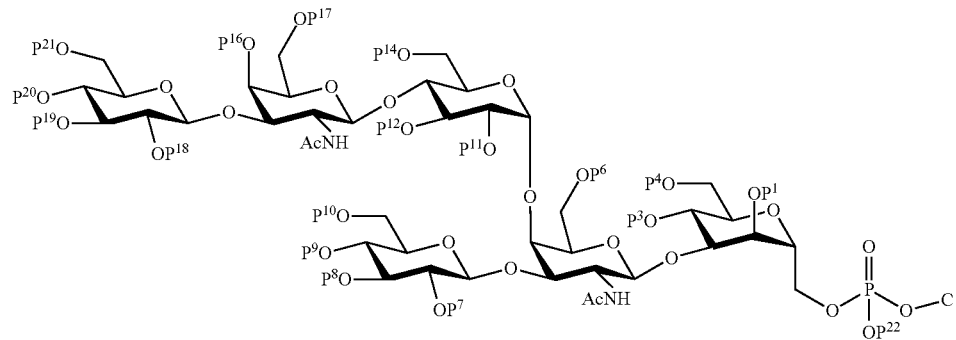
(17d)
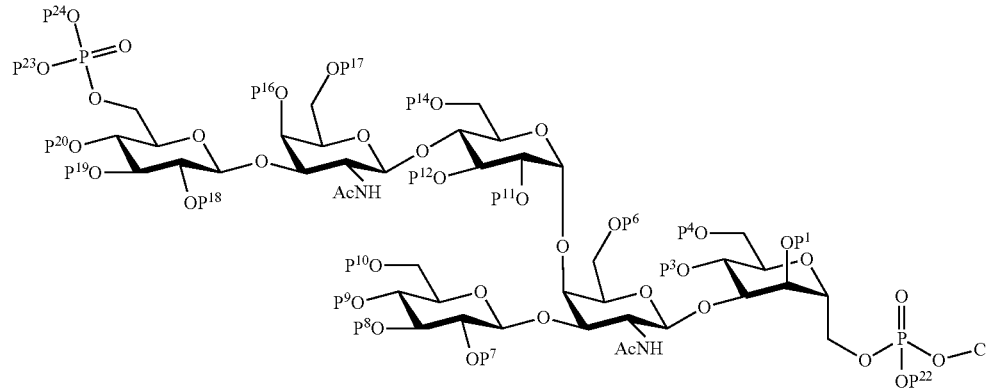
(17e)

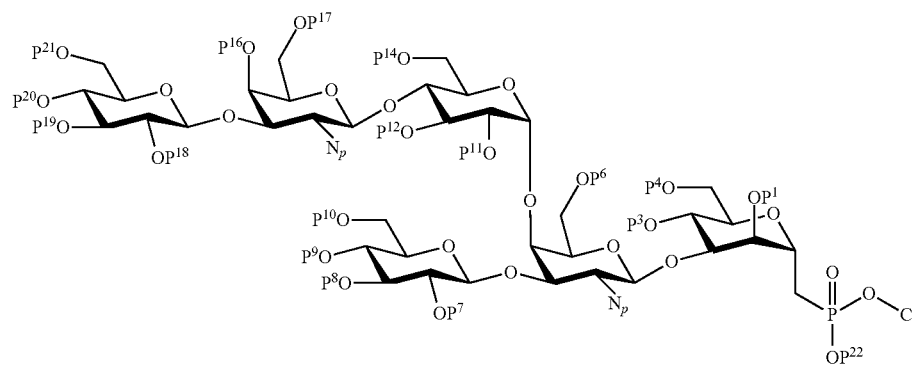
(17f)
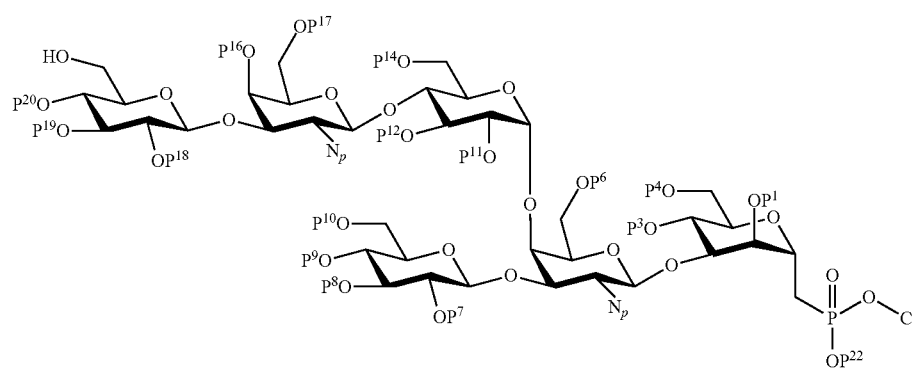
(17g)
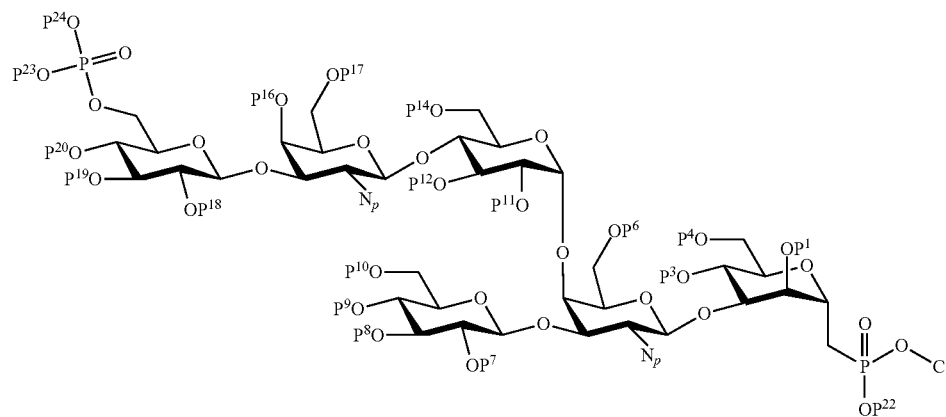
(17h)
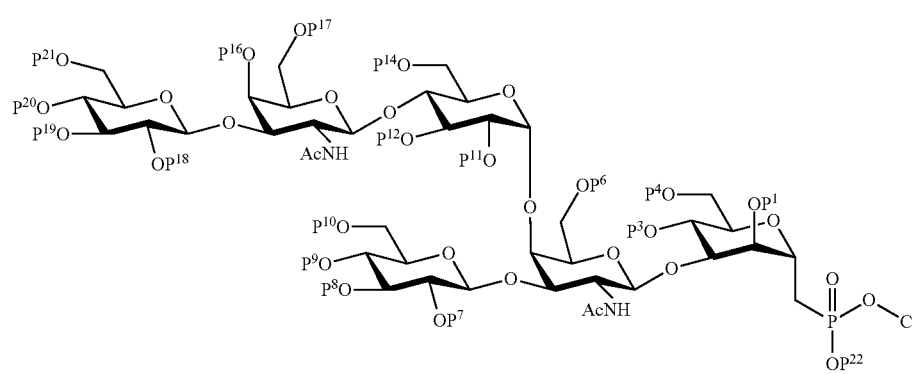
(17i)

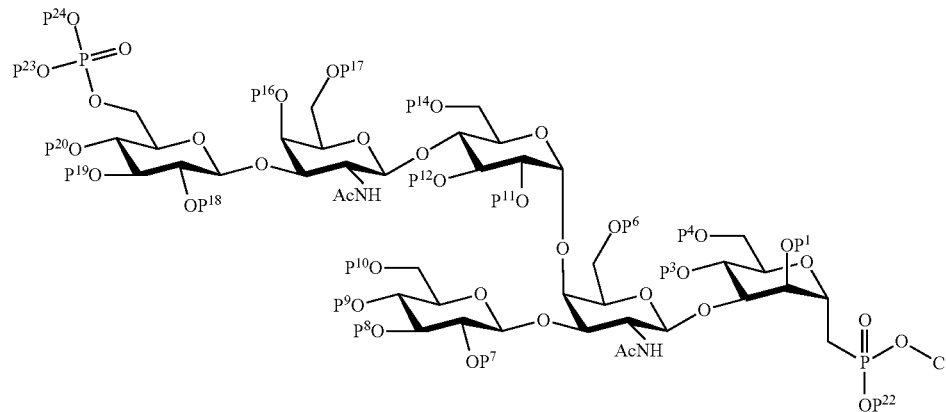
(17j)
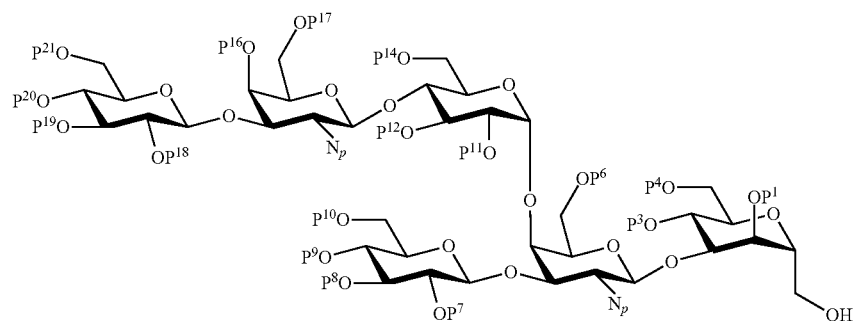
(17k)
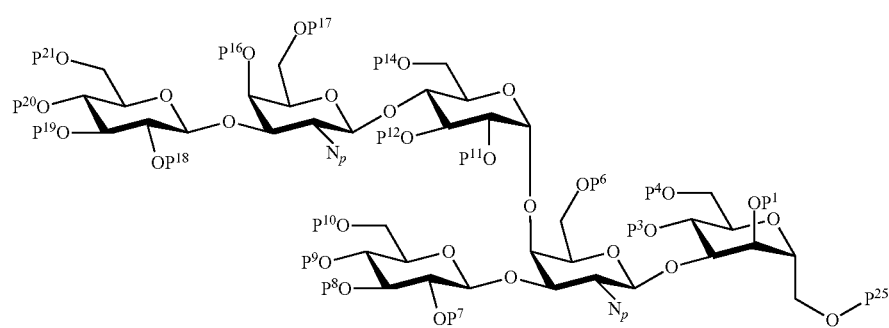
(17m)
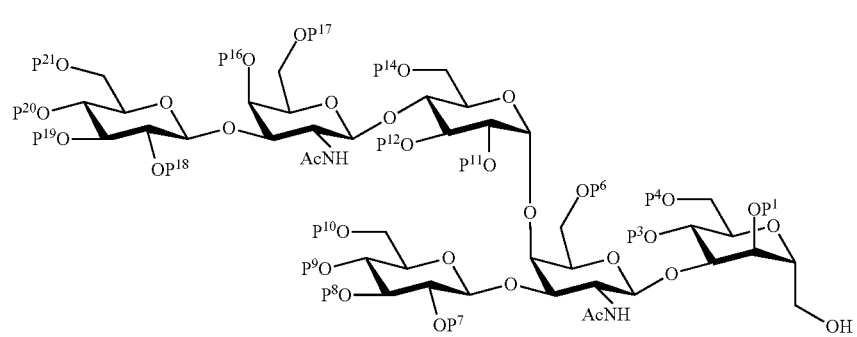
(17n)

-continued

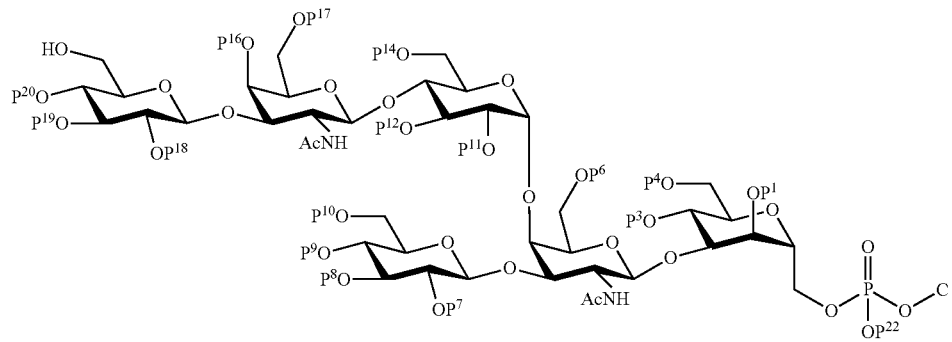

(17o)

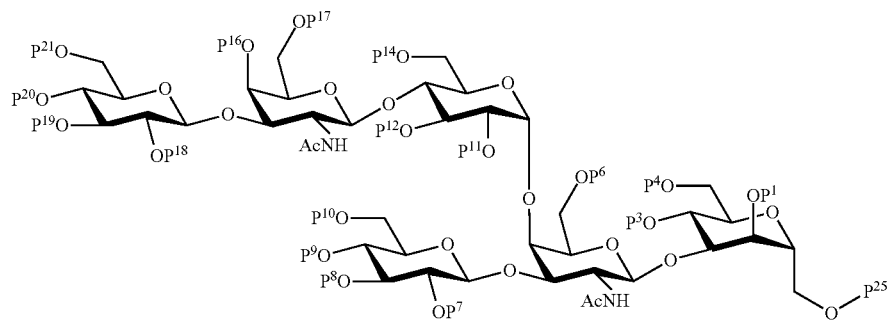

(17p)

wherein C represents -L-$E_p$ with Ep being a solid support or a protected end group E, $P^1$, $P^2$, $P^3$, $P^4$, $P^5$, $P^6$, $P^7$, $P^8$, $P^9$, $P^{10}$, $P^{11}$, $P^{12}$, $P^{13}$, $P^{14}$, $P^{15}$, $P^{16}$, $P^{17}$, $P^{18}$, $P^{19}$, $P^{20}$, $P^{21}$, $P^{22}$, $P^{23}$, $P^{24}$ and $P^{25}$ represent protecting groups, Np represents a protected amino group, LG represents a leaving group and E and L have the same meanings as defined above.

More preferred are the intermediate compounds of the general formulae (I), (II), (II-a), (II-b), (III), (III-a) or (III-b), wherein the intermediate compound has any one of the general formulae (I2a), (I2b), (I2c), (I2d), (I2e), (I2f), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i), (I5j), (I6a), (I6b), (I6c), (I6d), (I6e), (I6f), (I6g), (I6h), (I7a), (I7b), (I7c), (I7d), (I7e), (I7f), (I7g), (I7h), (I7i), (I7j), (I7k), (I7m), (I7n), (I7o) or (I7p).

In formulae (I2a), (I2b), (I2c), (I2d), (I2e), (I2f), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i), (I5j), (I6a), (I6b), (I6c), (I6d), (I6e), (I6f), (I6g), (I6h), (I7a), (I7b), (I7c), (I7d), (I7e), (I7f), (I7g), (I7h), (I7i), (I7j), (I7k), (I7m), (I7n), (I7o) or (I7p) preferably the linker -L- represents -$L^a$-, -$L^a$-$L^e$-, -$L^a$-$L^b$-$L^e$-, or -$L^a$-$L^d$-$L^e$-;
- -$L^a$- represents —$(CH_2)_o$—, —$(CH_2$—$CH_2$—$O)_o$—$C_2H_4$—, or —$(CH_2$—$CH_2$—$O)_o$—$CH_2$;
- -$L^b$- represents —O—;
- -$L^d$- represents —$(CH_2)_q$—, —$(CH(OH))_q$—, —$(CF_2)_q$—, —$(CH_2$—$CH_2$—$O)_q$—$C_2H_4$—, —$(CH_2$—$CH_2$—$O)_q$—$CH_2$—,
- -$L^e$- represents —$(CH_2)_{p1}$—, —$(CF_2)_{p1}$—, —$C_2H_4$—(O—$CH_2$—$CH_2)_{p1}$—, —$CH_2$—(O—$CH_2$—$CH_2)_{p1}$— or —$(CH_2)_{p1}$—O—$(CH_2)_{p2}$—; and
- o, q, p1 and p2 are independently of each other an integer selected from 1, 2, 3, 4, 5, and 6.

An especially preferred intermediate is an intermediate of formula (I2a), (I2b), (I2c), (I2d), (I2e), (I2f), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i), (I5j), (I6a), (I6b), (I6c), (I6d), (I6e), (I6f), (I6g), (I6h), (I7a), (I7b), (I7c), (I7d), (I7e), (I7f), (I7g), (I7h), (I7i), (I7j), (I7k), (I7m), (I7n), (I7o) or (I7p), wherein -L- represents —$(CH_2)_o$— and o is an integer selected from 2, 5 and 6.

$P^1$, $P^2$, $P^3$, $P^4$, $P^5$, $P^6$, $P^7$, $P^8$, $P^9$, $P^{10}$, $P^{11}$, $P^{12}$, $P^{13}$, $P^{14}$, $P^{15}$, $P^{16}$, $P^{17}$, $P^{18}$, $P^{19}$, $P^{20}$, $P^{21}$, $P^{22}$, $P^{23}$, $P^{24}$ and $P^{25}$ are suitable protecting groups for hydroxyl groups, more preferably different suitable protecting groups for hydroxyl groups capable of being removed subsequently one after another by a suitable sequence of deprotection reactions. Preferred protecting groups for hydroxyl groups are acetyl, phenyl, benzyl, isopropylidene, benzylidene, benzoyl, p-methoxybenzyl, p-methoxybenzylidene, p-methoxyphenyl, p-bromobenzylidene, p-nitrophenyl, allyl, acetyl, isopropyl, p-bromobenzyl, dimethoxytrityl, trityl, 2-naphthylmethyl, pivaloyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl, levulinoyl.

Thus, intermediates (I2a), (I2b), (I2c), (I2d), (I2e), (I2f), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i), (I5j), (I6a), (I6b), (I6c), (I6d), (I6e), (I6f), (I6g), (I6h), (I7a), (I7b), (I7c), (I7d), (I7e), (I7f), (I7g), (I7h), (I7i), (I7j), (I7k), (I7m), (I7n), (I7o) or (I7p) are especially preferred when protecting groups $P^3$, $P^4$, $P^8$-$P^{12}$, $P^{14}$, $P^{16}$-$P^{20}$ and $P^{22}$-$P^{24}$ are benzyl groups or acetyl groups, protecting group $P^1$ is a benzoyl group, protecting groups $P^7$ and $P^{18}$ are acetyl groups, protecting group $P^{26}$ is a benzyl group and protecting group $P^{27}$ is a benzyloxycarbonyl group (Cbz). Preferably, protecting group $P^{21}$ is p-bromobenzyl or tert-butyldiphenylsilyl (TBDPS). Preferably, protecting group $P^{25}$ is a 2-naphthylmethyl group.

Preferably, Np is selected from —$N_3$, —NH—CO—$CCl_3$ and —NH—CO—O—$CH_2$—$CCl_3$ (Troc). Thus, intermediates (I2a), (I2b), (I2c), (I2d), (I2e), (I2f), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i), (I5j), (I6a), (I6b), (I6c), (I6d), (I6e), (I6f), (I6g), (I6h), (I7a), (I7b), (I7c), (I7d), (I7e), (I7f), (I7g), (I7h), (I7i), (I7j), (I7k), (I7m), (I7n), (I7o) or carrier to provide conjugates, which present increased immunogenicity in comparison with the saccharide. Hence, under the scope of the present application is covered also a conjugate comprising a saccharide fragment

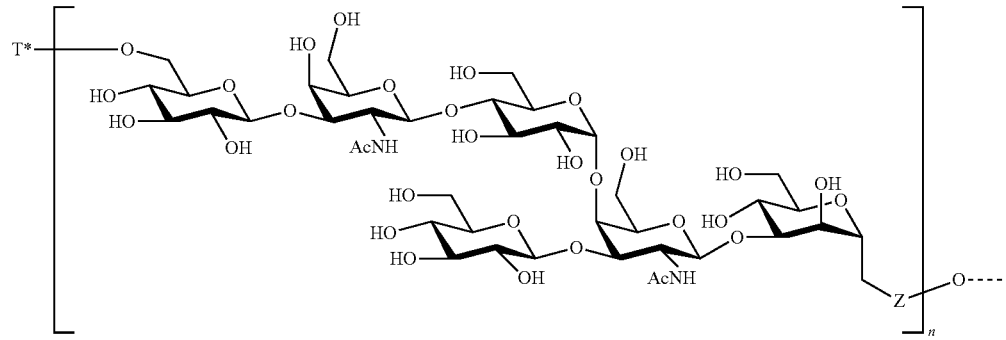

(I7p) are preferred when Np is selected from —$N_3$, —NH—CO—$CCl_3$ and —NH—CO—O—$CH_2$—$CCl_3$ (Troc). Particularly preferred are intermediates (I2a), (I2b), (I2c), (I2d), (I2e), (I2f), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i), (I5j), (I6a), (I6b), (I6c), (I6d), (I6e), (I6f), (I6g), (I6h), (I7a), (I7b), (I7c), (I7d), (I7e), (I7f), (I7g), (I7h), (I7i), (I7j), (I7k), (I7m), (I7n), (I7o) or (I7p) when Np represents —NH—CO—O—$CH_2$—$CCl_3$ (Troc).

Glycoconjugates

Another aspect of the present invention refers to a conjugate comprising a saccharide of general formula (I) covalently bound or covalently linked to an immunogenic carrier through the terminal group E of the —O-L-E group. In other words, another aspect of the present invention is directed to a saccharide of any of the general formulae (I), (II), (II-a), (II-b), (III), (III-a) or (III-b) conjugated with an immunogenic carrier through the terminal group E of the —O-L-E group. A conjugate comprising a synthetic saccharide of the general formula (I), (II), (II-a), (II-b), (III), (III-a) or (III-b), covalently bound or covalently linked to an immunogenic carrier through the terminal group E of the —O-L-E group is also defined as a conjugate obtained by reacting a saccharide of any of the general formulae (I), (II), (II-a), (II-b), (III), (III-a) or (III-b) with an immunogenic carrier. Surprisingly, said conjugate proved to be efficient as a vaccine for immunization against diseases associated with *Clostridium difficile* bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, the saccharides of general formulae (I), (II), (II-a), (II-b), (III), (III-a) or (III-b) are conjugated to an immunogenic carrier to provide conjugates, which present increased immunogenicity in comparison with the saccharide. Hence, under the scope of the present application is covered also a conjugate comprising a saccharide fragment wherein n, Z and T* have the meanings defined herein, covalently linked through the O atom to an immunogenic carrier.

Said conjugate comprises at least one synthetic saccharide of the general formula (I) and an immunogenic carrier to which the at least one saccharide (I) is covalently bound.

Surprisingly it was found that immunization with a conjugate comprising a saccharide of general formula (I) covalently linked to an immunogenic carrier results in the production of high titers of antibodies specific to the carbohydrate part of the saccharide of general formula (I). Said antibodies are cross-reacting with the natural *Clostridium difficile* PS-II cell-wall saccharide and present opsonophagocytosis and bactericidal activity, thus conferring protection against *Clostridium difficile* bacteria.

In this context the term "immunogenic carrier" is defined as a structure, which is conjugated to the saccharide to form a conjugate that presents an increased immunogenicity in comparison with the saccharide per se. Thus, the conjugation of the saccharides of the general formulae (I), (II), (II-a), (II-b), (III), (III-a) or (III-b) to the immunogenic carrier has as effect the stimulation of the immune response against the saccharide of general formula (I) without inducing an immune response against said immunogenic carrier.

Preferred immunogenic carriers are carrier proteins (CP) or glycosphingolipids with immunomodulatory properties. For the person skilled in the art, a carrier protein (CP) is a protein that is non-toxic and non-reactogenic and obtainable in sufficient amount and purity. The carrier protein is selected from the group comprising or consisting of: a diphtheria toxoid, such as $CRM_{197}$, a mutated diphtheria toxoid, a modified diphtheria toxoid, a mutated and modified diphtheria toxoid, a tetanus toxoid, a modified tetanus toxoid, a mutated tetanus toxoid, non-lipidated cell-surface liporotein (protein D) of non-typeable *Haemophilus influenzae*, outer membrane protein (OMP) complex of *Neisseria meningitidis*, bovine serum albumin (BSA), keyhole limpet hemocyanine (KLH) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence.

Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Preferably, the saccharide of general formula I is conjugated to the non-toxic mutated diphtheria toxin $CRM_{197}$, which is modified by maleimide. In yet another preferred embodiment, the saccharide of general formula I is conjugated to the non-toxic mutated diphtheria toxin $CRM_{197}$, which is modified by α-bromoacetamide. In the most preferred embodiment, the saccharide of general formula I is conjugated to the non-toxic mutated diphtheria toxin $CRM_{197}$, which is modified by N-hydroxysuccinimide adipate.

Preferred is a conjugate of general formula (IV)

(IV)

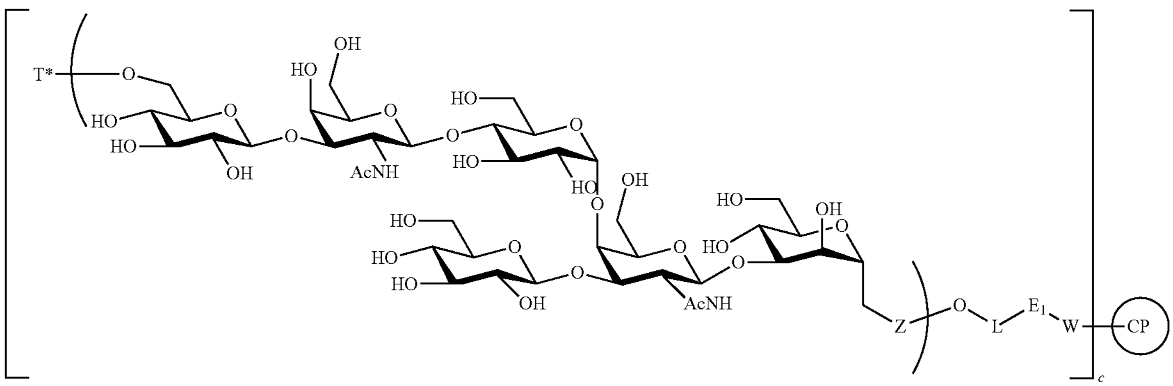

Activated esters include N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarate (DSG), disuccinimidyl adipate (DSA), 2-pyridyldithiol-tetraoxatetradecane-N-hydroxysuccinimide (PEG-4-SPDP) (see FIG. 2).

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the saccharides of general formula I are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines for diseases such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker of the compounds of general formula (I).

Said functional group X of the interconnecting molecules is selected of the group comprising or consisting of maleimide; α-iodoacetyl; α-bromoacetyl; and N-hydroxysuccinimide ester (NHS), aldehyde, imidoester, carboxylic acid, alkyl sulfonate, sulfonyl chloride, epoxide, anhydride, carbonate (see FIG. 3).

wherein c is comprised between 2 and 18;

$-E_1-$ represents a covalent bond, —NH—, —O—NH—, —O—, —S—, —CO—, —CH═CH—, —CONH—, —CO—NHNH—, 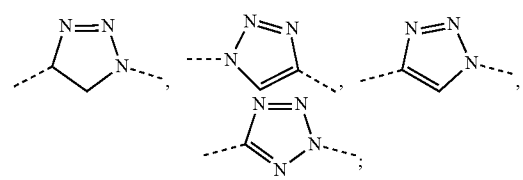 —W— is selected from:

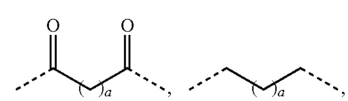

And 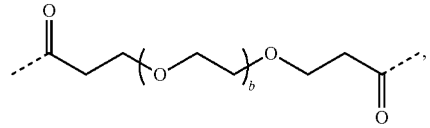 a represents an integer selected from 1, 2, 3, 4, 5, 6, 7, 8, 9 and 10, b represents an integer selected from 1, 2, 3 and 4, CP is a carrier protein; and n, L, Z and T* have the meanings as defined herein.

Preferably $E_1$ is a covalent bond, —NH—, —CH═CH—, —CONH—,

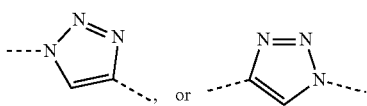

Preferably CP is $CRM_{197}$. Thus, in one embodiment of the present invention the conjugate is of general formula (IV), wherein CP is $CRM_{197}$ and c, $-E_1-$, W, n, L, Z and T* have the meanings as defined herein.

Preferably, in general formula (IV) the linker -L- is selected from: $-L^a-$, $-L^a-L^e-$, $-L^a-L^b-L^e-$, and $-L^a-L^d-L^e-$;

- $-L^a-$ is selected from: $—(CH_2)_o—$, $—(CH_2—CH_2—O)_o—C_2H_4—$, $—(CH_2—CH_2—O)_o—CH_2$;
- $-L^b-$ represents $—O—$;
- $-L^d-$ is selected from: $—(CH_2)_q—$, $—(CF_2)_q—$, $—(CH_2—CH_2—O)_q—C_2H_4—$, and $—(CH_2—CH_2—O)_q—CH_2—$;
- $-L^e-$ is selected from: $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ and $—(CH_2)_{p1}—O—(CH_2)_{p2}—$;

and o, q, p1 and p2 are independently of each other an integer selected from 1, 2, 3, 4, 5, and 6.

Also a conjugate of general formula (IV), wherein —W— represents

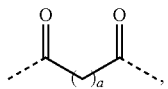

and a is an integer selected from 2, 3, 4, 5 and 6 is preferred.

A conjugate of general formula (IV), wherein the linker -L- is selected from: $L^a$, $-L^a-L^e-$, $-L^a-L^b-L^e-$, and $-L^a-L^d-L^e-$;
- $-L^a-$ is selected from: $—(CH_2)_o—$, $—(CH_2—CH_2—O)_o—C_2H_4—$, $—(CH_2—CH_2—O)_o—CH_2$;
- $-L^b-$ represents $—O—$;
- $-L^d-$ is selected from: $—(CH_2)_q—$, $—(CF_2)_q—$, $—(CH_2—CH_2—O)_q—C_2H_4—$, and $—(CH_2—CH_2—O)_q—CH_2—$;
- $-L^e-$ is selected from: $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ and $—(CH_2)_{p1}—O—(CH_2)_{p2}—$;

o, q, p1 and p2 are independently of each other an integer selected from 1, 2, 3, 4, 5, and 6;
—W— represents

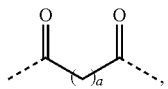

and a is an integer selected from 2, 3, 4, 5 and 6 is especially preferred.

Even more preferred is a conjugate of general formula (IV), wherein n is selected from 1, 2 or 3;
the linker -L- is selected from: $L^a$, $-L^a-L^e-$, $-L^a-L^b-L^e-$, and $-L^a-L^d-L^e-$;
- $-L^a-$ is selected from: $—(CH_2)_o—$, $—(CH_2—CH_2—O)_o—C_2H_4—$, $—(CH_2—CH_2—O)_o—CH_2$;
- $-L^b-$ represents $—O—$;
- $-L^d-$ is selected from: $—(CH_2)_q—$, $—(CF_2)_q—$, $—(CH_2—CH_2—O)_q—C_2H_4—$, and $—(CH_2—CH_2—O)_q—CH_2—$;
- $-L^e-$ is selected from: $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ and $—(CH_2)_{p1}—O—(CH_2)_{p2}—$;

o, q, p1 and p2 are independently of each other an integer selected from 1, 2, 3, 4, 5, and 6;
—W— represents

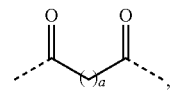

and a is an integer selected from 2, 3, 4, 5 and 6.

Particularly preferred is a conjugate of general formula (IV), wherein the linker -L- represents $—(CH_2)_o—$,
o is an integer selected from 2, 3, 4, 5 and 6;
—W— represents

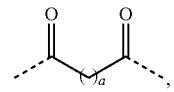

and a is an integer selected from 2, 3, 4, 5 and 6.

Particularly preferred is a conjugate of general formula (IV), wherein n represents an integer from 1, 2 or 3;
the linker -L- represents $—(CH_2)_o—$,
o is an integer selected from 2, 3, 4, 5 and 6;
—W— represents

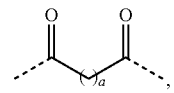

and a is an integer selected from 2, 3, 4, 5 and 6.

Particularly preferred is a conjugate of general formula (IV), wherein n represents an integer from 1, 2 or 3;
the linker -L- represents $—(CH_2)_o—$,
o is an integer selected from 2, 3, 4, 5 and 6;
—W— represents

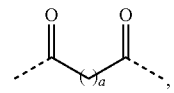

and a is an integer selected from 2, 3, 4, 5 and 6:
and Z represents

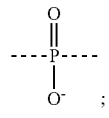

Preferably c is comprised between 2 and 18, more preferably between 5 and 15, even more preferably between 8 and 12. It is also preferred that n represents 1.

More preferred is a conjugate of any one of the formulae (IV-1)-(IV-4):

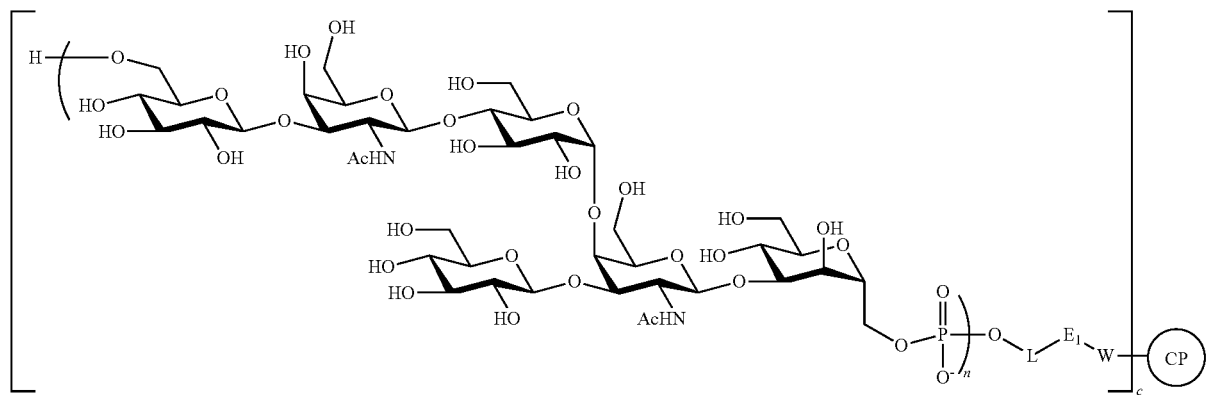
(IV-1)
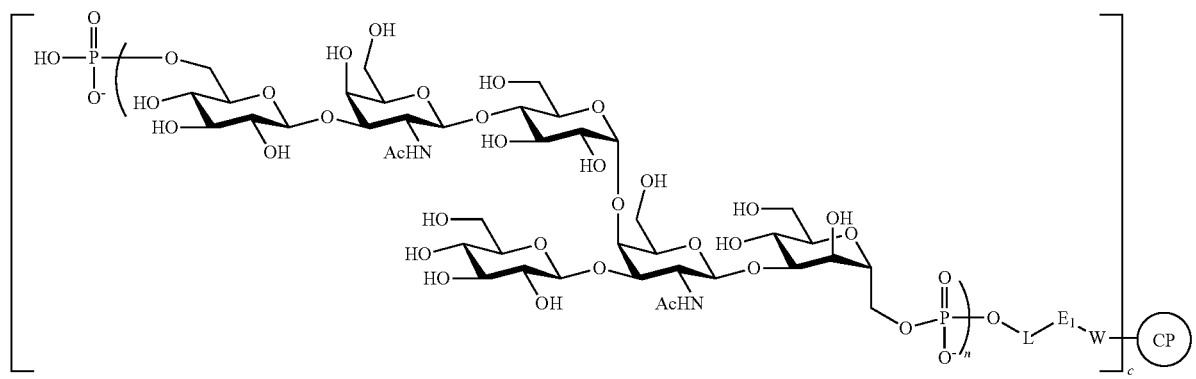
(IV-2)
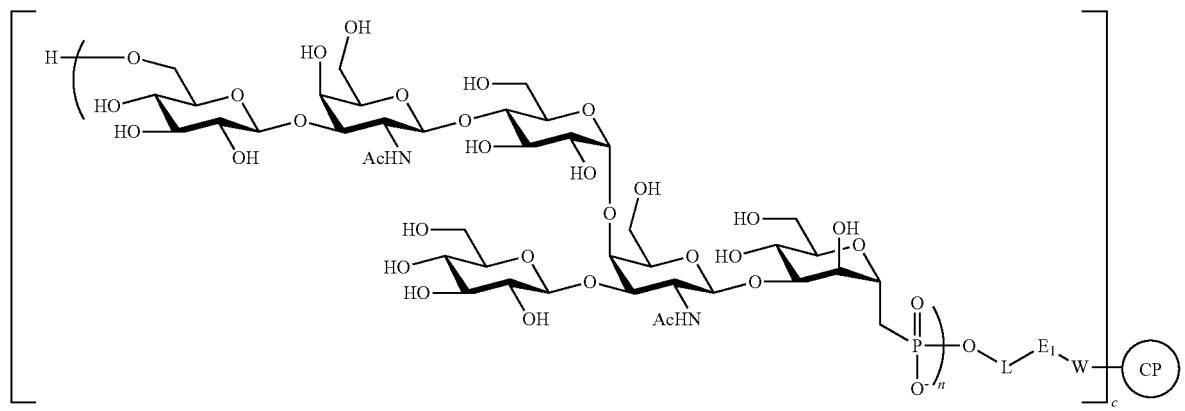
(IV-3)

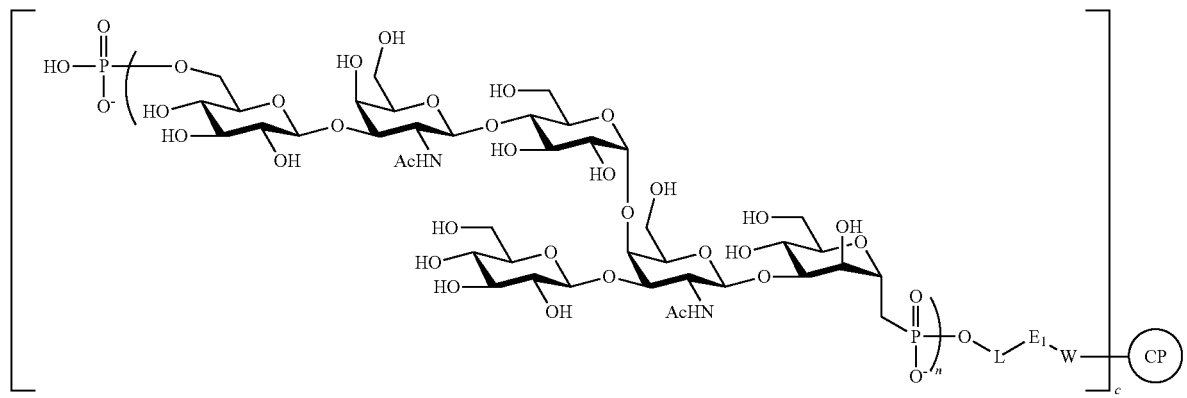

(IV-4)

wherein L, $E_1$, W, c, CP, and n have the same meanings as defined above.

Particularly preferred is a conjugate of formula (IV-2), wherein L is —$(CH_2)_5$—, $E_1$ is —NH—, n is an integer selected from 1 or 2, and c and W have the same meaning as defined above.

Preferred is also a conjugate of general formula (V)

—W— is selected from:

 , And

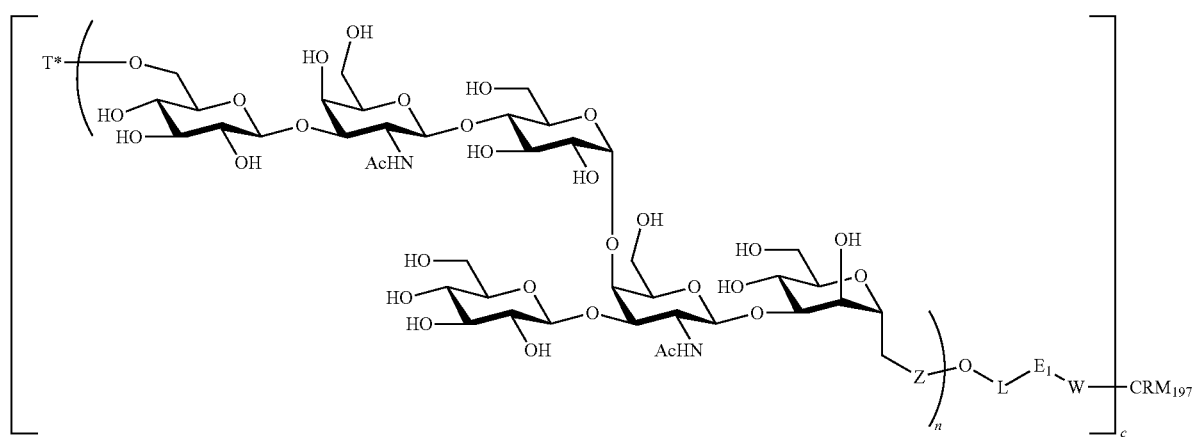

(V)

wherein
c is comprised between 2 and 18;
-$E_1$- represents a covalent bond, —NH—, —O—NH—, —O—, —S—, —CO—, —CH=CH—, —CONH—, —CO—NHNH—,

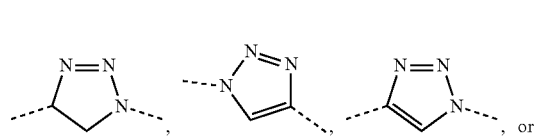 , or

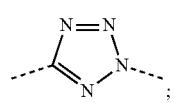 ;

-continued

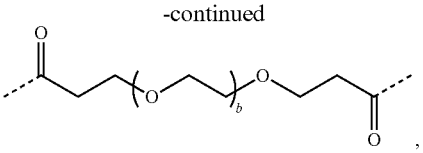 , a represents an integer selected from 1, 2, 3, 4, 5, 6, 7, 8, 9 and 10,
b represents an integer selected from 1, 2, 3 and 4; and
n, L, Z and T* have the meanings as defined herein.
A conjugate of general formula (V), wherein
the linker -L- is selected from: $L^a$, -$L^a$-$L^e$-, -$L^a$-$L^b$-$L^e$-, and -$L^a$-$L^d$-$L^e$-;
-$L^a$- is selected from: —$(CH_2)_o$—, —$(CH_2$—$CH_2$—$O)_o$—$C_2H_4$—, —$(CH_2$—$CH_2$—$O)_o$—$CH_2$;
-$L^b$- represents —O—;

-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—$O$—$(CH_2)_{p2}$—;

o, q, p1 and p2 are independently of each other an integer selected from 1, 2, 3, 4, 5, and 6;

—W— represents

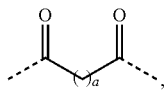

and a is an integer selected from 2, 3, 4, 5 and 6 is especially preferred.

Even more preferred is a conjugate of general formula (V), wherein n is selected from 1, 2 or 3;

the linker -L- is selected from: $L^a$, -$L^a$-$L^e$-, $L^a$ $L^b$ $L^e$ and -$L^a$-$L^d$-$L^e$-;

-$L^a$- is selected from: —$(CH_2)_o$—, —$(CH_2$—$CH_2$—$O)_o$—$C_2H_4$—, —$(CH_2$—$CH_2$—$O)_o$—$CH_2$;

-$L^b$- represents —O—;

-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—$O$—$(CH_2)_{p2}$—;

o, q, p1 and p2 are independently of each other an integer selected from 1, 2, 3, 4, 5, and 6;

—W— represents

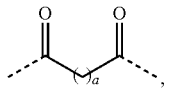

and a is an integer selected from 2, 3, 4, 5 and 6.

Particularly preferred is a conjugate of general formula (V), wherein the linker -L-represents —$(CH_2)_o$—, o is an integer selected from 2, 3, 4, 5 and 6;

—W— represents

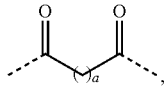

and a is an integer selected from 2, 3, 4, 5 and 6.

Particularly preferred is a conjugate of general formula (V), wherein n represents an integer from 1, 2 or 3;

the linker -L- represents —$(CH_2)_o$—, o is an integer selected from 2, 3, 4, 5 and 6;

—W— represents

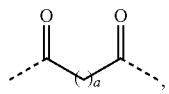

and a is an integer selected from 2, 3, 4, 5 and 6.

Particularly preferred is a conjugate of general formula (V), wherein n represents an integer from 1, 2 or 3;

the linker -L- represents —$(CH_2)_o$—, o is an integer selected from 2, 3, 4, 5 and 6;

—W— represents

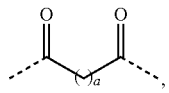

and a is an integer selected from 2, 3, 4, 5 and 6:

and Z represents

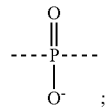

Particularly preferred is a conjugate of general formula (V), wherein n represents an integer from 1, 2 or 3;

the linker -L- represents —$(CH_2)_o$—, o is an integer selected from 2, 3, 4, 5 and 6;

—W— represents

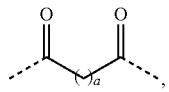

and a is an integer selected from 2, 3, 4, 5 and 6:

and T* represents a phosphate group.

Also preferred is a conjugate of general formula (IV), wherein the group —O-L-E is selected from the group consisting of:

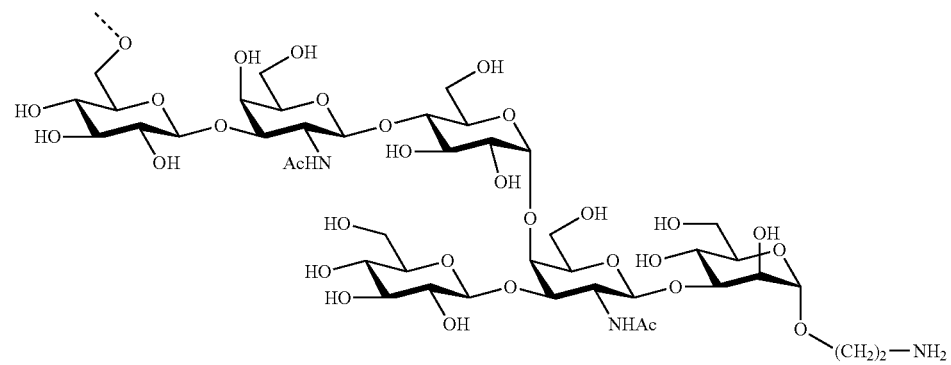

-continued
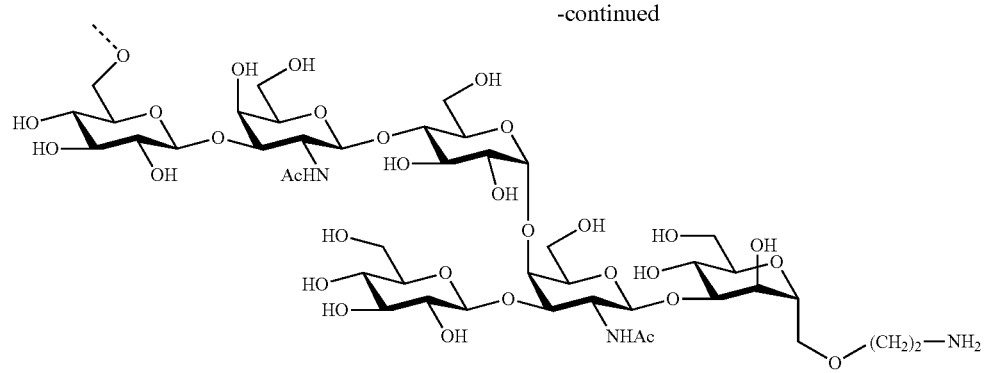
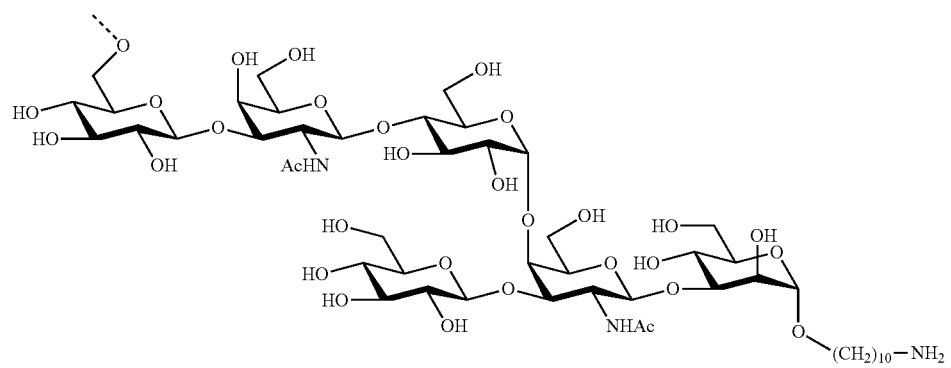
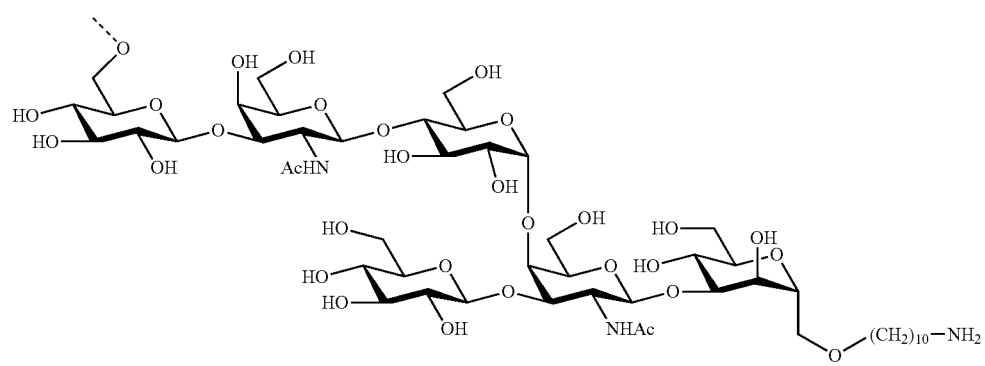
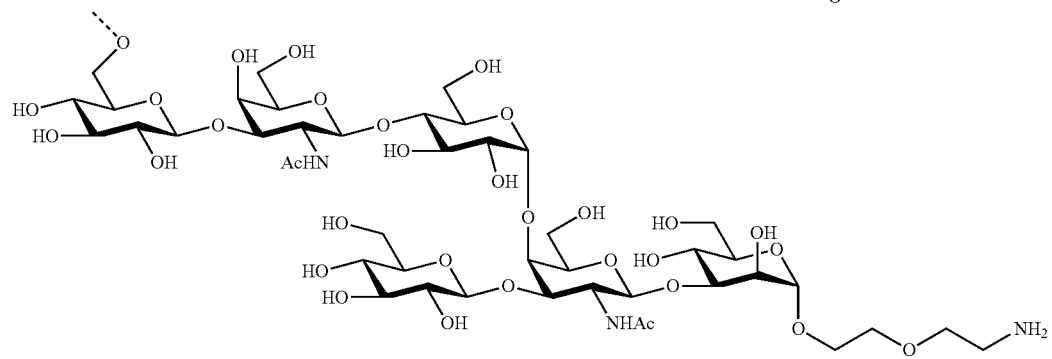

-continued
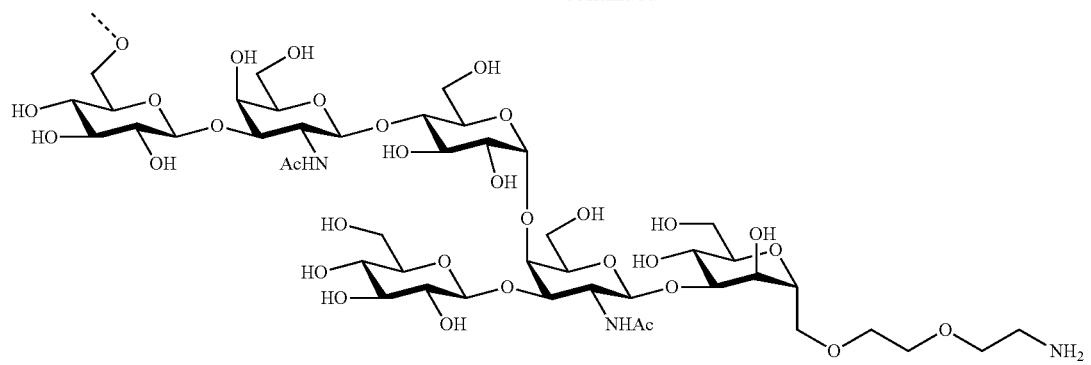
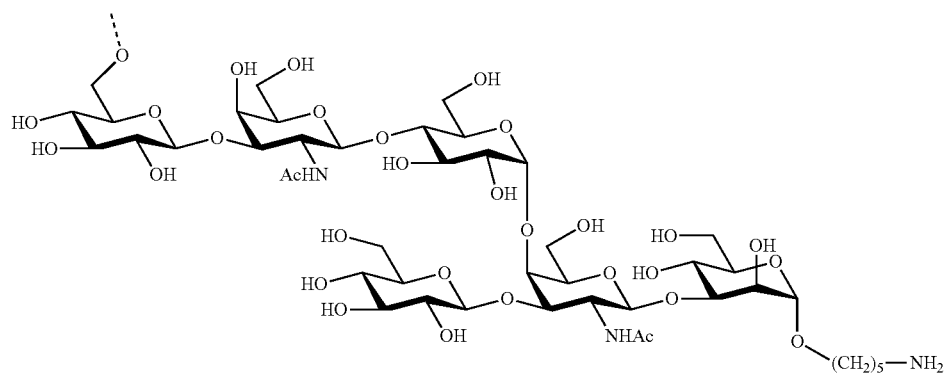
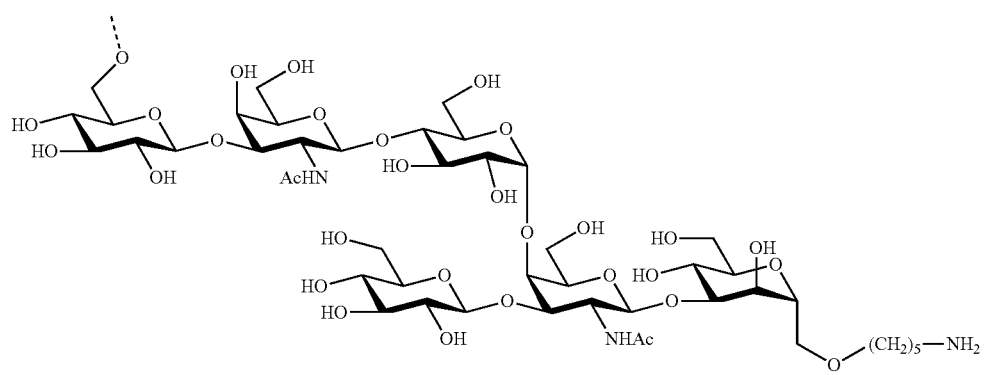
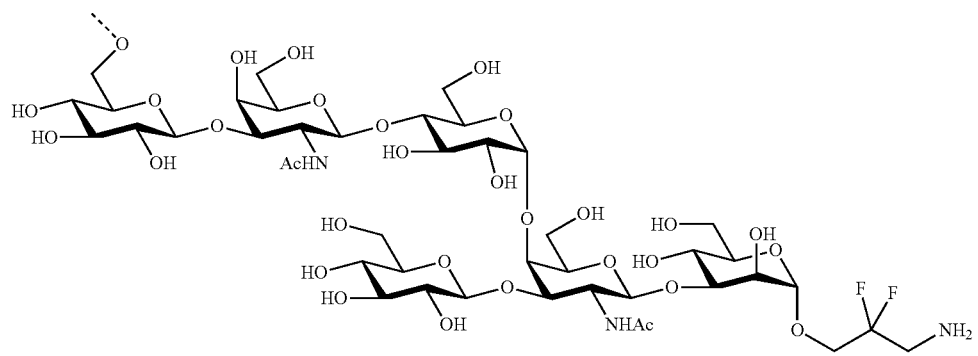

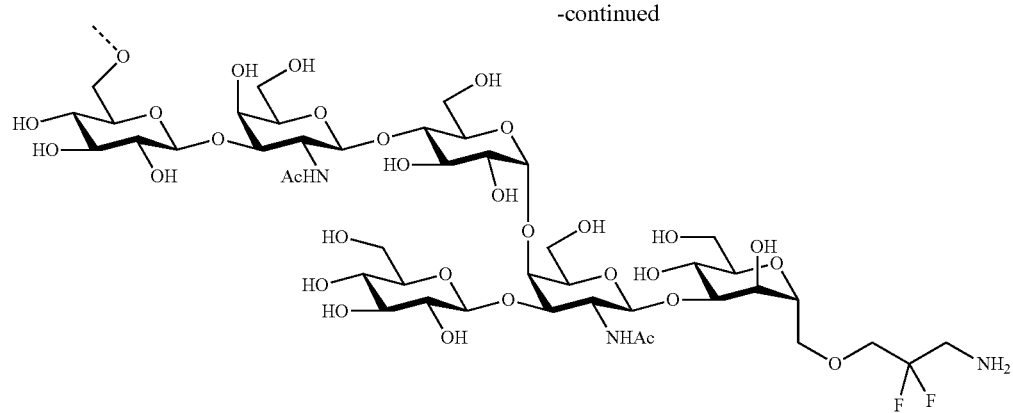
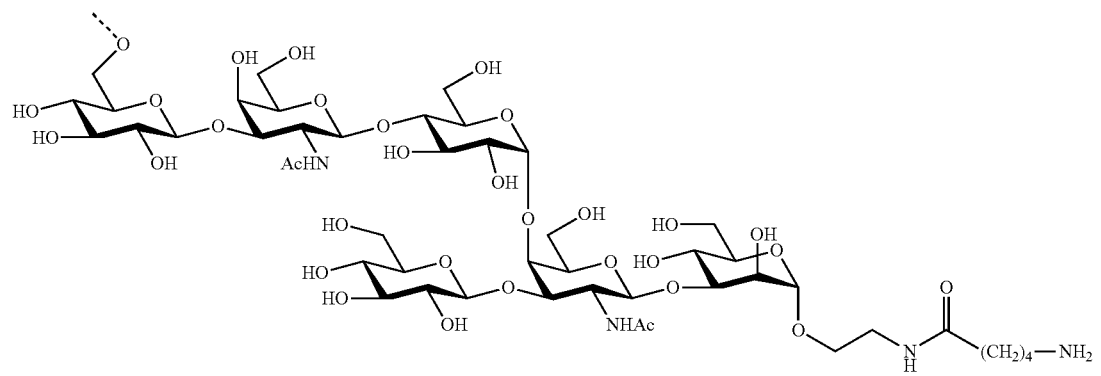
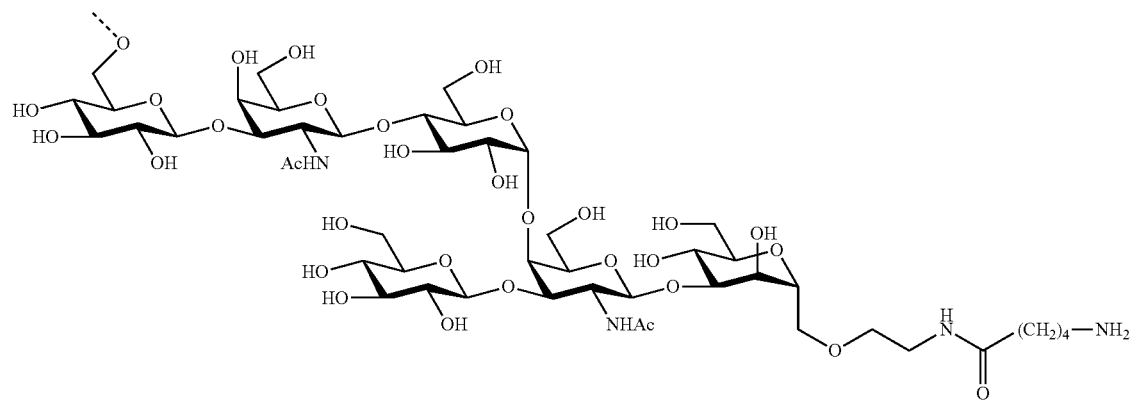
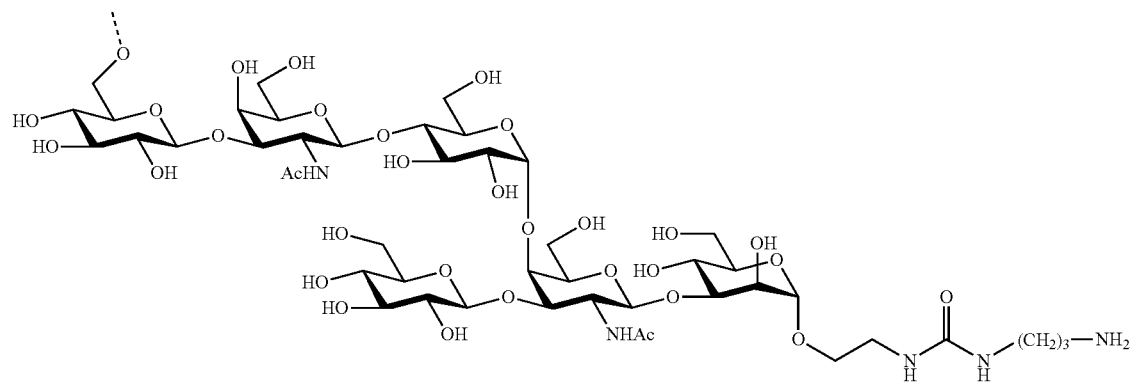

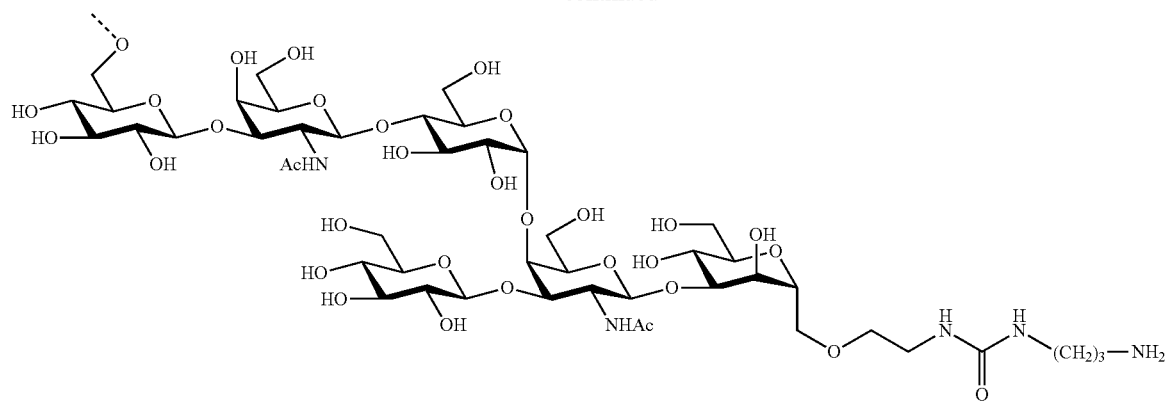
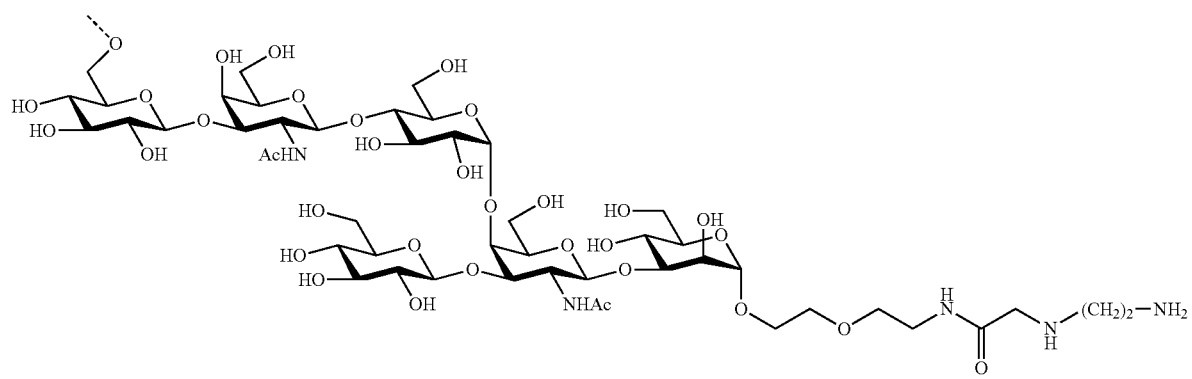
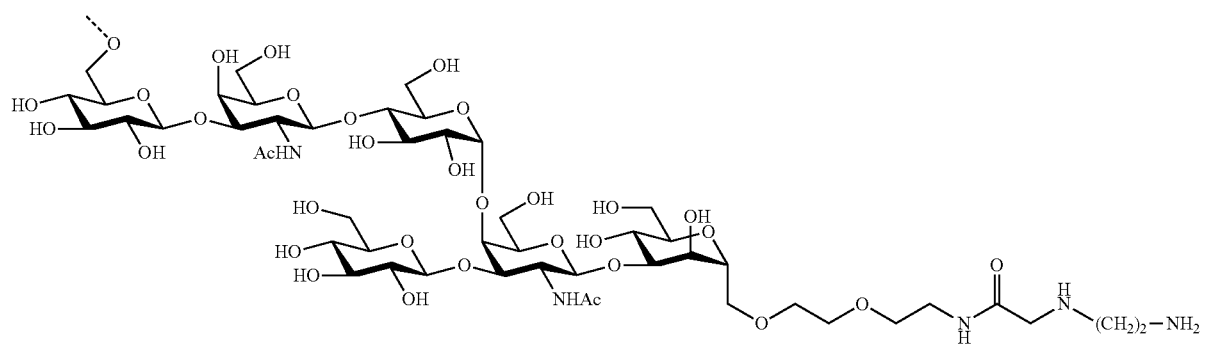
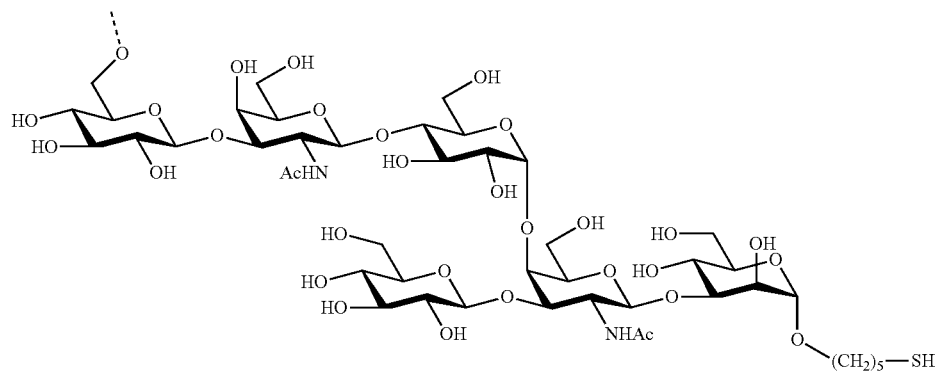

181 182
-continued
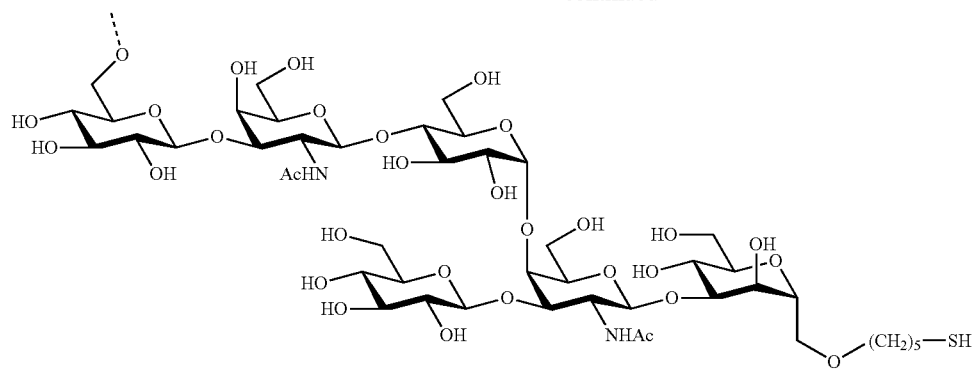
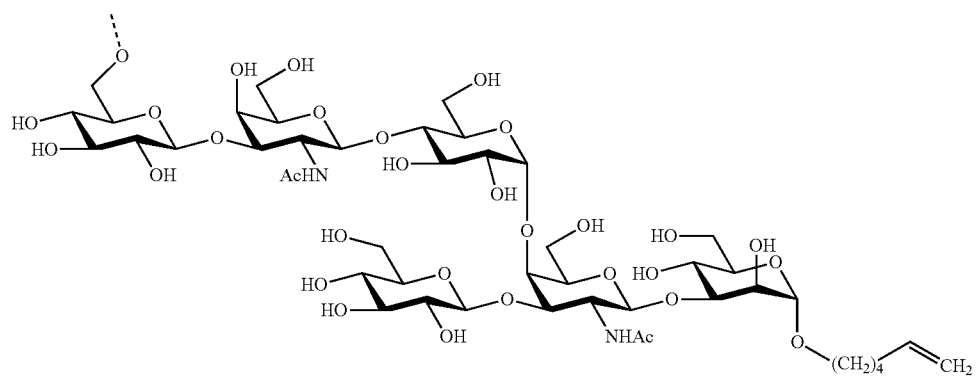
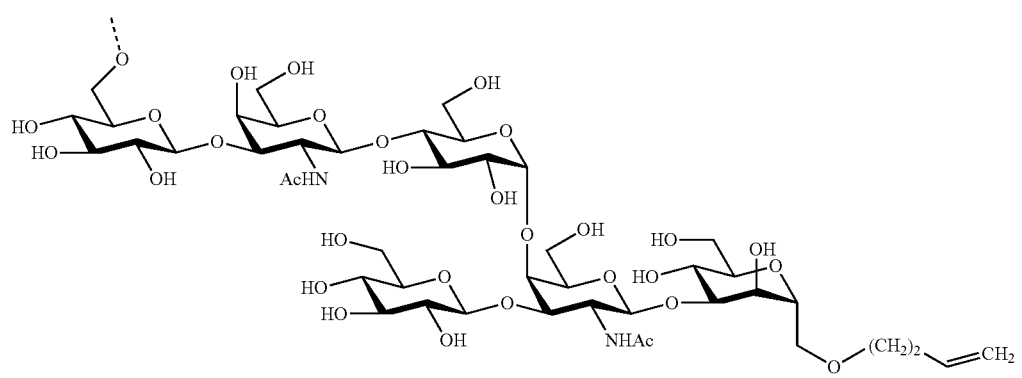
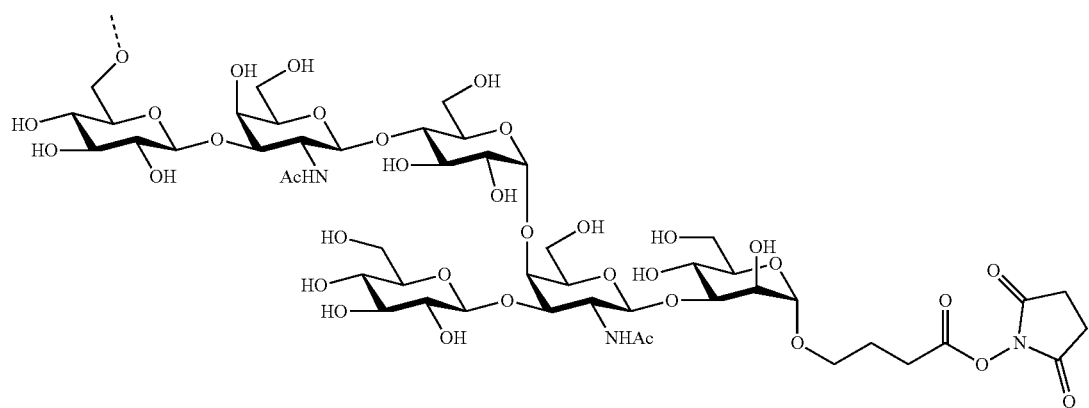

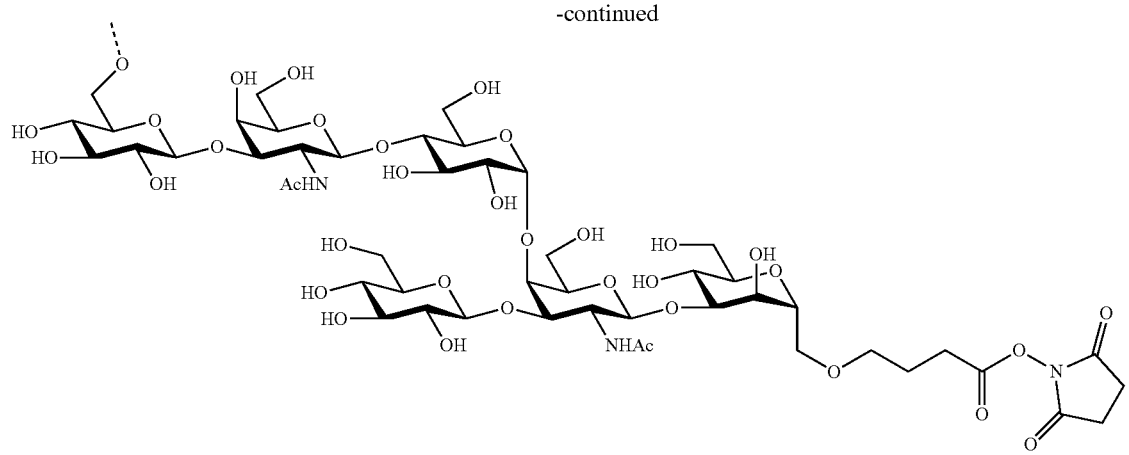
More preferred is a conjugate of any one of the formulae (V-1)-(V-4):
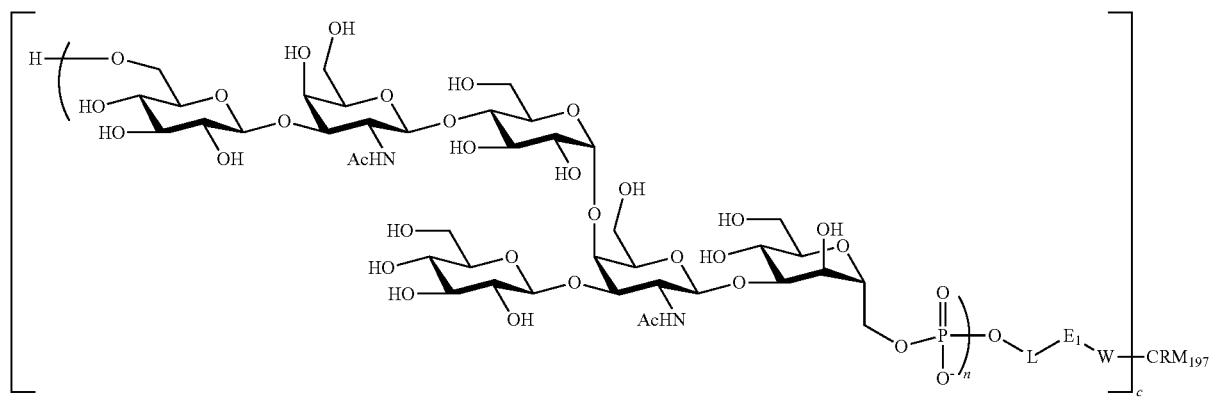
(V-1)
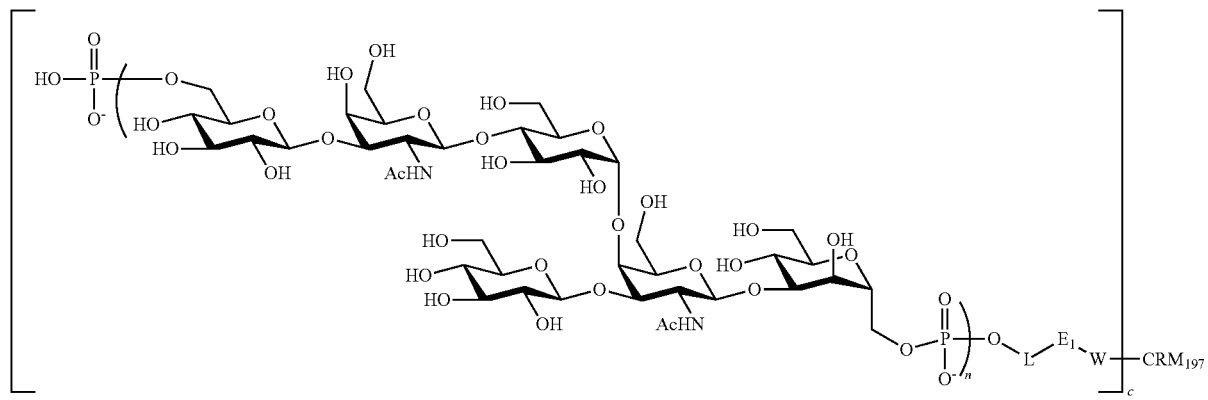
(V-2)

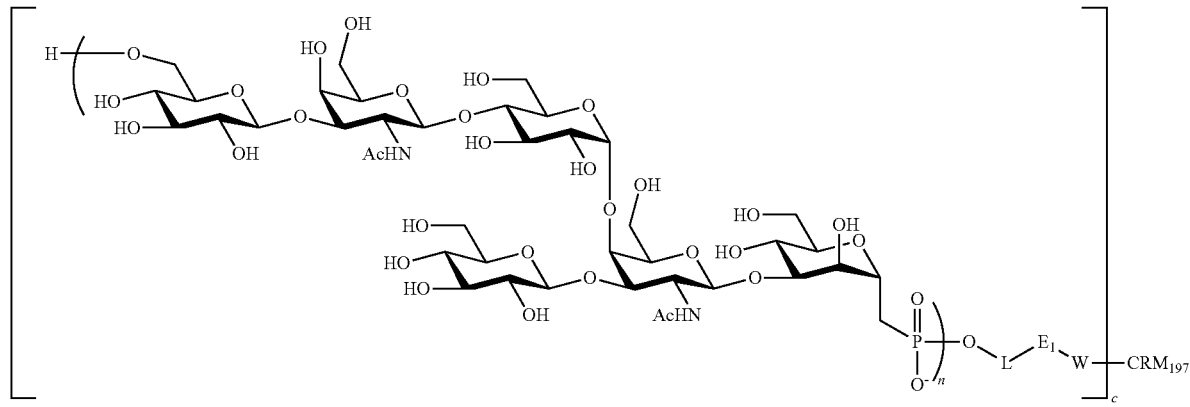

(V-3)

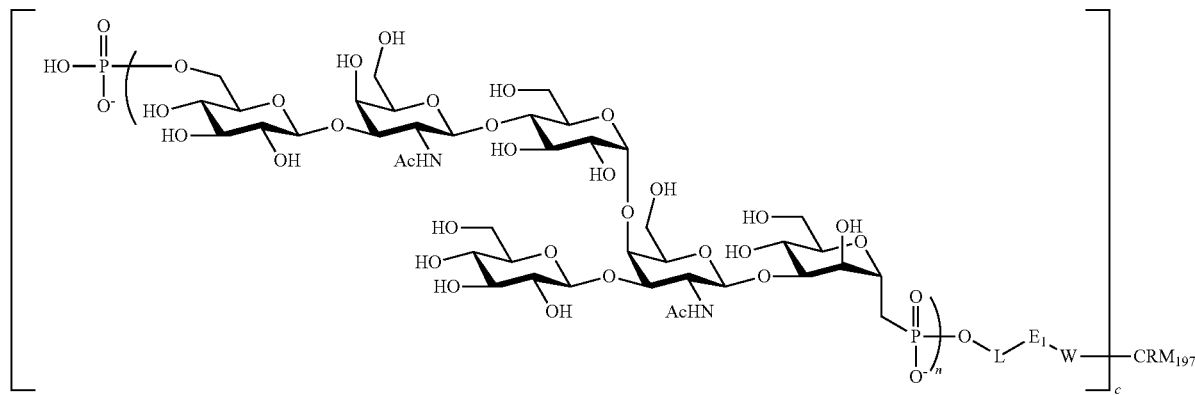

(V-4)

wherein L, $E_1$, W, c, and n have the same meanings as defined above.

More preferred is a conjugate of any one of the formulae (IV), (IV-1)-(IV-4), (V) and (V-1)-(V-4), wherein n is an integer from 1 to 3.

More preferred the conjugate of any one of the formulae (IV), (IV-1)-(IV-4), (V) and (V-1)-(V-4), wherein c is selected from 4 to 10.

Preferably —W— represents

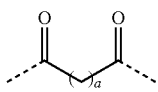

and a is an integer selected from 2, 3, 4, 5 and 6.

Thus, a conjugate of general formula (IV), (IV-1)-(IV-4), (V) and (V-1)-(V-4), wherein —W— represents

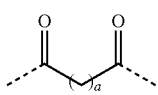

and a is an integer selected from 2, 3, 4, 5 and 6, is especially preferred.

Preferably, the linker -L- represents $L^a$, $-L^a-L^e-$, $-L^a-L^b-L^e-$, or $-L^a-L^d-L^e-$;

- $-L^a-$ represents $—(CH_2)_o—$, $—(CH_2—CH_2—O)_o—C_2H_4—$, or $—(CH_2—CH_2—O)_o—CH_2$;
- $-L^b-$ represents $—O—$;
- $-L^d-$ represents $—(CH_2)_q—$, $—(CH(OH))_q—$, $—(CF_2)_q—$, $—(CH_2—CH_2—O)_q—C_2H_4—$, or $—(CH_2—CH_2—O)_q—CH_2—$;
- $-L^e-$ represents $—(CH_2)_{p1}—$, $—(CF_2)_{p1}—$, $—C_2H_4—(O—CH_2—CH_2)_{p1}—$, $—CH_2—(O—CH_2—CH_2)_{p1}—$ or $(CH_2)_{p1}—O—(CH_2)_{p2}—$; and
- o, q, p1 and p2 are independently of each other an integer selected from 1, 2, 3, 4, 5, and 6

In the most preferred embodiment, $E_1$ is a covalent bond, —NH—, —CH=CH—, —CONH—,

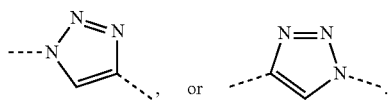

Also preferred is a conjugate of general formula (IV), (IV-1)-(IV-4), (V) and (V-1)-(V-4) wherein the group —O-L-E is selected from the group consisting of:

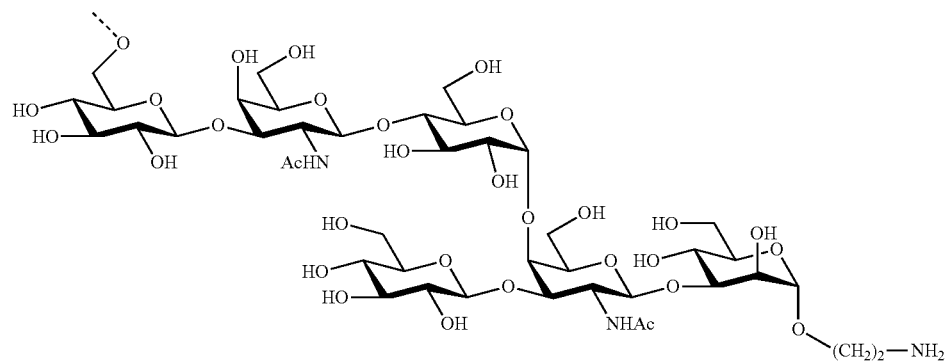
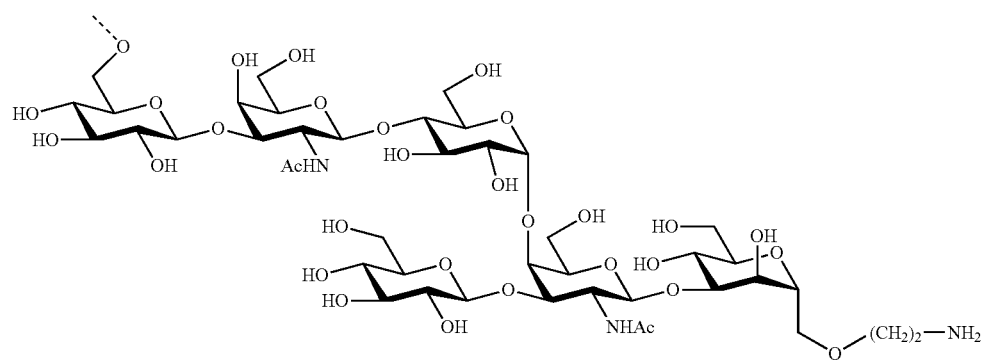
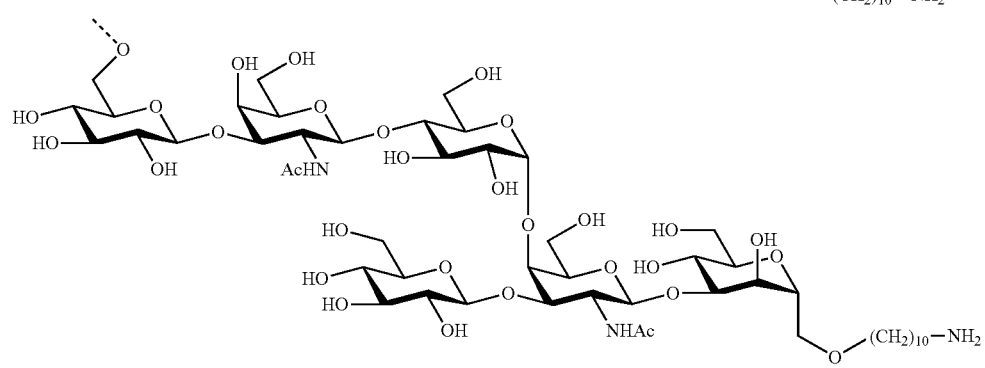

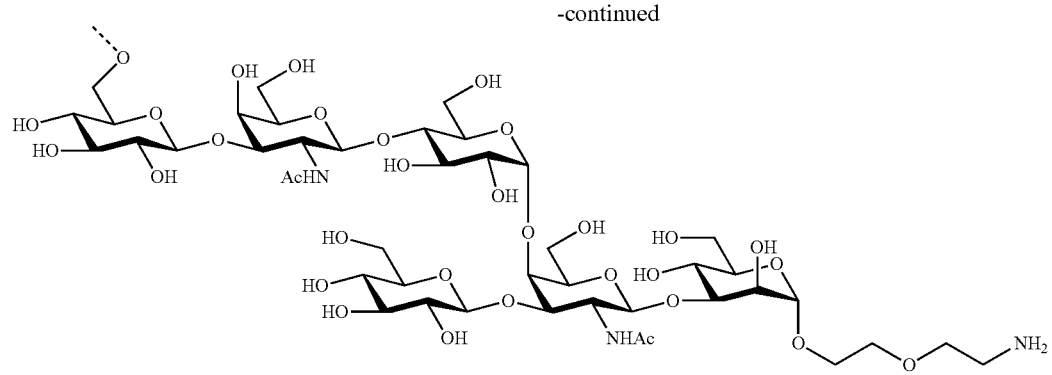
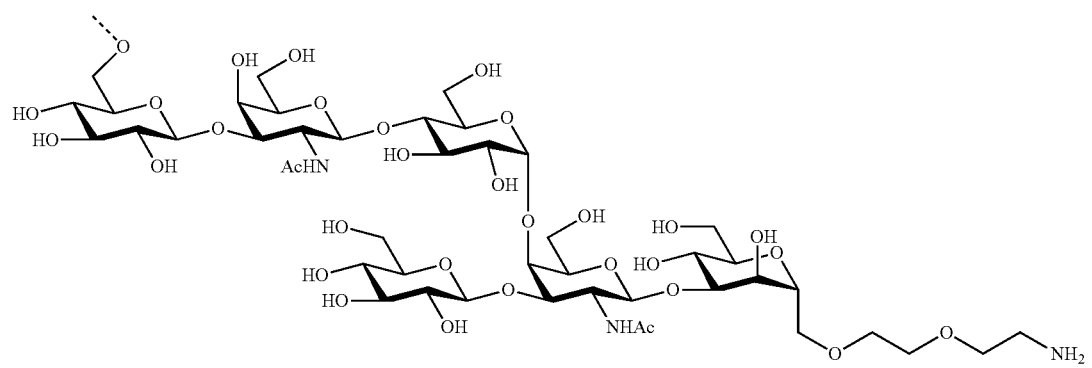
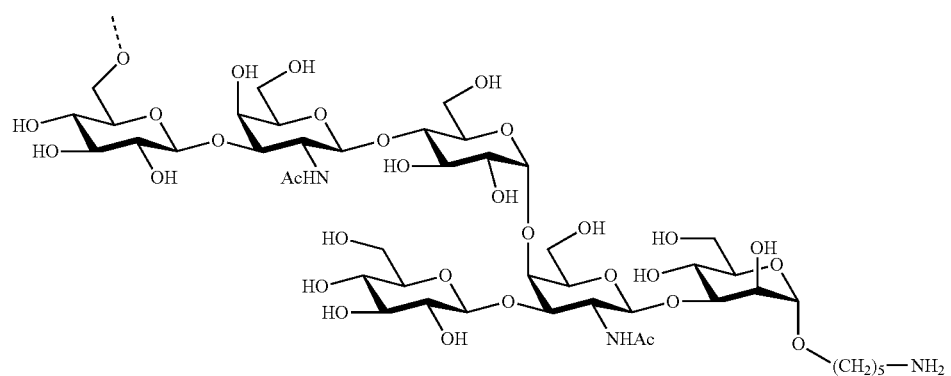
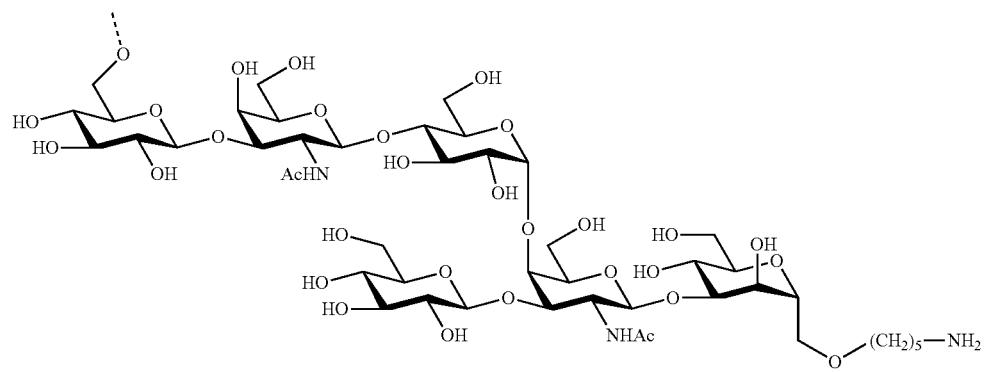

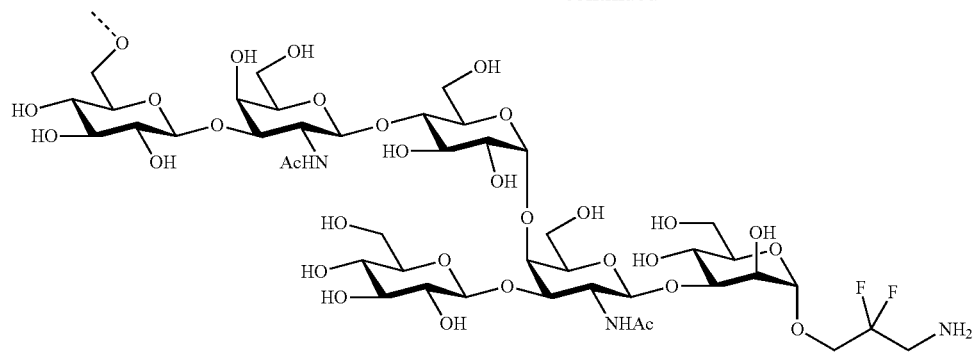
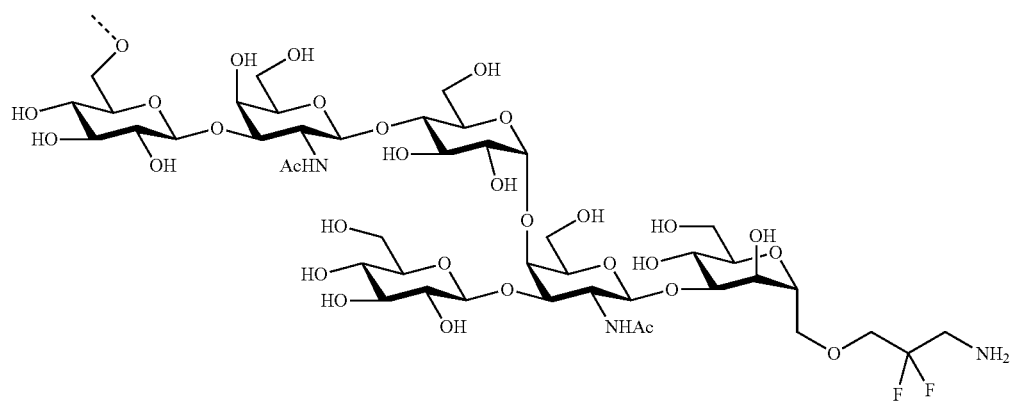
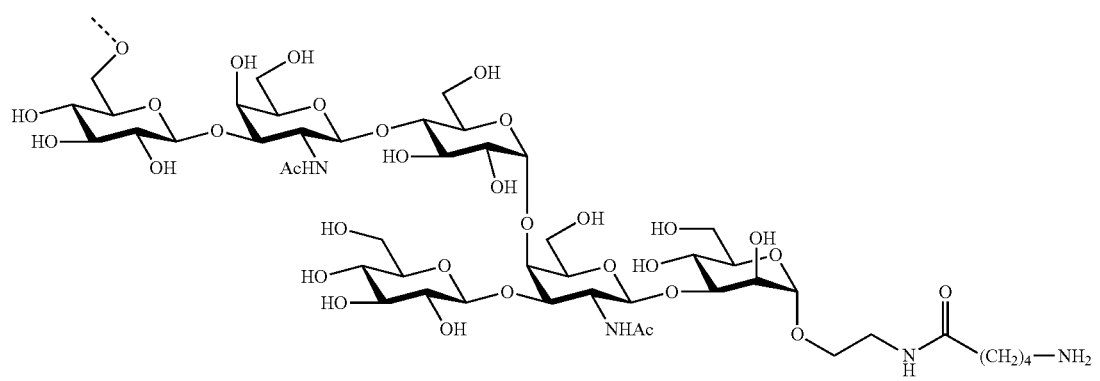
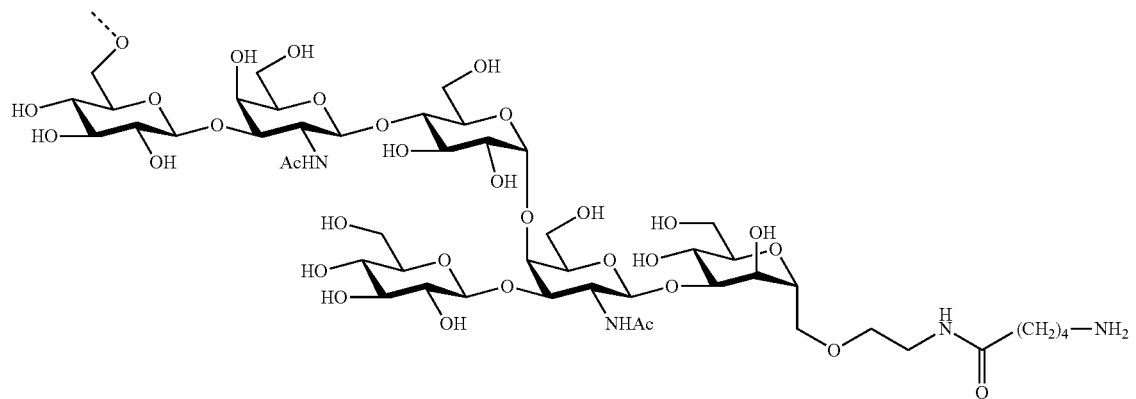

193                                                      194
-continued
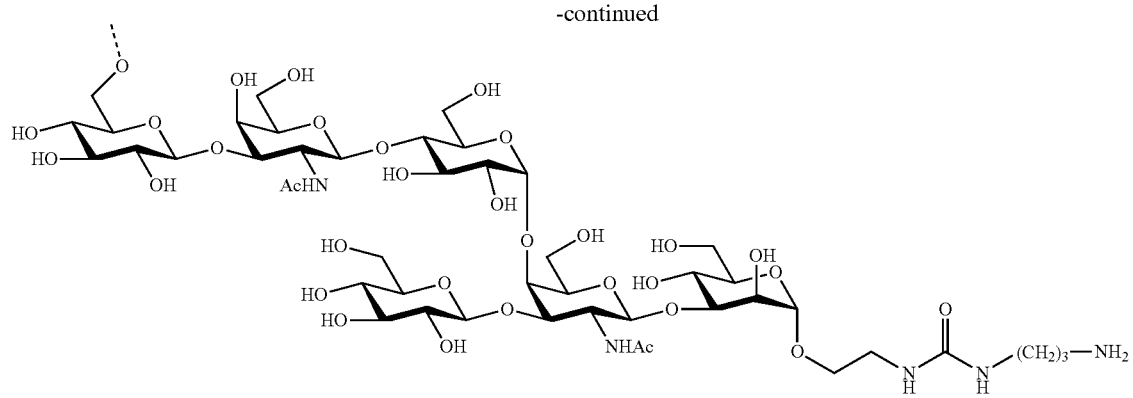
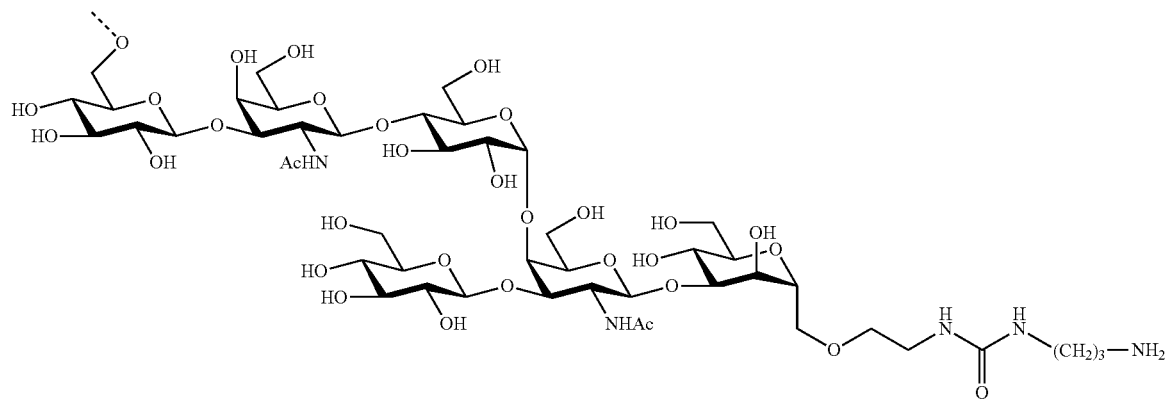
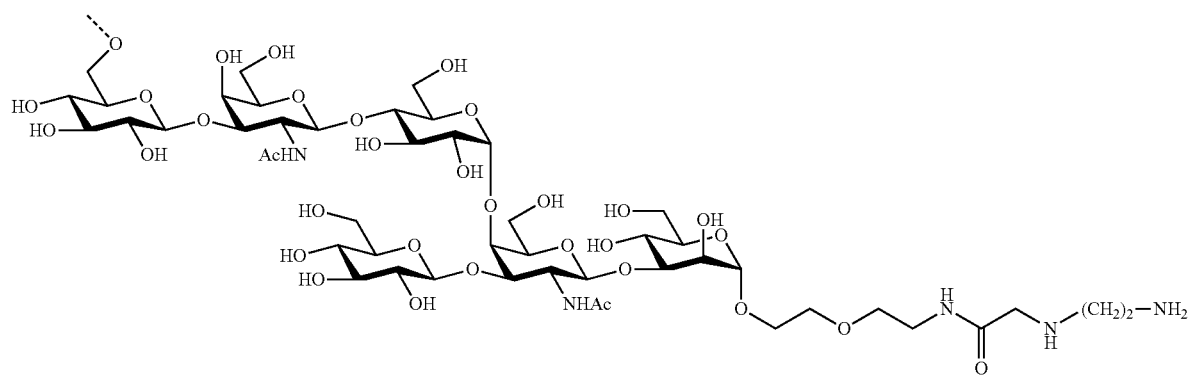
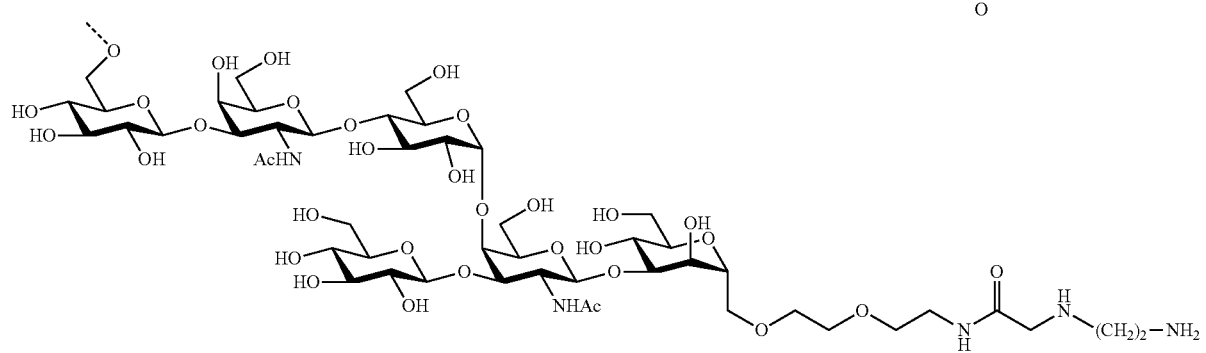

195
196
-continued
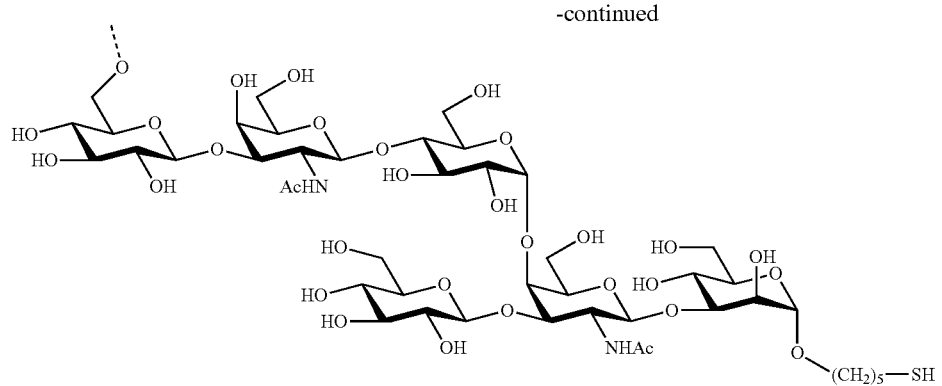
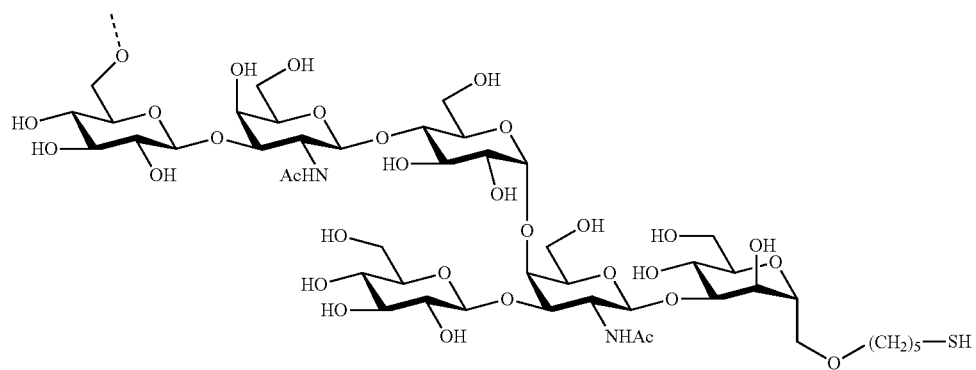
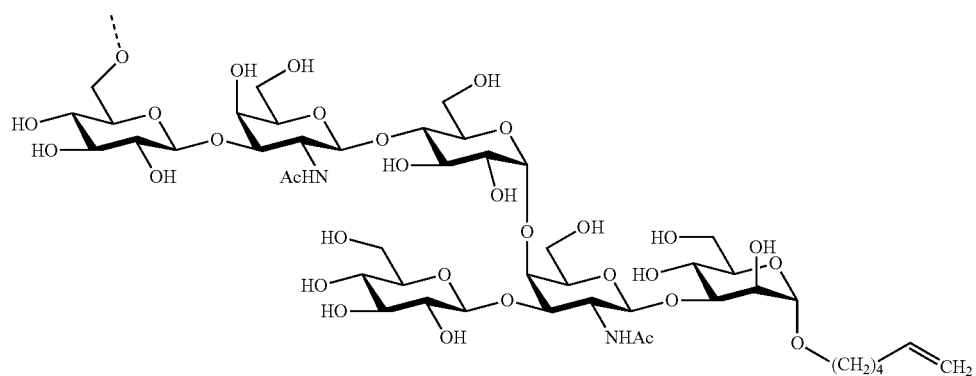
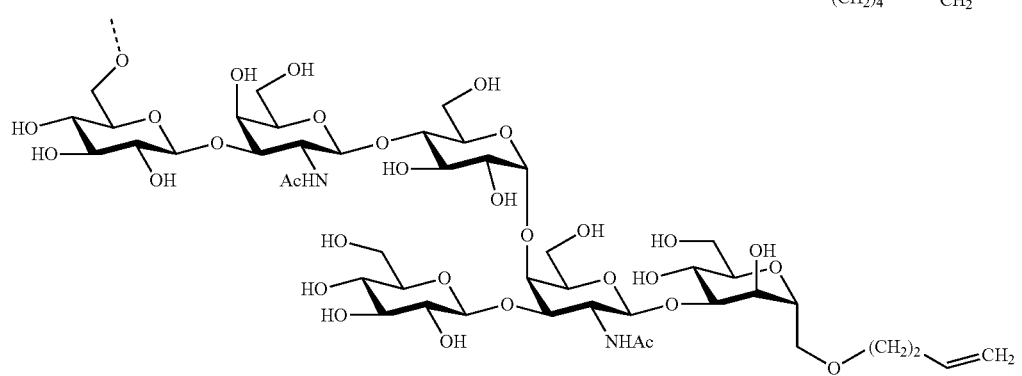

-continued

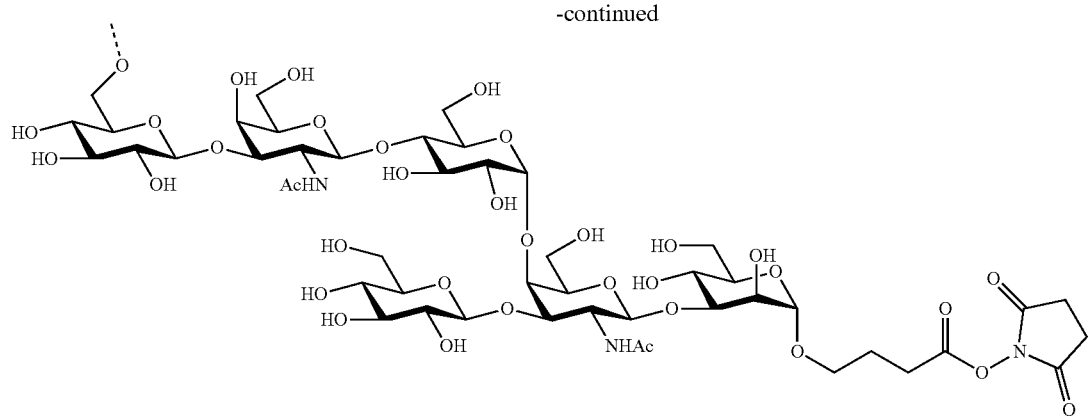

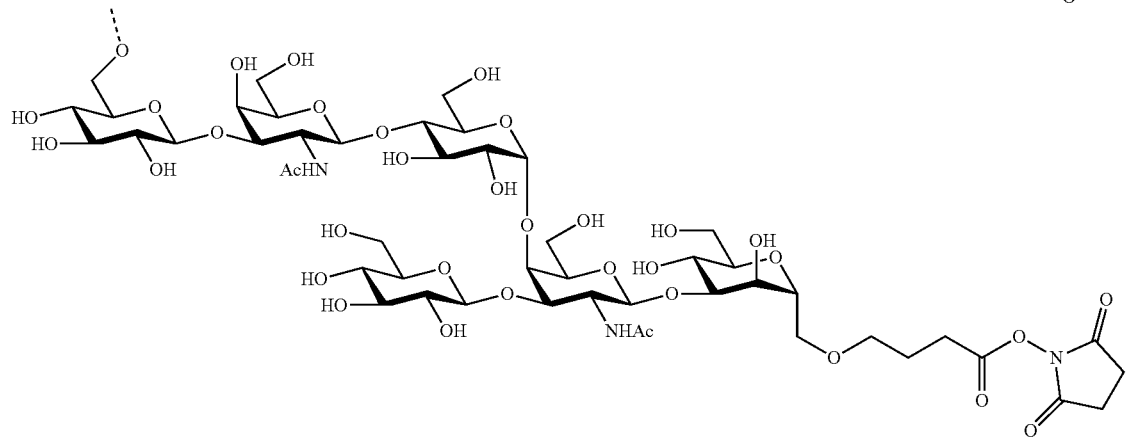

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci.* USA, 1998, 95, 5690).

The conjugates of the saccharides of general formula I with a glycosphingolipid with immunomodulatory properties have the advantage of being heat stable. To be suitable for conjugation, on the glycosphingolipid with immunomodulatory properties a functionality is introduced. Said functionality is prone to react directly with the terminal amino group of the linker of the saccharides of general formula I to provide conjugates of the saccharides of general formula I, or with the functional group Y of the interconnecting molecule to provide the modified glycosphingolipid with immunomodulatory properties.

Preferably, said functionality is introduced at the C6 of the carbohydrate moiety of the glycosphingolipid with immunomodulatory properties. Thus, the glycosphingolipid with immunomodulatory properties is functionalized with a functionality, which is prone of reacting with the terminal amino group of the saccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride. A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the C6 of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS), 2-pyridyldithiols.

Said functional group X of the interconnecting molecules is selected of the group comprising or consisting of maleimide, α-iodoacetyl, α-bromoacetyl, N-hydroxysuccinimide ester (NHS), aldehyde, carboxylic acid, epoxyde, alkyl sulfonate, sulfonyl chloride, anhydride, carbonate.

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

Vaccines containing at least one conjugate of the present invention cause fewer side effects and/or non-protective immune responses in comparison to vaccines containing isolated (and not synthesized) mixtures of saccharides obtained by non-selective cleavage of the capsular polysaccharide of *C. difficile* or conjugates thereof. Moreover the inventive vaccines can be easier manufactured in accordance with the GMP regulations than the vaccines containing isolated mixtures of non-selectively cleaved capsular polysaccharides and are easier characterized, which makes stability and purity control easier as well as detection of kind and amount of impurities.

It was found that a conjugate comprising a saccharide of any one of general formulae (I), (II), (II-a), (II-b), (III), (III-a) or (III-b), and particularly a conjugate of any one of general formulae (IV), (IV-1)-(IV-4), (V) and (V-1)-(V-4), elicits a protective immune response in a human and/or animal host, and therefore is useful for prevention and/or treatment of diseases associated with *Clostridium difficile* bacteria. Thus, the conjugates comprising the saccharides of general formula (I) conjugated to an immunogenic carrier are useful for prevention and/or treatment of diseases associated with *Clostridium difficile* bacteria containing in their cell-wall saccharide one of the following saccharide fragments:

-6)-β-D-Glc-(1, 3)-β-D-GalNAc-(1, 4)-α-D-Glc-(1, 4)-[β-D-Glc-(1, 3)]-β-D-GalNAc-(1, 3)-α-D-Man-(1-;
-3)-α-D-Man-(1, 6)-β-D-Glc-(1, 3)-β-D-GalNAc-(1, 4)-α-D-Glc-(1, 4)-[β-D-Glc-(1, 3)]-β-D-GalNAc-(1;
-4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1;
-4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1;
-3)-β-D-GalNAc-(1, 4)-α-D-Glc-(1, 4)-[β-D-Glc-(1, 3)]-β-D-GalNAc-(1, 3)-α-D-Man-(1, 6)-β-D-Glc-(1.

Preferably, the bacterium containing in their cell-wall saccharide one of the above mentioned saccharide fragments is *Clostridium difficile*.

In a preferred embodiment, the conjugates comprising the saccharides of general formula I conjugated to an immunogenic carrier are useful for prevention and/or treatment of diseases associated with bacteria, and particularly with diseases associated with bacteria containing in their cell-wall polysaccharide one of the following saccharide fragments:
−6)-β-D-Glc-(1, 3)-β-D-GalNAc-(1, 4)-α-D-Glc-(1, 4)-[β-D-Glc-(1, 3)]-β-D-GalNAc-(1, 3)-α-D-Man-(1-; -3)-α-D-Man-(1, 6)-β-D-Glc-(1, 3)-β-D-GalNAc-(1, 4)-α-D-Glc-(1, 4)-[β-D-Glc-(1, 3)]-β-D-GalNAc-(1; −4)-[β-D-Glc-(1, 3)]-β-D-GalNAc-(1, 3)-α-D-Man-(1, 6)-β-D-Glc-(1, 3)-β-D-GalNAc-(1; −4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1; −3)-β-D-GalNAc-(1, 4)-α-D-Glc-(1, 4)-[β-D-Glc-(1, 3)]-β-D-GalNAc-(1, 3)-α-D-Man-(1, 6)-β-D-Glc-(1, and preferably with *Clostridium difficile*, wherein said diseases include diarrhea, pseudomembranous colitis and paralytic ileus.

Pharmaceutical Compositions

Another aspect of the present invention is directed to a pharmaceutical composition or a vaccine comprising at least one conjugate that comprises a saccharide of general formula (I) conjugated to an immunogenic carrier and/or at least one saccharide of general formula (I) together with at least one pharmaceutically acceptable adjuvant and/or excipient. Said pharmaceutical composition can be used for raising a protective immune response in a human and/or animal host. Ideally, the pharmaceutical composition is suitable for use in humans.

In another aspect of the present invention, said pharmaceutical composition or vaccine further comprises at least one cell-well saccharide or cell-wall saccharide fragment and/or protein conjugates thereof of *Clostridium difficile* bacteria selected from the group comprising or consisting of *Clostridium difficile* strains, 027, MOH718 and MOH900.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to oil emulsions (e.g. Freund's adjuvant), saponins, aluminum or calcium salts (e.g. alum), non-ionic block polymer surfactants, and many others.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions may include a physiological salt, such as a sodium salt e.g. to control tonicity. Sodium chloride (NaCl) is typical and may be present at between 1 and 20 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg.

Pharmaceutical compositions may include compounds (with or without an insoluble metal salt) in plain water (e.g. w.f.i.), but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range.

Pharmaceutical compositions typically have a pH between 5.0 and 9.5 e.g. between 6.0 and 8.0.

Pharmaceutical compositions are preferably sterile and gluten free.

Pharmaceutical compositions are suitable for administration to animal (and, in particular, human) patients, and thus include both human and veterinary uses. They may be used in a method of raising an immune response in a patient, comprising the step of administering the composition to the patient.

The pharmaceutical compositions of the present invention may be administered before a subject is exposed to *C. difficile* and/or after a subject is exposed to *C. difficile* bacteria.

In another aspect of the present invention, the present invention is directed to the use of at least one conjugate that comprises at least one saccharide of general formula (I) conjugated to an immunogenic carrier and/or at least one saccharide of general formula (I) for the manufacture of said pharmaceutical composition or said vaccine for prevention and/or treatment of diseases associated with *C. difficile* bacteria, particularly, diseases associated with *C. difficile* bacteria is selected from the group comprising or consisting of diarrhea, pseudomembranous colitis and paralytic ileus.

Preferred, the present invention refers to the use of at least one saccharide of any one of general formulae (I), (II), (II-a), (II-b), (III), (III-a) or (III-b) and/or at least one of the conjugates comprising at least one saccharide of any one of general formulae (I), (I), (II), (II-a), (II-b), (III), (III-a) or (III-b) for the manufacture of said pharmaceutical composition or said vaccine.

More preferred, the present invention refers to the use of at least one of the saccharides I'a-1-I'a-11, I'b-1-I'b-11 and I'c-1-I'c-11 and/or at least one of the conjugates comprising at least one of the saccharides I'a-1-I'a-11, I'b-1-I'b-11 and I'c-1-I'c-11 for the manufacture of said pharmaceutical composition or said vaccine.

Particularly, the present invention refers to the use of at least one conjugate of any one of general formulae (IV), (IV-1)-(IV-4), (V) and (V-1)-(V-4) for the manufacture of said pharmaceutical composition or said vaccine.

Pharmaceutical compositions may be prepared in unit dose form. In some embodiments a unit dose may have a volume of between 0.1-1.0 mL e.g. about 0.5 mL.

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. by an inhaler, using a fine powder or a spray. The composition may be prepared as a suppository. The composition may be prepared for nasal, aural or ocular administration e.g. as a spray or drops. Injectables for intramuscular administration are typical.

The pharmaceutical compositions may comprise an effective amount of an adjuvant i.e. an amount which, when administered to an individual, either in a single dose or as part of a series, is effective for enhancing the immune response to a co-administered *C. difficile* PS-II saccharide antigen.

This amount can vary depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range that can be determined through routine trials.

Formulation and administration of the vaccine of the present invention may be achieved according to any known method in the art.

A therapeutically effective dosage of one conjugate according to the present invention or of one saccharide of general formula (I) refers to that amount of the compound that results in an at least a partial immunization against a disease.

Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgment of the prescribing physician.

Another aspect of the present invention is directed to a method of inducing immune response against *C. difficile* in a human and/or animal host, said method comprising administering of the saccharide of general formula (I) and/or salt thereof and/or a conjugate thereof or pharmaceutical composition thereof to said human and/or animal host. A method of treating or preventing diseases caused by *C. difficile*, in a human and/or animal host according to the present invention comprises administering of at least one saccharide of general formula (I) and/or salt thereof and/or a conjugate thereof or pharmaceutical composition thereof to said human and/or animal host.

Immunological Assays

Yet another aspect of the present invention refers to saccharide of general formula (I) for use as marker in immunological assays for detection of antibodies against bacteria containing in their cell-wall polysaccharide one of the following saccharide fragments:

-6)-β-D-Glc-(1, 3)-β-D-GalNAc-(1, 4)-α-D-Glc-(1, 4)-[β-D-Glc-(1, 3)]-β-D-GalNAc-(1, 3)-α-D-Man-(1-;

-3)-α-D-Man-(1, 6)-β-D-Glc-(1, 3)-β-D-GalNAc-(1, 4)-α-D-Glc-(1, 4)-[β-D-Glc-(1, 3)]-β-D-GalNAc-(1;

-4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1;

-4)-α-D-Glc-(1, 4)-[β-D-Glc-(1, 3)]-β-D-GalNAc-(1, 3)-α-D-Man-(1, 6)-β-D-Glc-(1, 3)-β-D-GalNAc-(1;

-3)-β-D-GalNAc-(1, 4)-α-D-Glc-(1, 4)-[β-D-Glc-(1, 3)]-β-D-GalNAc-(1, 3)-α-D-Man-(1, 6)-β-D-Glc-(1.

Such assays comprise, for instance, microarray and ELISA useful for detection of antibodies against bacteria containing in their cell-wall polysaccharide one of the above mentioned saccharide fragments, such as *C. difficile*.

The saccharides of the present invention can be easily conjugated to solid supports for providing immunological assays useful for detection of antibodies against *C. difficile*. Said solid supports present on their surface a functionality that is prone to react with the amino group of saccharides of general formula (I) or with the functional group Y of the interconnecting molecule to provide modified solid supports, presenting on their surface the functional group X of the interconnecting molecule that can further react with the amino group of saccharides of general formula (I). In an embodiment according to the present invention the solid supports are microarray slides, which present on their surface a functionality that is prone to react with the functional group Y of the interconnecting molecule to provide modified microarray slides, presenting of their surface the functional group X of the interconnecting molecule. Examples of such microarray slides include, but are not restricted to Corning® epoxide coated slides or Corning® GAPS™ II coated slides.

In a preferred embodiment the solid supports are microarray slides presenting on their surface a functionality that is prone to react with the amino group of saccharides of general formula (I), and more preferably an N-hydroxysuccinimide (NHS) activated ester. Such microarray slides are for example CodeLink® NHS slides.

DESCRIPTION OF THE FIGURES

FIG. 2 provides examples of functional group X of the interconnecting molecule according to the present invention.

Figure 1:
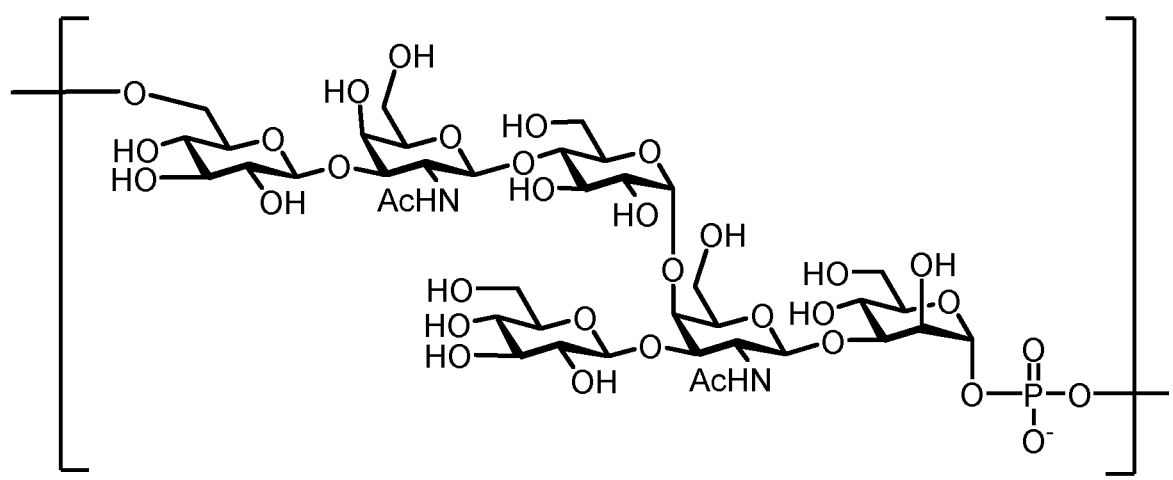
FIG. 1 shows the chemical structure of the repeating unit of C. difficile PS-II cell-wall saccharide.
Figure 3:
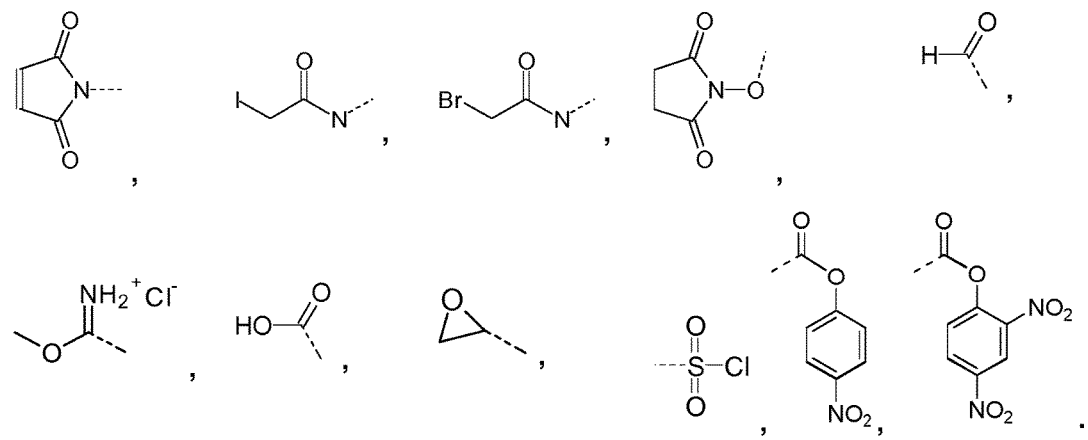
FIG. 3 provides examples of functional group X of the interconnecting molecule according to the present invention.
Figure 4:
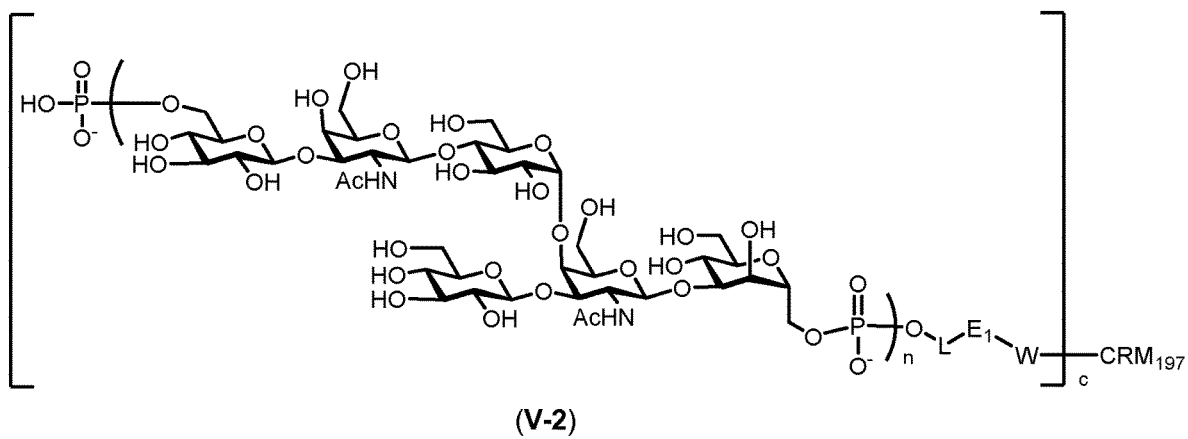
FIG. 4 shows a $CRM_{197}$ conjugate of the general formula (V-2) as preferred compounds of the present application.
Figure 5:
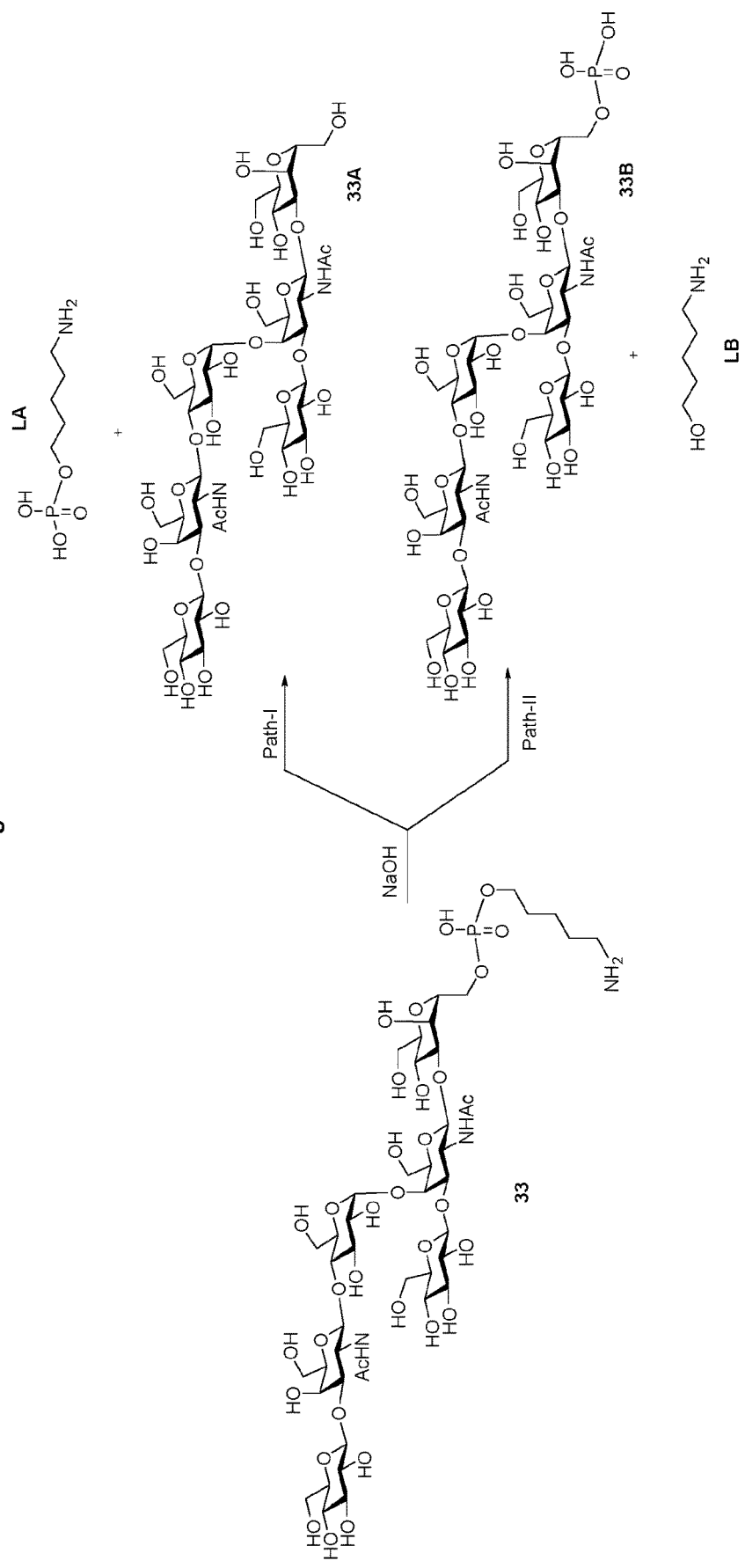
FIG. 5 shows two paths how the compound 33 could be cleaved by NaOH treatment. Path I shows the cleavage at the phosphate group where the phosphate group remains at the linker part and compound LA, 5-aminopentyl dihydrogen phosphate, is formed. Path II shows the cleavage at the phosphate group where the phosphate group remains at the saccharide moiety (compound 33B) and compound LB, 5-aminopentane-1-ol, is formed.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

A. Chemical Synthesis

General Information:

Commercial grade solvents were used unless stated otherwise. Dry solvents were obtained from a Waters Dry Solvent System. Solvents for chromatography were distilled prior to use. Sensitive reactions were carried out in heat-dried glassware and under an argon atmosphere. Analytical thin layer chromatography (TLC) was performed on Kieselgel 60 F254 glass plates precoated with a 0.25 mm thickness of silica gel. Spots were visualized by staining with vanillin solution (6% (w/v) vanillin and 10% (v/v) sulfuric acid in 95% EtOH) or Hanessian's stain (5% (w/v) ammonium molybdate, 1% (w/v) cerium(II) sulfate and 10% (v/v) sulfuric acid in water). Silica column chromatography was performed on Fluka Kieselgel 60 (230-400 mesh).

$^1H$, $^{13}C$ and two-dimensional NMR spectra were measured with a Varian 400-MR spectrometer at 296 K. Chemical shifts (d) are reported in parts per million (ppm) relative to the respective residual solvent peaks ($CDCl_3$: d 7.27 in $^1H$ and 77.23 in $^{13}C$ NMR; $CD_3OD$: d 3.31 in $^1H$ and 49.15 in $^{13}C$ NMR). The following abbreviations are used to indicate peak multiplicities: s singlet; d doublet; dd doublet of doublets; t triplet; dt doublet of triplets; q quartet; m multiplet. Coupling constants (J) are reported in Hertz (Hz). Optical rotation (OR) measurements were carried out with a Schmidt & Haensch UniPol L1000 polarimeter at λ=589 nm and a concentration (c) expressed in g/100 mL in the solvent noted in parentheses. High resolution mass spectrometry (HRMS) was performed at the Free University Berlin, Mass Spectrometry Core Facility, with an Agilent 6210 ESI-TOF mass spectrometer. Infrared (IR) spectra were measured with a Perkin Elmer 100 FTIR spectrometer.

A.1 Abbreviations

ACN acetonitrile
AcOH acetic acid
AIBN azobisisobutyronitrile
Alhydrogel Aluminium Hydroxide Gel Adjuvant, Al: 10 mg/mL (Brenntag)
Alloc allyloxycarbonyl
aq. aqueous
$BH_3$ borane
$BBr_3$ boron tribromide
Boc tert-butoxycarbonyl
BnBr benzyl bromide br. broad
CAS CAS Registry Number (CAS=Chemical Abstracts Service)
CHCl$_3$ chloroform
cHex cyclohexane
d doublet
dd doublet of doublets
DCM dichloromethane
DDQ 2,3-dichloro-5,6-dicyano-1,4-benzoquinone
DEAD diethyl azodicarboxylate
DIPEA N,N-diisopropyl-ethylamine
DMAP dimethylaminopyridine
DME dimethoxyethane
DMF dimethylformamide
DMSO dimethylsulfoxide
DPPA diphenylphosphoryl azide
EDC.HCl N1-((ethylimino)methylene)-N3,N3-dimethyl-propane-1,3-diamine hydrochloride
ES electrospray
Et$_2$O diethyl ether
EtOAc ethyl acetate
FCS fetal calf serum
FmocCl 9-fluorenylmethoxycarbonyl chloride
GSDMD Gasdermin-D
h hour
HCl hydrochloric acid
HEK293T embryonic kidney fibroblast cell line
H$_2$O water
HOBt.H$_2$O 1H-benzo[d][1,2,3]triazol-1-ol hydrate
hPBMC human Peripheral Blood Mononuclear Cells
IC$_{50}$ half maximal inhibitory concentration
K$_2$CO$_3$ potassium carbonate
LDH lactate dehydrogenase
LiAlH$_4$ lithium aluminium hydride
m multiplet
MeCN acetonitrile
MeOH methanol
MeI methyl iodide
MgSO$_4$ magnesium sulphate
min minutes
MS mass spectrometry
Na$_2$CO$_3$ sodium carbonate
NaCNBH$_3$ sodium cyanoborohydride
NaHCO$_3$ sodium hydrogencarbonate
NaH sodium hydride
NaOH sodium hydroxide
NAP 2-naphthylmethyl
NapBr 2-naphthylmethylbromide
NaPi buffer phosphate-buffered saline (PBS)
Na$_2$SO$_4$ sodium sulphate
NBS N-bromosuccinimide
NCS N-chlorosuccinimide
NET neutrophil extracellular traps
NIS N-iodosuccinimide
NMR nuclear magnetic resonance
PBBBr p-bromobenzylbromide
PBS=NaPi phosphate-buffered saline
Pd/C palladium on carbon
Pd(PPh$_3$)$_4$ Tetrakis(triphenylphosphine)palladium(0)
PMA phorbol 12-myristate 13-acetate
PPh$_3$ triphenylphosphine
PTFE polytetrafluoroethylene
q quartet
RBF round bottom flask
rt room temperature
s singlet
sat. saturated
sep septet
t triplet
TBAF tetrabutylammonium fluoride
TFA trifluoroacetic acid
THF tetrahydrofuran
THP1 acute monocytic leukaemia cancer cell line
TLC thin layer chromatography
TMSOTf trimethylsilyl trifluoromethanesulfonate
TsOH tosic acid
Wt weight A.2 Synthesis of Hexasaccharide 33

Synthesis of 2

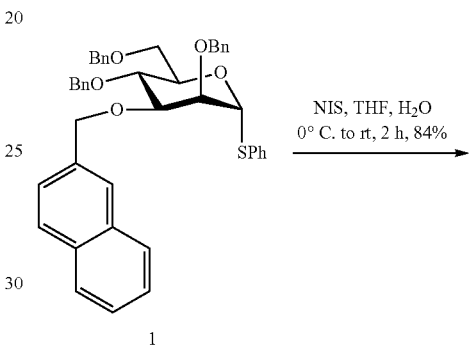

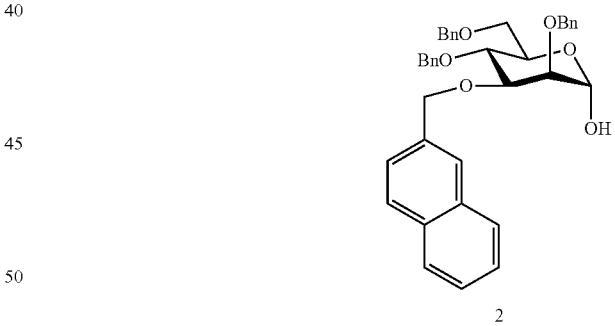

NIS (3.0 equiv.) was added to a cooled solution of 1 (obtained according to *Chem. Eur. J.* 2014, 20, 3578-3583) in THF:H$_2$O (4:1, 25 mL/1 g) at 0° C. After 10 min, reaction mixture was brought to rt and stirred for 2h. After complete consumption of starting material, THF was removed under reduced pressure and the obtained crude residue was dissolved in EtOAc and washed with aq. Na$_2$S$_2$O$_3$ and aq. NaHCO$_3$. Separated organic layer was dried over Na$_2$SO$_4$, concentrated and the crude product was purified by automated flash column chromatography on silica gel (0-60% EtOAc in cyclohexane) to afford the desired hemiacetal 2 (84%) as foam. HRMS (ESI+) Calculated for C$_{38}$H$_{38}$O$_6$Na$^+$ [M+Na]$^+$ 613.2566. found 613.2574.

Synthesis of 3

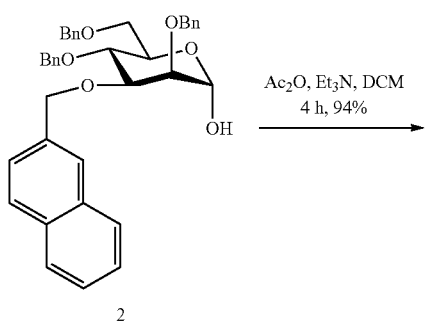

Ac₂O (2.0 equiv.) and trimethylamine (6.0 equiv.) were added to a clear solution of 2 in DCM (10 mL/1 g) and kept for stirring at rt for 4h. After complete consumption of starting material, solvents were removed under vacuum and the crude product was purified by automated flash column chromatography on silica gel (0-50% EtOAc in cyclohexane) to afford the desired product 3 (94%) as viscous liquid. HRMS (ESI+) Calculated for $C_{40}H_{40}O_7Na^+$ [M+Na]⁺ 655.2672. found 655.2679.

Synthesis of 4

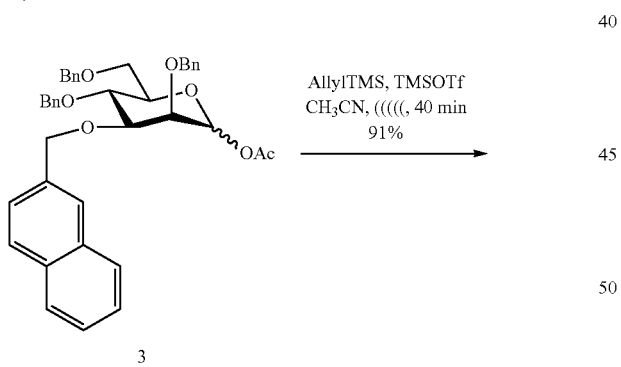

Allyl trimethylsilane (2.0 equiv.) was added to a clear solution of 3 in dry acetonitrile (20 mL/1 g) at room temperature and followed by dropwise addition of TMSOTf (0.5 equiv.). The flask was sealed and placed in an ultrasonic cleaning bath (frequency 80 Hz, 100% power 230 V, rt) until the reaction was complete by TLC (40 min)). After complete consumption of starting material, the reaction mixture was quenched with aq. NaHCO₃, diluted with EtOAc and washed with brine. The separated organic layers were dried over Na₂SO₄, concentrated and the crude product was purified by automated flash column chromatography on silica gel (0-60% EtOAc in cyclohexane) to afford the desired C-glycoside 4 as oil (91%). HRMS (ESI+) Calculated for $C_{41}H_{42}O_5Na^+$ [M+Na]⁺ 637.2930. found 637.2929.

Synthesis of 5

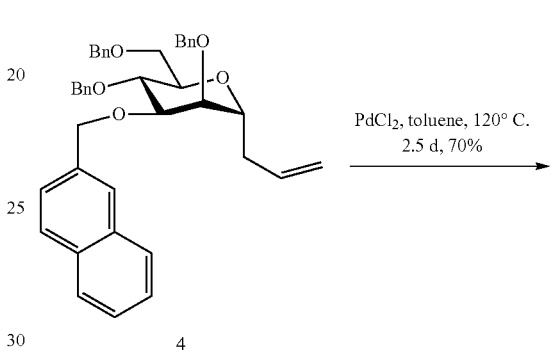

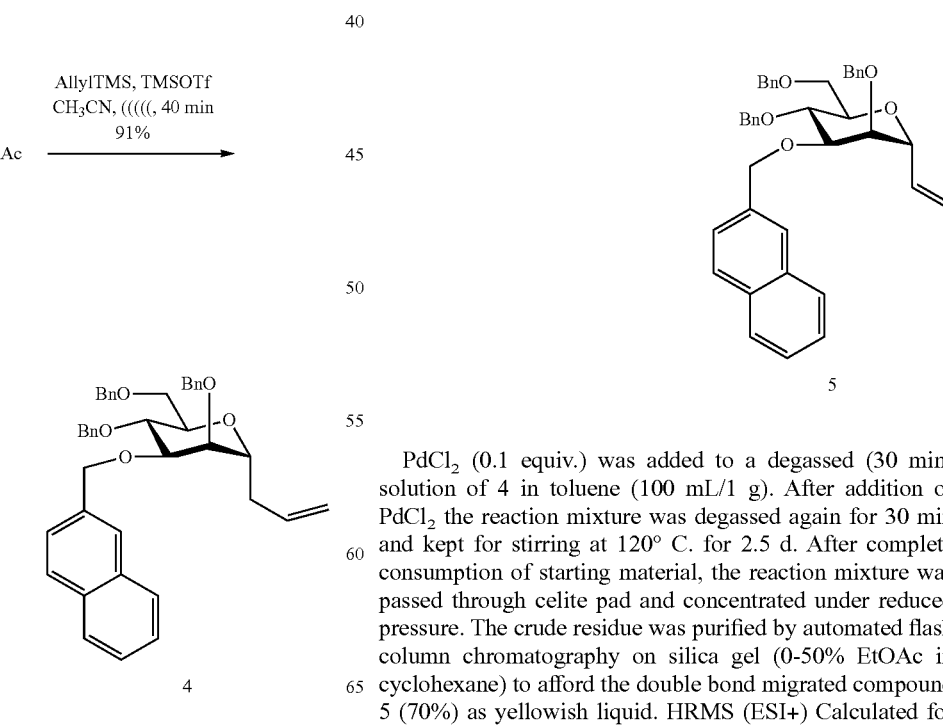

PdCl₂ (0.1 equiv.) was added to a degassed (30 min) solution of 4 in toluene (100 mL/1 g). After addition of PdCl₂ the reaction mixture was degassed again for 30 min and kept for stirring at 120° C. for 2.5 d. After complete consumption of starting material, the reaction mixture was passed through celite pad and concentrated under reduced pressure. The crude residue was purified by automated flash column chromatography on silica gel (0-50% EtOAc in cyclohexane) to afford the double bond migrated compound 5 (70%) as yellowish liquid. HRMS (ESI+) Calculated for $C_{41}H_{42}O_5Na^+$ [M+Na]⁺ 637.2930. found 637.2942.

Synthesis of 6

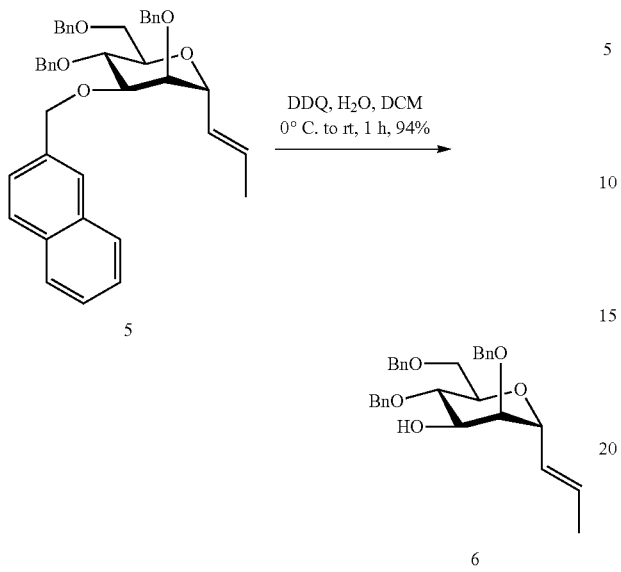

DDQ (1.2 equiv.) was added to a biphasic solution of 5 in DCM:H$_2$O (19:1, 20 mL/1 g) at 0° C. After 10 min at 0° C., the reaction mixture was warmed to room temperature and stirred at room temperature for 1 h. After complete consumption of starting material, reaction mixture was diluted with DCM and extracted with aq. NaHCO$_3$ and brine. The organic layer was dried over Na$_2$SO$_4$, filtered, and the filtrate was concentrated to obtain the crude product. The crude product was purified by automated flash chromatography on silica gel (0-80% EtOAc in cyclohexane) to give the desired product 6 as white oil (94%). HRMS (ESI+) Calculated for C$_{30}$H$_{34}$O$_5$Na$^+$ [M+Na]$^+$ 497.2304. found 497.2312.

Synthesis of 7

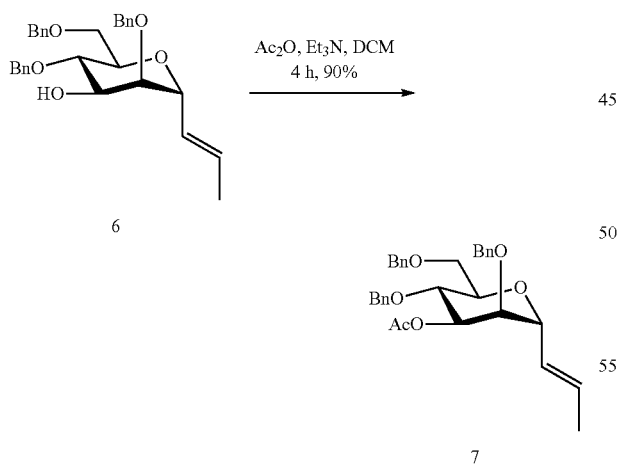

Ac$_2$O (2.0 equiv.) and trimethylamine (6.0 equiv.) were added to a clear solution of 6 in DCM (10 mL/1 g) and kept for stirring at rt for 4 h. After complete consumption of starting material, solvents were removed under vacuum and the crude product was purified by automated flash column chromatography on silica gel (0-50% EtOAc in cyclohexane) to afford the desired product 7 (90%) as viscous liquid. HRMS (ESI+) Calculated for C$_{32}$H$_{36}$O$_6$Na$^+$ [M+Na]$^+$ 539.2410. found 539.2419.

Synthesis of 8

Ozone was bubbled through a cooled solution of 7 in DCM:MeOH (1:1, 170 mL/1 g) at −78° C. until a blue color was persisted. To remove residual O$_3$, pure O$_2$ was bubbled through the reaction mixture until the solution turned clear. Then, NaBH$_4$ was added at −78° C., and the reaction mixture was stirred for 30 min at the same temperature. After complete consumption of starting material, the reaction mixture was quenched with aq. NH$_4$Cl at −78° C. and washed with DCM. Separated organic layers were dried over Na$_2$SO$_4$ and concentrated under reduced pressure. The crude residue was purified by automated flash column chromatography on silica gel (0-100% EtOAc in cyclohexane) to afford the desired compound 8 (60% over 2 steps) as yellowish liquid. HRMS (ESI+) Calculated for C$_{30}$H$_{34}$O$_7$Na$^+$ [M+Na]$^+$ 529.2202. found 529.2220.

Synthesis of 9

To a solution of 8 in methanol (10 mL/1 g) was added sodium methoxide in MeOH (0.5 M, 10 mL) and the mixture was kept for stirring at rt for 1 h. After complete consumption of 8, AcOH (1 mL) was added until the pH of the reaction mixture was acidic. After neutralization, reaction mixture was concentrated, and the crude residue was purified by flash column chromatography (0-100%, EtOAc in cyclohexane) to give the desired compound 9 (90%) as paste. HRMS (ESI+) Calculated for C$_{28}$H$_{32}$O$_6$Na$^+$ [M+Na]$^+$ 487.2097. found 487.2111.

Alternative Synthesis of 9—Compound 10

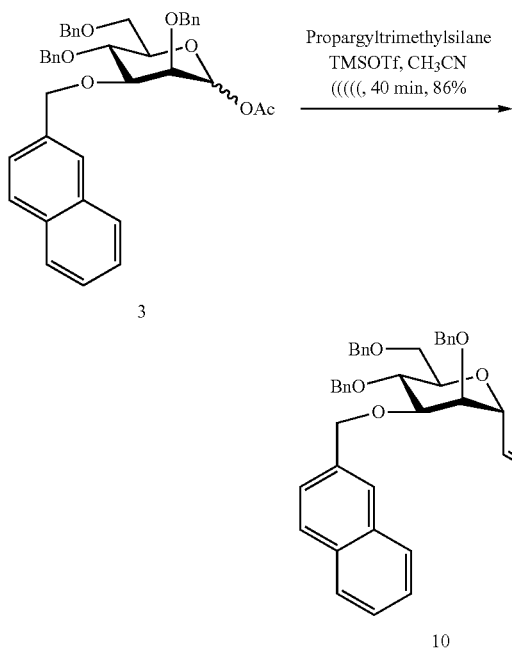

Propargyltrimethylsilane (9.11 mL, 61.5 mmol, 2.0 equiv.) was added to a clear solution of 3 (19.5 g, 30.8 mmol) in dry acetonitrile (390 mL) at room temperature and followed by dropwise addition of TMSOTf (2.8 mL, 15.4 mmol, 0.5 equiv.). The flask was sealed and placed in an ultrasonic cleaning bath (frequency 80 Hz, 100% power 230 V, 5-10° C.) until the reaction was complete by TLC (40 min)). After complete consumption of starting material, the reaction mixture was quenched with aq. NaHCO3, diluted with EtOAc and washed with brine. The separated organic layers were dried over $Na_2SO_4$, concentrated and the crude product was purified by automated flash column chromatography on silica gel (0-60% EtOAc in cyclohexane) to afford the desired C-glycoside 10 as oil (16.2 g, 86%). HRMS (ESI+) Calcd for $C_{41}H_{40}O_5Na^+$ [M+Na]$^+$ 635.2773. found 635.2786.

Alternative Synthesis of 9—Compound 11

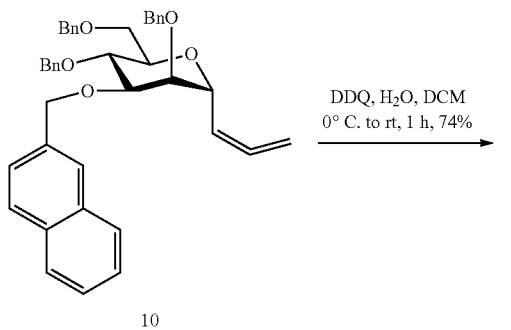

DDQ (18.7 g, 82.0 mmol, 1.2 equiv.) was added to a biphasic solution of 10 (42 g, 68.5 mmol) in DCM:$H_2O$ (19:1, 950 mL) at 0° C. After 10 min at 0° C., the reaction mixture was warmed to room temperature and stirred at room temperature for 1 h. After complete consumption of starting material, reaction mixture was diluted with DCM and extracted with aq. NaHCO3 and brine. The organic layer was dried over $Na_2SO_4$, filtered, and the filtrate was concentrated to obtain the crude product. The crude product was purified by automated flash chromatography on silica gel (0-80% EtOAc in cyclohexane) to give the desired product 11 as white oil (24 g, 74%, only α-isomer). HRMS (ESI+) Calcd for $C_{30}H_{32}O_5Na^+$ [M+Na]$^+$ 495.2147. found 495.2151.

Alternative Synthesis of 9—Compound 9

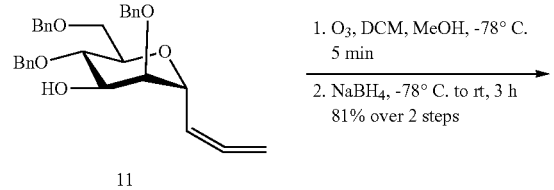

Ozone was bubbled through a cooled solution of 11 (10.6 g, 22.4 mmol) in DCM:MeOH (1:1, 1 L) at −78° C. until a blue color was persisted. To remove residual $O_3$, pure $O_2$ was bubbled through the reaction mixture until the solution turned clear. Then, NaBH4 (5.1 g, 135.0 mmol, 6.0 equiv.) was added at −78° C., and the reaction mixture was gradually brought to RT over 3 h and stirred at RT for 45 min. After complete consumption of starting material, the reaction mixture was quenched with aq. NH4Cl and washed with DCM three times. Separated organic layers were dried over $Na_2SO_4$ and concentrated under reduced pressure. The crude residue was purified by automated flash column chromatography on silica gel (0-100% EtOAc in cyclohexane) to afford the desired compound 9 (8.4 g, 81% over 2 steps) as oil (sticky white solid after drying under vacuum). HRMS (ESI+) Calcd for $C_{28}H_{32}O_6Na^+$ [M+Na]$^+$ 487.2097. found 487.2106.

Synthesis of 12

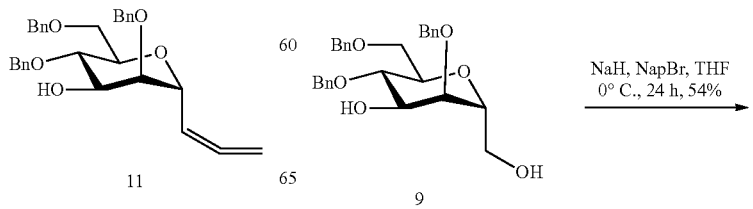

-continued

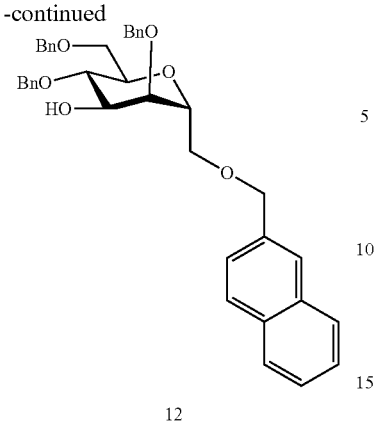

12

Sodium hydride (2.0 equiv., 60% in mineral oil) was added at 0° C. to a stirred solution of 9 in THF (20 mL/1 g). After 10 min, NapBr (1.05 equvi.) was added and the mixture was stirred for 24 h at 0° C. After 24 h, reaction mixture was quenched with MeOH, water, and extracted with EtOAc. The combined organic layers were washed with brine, dried over Na$_2$SO$_4$, filtered, and concentrated. The crude residue obtained was purified by automated flash column chromatography on silica gel (0-100%, EtOAc in cyclohexane) to give the desired compound 12 (54%) as paste. HRMS (ESI+) Calculated for C$_{39}$H$_{40}$O$_6$Na$^+$ [M+Na]$^+$ 627.2723. found 627.2748.

Synthesis of 14

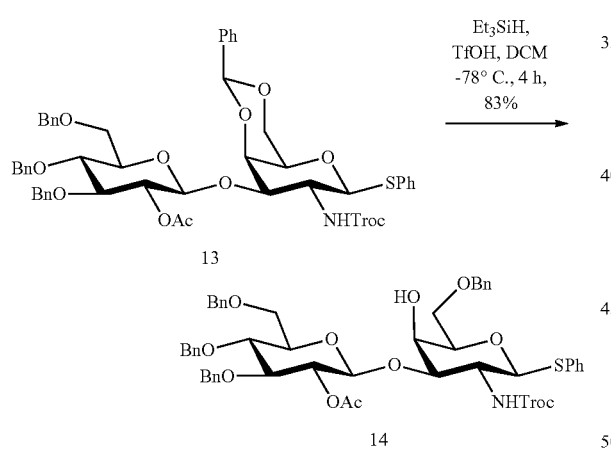

Et$_3$SiH (3.0 equiv.), TfOH (3.3 equiv.) were added to a cooled solution of 13 (obtained according to *Org. Lett.* 2011, 13, 378-381) in DCM (10 mL/1 g) with freshly activated molecular sieves (4 Å) at −78° C. The reaction mixture was stirred at the same temperature for 4 h. After complete consumption of starting material, reaction mixture was quenched with Et$_3$N (1 mL) and diluted with DCM. The solution was washed with aq. NaHCO$_3$ and brine. The organic layer was dried over Na$_2$SO$_4$, filtered and concentrated. The crude residue was purified by automated flash column chromatography on silica gel (0-100%, EtOAc in cyclohexane) to give the desired 4-OH compound 14 (83%) as white solid. HRMS (ESI+) Calculated for C$_{51}$H$_{54}$Cl$_3$NO$_{12}$NaS$^+$ [M+Na]$^+$ 1034.2300. found 1034.2406.

Synthesis of 15

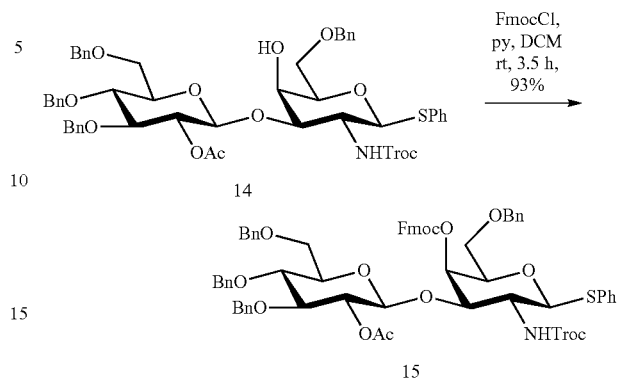

FmocCl (2.0 equiv.) and pyridine (3.0 equiv.) were added to a clear solution of 14 in DCM (10 mL/1 g) and kept for stirring at rt for 3.5 h. After complete consumption of starting material, reaction mixture was diluted with DCM and it was washed with brine. The organic layer was dried over Na$_2$SO$_4$, filtered and concentrated. The crude residue was purified by automated flash column chromatography on silica gel (0-100%, EtOAc in cyclohexane) to give the desired compound 15 (93%) as white solid. HRMS (ESI+) Calculated for C$_{66}$H$_{64}$Cl$_3$NO$_{14}$NaS$^+$ [M+Na]$^+$ 1256.2981. found 1256.3125.

Synthesis of 16

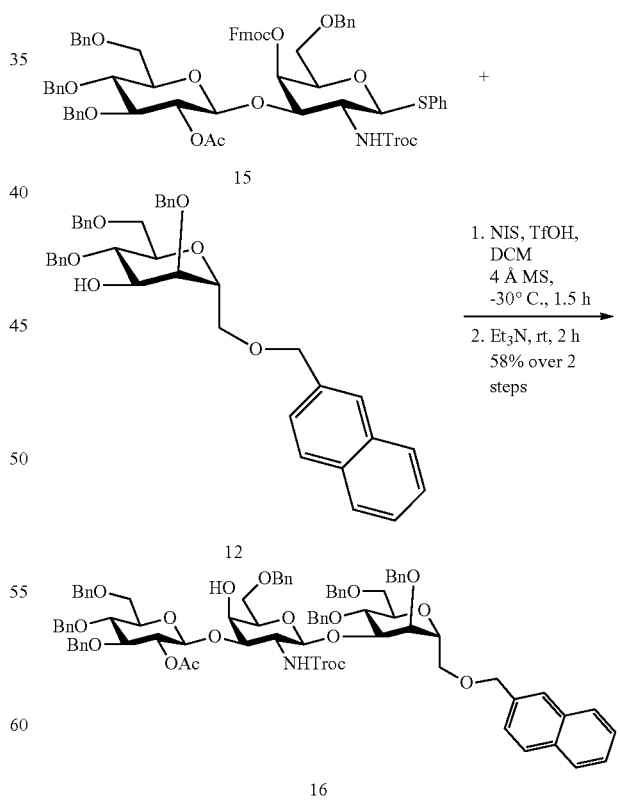

NIS (1.4 equiv.) and TfOH (0.26 equiv.) were added to a cooled solution of acceptor 15 (1.0 equiv.) and donor 12 (1.2 equiv.) in DCM (0.06 M) in presence of 4 Å MS at −30° C.

After 1.5 h, starting material was completely consumed, then Et$_3$N (1.4 equiv.) was added and kept for stirring at rt for 2 h. After 2 h, reaction mixture was diluted with DCM and MS were filtered. The organic layer was washed with aq. Na$_2$S$_2$O$_3$ and the separated organic layer was dried over Na$_2$SO$_4$, filtered and concentrated. The crude residue was purified by automated flash column chromatography on silica gel (0-100%, EtOAc in cyclohexane) to give the desired trisaccharide acceptor 16 (58% over 2 steps) as white solid. HRMS (ESI+) Calculated for C$_{84}$H$_{88}$Cl$_3$NO$_{18}$Na$^+$ [M+Na]$^+$ 1528.4935. found 1528.5037.
Synthesis of 18

NIS (1.5 equiv.) and TfOH (0.4 equiv.) were added to a cooled solution of acceptor 16 (1.0 equiv.) and donor 17 (obtained according to *J. Org. Chem.* 2016, 81, 162-184) (1.5 equiv.) in toluene:dioxane (4:1, 0.03 M) in presence of 4 Å MS at 0° C. After 2 min, reaction mixture was kept at rt and stirred for 30 min. After 30 min, reaction mixture was quenched with Et$_3$N, diluted with DCM and MS were filtered. The organic layer was washed with aq. Na$_2$S$_2$O$_3$ and the separated organic layer was dried over Na$_2$SO$_4$, filtered and concentrated. The crude residue was purified by automated flash column chromatography on silica gel (0-100%, EtOAc in cyclohexane) to give the desired tetrasaccharide 18 (76%) as white solid. HRMS (ESI+) Calculated for C$_{111}$H$_{114}$Cl$_3$NO$_{23}$Na$^+$ [M+Na]$^+$ 1958.6745. found 1958.6871.

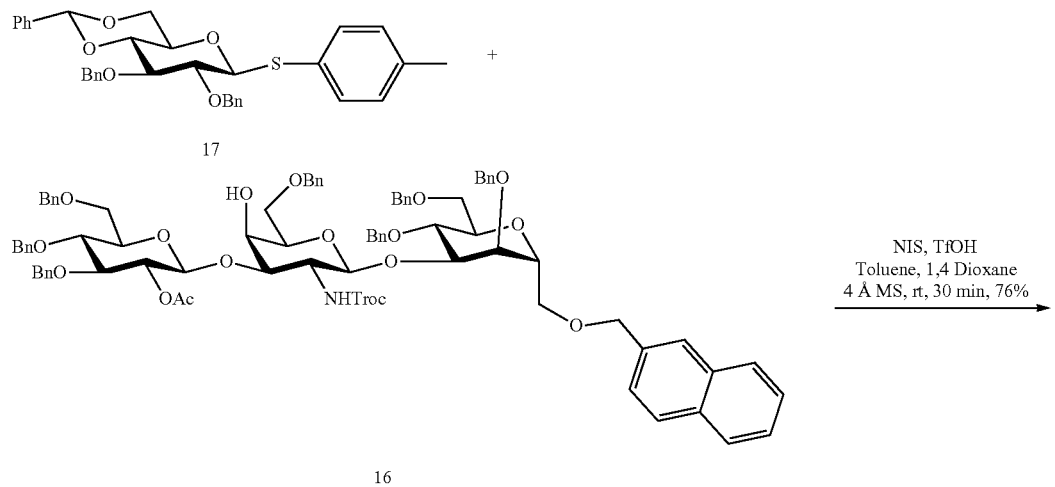

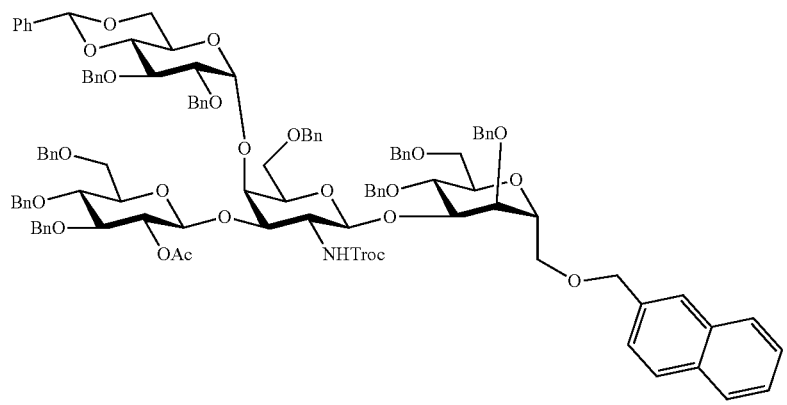

Synthesis of 19

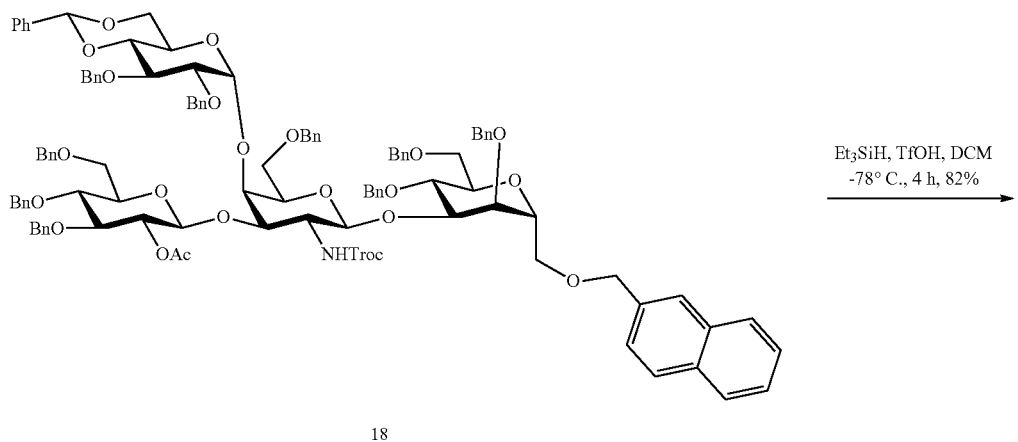

18

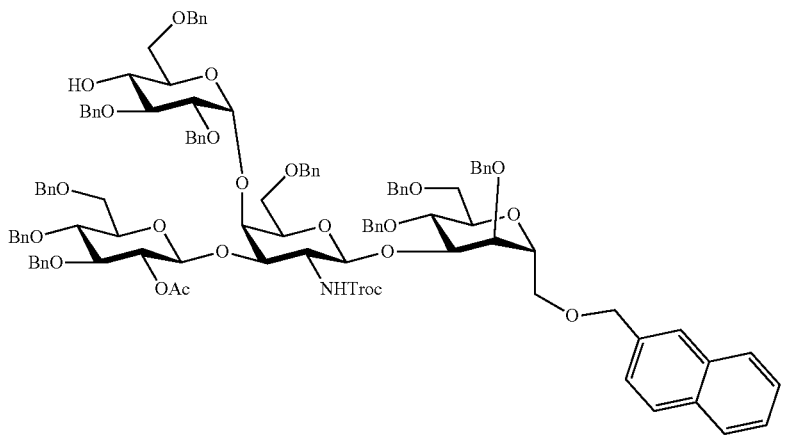

19

Et$_3$SiH (3.0 equiv.), TfOH (3.3 equiv.) were added to a cooled solution of 18 in DCM (10 mL/1 g) in presence of freshly activated molecular sieves (4 Å) at −78° C. The reaction mixture was stirred at the same temperature for 4 h. After complete consumption of starting material, reaction mixture was quenched with Et$_3$N (1 mL) and diluted with DCM. The solution was washed with aq. NaHCO$_3$ and brine. The organic layer was dried over Na$_2$SO$_4$, filtered and concentrated. The crude residue was purified by automated flash column chromatography on silica gel (0-100%, EtOAc in cyclohexane) to give the desired tetrasaccharide 19 (82%) as white solid. HRMS (ESI+) Calculated for C$_{111}$H$_{116}$Cl$_3$NO$_{23}$Na$^+$ [M+Na]$^+$ 1960.6901. found 1960.7024.

Synthesis of 21

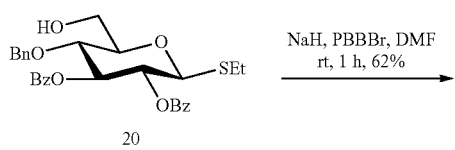

20

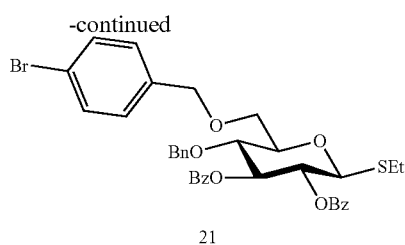

21

Sodium hydride (2.0 equiv., 60% in mineral oil) was added at 0° C. to a stirred solution of 20 (obtained according to *Tetrahedron: Asymmetry*, 2000, 11, 481-492) in DMF (10 mL/1 g). After 10 min, PBBBr (1.1 equvi.) was added and the mixture was brought to rt. After stirring at rt for 1 h, reaction mixture was quenched with NH$_4$Cl and extracted with EtOAc. The combined organic layers were washed with brine, dried over Na$_2$SO$_4$, filtered, and concentrated. The crude residue obtained was purified by automated flash column chromatography on silica gel (0-100%, EtOAc in cyclohexane) to give the desired compound 21 (62%) as paste. HRMS (ESI+) Calculated for C$_{36}$H$_{35}$BrO$_7$NaS$^+$ [M+Na]$^+$ 713.1185. found 713.1225.

Synthesis of 22

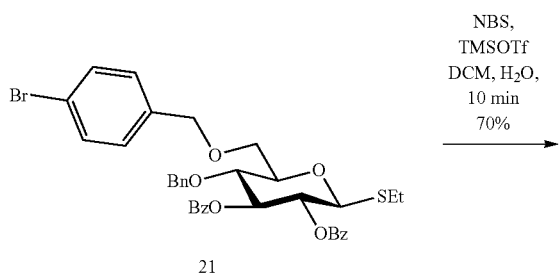

NBS (1.1 equiv.) and TMSOTf (0.1 equiv.) was added to a cooled solution of 21 in DCM:H$_2$O (20:1, 10 mL/1 g) at 0° C. After 10 min, reaction mixture was quenched with aq., NaHCO$_3$ and diluted with DCM. The organic layer was washed with brine. Separated organic layer was dried over Na$_2$SO$_4$, concentrated and the crude product was purified by automated flash column chromatography on silica gel (0-60% EtOAc in cyclohexane) to afford the desired hemi-acetal 22 (70%) as foam. HRMS (ESI+) Calculated for C$_{34}$H$_{31}$BrO$_8$Na$^+$ [M+Na]$^+$ 669.1100. found 669.1132.

Synthesis of 23

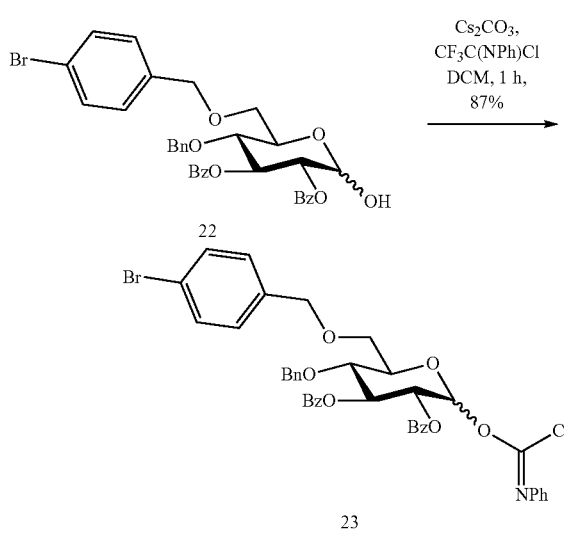

Cs$_2$CO$_3$ (3.0 equiv.), CF$_3$C(NPh)Cl (3.0 equiv.) were added to a stirred solution of 22 in DCM (10 mL/1 g) at 0° C. After 10 min., the mixture was brought to rt and stirred for 1 h. After complete consumption of 22, reaction mixture was filtered, and the filtrate was concentrated. The obtained crude residue was purified by automated flash column chromatography on silica gel (0-60% EtOAc in cyclohexane) to afford the desired imidate donor 23 (87%) as foam.

Synthesis of 25

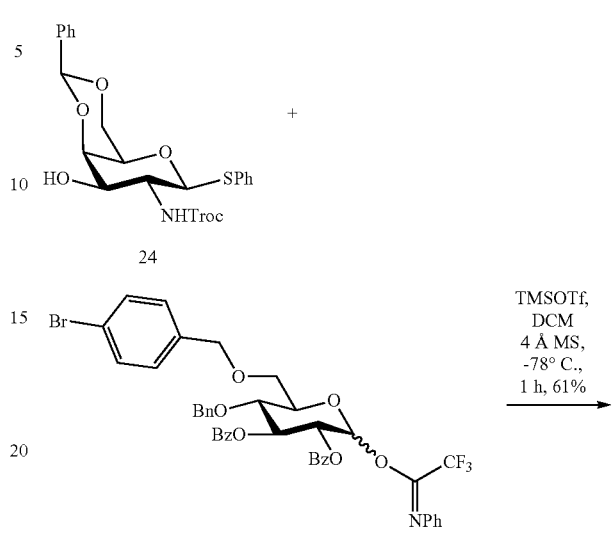

The thioglycoside acceptor 24 was synthesized according to Danieli, E.; Lay, L.; Proietti, D.; Berti, F.; Costantino, P.; Adamo, R. Org Lett. 2011, 13, 378-381. TMSOTf in DCM (0.1 M, 0.2 equiv.) was added to a mixture of thioglycoside acceptor 24 (1.0 equiv.) and freshly dried 4 Å MS in DCM at −78° C. After 2 min, a solution of the imidate 23 (1.2 equiv.) in DCM was added. After 1 h, the reaction mixture was quenched with Et$_3$N, and then filtered through a pad of Celite. The filtrate was concentrated, and the crude residue was purified by automated flash column chromatography on silica gel (0-100% EtOAc in cyclohexane) to afford the desired disaccharide 25 (61%) as solid. HRMS (ESI+) Calculated for C$_{56}$H$_{51}$BrCl$_3$NO$_{13}$NaS$^+$ [M+Na]$^+$ 1186.1207. found 1186.1314.

Synthesis of 26

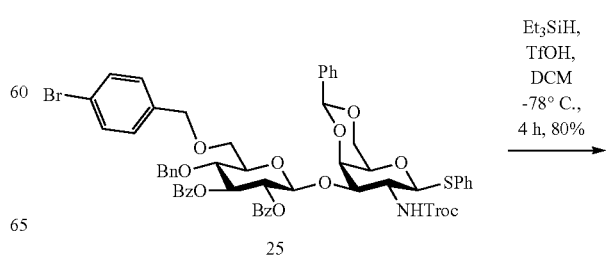

Synthesis of 27

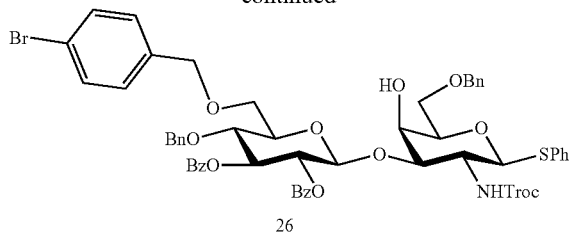

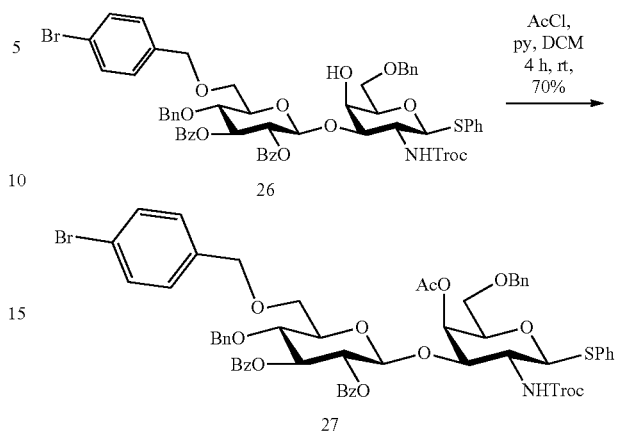

Et₃SiH (3.0 equiv.), TfOH (3.3 equiv.) were added to a cooled solution of 25 in DCM (10 mL/1 g) with freshly activated molecular sieves (4 Å) at −78° C. The reaction mixture was stirred at the same temperature for 4 h. After complete consumption of starting material, reaction mixture was quenched with Et₃N (1 mL) and diluted with DCM. The solution was washed with aq. NaHCO₃ and brine. The organic layer was dried over Na₂SO₄, filtered and concentrated. The crude residue was purified by automated flash column chromatography on silica gel (0-100%, EtOAc in cyclohexane) to give the desired 4-OH compound 26 (80%) as white solid. HRMS (ESI+) Calculated for $C_{56}H_{53}Cl_3NBrO_{13}NaS^+$ $[M+Na]^+$ 1188.1364. found 1188.1436.

AcCl (2.0 equiv.) and pyridine (3.0 equiv.) were added to a clear solution of 26 in DCM (10 mL/1 g) at 0° C. and kept for stirring at rt for 3.5 h. After complete consumption of starting material, reaction mixture was diluted with DCM and it was washed with brine. The organic layer was dried over Na₂SO₄, filtered and concentrated. The crude residue was purified by automated flash column chromatography on silica gel (0-100%, EtOAc in cyclohexane) to give the desired compound 27 (70%) as white solid. HRMS (ESI+) Calculated for $C_{58}H_{55}Cl_3NBrO_{14}NaS^+$ $[M+Na]^+$ 1230.1469. found 1230.1563.

Synthesis of 28

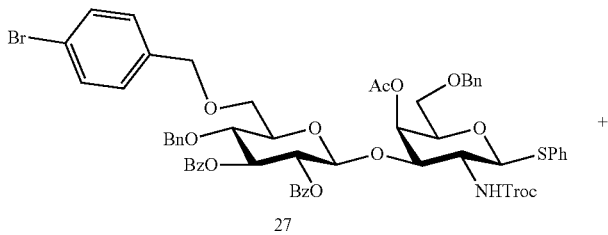

+

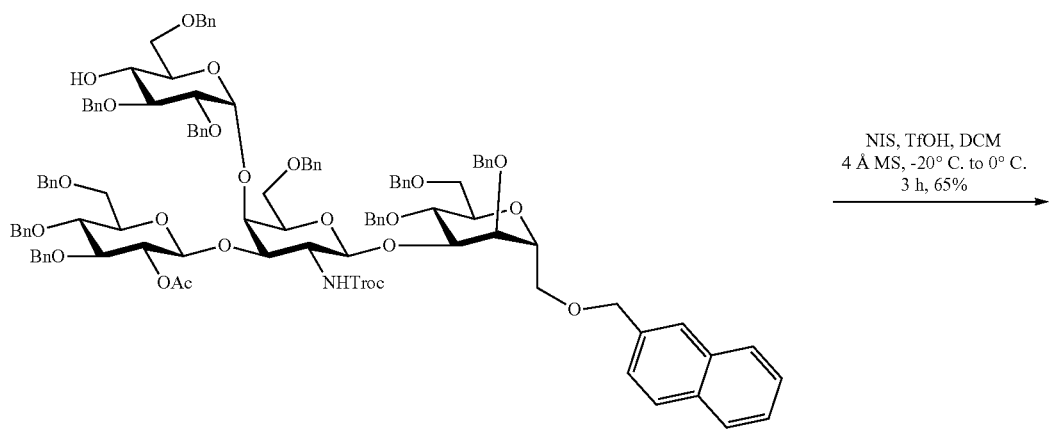

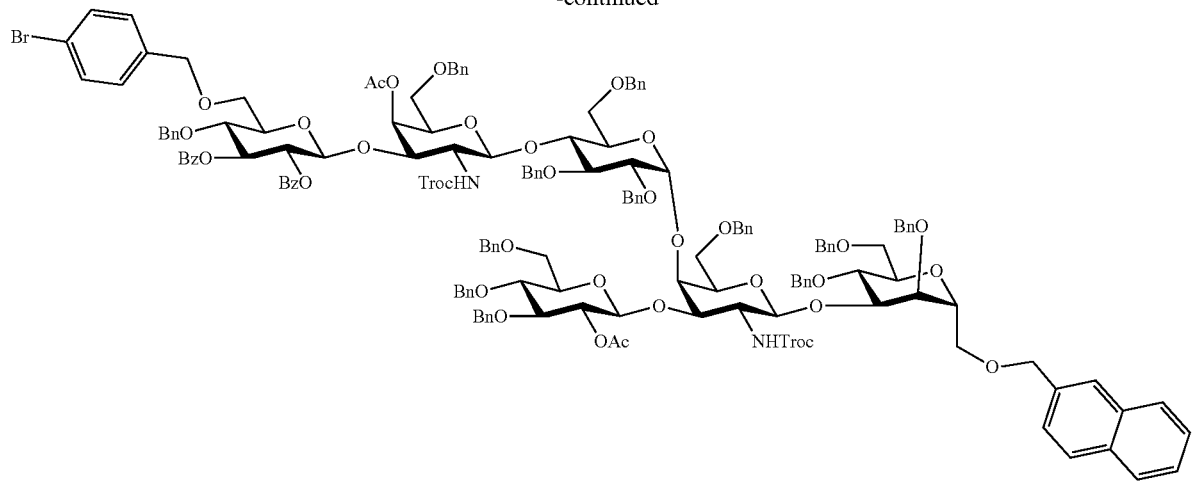

28

NIS (1.8 equiv.) and TfOH (0.4 equiv.) were added to a cooled solution of acceptor 19 (1.0 equiv.) and donor 27 (1.8 equiv.) in DCM (0.025 M) in presence of 4 Å MS at −20° C. Then the reaction mixture was gradually warmed to 0° C. during 3 h. After 3 h, reaction mixture was quenched with Et₃N, diluted with DCM and MS were filtered. The organic layer was washed with aq. Na₂S₂O₃ and the separated organic layer was dried over Na₂SO₄, filtered and concentrated. The crude residue was purified by automated flash column chromatography on silica gel (0-100%, EtOAc in cyclohexane) to give the desired hexasaccharide 28 (65%) as white solid. HRMS (ESI+) Calculated for $C_{163}H_{165}Cl_6N_2BrO_{37}Na^+$ $[M+Na]^+$ 3060.8258. found 3060.8275.

Synthesis of 29

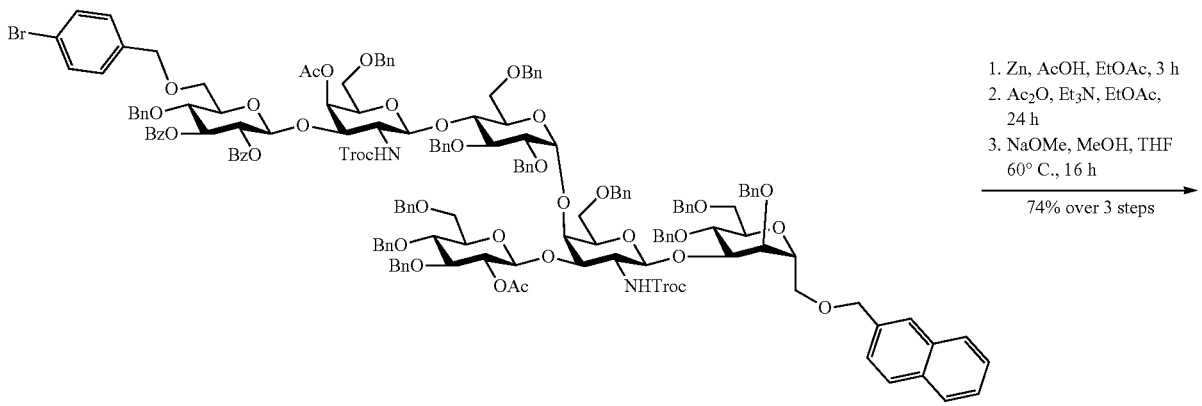

28

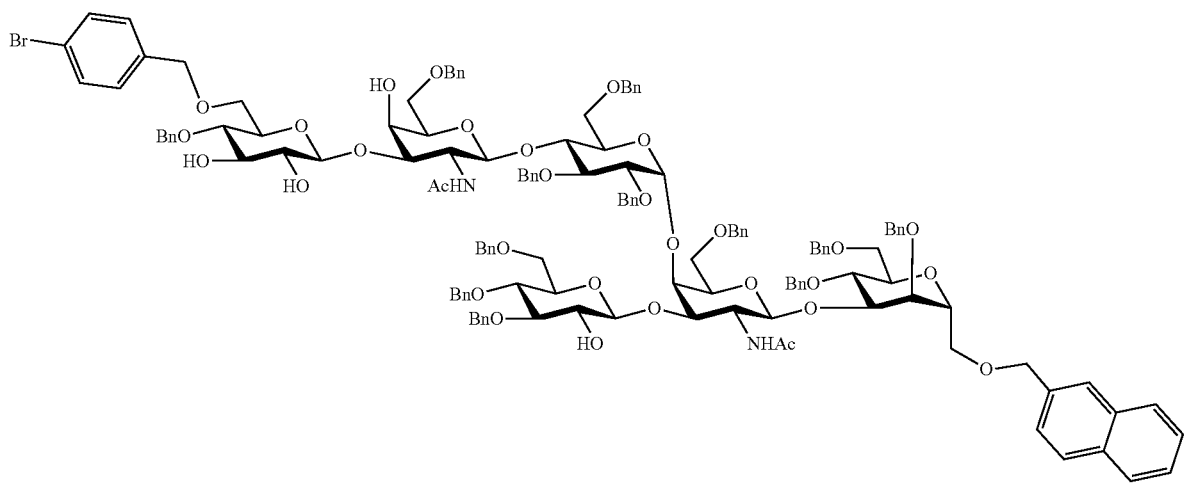

29

To a clear solution of 28 in EtOAc (2.0 mM) were added Zn (100 equiv.), and AcOH (100 equiv.) and the reaction mixture was kept for stirring at room temperature 3 h. After complete consumption of starting material, reaction mixture was filtered through celite pad and concentrated. The residue obtained after solvents removal was dissolved in EtOAc (2.0 mM), Et$_3$N (0.5 mL) and Ac$_2$O (0.5 mL) were added. After stirring at rt for 2.5 d, the reaction mixture was concentrated. The crude obtained after solvent removal was dissolved in THF and methanol. To this clear solution 0.5 M NaOMe (3 mL) was added and kept for reflux at 65° C. After 16 h, reaction mixture was neutralized with AcOH and solvents were removed. The crude residue was purified by automated flash column chromatography on silica gel (0-100%, EtOAc in cyclohexane) to give the desired hexasaccharide 29 (74% over 3 steps) as white solid. HRMS (ESI+) Calculated for C$_{143}$H$_{155}$N$_2$BrO$_{31}$Na$^+$ [M+Na]$^+$ 2500.9708. found 2500.9739.

Synthesis of 30

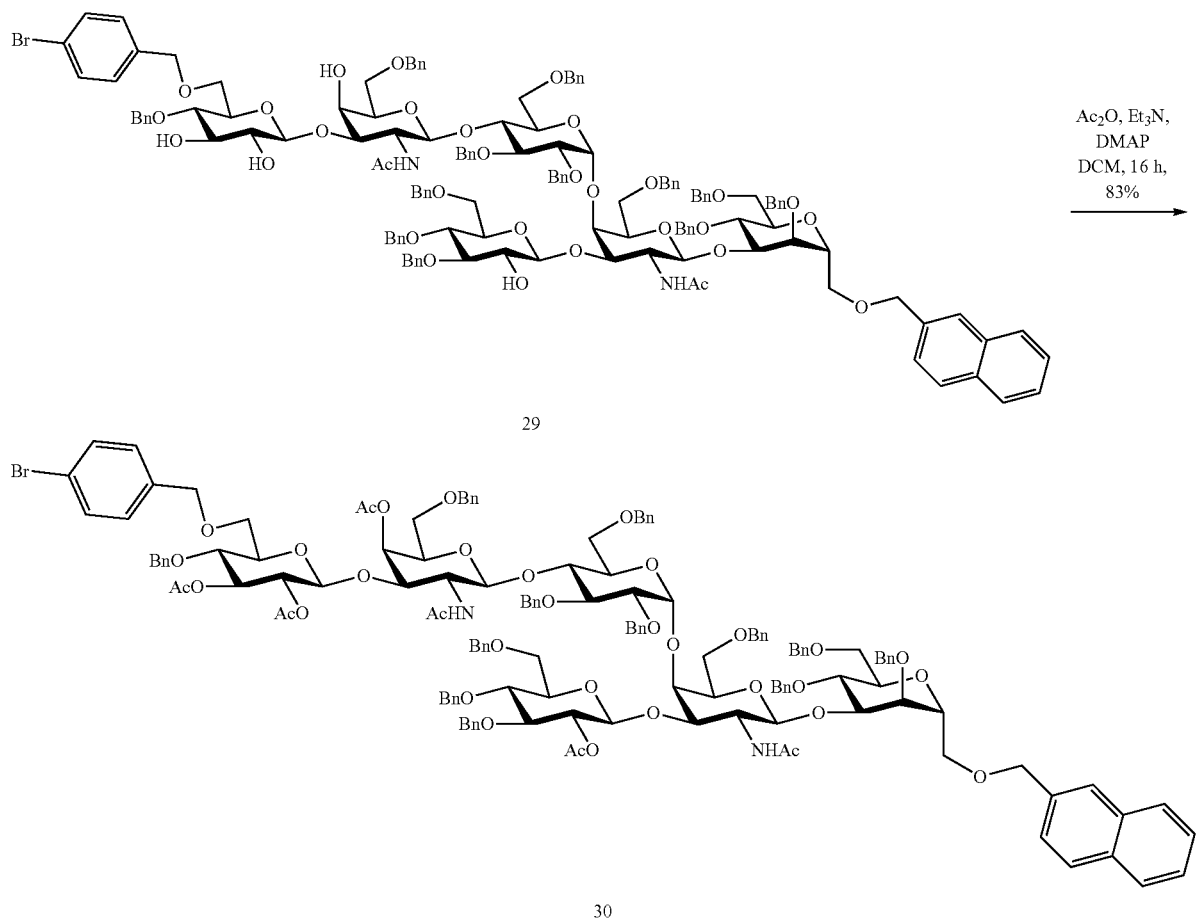

Ac$_2$O (8.0 equiv.) and trimethylamine (8.0 equiv.) were added to a clear solution of 29 in DCM (10 mL/1 g) and kept for stirring at rt for 16 h. After complete consumption of starting material, solvents were removed under vacuum and the crude product was purified by automated flash column chromatography on silica gel (0-100% EtOAc in cyclohexane) to afford the desired product 30 (83%) as viscous liquid. HRMS (ESI+) Calculated for C$_{151}$H$_{163}$N$_2$BrO$_{35}$Na$^+$ [M+Na]$^+$ 2669.0131. found 2669.0407.

Synthesis of 31

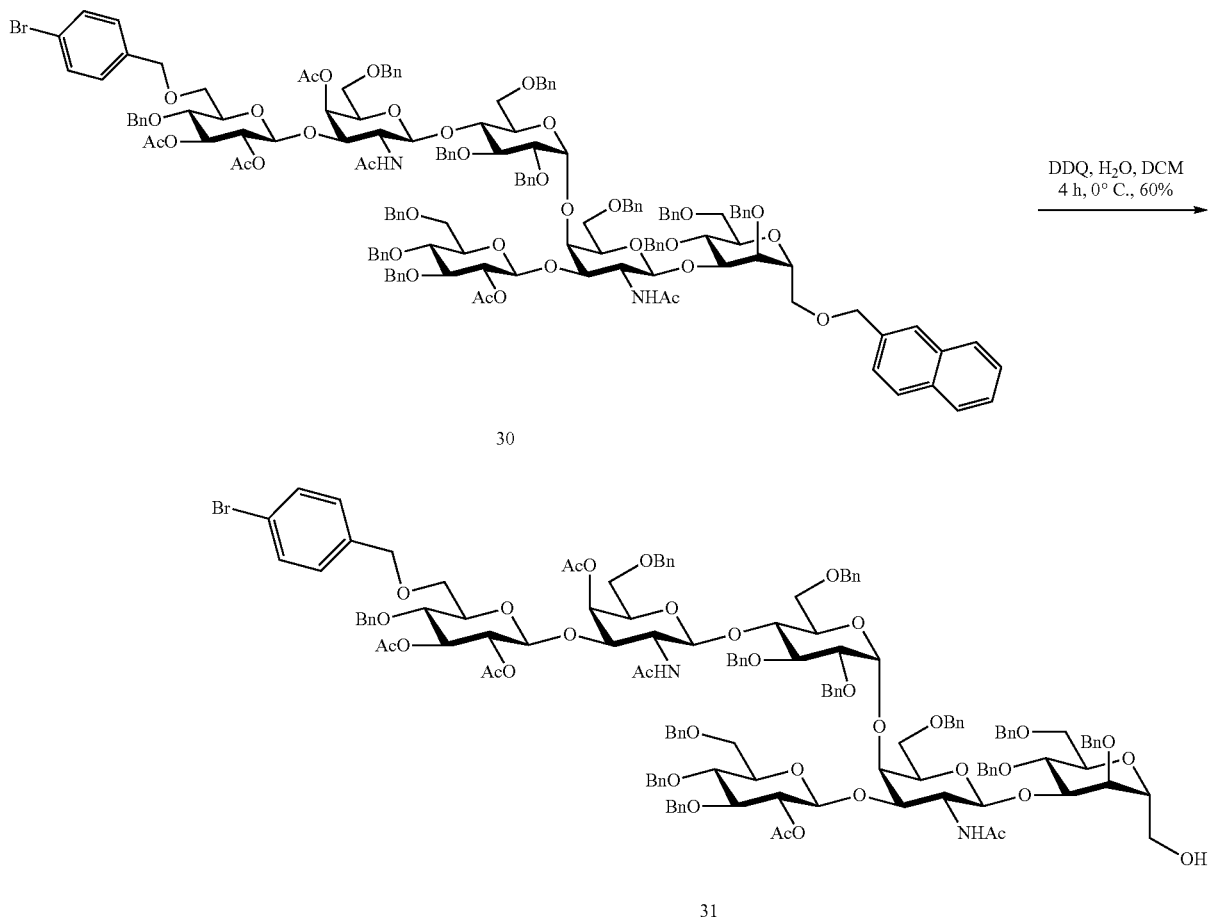

DDQ (1.1 equiv.) was added to a cooled solution of 30 in DCM:H$_2$O at 0° C. After stirring the reaction mixture at the same temperature for 4 h, reaction was diluted with DCM and extracted with NaHCO$_3$ aq. sat. solution and brine. The organic layer was dried over Na$_2$SO$_4$, filtered, and the filtrate was concentrated to obtain the crude product. The crude product was purified by automated flash column chromatography on silica gel (0-100% EtOAc in cyclohexane) to afford the desired product 31 (60%) as viscous liquid. HRMS (ESI+) Calculated for C$_{140}$H$_{155}$N$_2$BrO$_{35}$Na$^+$ [M+Na]$^+$ 2527.9559. found 2527.9731.

Synthesis of 32

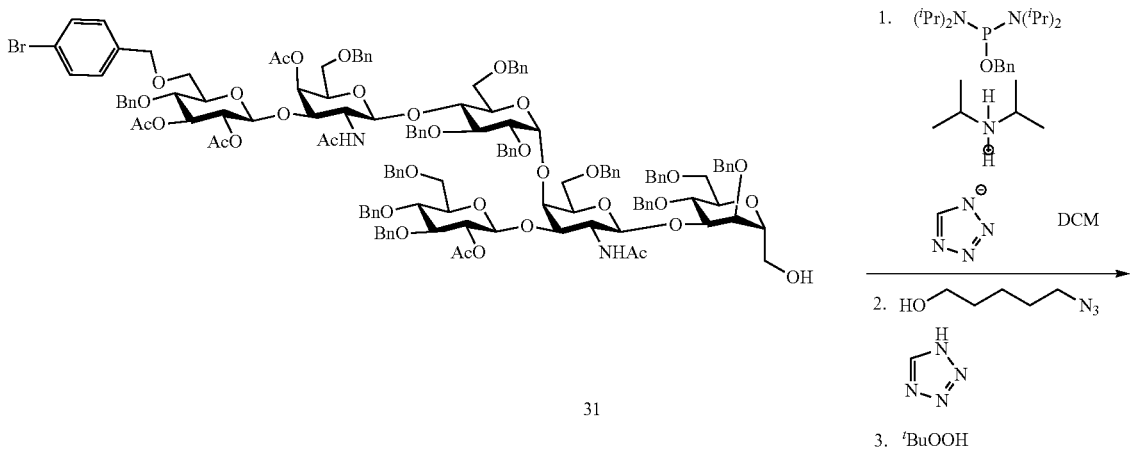

-continued

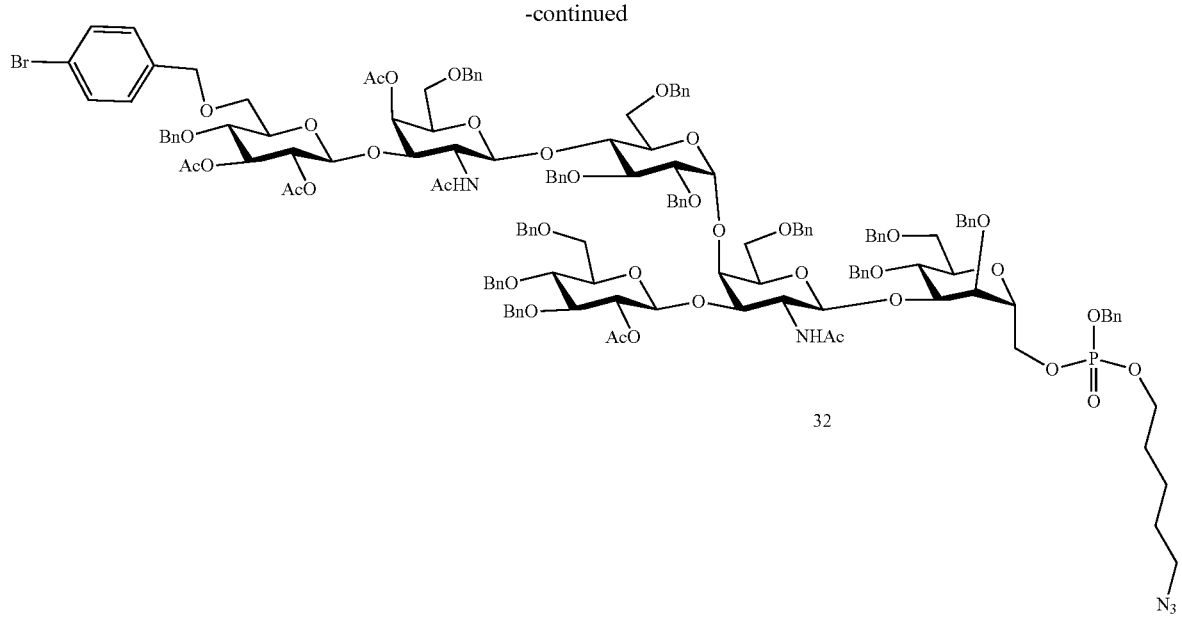

32

To a solution of 31 in DCM, were added bis(diisopropylamino)-benzyloxyphosphine (2.0 equiv.) and diisopropylammonium tetrazolide (1.5 equiv.) and the solution was stirred at rt for 1.5 h. Then, 5-azido pentanol (8.0 equiv.) and tetrazole (9.0 equiv. 0.45 M solution in CAN) were added and kept for stirring at room temperature for 2 h. After 2 h, t-butyl peroxide (6.0 equiv., 5.0-6.0 M solution in decane) was added and the reaction mixture stirred for 1 h. After 1 h, reaction mixture was diluted with DCM and quenched with NaHCO$_3$ aq. sat. solution. The aqueous layer was extracted with DCM. The combined organic layer was washed with brine, dried over Na$_2$SO$_4$, filtered, and the filtrate was concentrated under vacuum to obtain the crude product. The crude product was purified by automated flash column chromatography on silica gel (0-100% EtOAc in cyclohexane) to afford the desired product 32 (37% over 3 steps) as viscous liquid. MALDI Calculated for $C_{152}H_{171}N_5BrO_{38}PH^+$ [M+H]$^+$ 2786.0635. found 2786.870.

Synthesis of 33

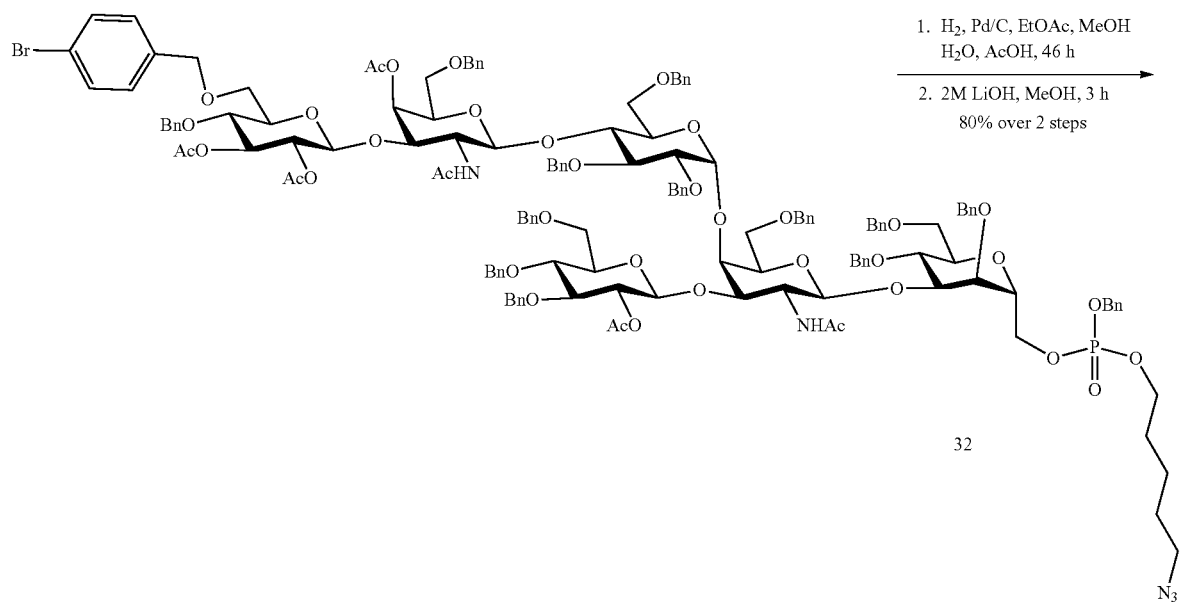

32

1. H$_2$, Pd/C, EtOAc, MeOH
   H$_2$O, AcOH, 46 h
2. 2M LiOH, MeOH, 3 h
   80% over 2 steps -continued

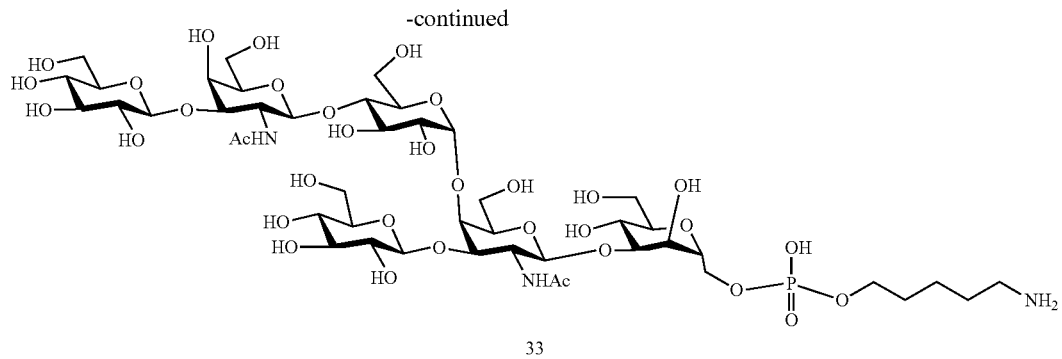

33

Pd/C (6 mg) was added to a clear solution of 32 (6 mg) in EtOAc:MeOH:H₂O:AcOH. Obtained inhomogeneous mixture was stirred under hydrogen atmosphere at rt for 40 h. After 40 h, reaction mixture was filtered through PTFE filter and concentrated under vacuum at 30° C. bath temperature of rotary evaporator for 10 min to remove methanol, EtOAc, AcOH and water. The crude product obtained after solvents removal was dissolved in MeOH, water and to this LiOH (2 N in water) was added at 0° C. The reaction mixture was stirred at 0° C. for 3 h. After 3 h, the reaction mixture was quenched with AcOH (30 μL) and the solvents were removed under reduced pressure and the obtained crude residue was purified with C18 reverse phase column chromatography using water and acetonitrile as solvents to give the desired final compound 33 (80% over 2 steps) as a white solid. HRMS (ESI+) Calculated for $C_{46}H_{82}N_3PO_{34}^+$ [M−Na+2H]⁺ 1252.4551. found 1252.4578.

Synthesis of 34

Pd/C (2 mg) was added to a clear solution of 29 in EtOAc:MeOH:H₂O:AcOH and the obtained inhomogeneous mixture was stirred under hydrogen atmosphere at rt for 40 h. After 40 h, reaction mixture was filtered through PTFE filter and concentrated under vacuum at 30° C. bath temperature of rotary evaporator for 10 min to remove methanol, EtOAc, AcOH and water. The crude product was purified with C18 reverse phase column chromatography using water and acetonitrile as solvents to give the desired final compound 34 (82%) as a white solid. HRMS (ESI+) Calculated for $C_{41}H_{70}N_2O_{31}^+$ [M+Na]⁺ 1109.3860. found 1109.3853.

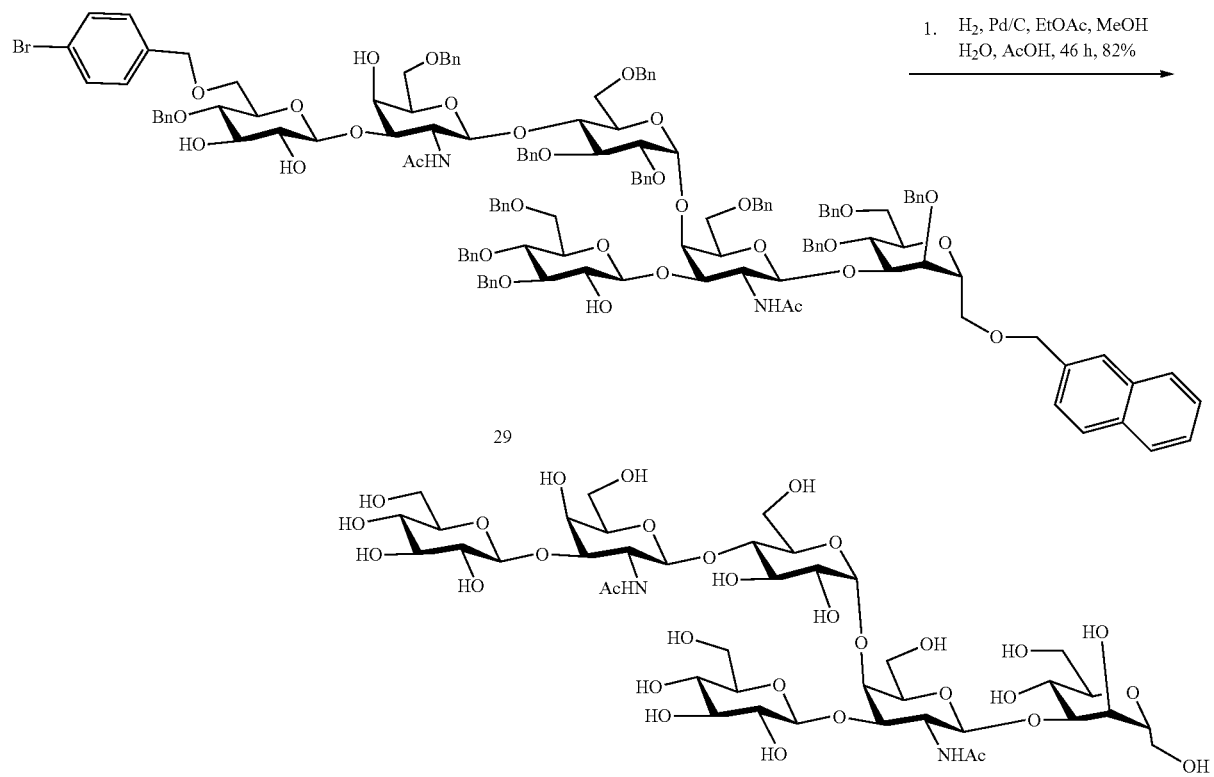

Conjugation of 33 with $CRM_{197}$ or BSA

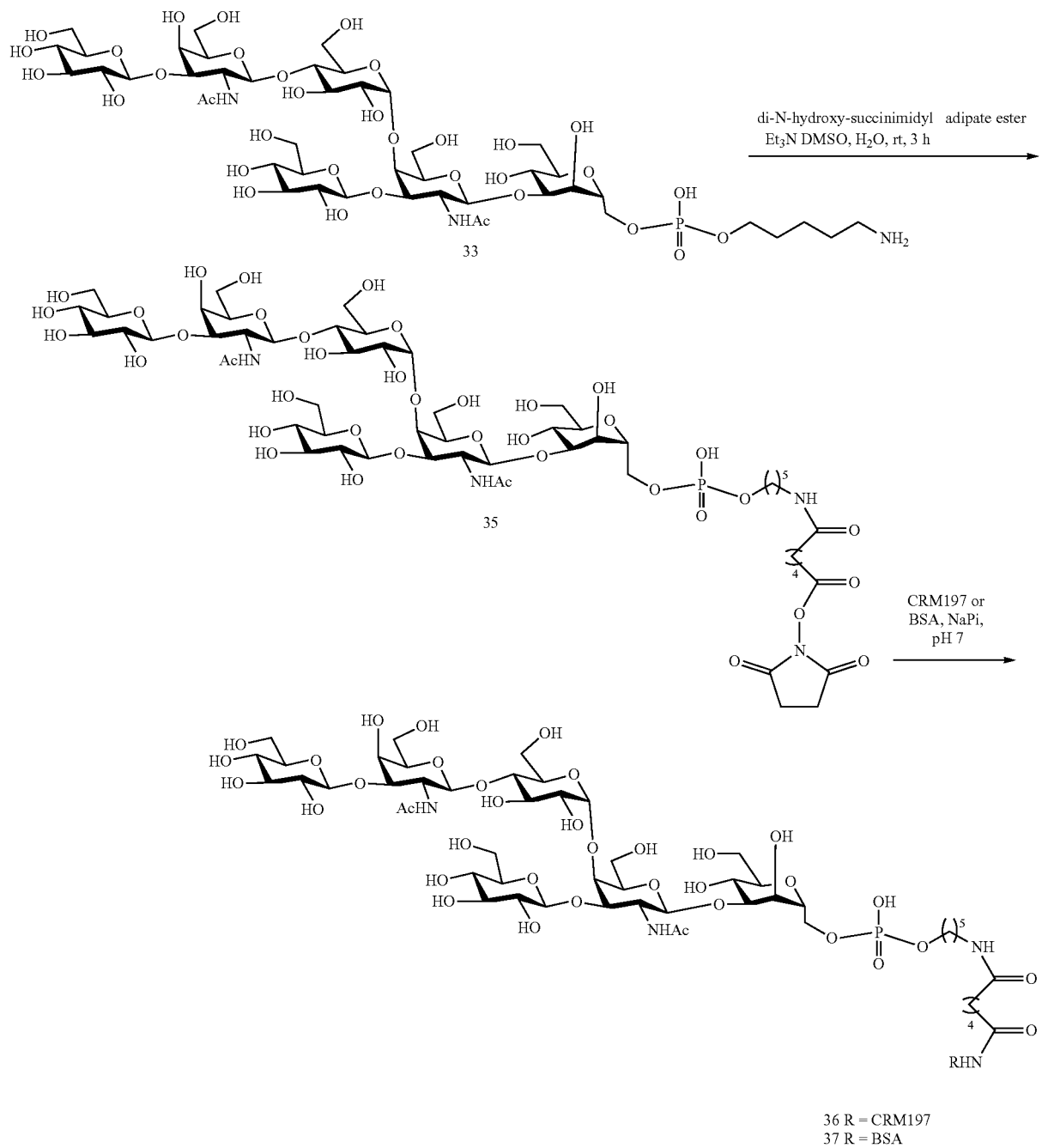

Antigen 33 (1.0 equiv.) was dissolved in DMSO-H₂O at rt in a 2 mL vial. Triethylamine (35.0 equiv.) was added to it. The mixture was added to the activated adipate-NHS ester (10 equiv.) in DMSO in an Eppendorf vial and stirred for 3 h at rt. The Antigen-NHS ester was precipitated out by adding 10 volume of EtOAc and centrifuged, supernatant was removed carefully. Washed the precipitate with EtOAc (1 mL×3), dried and taken for the next step. 1 mg of protein in NaPi buffer (~100 μL) was added to reaction vial containing the Antigen-NHS ester 35 in 50 μL of NaPi buffer (pH 7.0) dropwise. The vial was finally rinsed with 50 μL of buffer solution and transferred to the reaction vial completely. The reaction mixture was stirred at rt for 22 h. Antigen-protein conjugate solution was transferred to the Amicon Ultra-0.5 mL, centrifuged for 6 minutes at room temperature. Added 300 μL of buffer to the reaction vial, rinsed and transferred to the filter and centrifuged again. Additional washings were done using 1×PBS solution for three more times. After the final wash the conjugate was stored in 1×PBS solution at 2-8° C. The conjugates were analysed using MALDI, (loading of 4-12 antigens on protein was obtained), SDS-page, BCA estimation, SEC-HPLC.

A.3 Synthesis of Hexasaccharide 54

Synthesis of 41

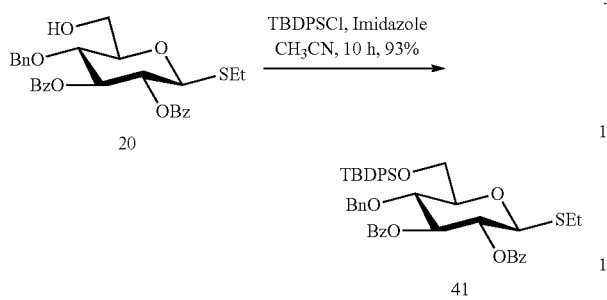

TBDPSCl (1.1 equiv.) and trimethylamine (2.8 equiv.) were added to a clear solution of 20 in CH$_3$CN (10 mL/1 g) and kept for stirring at rt for 10 h. After complete consumption of starting material, solvents were removed under vacuum and the crude product was purified by automated flash column chromatography on silica gel (0-100% EtOAc in cyclohexane) to afford the desired product 41 (93%) as viscous liquid. HRMS (ESI+) Calculated for C$_{45}$H$_{48}$O$_7$SSiNa$^+$ [M+Na]$^+$ 783.2788. found 783.2767.

Synthesis of 42

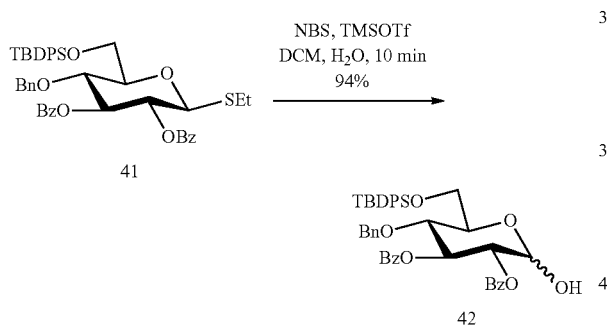

The procedure described for the synthesis of compound 22 used for the synthesis of compound 42 (94%). HRMS (ESI+) Calculated for C$_{43}$H$_{44}$O$_8$SiNa$^+$ [M+Na]$^+$ 739.2703. found 739.2700.

Synthesis of 43

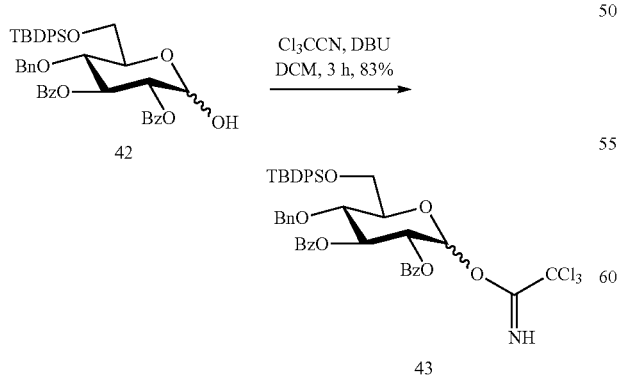

To a cooled solution of 42 in DCM at 0° C. was added trichloroacetonitrile (6.0 equiv.) and DBU (0.2 equiv.). After 3 h at 0° C., the reaction was complete, and the solvent was evaporated. The crude product was purified by automated flash column chromatography on silica gel (0-100% EtOAc in cyclohexane) to afford the desired product 43 (83%) as viscous liquid.

Synthesis of 44

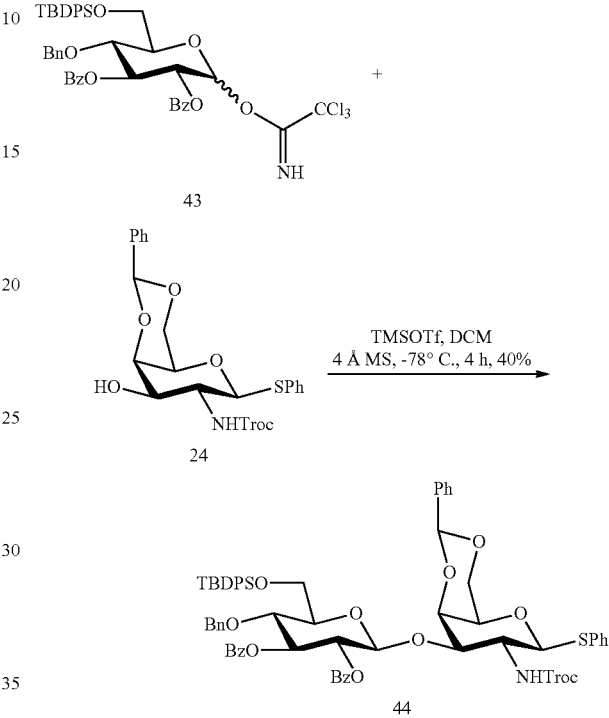

The procedure described for the synthesis of compound 25 used for the synthesis of compound 44 (40%). HRMS (ESI+) Calculated for C$_{65}$H$_{64}$O$_{13}$SiSNCl$_3$Na$^+$ [M+Na]$^+$ 1256.2801. found 1256.2645.

Synthesis of 45

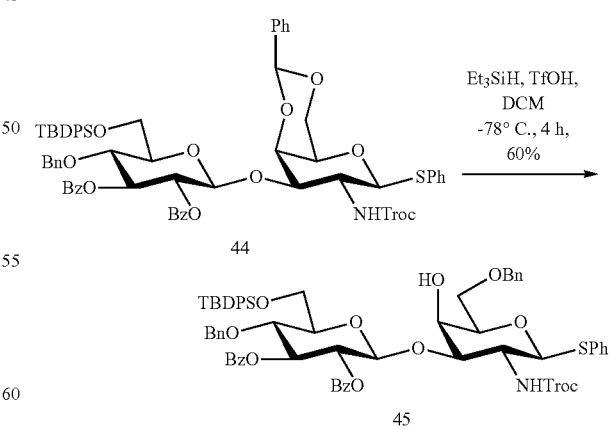

The procedure described for the synthesis of compound 26 used for the synthesis of compound 45 (60%). HRMS (ESI+) Calculated for C$_{65}$H$_{66}$O$_{13}$SiSNCl$_3$Na$^+$ [M+Na]$^+$ 1256.2987. found 1256.2974.

Synthesis of 46
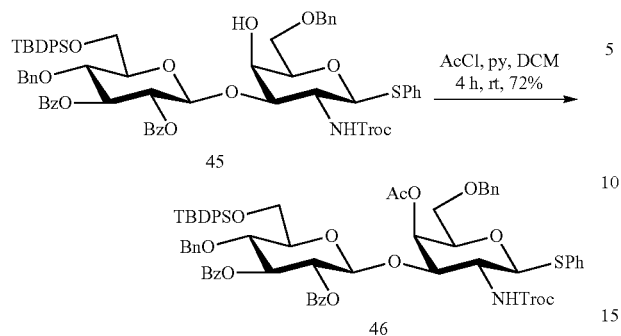
The procedure described for the synthesis of compound 27 used for the synthesis of compound 46 (60%). HRMS (ESI+) Calculated for $C_{67}H_{68}O_{14}SiSNCl_3Na^+$ [M+Na]+ 1300.3064. found 1300.3090.
Synthesis of 47
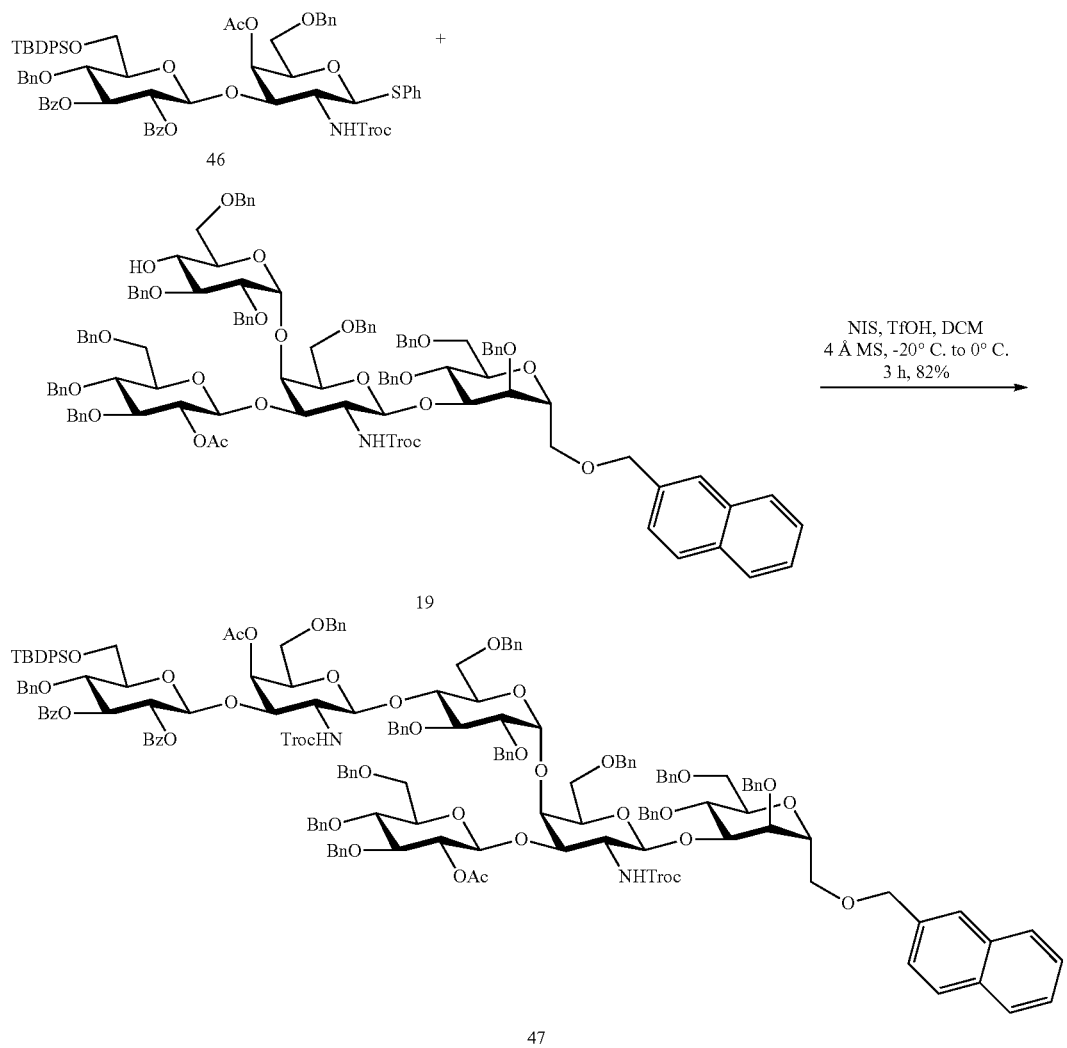
The procedure described for the synthesis of compound 28 used for the synthesis of compound 47 (82%). HRMS (ESI+) Calculated for $C_{172}H_{178}O_{37}SiN_2Cl_6Na^+$ [M+Na]+ 3127.9728. found 3127.9728.

Synthesis of 48
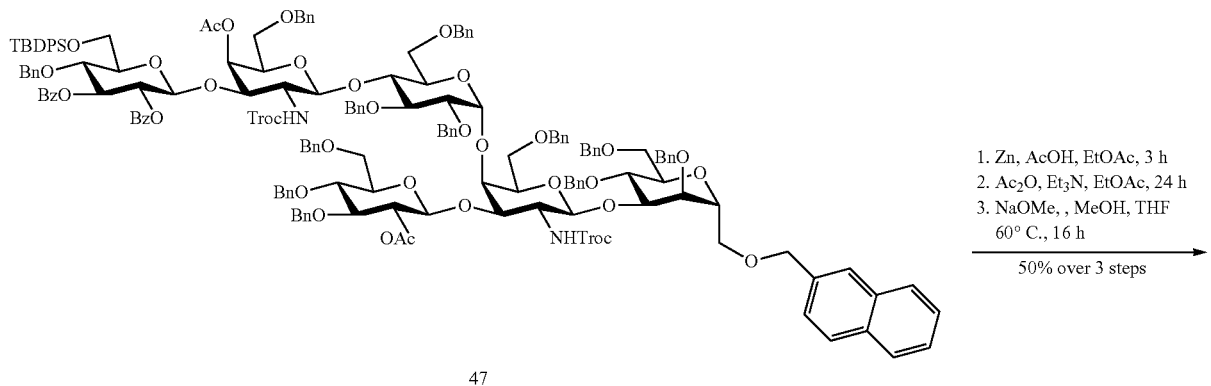
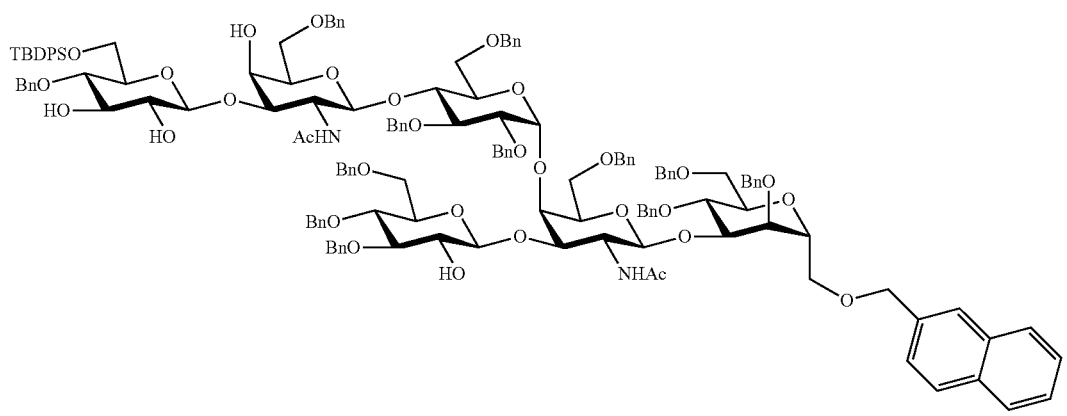
The procedure described for the synthesis of compound 29 used for the synthesis of compound 48 (50%). HRMS (ESI+) Calculated for $C_{152}H_{168}O_{31}SiN_2Na^+$ $[M+Na]^+$ 2568.1298. found 2568.1322.
Synthesis of 49
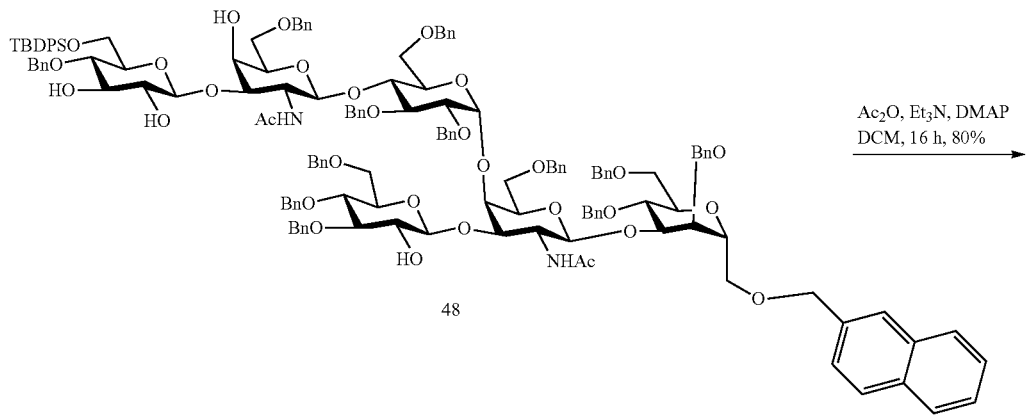

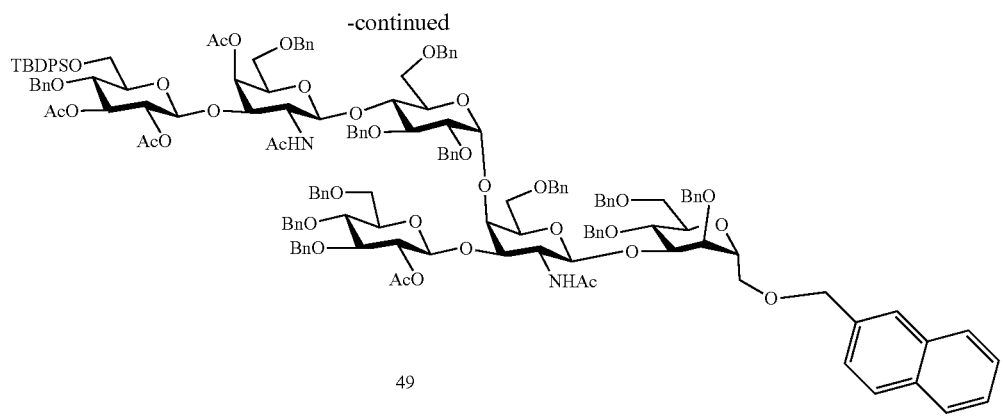
49
The procedure described for the synthesis of compound 30 used for the synthesis of compound 49 (80%). HRMS (ESI+) Calculated for $C_{160}H_{176}O_{35}SiN_2Na^+$ [M+Na]$^+$ 2737.1754. found 2737.2001.
Synthesis of 50
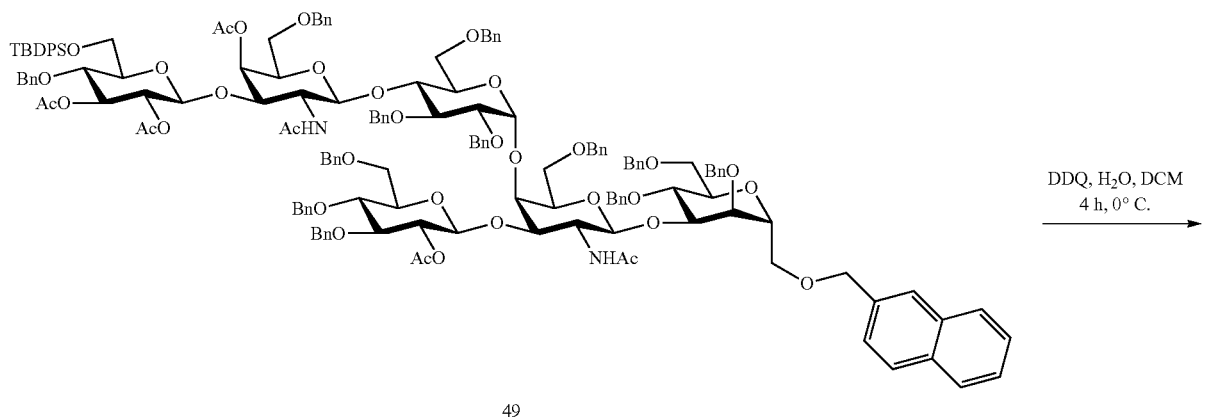
49
DDQ, H$_2$O, DCM
4 h, 0° C.
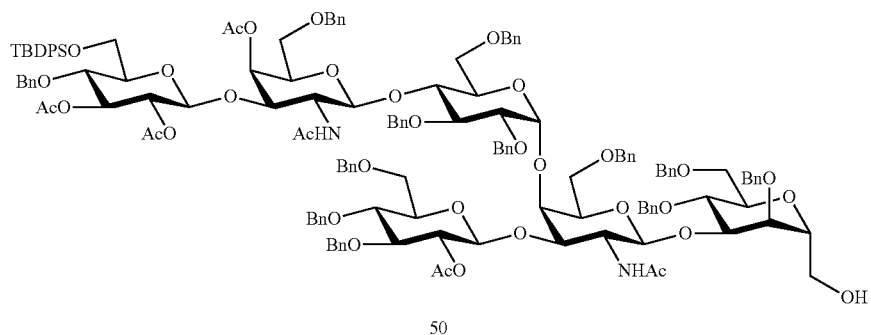
50
The procedure described for the synthesis of compound 31 used for the synthesis of compound 50 (70%). HRMS (ESI+) Calcd for $C_{149}H_{168}O_{35}SiN_2Na^+$ [M+Na]$^+$ 2596.1095. found 2595.9954 and 2596.9997.

Synthesis of 51
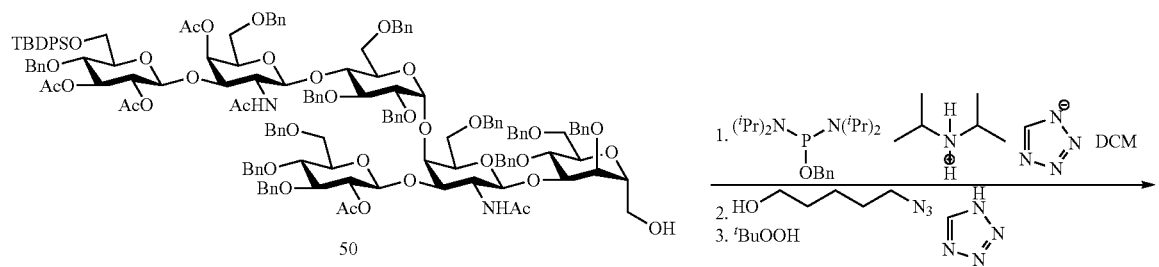
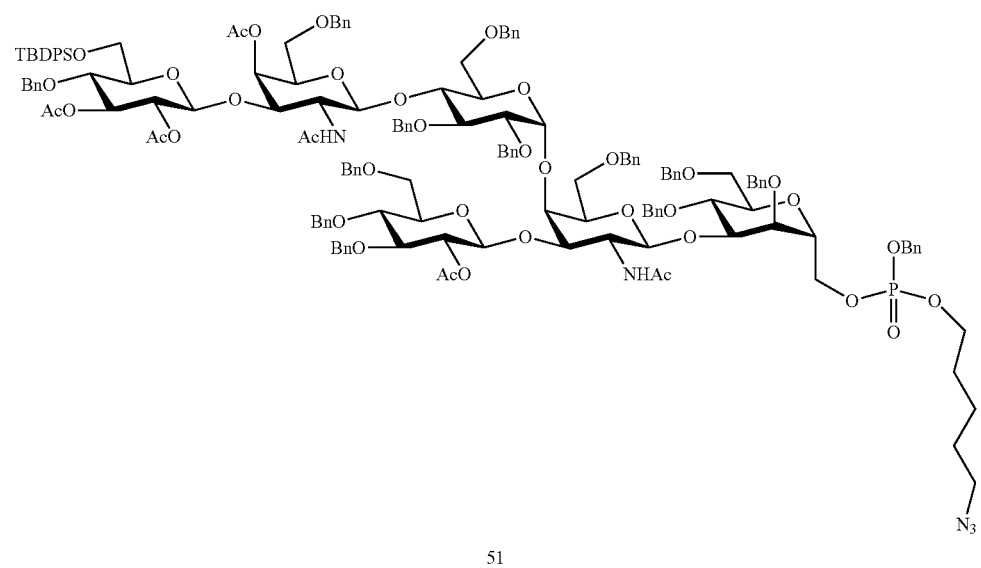
The procedure described for the synthesis of compound 32 used for the synthesis of compound 51.
Synthesis of 52
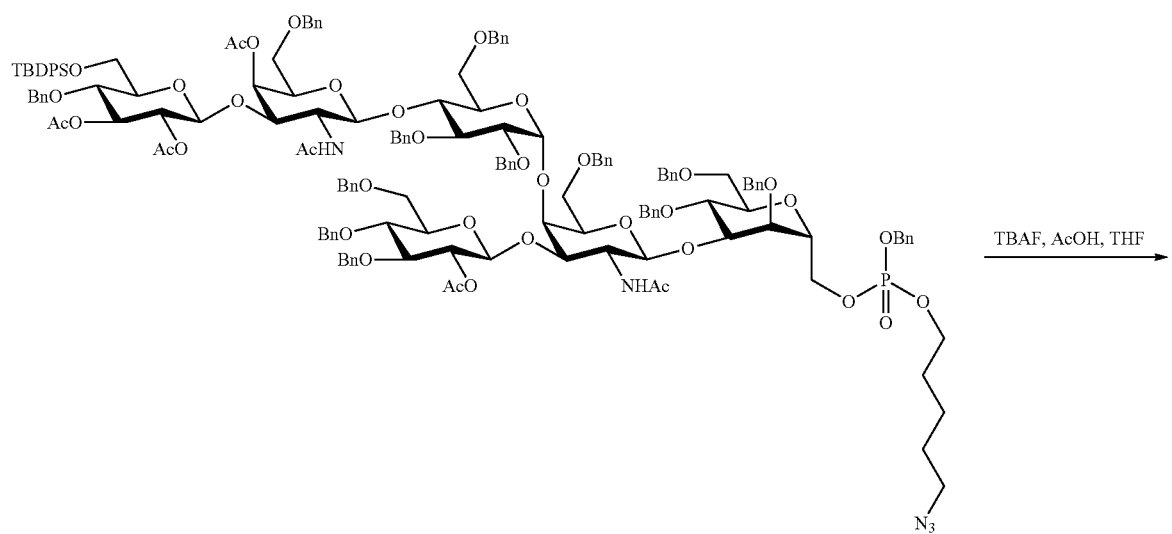

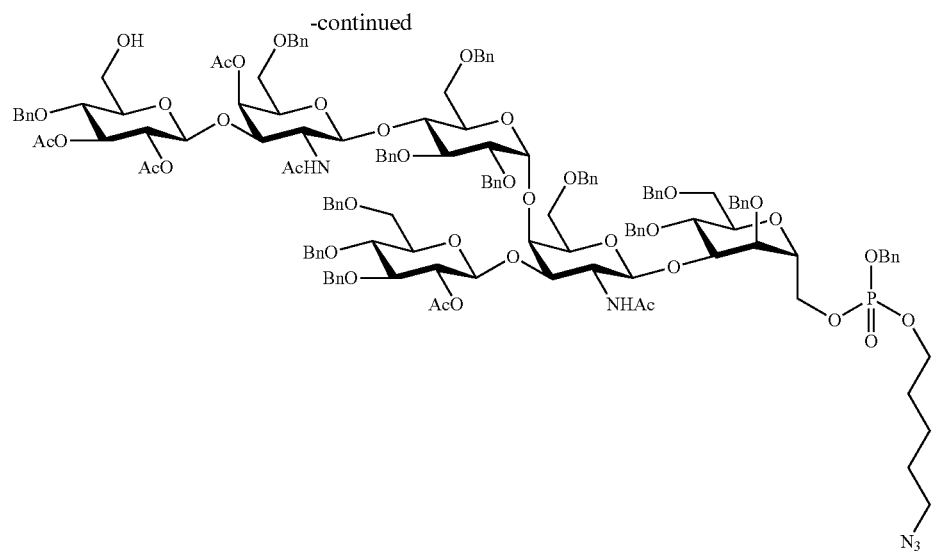

52

A premixed solution of TBAF and AcOH was added to a clear solution of 51 in THF at rt and the reaction mixture was kept for stirring at rt for 3 h. After complete consumption of starting material, reaction mixture was diluted with DCM and concentrated under vacuum to obtain the crude product. The crude product was purified by automated column chromatography on silica gel using EtOAc in n-hexane (gradient, 0 to 100%) as the eluent.

Synthesis of 53

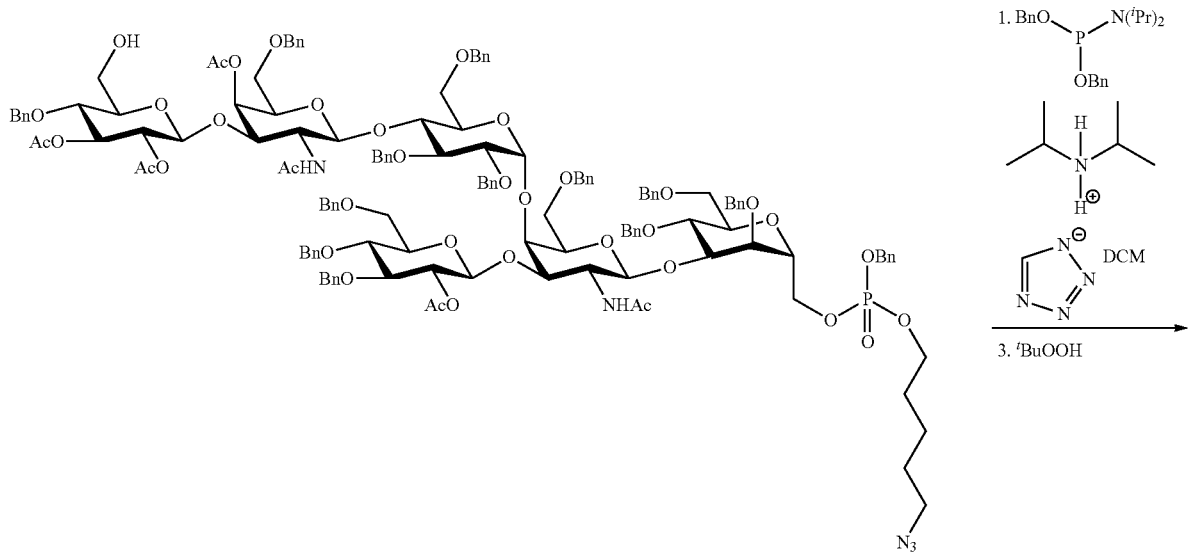

52

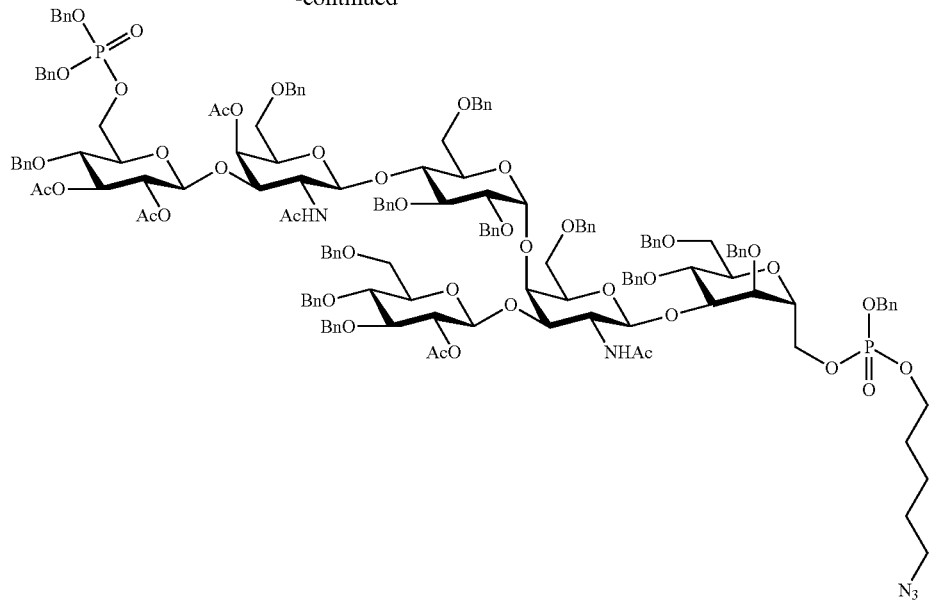

53

To a solution of 52 in DCM, were added dibenzyl N,N-diisopropylphosphoramidite (2.0 equiv.) and diisopropylammonium tetrazolide (1.5 equiv.) and the solution was stirred at rt for 1.5 h. Then, t-butyl peroxide (6.0 equiv., 5.0-6.0 M solution in decane) was added and the reaction mixture stirred for 1 h. After 1 h, reaction mixture was diluted with DCM and quenched with NaHCO$_3$ aq. sat. solution. The aqueous layer was extracted with DCM. The combined organic layer was washed with brine, dried over Na$_2$SO$_4$, filtered, and the filtrate was concentrated under vacuum to obtain the crude product. The crude product was purified by automated flash column chromatography on silica gel (0-100% EtOAc in cyclohexane) to afford the desired product 53.

Synthesis of 54

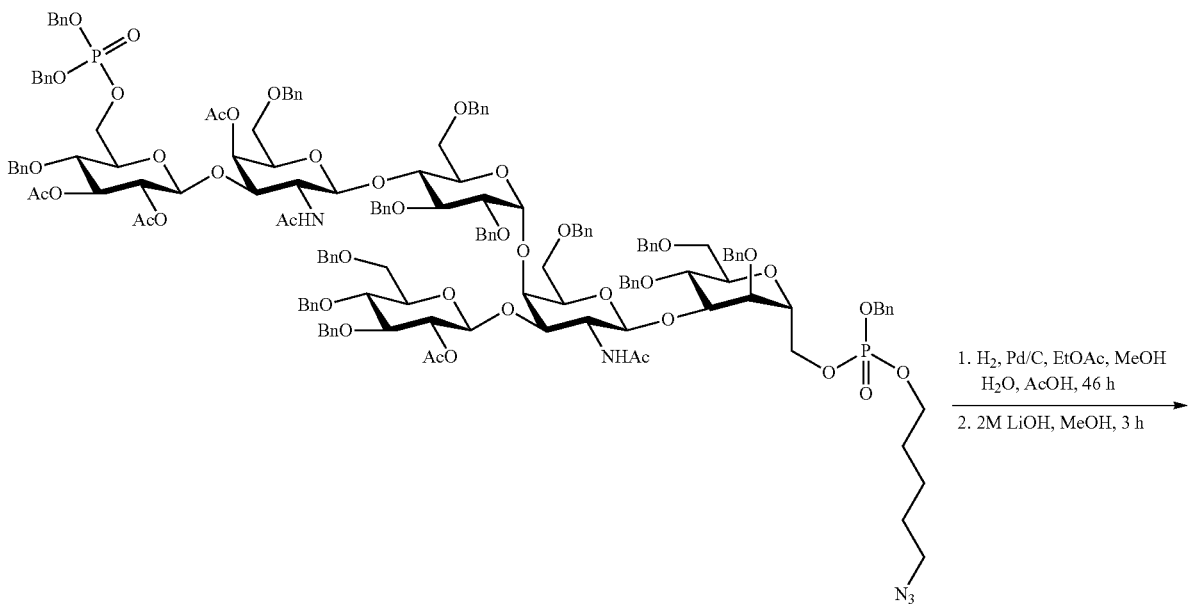

53

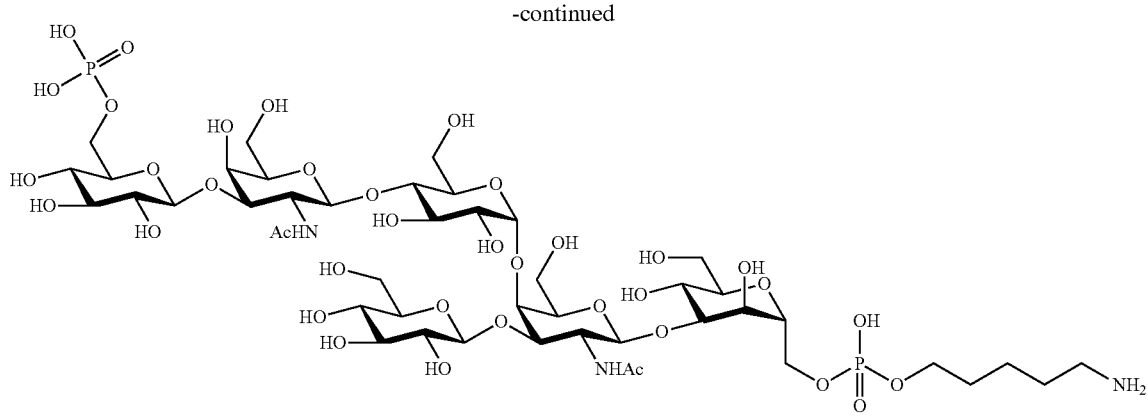
54
The procedure described for the synthesis of compound 33 used for the synthesis of compound 54.
Conjugation of 54 with CRM$_{197}$ and BSA
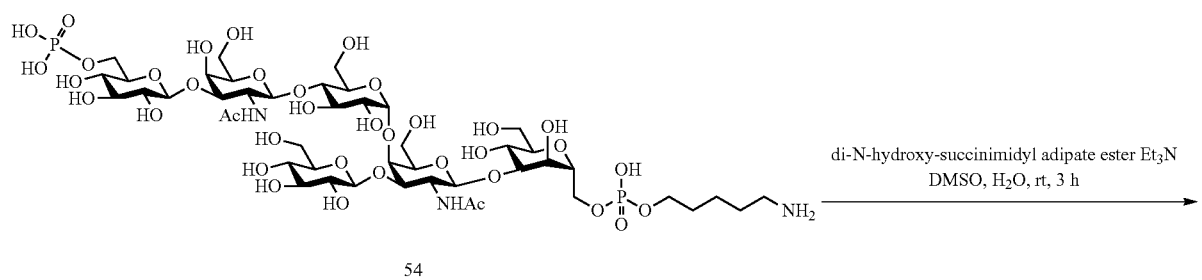
54
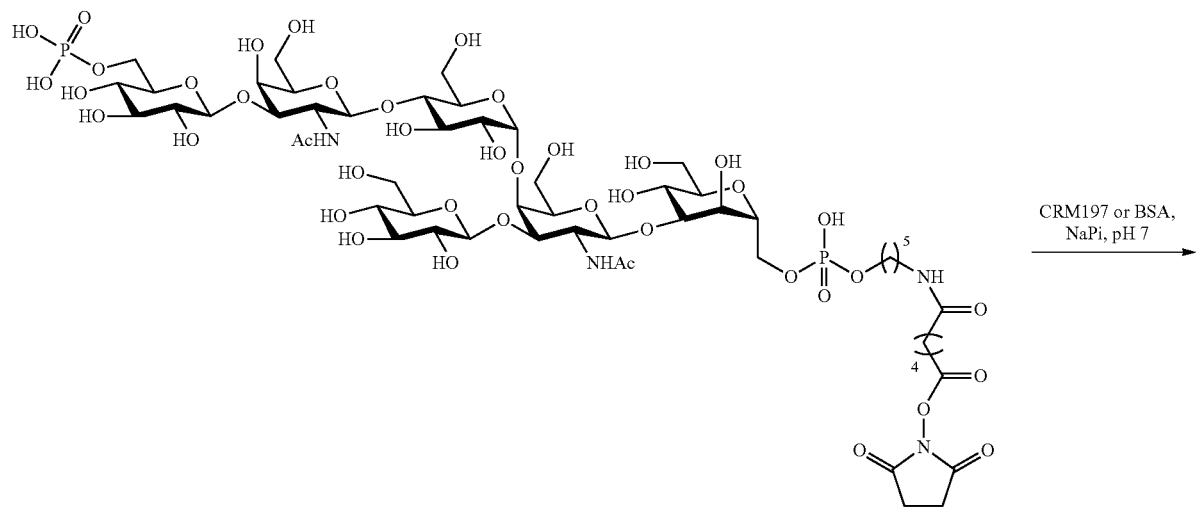
55

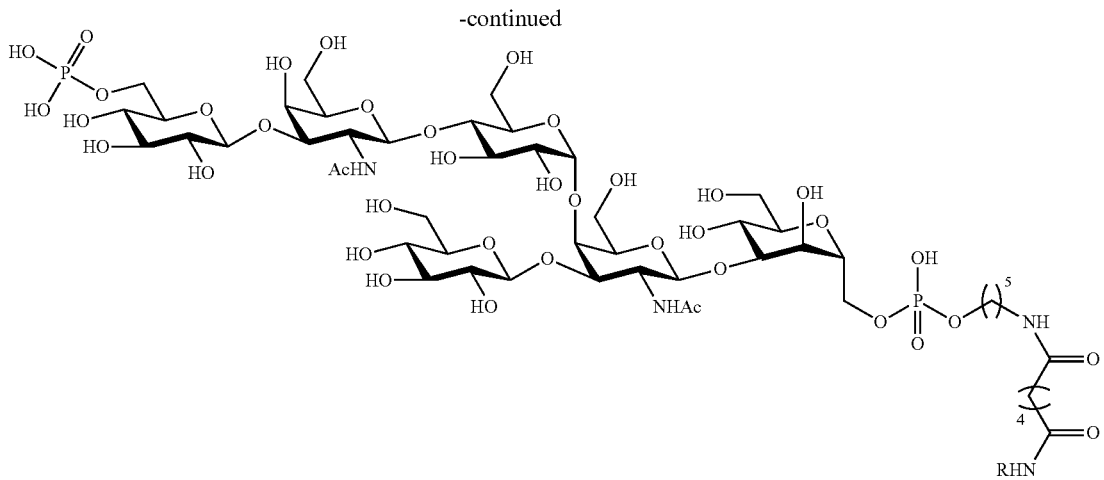

56 R = CRM197
57 R = BSA

The procedure described for the synthesis of glycoconjugates 36 and 37 was also used for the synthesis of 56 and 57.

A.4 Alternative Synthesis of Hexasaccharide 54

Synthesis of 58

Diphenyl phosphite was added to a clear solution of 48 in pyridine, and the reaction mixture was stirred at room temperature under nitrogen for 2 h. After 2 h, 1 M TEAB solution was added to the reaction mixture at 0° C. After 5 min, ice bath was removed and the stirring was continued for another 2 h at rt. After complete consumption of starting

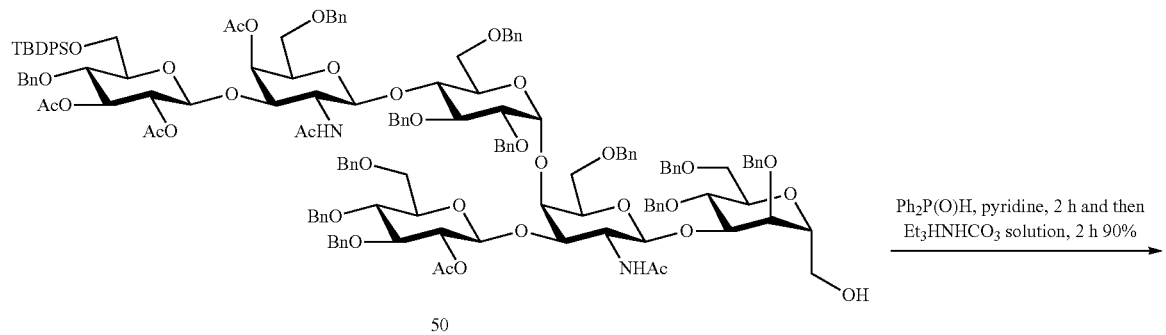

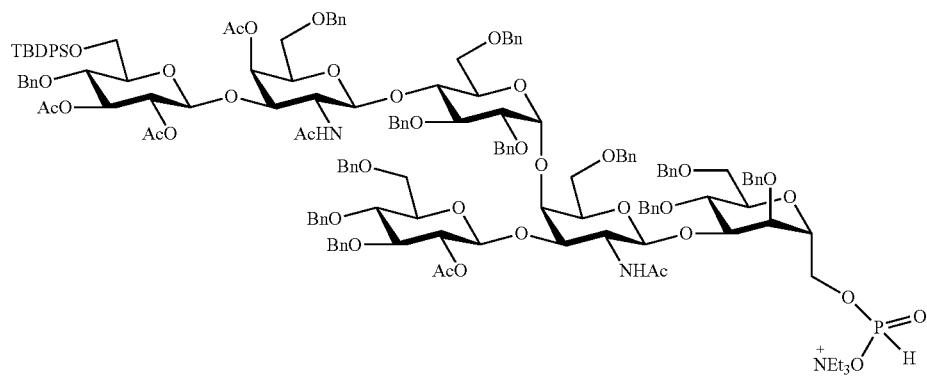

material, reaction mixture was diluted with DCM and the organic layer was washed successively with 1 M TEAB solution and concentrated under reduced pressure. The crude product was purified by automated flash column chromatography (EA:DCM:MeOH with 2% Et$_3$N) to give pure H-phosphonate derivative 58 (90%) as viscous liquid. HRMS (ESI+) Calcd for $C_{155}H_{184}N_3PSiO_{37}^+$ [M]$^+$ 2740.2189. found 2740.2132.

Synthesis of 59

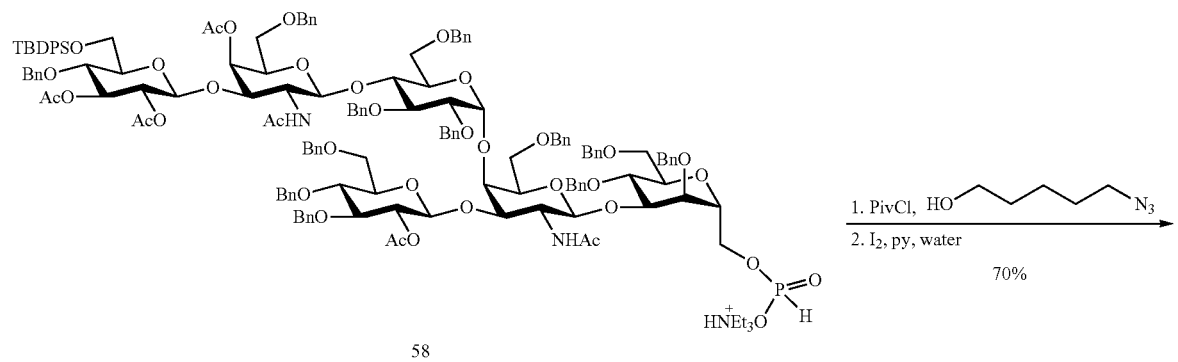

58

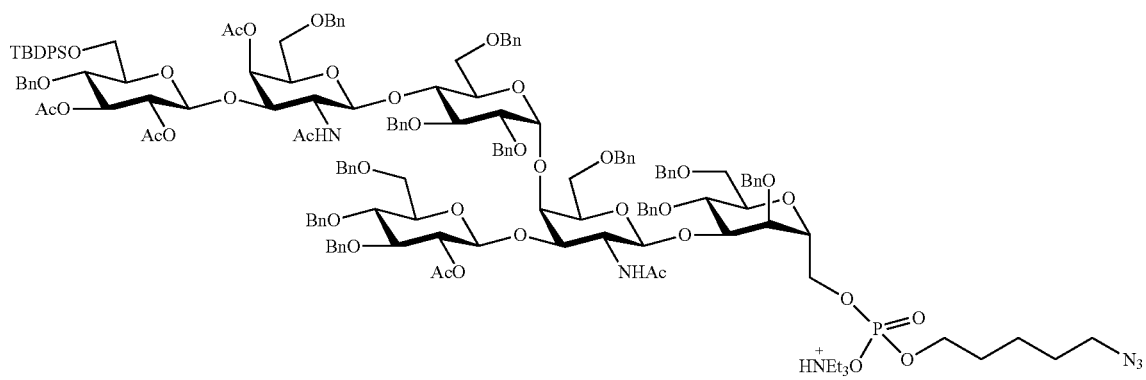

59

H-phosphonate 58 (1.0 equiv.) and linker (4.0 equiv.) were co-evaporated with pyridine and dried under vacuum for 30 min. After that, it was dissolved in py and to this PivCl (2.0 equiv.) was added. The reaction mixture was kept for stirring at rt for 2 h. After 2 h, the reaction was cooled to −40° C., a freshly prepared solution of I$_2$ in Py:H$_2$O (20:1) was added and the reaction mixture was kept for stirring at the same temperature for 1.5 h and later brought to rt and stirred at rt for 15 min. Then, TEAB (10 mL) was added to the mixture and diluted with dichloromethane, washed successively with 10% aq. sodium thiosulfate, 1 M aq. triethylammonium hydrogen carbonate (TEAB), dried over Na$_2$SO$_4$, filtered and concentrated. The residue was purified by automated flash column chromatography (ethyl acetate: DCM:MeOH) together with 2% trimethylamine as eluents give the desired product 59 (70%) as viscous liquid. Maldi (ESI+) Calcd for $C_{154}H_{178}N_5PNaSiO_{38}^+$ [M-Et$_3$N+Na]$^+$ 2789.1635. found 2788.0.

Synthesis of 60

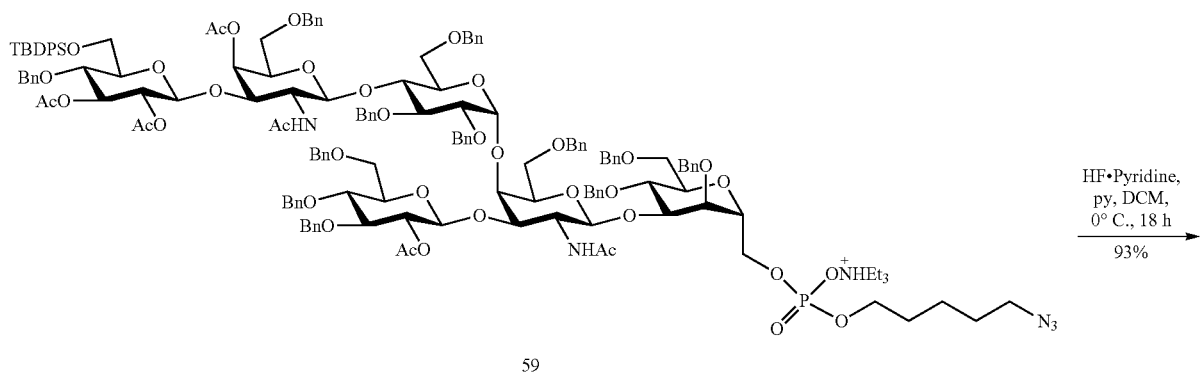

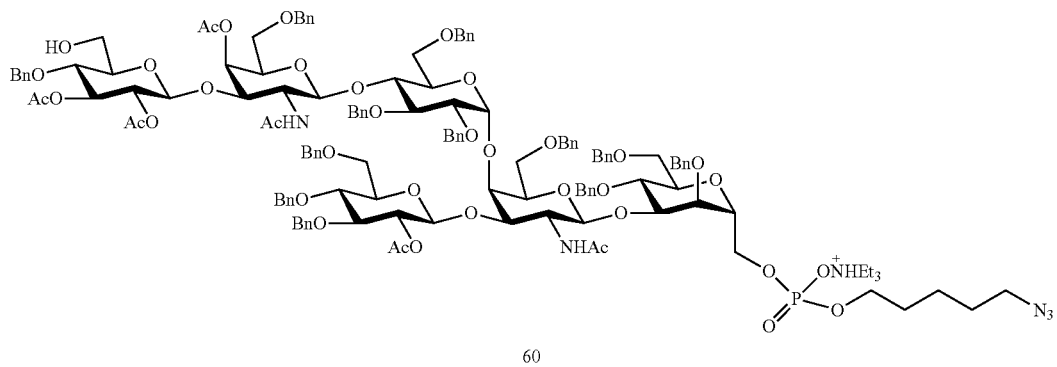

To a solution of 59 in DCM and pyridine at 0° C. was added HF solution (70% in pyridine, 0.3 mL) drop wisely. The reaction mixture was stirred at the same temperature for 18 h. Then, the reaction mixture was diluted with DCM, washed with saturated aqueous $NaHCO_3$ solution, and TEAB buffer. The organic phase was separated and dried ($Na_2SO_4$) and concentrated under reduced pressure. The residue was purified by automated flash column chromatography (ethyl acetate:DCM:MeOH) together with 2% trimethylamine as eluents give the desired product 60 as viscous liquid. Maldi (ESI+) Calcd for $C_{138}H_{160}N_5PNaO_{38}{}^+$ [M-$Et_3$N+Na]$^+$ 2550.7585. found 2549.698.

Synthesis of 54

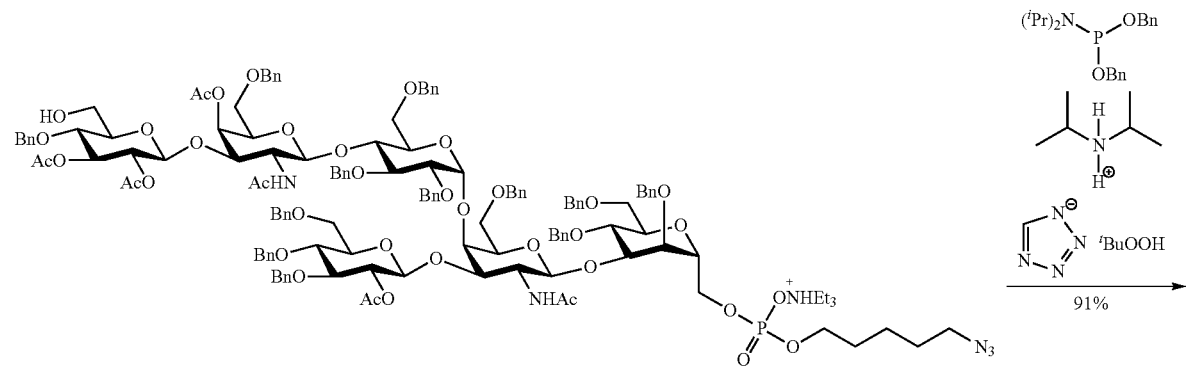

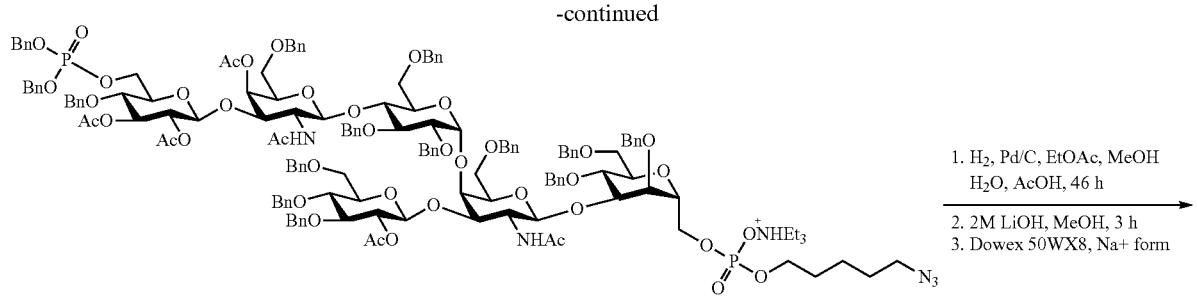

61

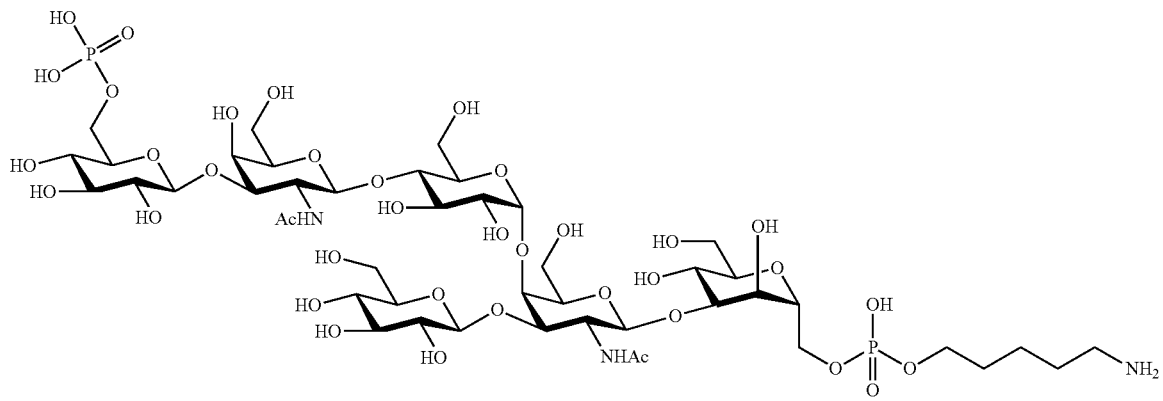

54

To a solution of 60 in DCM was added dibenzyl diisopropylphosphoramidite (2.0 equiv.) and diisopropylammonium tetrazolide (2.0 equiv.) and the solution stirred at room temperature for 1.5 h. Then, t-butyl peroxide 5.0-6.0 M solution in decane (6.0 equiv.) was added at room temperature and the reaction mixture stirred for 1 h. The reaction mixture was diluted with DCM and washed with NaHCO$_3$ aq. sat. solution and TEAB buffer. The aqueous layer was extracted with DCM (2×10 mL). The combined organic layer was dried over Na$_2$SO$_4$ (0.5 g), filtered, and the filtrate was concentrated under vacuum to obtain the crude product. The crude product was purified by automated flash chromatography using EtOAc:DCM:MeOH with 2% trimethylamine to obtain the desired product 61 as viscous oil (91%). Title compound 54 was obtained in 60% yield from compound 61 by the procedure described for the synthesis of compound 33. HRMS (ESI+) Calcd for C$_{46}$H$_{83}$N$_3$P$_2$NaO$_{37}$$^+$ [M+Na]$^-$ 1354.4078. found 1354.9623.

A.5 Alternative Synthesis of Hexasaccharide 54

Synthesis of 62

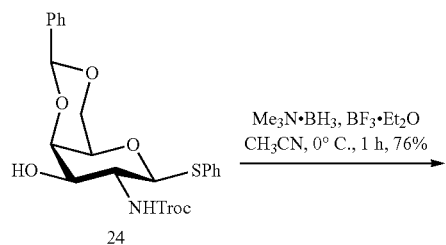

24

-continued

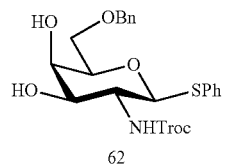

62

Me$_3$N·BH$_3$ (21.2 g, 291 mmol, 5.4 equiv.), BF$_3$·Et$_2$O (42.2 mL, 291 mmol, 5.4 equiv.) were added to a cooled solution of 24 (28.8 g, 54 mmol) in CH$_3$CN (1.5 L) at 0° C. The reaction mixture was stirred at the same temperature for 1 h. After complete consumption of starting material, reaction mixture was quenched with Et$_3$N (30 mL) and MeOH (50 mL). Then Reaction mixture was diluted with EtOAc (1 L), washed with 1 M HCl (three times, sometimes it is difficult to see 2 layers then add brine to get better) and followed by aq. NaHCO3 until pH of the organic layer becomes neutral. The separated organic layer was dried over Na$_2$SO$_4$, filtered and concentrated. The product 62 (22 g, 76%) white solid was pure used for the next step. HRMS (ESI+) Calcd for C$_{22}$H$_{24}$Cl$_3$NO$_6$SNa$^+$ [M+Na]$^+$ 558.0288. found 558.0332.

Synthesis of 64

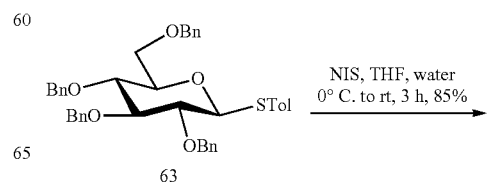

63

263

-continued

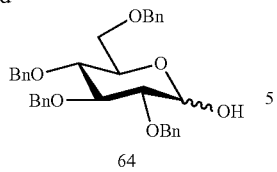
64

The procedure described for the synthesis of compound 2 used for the synthesis of compound 64 (85%). HRMS (ESI+) Calcd for $C_{34}H_{40}O_6N^+$ [M+NH$_4$]$^+$ 558.2856. found 558.2976.

Synthesis of 65

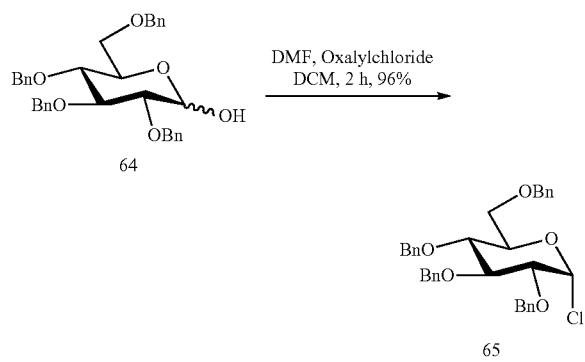

To a stirred solution of 64 (24.5 g, 45.3 mmol) in anhydrous DCM (360 mL), anhydrous DMF (1 mL, 13.6 mmol, 0.30 equiv.) and (COCl)$_2$ (10.3 mL, 118.0 mmol, 2.6 equiv.) were added at 0° C. After 5 min. reaction mixture was brought to rt and stirred at r.t. for 2 h. After complete consumption of starting material the reaction mixture was cooled to 0° C. quenched with Et$_3$N. The salt formed was filtered through short pad of celite and washed with DCM (Do not wash with lot of DCM, salt will dissolve and pass through celite). Then, the filtrate was concentrated under reduced pressure and purified by silica gel column chromatography using ethyl acetate:cyclohexane (0-40% with 2% Et$_3$N) to afford the desired glycosyl chloride 65 (24 g, 96%) as the viscous liquid. HRMS (ESI+) Calcd for $C_{34}H_{35}O_5ClNa^+$ [M+Na]$^+$581.2071. found 581.2206.

Synthesis of 66

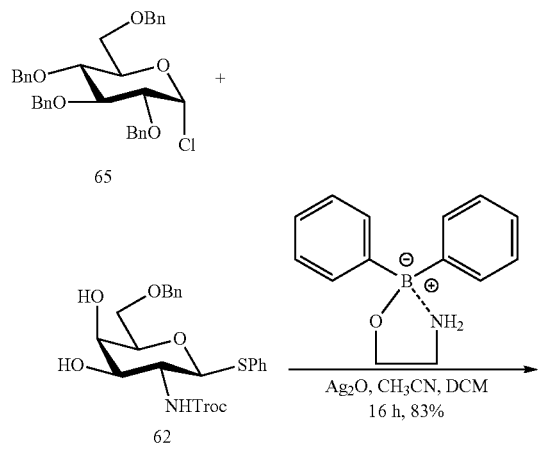

264

-continued

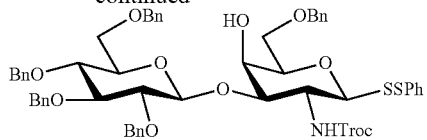
66

To a turbid of glycosyl chloride 65 (16.2 g, 28.9 mmol, 1.15 equiv.) and acceptor 62 (13.5 g, 25.1 mmol) in acetonitrile (200 mL) and DCM (80 mL), were added Ag$_2$O (8.8 g, 37.7 mmol, 1.5 equiv. dried under vacuum at 80° C. for 3 h before use) and 2-aminoethyl diphenylborinate (0.57 g, 2.51 mmol, 0.1 equiv.). After being stirred at rt. for 16 h, the mixture was diluted with DCM (80 mL), acetone (80 mL) and filtered through celite, sand and washed with DCM and Acetone till the filtrate showed no product. All the filtrate fractions were combined and concentrated. The residue was dissolved in EtOAc (300 mL) and kept at 55° C. till the solid dissolves and becomes the clear solution. Then this clear solution was filtered through filter paper and washed with hot EtOAc and kept for recrystallization. After 1 h white solid was crystalized and it was separated from the solution to give the desired disaccharide 66 as white solid (22 g, 83%). HRMS (ESI+) Calcd for $C_{56}H_{58}Cl_3NO_{11}SNa^+$ [M+Na]$^+$ 1080.2696. found 1080.2904.

Synthesis of 67

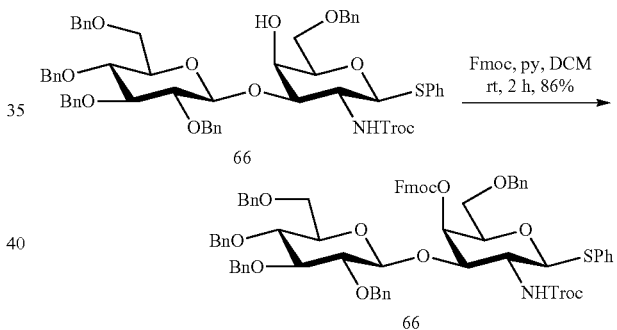

FmocCl (16.87 g, 63.2 mmol, 2.0 equiv.) and pyridine (7.67 mL, 95.0 mmol, 3.0 equiv.) were added to a clear solution of 66 (33.5 g, 31.6 mmol) in DCM (330 mL) and kept for stirring at rt for 2 h. After complete consumption of starting material, reaction mixture was diluted with DCM and it was washed with brine. The organic layer was dried over Na$_2$SO$_4$, filtered and concentrated. The crude residue was purified by automated flash column chromatography on silica gel (0-100%, EtOAc in cyclohexane) to give the desired compound 67 (34.7 g, 86%) as white solid. HRMS (ESI+) Calcd for $C_{71}H_{68}Cl_3NO_{13}SNa^+$ [M+Na]$^+$ 1302.3375. found 1302.3694.

Synthesis of 69

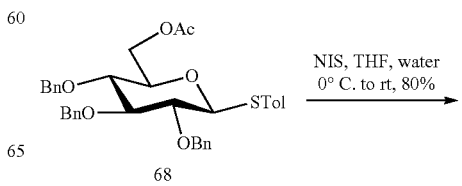
68

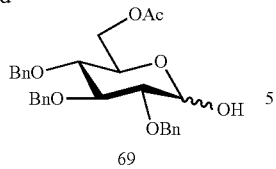

69

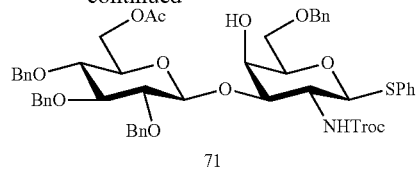

71

The procedure described for the synthesis of compound 2 used for the synthesis of compound 69 (80%). HRMS (ESI+) Calcd for $C_{29}H_{36}O_7N^+$ [M+NH$_4$]$^+$ 510.2492. found 510.2527.

Synthesis of 70

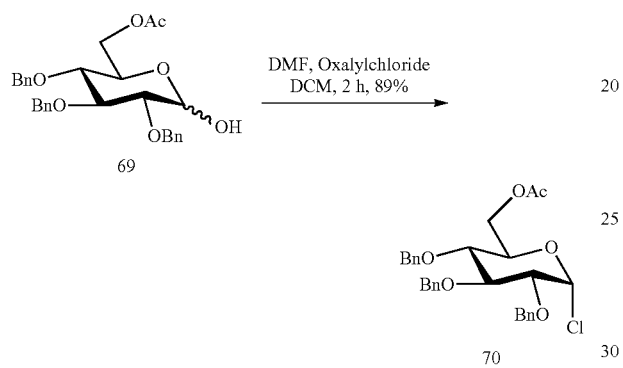

To a stirred solution of 69 (18.0 g, 36.5 mmol) in anhydrous DCM (290 mL), anhydrous DMF (0.85 mL, 11.0 mmol, 0.30 equiv.) and (COCl)$_2$ (8.3 mL, 95.0 mmol, 2.6 equiv.) were added at 0° C. After 5 min. reaction mixture was brought to rt and stirred at r.t. for 2 h. After complete consumption of starting material the reaction mixture was cooled to 0° C. quenched with Et$_3$N. The salt formed was filtered through short pad of celite and washed with DCM. Then, the filtrate was concentrated under reduced pressure and purified by silica gel column chromatography using ethyl acetate:cyclohexane (0-40% with 2% Et$_3$N) to afford the desired glycosyl chloride 70 (16.7 g, 89%) as the viscous liquid. HRMS (ESI+) Calcd for $C_{29}H_{31}O_6ClNa^+$ [M+Na]$^+$ 533.1707. found 533.1752.

Synthesis of 71

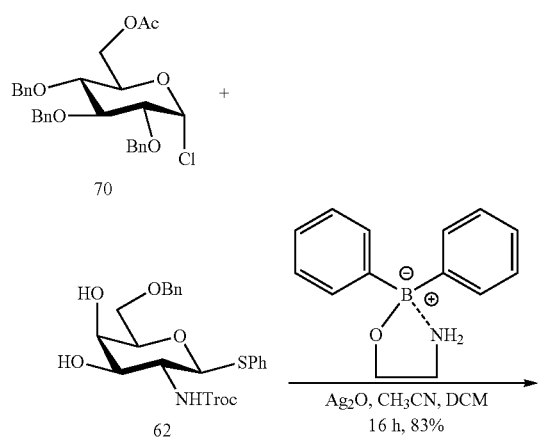

To a turbid of glycosyl chloride 70 (16.5 g, 32.3 mmol, 1.15 equiv.) and acceptor 62 (15.07 g, 28.1 mmol) in acetonitrile (200 mL) and DCM (80 mL), were added Ag$_2$O (9.76 g, 42.1 mmol, 1.5 equiv. dried under vacuum at 80° C. for 3 h before use) and 2-aminoethyl diphenylborinate (0.63 g, 2.81 mmol, 0.1 equiv.). After being stirred at rt. for 16 h, the mixture was diluted with DCM (80 mL), acetone (80 mL) and filtered through celite, sand and washed with DCM and Acetone till the filtrate showed no product. All the filtrate fractions were combined and concentrated. The residue was dissolved in EtOAc (400 mL) and kept at 55° C. till the solid dissolves and becomes the clear solution. Then this clear solution was filtered through filter paper and washed with hot EtOAc and kept for recrystallization. After 1 h white solid was crystalized and it was separated from the solution to give the desired disaccharide 71 as white solid (23 g, 81%). HRMS (ESI+) Calcd for $C_{51}H_{54}Cl_3NO_{12}SNa^+$ [M+Na]$^+$ 1032.2330. found 1032.2423.

Synthesis of 72

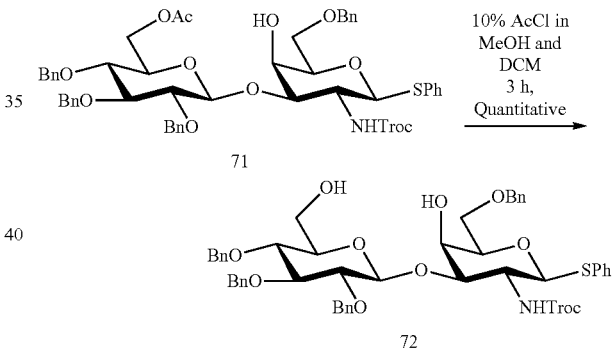

AcCl (40 mL) was added to a turbid of 71 (18.87 g, 18.66 mmol) in MeOH (200 mL) and DCM (200 mL) at 0° C. After 5 minutes, ice bath was removed and kept at rt for stirring. After stirring at room temperature for 3 h, the reaction mixture was diluted with DCM and washed with water and aq. NaHCO$_3$. The separated organic layer was dried over Na$_2$SO$_4$, filtered and concentrated on a rotary evaporator to yield the desired compound 72 (18.09 g, quantitative) as white solid. HRMS (ESI+) Calcd for $C_{49}H_{52}Cl_3NO_{11}SNa^+$ [M+Na]$^+$ 990.2224. found 990.2301.

Synthesis of 73

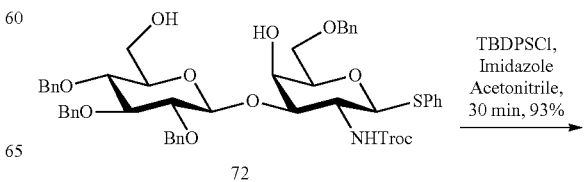

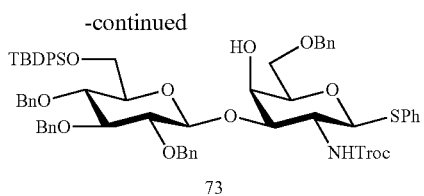

To a suspension of 72 (18.05 g, 18.6 mmol) in acetonitrile (370 mL) was added imidazole (3.56 g, 52.3 mmol, 2.8 equiv.) and TBDPSCl (7.2 mL, 28.0 mmol, 1.5 equiv.). After 5 minutes reaction mixture was completely clear and left for stirring at rt for 30 minutes. After 30 minutes, the reaction mixture was diluted with EtOAc and washed with brine. The separated organic layer was dried over $Na_2SO_4$, filtered and concentrated. The crude residue obtained after solvents removal was purified by automated silica gel flash chromatography using ethyl acetate and cyclohexane as the eluents to give the desired product 73 (20.9 g, 93%) as solid. HRMS (ESI+) Calcd for $C_{65}H_{70}Cl_3NO_{11}SSiNa^+$ $[M+Na]^+$ 1228.3402. found 1228.3481.

Synthesis of 74

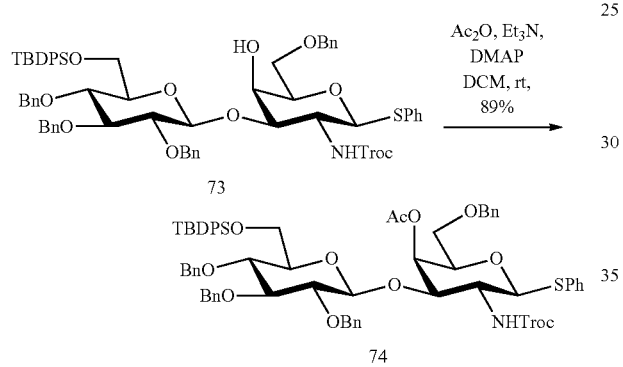

To a clear solution of 73 (18.69 g, 15.47 mmol) in DCM (200 mL) were added $Et_3N$ (19 mL, 139.0 mmol, 9.0 equiv.), aceticanhydride (4.4 mL, 46.4 mmol, 3.0 equiv.) and DMAP (0.189 g, 1.547 mmol, 0.1 equiv.) and kept for stirring at rt for 18 h. After 18 h, reaction mixture was diluted with DCM and washed with aq. $NaHCO_3$. The separated organic layer dried over $Na_2SO_4$ and concentrated. The crude residue obtained after solvents removal was purified by automated flash chromatography on silica gel (cyclohexane-EtOAc) to yield the desired product 74 as foam (17.2 g, 89%). HRMS (ESI+) Calcd for $C_{67}H_{72}Cl_3NO_{12}SSiNa^+$ $[M+Na]^+$ 1272.3478. found 1272.3530.

Synthesis of 76

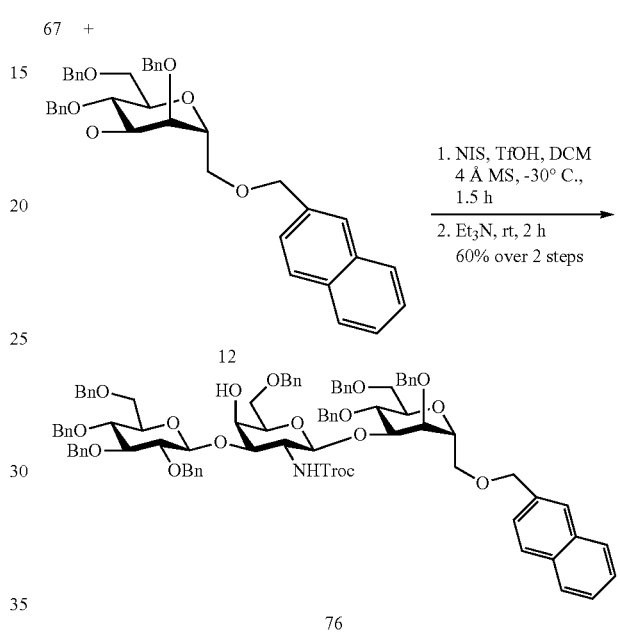

The procedure described for the synthesis of compound 16 used for the synthesis of compound 76 (60% over 2 steps). HRMS (ESI+) Calcd for $C_{82}H_{86}O_{17}NNaCl_3^+$ $[M+Na]^+$ 1574.5329. found 1574.5624.

Synthesis of 77

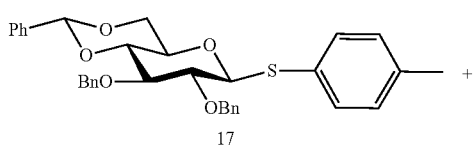

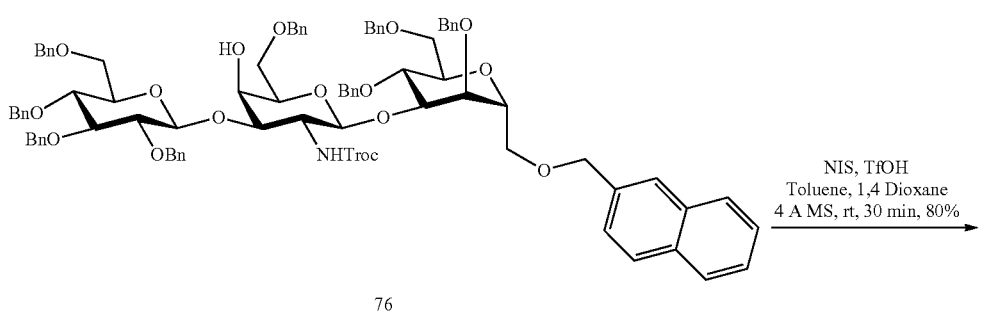

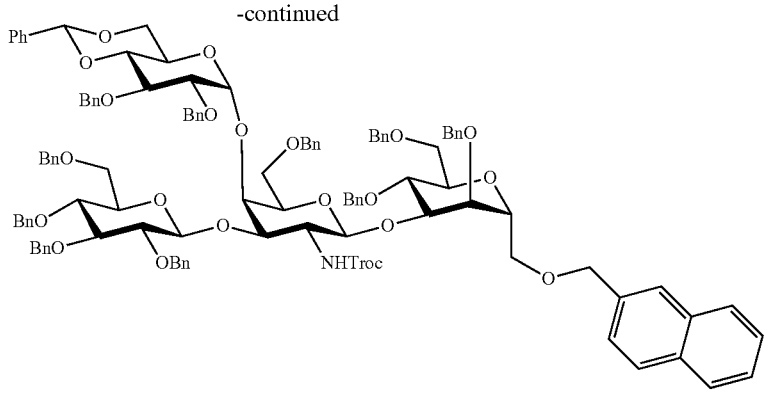
77
The procedure described for the synthesis of compound 18 used for the synthesis of compound 77 (80%). HRMS (ESI+) Calcd for $C_{116}H_{122}O_{22}N_2Cl_3^+$ [M+NH$_4$]$^+$ 2000.7565. found 2000.7588.
Synthesis of 78
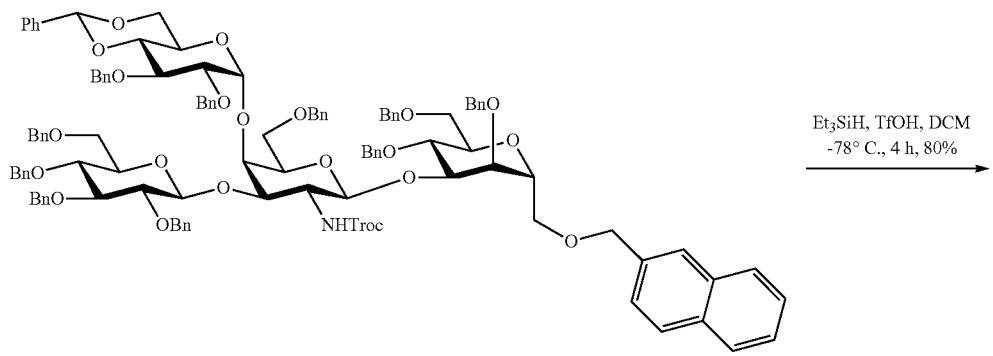
77
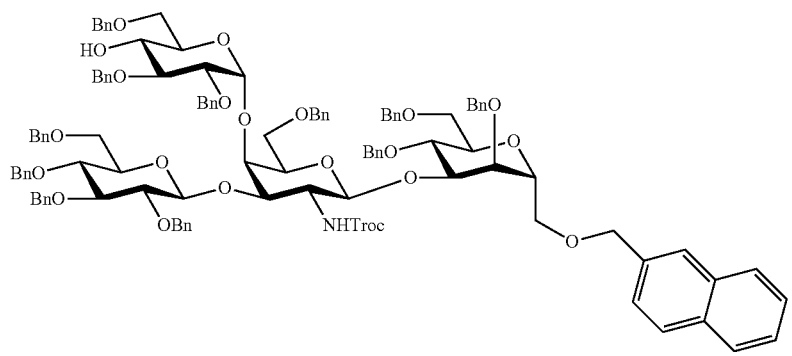
78
The procedure described for the synthesis of compound 19 used for the synthesis of compound 78 (80%). HRMS (ESI+) Calcd for $C_{116}H_{124}O_{22}N_2Cl_3^+$ [M+NH$_4$]$^+$ 2001.7711. found 2001.6469.

Synthesis of 79
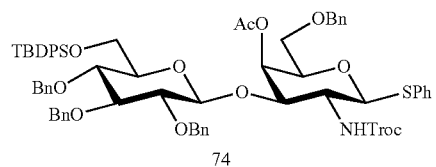
74
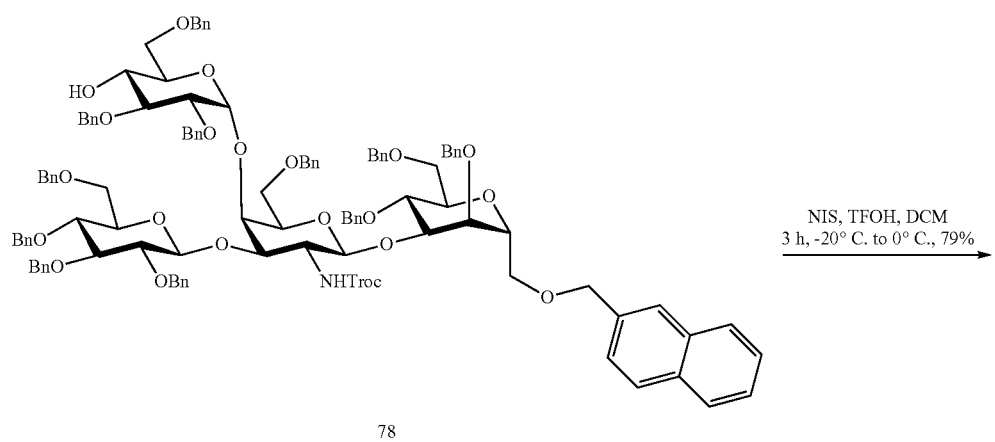
78
NIS, TFOH, DCM
3 h, -20° C. to 0° C., 79%
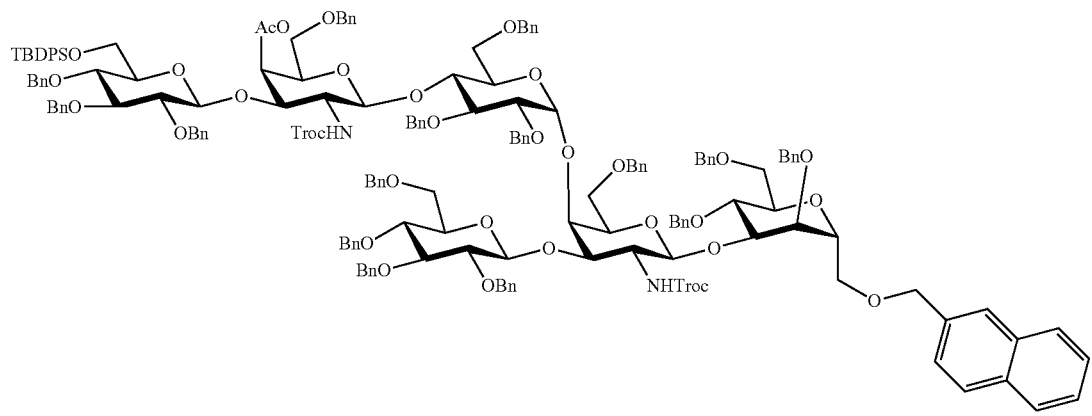
79
The procedure described for the synthesis of compound 28 used for the synthesis of compound 79 (79%). HRMS (ESI+) Calcd for $C_{177}H_{186}O_{34}N_2Cl_6Na^+$ [M+Na]$^+$ 3147.0689. found 3147.1184.
Synthesis of 80
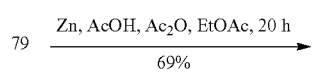
Zn, AcOH, Ac$_2$O, EtOAc, 20 h
69%

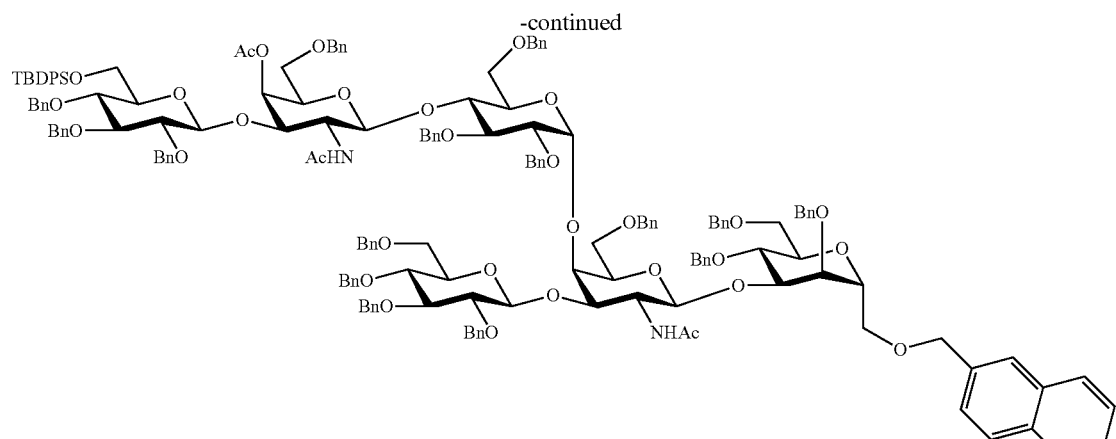

80

To a clear solution of 79 in EtOAc (2.0 mM) were added Zn (100 equiv.), AcOH (100 equiv.), Ac$_2$O and the reaction mixture was kept for stirring at room temperature 20 h. After complete consumption of starting material, reaction mixture was filtered through celite pad and concentrated. The crude residue was purified by automated flash column chromatography on silica gel (0-100%, EtOAc in cyclohexane) to give the desired hexasaccharide 80 (69%) as white solid. HRMS (ESI+) Calcd for $C_{175}H_{188}N_2O_{32}Si^+$ [M]$^+$ 2858.2948. found 2858.3062.

Synthesis of 81

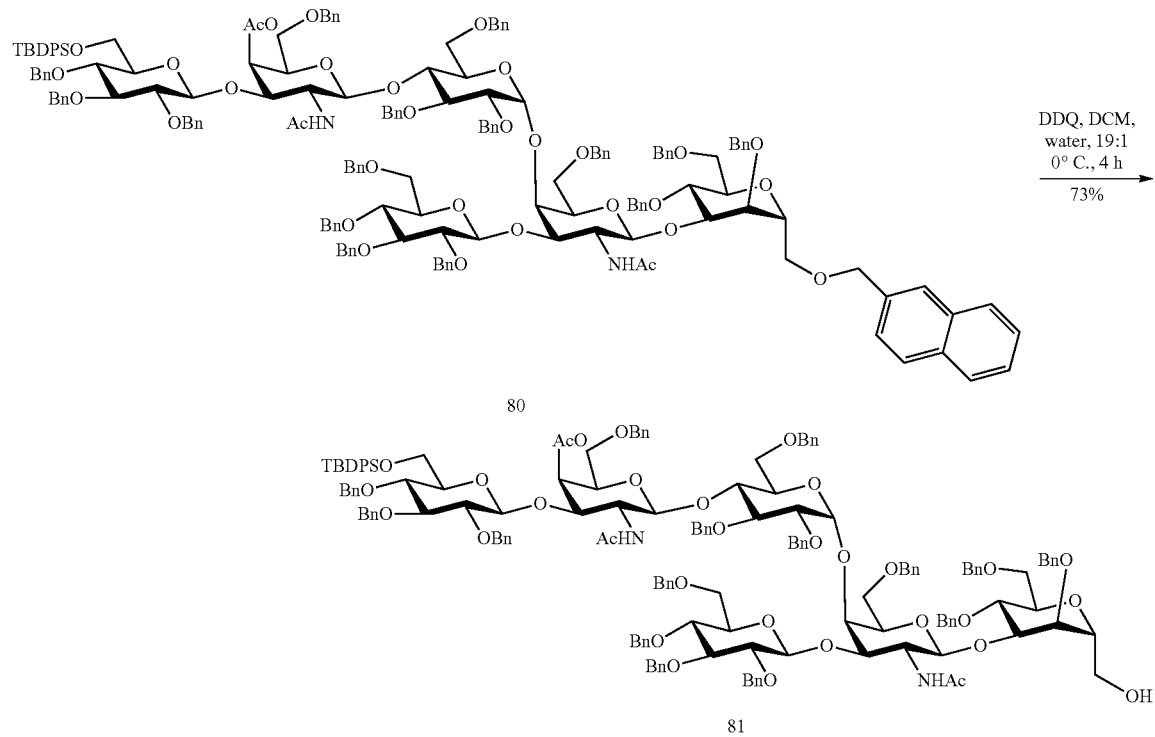

The procedure described for the synthesis of compound 31 used for the synthesis of compound 81 (73%). HRMS (ESI+) Calcd for $C_{164}H_{180}O_{32}N_2Si^+$ [M]$^+$ 2718.2322, found 2718.2347.

Synthesis of 82
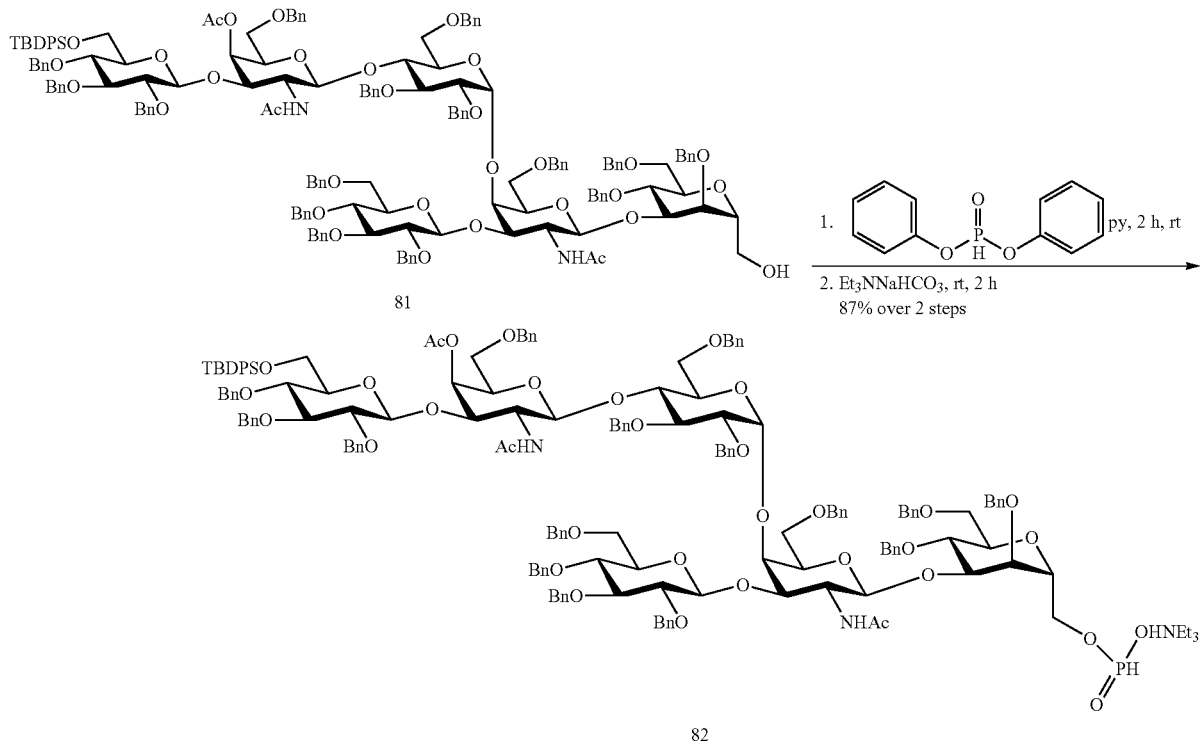
The procedure described for the synthesis of compound 58 used for the synthesis of compound 82 (87%). HRMS (ESI+) Calcd for $C_{164}H_{181}O_{34}N_2SiP^+$ [M-Et$_3$N]$^+$ 2782.2036. found 2782.2077.
Synthesis of 83
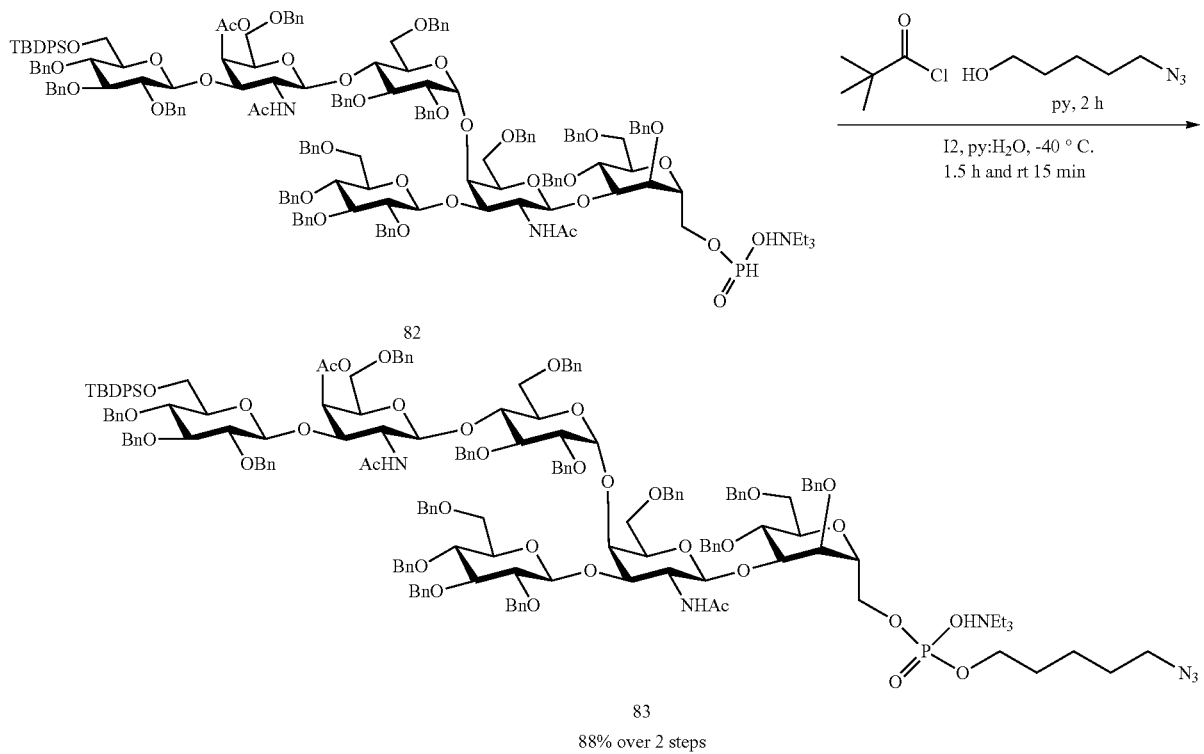

The procedure described for the synthesis of compound 59 used for the synthesis of compound 83 (88%). HRMS (ESI+) Calcd for $C_{169}H_{190}O_{35}N_5SiP^+$ [M-Et$_3$N]$^+$ 2910.2815. found 2910.2841.
Synthesis of 84
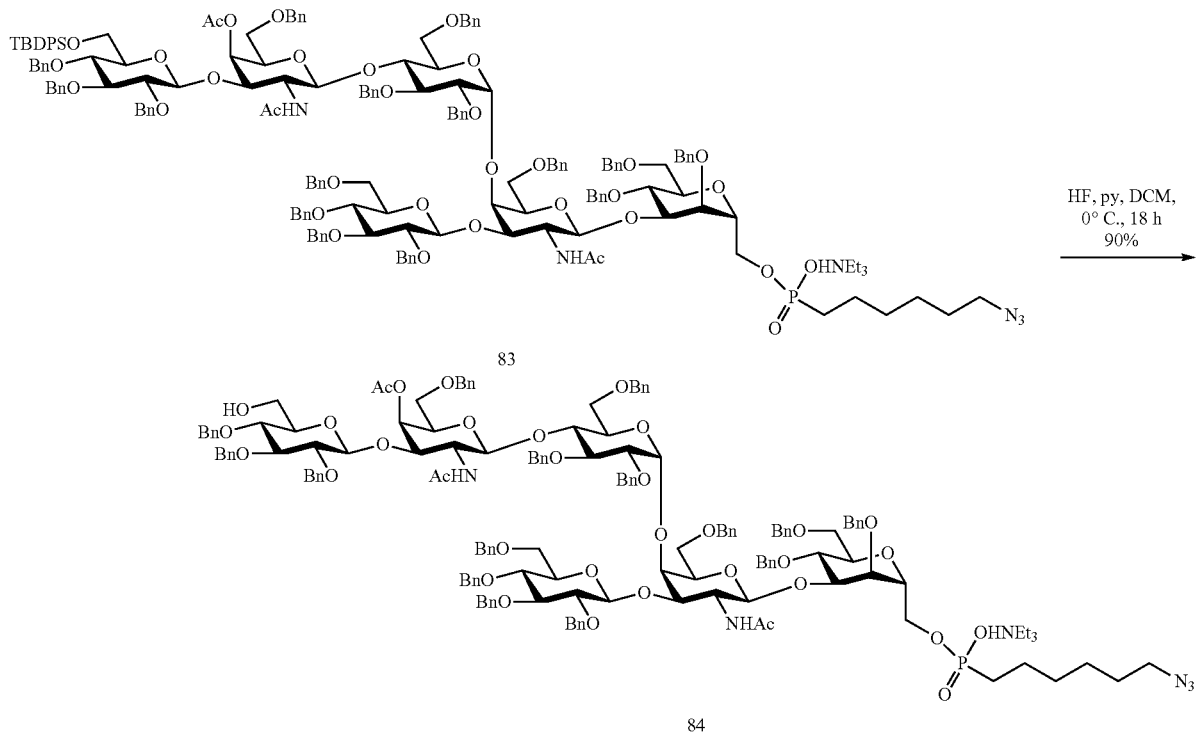
The procedure described for the synthesis of compound 60 used for the synthesis of compound 84 (90%). HRMS (ESI+) Calcd for $C_{153}H_{172}O_{35}N_5P^+$ [M-Et$_3$N]$^+$ 2672.1638. found 2672.1759.
Synthesis of 33
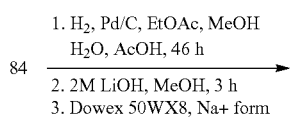
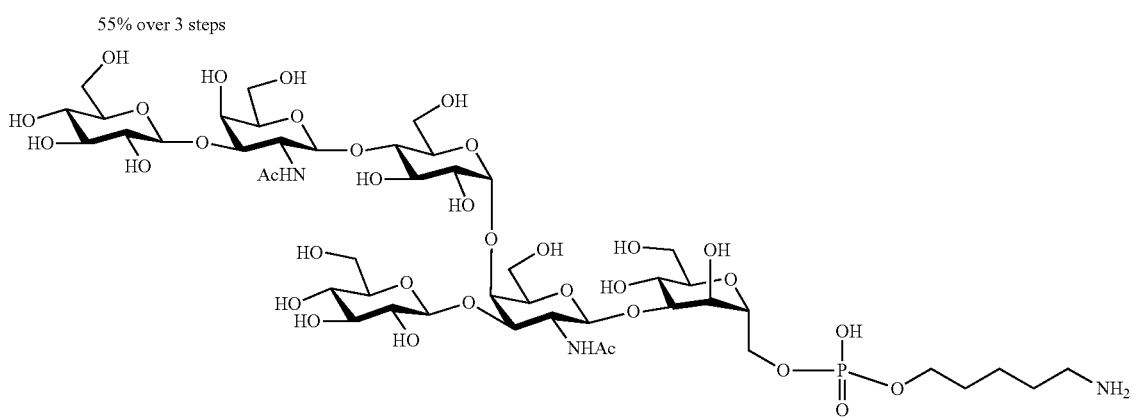

The procedure described for the synthesis of compound 33 from 32 used for the synthesis of compound 33 (55%). HRMS (ESI+) Calcd for $C_{46}H_{82}N_3PO_{34}{}^+$ [M-Na+2H]$^+$ 1252.4551. found 1252.4574.

Synthesis of 85

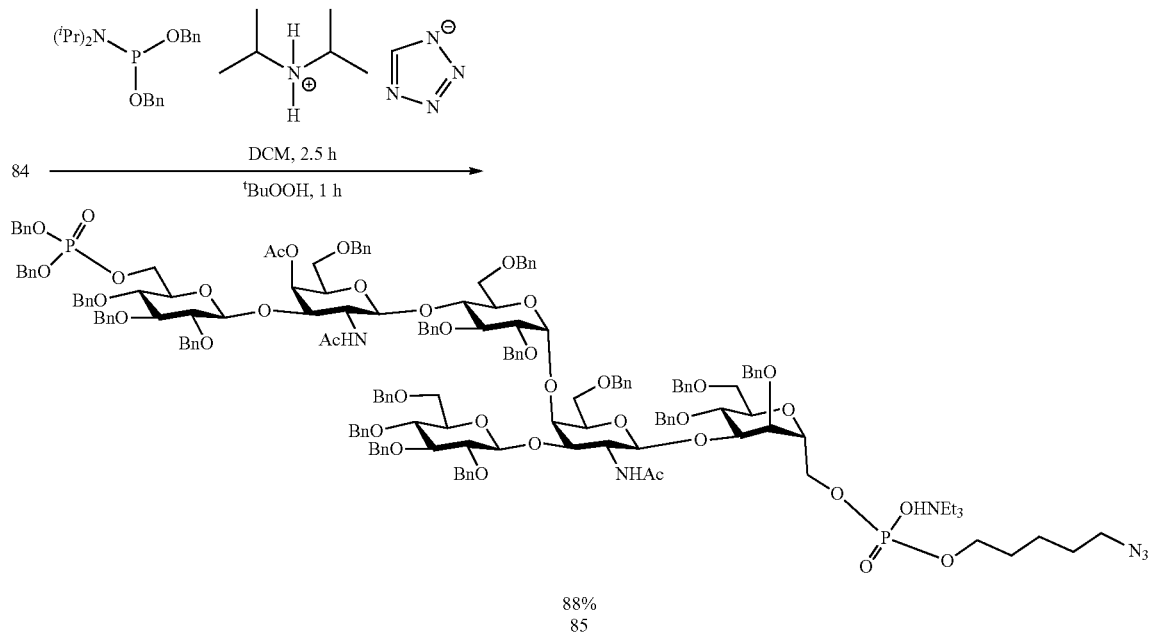

To a solution of 84 in DCM, were added dibenzyl N,N-diisopropylphosphoramidite (2.0 equiv.) and diisopropylammonium tetrazolide (1.5 equiv.) and the solution was stirred at rt for 2.5 h. Then, t-butyl peroxide (6.0 equiv., 5.0-6.0 M solution in decane) was added and the reaction mixture stirred for 1 h. After 1 h, reaction mixture was diluted with DCM and quenched with NaHCO$_3$ aq. sat. solution. The aqueous layer was extracted with DCM. The combined organic layer was washed with brine, dried over Na$_2$SO$_4$, filtered, and the filtrate was concentrated under vacuum to obtain the crude product. The crude product was purified by automated flash column chromatography on silica gel (0-100% EtOAc in cyclohexane) to afford the desired product 85 (88%). HRMS (ESI+) Calcd for $C_{167}H_{185}O_{38}N_5P_2{}^+$ [M-Et$_3$N]$^+$ 2932.2240. found 2932.2147.

Synthesis of 54

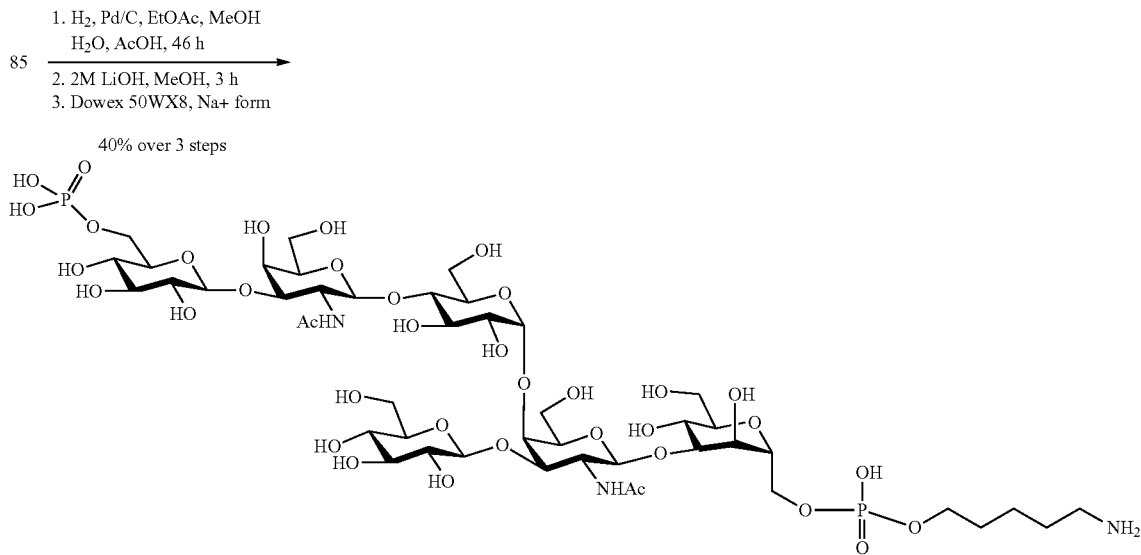

Pd/C (20 mg) was added to a clear solution of 85 (20 mg) in EtOAc:MeOH:H₂O:DCM. Obtained inhomogeneous mixture was stirred under hydrogen atmosphere at rt for 40 h. After 40 h, reaction mixture was filtered through PTFE filter and concentrated under vacuum at 30° C. bath temperature of rotary evaporator for 10 min to remove methanol, EtOAc, DCM and water. The crude product obtained after solvents removal was dissolved in MeOH, water and to this LiOH (2 N in water) was added at 0° C. The reaction mixture was stirred at 0° C. for 3 h. After 3 h, the reaction mixture was quenched with AcOH and the solvents were removed under reduced pressure and the obtained crude residue was purified with C18 reverse phase column chromatography using water and acetonitrile as solvents to give the desired final compound 54 in salt form. Then triethylamine salt was exchanged with Dowex resin to give the desired compound with sodium salt. (40% over 3 steps) as a white solid. HRMS (ESI+) Calcd for $C_{46}H_{83}N_3P_2O_{37}^+$ [M−Na+H]⁺ 1332.4214. found 1332.4242.

Synthesis of 86

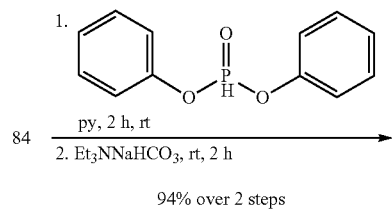

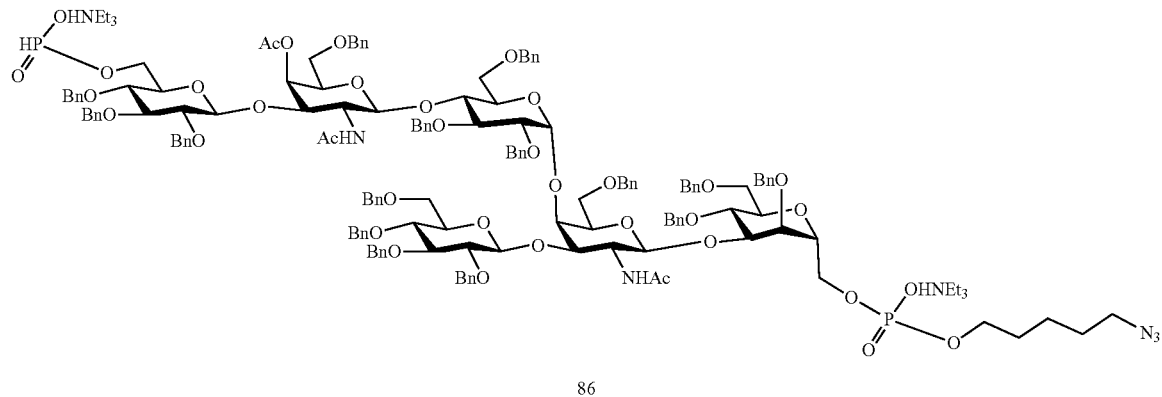

The procedure described for the synthesis of compound 58 used for the synthesis of compound 86 (94%). HRMS (ESI+) Calcd for $C_{165}H_{203}O_{37}N_7P_2^+$ [M−2×Et₃N+H]⁺ 2735.1318. found 2735.1356.

Synthesis of 87

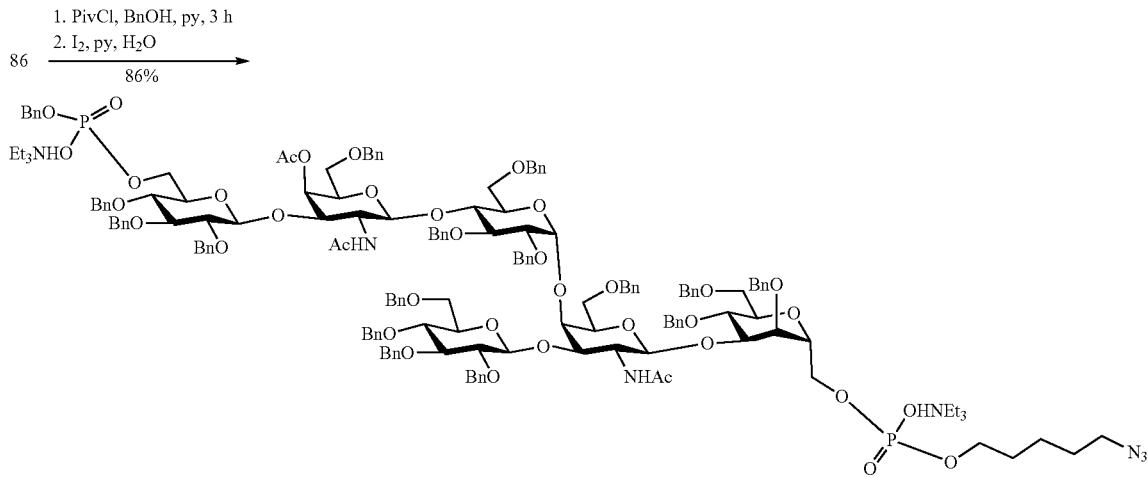

H-phosphonate 86 (1.0 equiv.) and benzyl alcohol (10.0 equiv.) were co-evaporated with pyridine and dried under vacuum for 30 min. After that, it was dissolved in py and to this PivCl (5.0 equiv.) was added. The reaction mixture was kept for stirring at rt for 2 h. After 2 h, the reaction was cooled to −40° C., a freshly prepared solution of $I_2$ in Py:$H_2O$ (20:1) was added and the reaction mixture was kept for stirring at the same temperature for 1.5 h and later brought to rt and stirred at rt for 15 min. Then, TEAB (10 mL) was added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue was purified by automated flash column chromatography (ethyl acetate:DCM:MeOH) together with 2% trimethylamine as eluents give the desired product 87 (86%) as viscous liquid. Maldi (ESI+) Calcd for $C_{160}H_{179}N_5P_2O_{38}^+$ [M+H-2×$Et_3$N]$^+$ 2842.1770. found 2842.1638.

Synthesis of 54

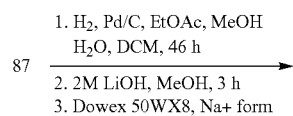

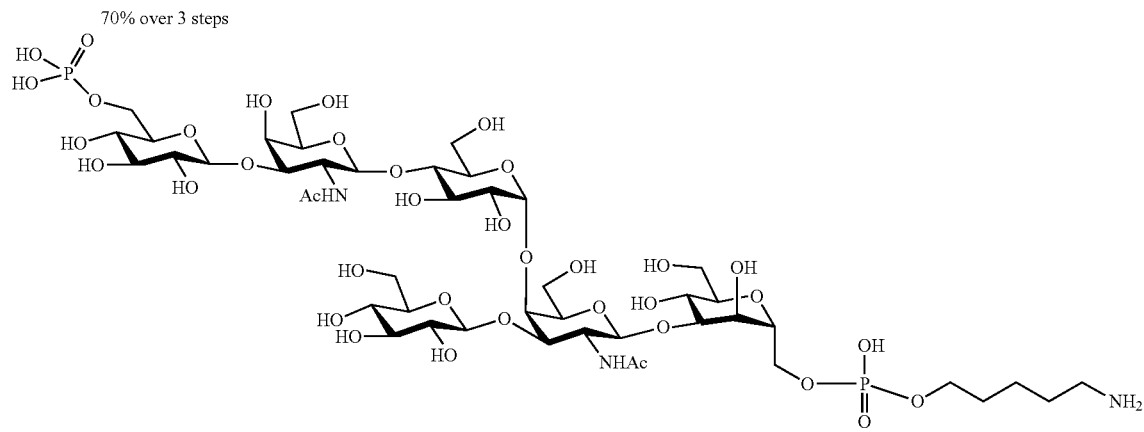

54

Pd/C (20 mg) was added to a clear solution of 87 (20 mg) in EtOAc:MeOH:$H_2$O:DCM. Obtained inhomogeneous mixture was stirred under hydrogen atmosphere at rt for 40 h. After 40 h, reaction mixture was filtered through PTFE filter and concentrated under vacuum at 30° C. bath temperature of rotary evaporator for 10 min to remove methanol, EtOAc, DCM and water. The crude product obtained after solvents removal was dissolved in MeOH, water and to this LiOH (2 N in water) was added at 0° C. The reaction mixture was stirred at 0° C. for 3 h. After 3 h, the reaction mixture was quenched with AcOH and the solvents were removed under reduced pressure and the obtained crude residue was purified with C18 reverse phase column chromatography using water and acetonitrile as solvents to give the desired final compound 54 in salt form. Then triethylamine salt was exchanged with Dowex resin to give the desired compound with sodium salt. (70% over 3 steps) as a white solid. HRMS (ESI+) Calcd for $C_{46}H_{83}N_3P_2O_{37}^+$ [M-3Na+4H]$^+$ 1332.4214. found 1332.4232.

A.6 Synthesis of Dodecasaccharide 92
Synthesis of 88
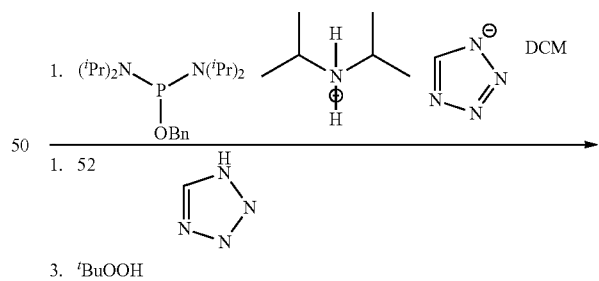
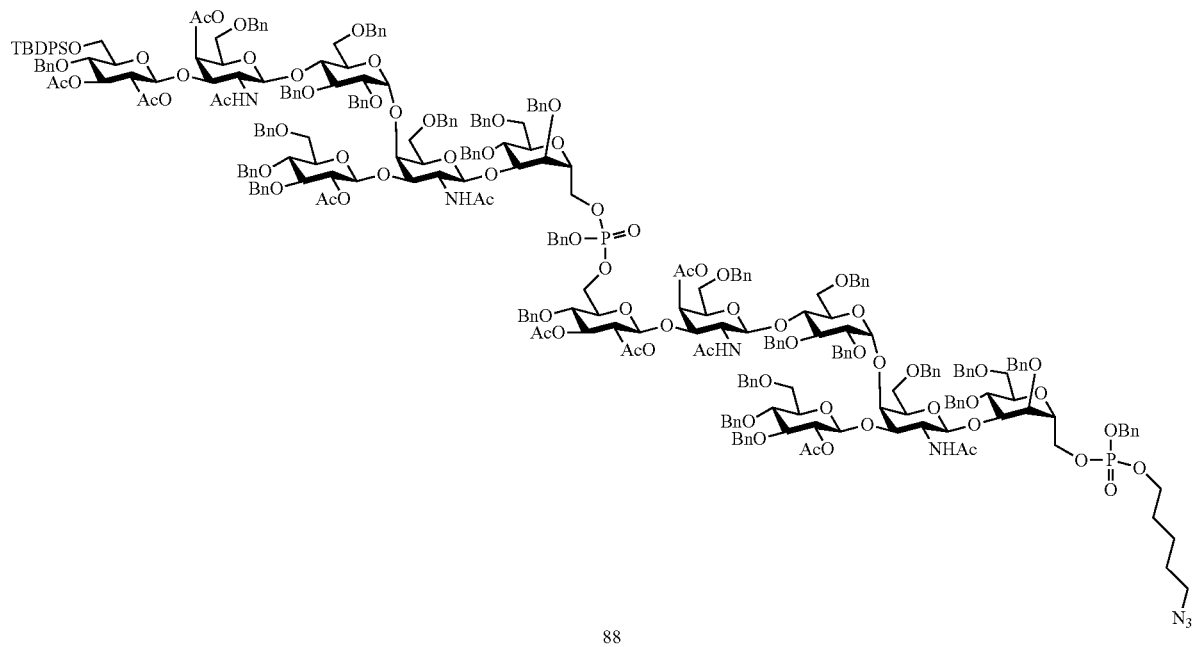
88
The procedure described for the synthesis of compound 32 is used for the synthesis of compound 88, here the only change is, in second step instead of a linker compound 52 is used as nucleophile.
Synthesis of 89

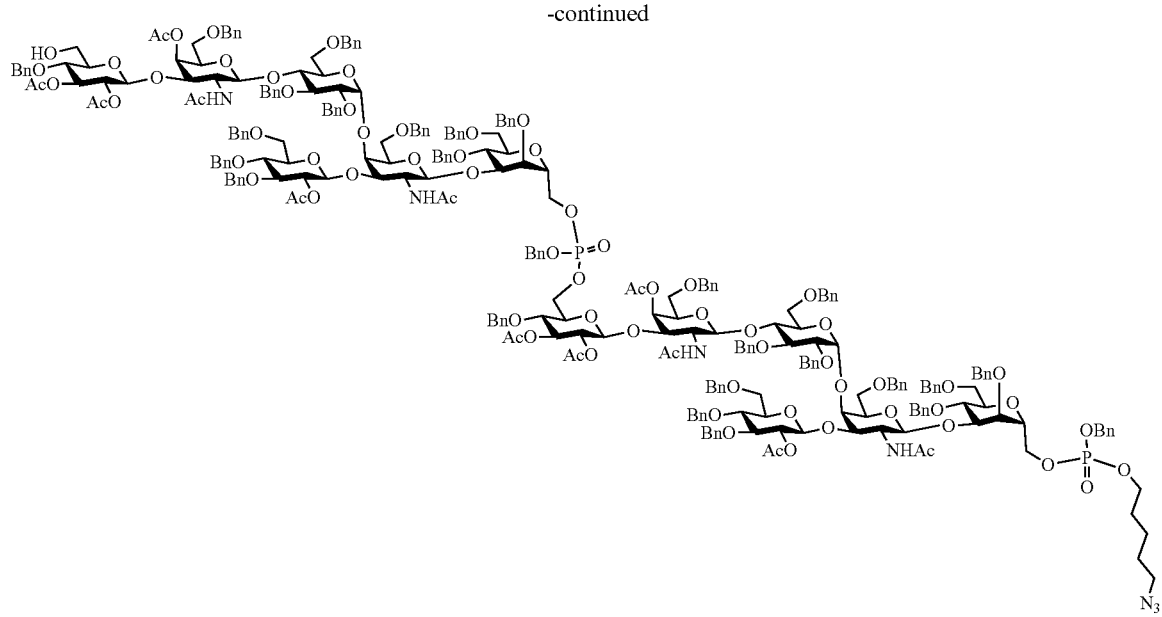
89
The procedure described for the synthesis of compound 52 is used for the synthesis of compound 89.
Synthesis of 90
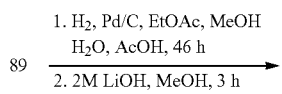
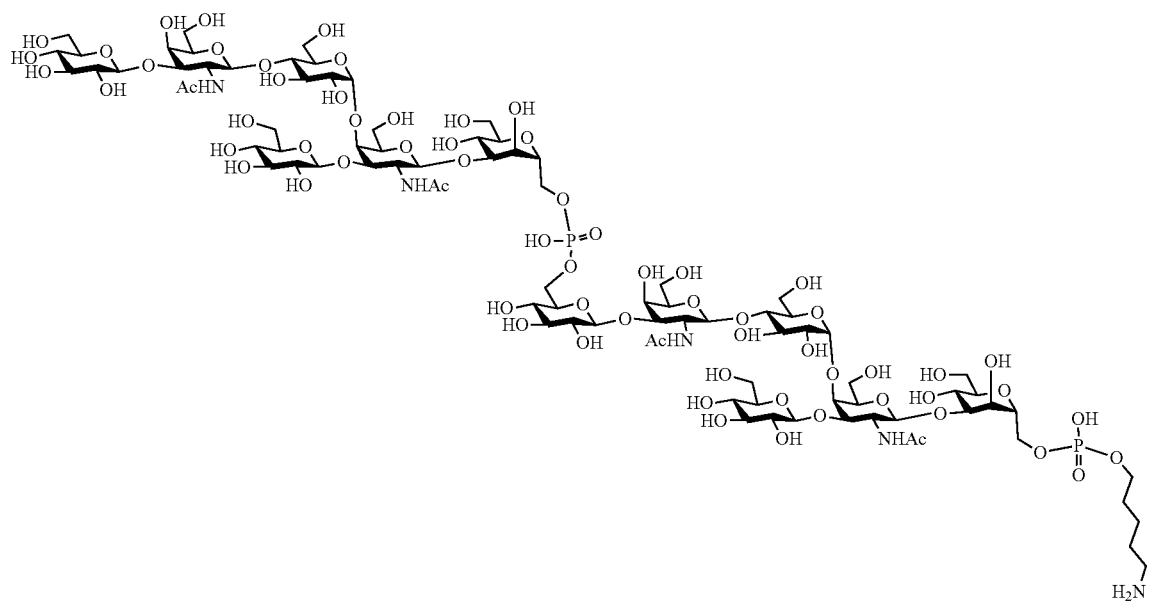
90
The procedure described for the synthesis of compound 33 is used for the synthesis of compound 90.
Synthesis of 91

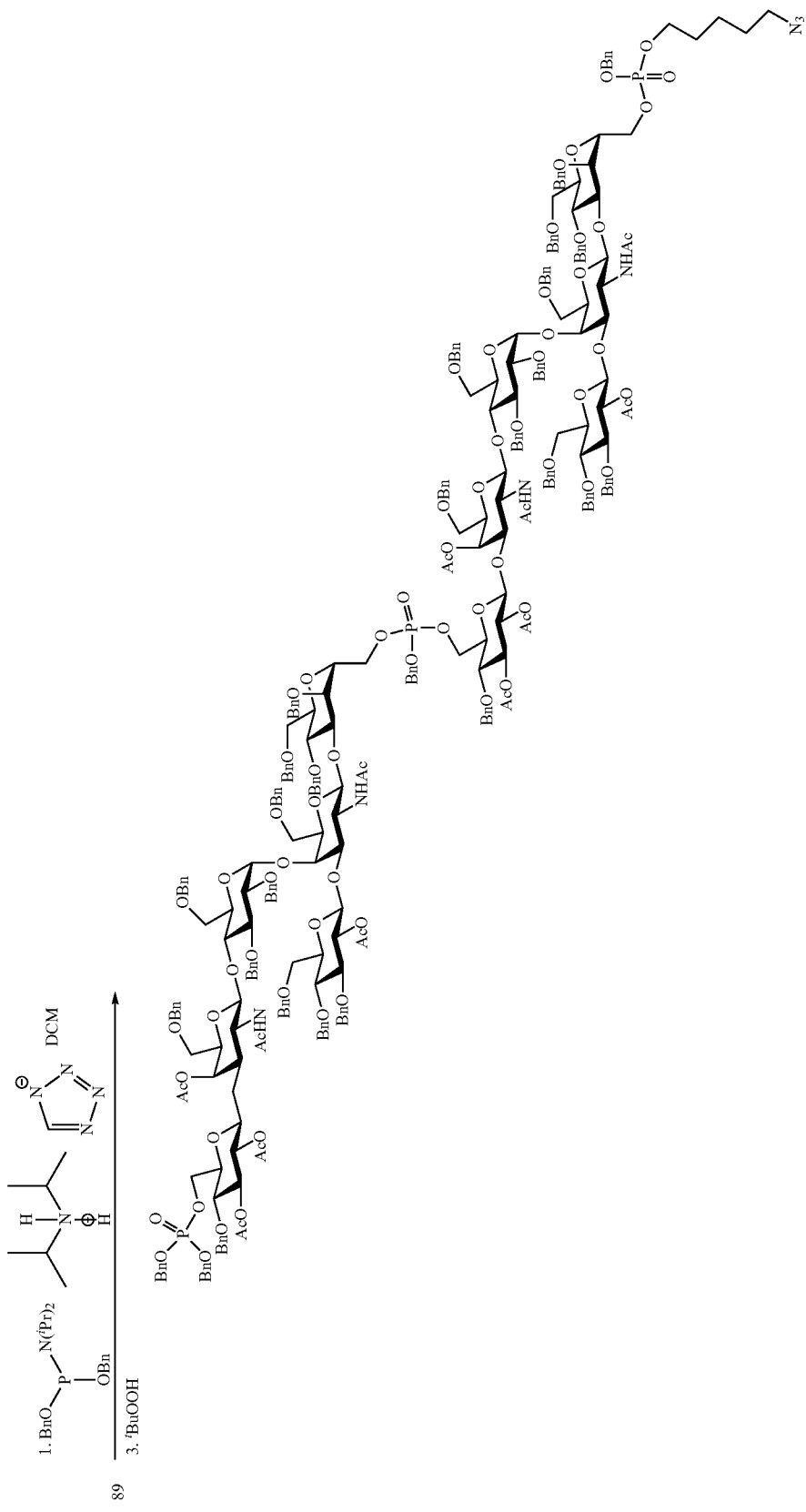

The procedure described for the synthesis of compound 53 is used for the synthesis of compound 91.
Synthesis of 92
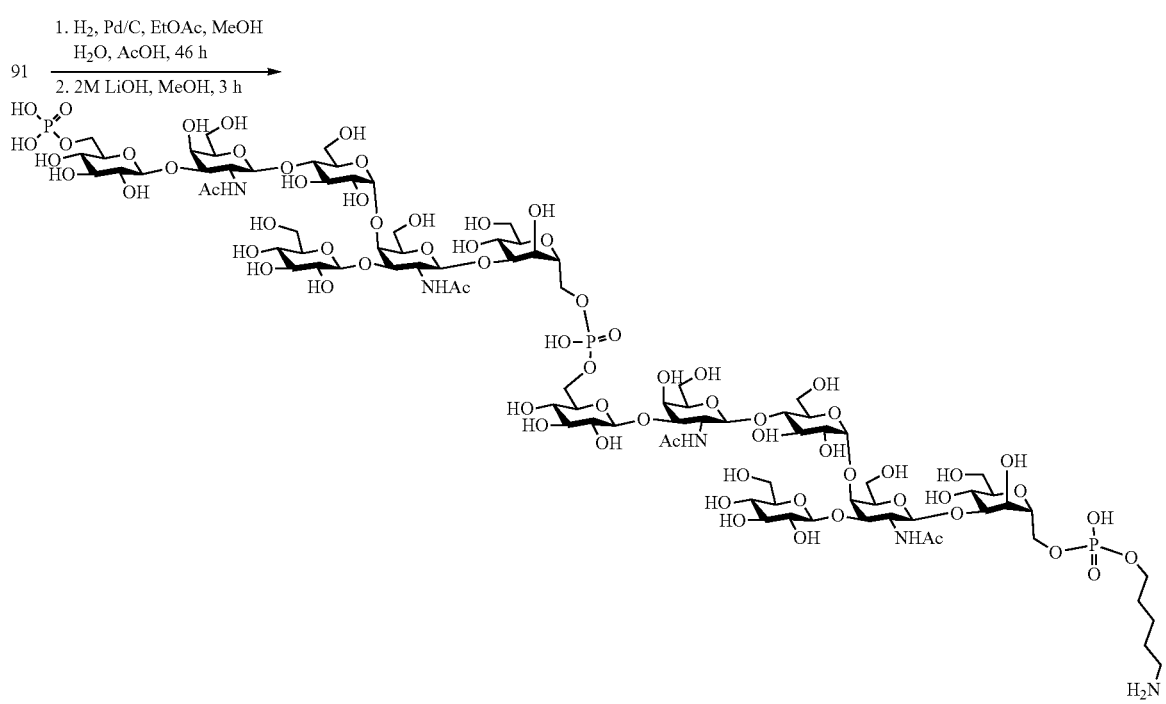
The procedure described for the synthesis of compound 33 is used for the synthesis of compound 92.
Conjugation of 92 with $CRM_{197}$ and BSA

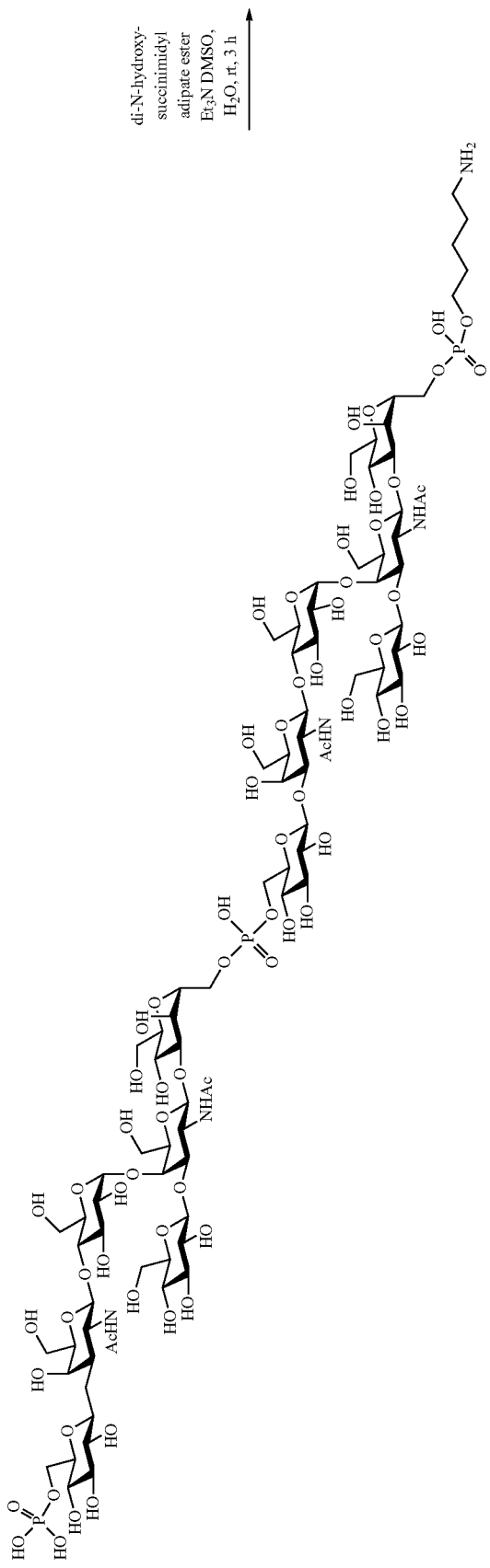
92

-continued
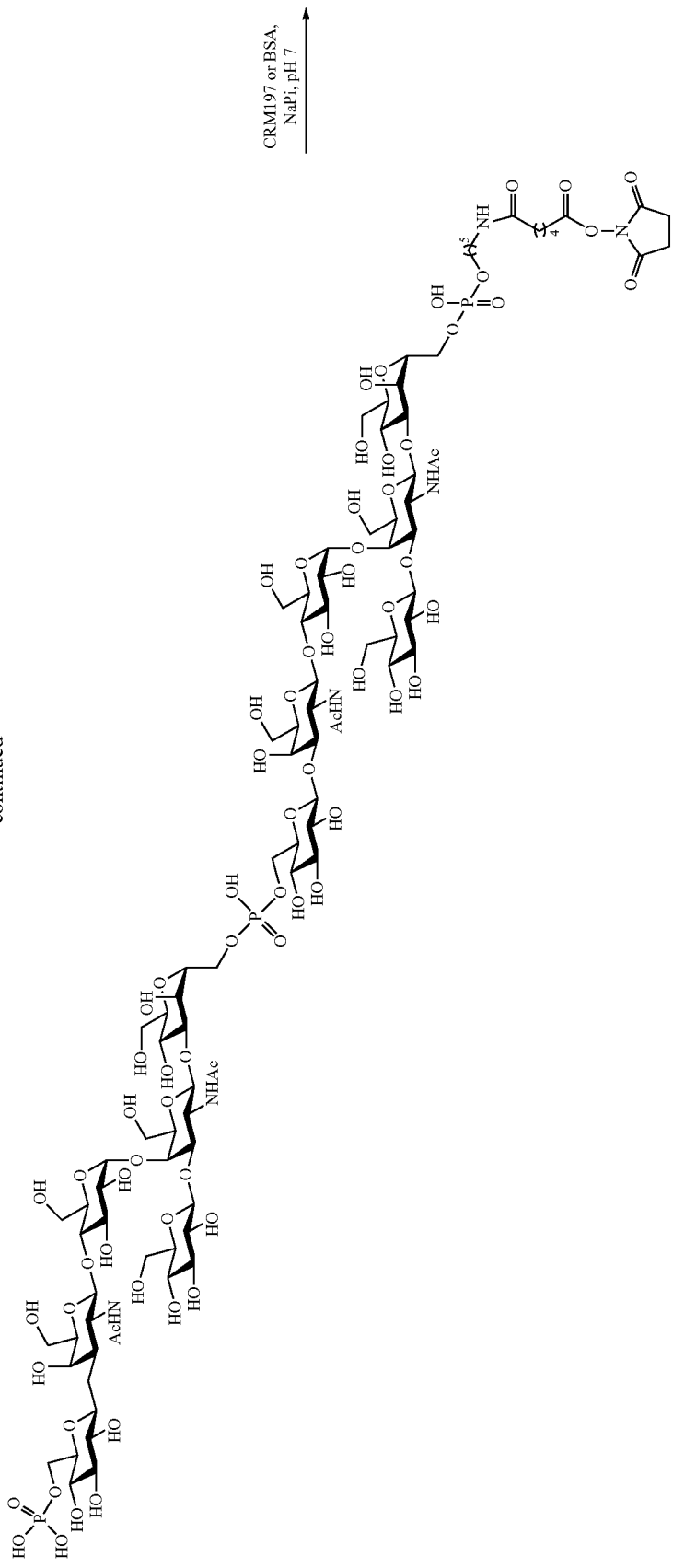

-continued
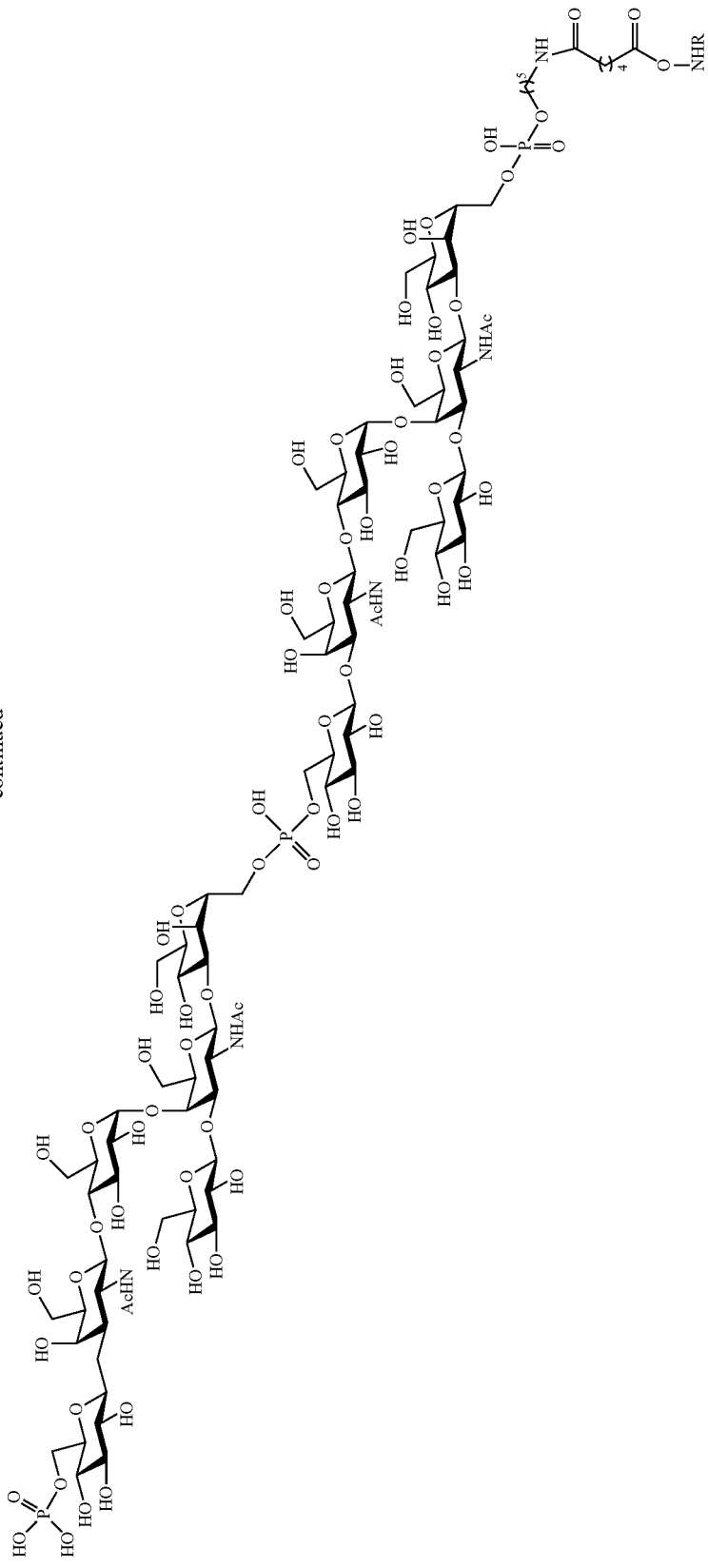
94 R = CRM197
95 R = BSA

The procedure described for the synthesis of glycoconjugates 36 and 37 was used for the synthesis of 94 and 95.

A.7 Alternative Synthesis of Dodecasaccharide 92

Synthesis of 96

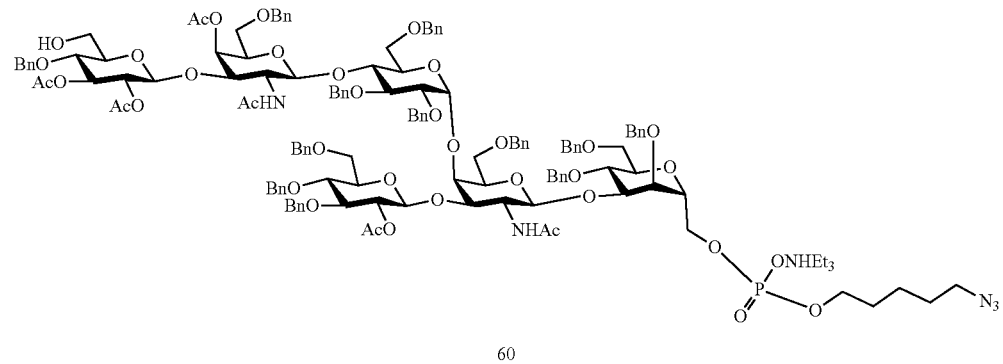

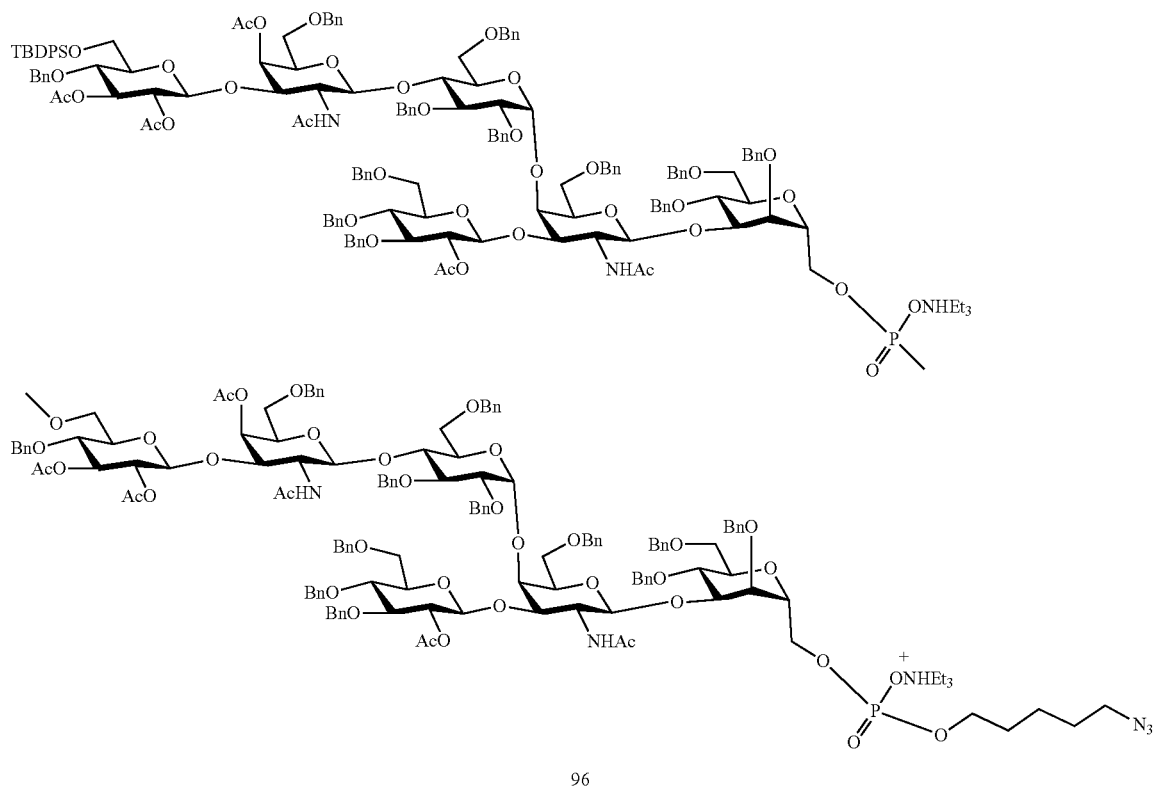

H-phosphonate 58 (1.2 equiv.) and acceptor 60 (1.0 equiv.) were co-evaporated with pyridine and dried under vacuum for 30 min. After that, it was dissolved in py and to this PivCl (1.3 equiv.) was added. The reaction mixture was kept for stirring at rt for 3 h. After 3 h, the reaction was cooled to −40° C., a freshly prepared solution of $I_2$ in Py:$H_2O$ (250 μL, 20:1) was added and the reaction mixture was kept for stirring at the same temperature for 1.5 h and later brought to rt and stirred at rt for 15 min. Then, TEAB (10 mL) was added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue was purified by automated flash column chromatography (ethyl acetate:DCM:MeOH) together with 2% trimethylamine as eluents give the desired product 96 (70%) as viscous liquid. MALDI (ESI+) Calcd for $C_{287}H_{325}K_2N_7O_{75}P_2Si^+$ [M−2Et$_3$N+2K]$^+$ 5237.0351. found 5237.718.

Synthesis of 97
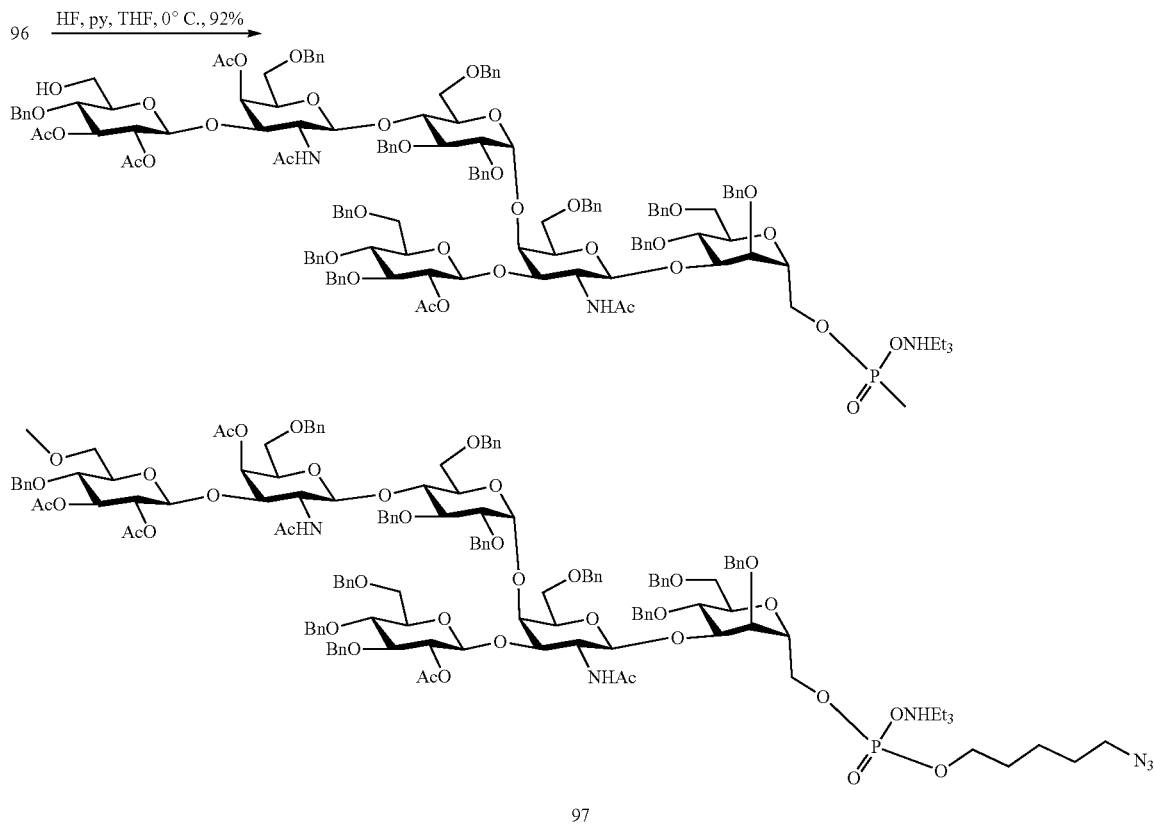
The procedure described for the synthesis of compound 60 was used for the synthesis of compound 97 (70%). Maldi (ESI+) Calcd for $C_{271}H_{309}N_7O_{75}P_2^+$ [M]$^+$ 4926.3745. found 4926.323.
Synthesis of 92

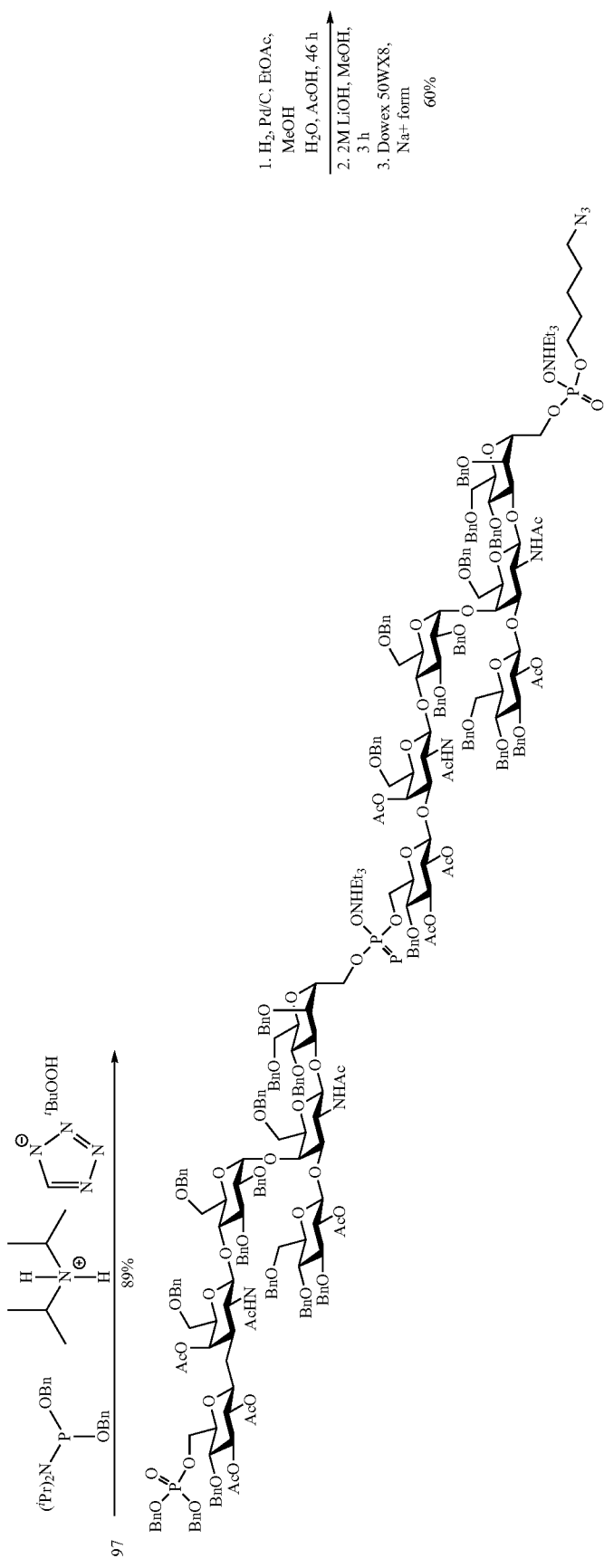

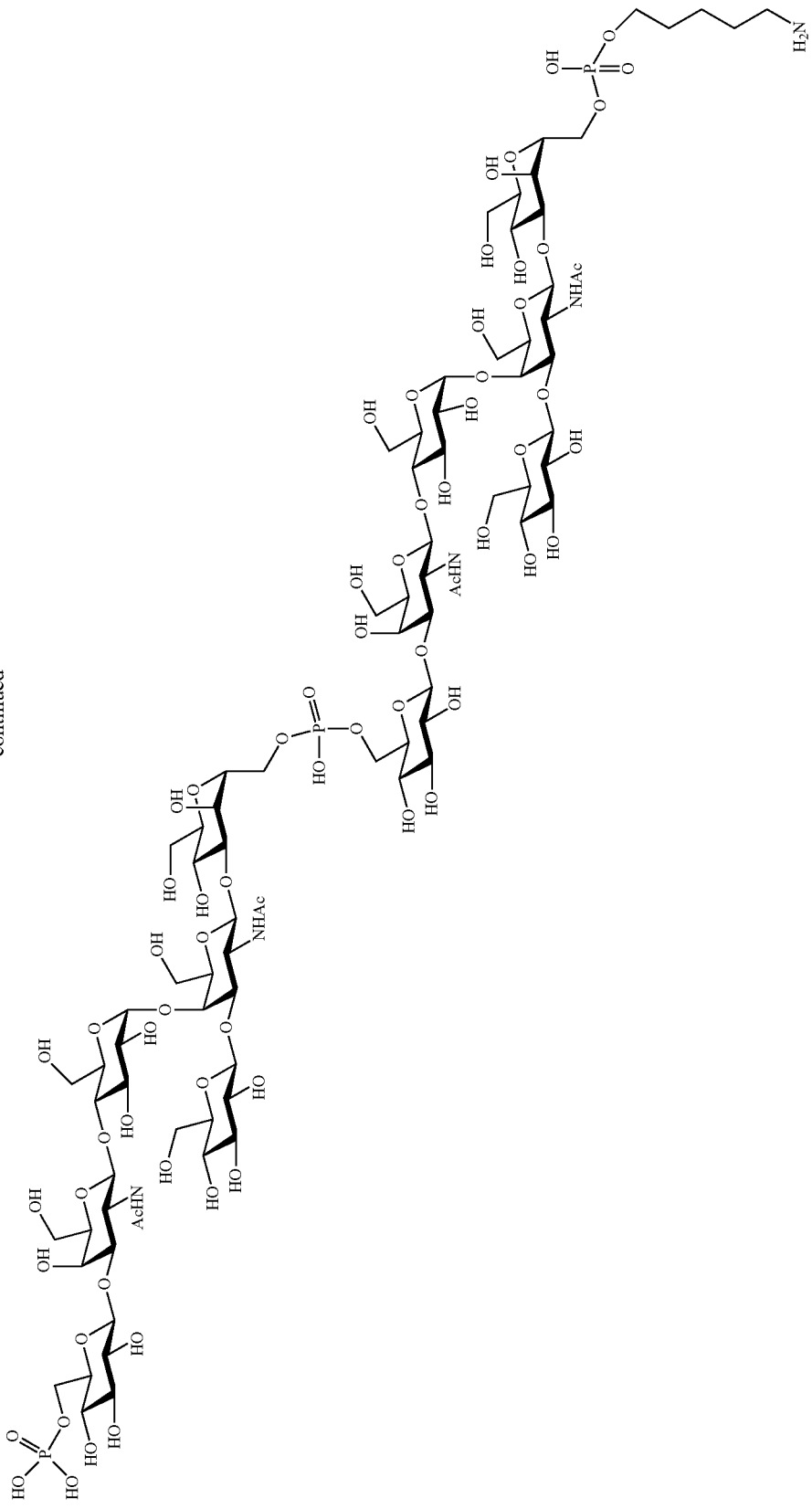
92

The procedure described for the synthesis of compound 61 was used for the synthesis of compound 98 (89%). The procedure described for the synthesis of compound 54 was used for the synthesis of compound 92.

A.8 Synthesis of Hexasaccharide 112

Synthesis of 99

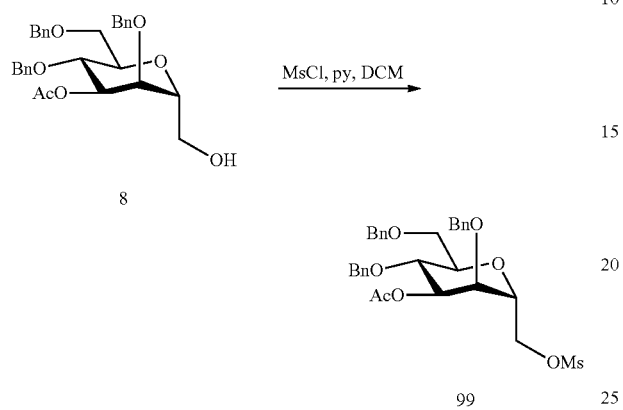

MsCl and pyridine (py) are added to a clear solution of 8 in DCM at 0° C. The reaction mixture is stirred at room temperature overnight and then diluted with DCM, washed with aq. NaHCO$_3$ solution, dried over Na$_2$SO$_4$ and concentrated to give the crude product. The residue is purified by automated silica gel chromatography (hexane/AcOEt) to give compound 99.

Synthesis of 100 and 101

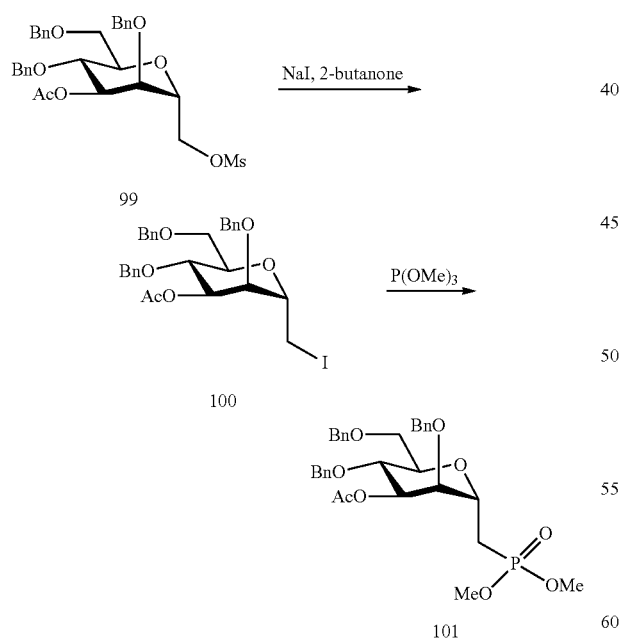

Sodium iodide is added to a clear solution of 99 in 2-butanone and the reaction mixture is stirred at 100° C. for overnight. Then, the solvent is removed, and the crude residue is dissolved in DCM, washed with aq. NaHSO$_3$, dried over Na$_2$SO$_4$ and concentrated to give the iodomethyl derivative 100. This iodo derivative is dissolved in freshly distilled trimethylphosphite and the solution is heated to 100° C. under vacuum (water pump) for 48 h. After concentration and silica gel chromatography phosphonate derivative 101 is obtained.

Synthesis of 102

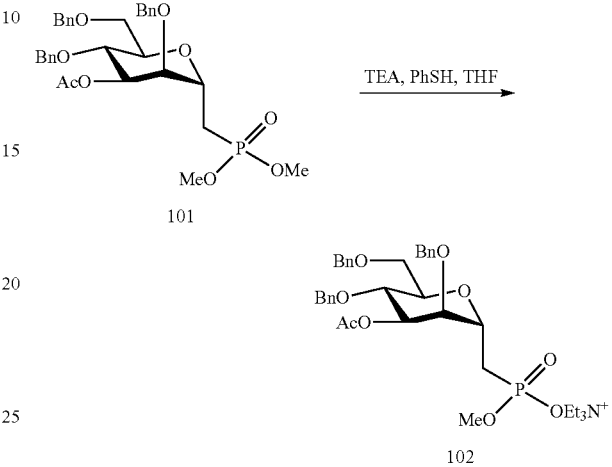

TEA and thiophenol are added to a clear solution of 101 in THF. The reaction mixture is stirred at room temperature for 24 h. After complete consumption of starting material, the reaction mixture is diluted with TEA and concentrated to give a crude residue, and it is purified by silica gel chromatography to give 102.

Synthesis of 103

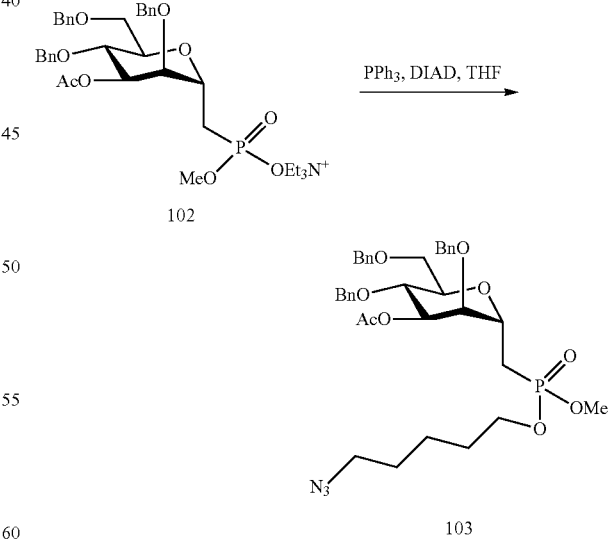

Phosphonate 102, linker and triphenylphosphine are dissolved in THF and the solution is cooled at 0° C. and to this DIAD is added. The mixture is stirred at room temperature for 24 h. After 24 h, the solution is concentrated and crude product is purified by silica gel chromatography to give 103.

Synthesis of 104

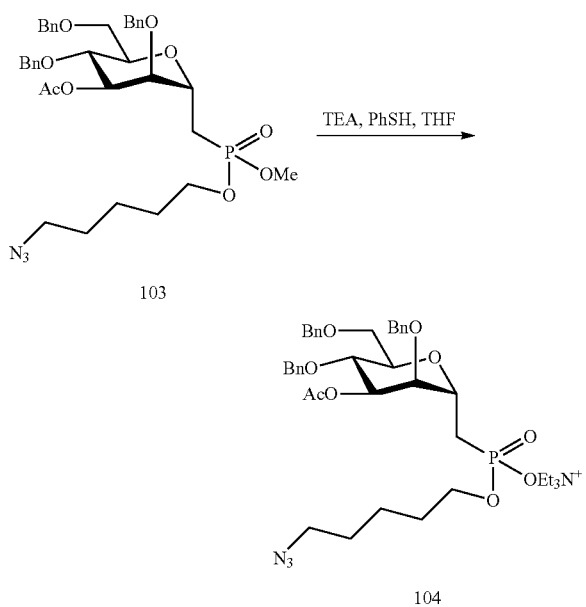

TEA and thiophenol are added to a clear solution of 103 in THF. The reaction mixture is stirred at room temperature for 24 h. After complete consumption of starting material, the reaction mixture is diluted with TEA and concentrated to give a crude residue, and it is purified by silica gel chromatography to give 104.

Synthesis of 105

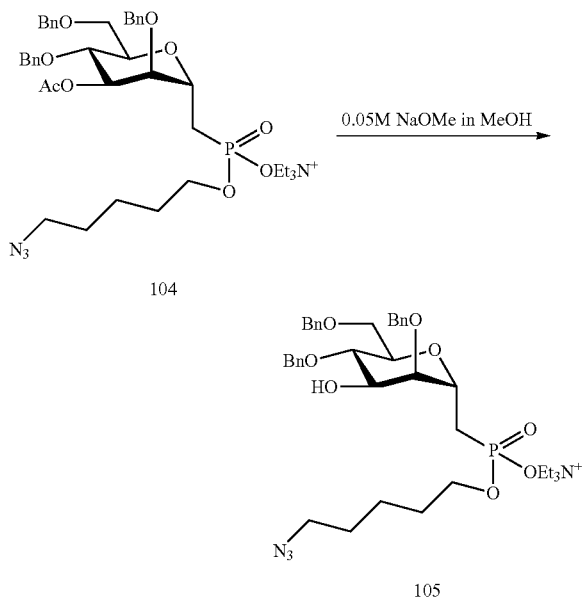

Phosphonate derivative 104 is dissolved in 0.05 M solution of NaOMe in MeOH and stirred at rt for 10 min. Then reaction mixture is quenched with AcOH and the solvents are removed under vacuum. The obtained crude residue is purified by silica gel chromatography to give 105.

Synthesis of 106

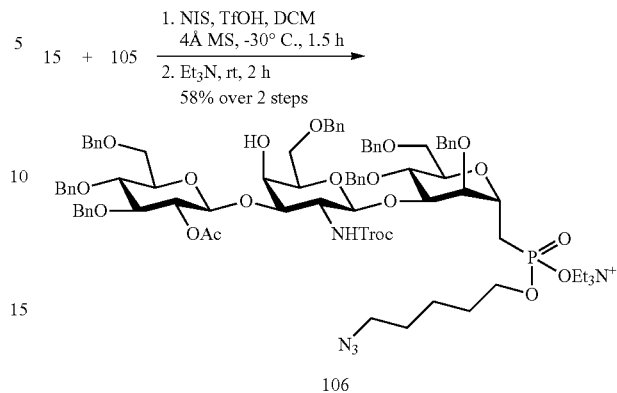

Reaction is performed in accordance with the synthesis of compound 16.

Synthesis of 107

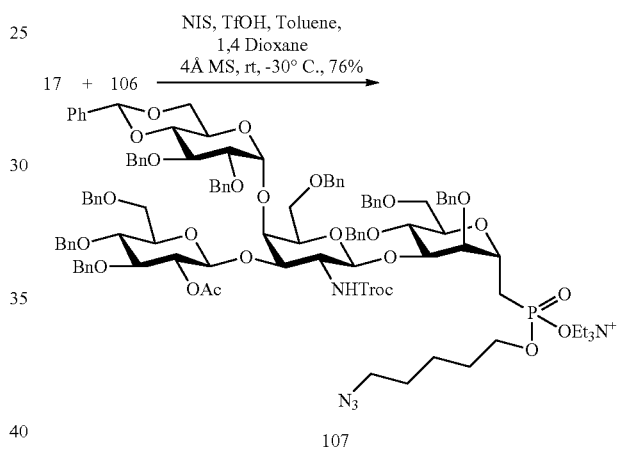

Reaction is performed in accordance with the synthesis of compound 18.

Synthesis of 108

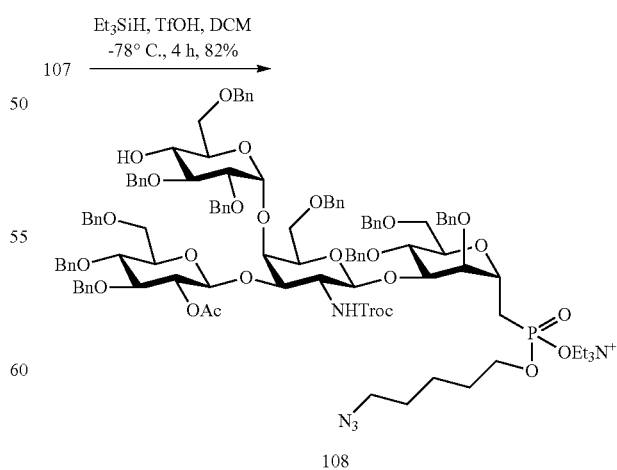

Reaction is performed in accordance with the synthesis of compound 19.

Synthesis of 109
$$27 + 108 \xrightarrow[\text{3 h, 65\%}]{\substack{\text{NIS, TfOH, DCM}\\\text{4Å MS, -20° C. to 0°.}}}$$
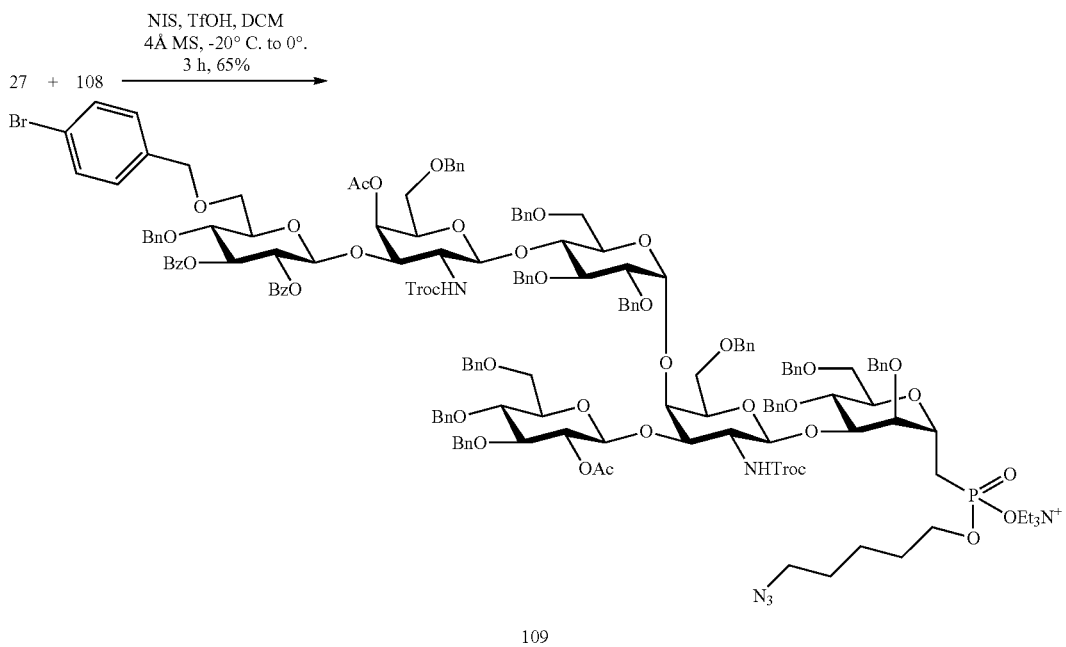
109
Reaction is performed in accordance with the synthesis of compound 28.
Synthesis of 110
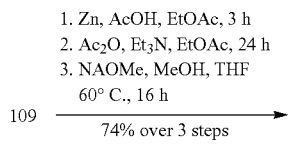
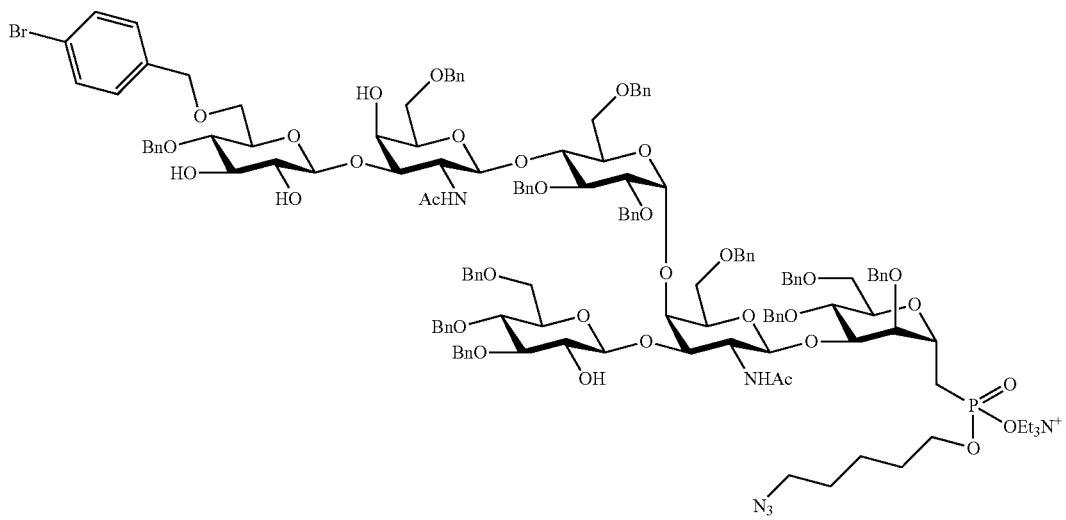
110
Reaction is performed in accordance with the synthesis of compound 29.

Synthesis of 111
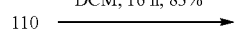
Ac₂O, Et₃N, DMAP
DCM, 16 h, 83%
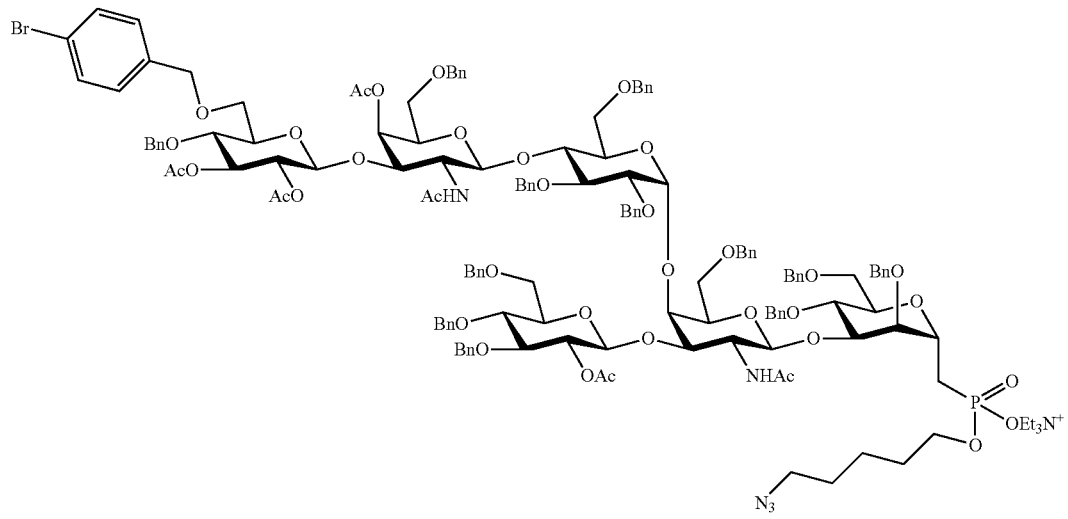
111
Reaction is performed in accordance with the synthesis of compound 30.
Synthesis of 112
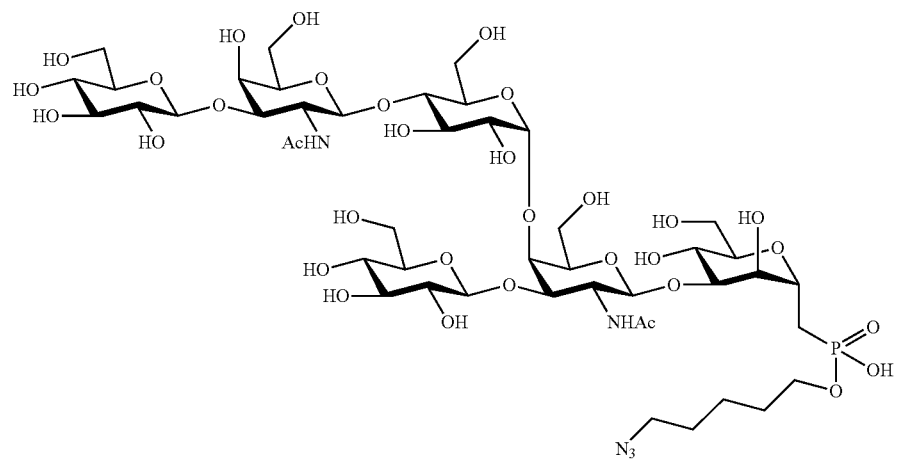
111 →
1. H₂, Pd/C, EtOAc, MeOH H₂O, AcOH 46 h
2. 2M LiOH, MeOH, 3 h
80% over 2 steps
112
Reaction is performed in accordance with the synthesis of compound 33.
Conjugation of 112 with CRM197 or BSA
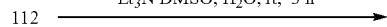
di-N-hydroxy-succinimidyl adipate ester
Et₃N DMSO, H₂O, rt, 3 h
112 →

-continued
315
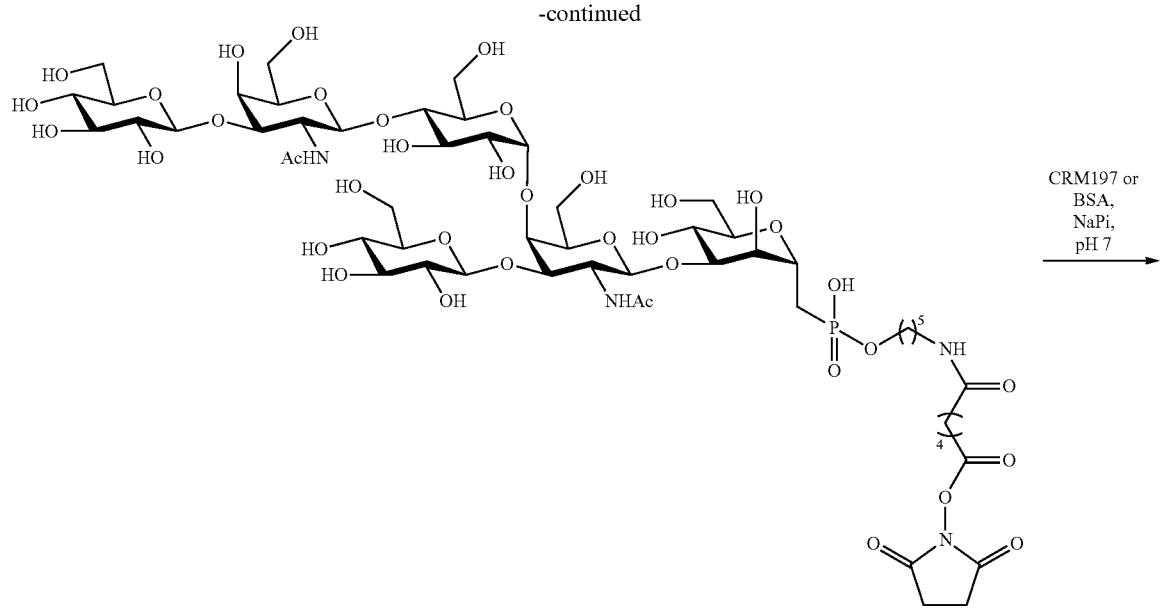
113
316
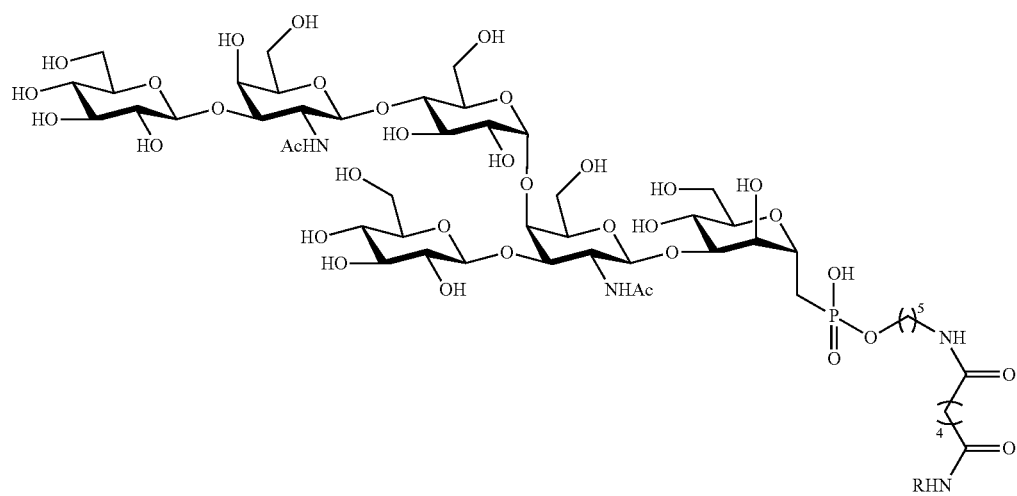
114 R = CRM197
115 R = BSA
Reaction is performed in accordance with the conjugation of compound 33.

A.8 Synthesis of Hexasaccharide 117

Synthesis of 116

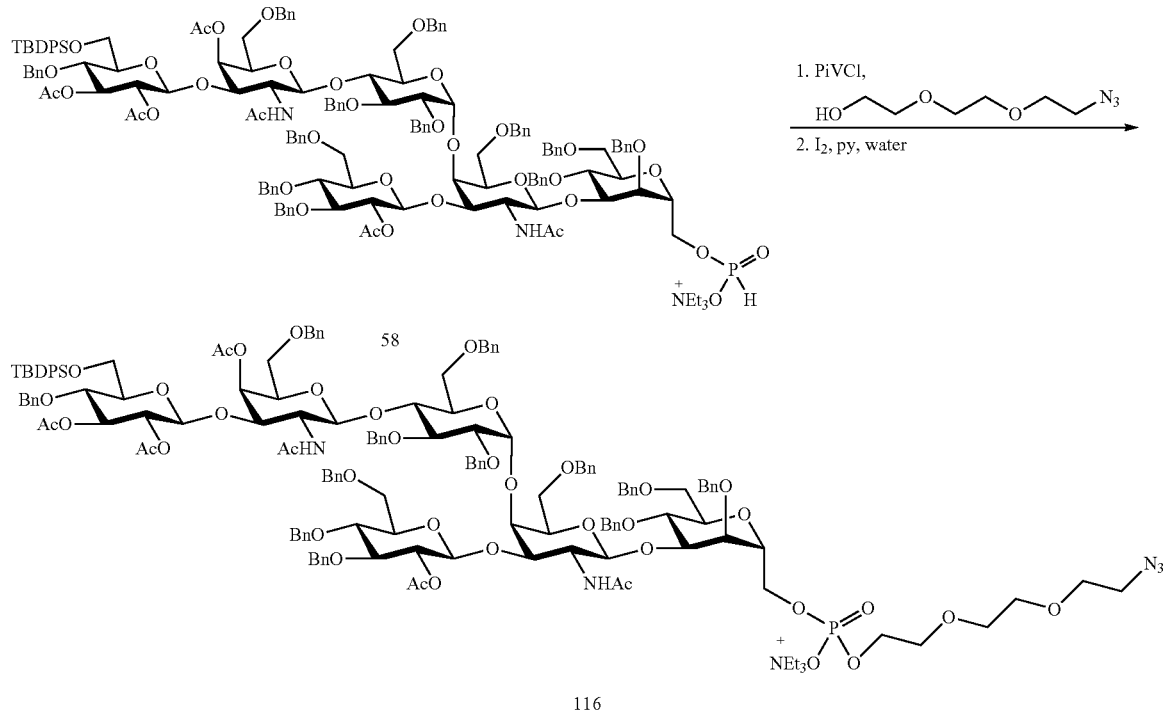

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction is cooled to −40° C., a freshly prepared solution of $I_2$ in pyridine: $H_2O$ (20:1) is added and the reaction mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue is purified by automated flash column chromatography (ethyl acetate:DCM:MeOH) together with 2% trimethylamine as eluents give the desired product 116 as viscous liquid.

Synthesis of 117

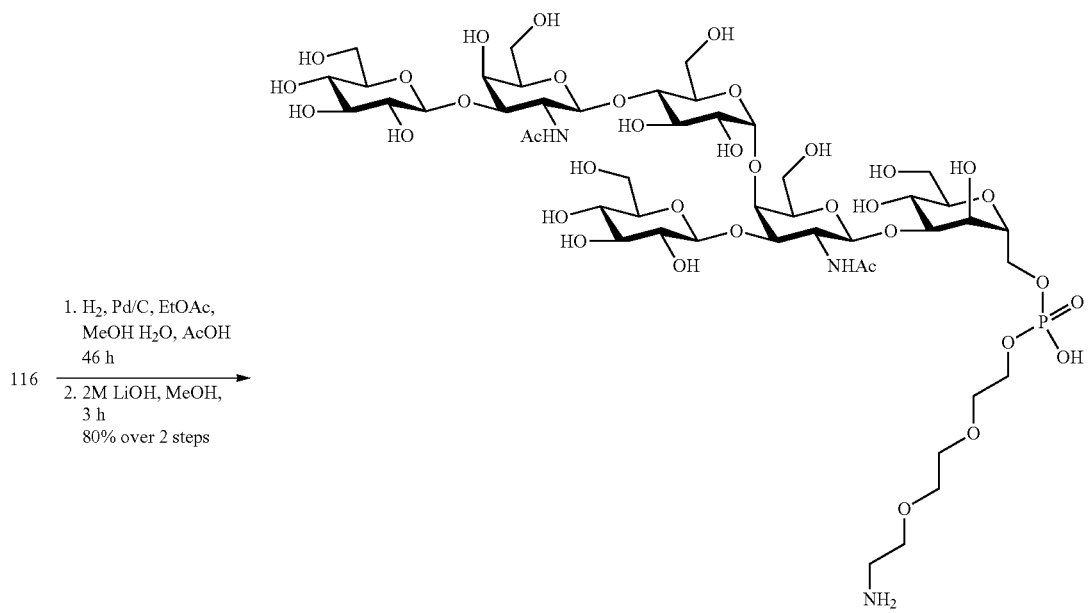

Reaction is performed in accordance with the synthesis of compound 31.
Conjugation of 117 with CRM$_{197}$ or BSA
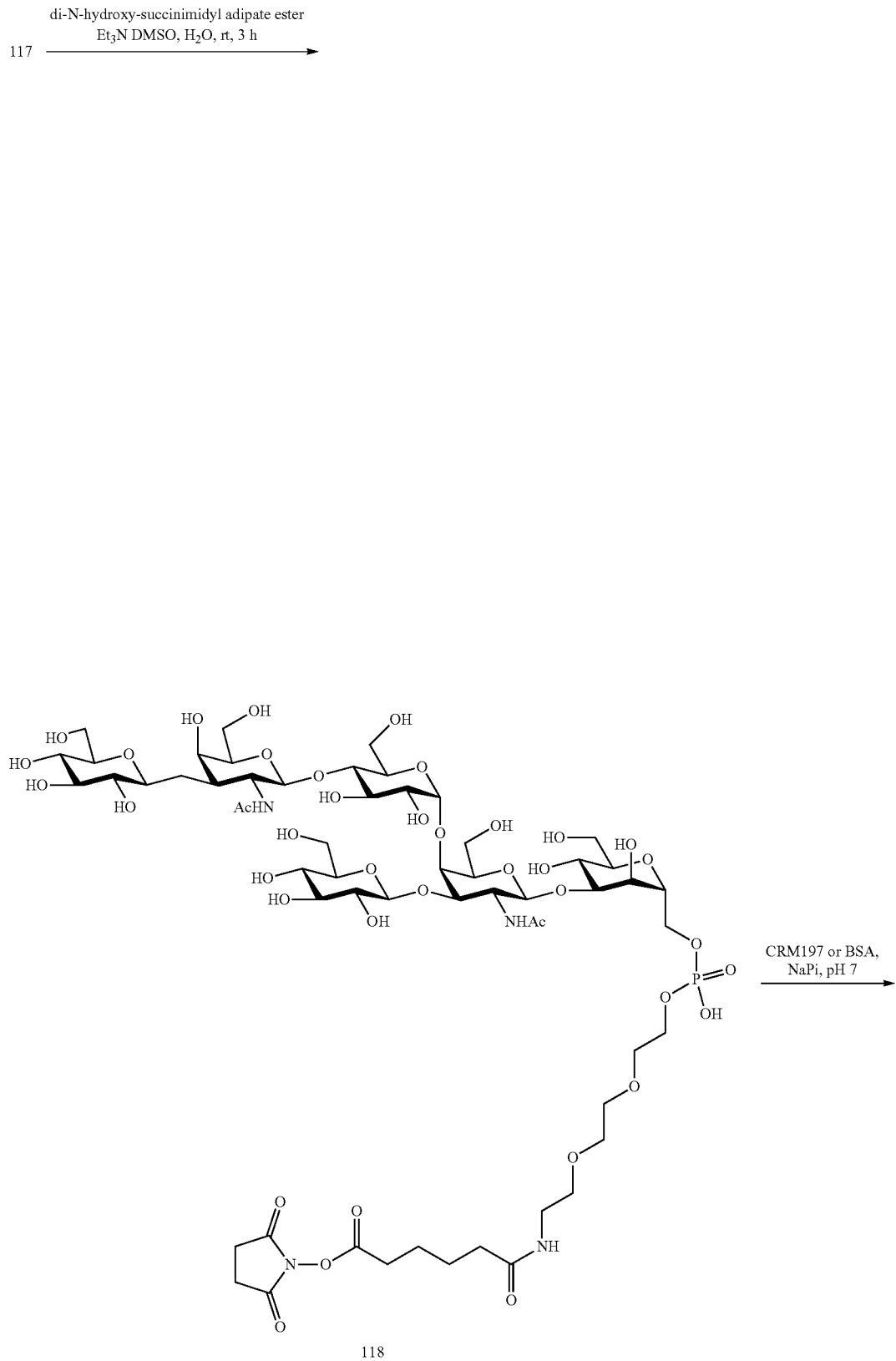

-continued
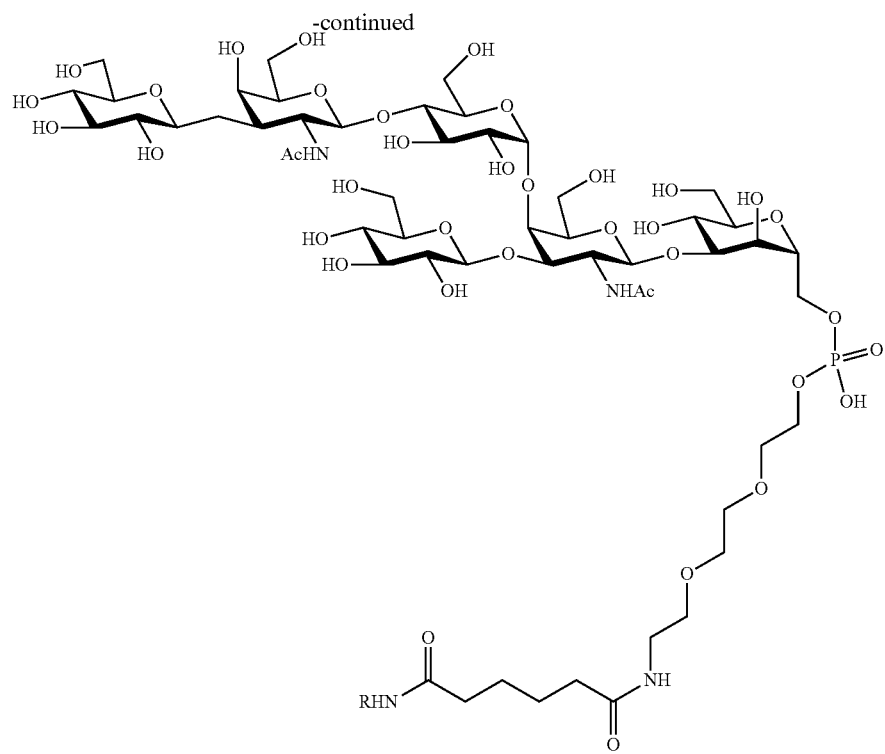
119 R = CRM197
120 R = BSA
Reaction is performed in accordance with the conjugation of compound 33.
A.9 Synthesis of Hexasaccharide 122
Synthesis of 121
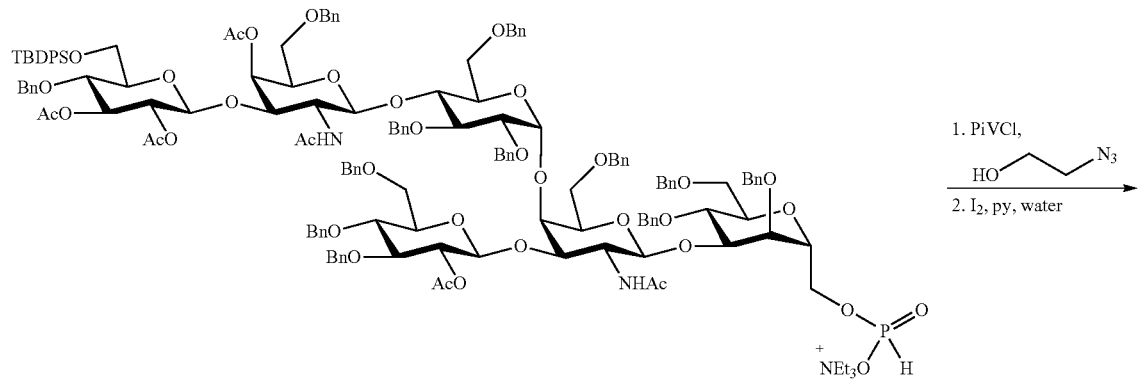

-continued

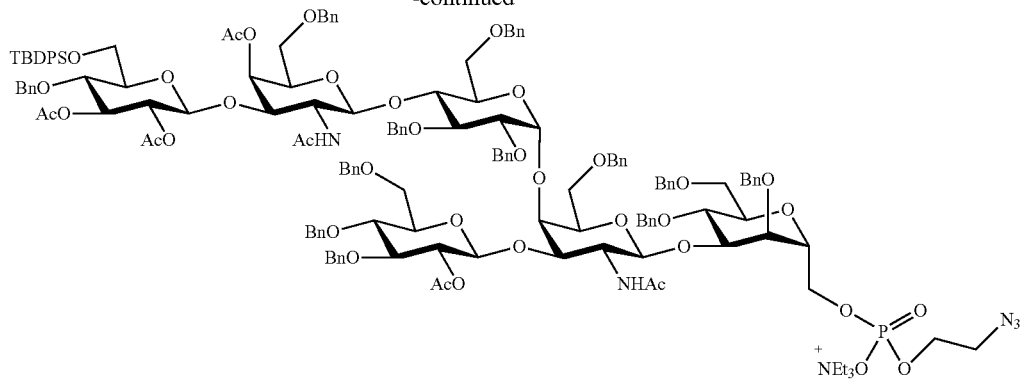

121

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction is cooled to −40° C., a freshly prepared solution of $I_2$ in pyridine: $H_2O$ (20:1) is added and the reaction mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue is purified by automated flash column chromatography (ethyl acetate:DCM:MeOH) together with 2% trimethylamine as eluents give the desired product 121 as viscous liquid.

Synthesis of 122

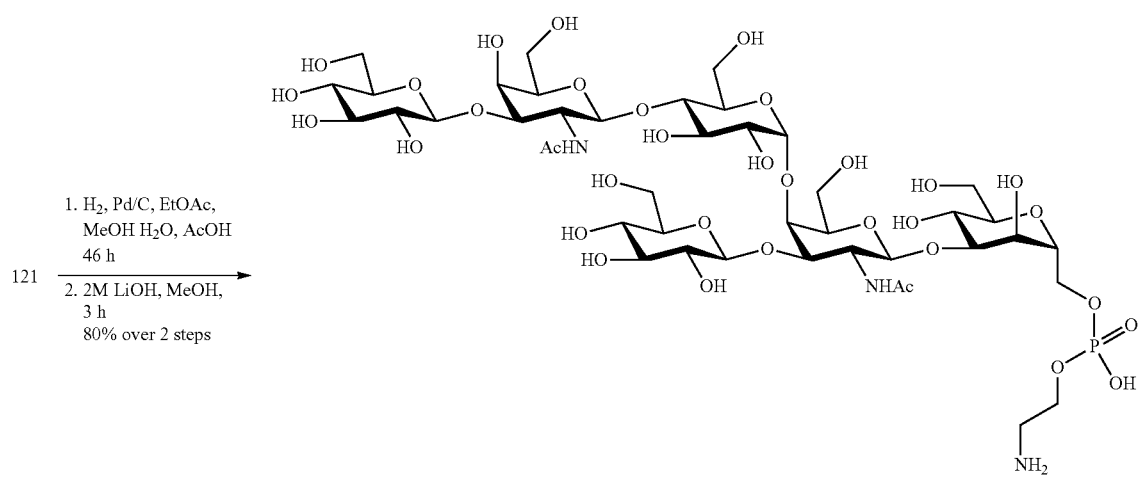

122

Reaction is performed in accordance with the synthesis of compound 33 and a TBS deprotection step.

Conjugation of 122 with CRM$_{197}$ or BSA
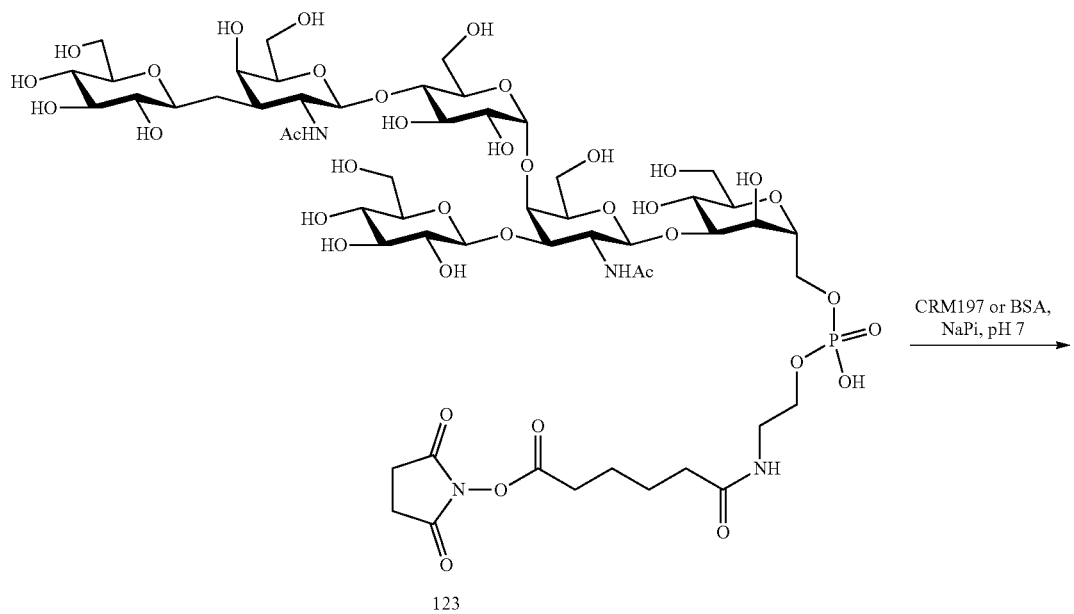
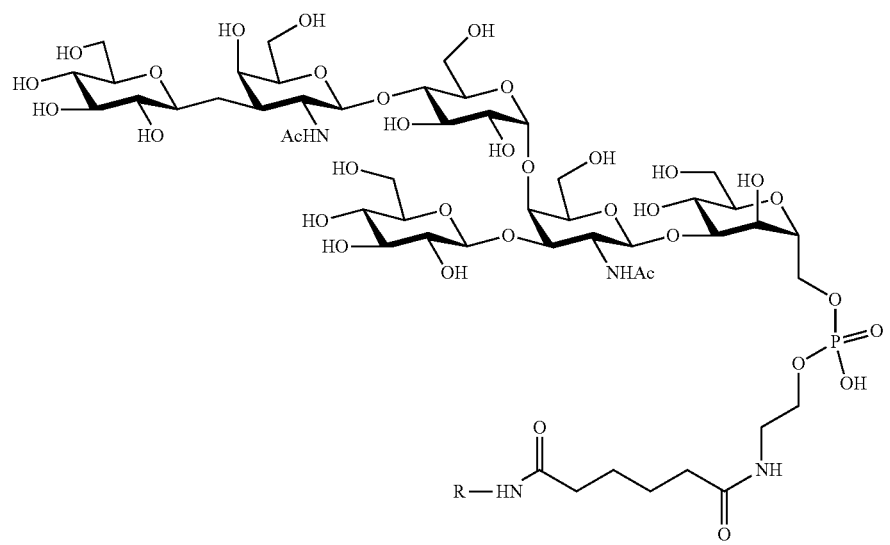
124 R = CRM197
125 R = BSA
Reaction is performed in accordance with the conjugation of compound 33.

A.10 Synthesis of Hexasaccharide 127

Synthesis of 126

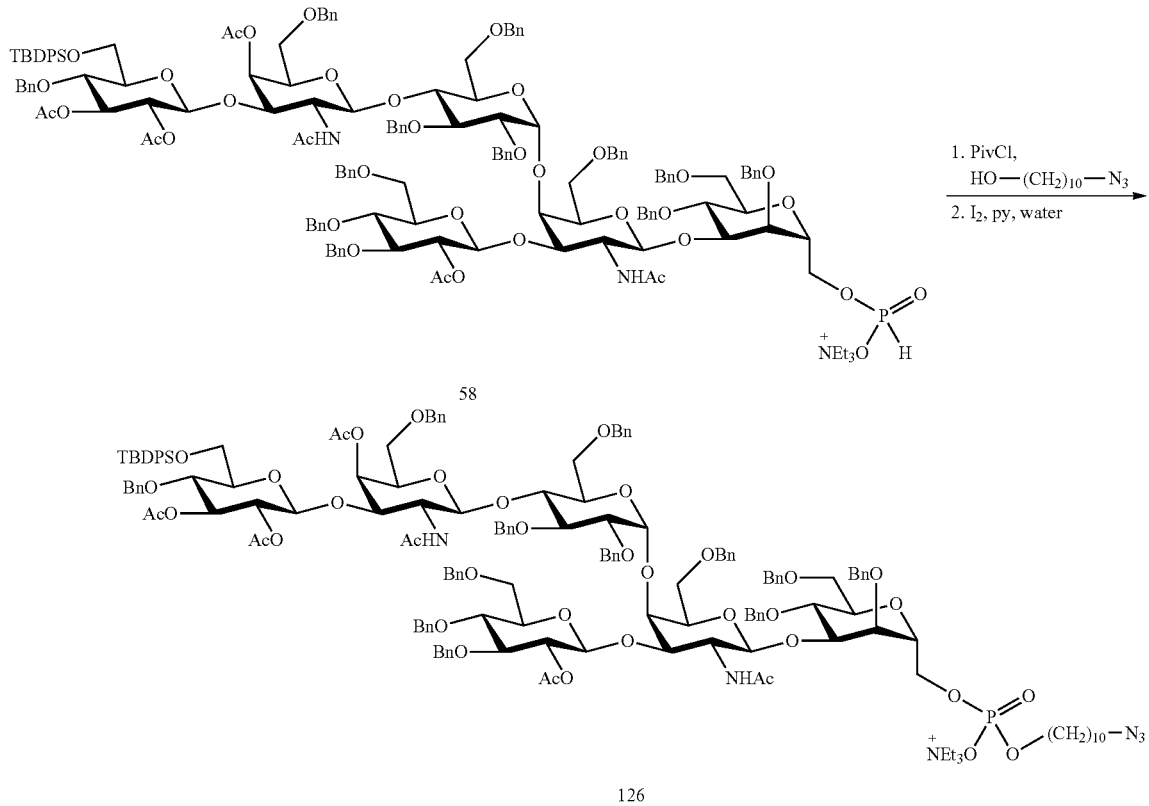

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction is cooled to −40° C., a freshly prepared solution of $I_2$ in pyridine: $H_2O$ (20:1) is added and the reaction mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue is purified by automated flash column chromatography (ethyl acetate:DCM:MeOH) together with 2% trimethylamine as eluents give the desired product 126 as viscous liquid.

Synthesis of 127

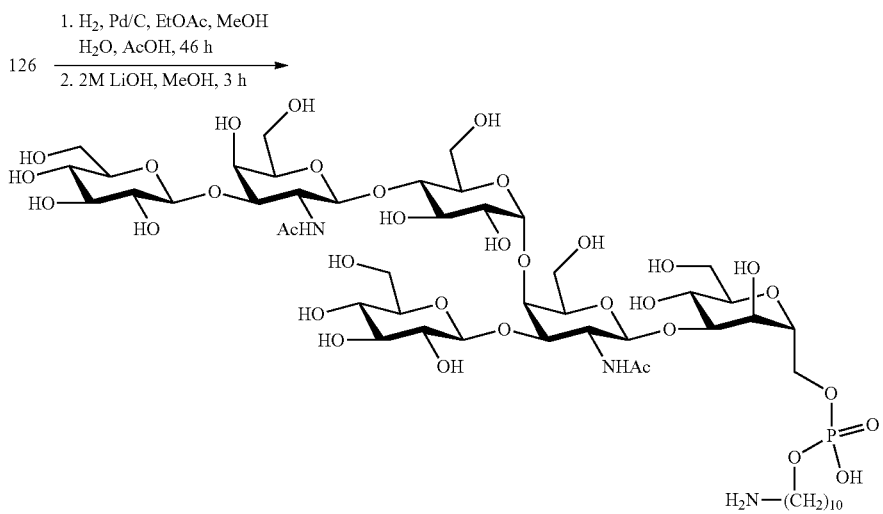

Reaction is performed in accordance with the synthesis of compound 33 and a TBS deprotection step.
Conjugation of 127 with CRM$_{197}$ or BSA
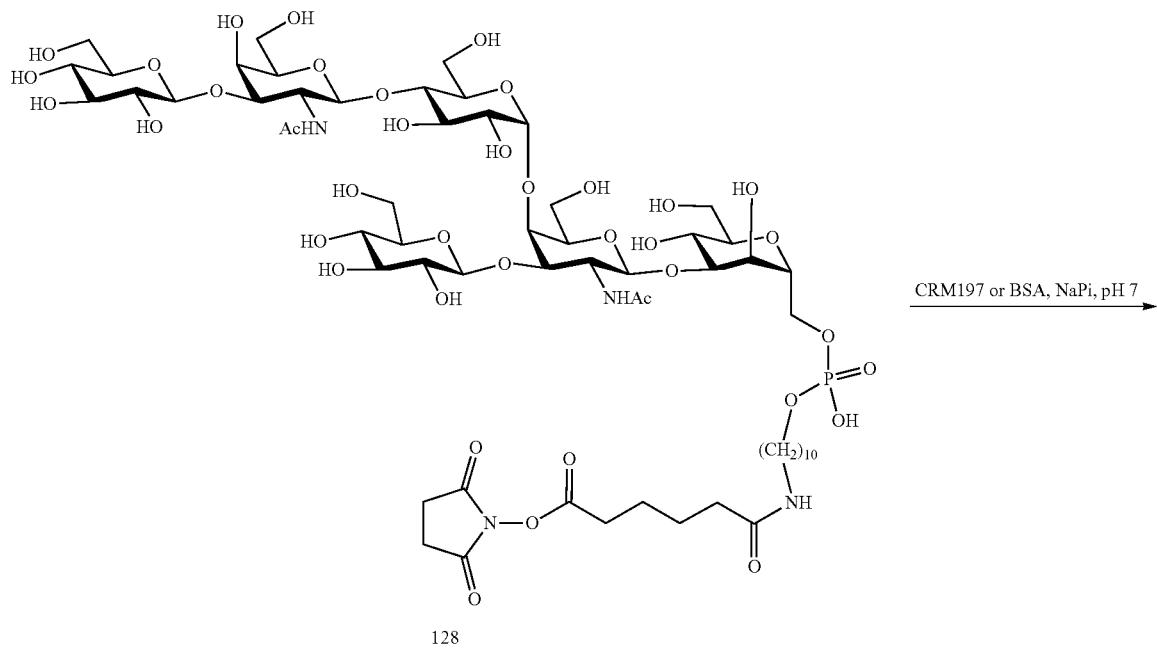
Reaction is performed in accordance with the conjugation of compound 33.

A.11 Synthesis of Hexasaccharide 132
Synthesis of 131

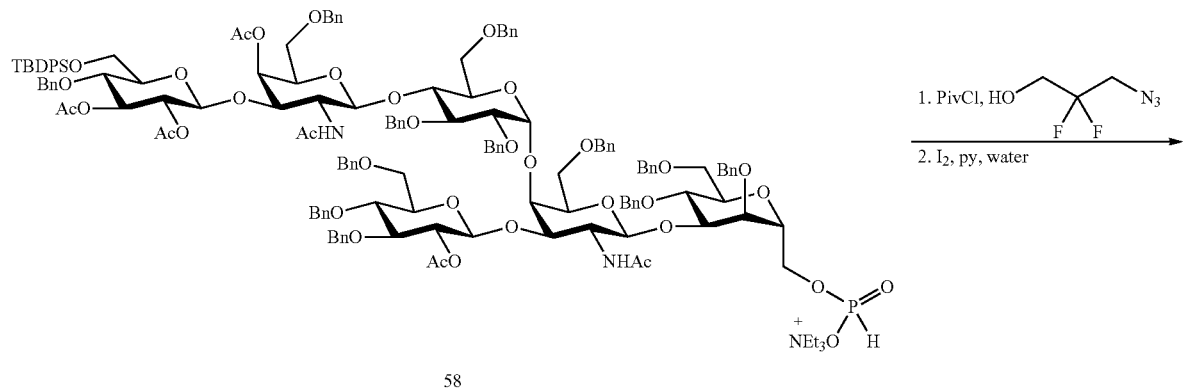

58

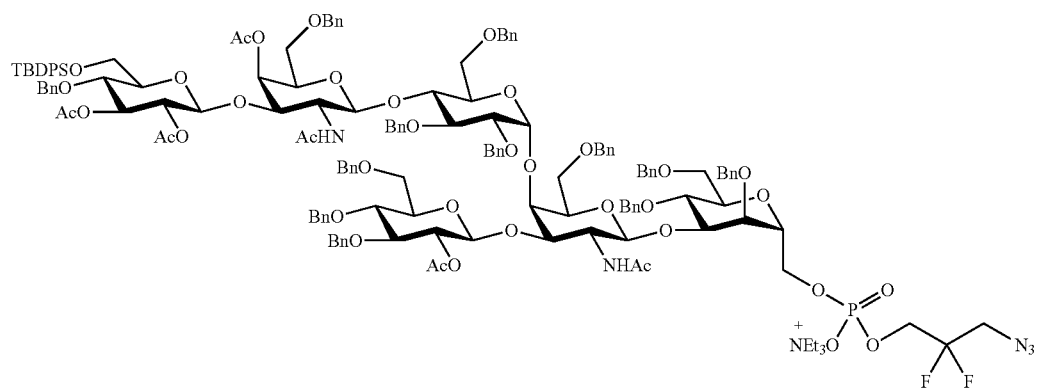

131

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction is cooled to −40° C., a freshly prepared solution of $I_2$ in pyridine: $H_2O$ (20:1) is added and the reaction mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue is purified by automated flash column chromatography (ethyl acetate:DCM:MeOH) together with 2% trimethylamine as eluents give the desired product 131 as viscous liquid.

Synthesis of 132

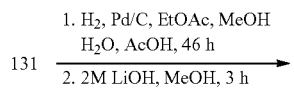

-continued
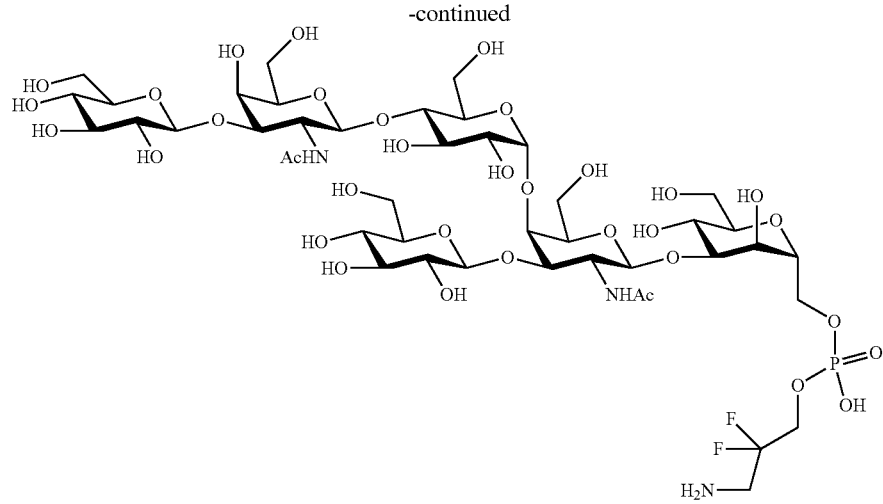
132
Reaction is performed in accordance with the synthesis of compound 33 and a TBS deprotection step.
Conjugation of 132 with CRM$_{197}$ or BSA
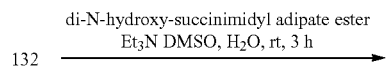
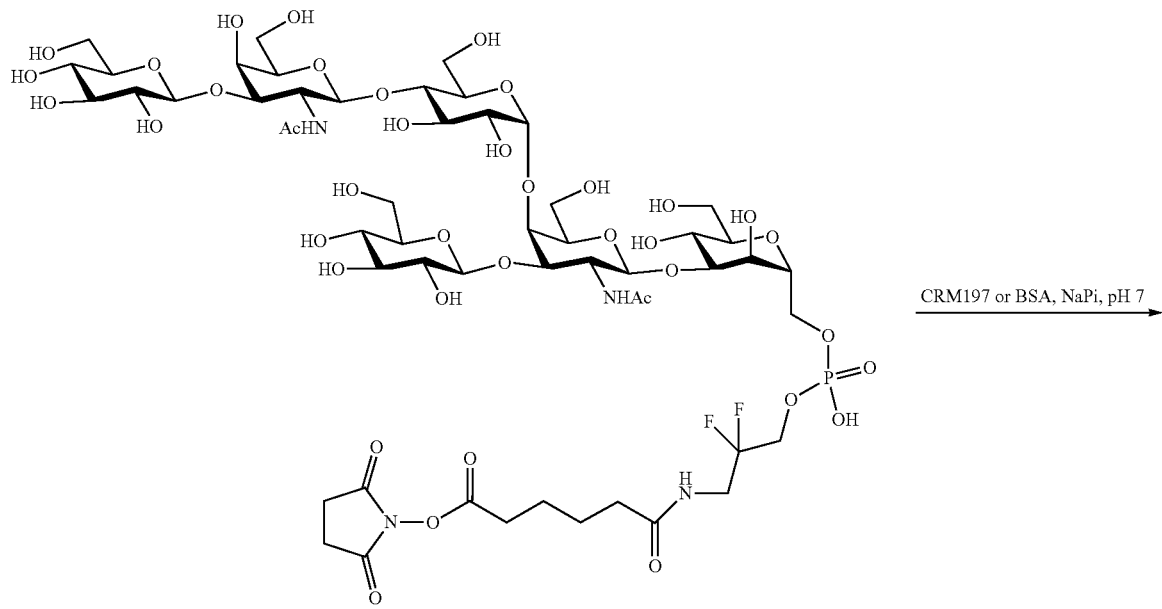
133

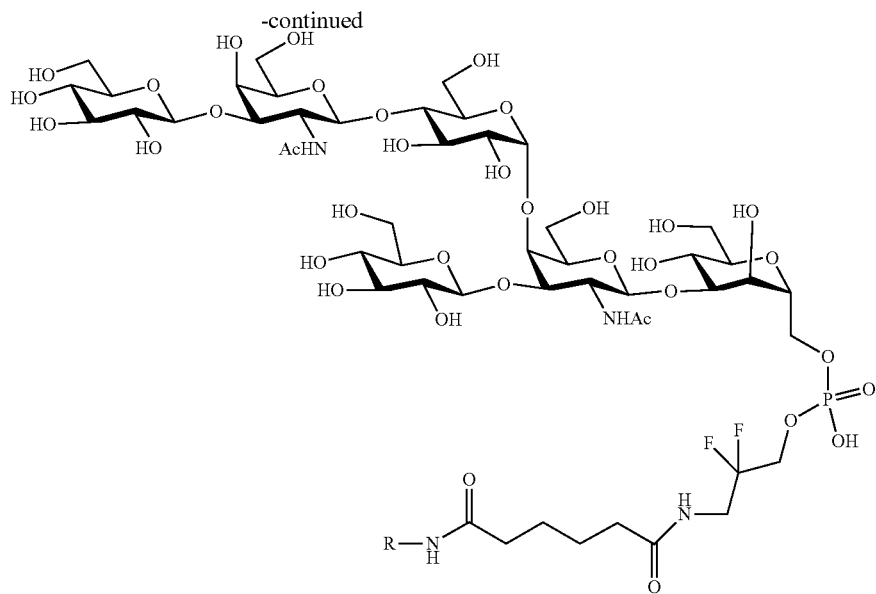
134 R= CRM197
135 R= BSA
Reaction is performed in accordance with the conjugation of compound 33.
A.12 Synthesis of Hexasaccharide 137
Synthesis of 136
H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the
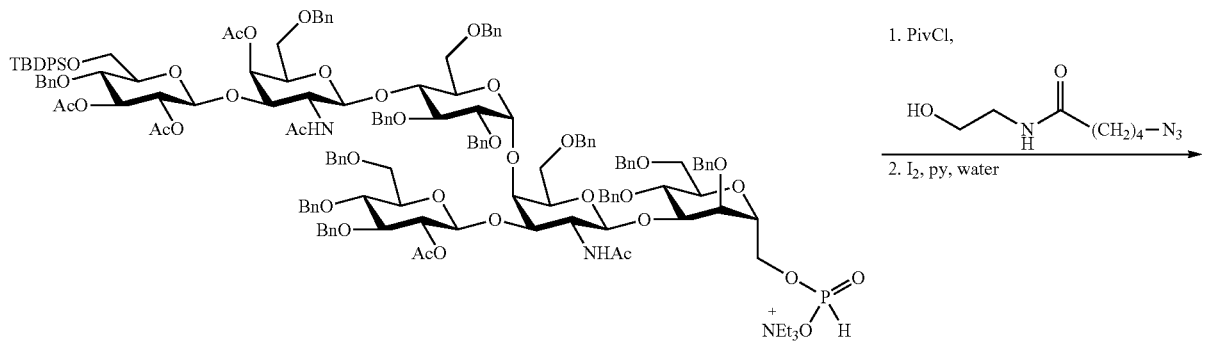
58
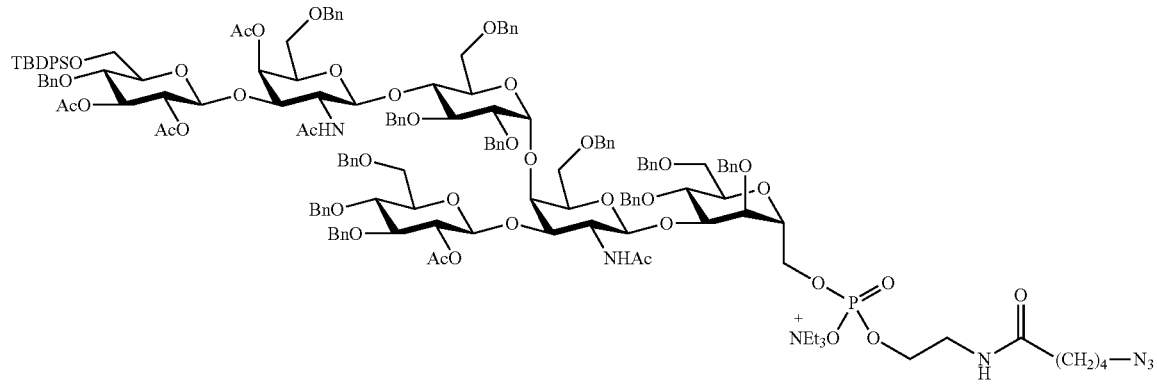
136 reaction is cooled to −40° C., a freshly prepared solution of I₂ in pyridine: H₂O (20:1) is added and the reaction mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over Na₂SO₄, filtered and concentrated. The residue is purified by automated flash column chromatography (ethyl acetate:DCM:MeOH) together with 2% trimethylamine as eluents give the desired product 136 as viscous liquid.

Synthesis of 137

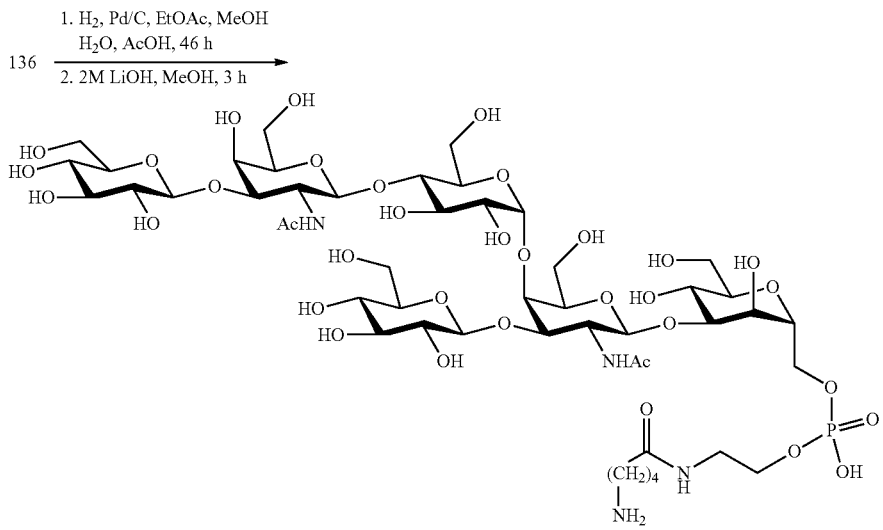

Reaction is performed in accordance with the synthesis of compound 33 and a TBS deprotection step.

Conjugation of 137 with CRM₁₉₇ or BSA

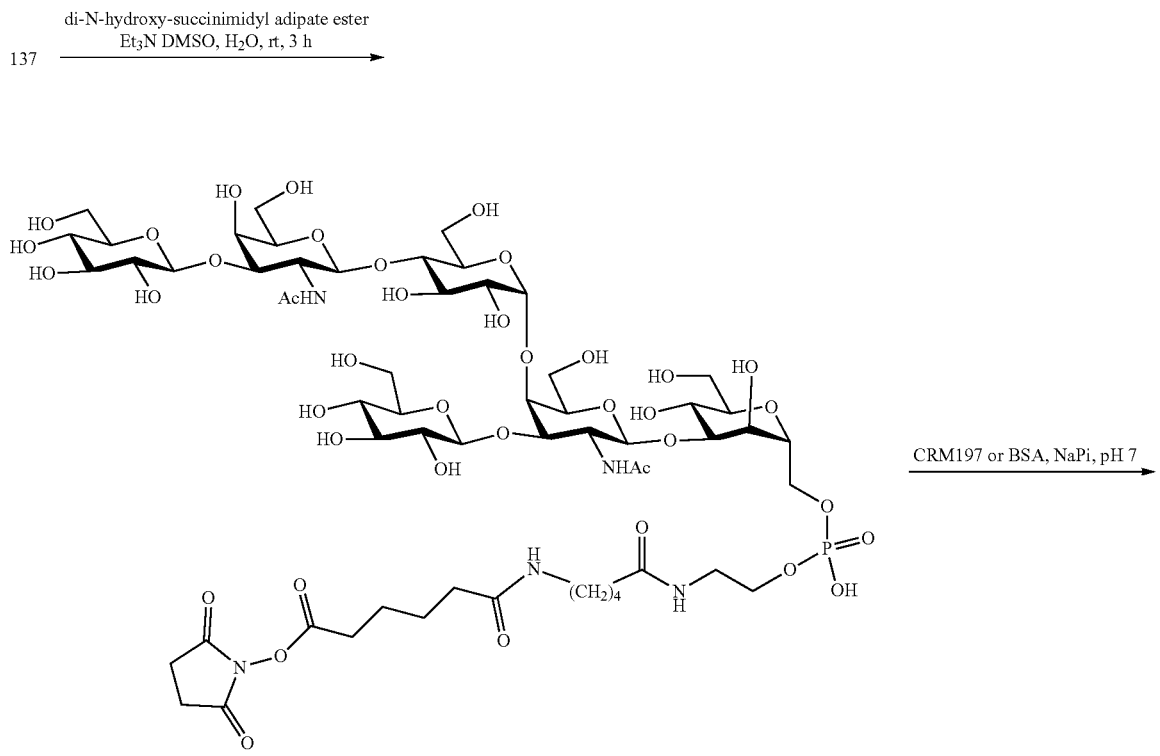

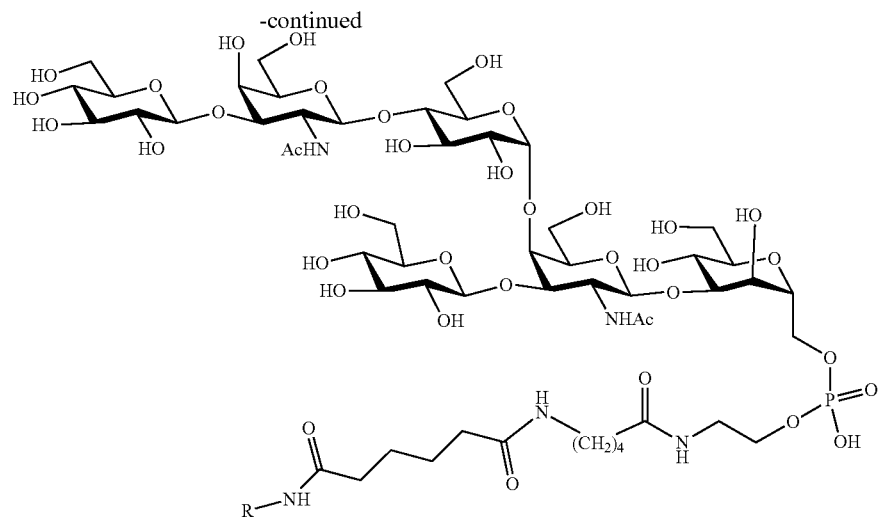

139 R= CRM197
140 R= BSA

Reaction is performed in accordance with the conjugation of compound 33.

A.13 Synthesis of Hexasaccharide 142

Synthesis of 141

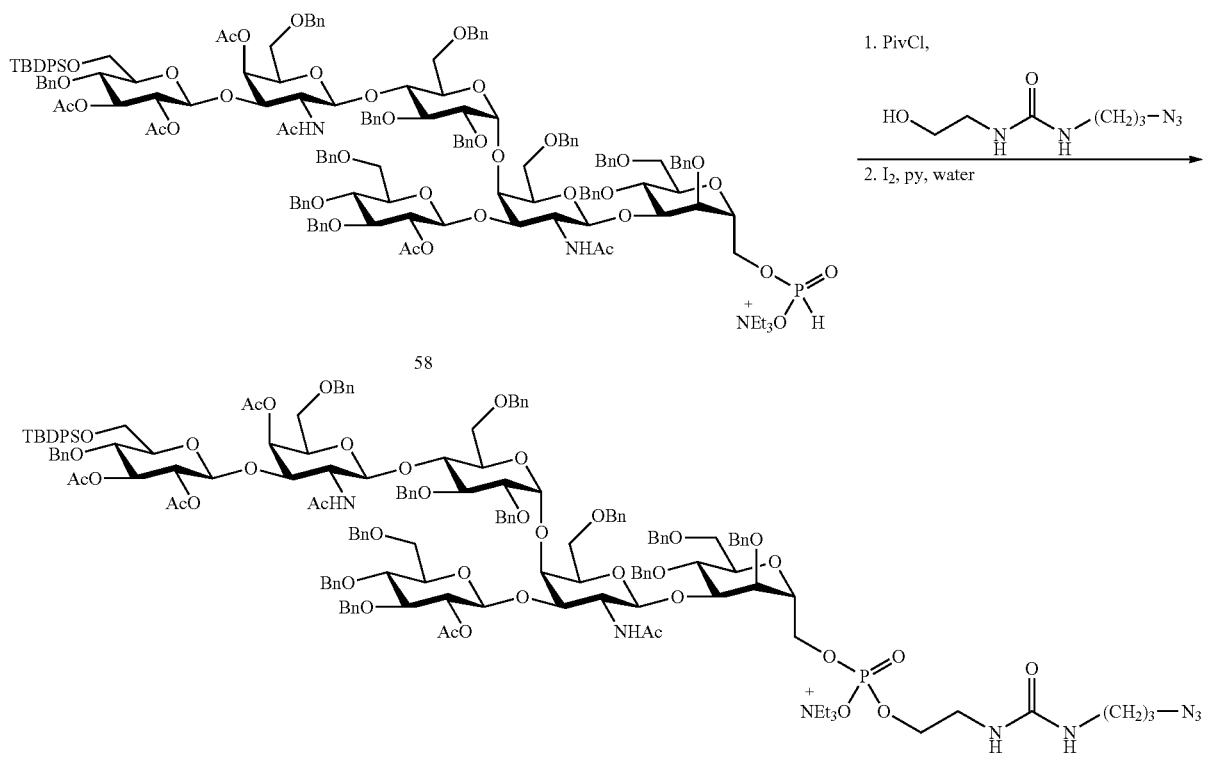

141

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction is cooled to −40° C., a freshly prepared solution of $I_2$ in pyridine: $H_2O$ (20:1) is added and the reaction mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue is purified by automated flash column chromatography (ethyl acetate:DCM:MeOH) together with 2% trimethylamine as eluents give the desired product 141 as viscous liquid.
Synthesis of 142
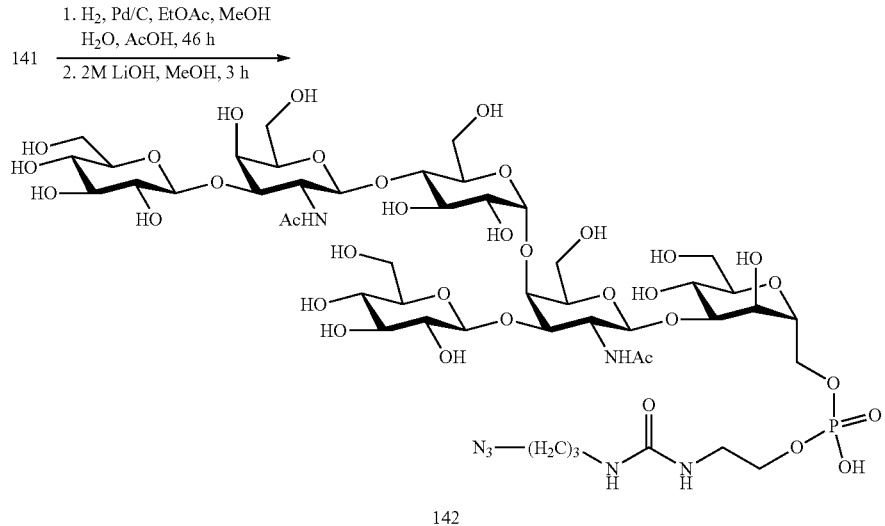
Reaction is performed in accordance with the synthesis of compound 33 and a TBS deprotection step.
Conjugation of 142 with CRM$_{197}$ or BSA
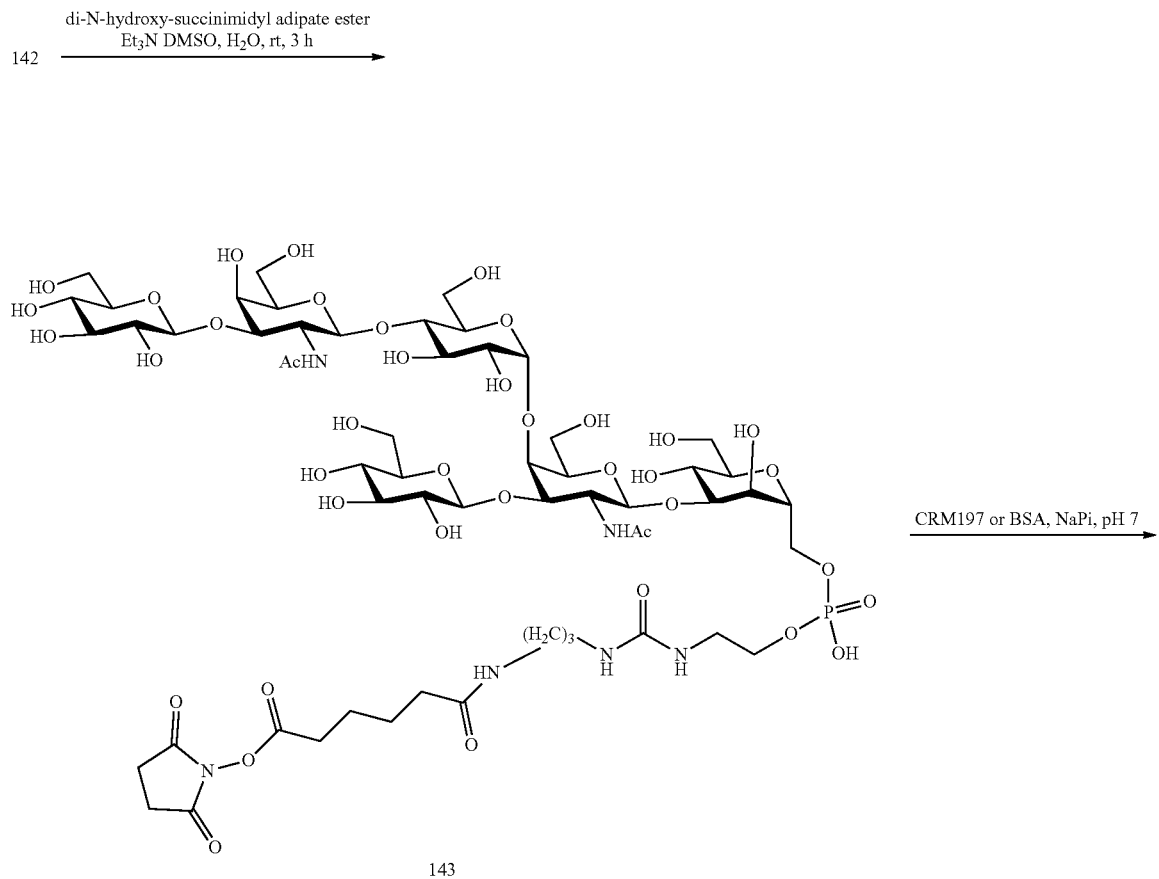

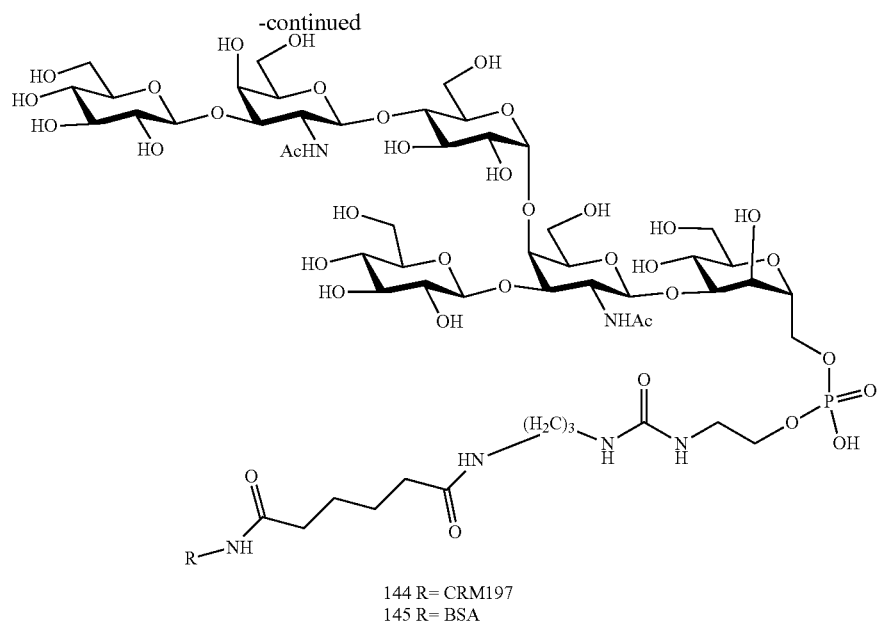

144 R= CRM197
145 R= BSA

Reaction is performed in accordance with the conjugation of compound 33.

A.14 Synthesis of Hexasaccharide 147

Synthesis of 146

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction is cooled to −40° C., a freshly prepared solution of $I_2$ in pyridine: $H_2O$ (20:1) is added and the reaction mixture

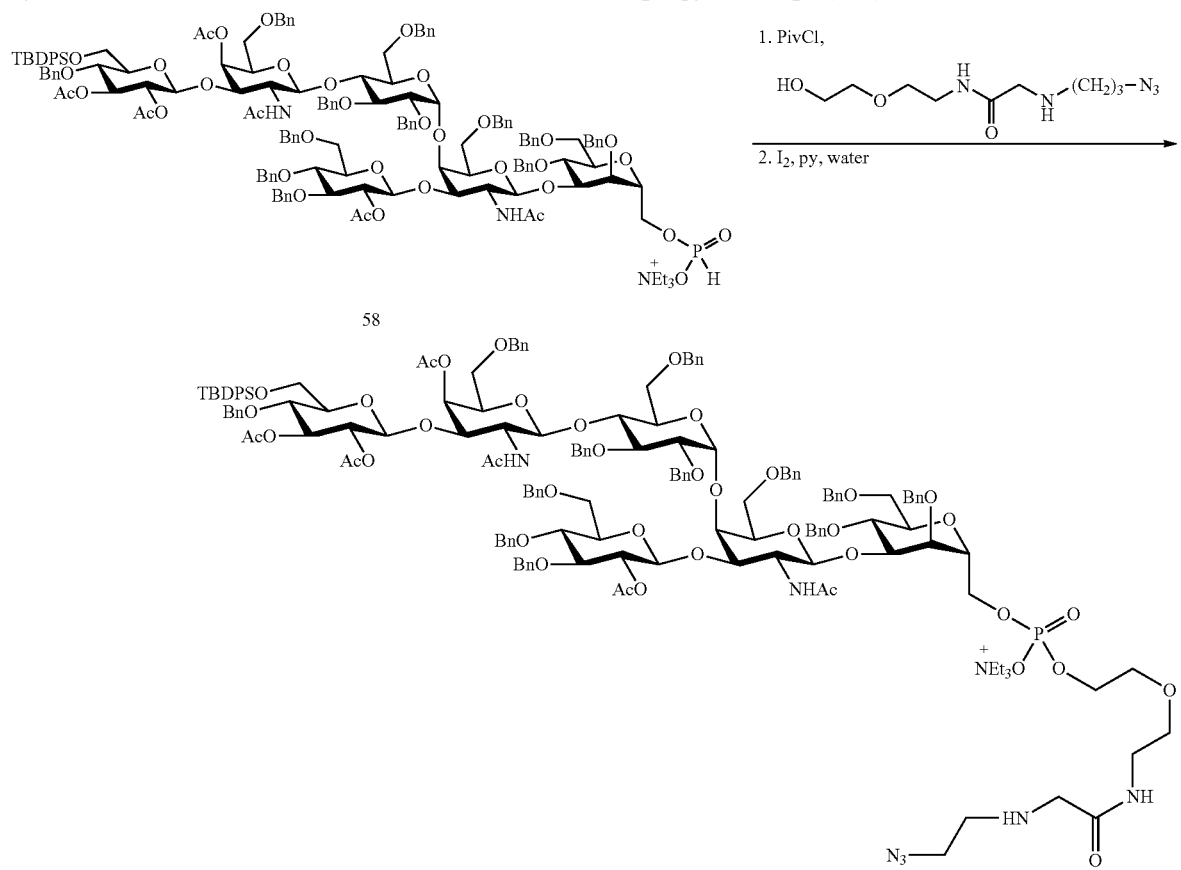

is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue is purified by automated flash column chromatography (ethyl acetate:DCM:MeOH) together with 2% trimethylamine as eluents give the desired product 146 as viscous liquid.

Synthesis of 142

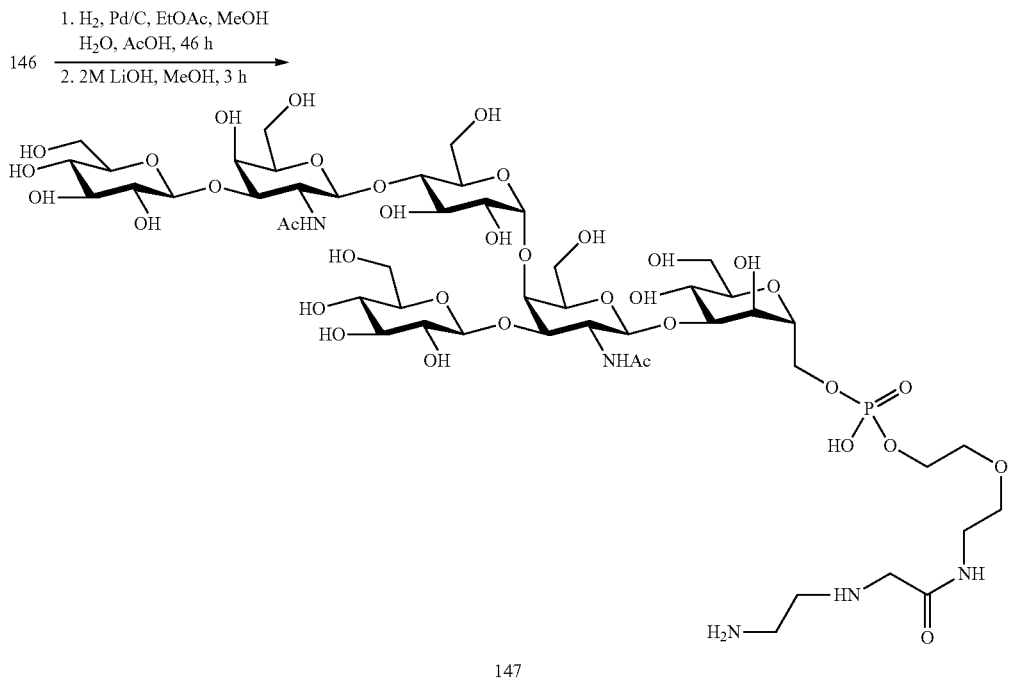

Reaction is performed in accordance with the synthesis of compound 33 and a TBS deprotection step.

Conjugation of 147 with $CRM_{197}$ or BSA

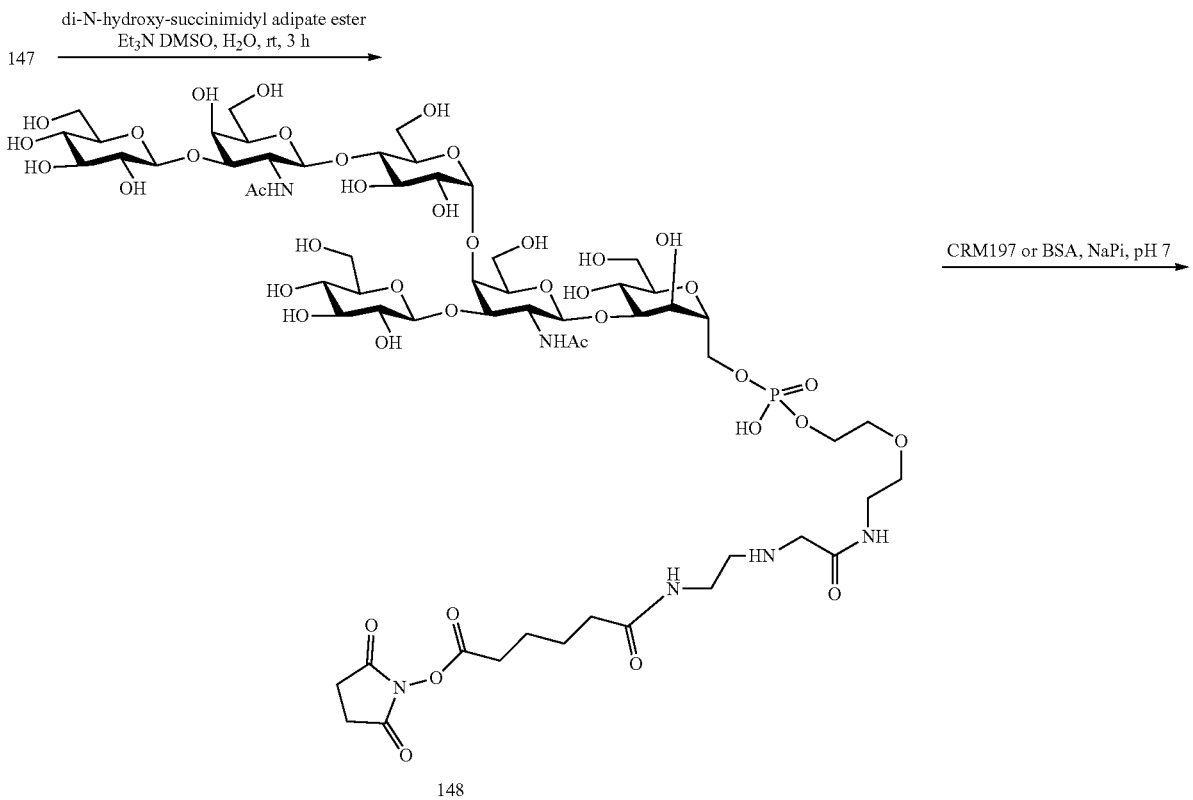

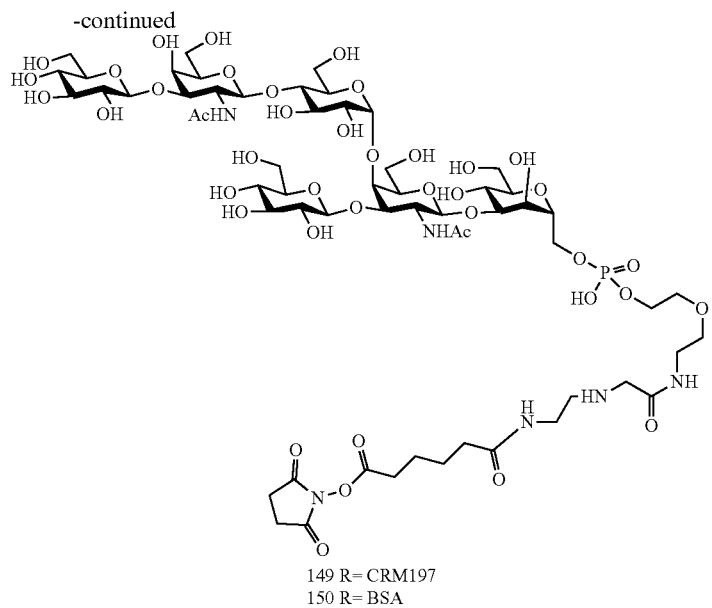

149 R= CRM197
150 R= BSA

Reaction is performed in accordance with the conjugation of compound 33.

A.15 Synthesis of Hexasaccharide 152

Synthesis of 151

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction was cooled to −40° C., a freshly prepared solution of $I_2$ in pyridine: $H_2O$ (20:1) is added and the reaction

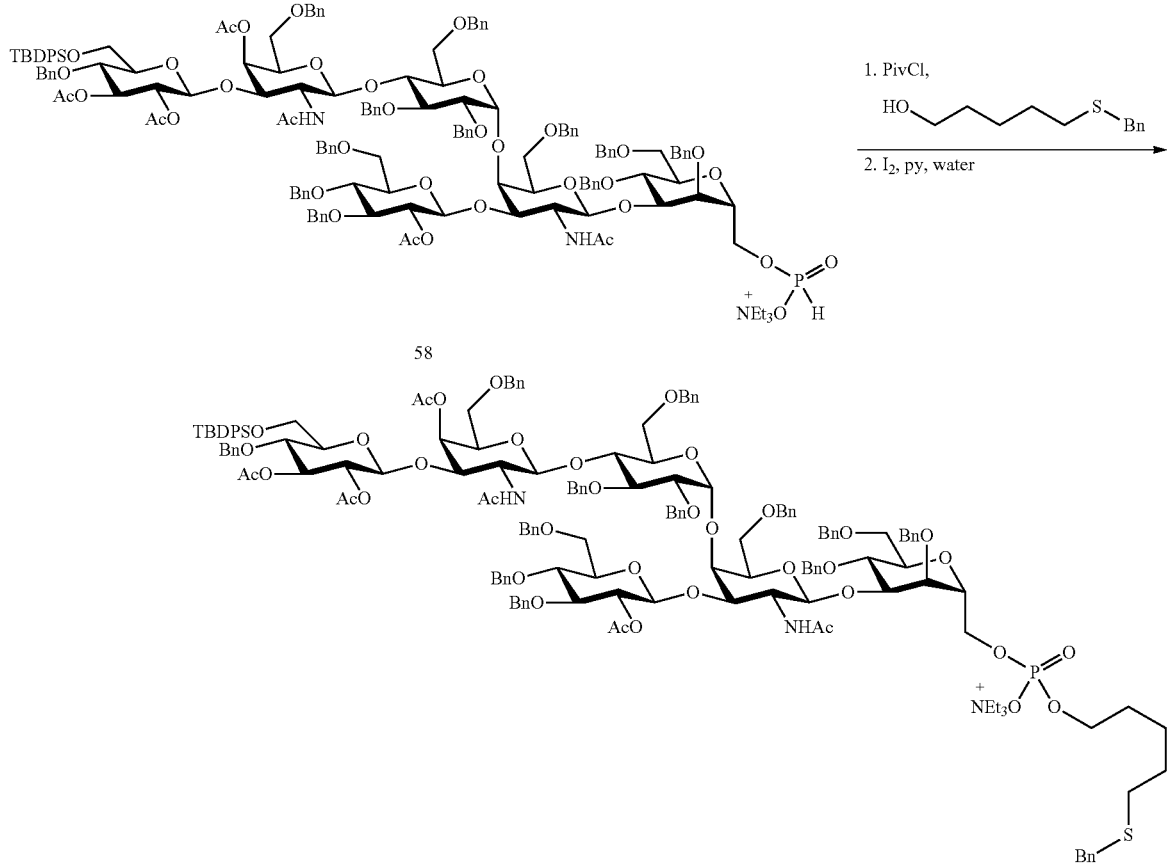

mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over Na$_2$SO$_4$, filtered and concentrated. The residue is purified by automated flash column chromatography (ethyl acetate: DCM: MeOH) together with 2% trimethylamine as eluents give the desired product 151 as viscous liquid.

Synthesis of 152

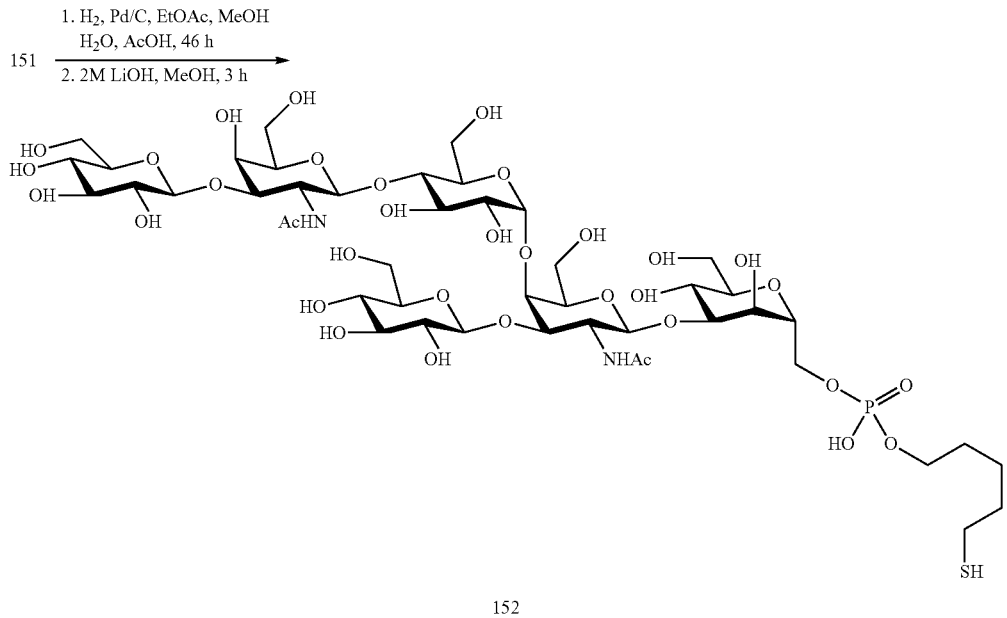

Reaction was performed in accordance with the synthesis of compound 33 and a TBS deprotection step.

Conjugation of 152 with CRM$_{197}$ or BSA

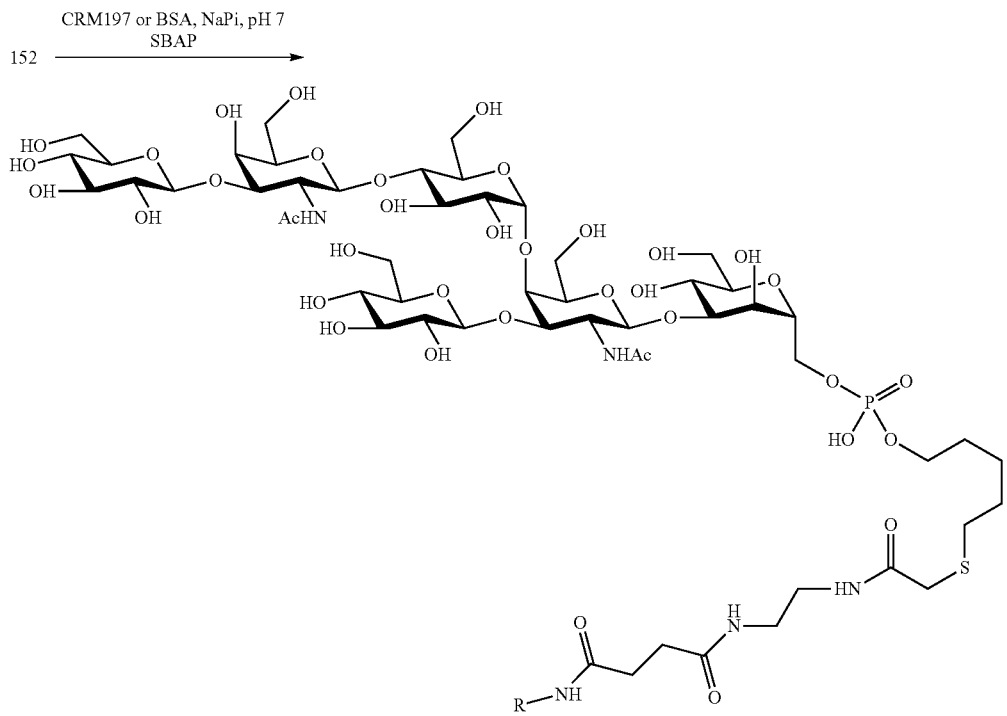

SBAP (N-succinimidyl-3-(bromoacetamido) propionate) is added to a stirred solution of protein in sodium phosphate buffer (NaPi, pH 7.4) at room temperature. The reaction mixture is stirred for one hour at room temperature and afterwards concentrated using membrane filtration and rebuffered in NaPi (pH 8.0). A solution of compound 152 in NaPi is added to the solution of activated protein and stirred at r.t. for 16 hours. The glycoconjugate is then washed with sterile water and treated with l-cysteine in sterile water. Purification of the glycoconjugate is achieved by membrane filtration.

A.16 Synthesis of Hexasaccharide 157

Synthesis of 156

H-phosphonate 58 and linker are co-evaporated with pyridine and dried under vacuum for 30 min. After that, it is dissolved in pyridine and to this PivCl is added. The reaction mixture is kept for stirring at r.t. for 2 h. After 2 h, the reaction is cooled to −40° C., a freshly prepared solution of $I_2$ in pyridine: $H_2O$ (20:1) is added and the reaction mixture is kept for stirring at the same temperature for 1.5 h and later brought to rt and stirred at rt for 15 min. Then, TEAB (10 mL) is added to the mixture and diluted with dichloromethane, washed successively with 10% aq. sodium thiosulfate, 1 M aq. triethylammonium hydrogen carbonate (TEAB), dried over $Na_2SO_4$, filtered and concentrated. The residue is purified by automated flash column chromatography (ethyl acetate:DCM:MeOH) together with 2% trimethylamine as eluents give the desired product 156 as viscous liquid.

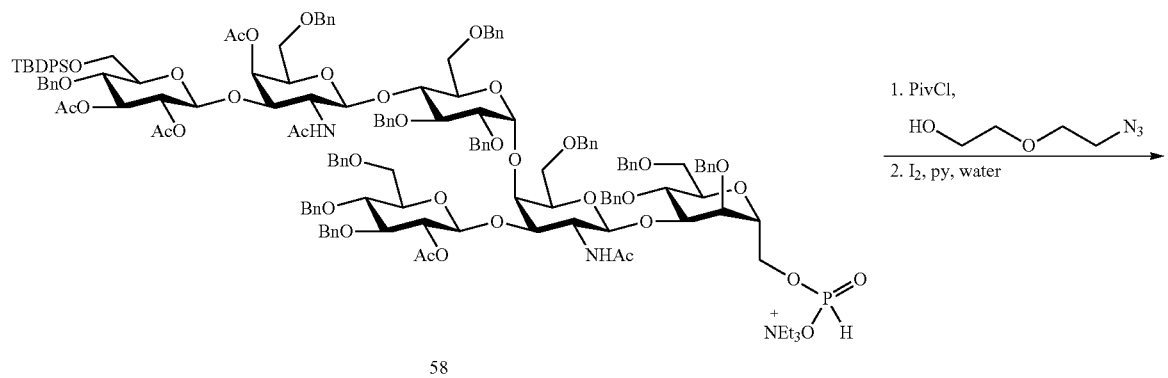

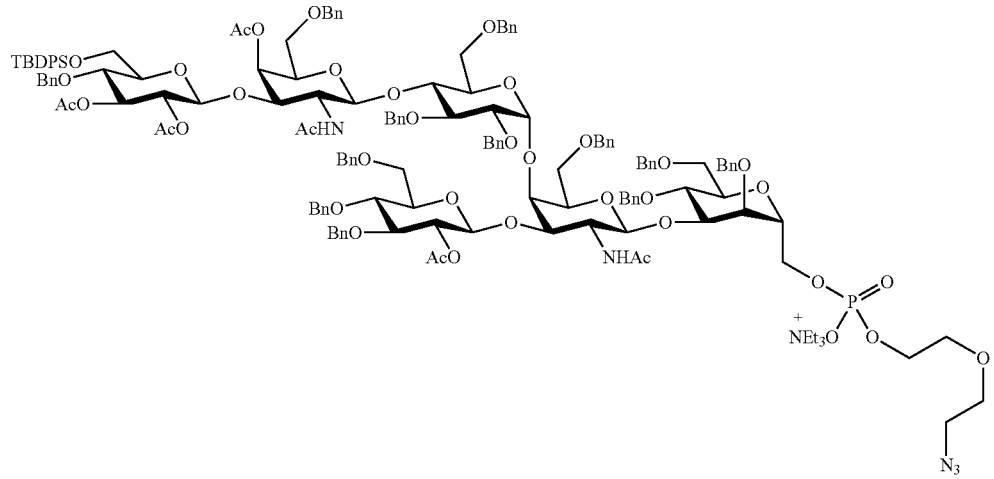

Synthesis of 157
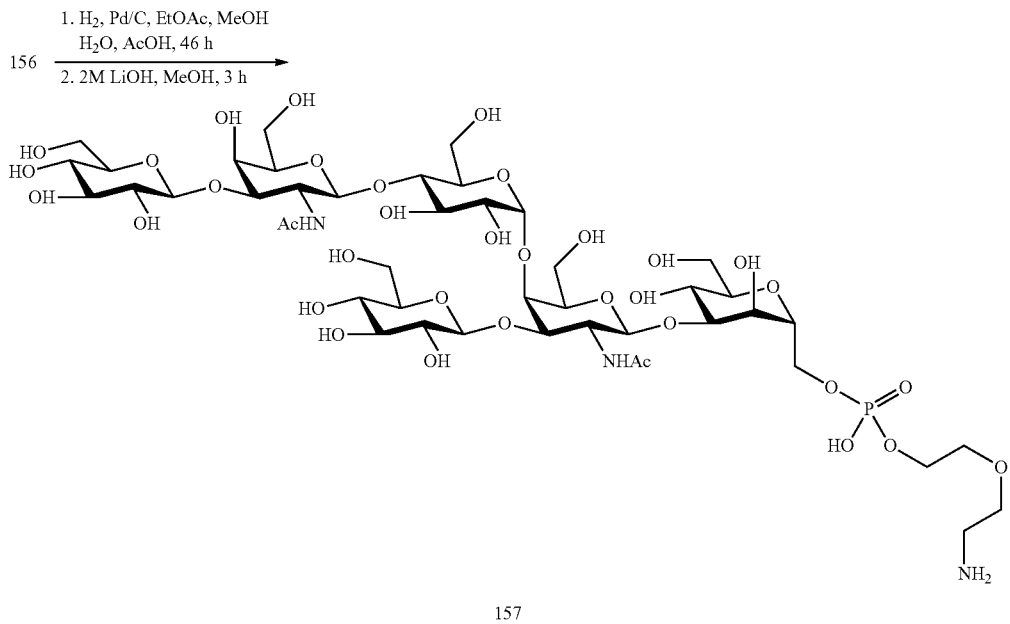
Reaction is performed in accordance with the synthesis of compound 33 and a TBS deprotection step.
Conjugation of 157 with CRM$_{197}$ or BSA
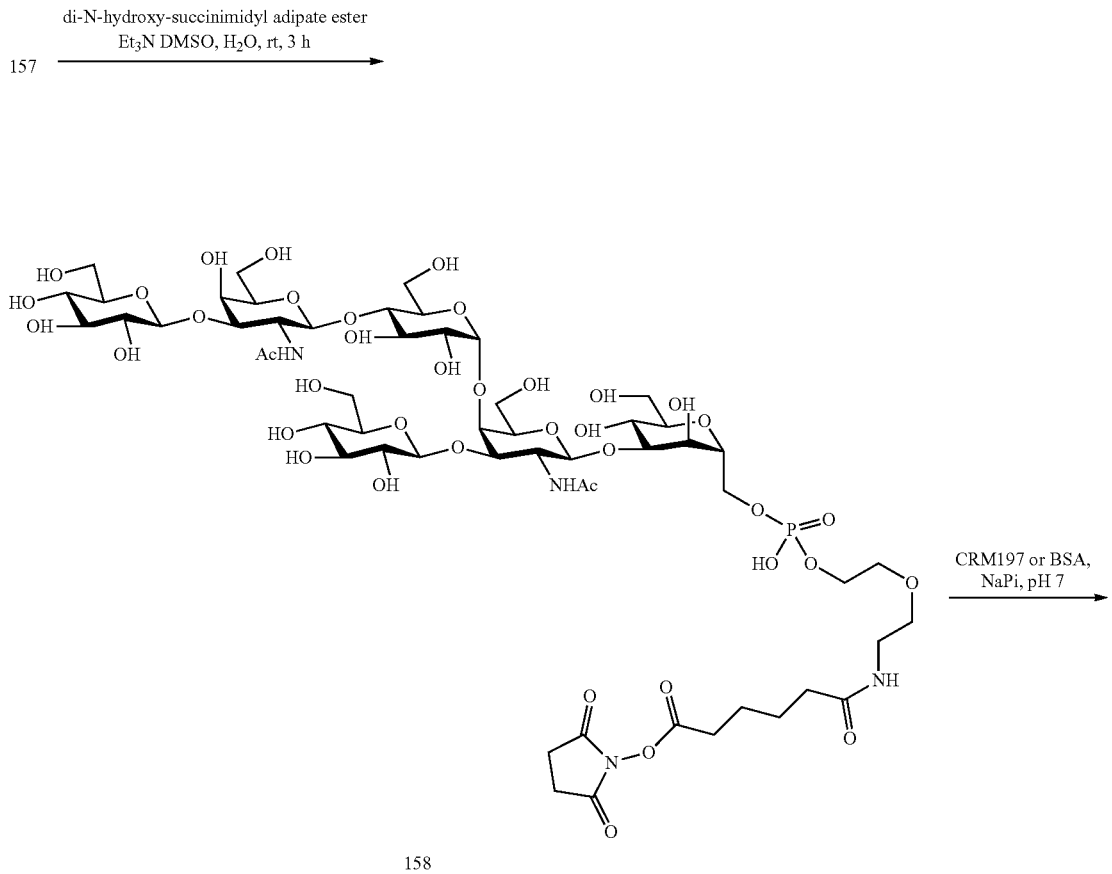

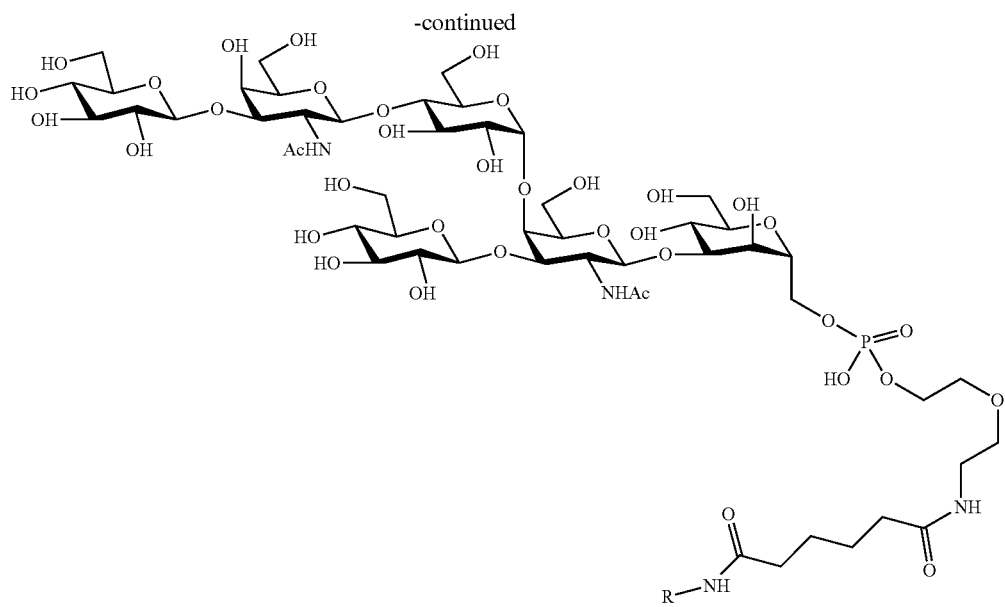
159 R = CRM197
160 R = BSA
Reaction is performed in accordance with the conjugation of compound 33.
A.17 Synthesis of Octadecasaccharides 162, 163, 164 and 165
Synthesis of 161
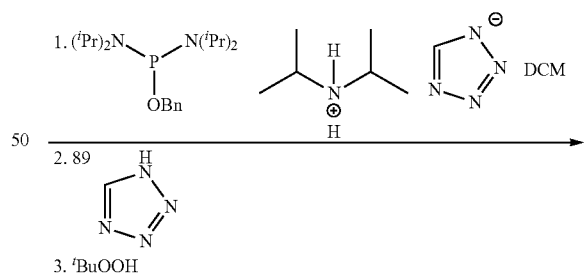

-continued
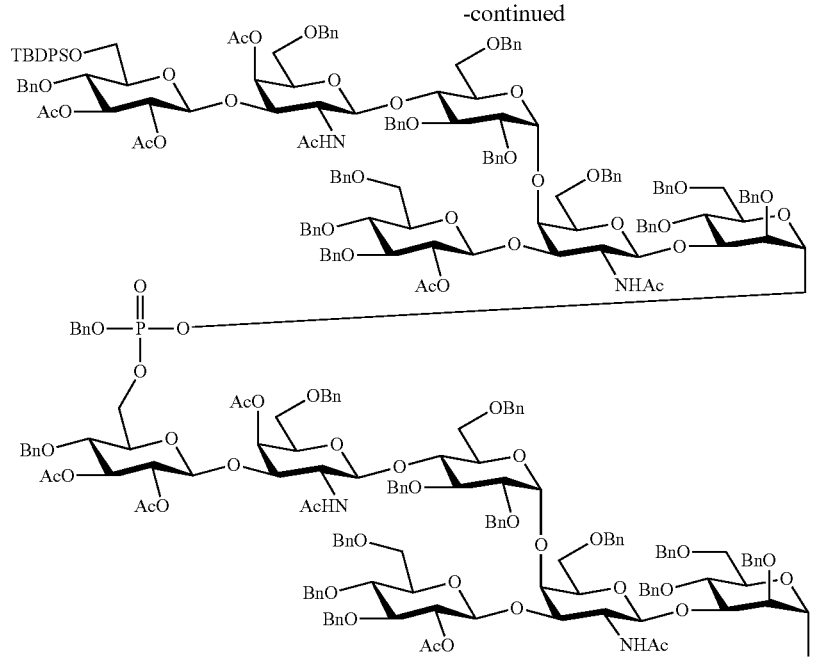
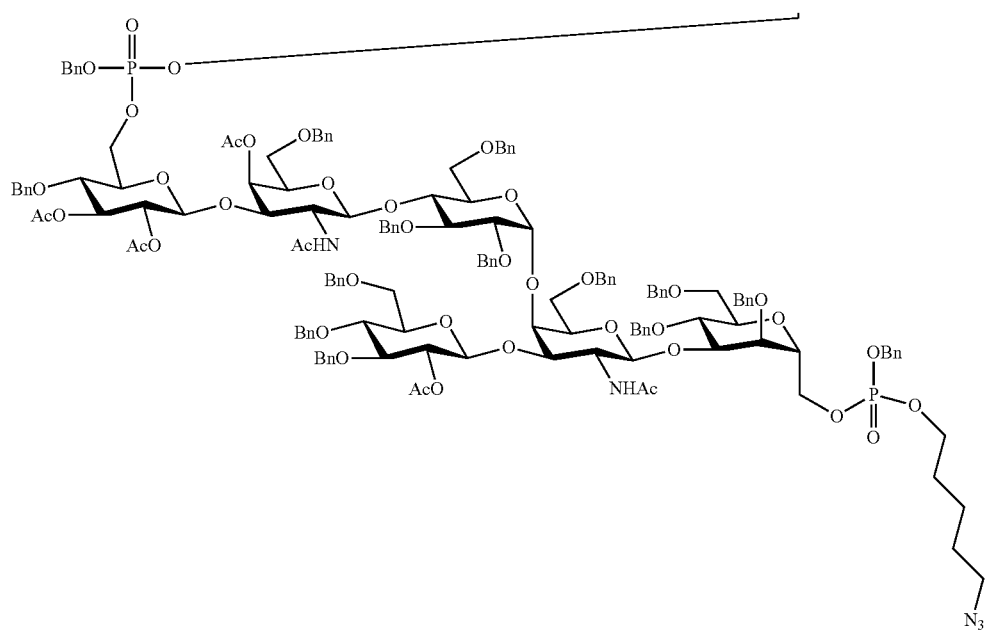
161
The procedure described for the synthesis of compound 32 is used for the synthesis of compound 161, here with the only change that in the second step instead of a linker compound 89 is used as nucleophile.

Synthesis of 162

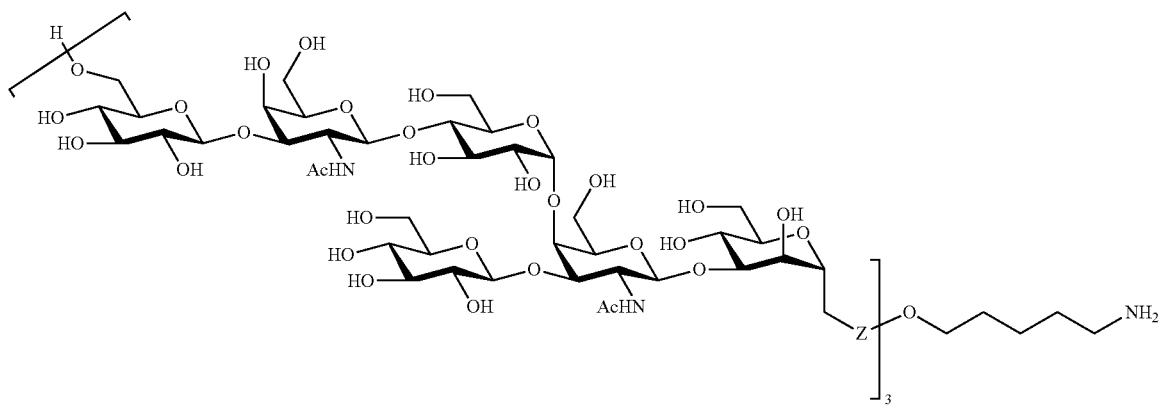

wherein Z represents

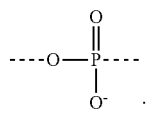

Compound 162 is synthesized from compound 161 as described for compound 89 (removal of the TBDPS protecting group) and thereafter as described for compound 90.

Synthesis of 163

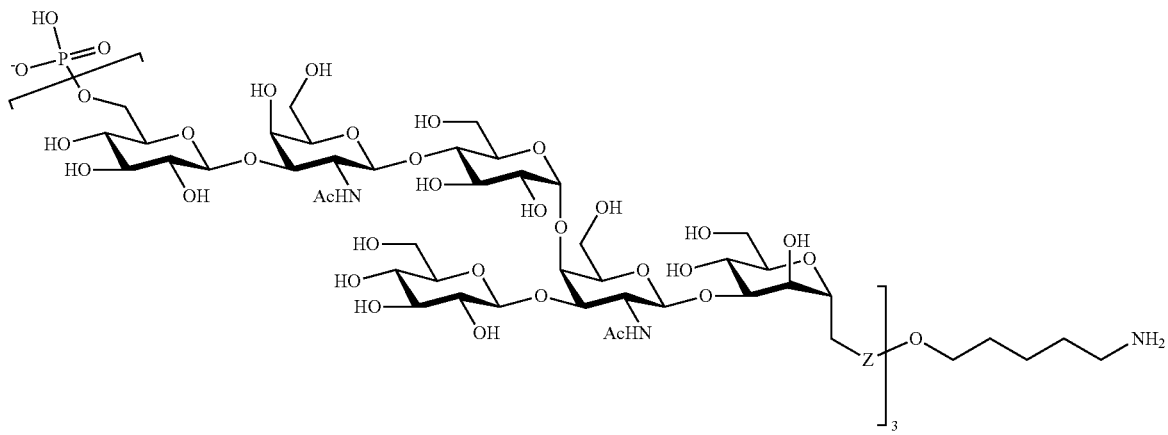

wherein Z represents

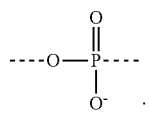

Compound 163 is synthesized from compound 161 as described for compound 89 (removal of the TBDPS protecting group) and thereafter as described for compounds 91 and 92.

Synthesis of 164
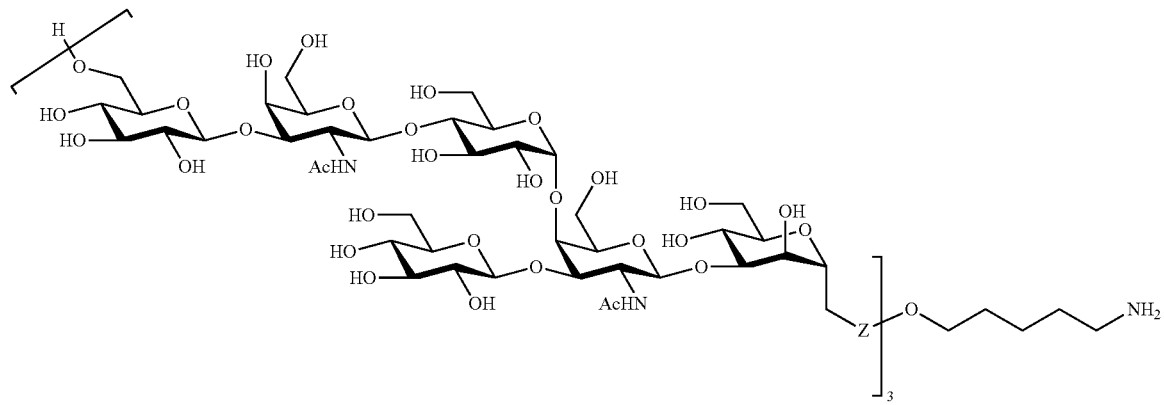
wherein Z represents
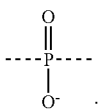
The phosphonate compound 164 is synthesized as described for compound 162.
Synthesis of 165
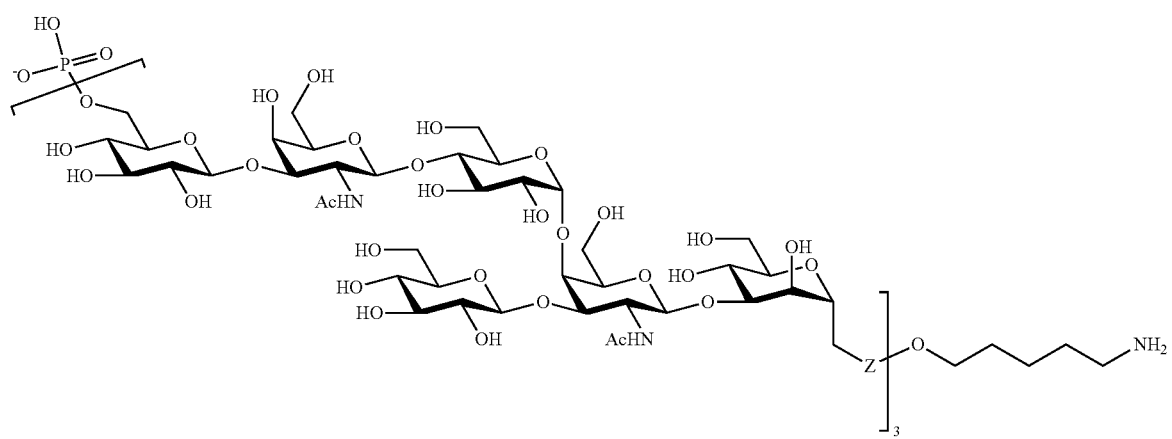
wherein Z represents
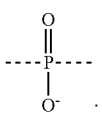
The phosphonate compound 165 is synthesized as described for compound 163.

A.18 Alternative Synthesis of Octadecasaccharides 162 and 163
Synthesis of 166
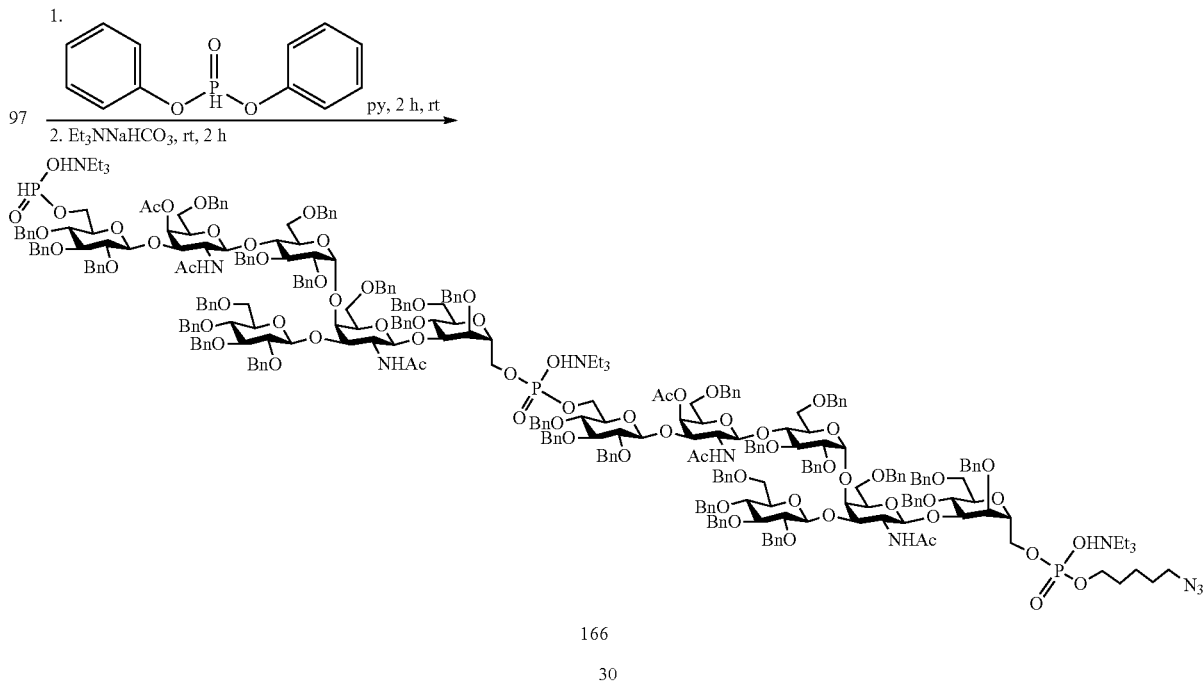
The procedure described for the synthesis of compound 86 is used for the synthesis of compound 166.
Synthesis of 167
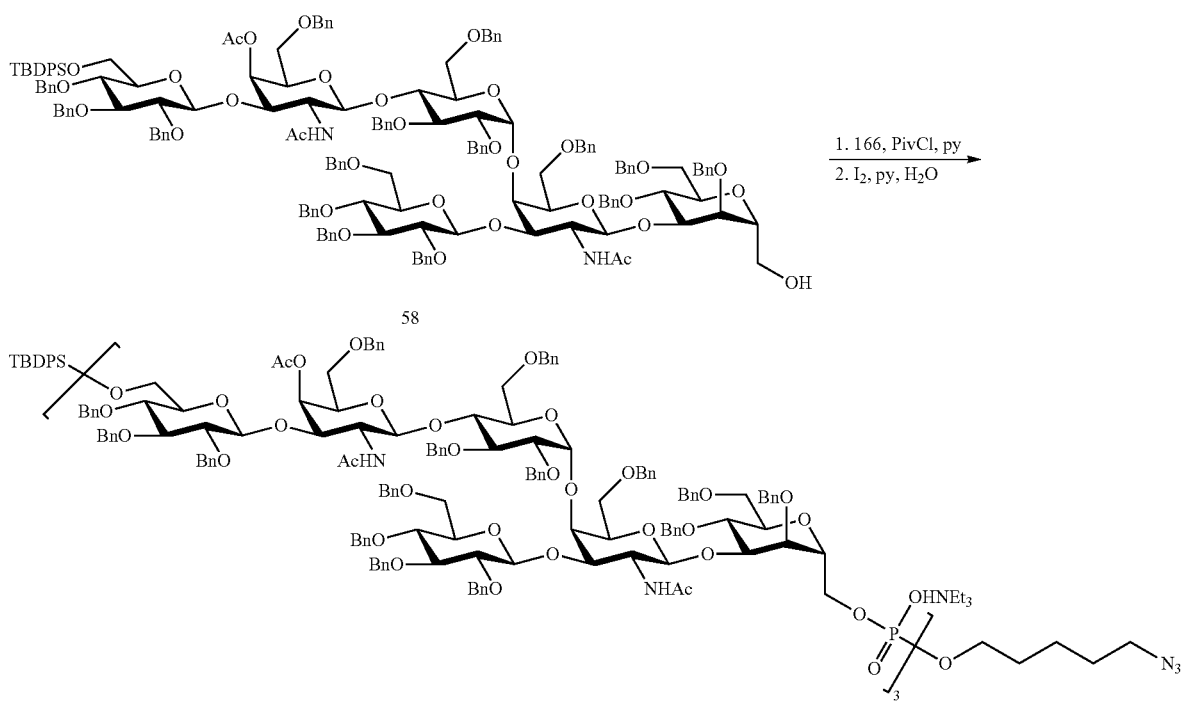
The procedure described for the synthesis of compound 96 is used for the synthesis of compound 167.

Synthesis of 162
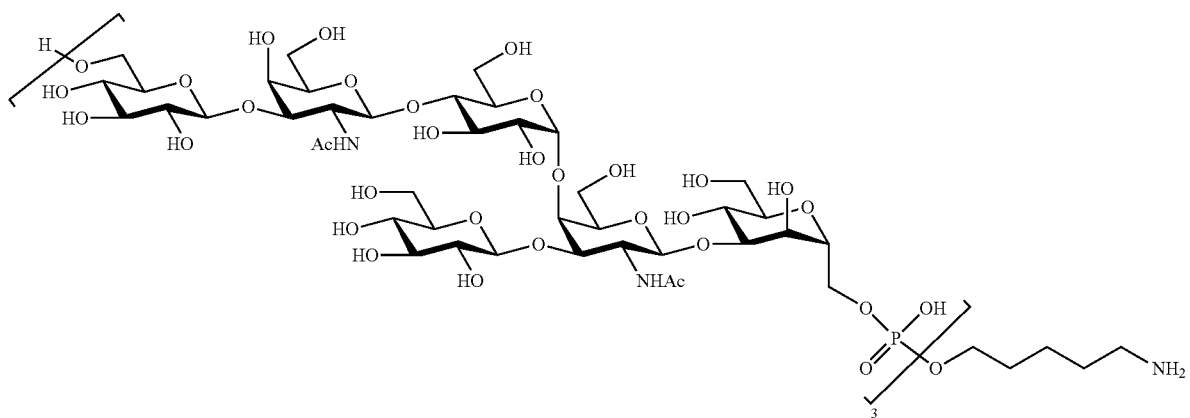
Compound 162 is synthesized from compound 167 as described for compound 33.
Synthesis of 168
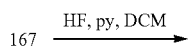
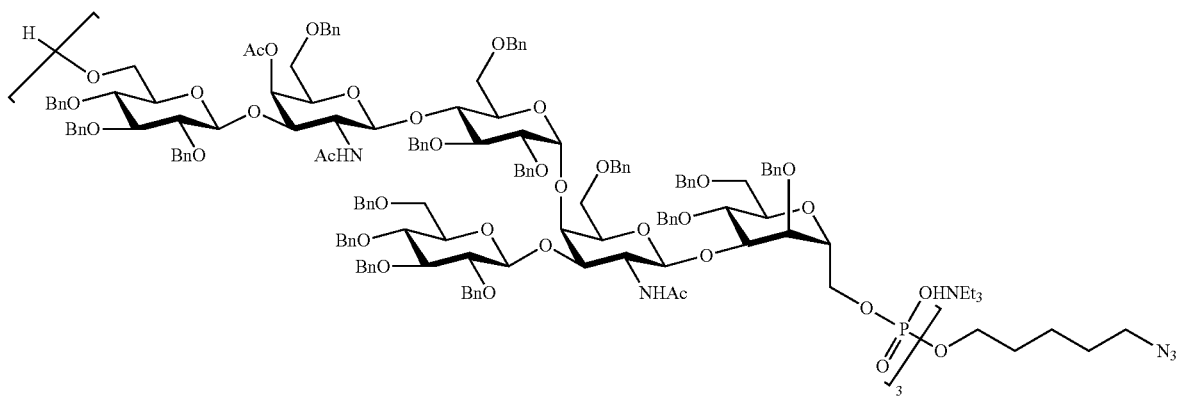
The procedure described for the synthesis of compound 60 is used for the synthesis of compound 168.
Synthesis of 169
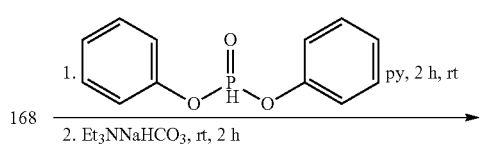

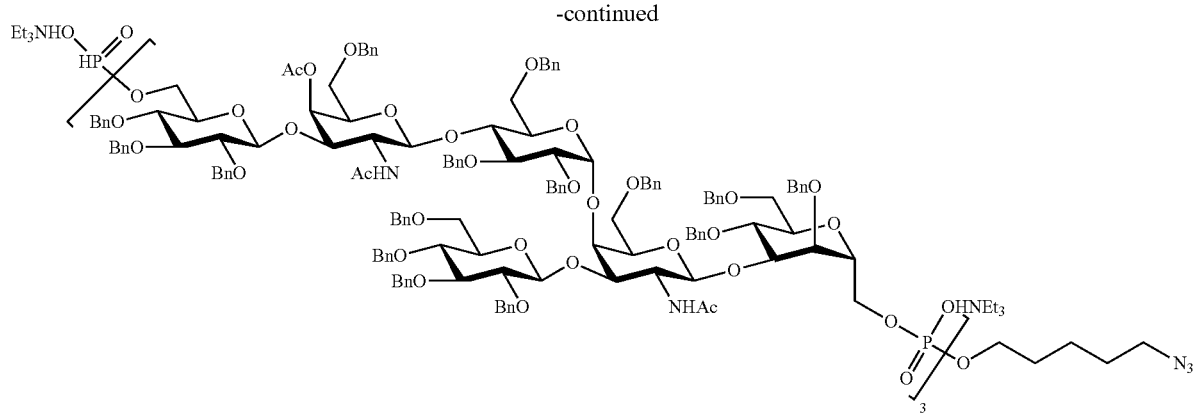
169
The procedure described for the synthesis of compound 86 is used for the synthesis of compound 169.
Synthesis of 170
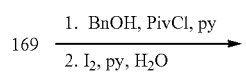
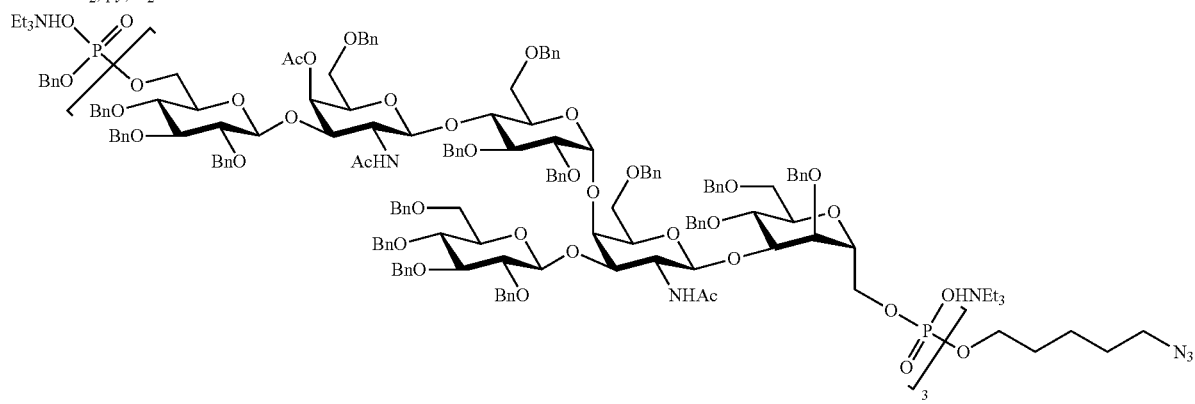
170
The procedure described for the synthesis of compound 87 is used for the synthesis of compound 170.
Synthesis of 163
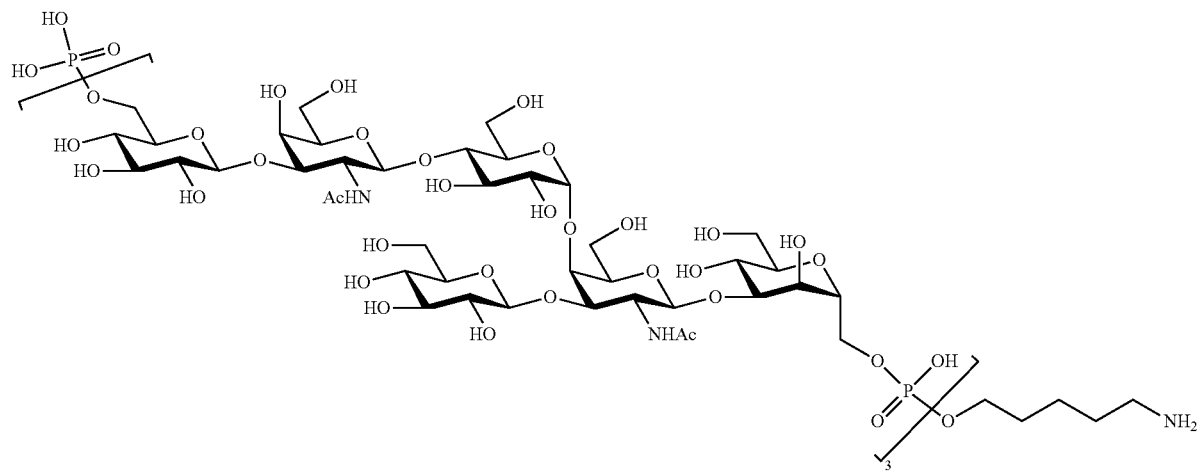
163

Compound 163 is synthesized from compound 170 as described for compound 54.

A.19 Synthesis of Tetracosasaccharides 172 and 173

Synthesis of 172

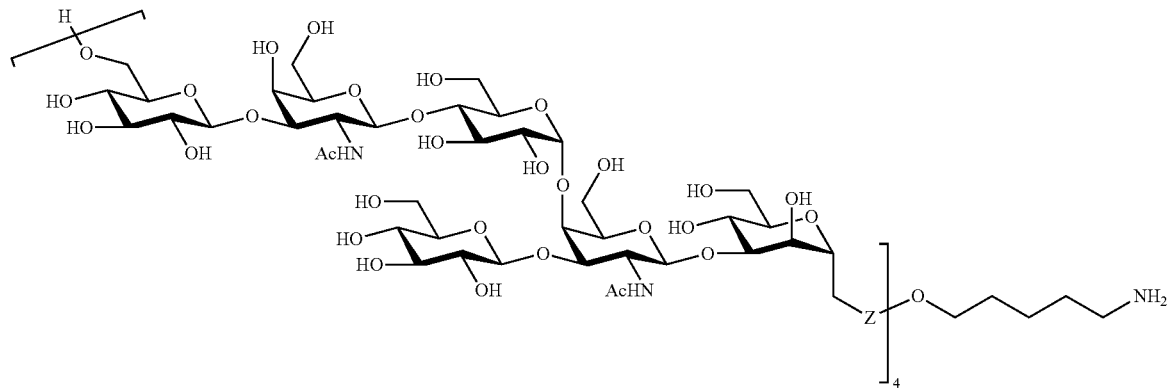

wherein Z represents

Compound 172 is synthesized from dodecasaccharide 89 which is attached to the dodecasaccharide 171

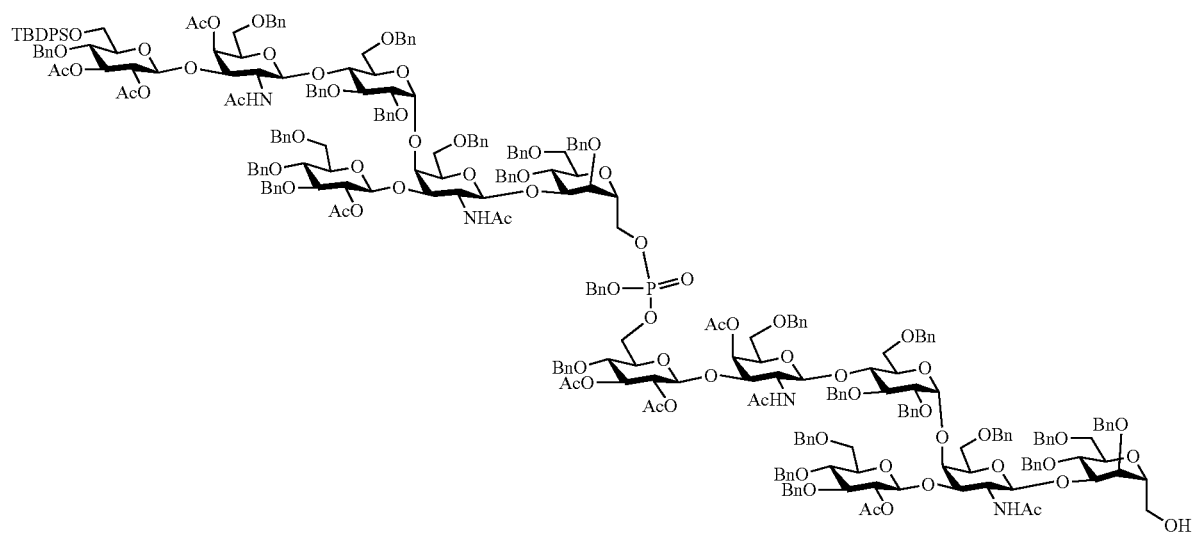

171 according to the procedure described for compound 88 following deprotection of the TBDPS group as described for compound 89 and subsequently complete deprotection as described for compound 90.

Synthesis of 173

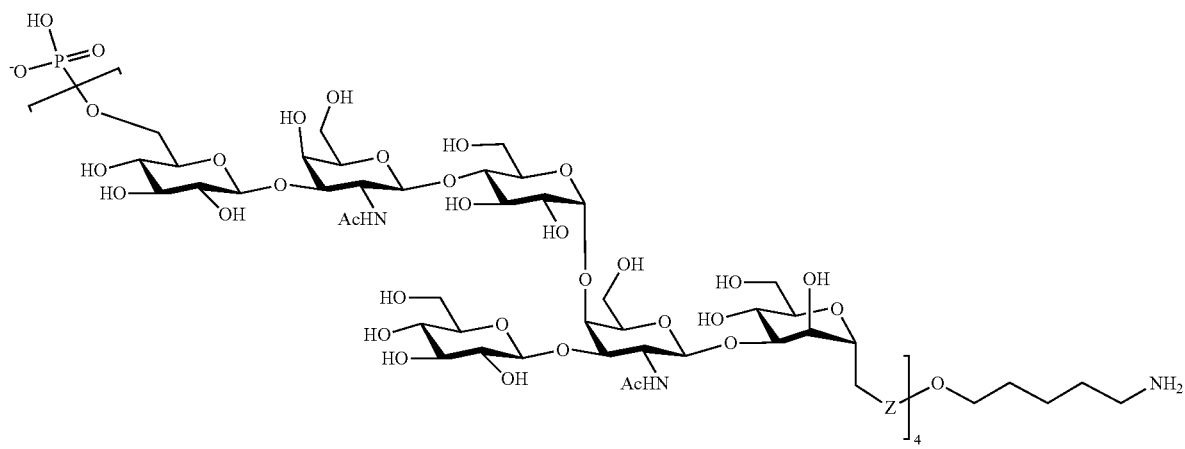

wherein Z represents

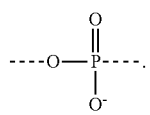

Compound 173 is synthesized from the dodecasaccharide 89 which is attached to the dodecasaccharide 171 according to the procedure described for compound 88 following deprotection of the TBDPS group as described for compound 89, phosphorylation as described for compound 91 and subsequently complete deprotection as described for compound 92.

A.20 Alternative Synthesis of Tetracosasaccharides 172 and 173

Synthesis of 174

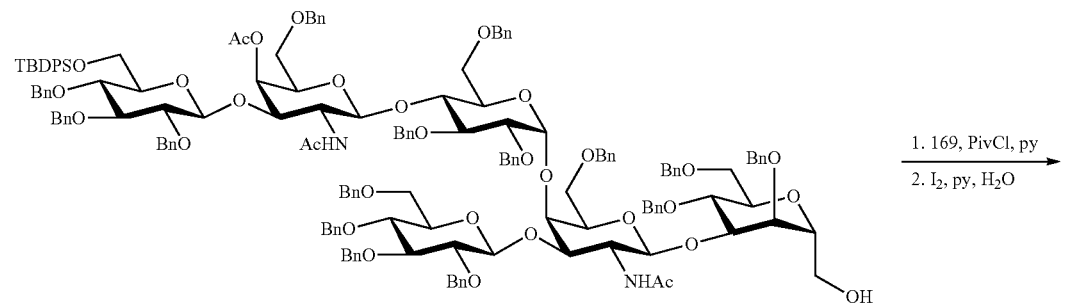

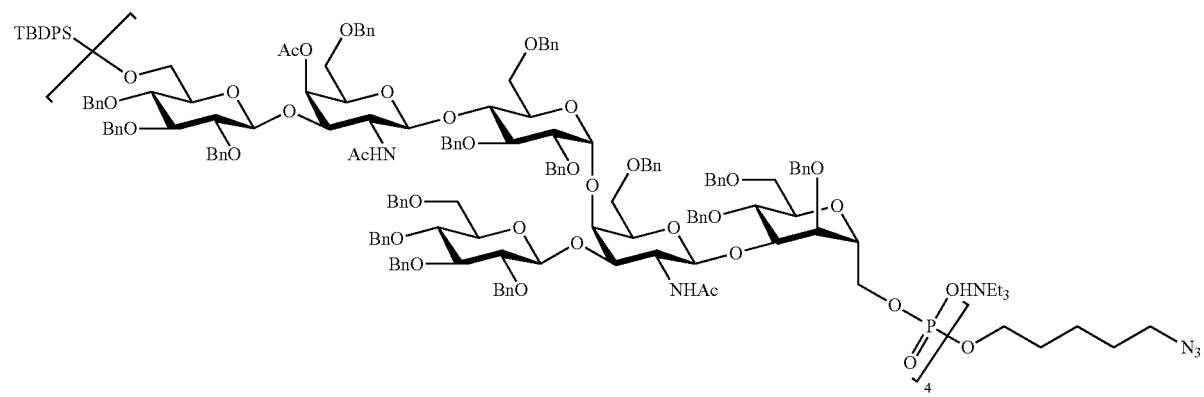

The procedure described for the synthesis of compound 96 is used for the synthesis of compound 174.
Synthesis of 172
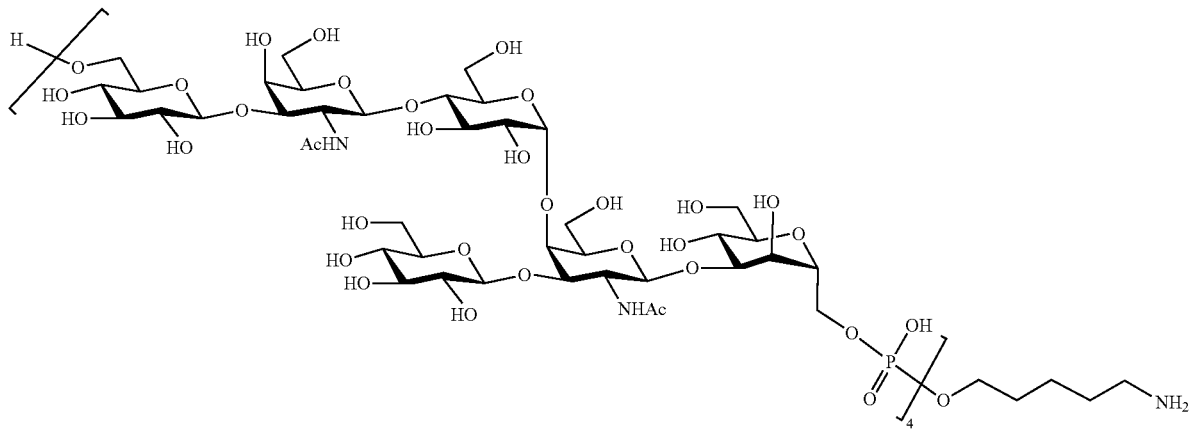
172
Compound 172 is synthesized from compound 174 as described for compound 33.
Synthesis of 175
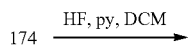
HF, py, DCM
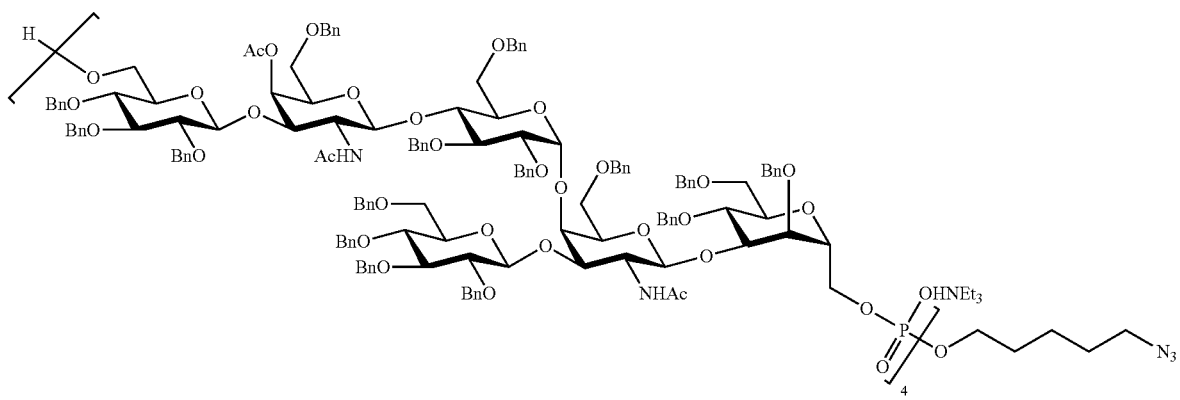
175
The procedure described for the synthesis of compound 60 is used for the synthesis of compound 175.
Synthesis of 176
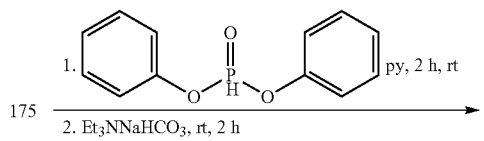

-continued
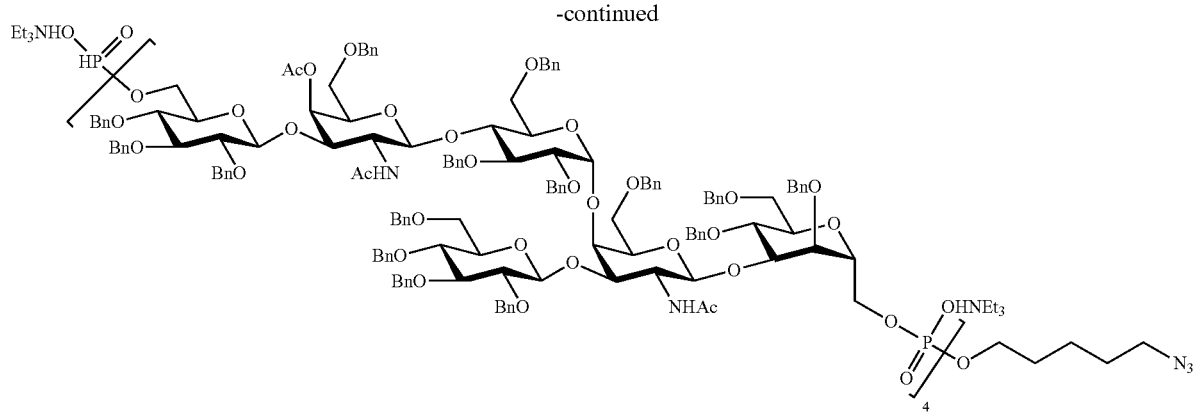
176
The procedure described for the synthesis of compound 86 is used for the synthesis of compound 176.
Synthesis of 177
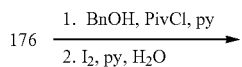
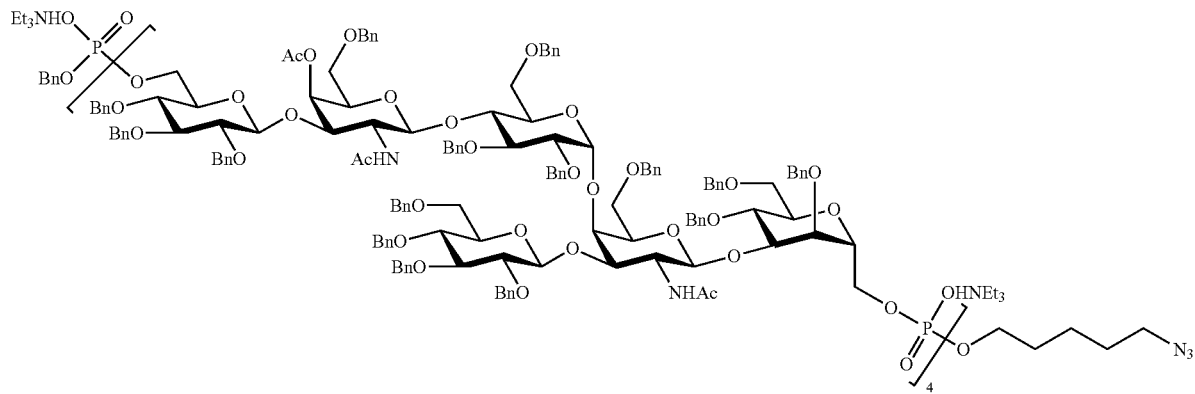
177
The procedure described for the synthesis of compound 87 is used for the synthesis of compound 177.

Synthesis of 173
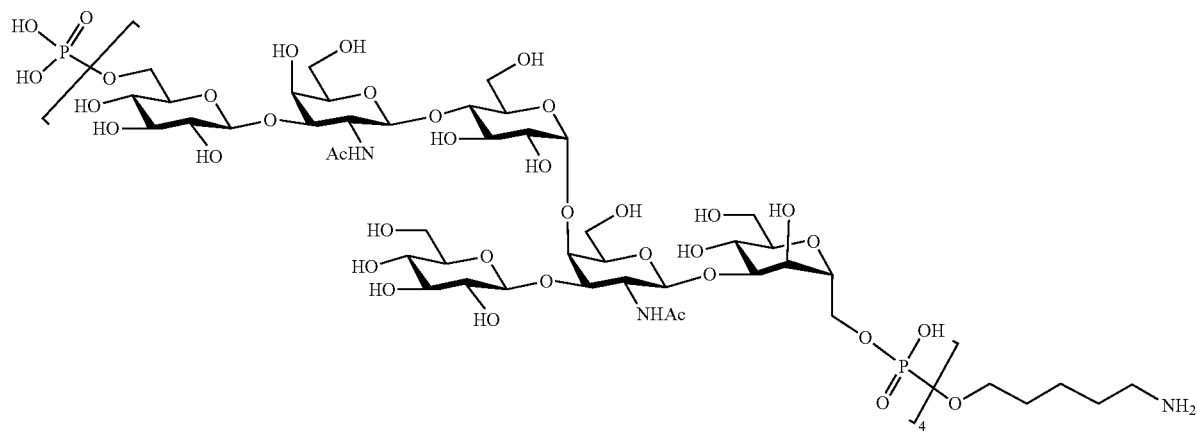
Compound 173 is synthesized from compound 177 as described for compound 54.
A.21 Synthesis of Triacontasaccharides 179 and 183
Synthesis of 178
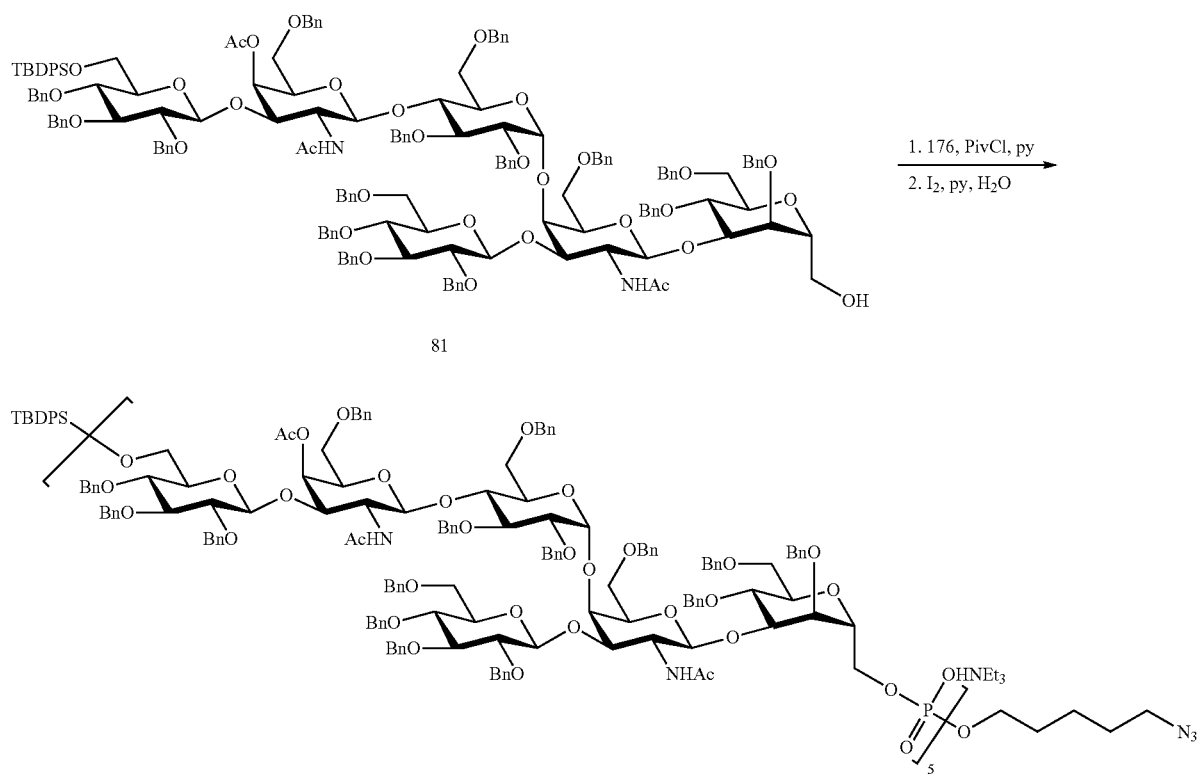
The procedure described for the synthesis of compound 96 is used for the synthesis of compound 178.

Synthesis of 179
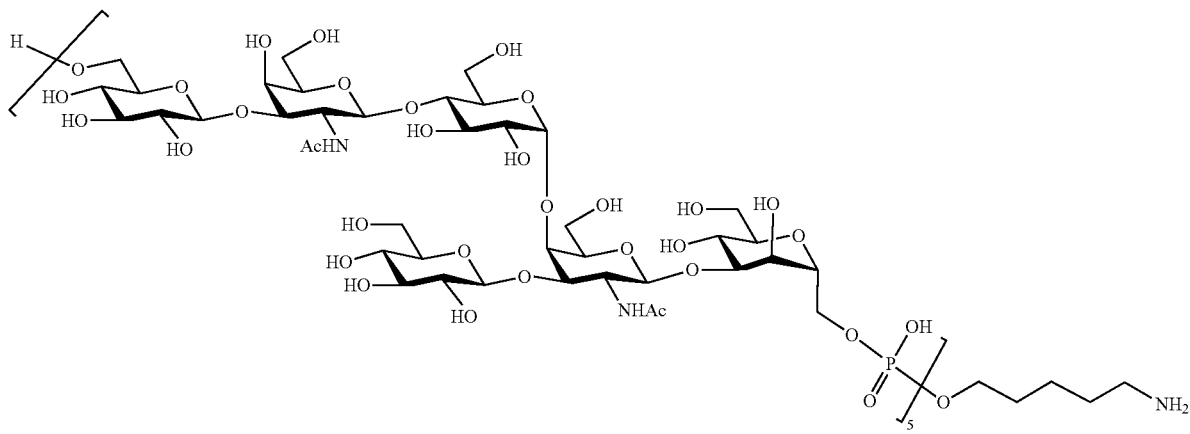
Compound 179 is synthesized from compound 178 as described for compound 33.
Synthesis of 180
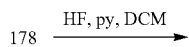
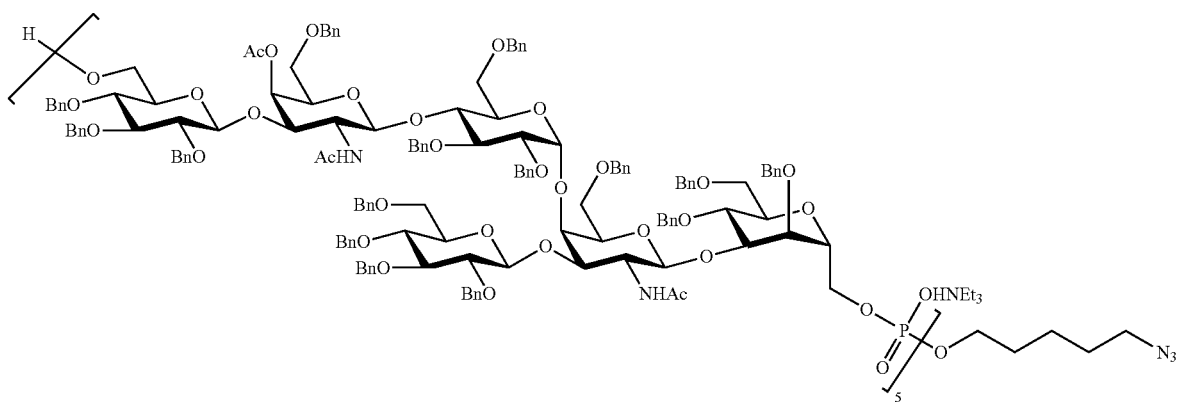
The procedure described for the synthesis of compound 60 is used for the synthesis of compound 180.
Synthesis of 181
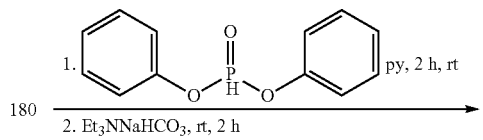

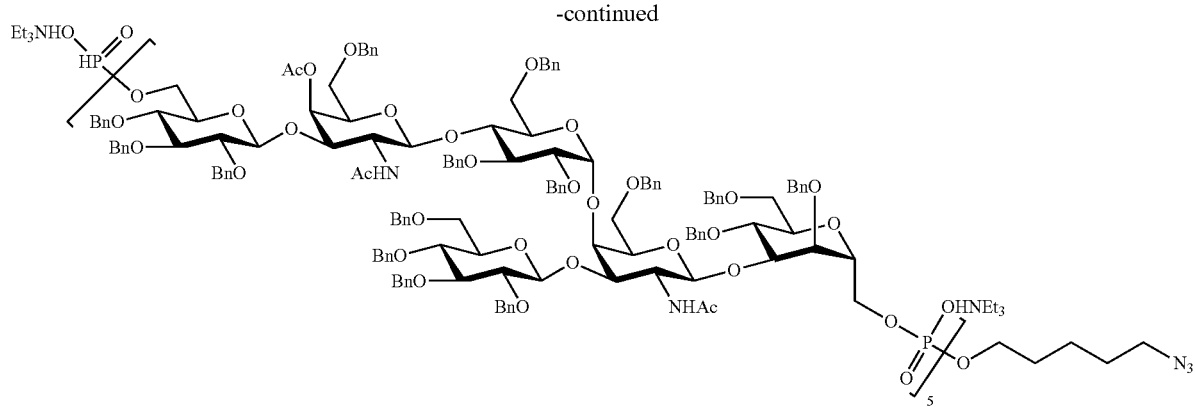
181
The procedure described for the synthesis of compound 86 is used for the synthesis of compound 181.
Synthesis of 182
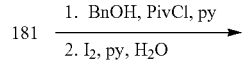
181 →
1. BnOH, PivCl, py
2. I₂, py, H₂O
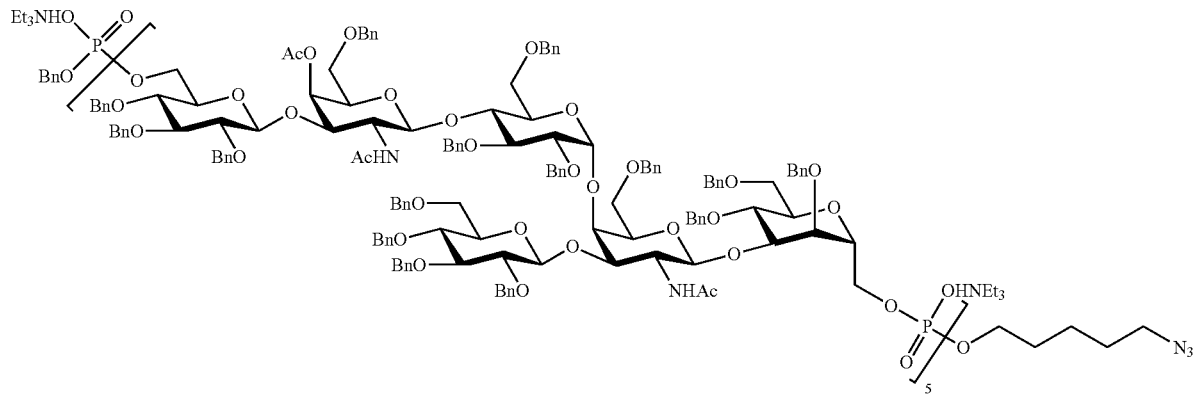
182
The procedure described for the synthesis of compound 87 is used for the synthesis of compound 182.

Synthesis of 183

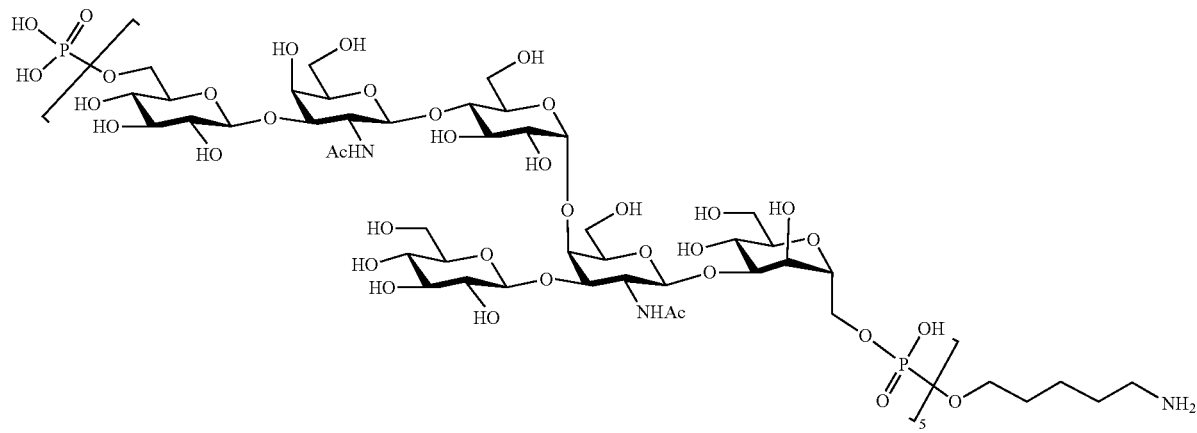

183

Compound 183 is synthesized from compound 182 as described for compound 54.

A.22 Synthesis of Hexatriacontasasaccharides 186 and 187

Synthesis of 185

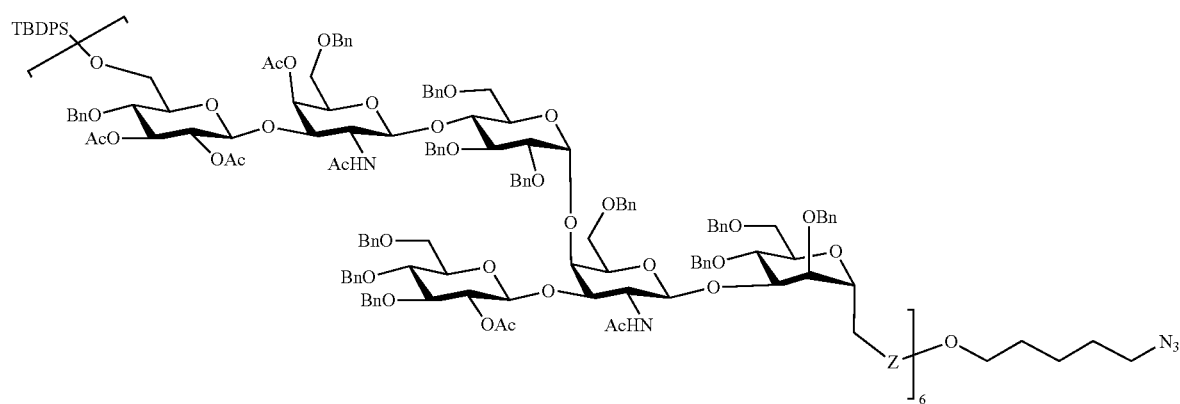

wherein Z represents

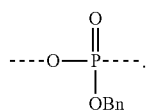

Compound 185 is synthesized from octadecasaccharide 161 from which the TBDPS protecting group is selectively removed according to the procedure described for compound 89. Thereafter the TBDPS deprotected trisaccharide is reacted with compound 184

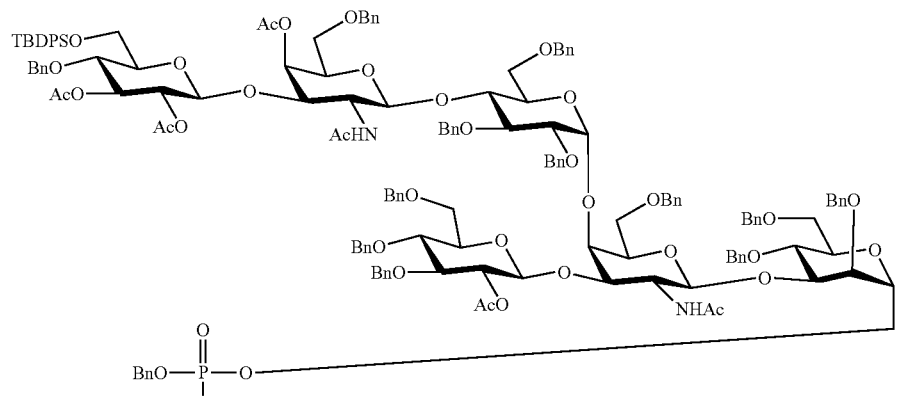
184
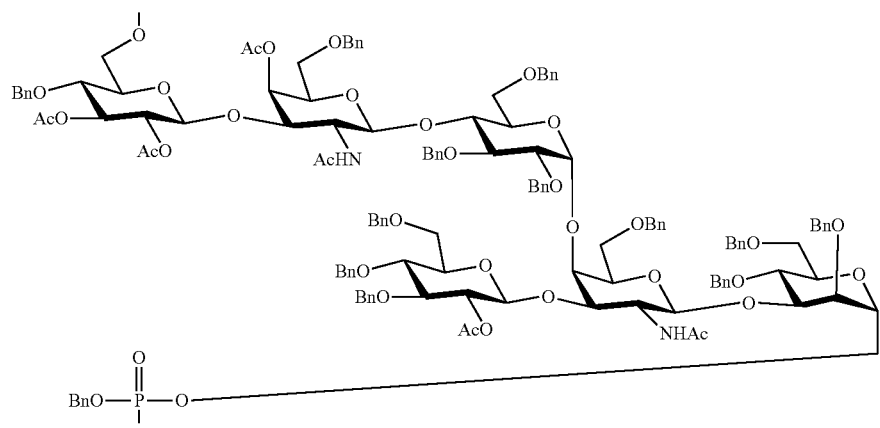
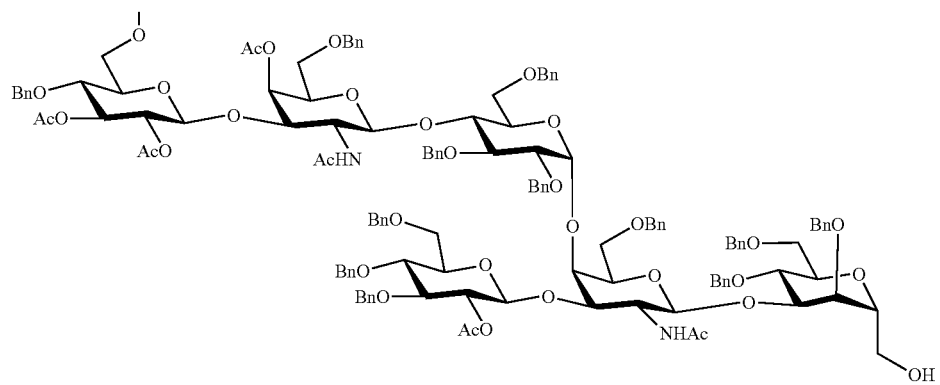
in order to obtain the saccharide 185.

Synthesis of 186

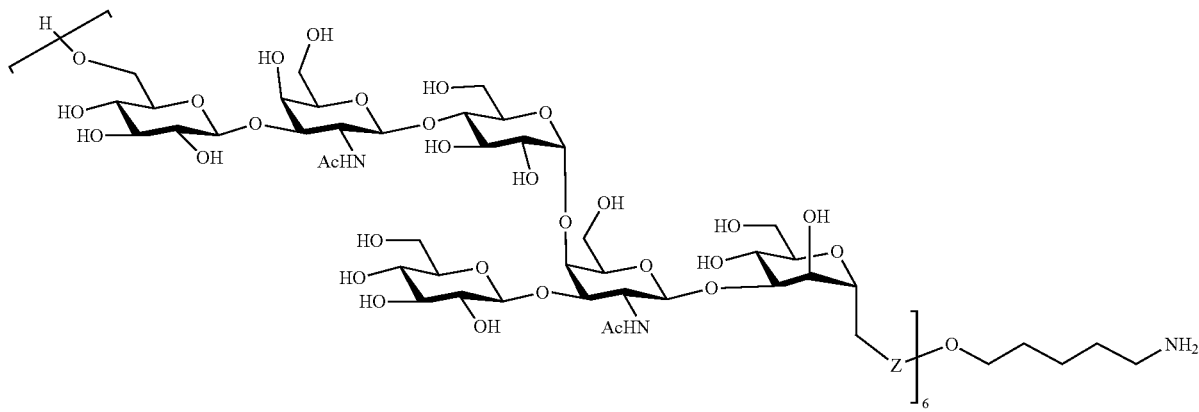

wherein Z represents

Compound 186 is synthesized from saccharide 185 which is converted according to the procedures described for compound 89 (removal of the TBDPS protecting group) and thereafter for compound 90 (removal of the TBDPS protecting group).

Synthesis of 187

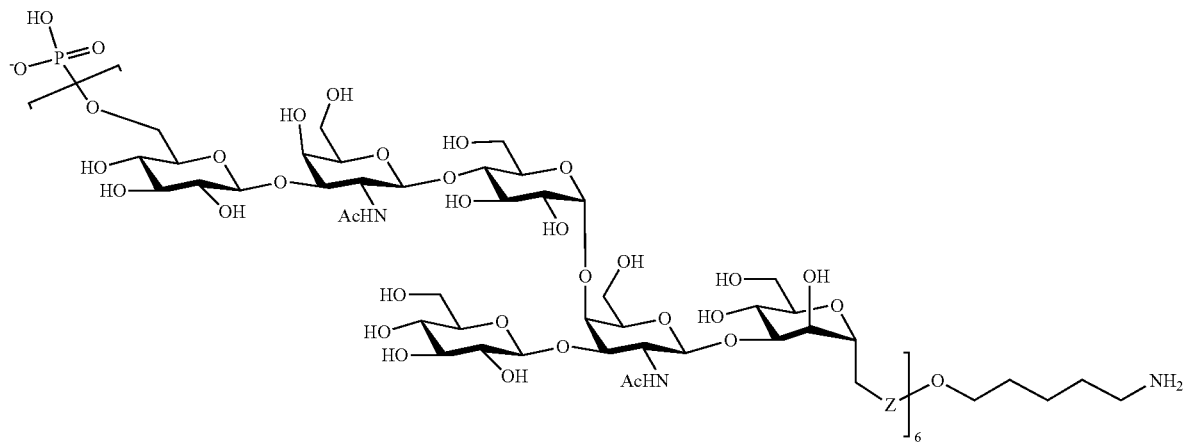

wherein Z represents

Compound 187 is synthesized from saccharide 185 which is converted according to the procedures described for compound 89 (removal of the TBDPS protecting group), phosphorylation as described for compound 91 and subsequently complete deprotection as described for compound 92.

A.23 Alternative Synthesis of Hexatriacontasasaccharides 186 and 187
Synthesis of 188
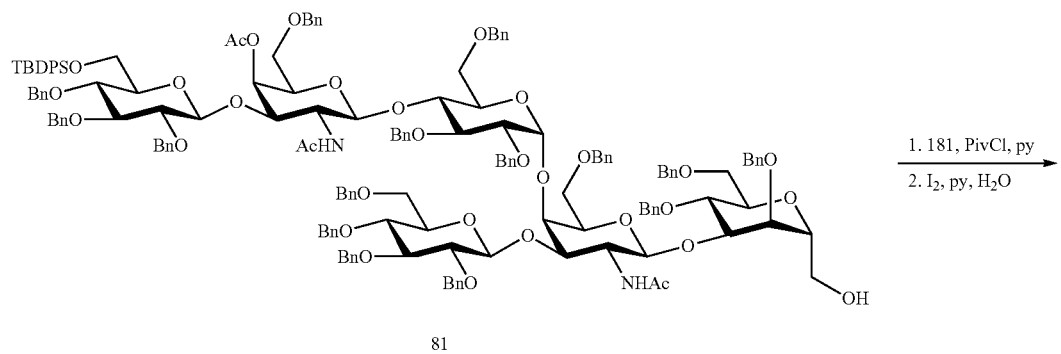
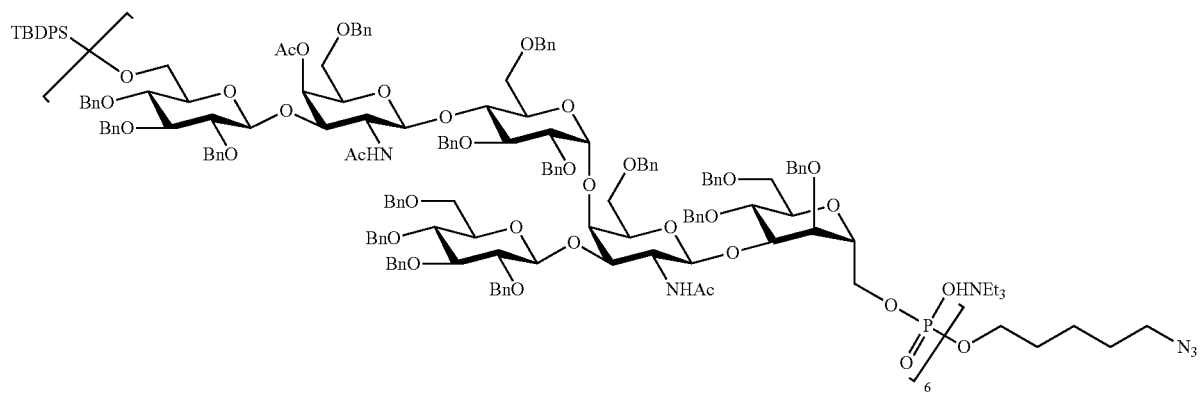
The procedure described for the synthesis of compound 96 is used for the synthesis of compound 188.
Synthesis of 186
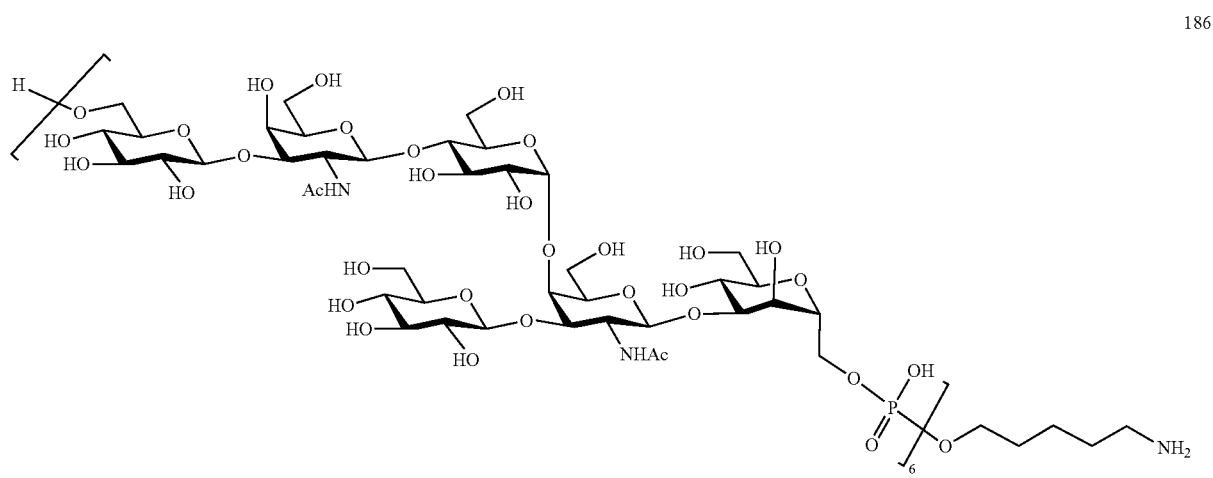
Compound 186 is synthesized from compound 188 as described for compound 33.

Synthesis of 189
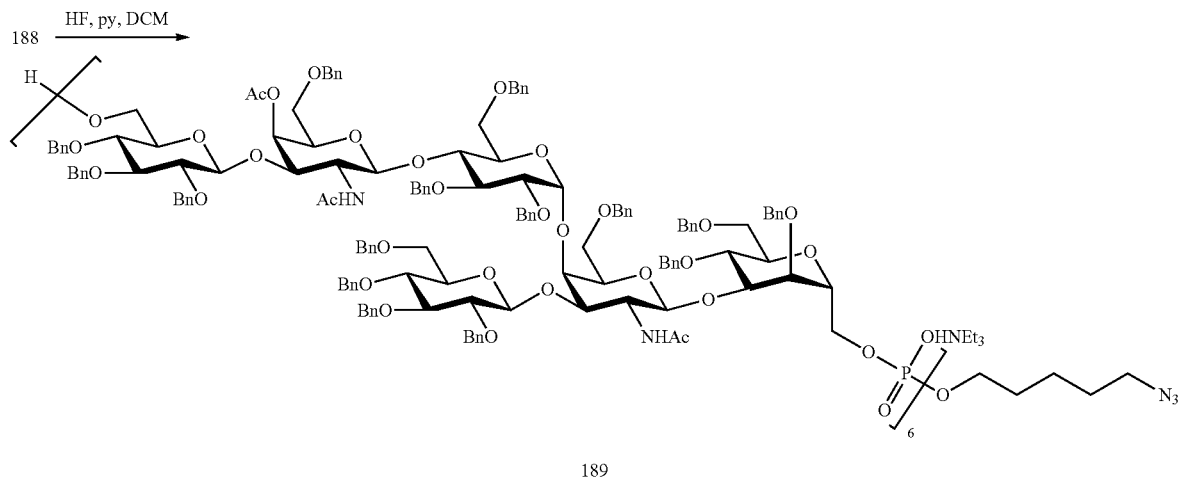
189
The procedure described for the synthesis of compound 60 is used for the synthesis of compound 189
Synthesis of 190
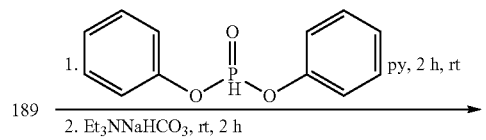
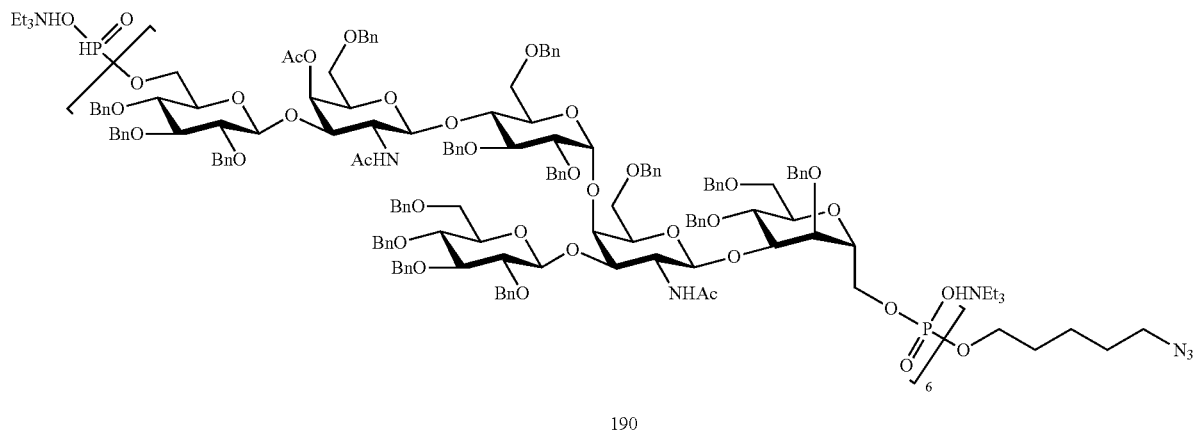
190
The procedure described for the synthesis of compound 86 is used for the synthesis of compound 190.
Synthesis of 191
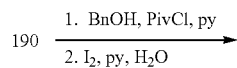

-continued
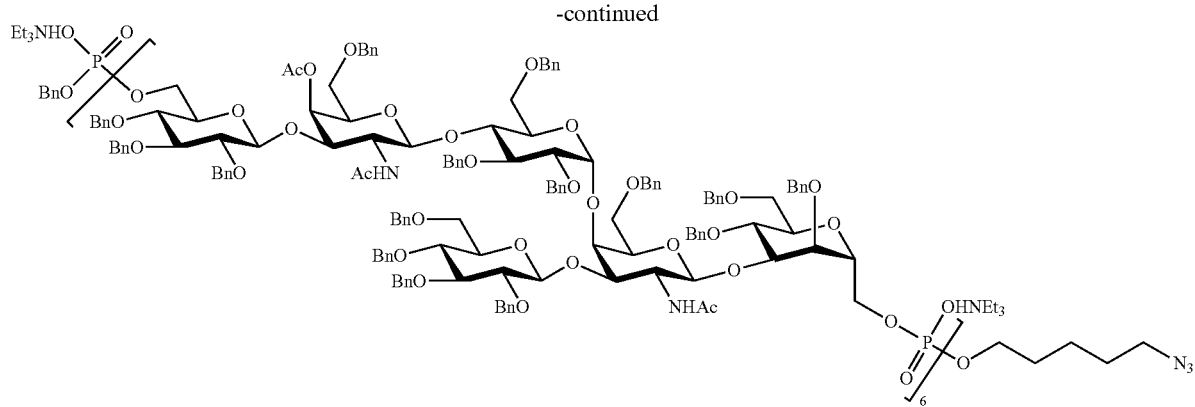
192
The procedure described for the synthesis of compound 87 is used for the synthesis of compound 191.
Synthesis of 187
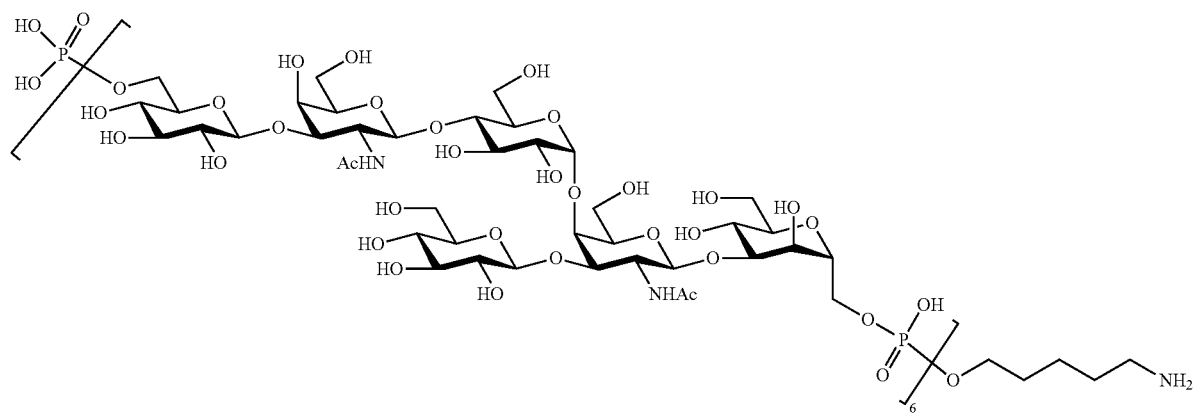
187
Compound 187 is synthesized from compound 191 as described for compound 54.
A.24 Synthesis of Oligosaccharides 193 and 197
Synthesis of 192
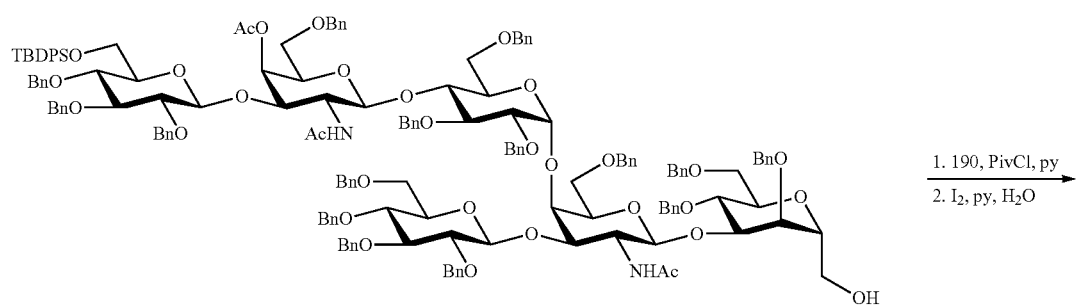
81
1. 190, PivCl, py
2. I₂, py, H₂O

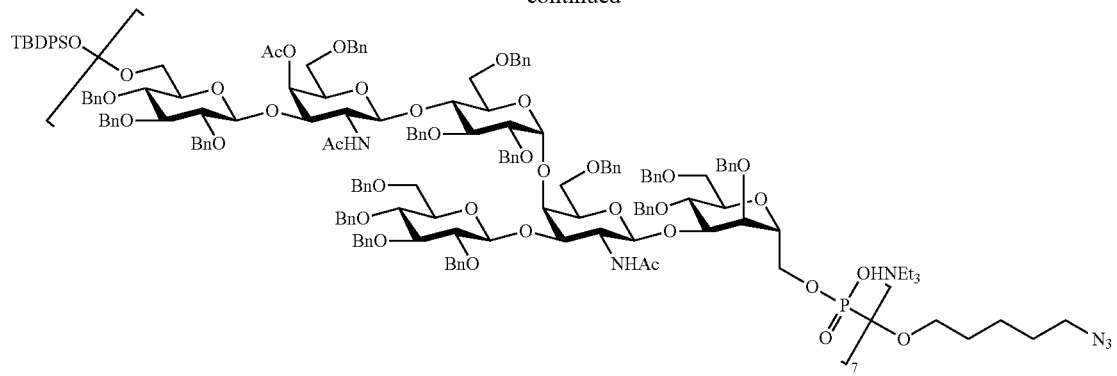
192
The procedure described for the synthesis of compound 96 is used for the synthesis of compound 192.
Synthesis of 193
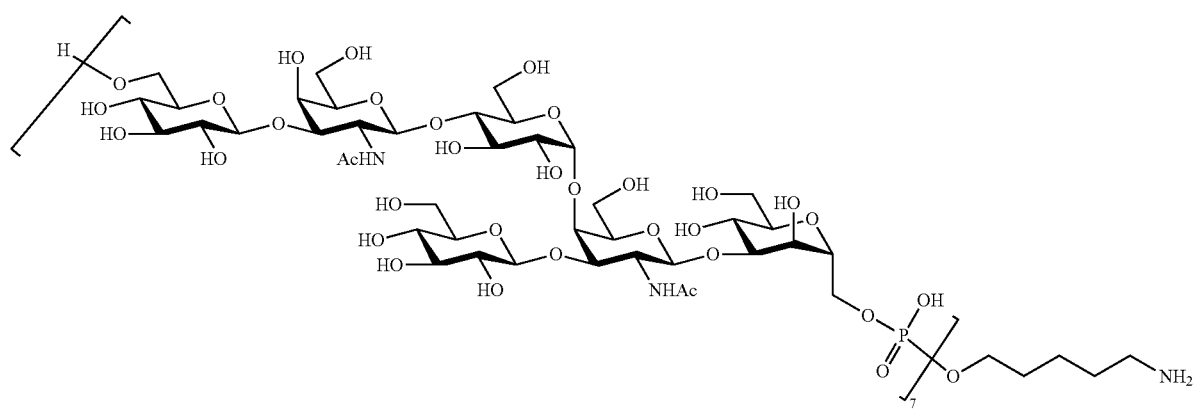
193
Compound 193 is synthesized from compound 192 as described for compound 33.
Synthesis of 194
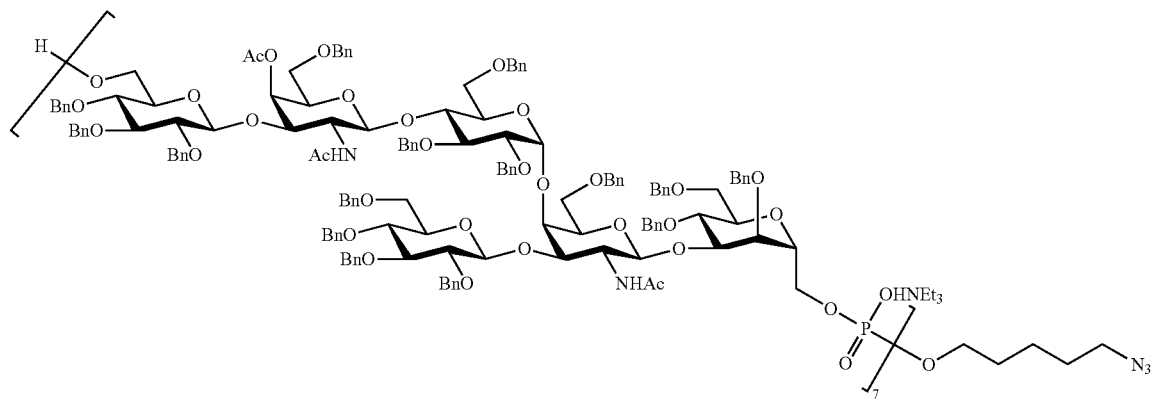
194

The procedure described for the synthesis of compound 60 is used for the synthesis of compound 194.
Synthesis of 195
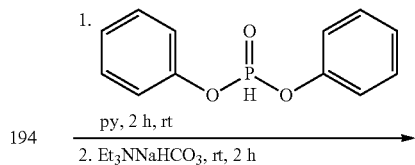
194 → 
1. (PhO)₂P(O)H, py, 2 h, rt
2. Et₃NNaHCO₃, rt, 2 h
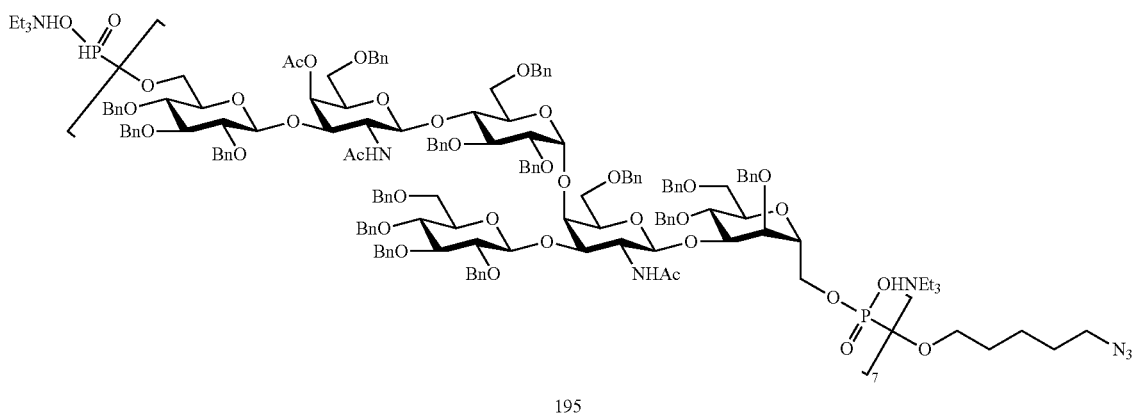
195
The procedure described for the synthesis of compound 86 is used for the synthesis of compound 195.
Synthesis of 196
195 →
1. BnOH, PivCl, py
2. I₂, py, H₂O
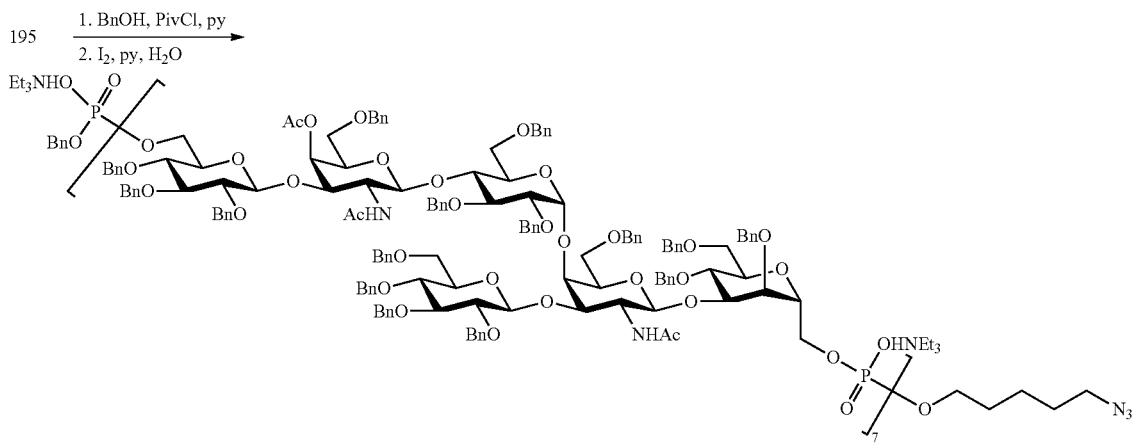
196
The procedure described for the synthesis of compound 87 is used for the synthesis of compound 196.

Synthesis of 197
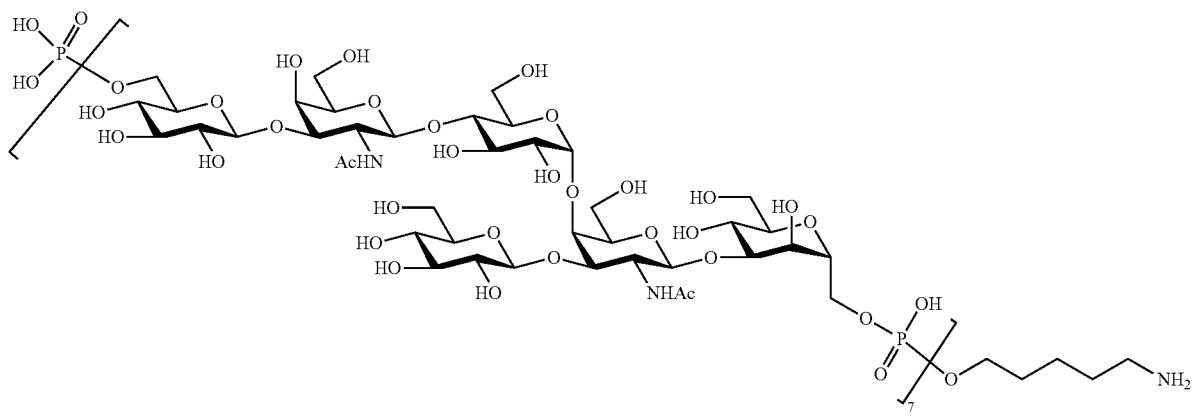
Compound 197 is synthesized from compound 196 as described for compound 54.
A.25 Synthesis of Oligosaccharides 199 and 203
Synthesis of 198
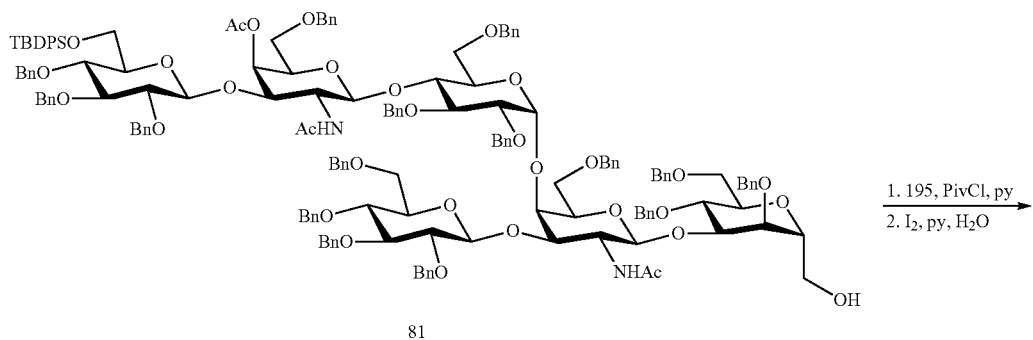
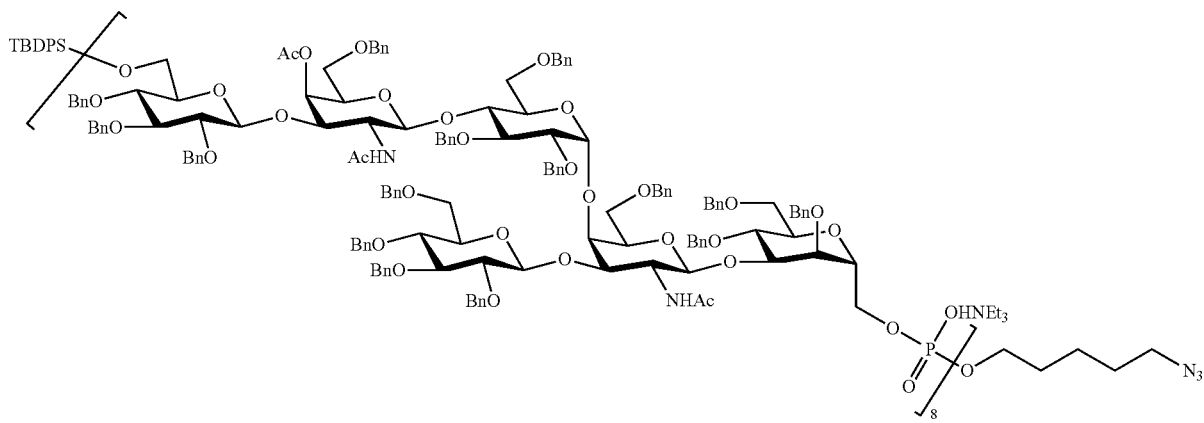
The procedure described for the synthesis of compound 96 is used for the synthesis of compound 198.

Synthesis of 199
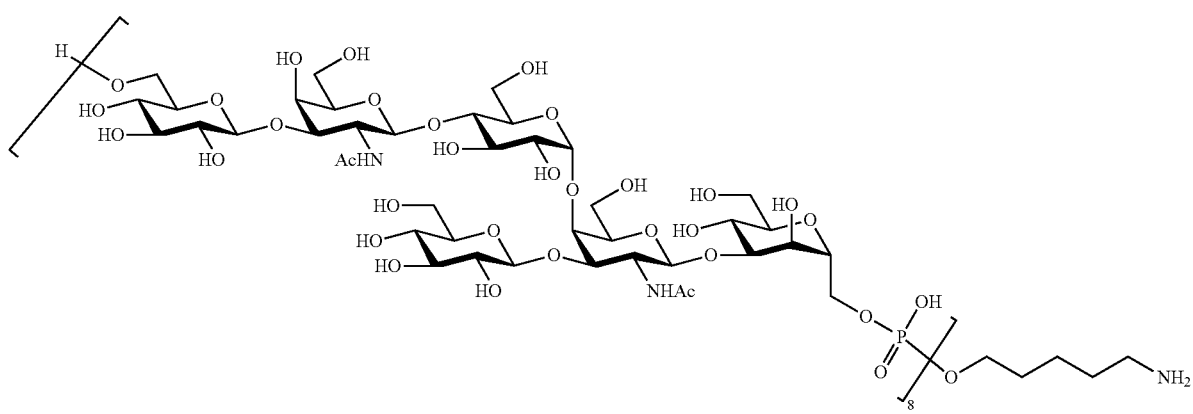
Compound 199 is synthesized from compound 198 as described for compound 33.
Synthesis of 200
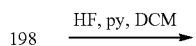
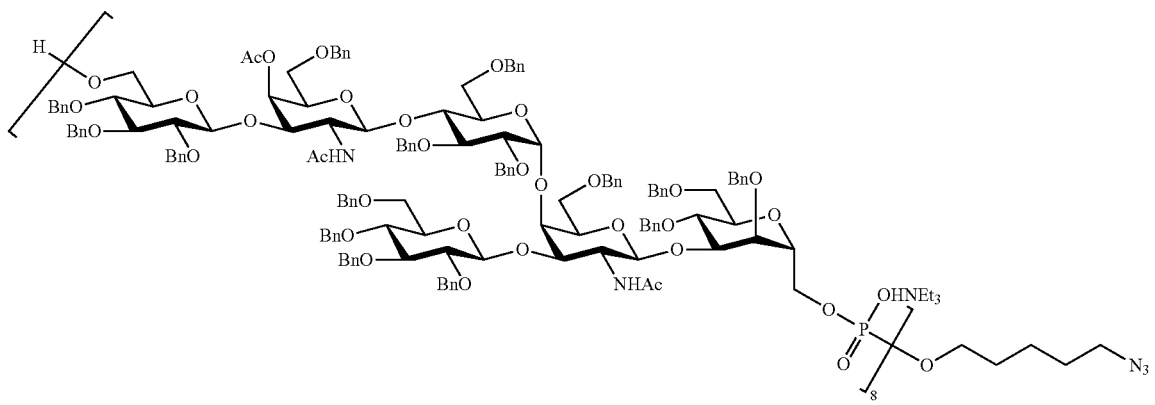
The procedure described for the synthesis of compound 60 is used for the synthesis of compound 200.
Synthesis of 201
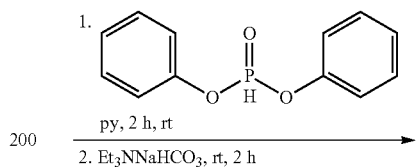

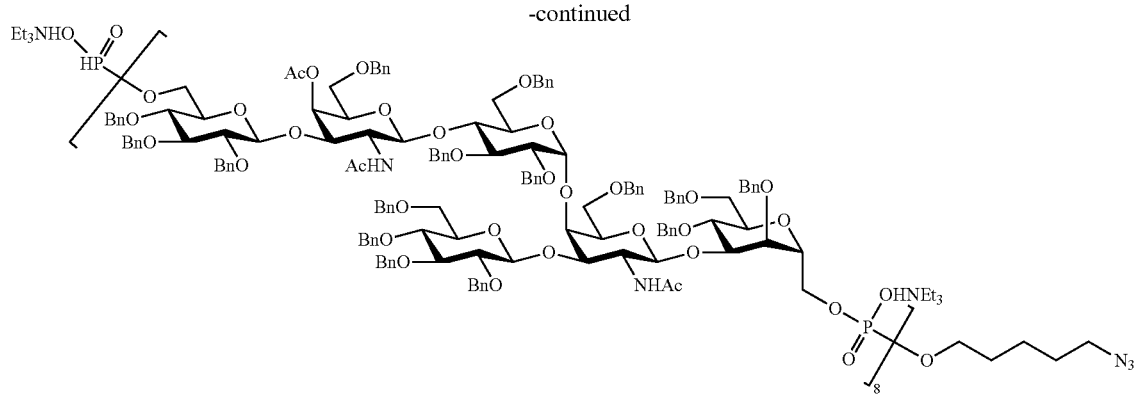
201
The procedure described for the synthesis of compound 86 is used for the synthesis of compound 201.
Synthesis of 202
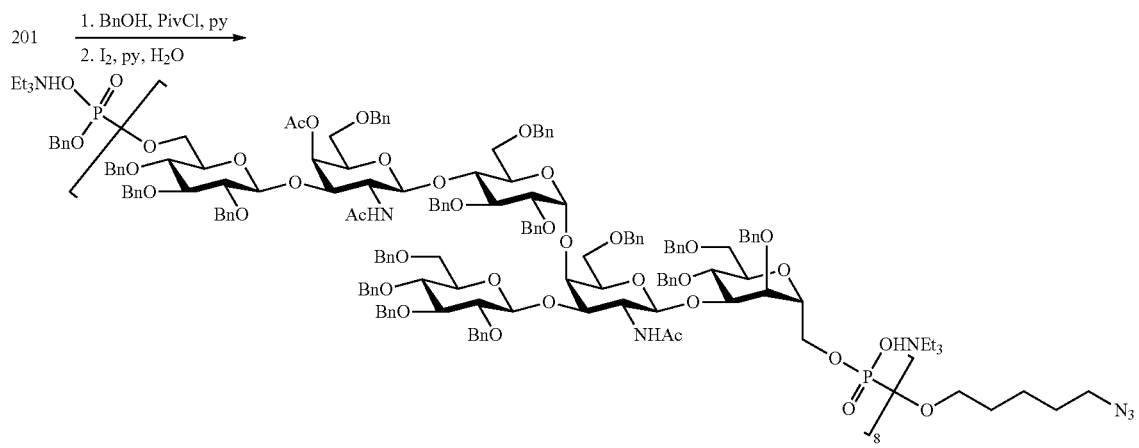
202
The procedure described for the synthesis of compound 87 is used for the synthesis of compound 202.
Synthesis of 203
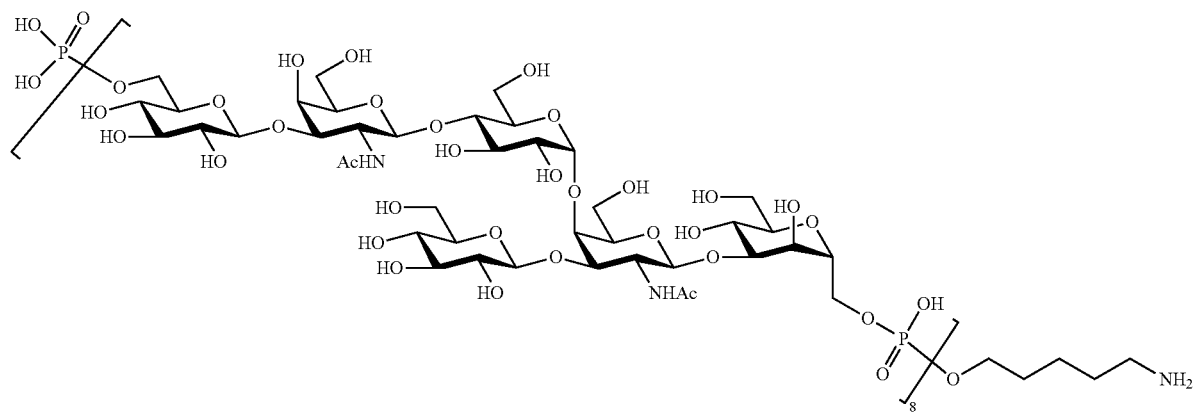
203
Compound 203 is synthesized from compound 202 as described for compound 54.

A.26 Synthesis of Oligosaccharides 205 and 209
Synthesis of 204
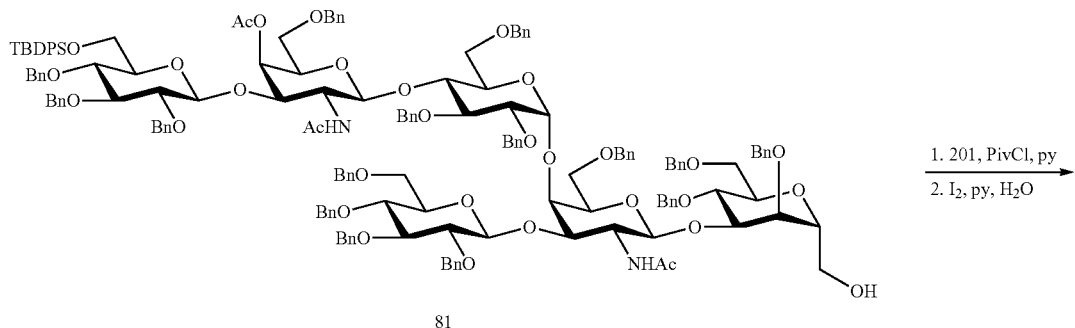
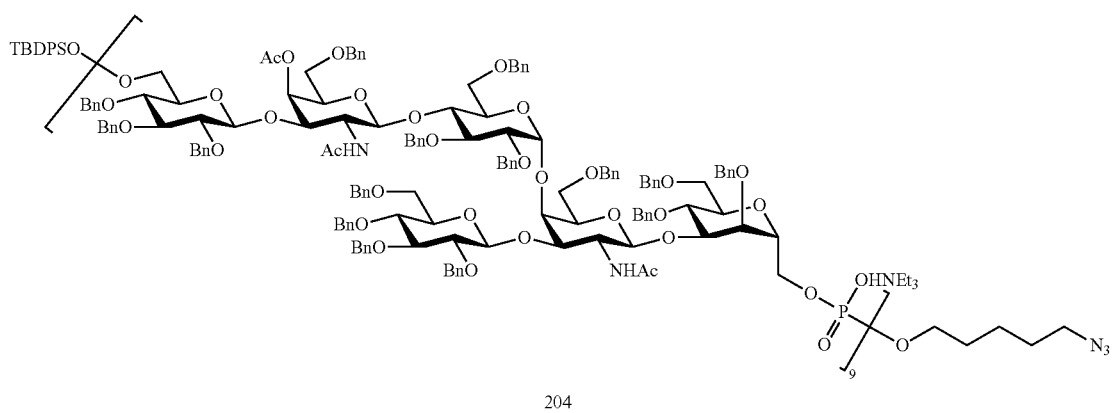
The procedure described for the synthesis of compound 96 is used for the synthesis of compound 204.
Synthesis of 205
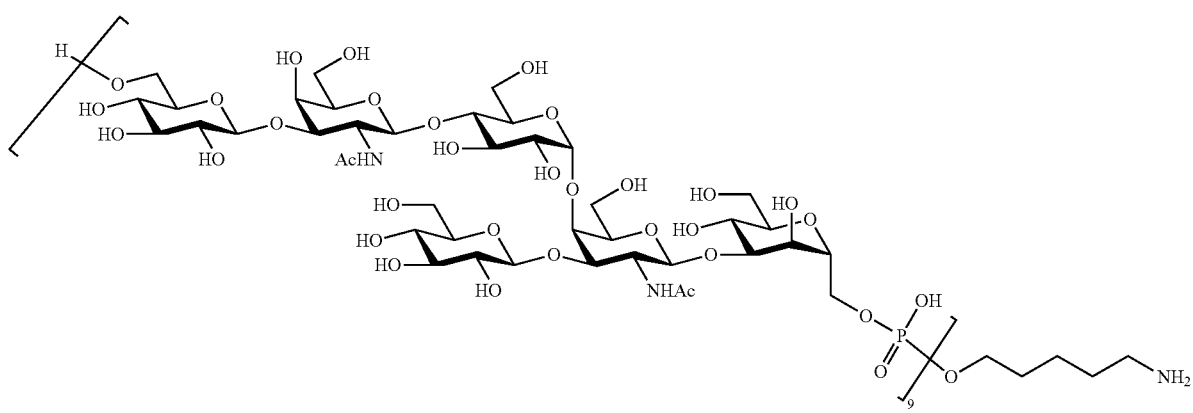
Compound 205 is synthesized from compound 204 as described for compound 33.
Synthesis of 206
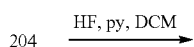

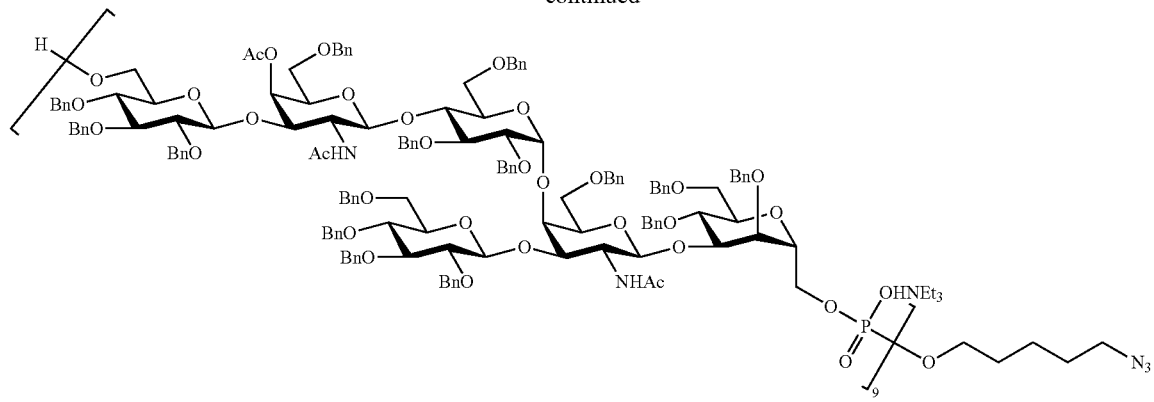
206
The procedure described for the synthesis of compound 60 is used for the synthesis of compound 206.
Synthesis of 207
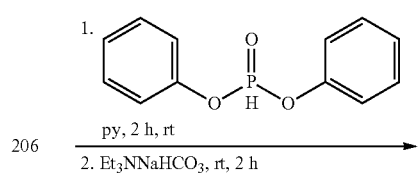
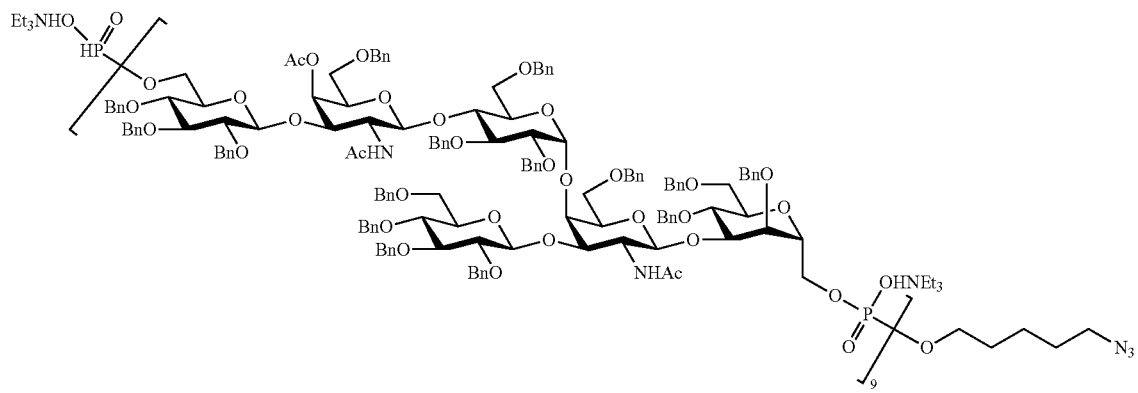
207
The procedure described for the synthesis of compound 86 is used for the synthesis of compound 207.
Synthesis of 208
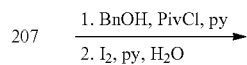

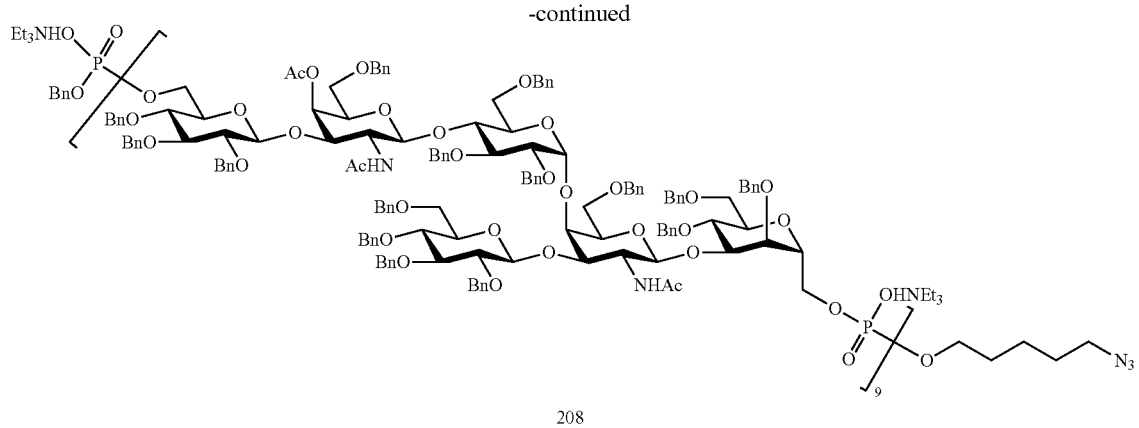
208
The procedure described for the synthesis of compound 87 is used for the synthesis of compound 208.
Synthesis of 209
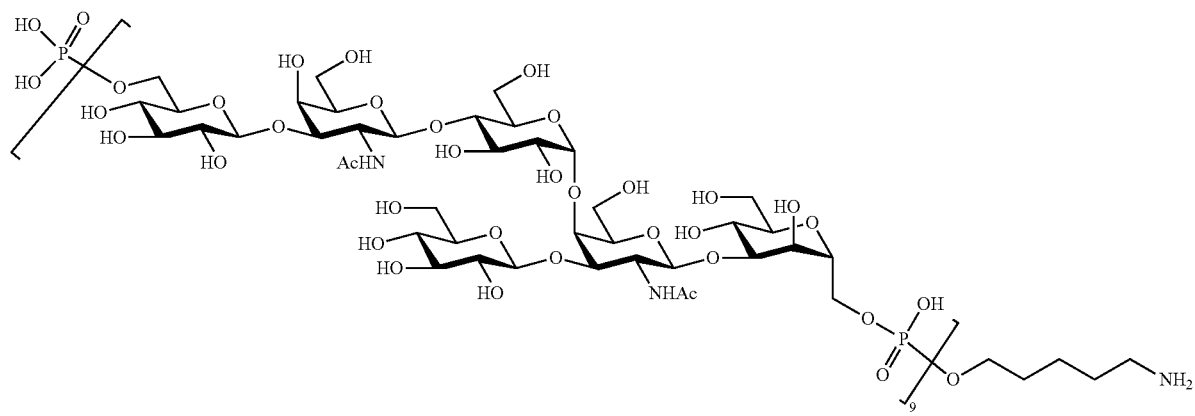
209
Compound 209 is synthesized from compound 208 as described for compound 54.
A.27 Synthesis of Oligosaccharides 211 and 215
Synthesis of 210
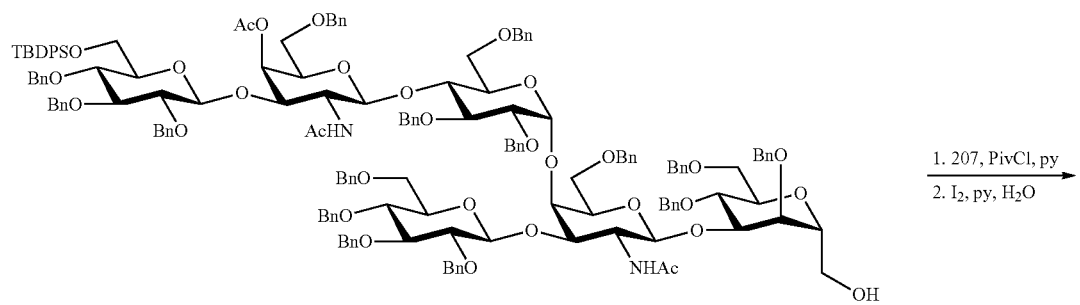
81
1. 207, PivCl, py
2. I$_2$, py, H$_2$O

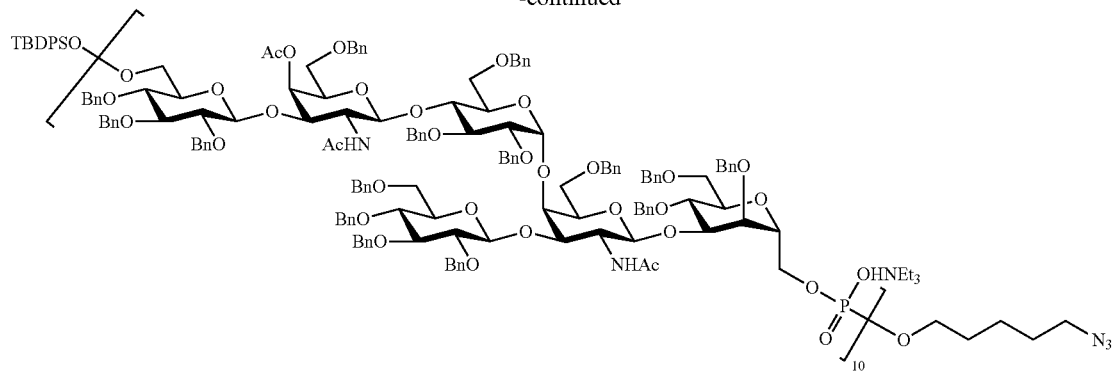
210
The procedure described for the synthesis of compound 96 is used for the synthesis of compound 210.
Synthesis of 211
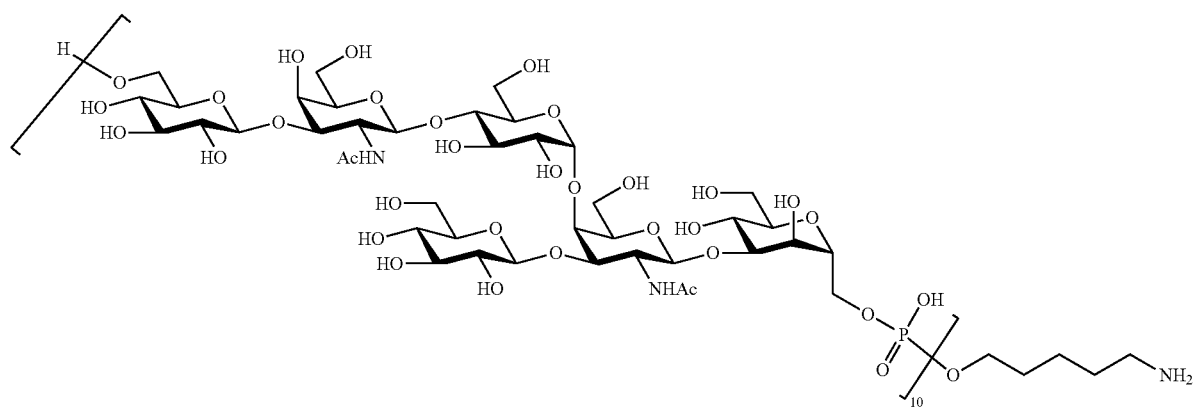
211
Compound 211 is synthesized from compound 210 as described for compound 33.
Synthesis of 212
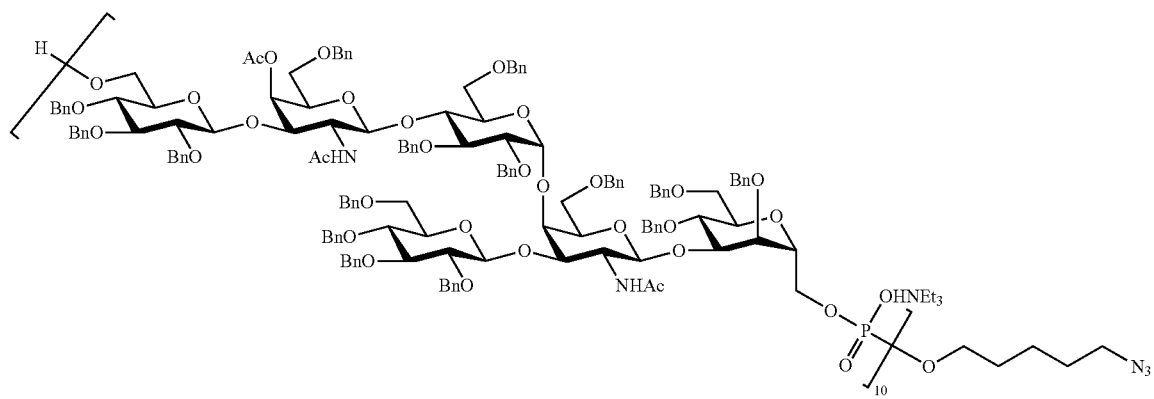
212

The procedure described for the synthesis of compound 60 is used for the synthesis of compound 212.
Synthesis of 213
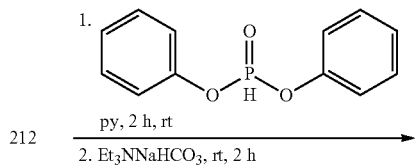
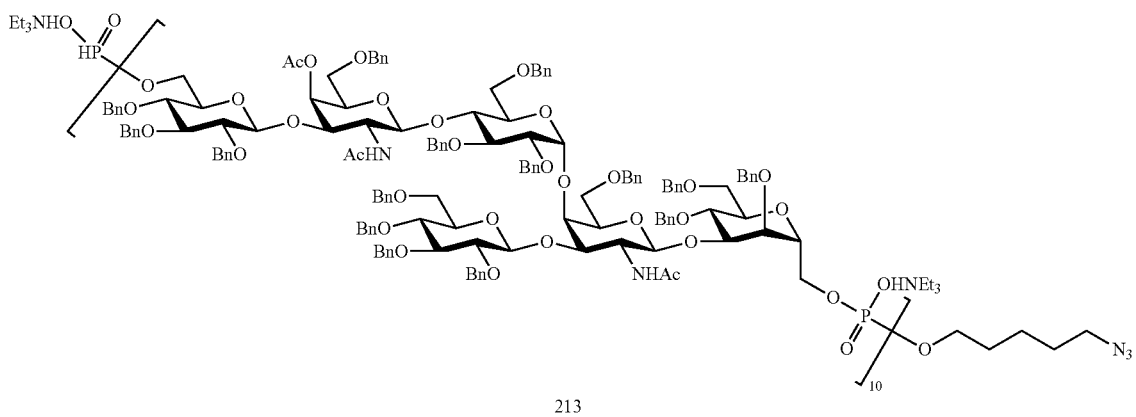
213
The procedure described for the synthesis of compound 86 is used for the synthesis of compound 213.
Synthesis of 214
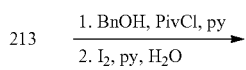
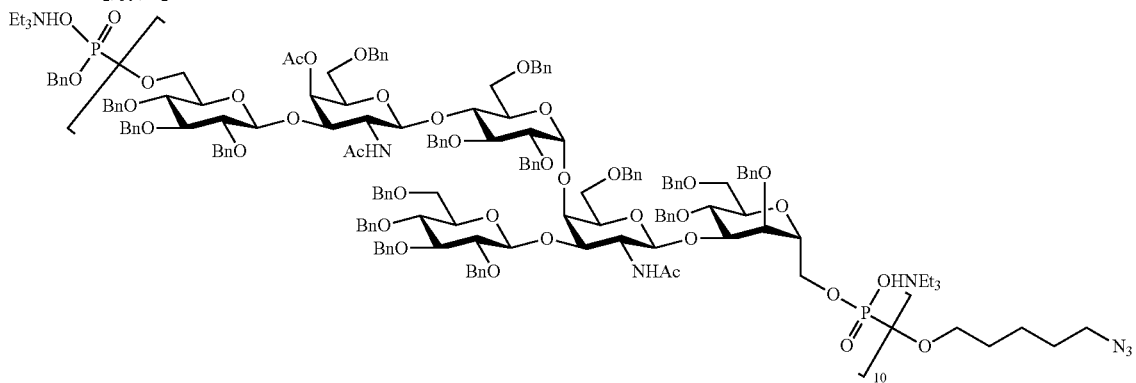
214
The procedure described for the synthesis of compound 87 is used for the synthesis of compound 214.

Synthesis of 215

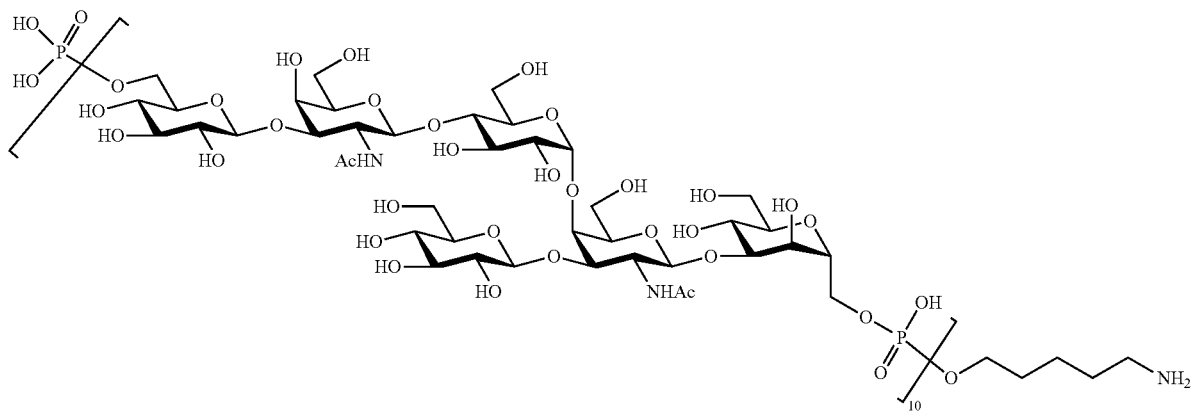

215

Compound 215 is synthesized from compound 214 as described for compound 54.

B. Stability Studies

Cleavage of the Phosphate Bond in Compound 33 with NaOH

Figure 6:
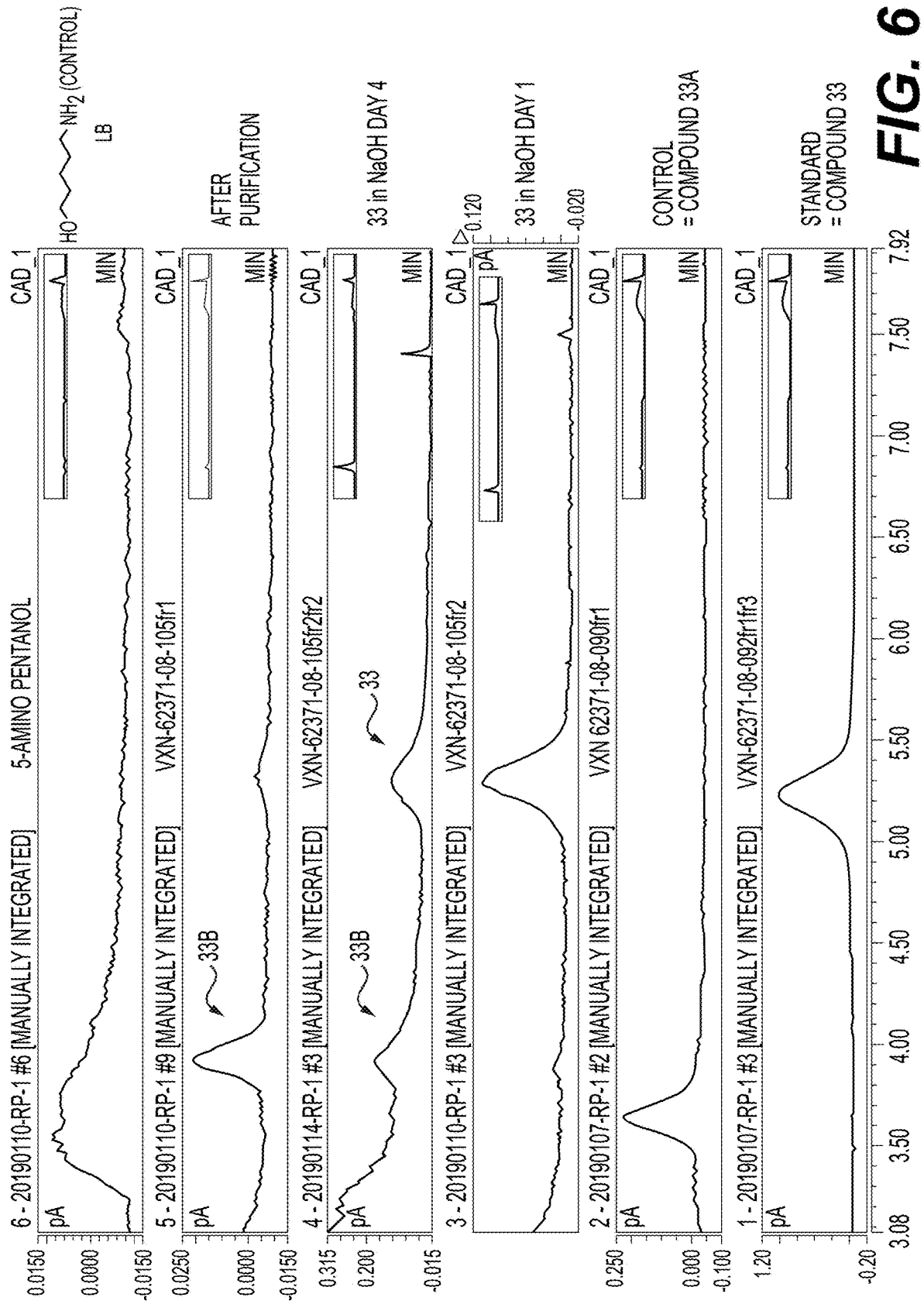
FIG. 6 shows HPLC plots from bottom to top of the following compounds: Compound 33 (standard), compound 33A (control), compound 33 after one day treatment with 0.1 M sodium hydroxide solution at room temperature and purified, compound 33 after four days treatment with 0.1 M sodium hydroxide solution at room temperature, purified compound 33B, compound LB. It is evident from FIG. 7 that compound 33 is fully stable under basic conditions for one day. After four days of treatment with NaOH at rt still 50% of compound 33 remains intact.
Figure 7:
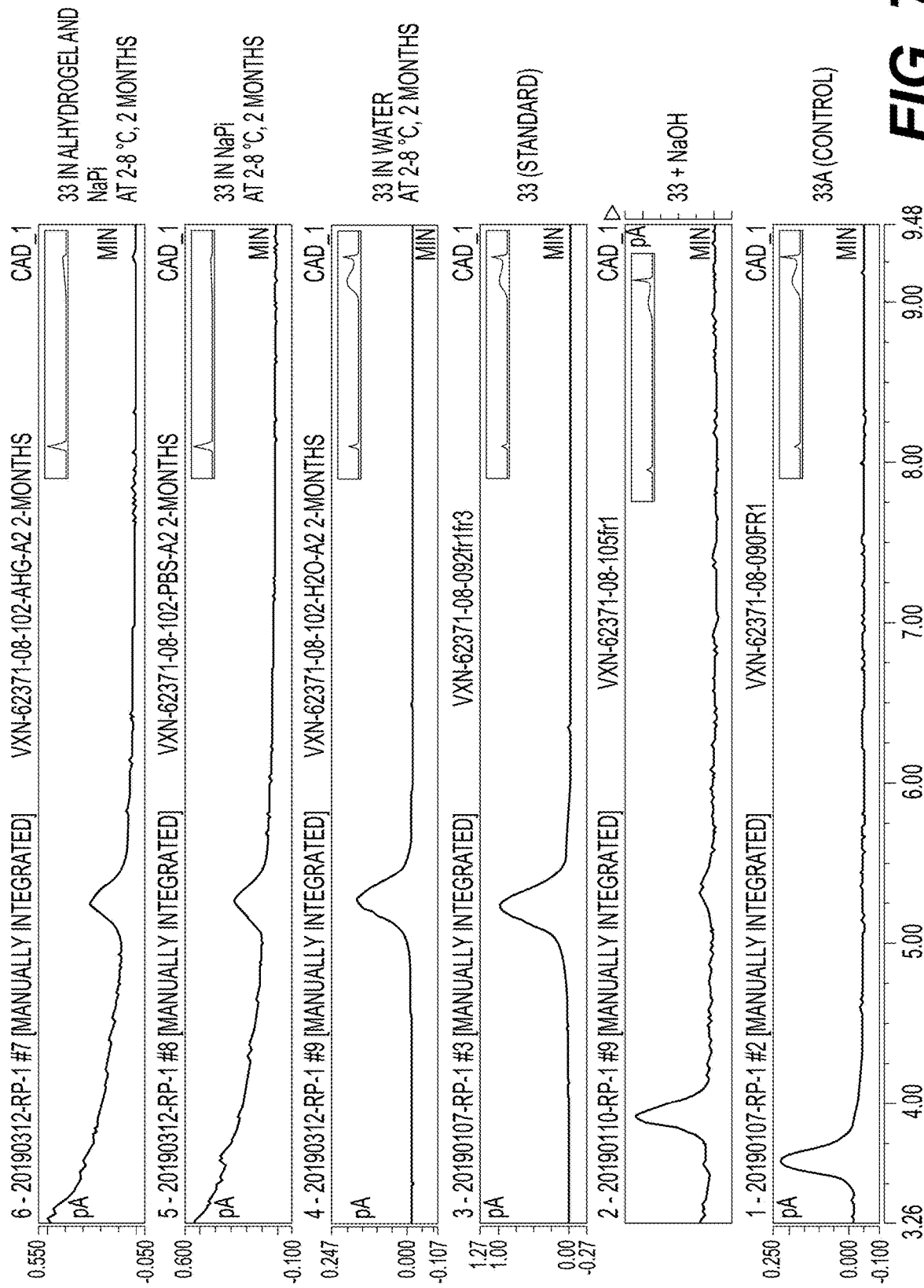
FIG. 7 shows HPLC plots from bottom to top of the following compounds: compound 33A (control), compound 33 after one day treatment with 0.1 M sodium hydroxide solution at room temperature and purified, compound 33 (standard), compound 33 after two months at 2° C.-8° C. in water, compound 33 after two months at 2° C.-8° C. in NaPi which is a synonym for PBS (phosphate-buffered saline), compound 33 after two months at 2° C.-8° C. in Alhydrogel and PBS. It is evident from FIG. 7 that compound 33 is fully stable at 2° C. to 8° C. over two months.

Next the stability of the compounds of the present invention was tested and assessed. The task was to find out how stable are compounds 33, 54, 90, 92, 112, 117, 162, 163, 164, 165, 172, and 173 under formulation conditions. Prior to the stability in Alhydrogel, PBS buffer and water, the compound 33 was treated with 0.1 M sodium hydroxide at room temperature. Here it was found that compound 33 is cleaving very slowly only under highly basic conditions. However, even after 4 days (10 μg of 33 in 200 μL) under these drastic conditions, only 50% of compound 33 was cleaved and still 50% of compound 33 was observed being intact in HPLC chromatogram (FIGS. 6 and 7).

Figure 8:
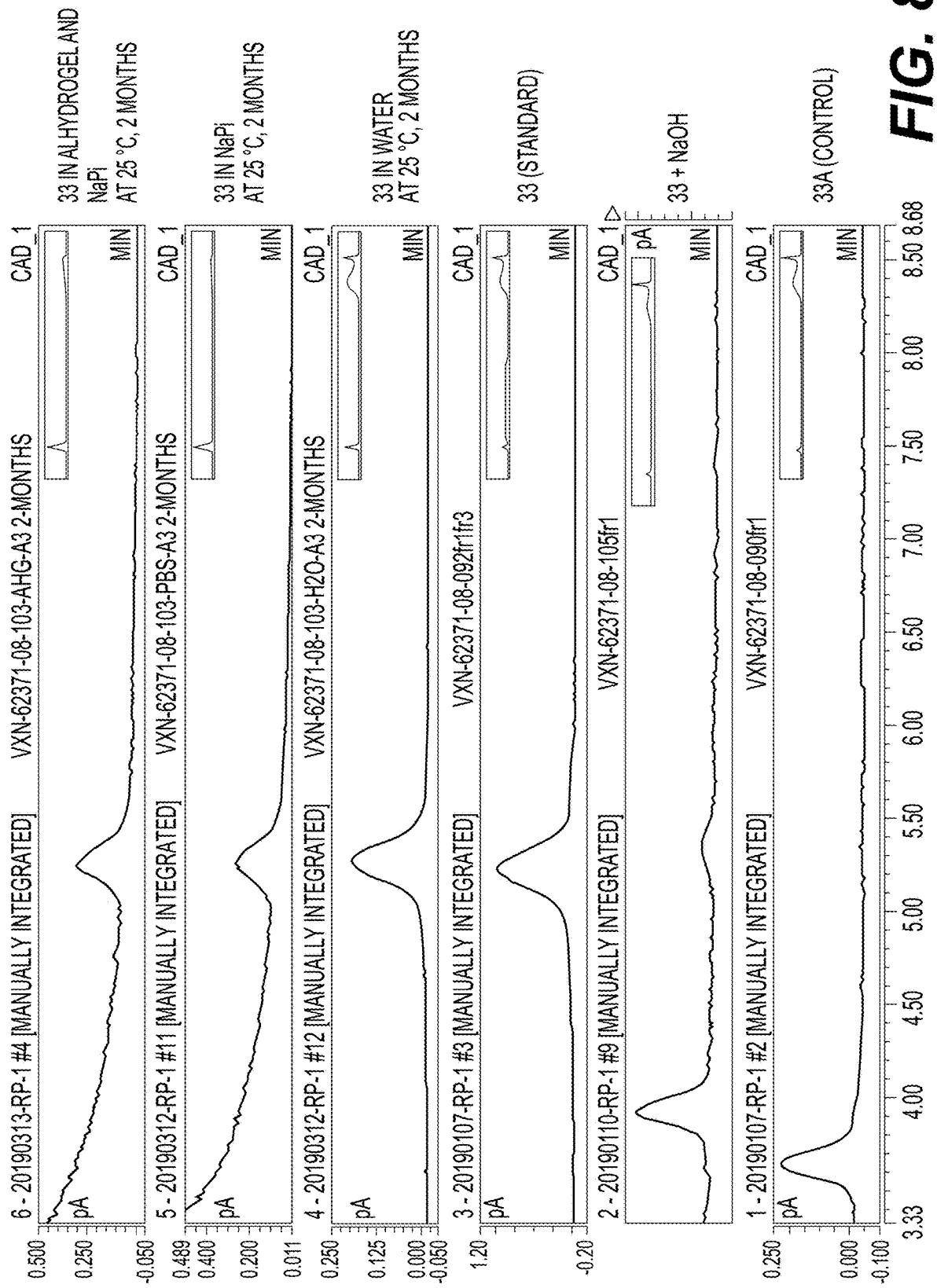
FIG. 8 shows HPLC plots from bottom to top of the following compounds: compound 33A (control), compound 33 after one day treatment with 0.1 M sodium hydroxide solution at room temperature and purified, compound 33 (standard), compound 33 after two months at 25° C. in water, compound 33 after two months at 25° C. in NaPi which is a synonym for PBS (phosphate-buffered saline), compound 33 after two months at 25° C. in Alhydrogel and PBS. It is evident from FIG. 8 that compound 33 is fully stable at 25° C. over two months.
Figure 9:
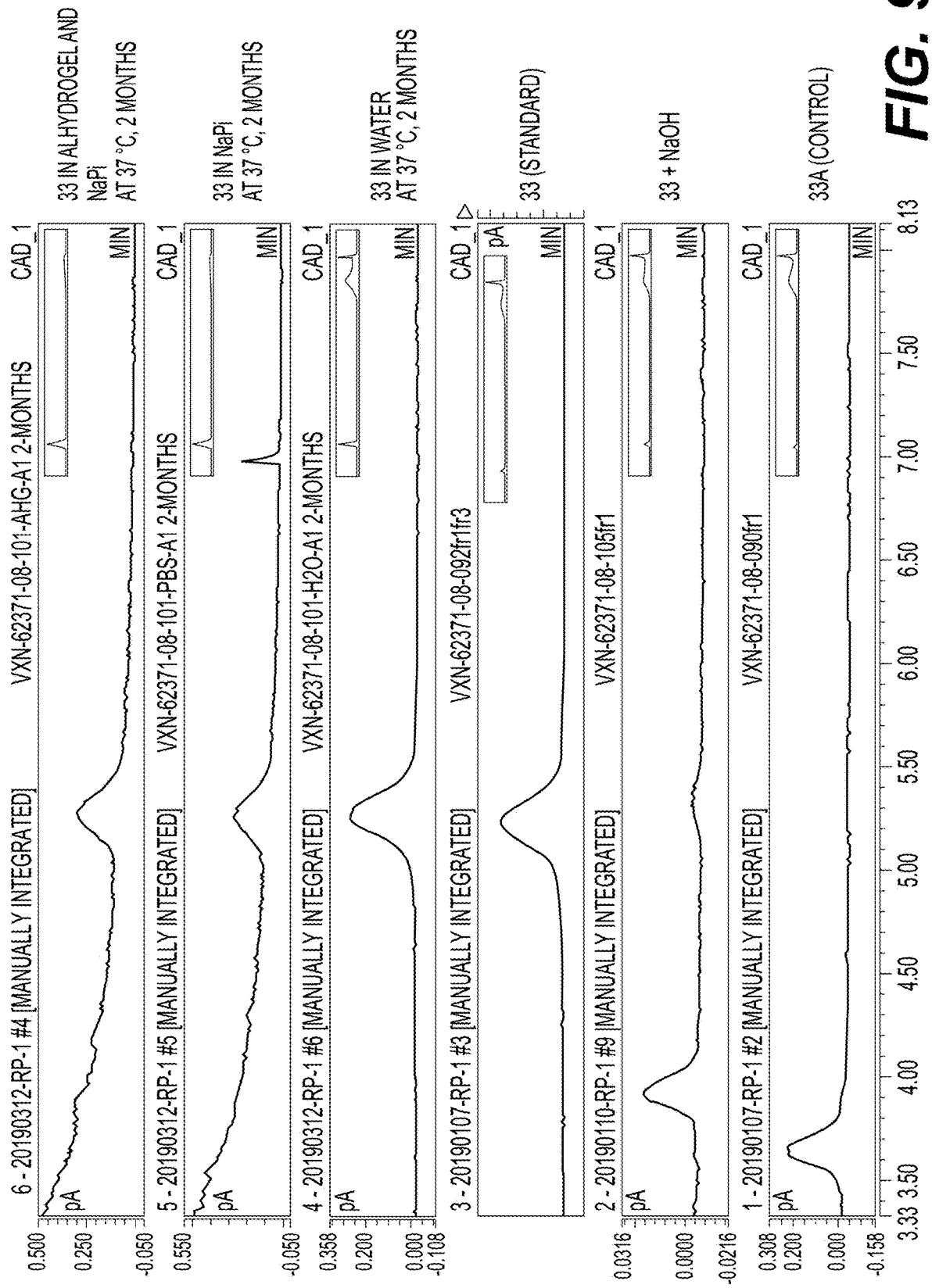
FIG. 9 shows HPLC plots from bottom to top of the following compounds: compound 33A (control), compound 33 after one day treatment with 0.1 M sodium hydroxide solution at room temperature and purified, compound 33 (standard), compound 33 after two months at 37° C. in water, compound 33 after two months at 37° C. in NaPi which is a synonym for PBS (phosphate-buffered saline), compound 33 after two months at 37° C. in Alhydrogel and PBS. It is evident from FIG. 9 that compound 33 is fully stable at 37° C. over two months.
Figure 10:
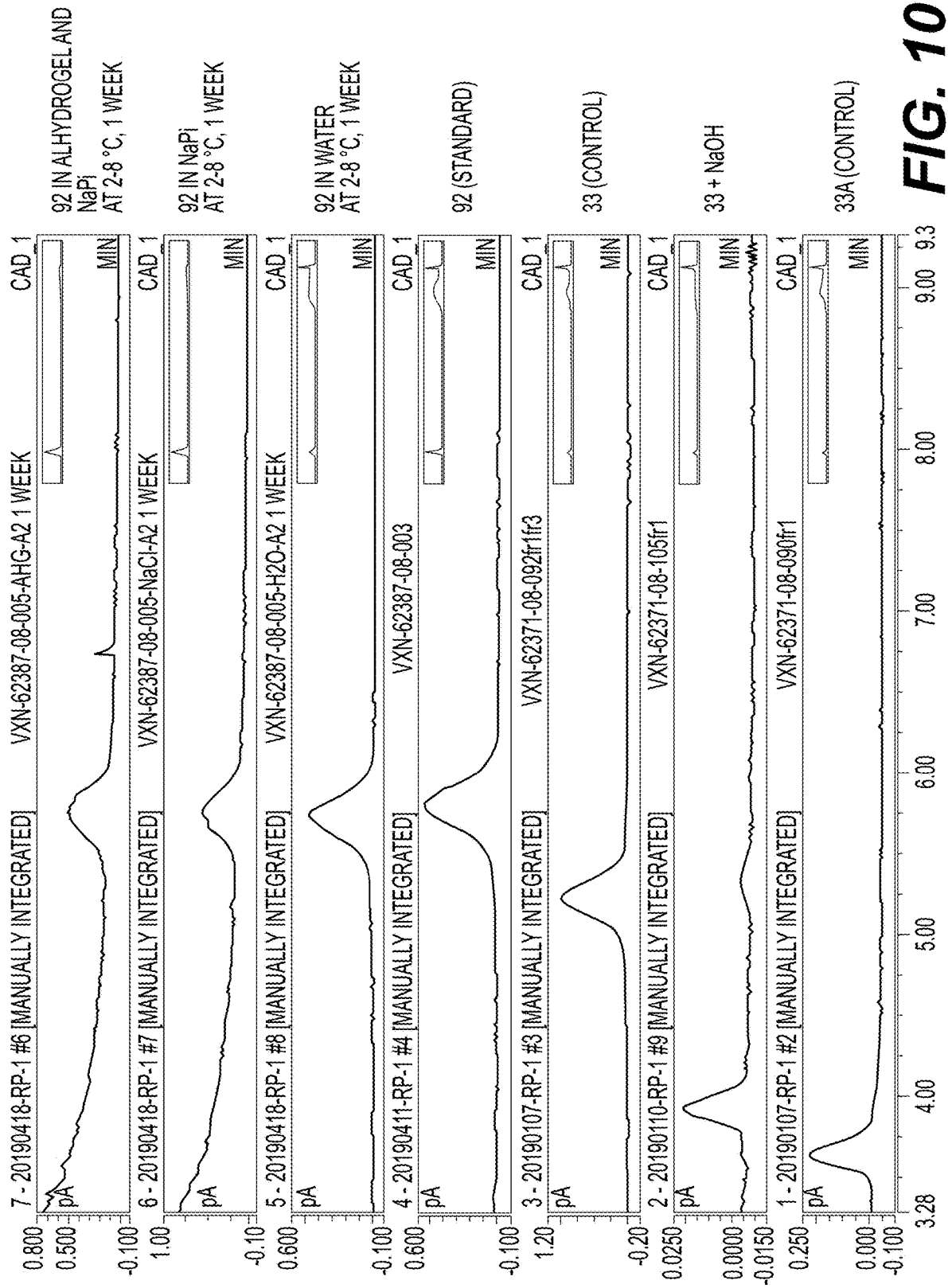
FIG. 10 shows HPLC plots from bottom to top of the following compounds: compound 33A (control), compound 33 after one day treatment with 0.1 M sodium hydroxide solution at room temperature and purified, compound 33 (control), compound 92 (standard), compound 92 after one week at 2-8° C. in water, compound 92 after one week at 2-8° C. in NaPi which is a synonym for PBS (phosphate-buffered saline), compound 92 after one week at 2-8° C. in Alhydrogel and PBS. It is evident from FIG. 10 that compound 92 is fully stable at 2-8° C. over one week.
Figure 11:
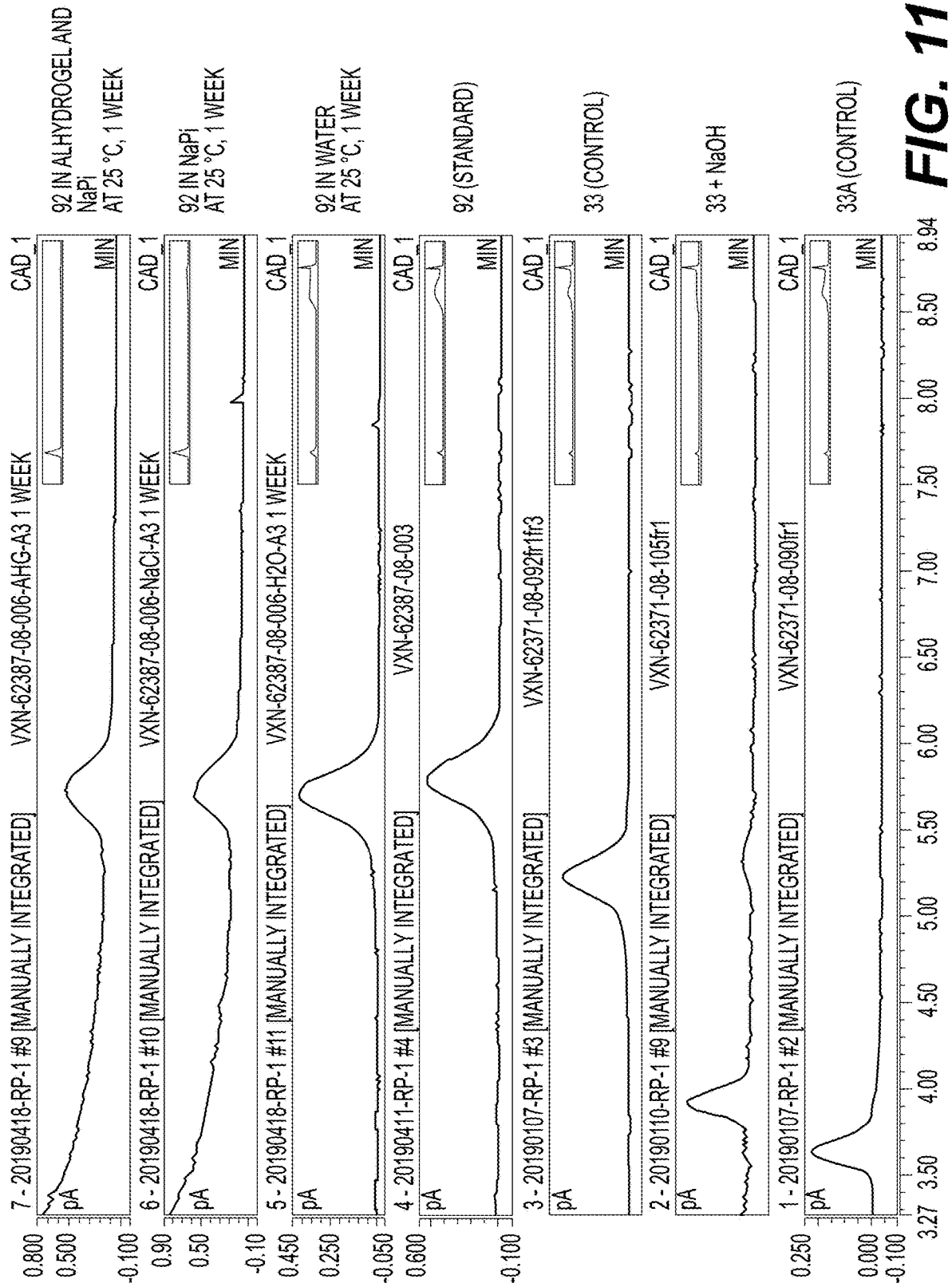
FIG. 11 shows HPLC plots from bottom to top of the following compounds: compound 33A (control), compound 33 after one day treatment with 0.1 M sodium hydroxide solution at room temperature and purified, compound 33 (control), compound 92 (standard), compound 92 after one week at 25° C. in water, compound 92 after one week at 25° C. in NaPi which is a synonym for PBS (phosphate-buffered saline), compound 92 after one week at 25° C. in Alhydrogel and PBS. It is evident from FIG. 11 that compound 92 is fully stable at 25° C. over one week.
Figure 12:
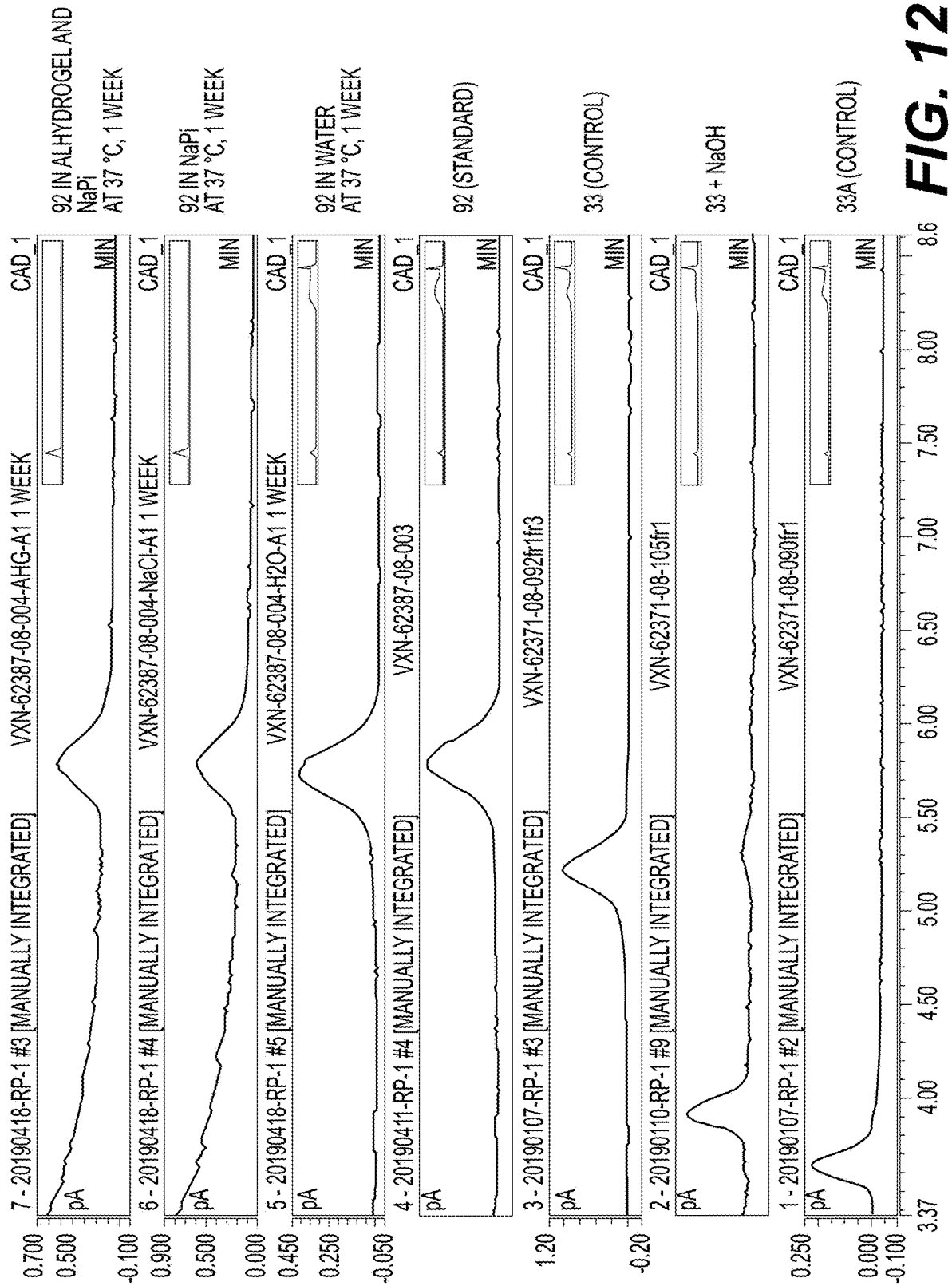
FIG. 12 shows HPLC plots from bottom to top of the following compounds: compound 33A (control), compound 33 after one day treatment with 0.1 M sodium hydroxide solution at room temperature and purified, compound 33 (control), compound 92 (standard), compound 92 after one week at 37° C. in water, compound 92 after one week at 37° C. in NaPi which is a synonym for PBS (phosphate-buffered saline), compound 92 after one week at 37° C. in Alhydrogel and PBS. It is evident from FIG. 12 that compound 92 is fully stable at 37° C. over one week.
Figure 13:
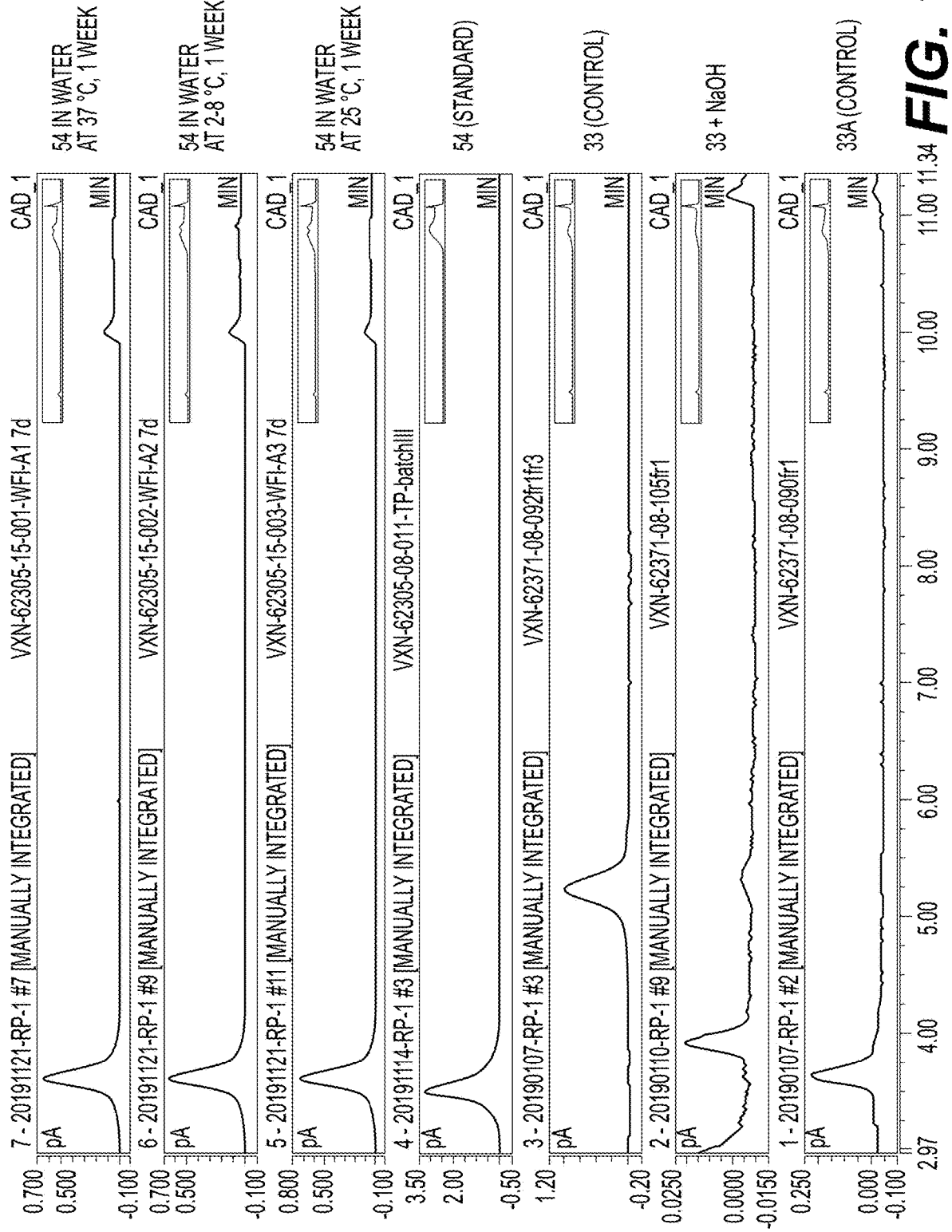
FIG. 13 shows HPLC plots from bottom to top of the following compounds: compound 33A (control), compound 33 after one day treatment with 0.1 M sodium hydroxide solution at room temperature and purified, compound 33 (control), compound 54 (standard), compound 54 after one week at 25° C. in water, compound 54 after one week at 2-8° C. in water, compound 54 after one week at 37° C. in water. It is evident from FIG. 13 that compound 54 is fully stable at 37° C. over one week.
Figure 14:
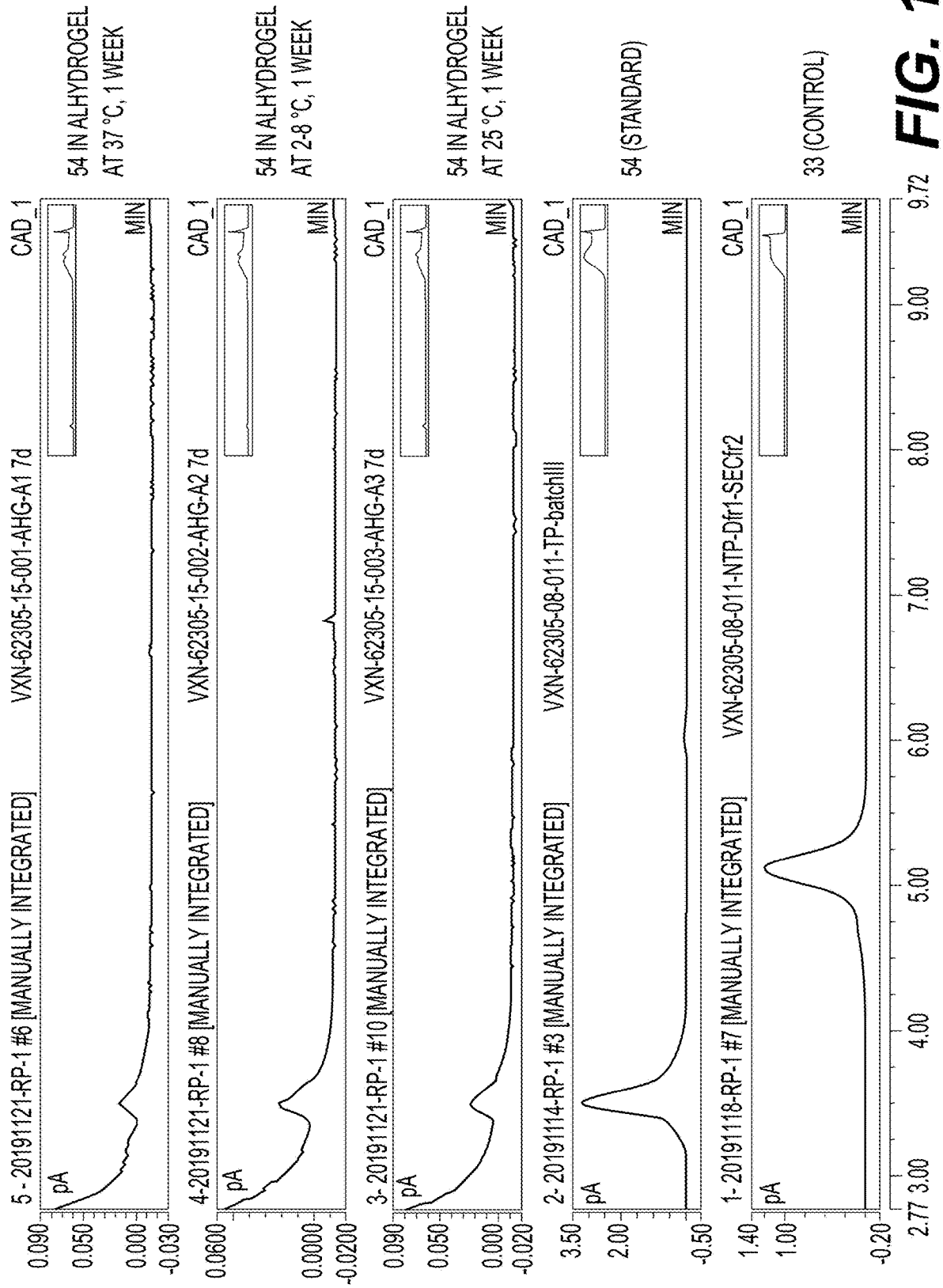
FIG. 14 shows HPLC plots from bottom to top of the following compounds: compound 33A (control), compound 54 (standard), compound 54 after one week at 25° C. in Alhydrogel, compound 54 after one week at 2-8° C. in Alhydrogel, compound 54 after one week at 37° C. in Alhydrogel. It is evident from FIG. 14 that compound 54 when formulated with Alhydrogel becomes mostly adsorbed to the aluminum hydroxide and that no conceivable cleavage products were formed, which are detectable by HPLC in the presence of aluminium hydroxide. Thus compound 54 is stable at 37° C. over one week.

Stability of Compound 33 Over Alhydrogel in PBS, PBS and Water:

Next the stability of the compound 33 under formulation conditions was scrutinized. Each formulation vial contains, 30 μg of 33 in i) Alhydrogel in PBS or ii) PBS alone or iii) water (overall volume of the solution is 500 μL). NaPi is used as a synonym for PBS herein. 60 μL of Alhydrogel containing 0.6 mg of Aluminium were used for each experiment. These three formulated solutions were kept at 37° C., 25° C. and 2-8° C. for 14 days. After every 24 h duration, 50 μL of the solution from each vial i) Alhydrogel in PBS, ii) PBS alone and iii) water at 37° C., 25° C. and 2-8° C. was aliquoted and analyzed by HPLC (FIGS. 8, 9, 10). From these studies it is evident that compound 33 is stable over the whole temperature range from 2° C. to 37° C. FIG. 8 shows the stability at 2-8° C. after 4 days, FIG. 9 at 2-8° C. after 14 days, FIG. 10 at 25° C. after 4 days, FIG. 11 at 25° C. after 14 days, FIG. 12 at 37° C. after 4 days, and FIG. 13 at 37° C. after 14 days.

In comparison to the natural polysaccharide PSII of *Clostridium difficile* the compounds 33, 54, and 90 were found to be sufficiently stable under the formulation conditions described above and 92, 112, 117, 162, 163, 164, 165, 172, and 173 are expected to be sufficiently stable under the formulation conditions described above.

It was also found that the natural polysaccharide PSII of *Clostridium difficile* composed of hexaglycosyl phosphate repeating units as shown below

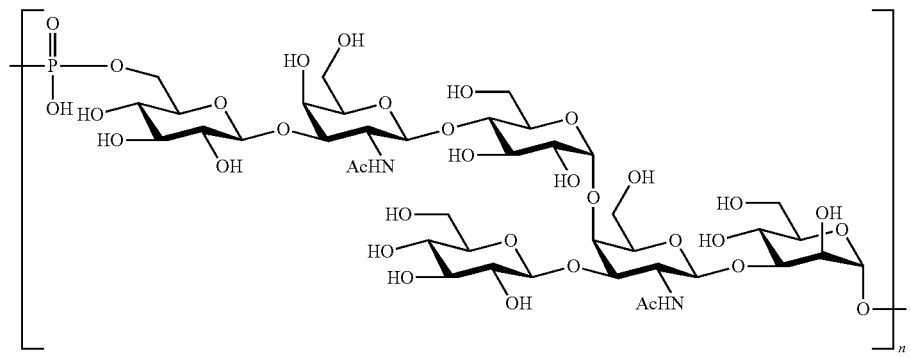

is not stable under NaOH treatment, not stable under acid conditions such as acetic acid and also not stable in solution at 2-8° C., 25° C. and 37° C. In was found that under these conditions the natural PSII degrades quickly to degradation products which no longer induce an immunological effect.

Therefore the stability experiments above demonstrate unambiguously that the compounds of the present invention are stable under conditions where the natural PSII decomposes to fragments no longer useful as vaccines, while the compounds disclosed herein are stable in solution and do not require to be lyophilized and re-dissolved, no cold storage, and do not require production and shipment applying an expensive working cold chain system.

C. Biological Experiments

SDS-PAGE Analysis.

The samples were mixed in a microfuge tube and heated for 5 min at 95° C. on a thermocycler. After cooling to room temperature for 5 min, the samples at approximately 2.5 µg were loaded onto the respective wells of a 10% polyacrylamide gel along with 10 µL of the marker. The samples were run at a constant voltage of 120 V for 1 h. Staining was done using the GelCode™ Blue Safe Protein Stain as per manufacture instructions. The gels were washed with deionized water overnight and scanned using the gel documentation system.

Size Exclusion Chromatography (SEC) of Glycoconjugates.

The glycoconjugates used for immunization studies were analyzed by SEC to observe a mass difference between the conjugated and unconjugated CRM protein. The samples were diluted in 50 mM Tris, 20 mM NaCl, pH 7.2 and run on an Agilent 1100 HPLC system fitted with Tosoh TSK G2000 column (SWxl, 7.8 mm×30 cm, 5 µm) and a Tosoh TSKgel® Guard Column (SWxl 6.0 mm×4 cm, 7 µm). The flow rate was kept at 1 mL/min.

Production of Glycoconjugate

The C. difficile PS-II synthetic antigens were conjugated to the carrier protein $CRM_{197}$ for immunization experiments and to Bovine Serum Albumin (BSA) as coating antigen for ELISA (see A. Chemical Synthesis). The resulting conjugates were sterile filtered using a 0.2 µM membrane filter prior to use. The conjugates were analyzed by MALDI analysis. The loading of the saccharide on the carrier protein was specifically calculated by subtracting the mass between the conjugated and unconjugated protein using MALDI analysis. The protein content was estimated using the micro BCA method following manufacture protocol.

Characterization of Glycoconjugates 36 (33-$CRM_{197}$), 56 (54-$CRM_{197}$) and 94 (92-$CRM_{197}$)

The C. difficile antigen glycoconjugates 36, 56 and 94 used for the immunization studies were analyzed for the conjugation efficiency and antigen content. MALDI-TOF MS analysis of the glycoconjugates revealed a good conjugation efficiency. The mass differences between the conjugated and unconjugated $CRM_{197}$ protein yielded a loading of about 7.5 (56) and about 5 (94) antigens per $CRM_{197}$ molecule.

Figure 24:
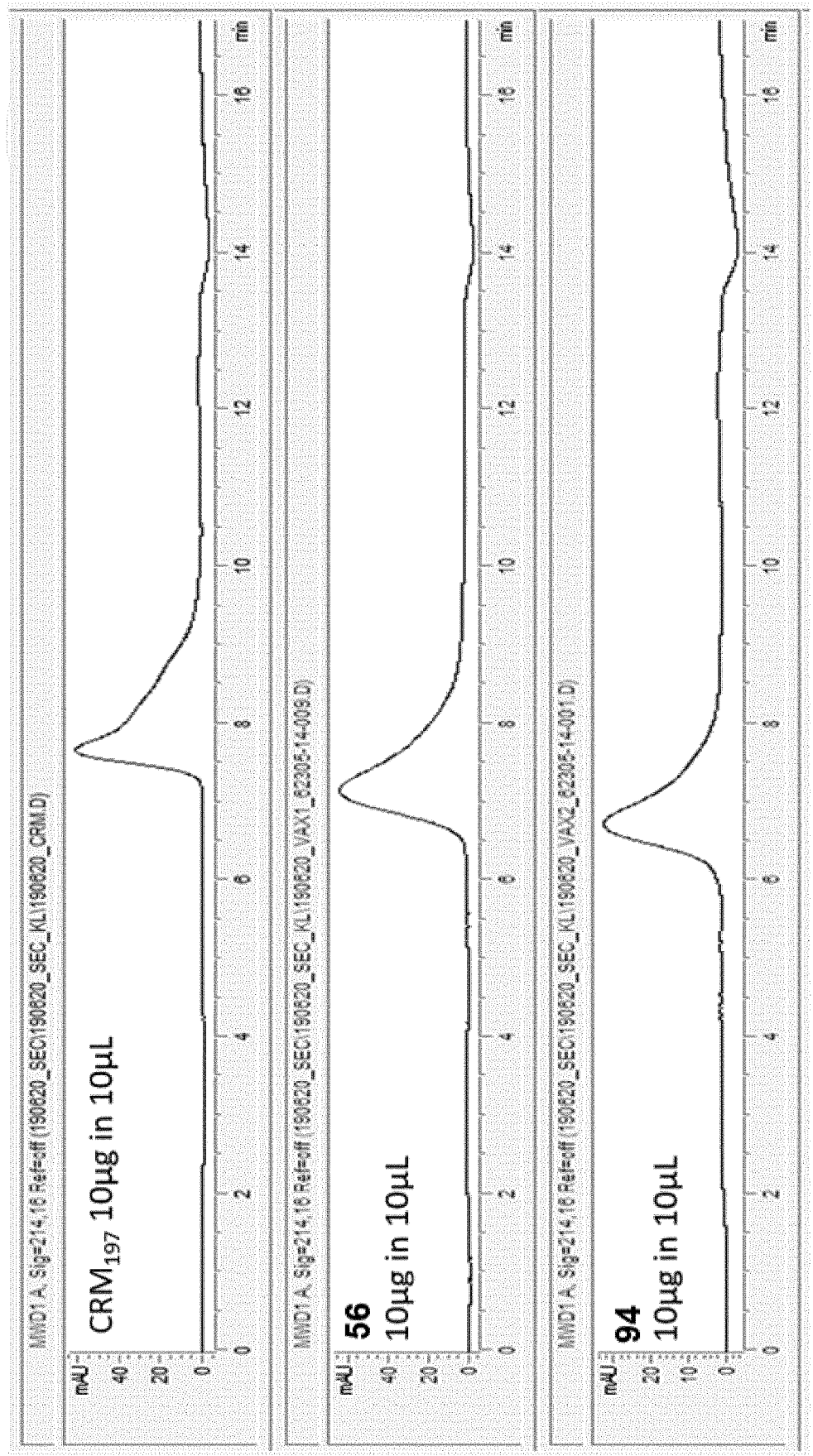
FIG. 24 shows SEC chromatograms of two glycoconjugates 94 and 56 used for immunization experiments. Unconjugated $CRM_{197}$ protein served as control.
Figure 25:
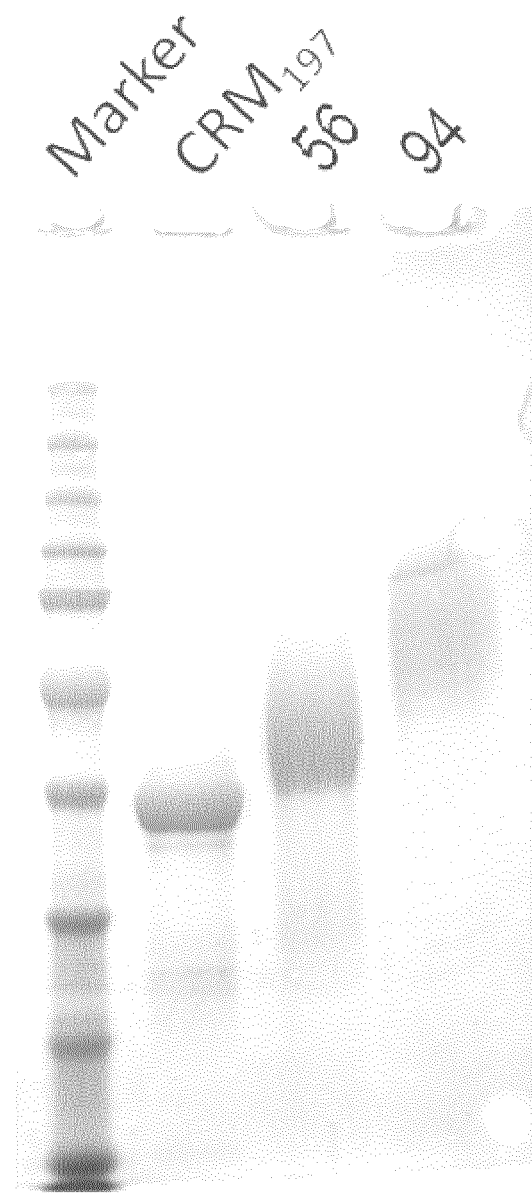
FIG. 25 shows SDS-PAGE of C. difficile glycoconjugates 94 and 56 (2.5 μg per well) used for immunization experiments resolved using a 10% polyacrylamide gel. Unconjugated $CRM_{197}$ protein served as control.

The glycoconjugates were also analyzed by a 10% SDS-PAGE and SEC that revealed a clear mass shift as compared to the unconjugated $CRM_{197}$ protein (FIGS. 24 and 25).

Immunization Studies

Study I—Immunological Evaluation of Semisynthetic Glycoconjugates of C. difficile Antigen PS-II Immunized in Rabbits.

1. Aim of the Study:

Evaluation of the IgG antibody response in rabbits immunized with C. difficile antigen PS-II semi-synthetic $CRM_{197}$ conjugate vaccine 36.

2. Materials:

ELISA plates (high-binding, EIA/RIA Plate, 96 well, flat bottom with low evaporation lid, company: Costar® 3361)
Detection antibody: Goat anti rabbit IgG peroxidase conjugate (Sigma, #A4914)
Blocking solution: 1% FCS (v/v) in PBS
Antibody diluent: PBS+1% BSA (w/v).
Wash Buffer: PBS+0.1% Tween 20 (PBS-T)
Developing solution: 1 Step™ Ultra TMB-ELISA developer. (ThermoScientific, Cat #: 34028)
Stop solution: 2M Sulphuric acid ($H_2SO_4$)
Plate reader: Anthos ht 2.
Software: WinRead 2.36 for absorbance measurements and GraphPad Prism 7 for data plotting and analysis.
Incomplete Freund's Adjuvant (IFA). InvivoGen; Cat: vac-ifa-10, Batch #: IFA-39-03; Exp Dt: September 2019
QuantiPro™ BCA Assay Kit (SIGMA) Product: QPBCA-1KT; Lot #: SLBR7451V; Pcode: 1002296464

3. Methods:

Formulation of Vaccines for Immunization

The C. difficile PS-II glycoconjugate 36 was formulated in Incomplete Freund's Adjuvant (IFA) for immunization in rabbits. Incomplete Freund's Adjuvant (IFA) from Invivogen was used for formulating the vaccines for rabbit immunization studies. Protocol was followed as per manufacture. Antigen: IFA concentration was kept at 1:1. The antigen dose per animal was kept at 2.5 µg/200 µL/animal (100 µL of antigen +100 µL IFA). IFA at the desired calculated volume (50% of the final immunization volume) was taken in a 15 mL sterile falcon. The calculated amount of the diluted antigen solution (Volume adjusted with PBS to 50% of the final immunization volume) was taken in a 3 mL sterile syringe, fitted with a 20 G needle. The DS solution was added into the falcon containing the IFA and immediately vortexed for 15 sec (5×). The color of the formulation changes from pale-yellow to milky-white on vortexing which indicates the formation of stable emulsion. The resulting vaccine formulation was briefly vortexed and aliquoted into 2 mL sterile tubes with the desired dose volumes. Prior to immunizations, the tubes containing the vaccine formulations were vortexed and then injected into animals.

Immunization Schedule

Rabbit immunizations were performed under specific pathogen-free conditions and were provided food and water ad libitum. Rabbits (n=4) were immunized sub cutaneous with the vaccine formulations at an injection volume of 200 µL/rabbit. The antigen dose for rabbit was kept at 2.5 µg/animal of PS-II antigen or corresponding volume of PBS for negative controls. Rabbits were immunized on day 0, 14 and 35. Blood was drawn on day 0, 7 and 42 for the determination of antibody titers.

4. Enzyme Linked Immunosorbent Assay (ELISA) of Sera Using In-House Antigen Coated Plates Coating of Plates with Antigen Antigen-BSA conjugates were used as the coating antigen. Antigen-BSA conjugates were dissolved at a concentration of 5 µg/mL in phosphate buffered saline (PBS) pH 7.4. 100 µL were coated per well and incubated overnight at 4° C. to get an antigen concentration of 0.5 µg/well.

Washing

After overnight adsorption of the antigen, the plates were washed 1× with PBS-T (200 µL/well) and the excess fluid per well was removed by inverting the plate and tapping on a clean dry tissue towel.

Blocking

The plates were blocked using 200 µL of the commercial blocking solution and incubated for 2h at RT.

Washing

After blocking, the plates were washed 3× with PBS-T (200 µL/well) and the excess fluid per well was removed by inverting the plate and by tapping on a clean dry tissue towel.

Dilution of Sera and Incubations

Pooled sera (n=4 rabbits) from different time-points of the different experimental groups were diluted to their respective dilutions in the antibody diluent (PBS+1% BSA). 100 µL of the diluted sera samples of the different experimental groups were added in duplicates to the corresponding wells and incubated on a shaker set at 250 rpm for 2h at RT. 100 µL/well of the antibody diluent (PBS+1% BSA) formed the experimental blank. After incubation with sera, the plates were washed 4× with PBS-T (200 µL/well) and the excess fluid per well was removed by inverting the plate and by tapping on a clean dry tissue towel.

Incubation (Detection Antibody)

The corresponding detection antibody, anti-rabbit IgG HRP conjugate was diluted 1:10,000 in the antibody diluent (PBS+1% BSA) and 100 µL/well was added and incubated on a shaker at 250 rpm for 1 h at RT. After the incubation with detection antibody, the plates were washed 5× with PBS-T (200 µL/well) and the excess fluid per well was removed by inverting the plate and by tapping on a clean dry tissue towel.

Substrate Addition

To each well, 100 µL of the ready to use TMB substrate (normalized to RT form 4° C.) was added and incubated in dark for 15 min. The blue color of the enzymatic reaction was stopped by adding 50 µL/well of 2M $H_2SO_4$ solution resulting in a yellow colored solution. The absorption of the yellow colored solution was measured at 450 nm using a plate reader.

Results

The absorption values were analyzed by plotting a graph using the Graphpad Prism software.

Figure 15:
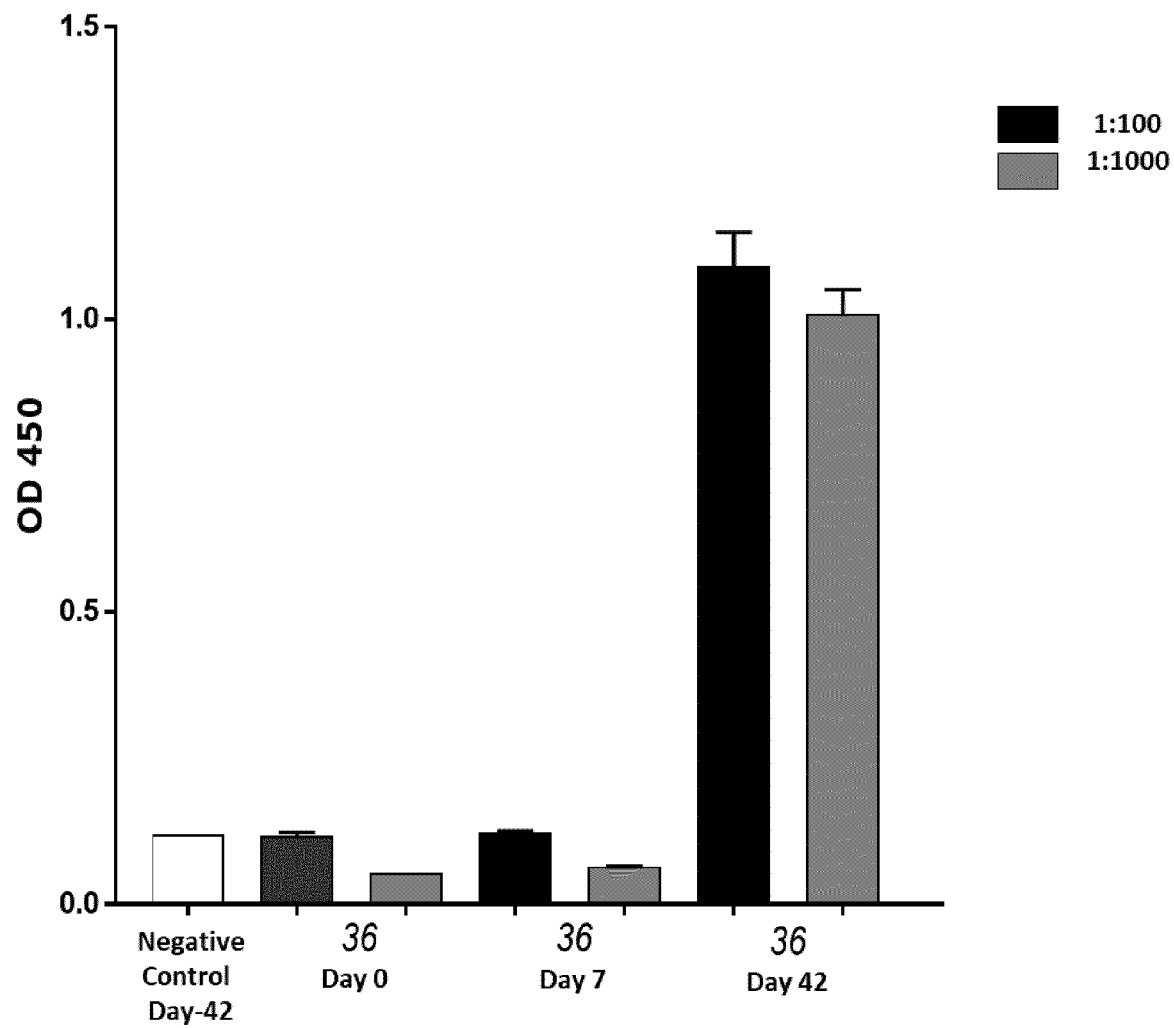
FIG. 15 shows ELISA titers of Day-0, Day-7 and Day-42 of pooled sera from rabbits (n=4) immunized with C. difficile saccharide 33-$CRM_{197}$ formulations (36). The sera obtained from the rabbits immunized with compound 36 were diluted 1:100, 1000 with 1% BSA-PBS. The diluted sera (100 μL) were added per well of a microtiter plate which was coated with 0.5 μg of the corresponding 33-BSA conjugate (compound 37). Detection was done using HRP conjugated goat anti-rabbit secondary antibody diluted to 1:10000 and developed using 3,3',5,5'-Tetramethylbenzidine (TMB) as a substrate. Absorbance was measured at 450 nm and the data were plotted using the Graphpad prism software. At day 42 a remarkable immunological response is evident from FIG. 15.

The ELISA data clearly show that sera from *C. difficile* PS-II conjugate 36 immunized rabbits recognize the corresponding antigens (see FIG. 15).

Study II—Immunological Evaluation of Semisynthetic Glycoconjugates of *C. difficile* Antigen PS-II Immunized in Rabbits and Mice.

1. Aim of the Study:

Evaluation of the IgG antibody response in rabbits and mice immunized with C. diff PS-II semi-synthetic $CRM_{197}$ conjugate vaccines 56 and 94.

2. Materials:

ELISA plates (high-binding, EIA/RIA Plate, 96 well, flat bottom with low evaporation lid, company: Costar® 3361)

Detection antibody: Goat anti rabbit IgG peroxidase conjugate (Sigma, #A4914) and anti-human IgG (H+L)-HRP, Nordic Immunology, Lot #:6276

Blocking solution: Roche, Ref: 11112589001; Lot: 21495200, Exp. Dt: July 2019.

Antibody diluent: PBS+1% BSA (w/v)

Wash Buffer: PBS+0.1% Tween 20 (PBS-T)

Developing solution: 1 Step™ Ultra TMB-ELISA developer. (ThermoScientific, Cat #: 34028)

Stop solution—2M Sulphuric acid ($H_2SO_4$)

Plate reader: Anthos ht 2

Software: WinRead 2.36 for absorbance measurements and GraphPad Prism 7 for data plotting and analysis Alum: Aluminium Hydroxide Gel Adjuvant (Alhydrogel 2%), Brenntag, Batch #:5447 Exp Dt: February 2020

QuantiPro™ BCA Assay Kit (SIGMA) Product: QPBCA-1KT; Lot #: SLBR7451V; Pcode: 1002296464

Mini-PROTEAN® TGX™ Gels—10%, 10 well (30 µL/well) Control Nr: 64175708

Precision Plus Dual Color, Cat: 1610374; Control Nr: 641798899

Gel Code™ Blue Safe Protein Stain; ThermoScientific; Ref: 1860957; Lot #: TA260266

*C. difficile* coated ELISA plates for strains 630 (tgc BIOMICS Lot #: 630-43411) and R20291 (tgc BIOMICS Lot #: R20291-43559) Exp. Dt: May 2020.

*C. difficile* positive patient plasma.

3. Methods

Formulation of Vaccines for Immunization in Aluminum Hydroxide (Alum) Adjuvant

All the formulations were prepared under sterile conditions. The glycoconjugates 56 and 94 (drug substances; DS) and PBS were mixed in the appropriate pre-calculated ratio in a 50 mL Falcon™ tube corresponding to the final formulation volume leaving out the volume of alum (0.25 mg/mL) required. This formed the DS-PBS mixture. The antigen/DS dose per animal was kept at 2.5 µg/500 µL/animal or 10 µg/500 µL/animal (rabbit studies) or at 0.5 µg/100 µL/animal or 2 µg/100 µL/animal (mouse studies). The DS-PBS mixtures were gently mixed (5×) using a serological pipette. To the DS-PBS mixtures, the corresponding volume of stock alum (10 mg/mL) was added to give a final alum ratio of 1:40 or 0.250 mg/mL. The mixtures were immediately mixed by gentle pipetting (20×) using a 5 mL serological pipette. The Falcon™ tubes were capped, wrapped with Parafilm® and allowed to mix on a shaker at 250 rpm for 2 h at room temperature (RT). After the incubation time of 2 h, the formulations were brought under the clean bench, aliquoted, and further stored at 4° C. until further use. The glycoconjugates formulated in Alum were characterized to determine the final alum concentration and the pH of the formulations.

Immunization Schedule

Mice and rabbit immunizations were performed under specific pathogen-free conditions and the animals were provided food and water ad libitum. Mice (n=7 or 8 per study arm) and rabbits (n=4 per study arm) were immunized subcutaneously with the vaccine formulations at an injection volume of 100 µL/mice, and 500 µL/rabbit with the different antigen doses. Mice were immunized on days 0, 14 and 28 and blood was collected on days 21 and 35. Rabbits were immunized on days 0, 14, 28 and 77 and blood was collected on days 0, 7, 21, 35, 77 and 84. Serum was prepared from the blood samples for serum antibody analyses.

4. Enzyme Linked Immunosorbent Assay (ELISA) of Sera Using In-House Antigen Coated Plates.

Coating of Plates with Antigen:

Conjugates 54-BSA and 92-BSA were used as coating antigens. The respective conjugates were diluted to a concentration of 5 µg/mL in phosphate buffered saline (PBS) pH 7.4. 100 µL were coated per well and incubated overnight at 4° C. to get an antigen concentration of 0.5 µg/well. For coating of the isolated PS-II polysaccharide the polysaccharide was diluted to 50 µg/mL in PBS with 10 mM imidazole and 100 µL per well were coated at 50° C. for 5 hours.

Washing:

After adsorption of the antigen, the plates were washed 1× with PBS-T (200 µL/well) and the excess fluid per well was removed by inverting the plate and tapping on a clean dry tissue towel.

Blocking:

The plates were blocked using 200 µL of the commercial blocking solution and incubated for 2h at RT.

Washing:

After blocking, the plates were washed 3× with PBS-T (200 µL/well) and the excess fluid per well was removed by inverting the plate and by tapping on a clean dry tissue towel.

Dilution of Sera and Incubations:

Pooled sera (n=4 rabbits or n=7-8 mice/group) from different time-points of the different experimental groups were diluted to their respective dilutions in the antibody diluent (PBS+1% BSA). 100 µL of the diluted sera samples of the different experimental groups were added in duplicates to the corresponding wells and incubated on a shaker set at 250 rpm for 2h at RT. For competition ELISA experiments, diluted sera were incubated on ice for 30 min with 10 or 50 µg of isolated PS-II polysaccharide or with PBS before addition to the ELISA plates. 100 µL/well of the antibody diluent (PBS+1% BSA) formed the experimental blank. After incubation with sera, the plates were washed 4× with PBS-T (200 µL/well) and the excess fluid per well was removed by inverting the plate and by tapping on a clean dry tissue towel.

Incubation with Detection Antibody:

The corresponding detection antibody, anti-rabbit or anti-mouse IgG HRP conjugate was diluted 1:10,000 in the antibody diluent (PBS+1% BSA) and 100 µL/well were added and incubated on a shaker at 250 rpm for 30 min at RT. After the incubation with detection antibody, the plates were washed 5× with PBS-T (200 µL/well) and the excess fluid per well was removed by inverting the plate and by tapping on a clean dry tissue towel.

Substrate Addition:

To each well, 100 µL of the ready to use TMB (3,3',5,5'-tetramethylbenzidine) substrate (normalized to RT from 4° C.) was added and incubated in dark for 15 min. The blue color of the enzymatic reaction was stopped by adding 50 µL/well of 2M $H_2SO_4$ solution resulting in a yellow colored solution. The absorption of the yellow colored solution was measured at 450 nm using a plate reader.

Results:

The absorption values were analyzed by plotting a graph using the GraphPad Prism software.

5. Enzyme Linked Immunosorbent Assay (ELISA) of Sera Using Commercial Pre-Coated Plates This procedure was identical to the above ELISA protocol, except that the coating step was omitted.

Figure 16:
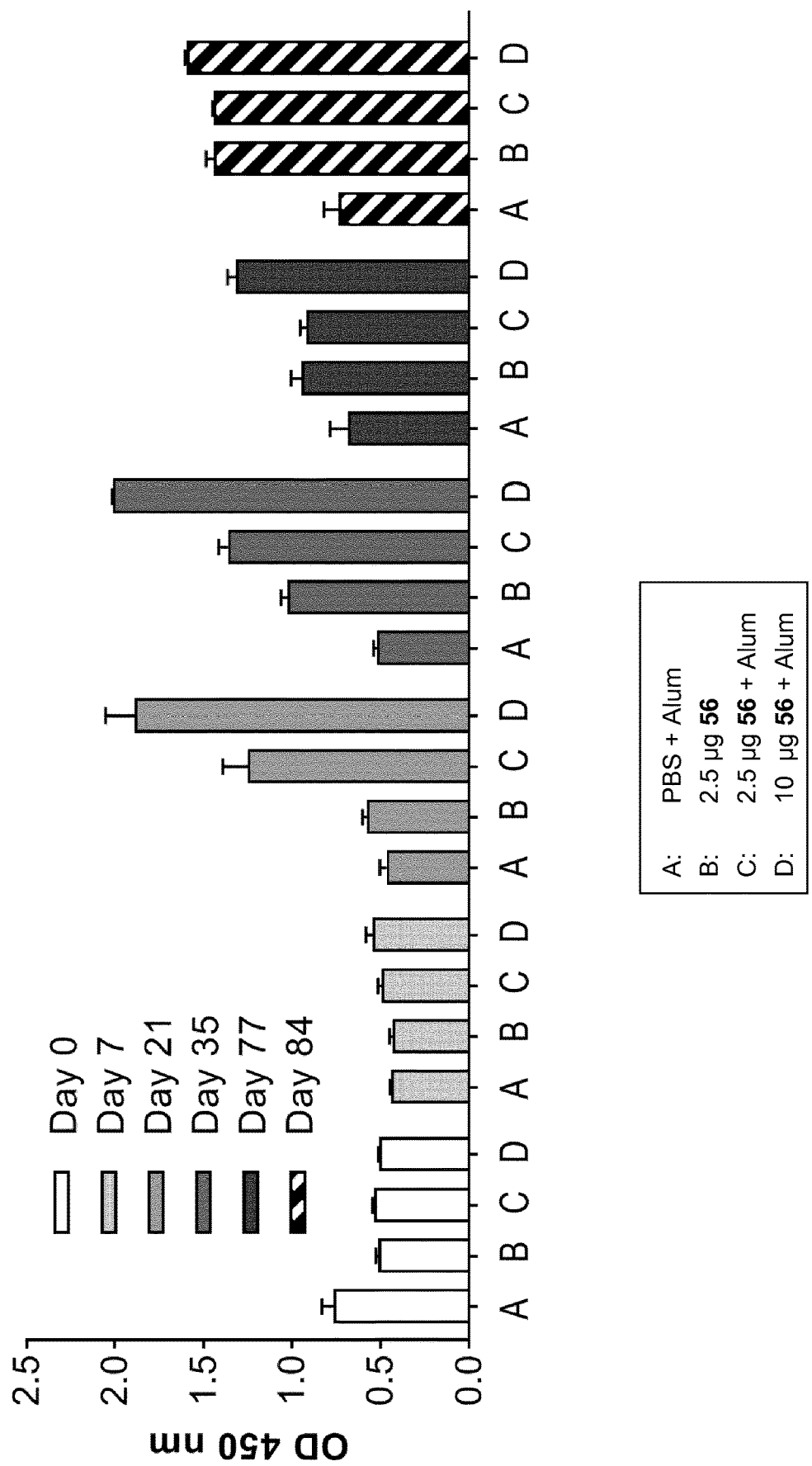
FIG. 16 shows ELISA titers of rabbit antisera against *C. difficile* strain 630 (pooled sera). Rabbits (4 animals per study arm) were immunized four times (days 0, 14, 28, 77) subcutaneously with 2.5 µg or 10 µg glycan antigen per injection with or without aluminum hydroxide (Alum) adjuvant, as indicated. PBS with Alum served as negative control. The immunogen was conjugate 56. Pooled sera from different timepoints (days 0, 7, 21, 35, 77 and 84) were tested for total IgG against formalin-inactivated *C. difficile* bacteria (strain 630) coated onto the ELISA plates. Coated ELISA plates purchased from tgcBIOMICS GmbH were blocked with 200 µL per well of commercial blocking reagent (Roche, ref. 11112589001) for 2 hours. Sera were diluted 1:100 with 1% (w/v) BSA in PBS and incubated for 1 hour at a volume of 100 µL per well. Total IgG was then detected using an HRP-conjugated goat anti-rabbit IgG secondary antibody (Sigma-Aldrich, ref. A4914) diluted to 1:10,000 in 1% (w/v) BSA in PBS for 30 min and developed using the TMB substrate (Thermo Scientific, ref. 34028). Absorbance was measured at 450 nm in a microplate reader and background-subtracted data were plotted using the GraphPad Prism software. It is evident from FIG. 16 that vaccination of rabbits with conjugate 56 induces IgG antibodies that bind to the surface of *C. difficile* bacteria, strain 630. Further, addition of Alum adjuvant leads to higher overall IgG titers.
Figure 17:
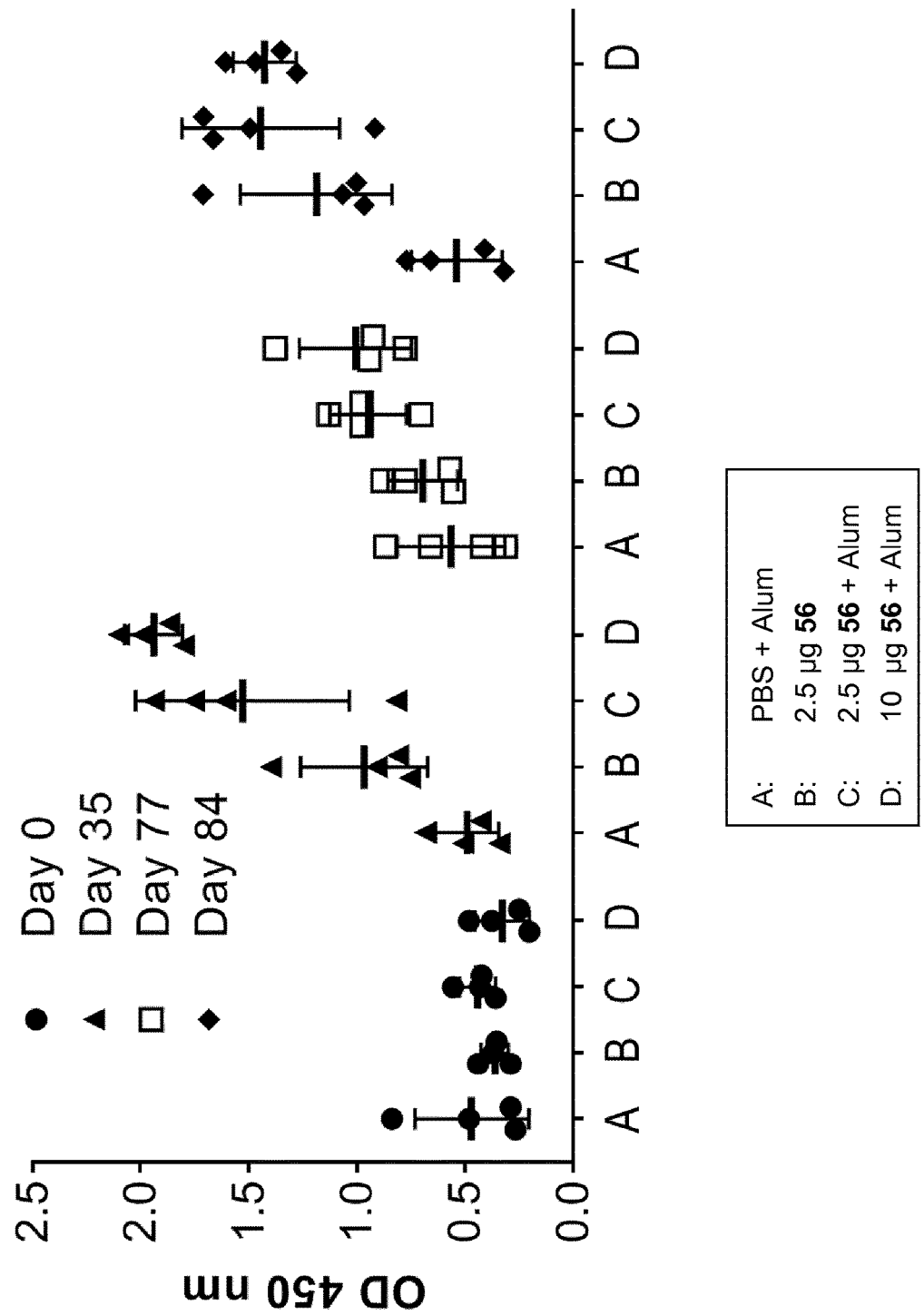
FIG. 17 shows ELISA titers of rabbit antisera against *C. difficile* strain 630 (individual sera). Rabbits (4 animals per study arm) were immunized four times (days 0, 14, 28, 77) subcutaneously with 2.5 µg or 10 µg glycan antigen per injection with or without aluminum hydroxide (Alum) adjuvant, as indicated. PBS with Alum served as negative control. The immunogen was conjugate 56. Sera from different timepoints (days 0, 35, 77 and 84) were tested for total IgG against formalin-inactivated *C. difficile* bacteria (strain 630) coated onto the ELISA plates. Coated ELISA plates purchased from tgcBIOMICS GmbH were blocked with 200 uL per well of commercial blocking reagent (Roche, ref. 11112589001) for 2 hours. Sera were diluted 1:300 with 1% (w/v) BSA in PBS and incubated for 1 hour at a volume of 100 µL per well. Total IgG was then detected using an HRP-conjugated goat anti-rabbit IgG secondary antibody (Sigma-Aldrich, ref. A4914) diluted to 1:10,000 in 1% (w/v) BSA in PBS for 30 min and developed using the TMB substrate (Thermo Scientific, ref. 34028). Absorbance was measured at 450 nm in a microplate reader and background-subtracted data were plotted using the GraphPad Prism software. It is evident from FIG. 17 that vaccination of rabbits with conjugate 56 induces IgG antibodies that bind to the surface of *C. difficile* bacteria, strain 630. Further, addition of Alum adjuvant leads to higher overall IgG titers.
Figure 18:
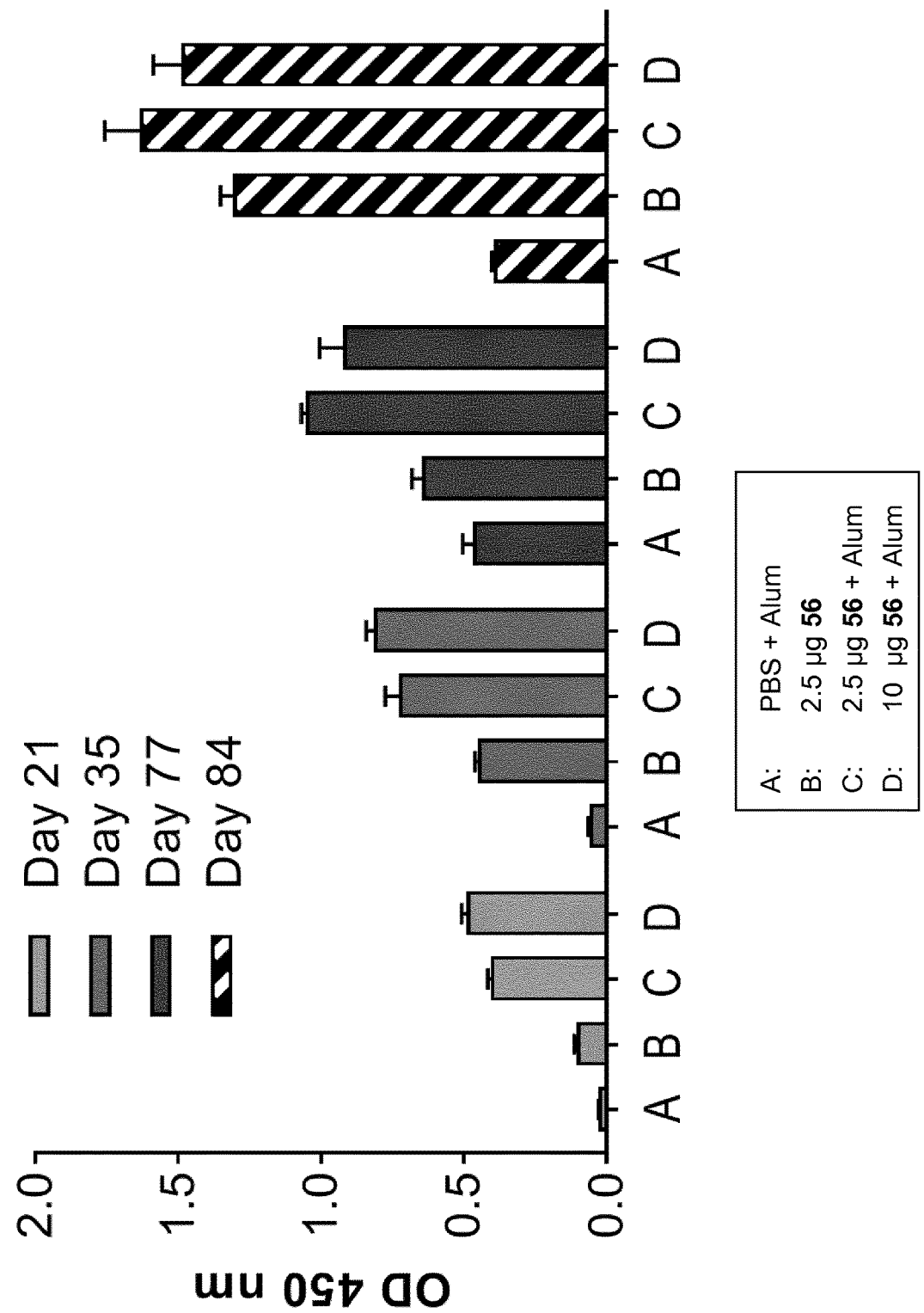
FIG. 18 shows ELISA titers of rabbit antisera against *C. difficile* strain R20291. Rabbits (4 animals per study arm) were immunized four times (days 0, 14, 28, 77) subcutaneously with 2.5 µg or 10 µg glycan antigen per injection with or without aluminum hydroxide (Alum) adjuvant, as indicated. PBS with Alum served as negative control. The immunogen was conjugate 56. Pooled sera from different timepoints (days 21, 35, 77 and 84) were tested for total IgG against formalin-inactivated *C. difficile* bacteria (strain R20291) coated onto the ELISA plates. Commercially available coated ELISA plates were blocked with 200 µL per well of commercial blocking reagent (Roche, ref. 11112589001) for 2 hours. Sera were diluted 1:100 with 1% (w/v) BSA in PBS and incubated for 1 hour at a volume of 100 µL per well. Total IgG was then detected using an HRP-conjugated goat anti-rabbit IgG secondary antibody (Sigma-Aldrich, ref. A4914) diluted to 1:10,000 in 1% (w/v) BSA in PBS for 30 min and developed using the TMB substrate (Thermo Scientific, ref. 34028). Absorbance was measured at 450 nm in a microplate reader and background-subtracted data were plotted using the GraphPad Prism software. It is evident from FIG. 18 that vaccination of rabbits with conjugate 56 induces IgG antibodies that bind to the surface of *C. difficile* bacteria, strain R20291. Further, addition of Alum adjuvant leads to higher overall IgG titers.
Figure 19:
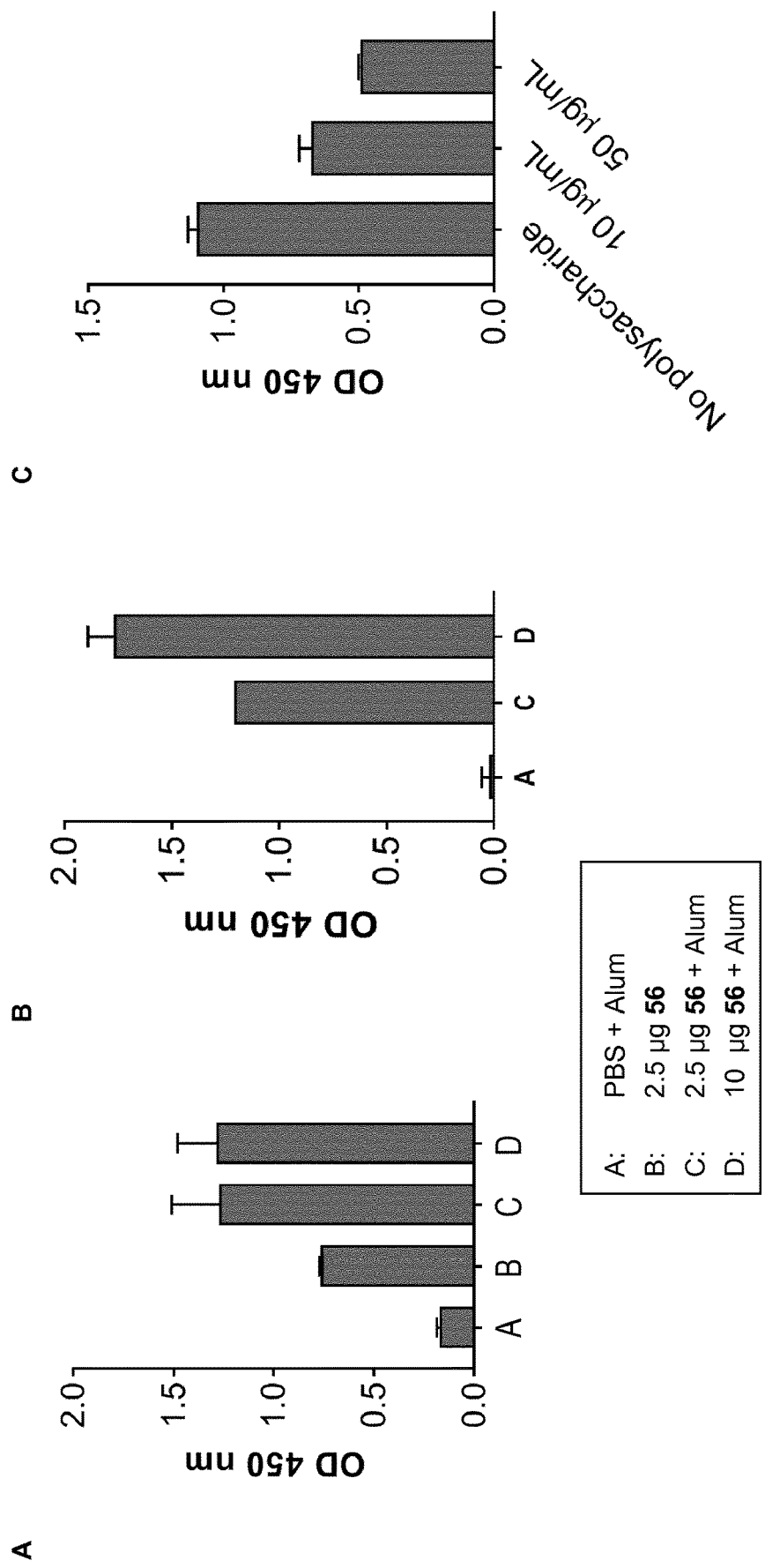
FIG. 19A shows ELISA titers of rabbit antisera (day 35) against *C. difficile* strain VPI10463. Rabbits (4 animals per study arm) were immunized four times (days 0, 14, 28, 77) subcutaneously with 2.5 µg or 10 µg glycan antigen per injection with or without aluminum hydroxide (Alum) adjuvant, as indicated. PBS with Alum served as negative control. The immunogen was conjugate 56. Pooled sera from day 35 were tested for total IgG against formalin-inactivated *C. difficile* bacteria (strain VPI10463) coated onto the ELISA plates. It is evident from FIG. 19A that vaccination of rabbits with conjugate 56 induces IgG antibodies that bind to the surface of *C. difficile* bacteria, strain VPI10463. Further, addition of Alum adjuvant leads to higher overall IgG titers.
FIG. 19B shows ELISA titers of rabbit antisera (day 35) against isolated *C. difficile* PS-II polysaccharide. Rabbits (4 animals per study arm) were immunized four times (days 0, 14, 28, 77) subcutaneously with 2.5 µg or 10 µg glycan antigen per injection with aluminum hydroxide (Alum) adjuvant, as indicated. PBS with Alum served as negative control. The immunogen was conjugate 56. Pooled sera from day 35 were tested for total IgG against isolated PS-II polysaccharide. It is evident from FIG. 19B that vaccination of rabbits with conjugate 56 induces IgG antibodies that bind to the isolated PS-II polysaccharide.
FIG. 19C shows ELISA titers of rabbit antisera (day 35) against *C. difficile* strain 630 with or without pre-incubation with isolated *C. difficile* PS-II polysaccharide. Rabbits (4 animals per study arm) were immunized four times (days 0, 14, 28, 77) subcutaneously with 10 µg glycan antigen per injection with aluminum hydroxide (Alum) adjuvant. The immunogen was conjugate 56. Pooled sera (diluted 1:100 in 1% (w/v) BSA in PBS) from day 35 were incubated on ice for 30 min with 10 or 50 µg of isolated PS-II polysaccharide or with PBS. The sera were then incubated for 1 hour (100 µL/well) on commercially available coated ELISA plates (*C. difficile* strain 630) that have been blocked beforehand with 200 µL per well of commercial blocking reagent (Roche, ref. 11112589001) for 2 hours. Total IgG was then detected using an HRP-conjugated goat anti-rabbit IgG secondary antibody (Sigma-Aldrich, ref. A4914) diluted to 1:10,000 in 1% (w/v) BSA in PBS for 30 min and developed using the TMB substrate (Thermo Scientific, ref. 34028). Absorbance was measured at 450 nm in a microplate reader and background-subtracted data were plotted using the GraphPad Prism software. It is evident from FIG. 19C that binding of rabbit antisera to *C. difficile* bacteria can be blocked with PS-II polysaccharide in a dose-dependent manner, indicating that anti-bacterial antibody responses are specific to the PS-II polysaccharide.
Figure 20:
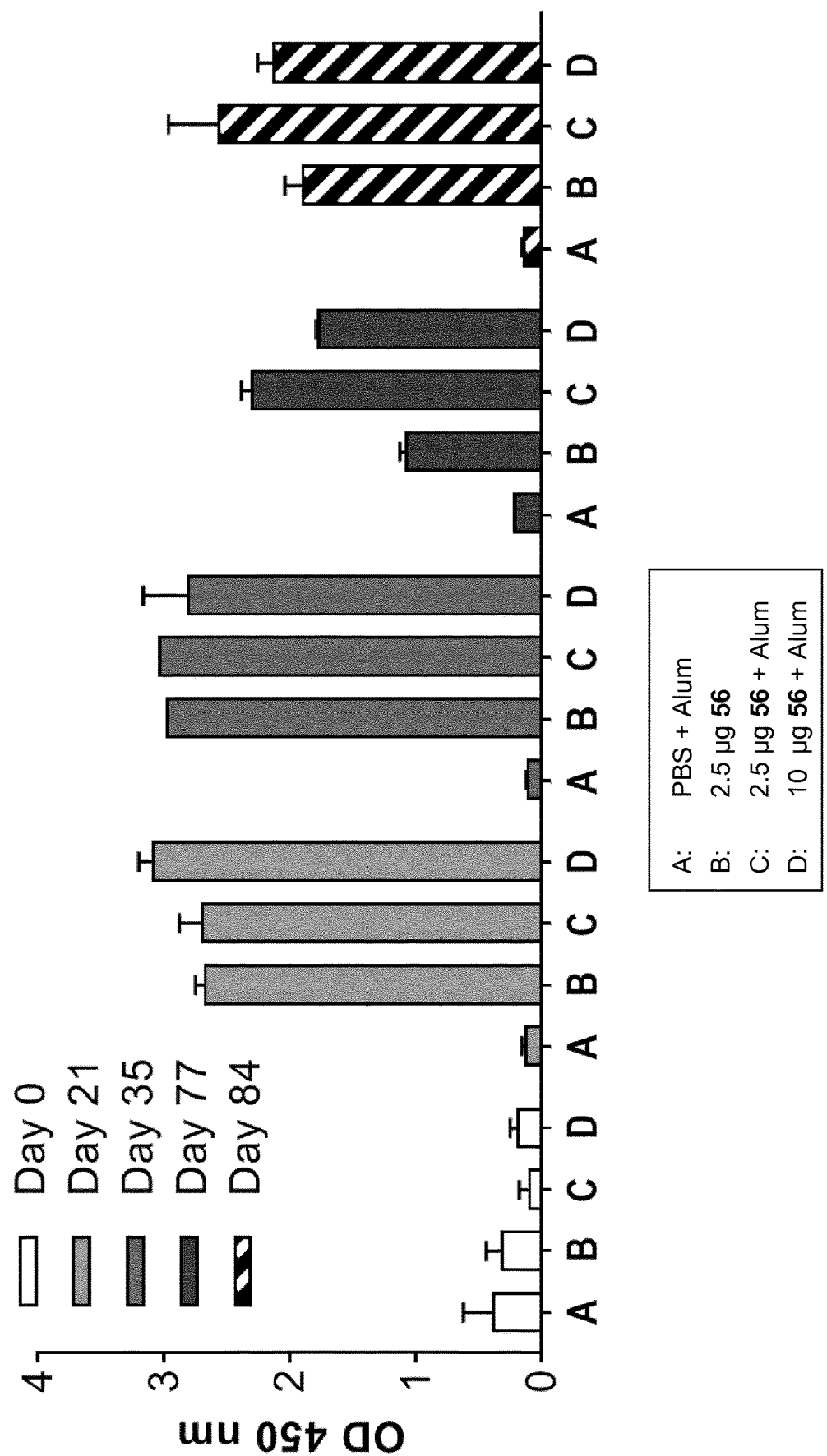
FIG. 20 shows ELISA titers of rabbit antisera against synthetic C. difficile PS-II hexasaccharide 54. Rabbits (4 animals per study arm) were immunized four times (days 0, 14, 28, 77) subcutaneously with 2.5 μg or 10 μg glycan antigen per injection with or without aluminum hydroxide (Alum) adjuvant, as indicated. PBS with Alum served as negative control. The immunogen was conjugate 56. Pooled sera from different timepoints (days 0, 21, 35, 77 and 84) were tested for total IgG against synthetic C. difficile PS-II hexasaccharide 54. It is evident from FIG. 20 that vaccination of rabbits with conjugate 56 induces IgG antibodies that bind to the synthetic immunogen 54. Further, addition of Alum adjuvant leads to higher overall IgG titers
Figure 21:
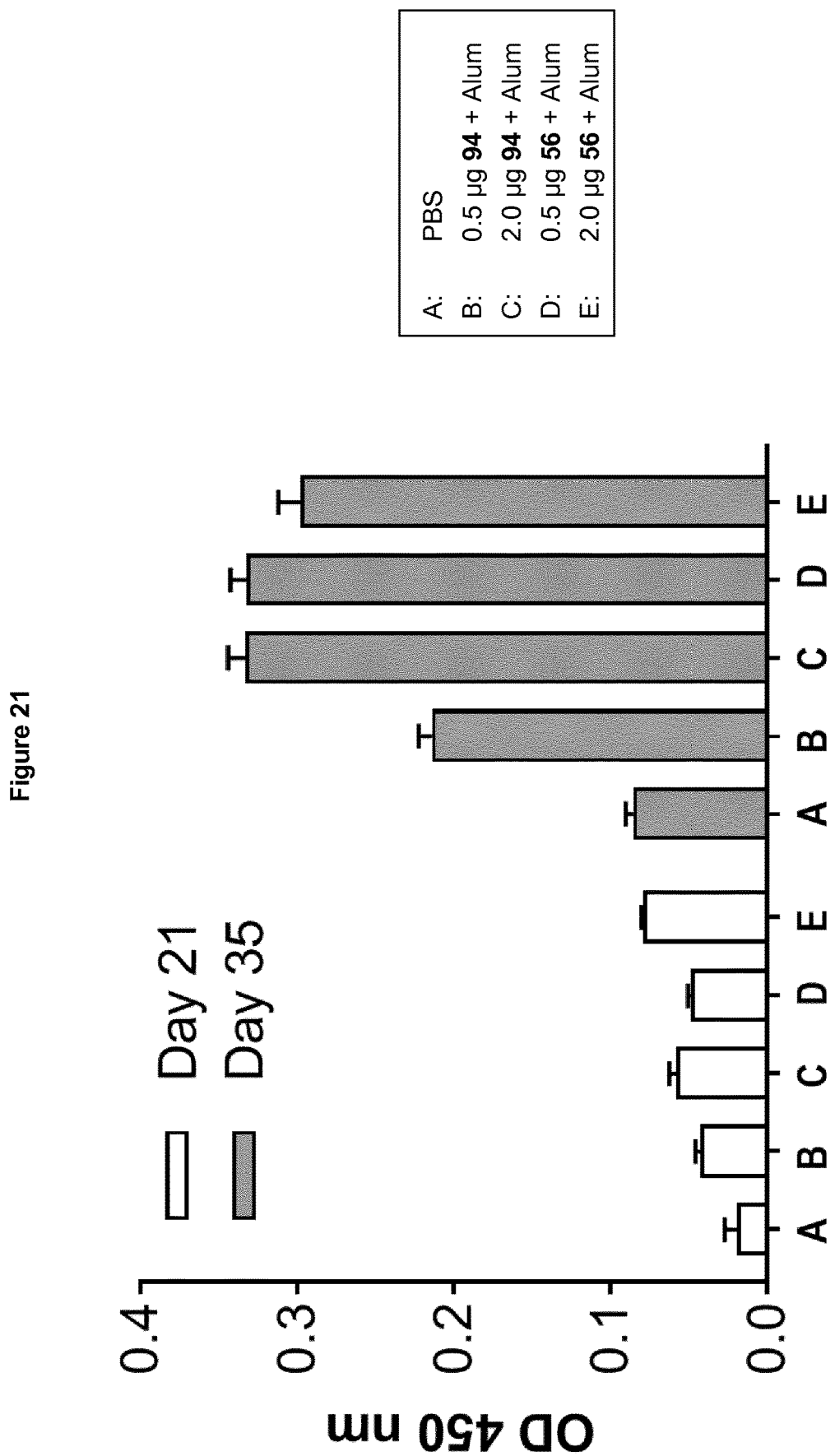
FIG. 21 shows ELISA titers of rabbit antisera against C. difficile strain 630. Mice (7 or 8 animals per study arm) were immunized two times (days 0, 14, 28) subcutaneously with either conjugate 94 or conjugate 56 at a dose of 0.5 or 2 μg glycan antigen per injection. PBS served as negative control and aluminum hydroxide (Alum) adjuvant was used for all immunizations. Pooled sera from days 21 and 35 were tested for total IgG against formalin-inactivated C. difficile bacteria (strain 630) coated onto the ELISA plates. It is evident from FIG. 21 that vaccination of mice with conjugate 94 or 56 induces IgG antibodies that bind to the surface of C. difficile bacteria, strain 630.
Figure 22:
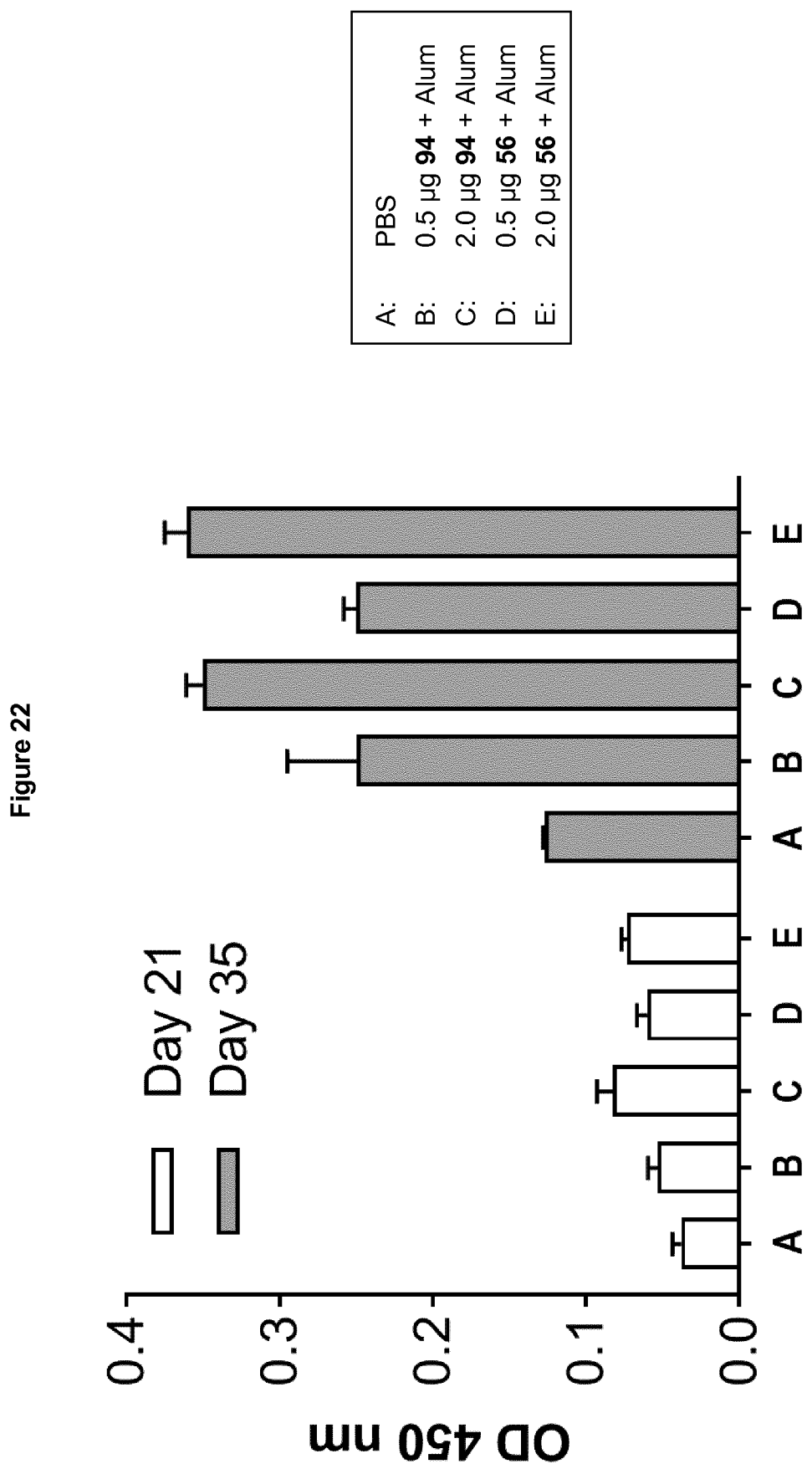
FIG. 22 shows ELISA titers of rabbit antisera against C. difficile strain R20291. Mice (7 or 8 animals per study arm) were immunized two times (days 0, 14, 28) subcutaneously with either conjugate 94 or 56 at a dose of 0.5 or 2 μg glycan antigen per injection. PBS served as negative control and aluminum hydroxide (Alum) adjuvant was used for all immunizations. Pooled sera from days 21 and 35 were tested for total IgG against formalin-inactivated C. difficile bacteria (strain R20291) coated onto the ELISA plates. It is evident from FIG. 22 that vaccination of mice with conjugate 94 or 56 induces IgG antibodies that bind to the surface of C. difficile bacteria, strain 630.
Figure 23:
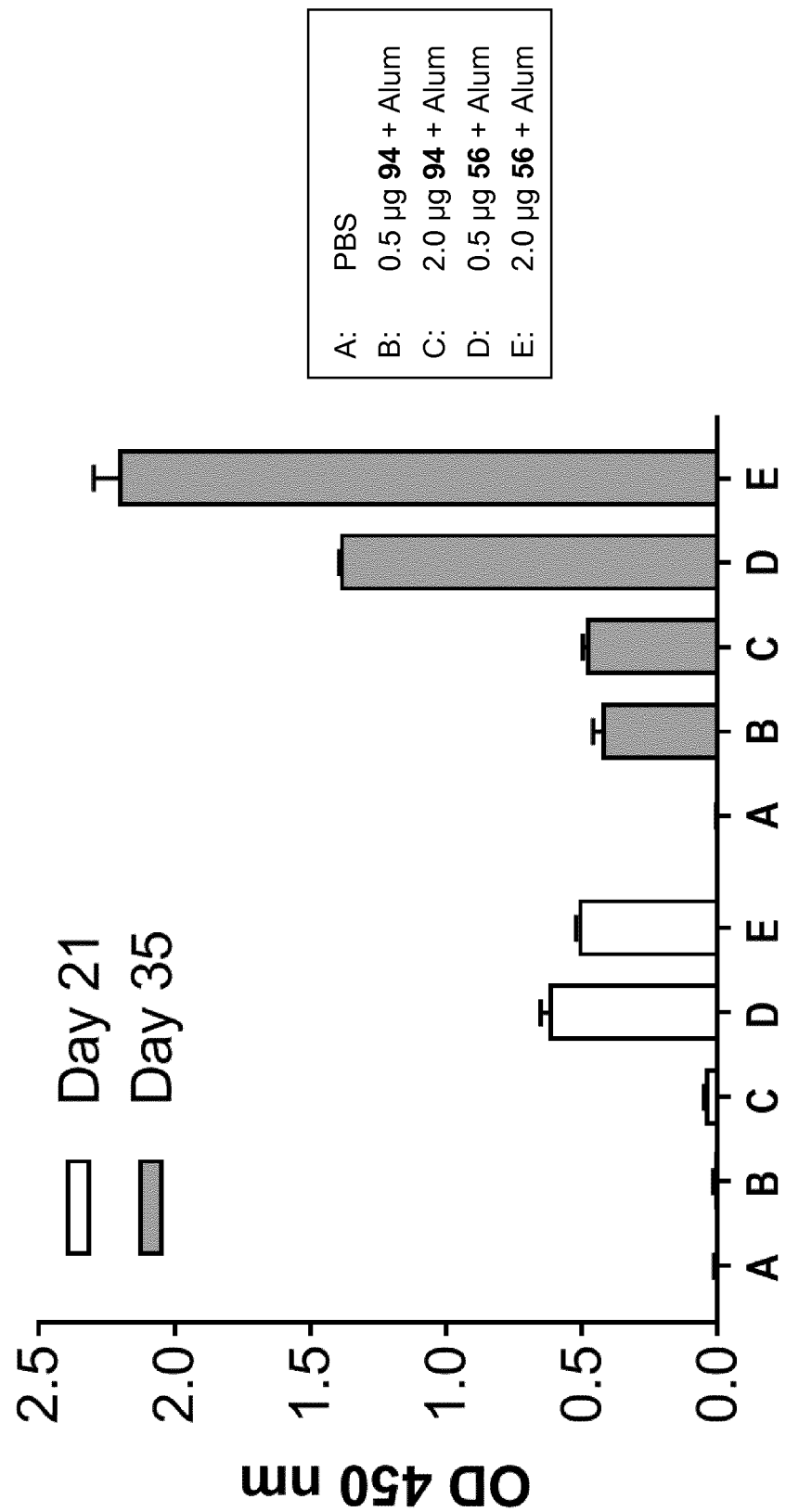
FIG. 23 shows ELISA titers of mouse antisera against synthetic C. difficile PS-II antigens. Mice (7 or 8 animals per study arm) were immunized two times (days 0, 14, 28) subcutaneously with either conjugate 94 or conjugate 56 at a dose of 0.5 or 2 μg glycan antigen per injection. PBS served as negative control and aluminum hydroxide (Alum) adjuvant was used for all immunizations. Pooled sera from days 21 and 35 were tested for total IgG against the respective synthetic C. difficile glycan antigen that was used for immunization. It is evident from FIG. 23 that vaccination of mice with conjugate 94 or 56 induces IgG antibodies that bind to the synthetic immunogens. Further, addition of Alum adjuvant leads to higher overall IgG titers.

Results:

Serum IgG from immunized rabbits recognizes the immunogen (FIG. 20), the isolated PS-II polysaccharide (FIGS. 19B and 19C) and *C. difficile* strains 630 (FIGS. 16 and 17), R20291 (FIG. 18) and VPI10463 (FIG. 19A). Serum IgG from immunized mice recognizes the respective immunogens (FIG. 23) and *C. difficile* strains 630 (FIG. 21) and R20291 (FIG. 22).

The herein provided data demonstrate that after immunization with a conjugate of the present invention, particularly conjugates 56 and 94, functional antibodies against oligosaccharides of the present invention as well as against the natural *C. difficile* PS-II polysaccharide, isolated and on the surface of bacteria, were elicited in rabbits and mice. These findings indicate the potential of these antibodies to confer protection infections with *C. difficile*.

The ELISA data further proves that the conjugates of the present invention are immunogenic and induce high antibody titers. Hence, ELISA analysis shows that the saccharides of the present invention are immunogenic in rabbits and mice and generate cross-reactive antibodies.

The invention claimed is:

1. A saccharide of general formula (I)

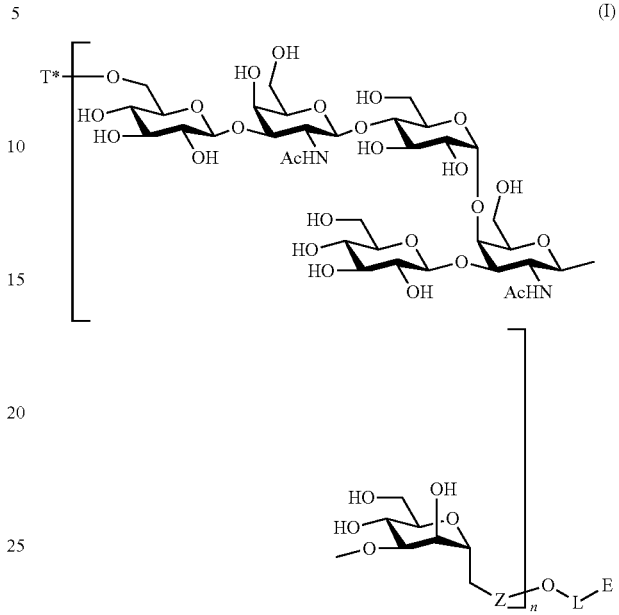

wherein
n is an integer selected from 1, 2, 3, 4, 5, 6, 7, 8, 9 or 10;
T*- is —P(=O)(OH)$_2$, —P(=O)(O$^-$)(OH) or —PO$_3^{2-}$;
Z is selected from

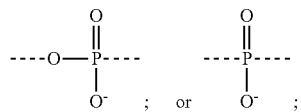

L is a linker;
E is —NH$_2$, —N$_3$, —CN, —O—NH$_2$, —CH=CH$_2$, —C≡CH, —Br, —Cl, —I, —CO$_2$R', —CONH—NH$_2$, —SH, —OH or —SAc; and
R' is —H, —Me, Et, 4-nitrophenyl, pentafluorophenyl, or N-succinimidyl;
or a diastereoisomer or a pharmaceutically acceptable salt thereof.

2. The saccharide according to claim 1, wherein Z is

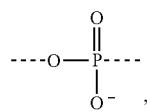

or a pharmaceutically acceptable salt thereof.

3. The saccharide according to claim 1, wherein
-L- is -L$^a$-, -L$^a$-L$^e$-, -L$^a$-L$^b$-L$^e$-, or -L$^a$-L$^d$-L$^e$-;
-L$^a$- is —(CH$_2$)$_o$—, —(CH$_2$—CH$_2$—O)$_o$—C$_2$H$_4$—, or —(CH$_2$—CH$_2$—O)$_o$—CH$_2$;
-L$^b$- is —O—;
-L$^d$- is —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;
-L$^e$- is —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and
o, q, p1 and p2 are independently of each other an integer selected from 1, 2, 3, 4, 5, or 6,
or a pharmaceutically acceptable salt thereof.

4. The saccharide according to claim 1 selected from the group consisting of:
(I′a-1)
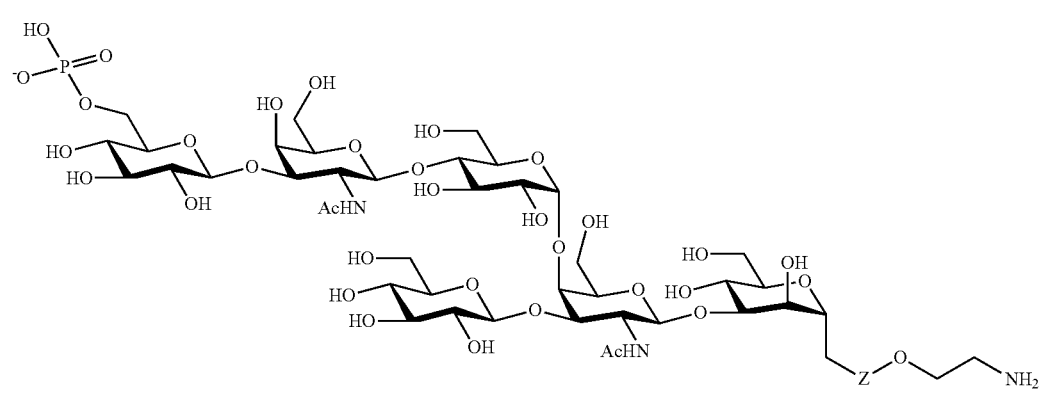
(I′a-2)
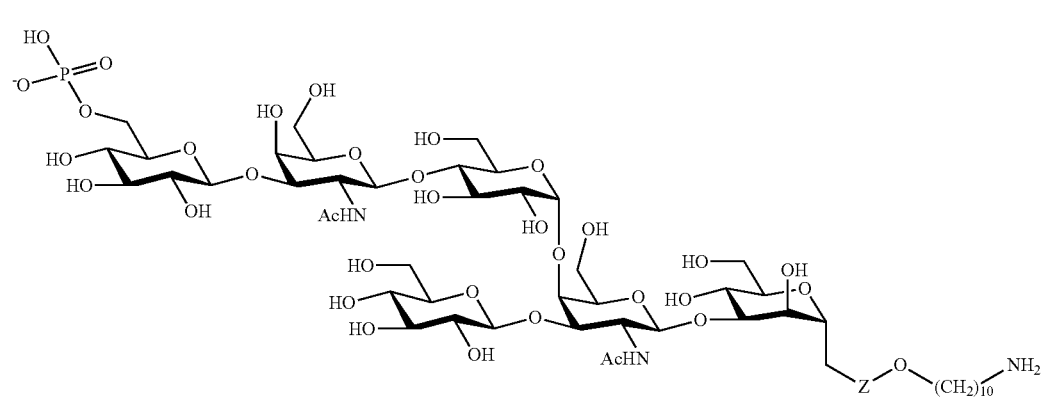
(I′a-3)
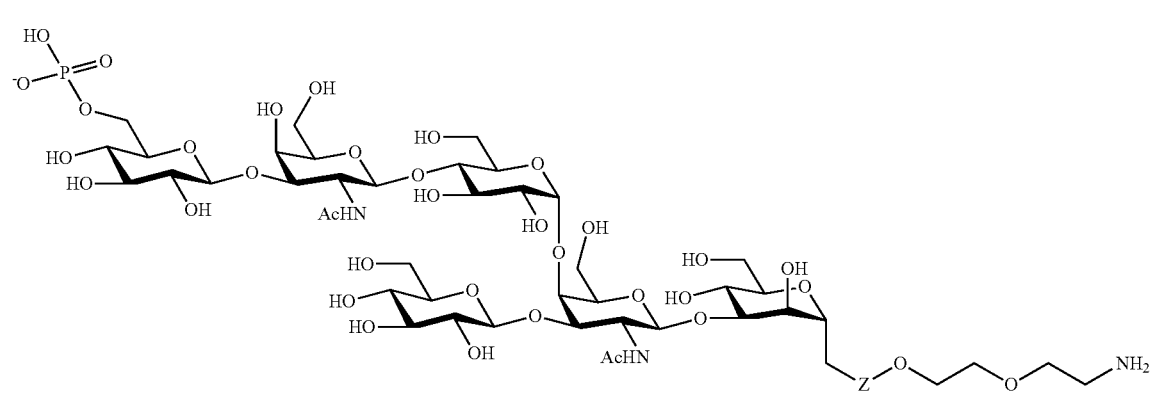
(I′a-4)
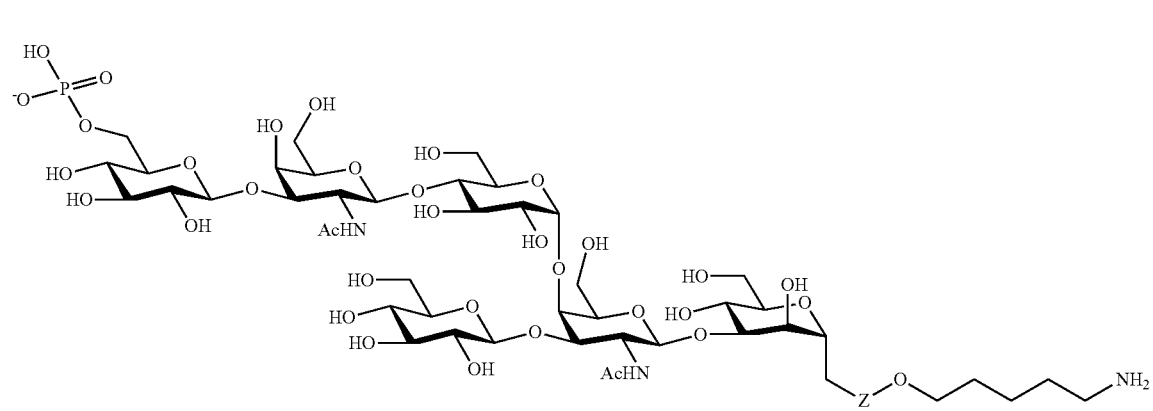

(I'a-5)
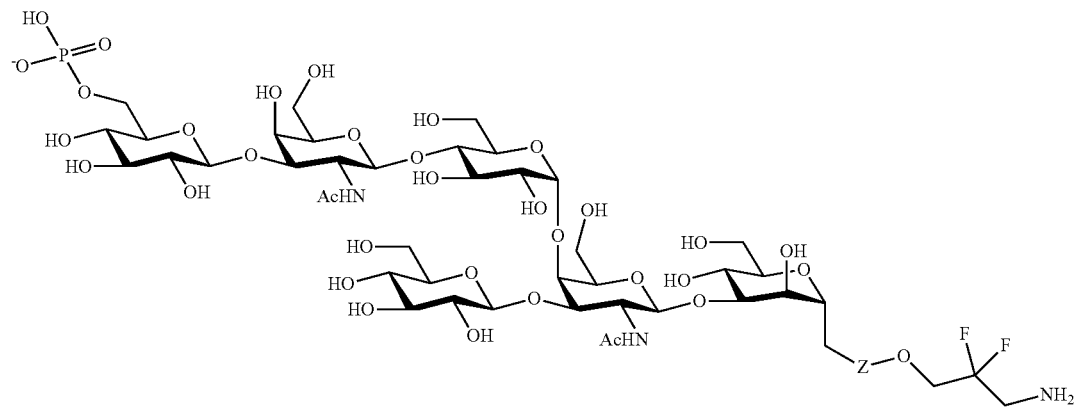
(I'a-6)
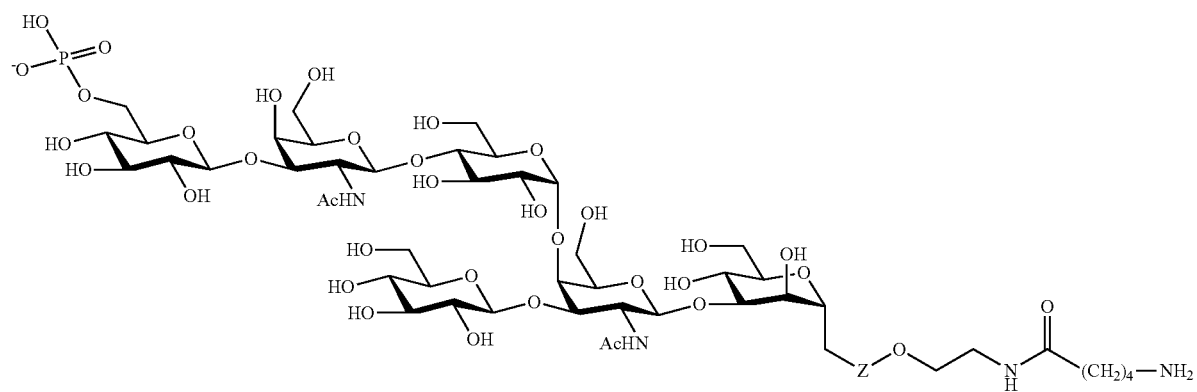
(I'a-7)
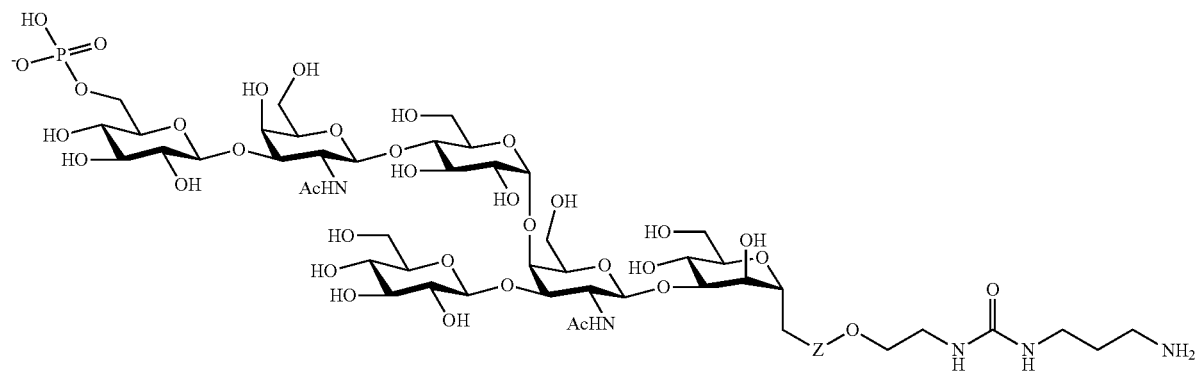
(I'a-8)
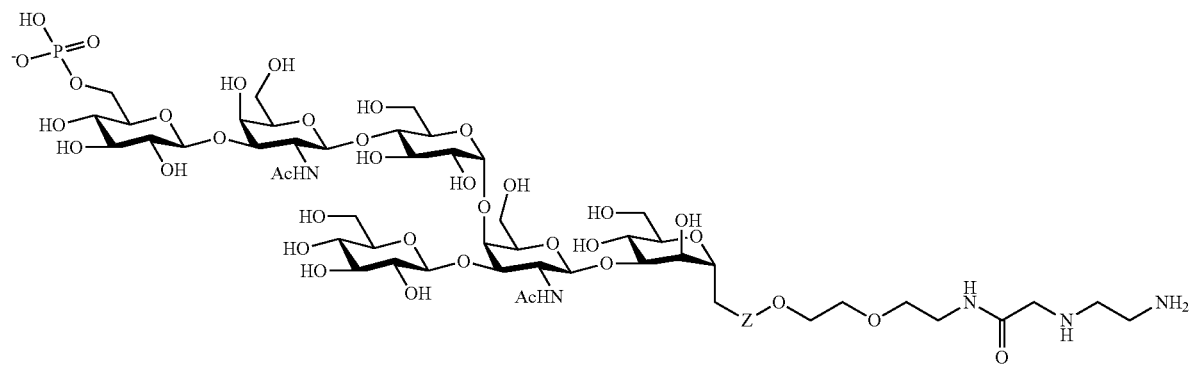

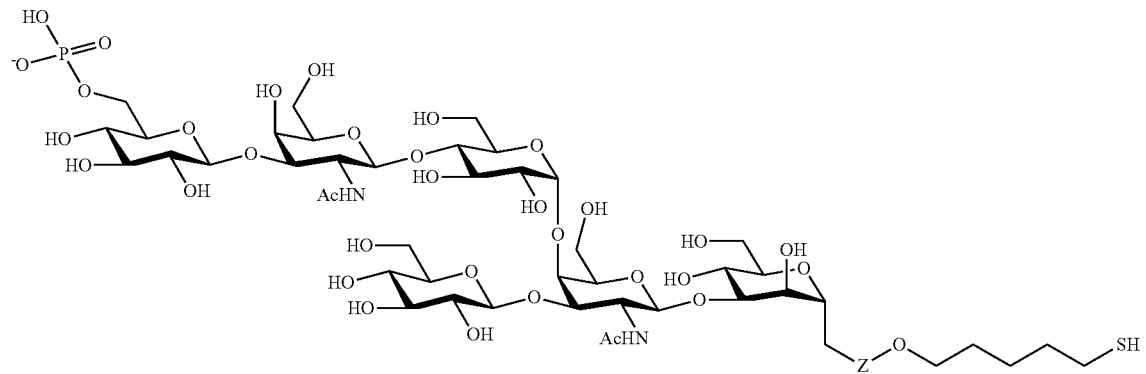
(I'a-9)
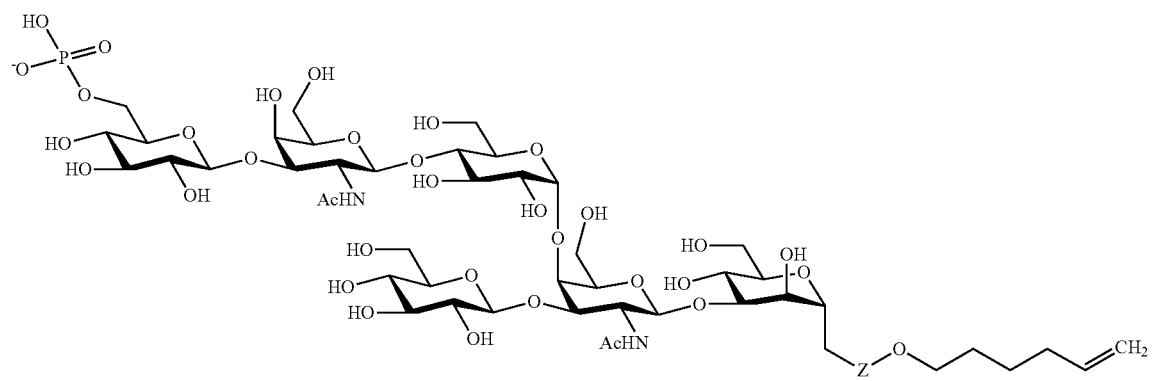
(I'a-10)
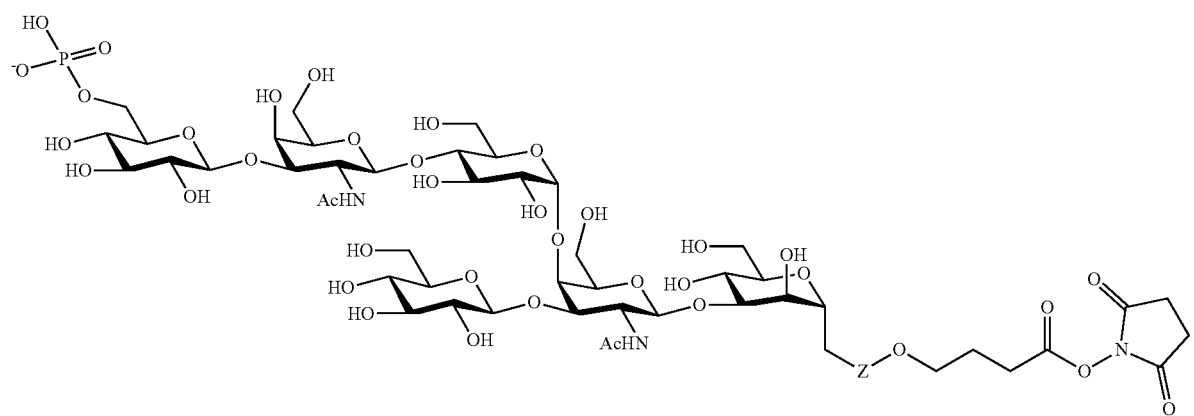
(I'a-11)

(I'a-12)
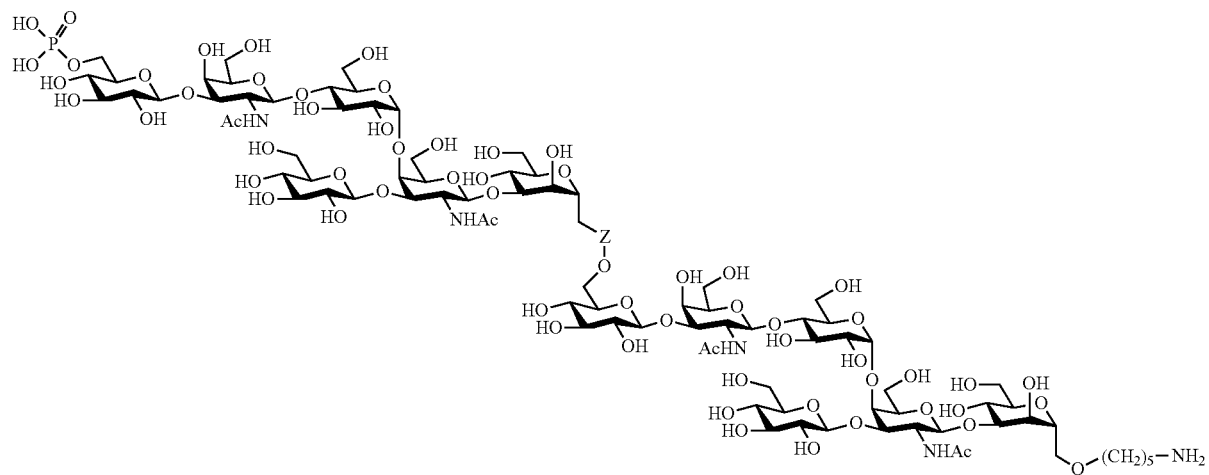
(I'a-13)
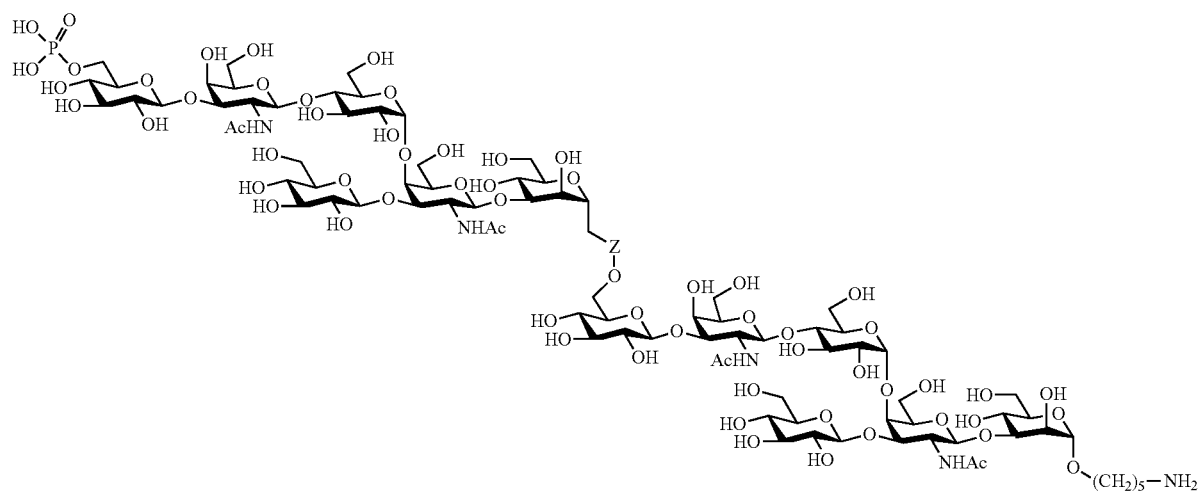
(I'b-1)
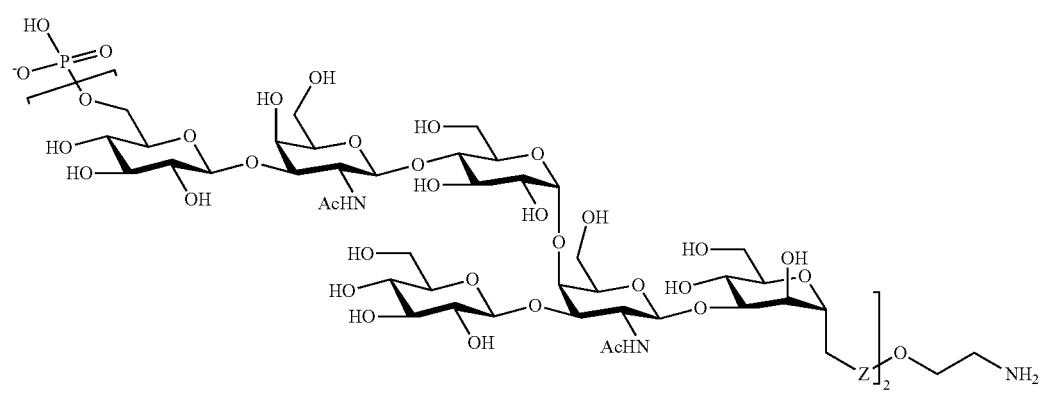

(I'b-2)
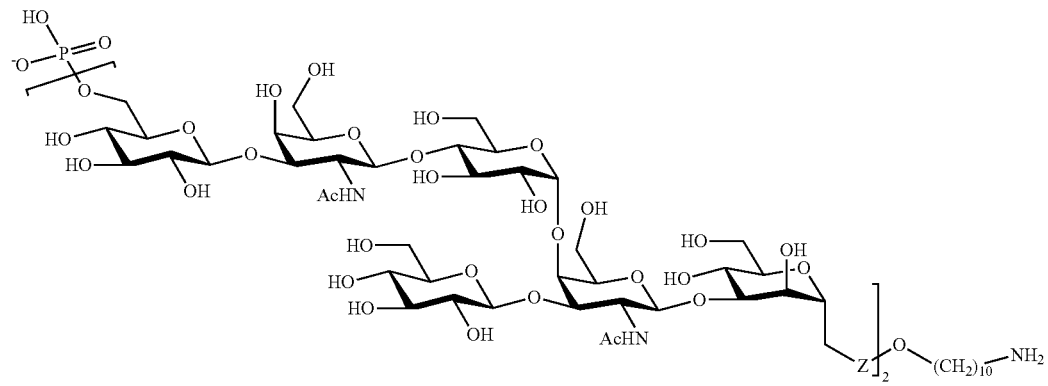
(I'b-3)
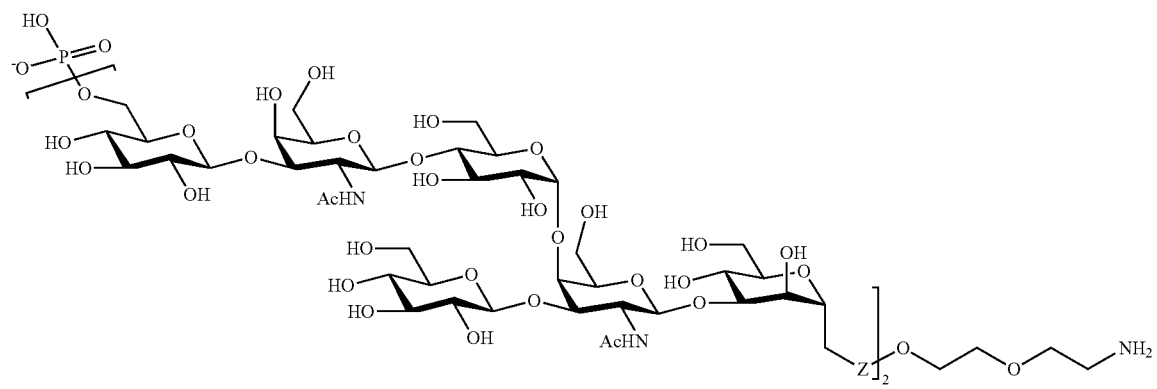
(I'b-4)
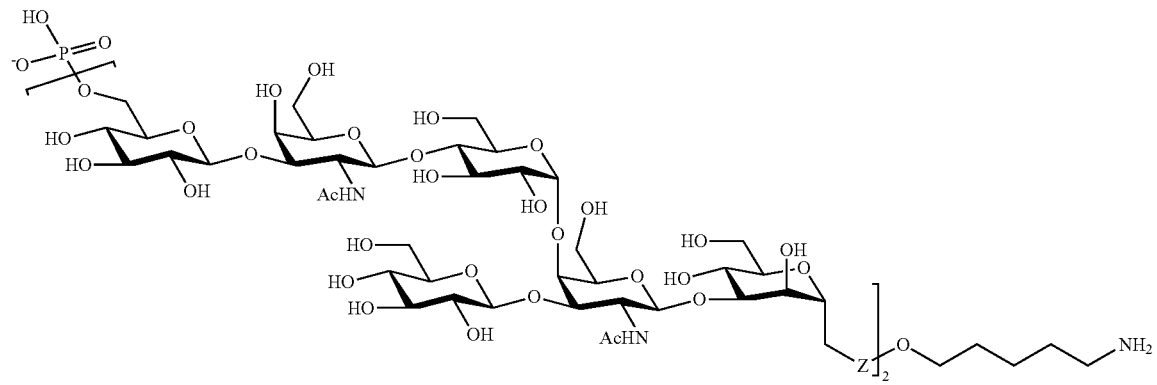
(I'b-5)
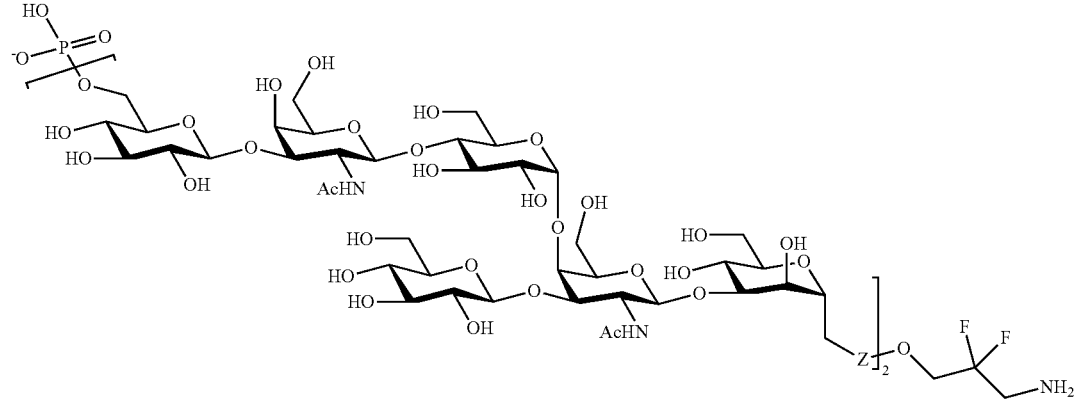

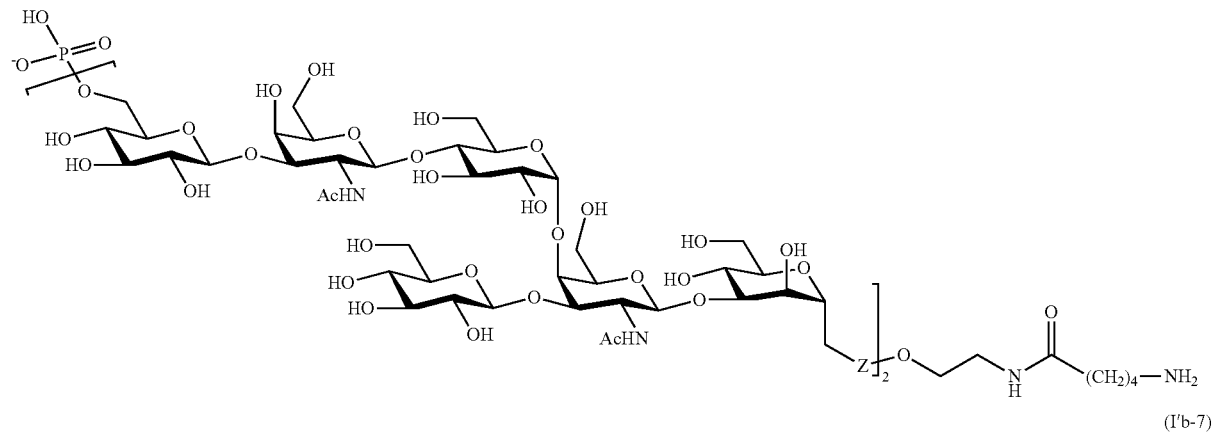
(I'b-6)
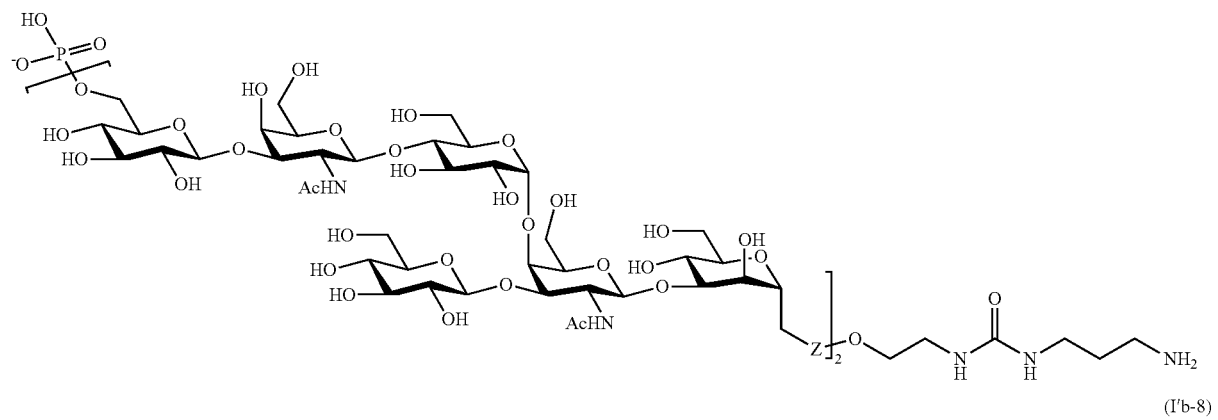
(I'b-7)
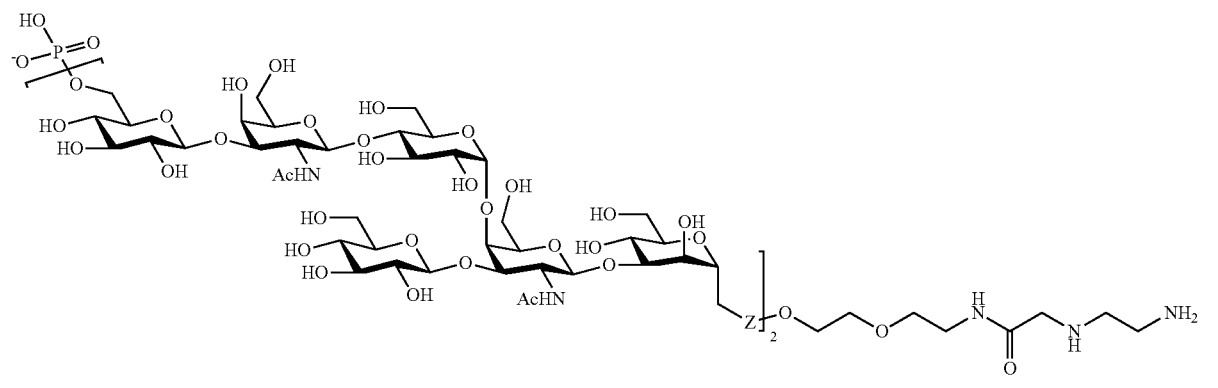
(I'b-8)
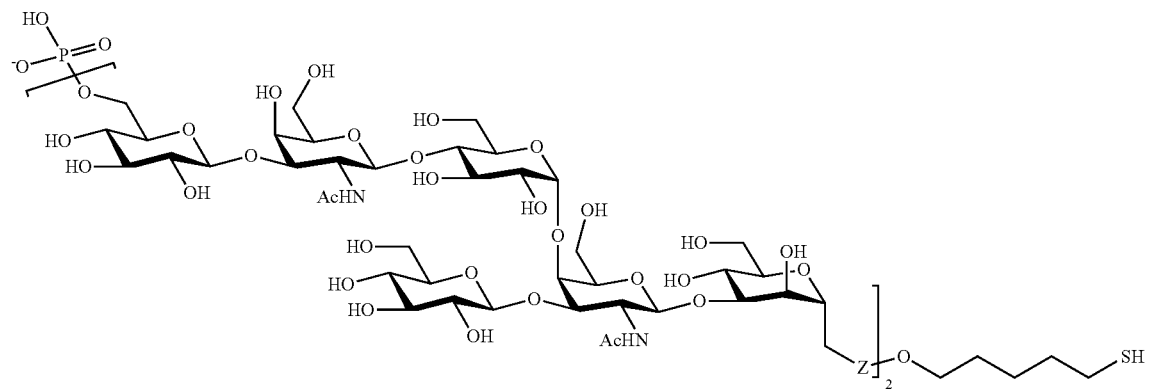
(I'b-9)

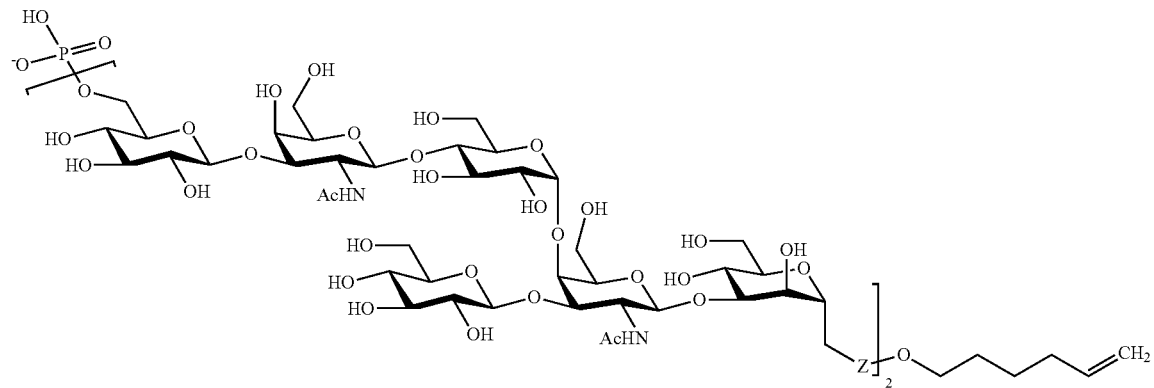
(I'b-10)
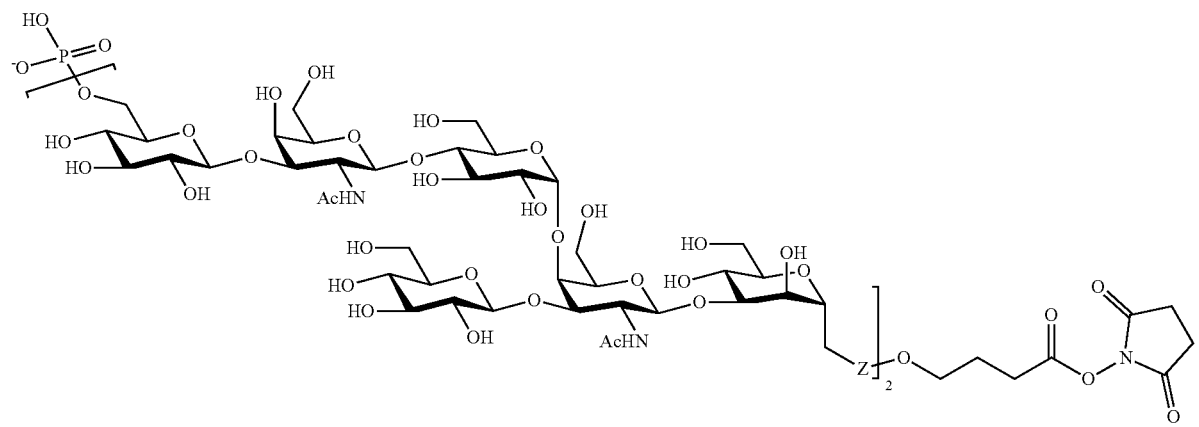
(I'b-11)
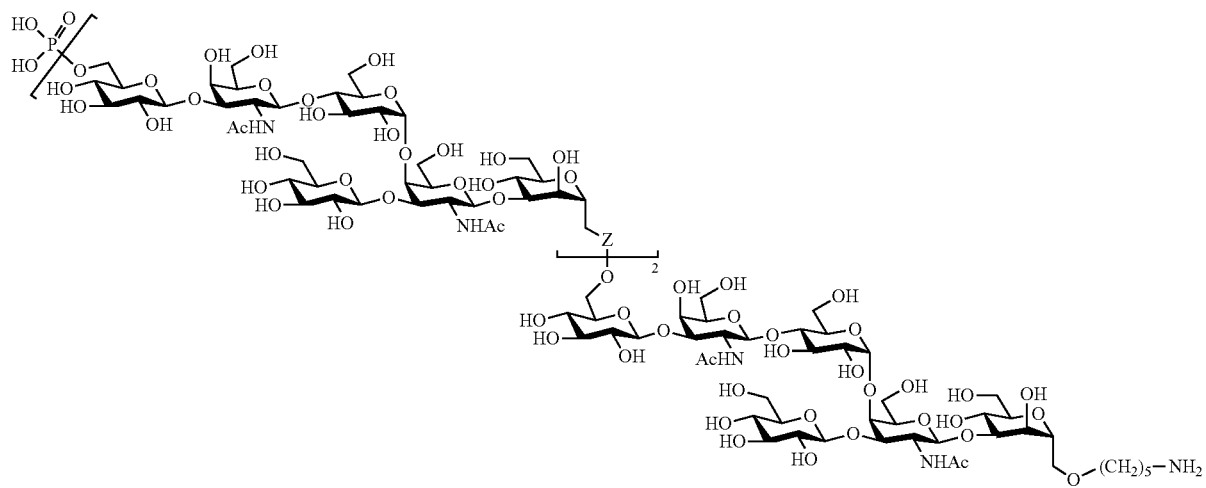
(I'b-12)

-continued
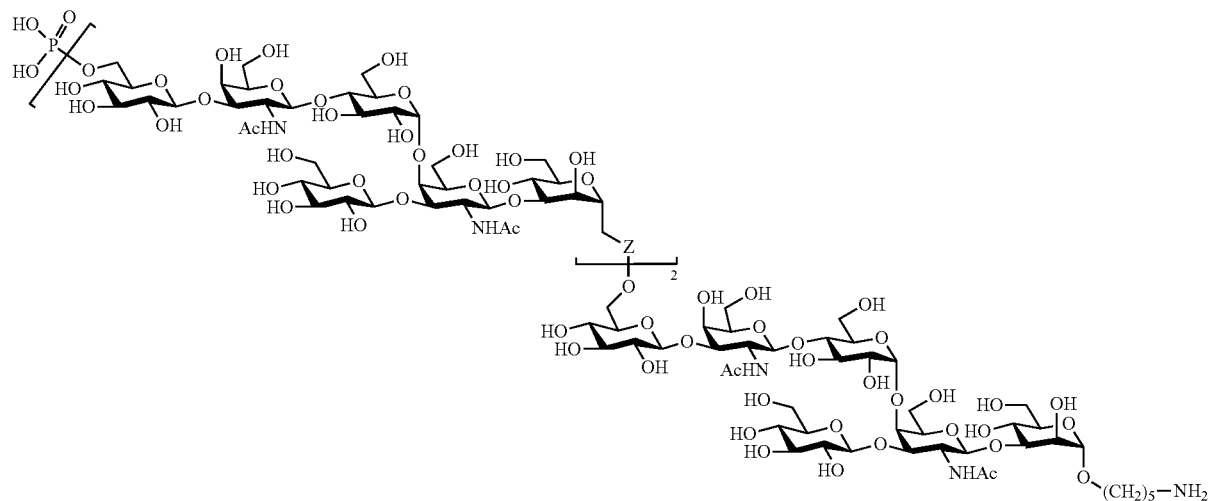
(I'b-13)
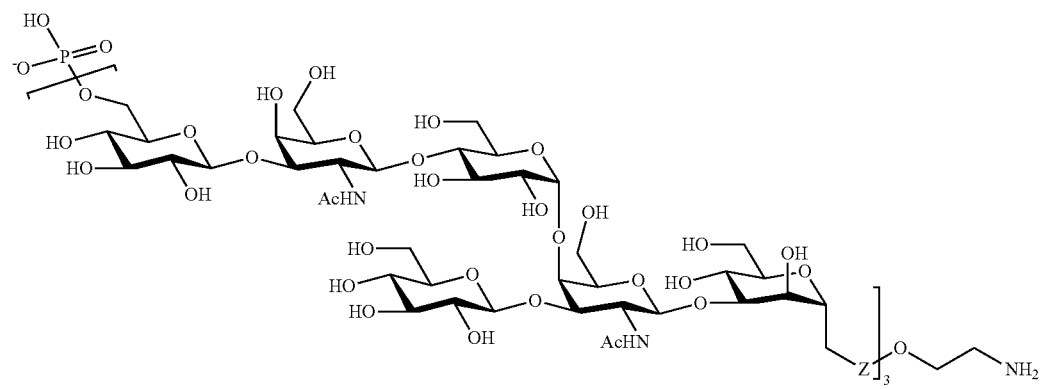
(I'c-1)
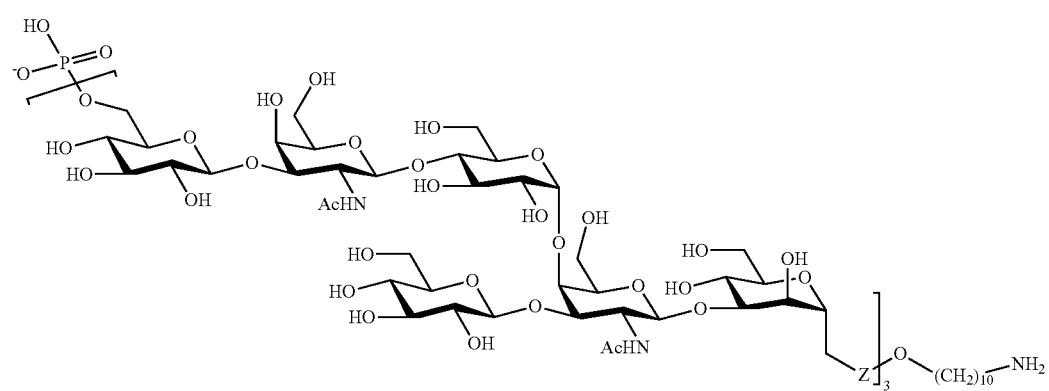
(I'c-2)

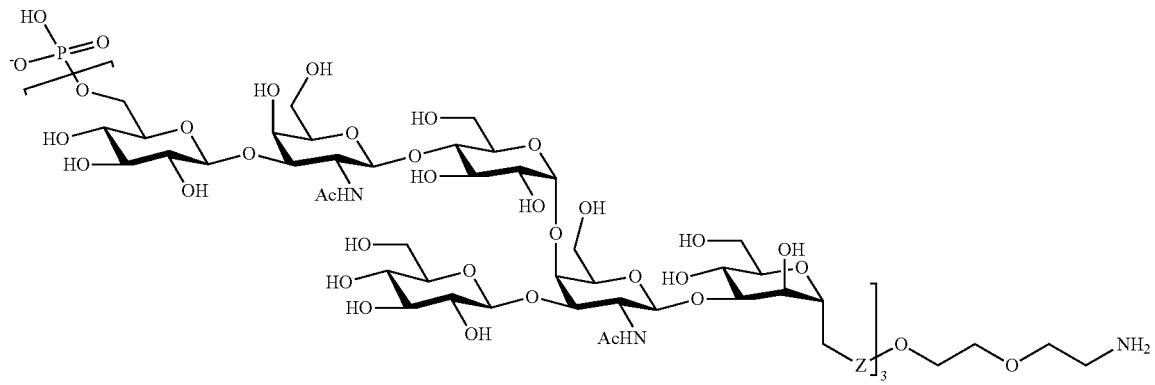
(I'c-3)
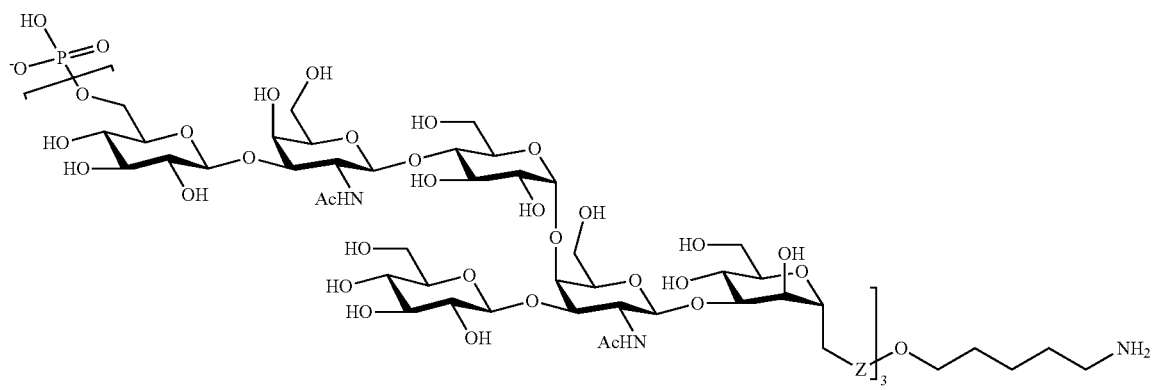
(I'c-4)
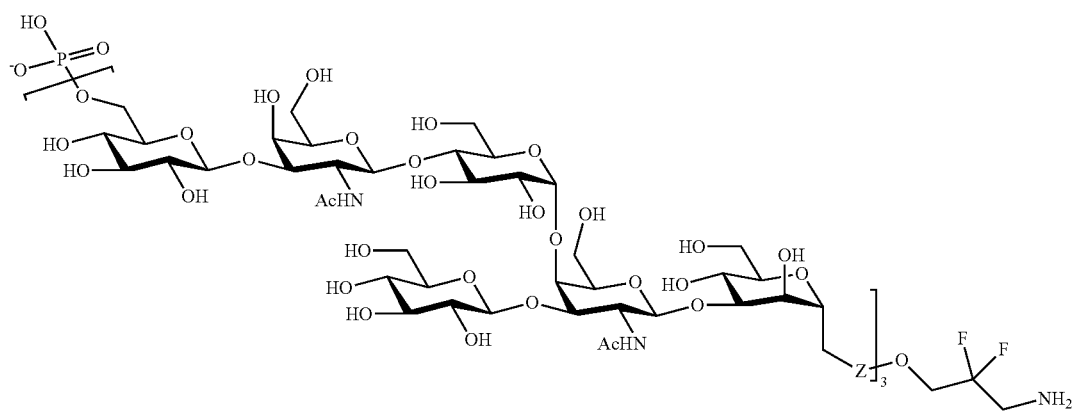
(I'c-5)
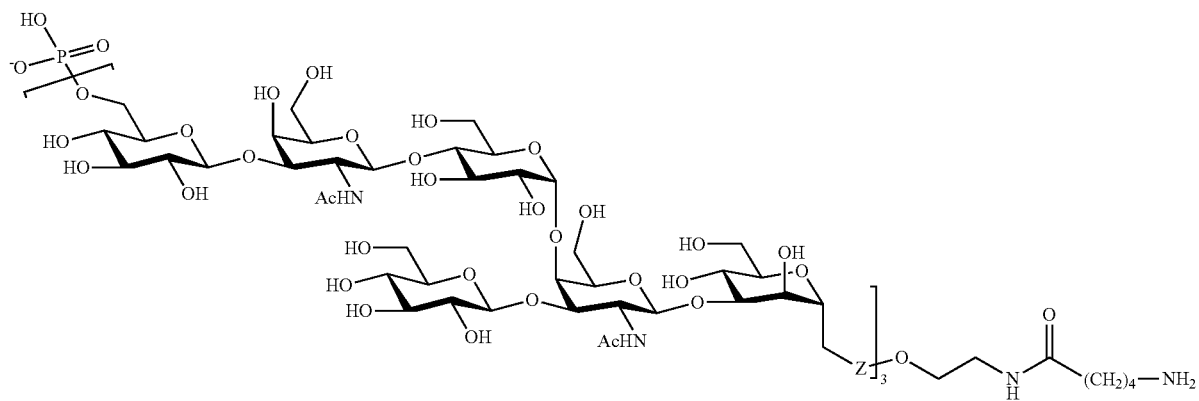
(I'c-6)

-continued
(I'c-7)
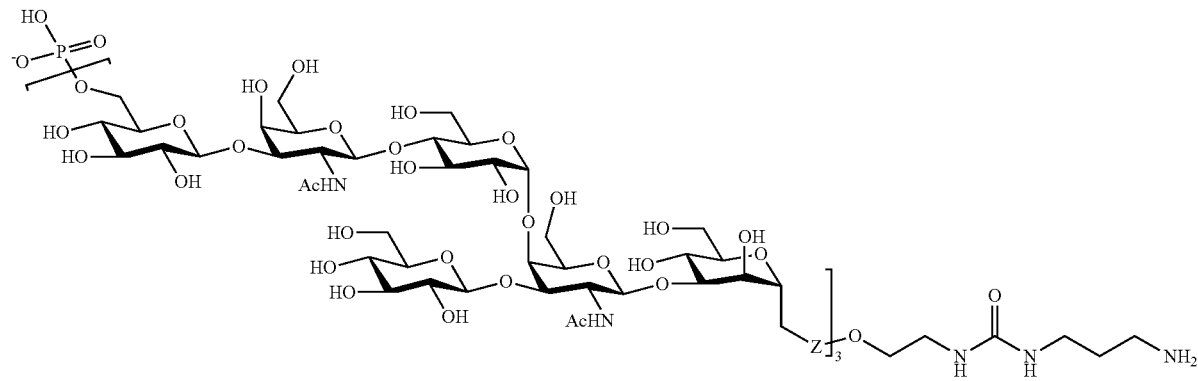
(I'c-8)
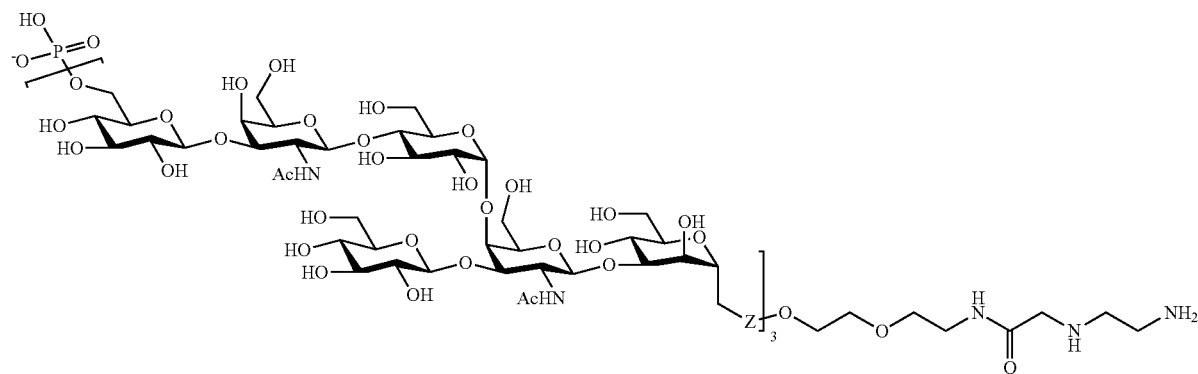
(I'c-9)
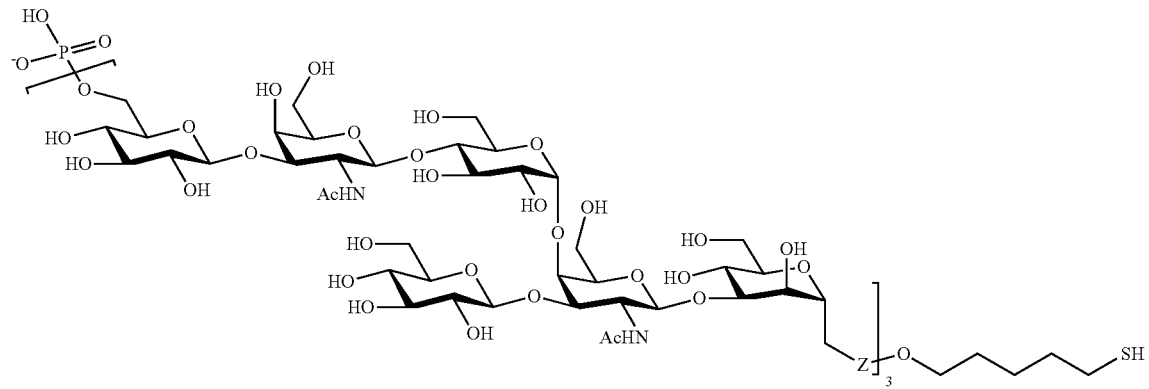
(I'c-10)
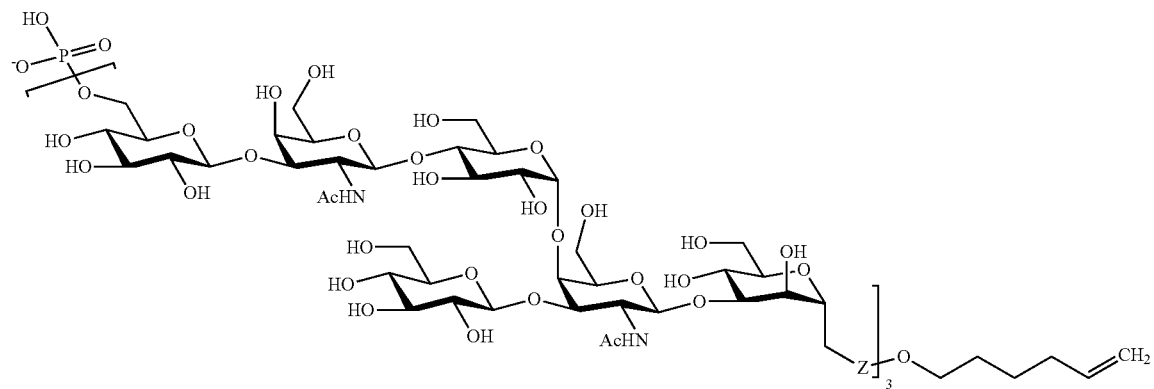

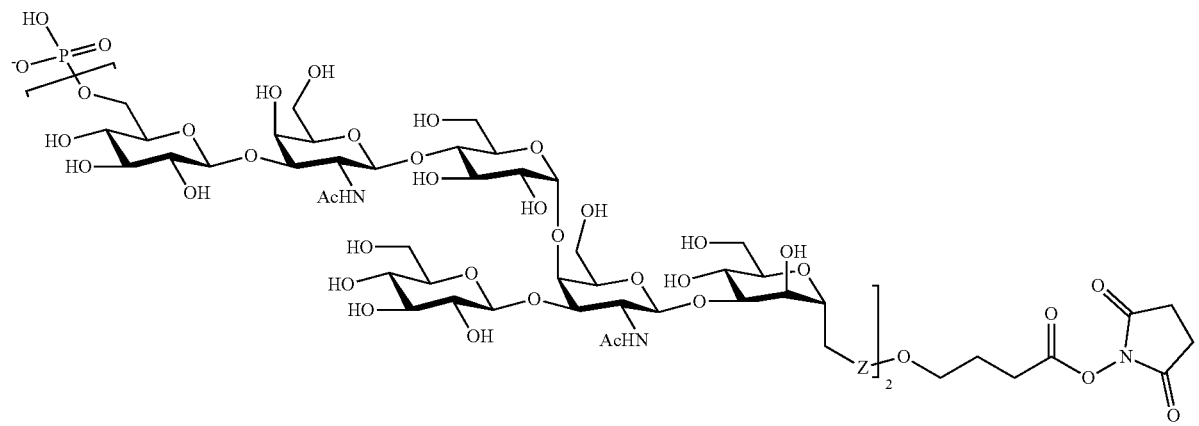
(I'c-11)
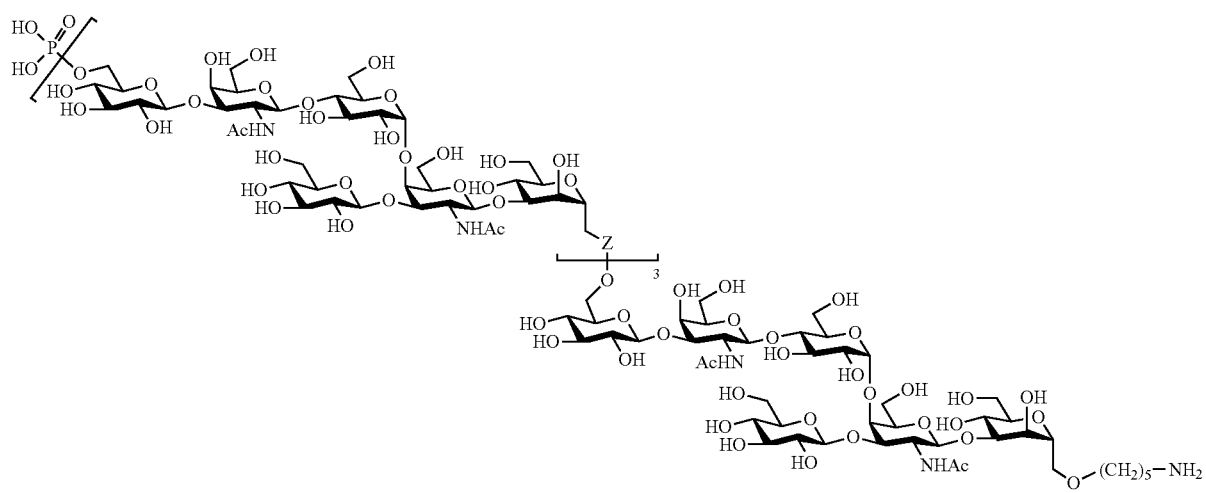
(I'c-12)
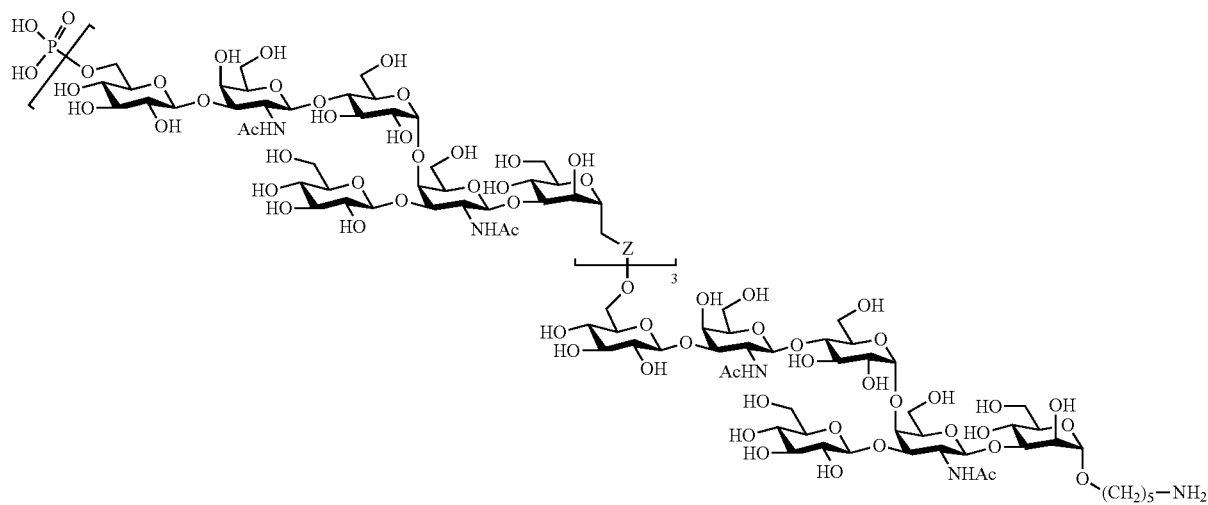
(I'c-13)

-continued
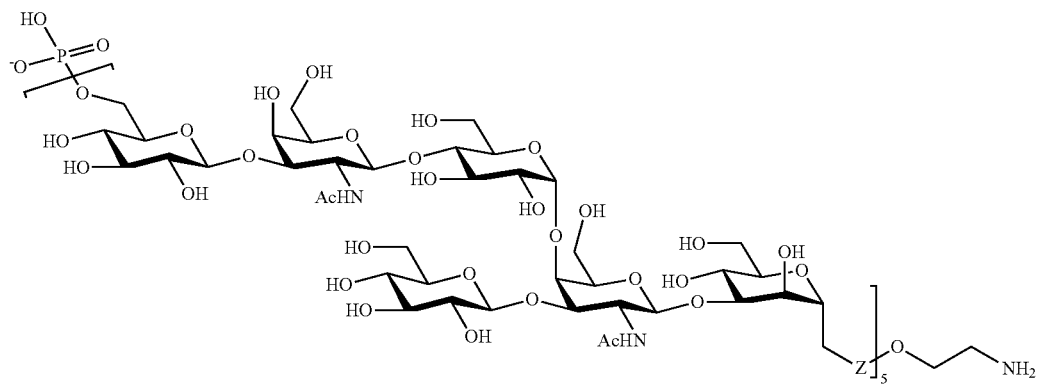
(I'd-1)
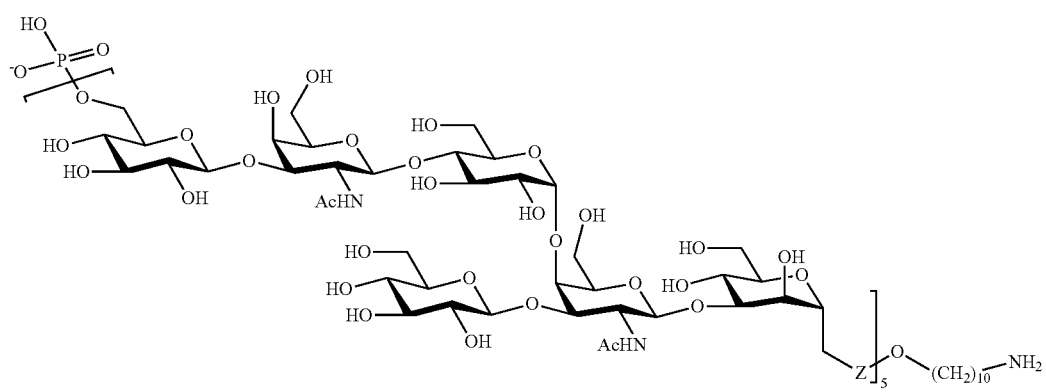
(I'd-2)
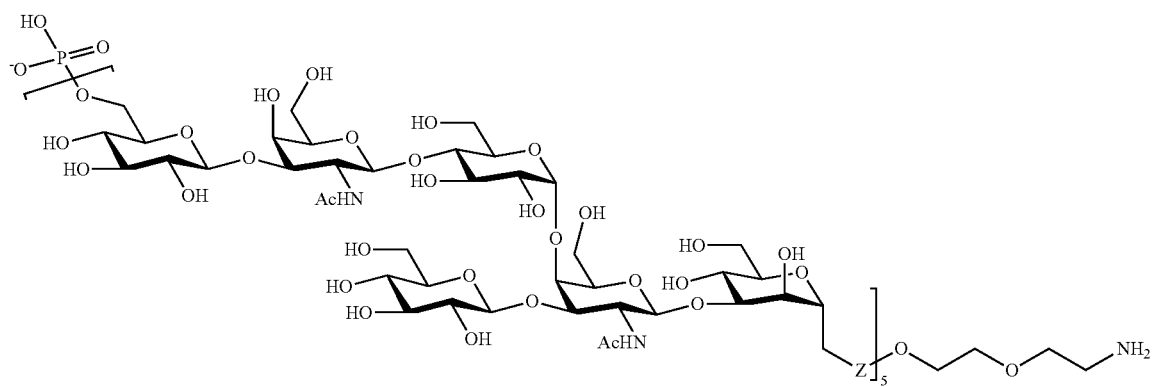
(I'd-3)
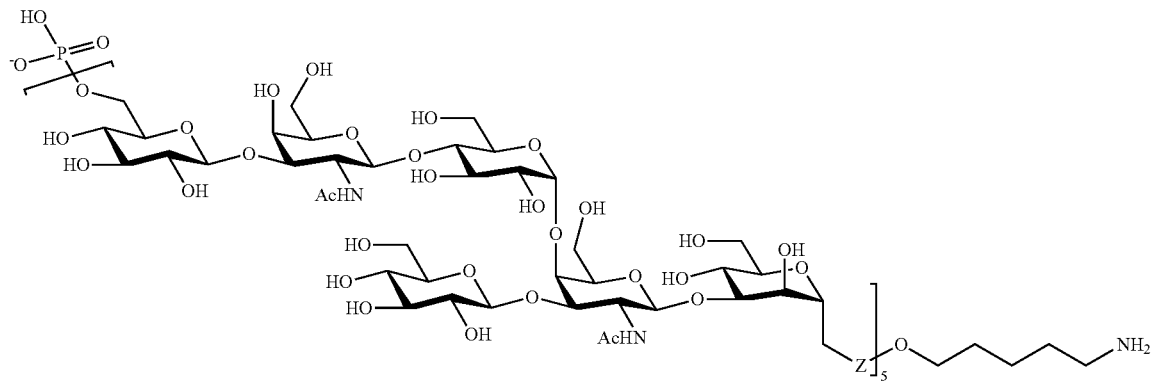
(I'd-4)

-continued
(I'd-5)
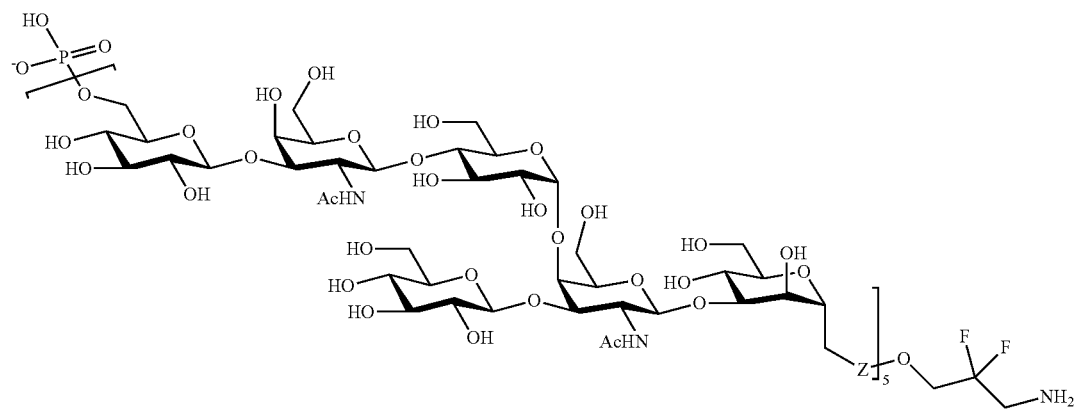
(I'd-6)
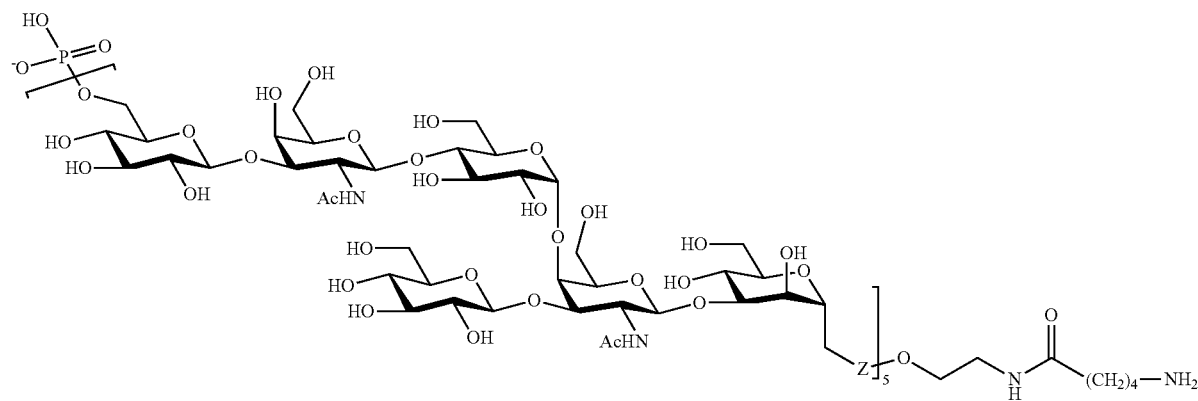
(I'd-7)
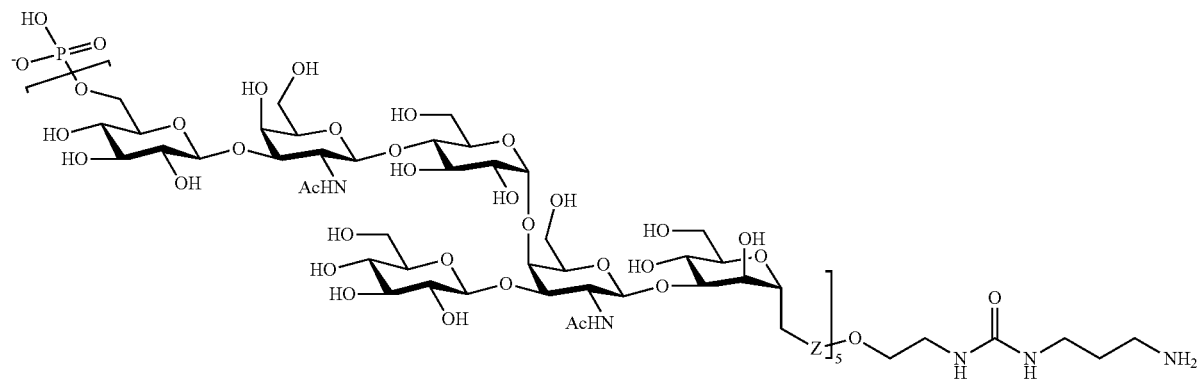
(I'd-8)
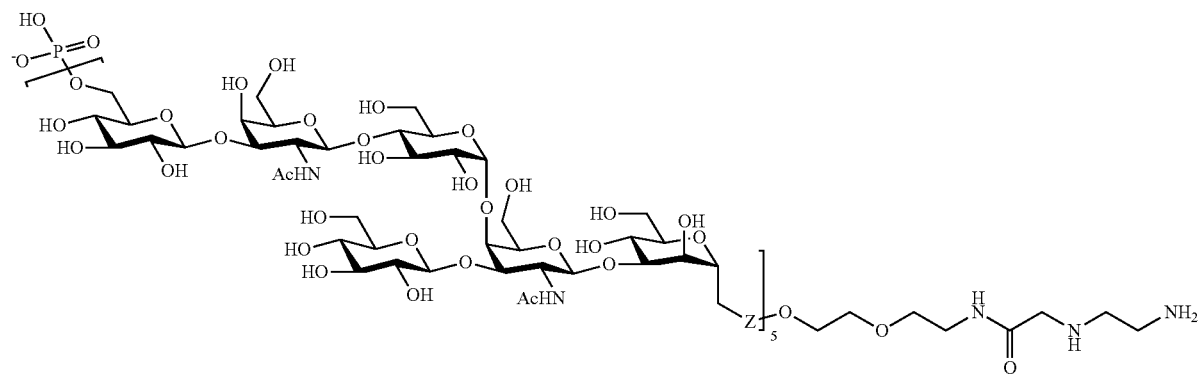

(I'd-9)
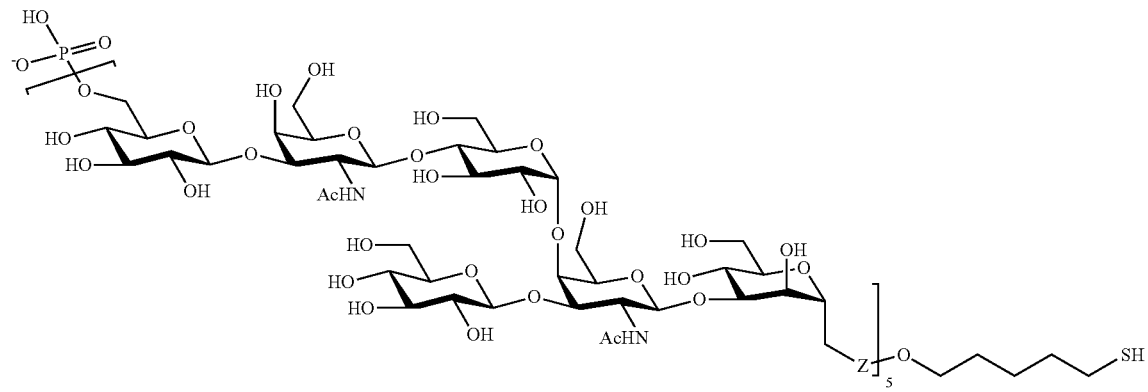
(I'd-10)
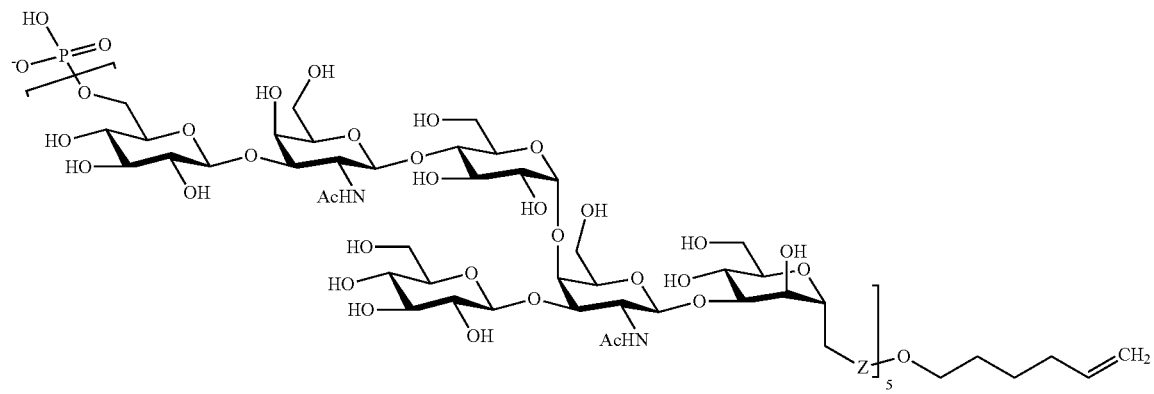
(I'd-11)
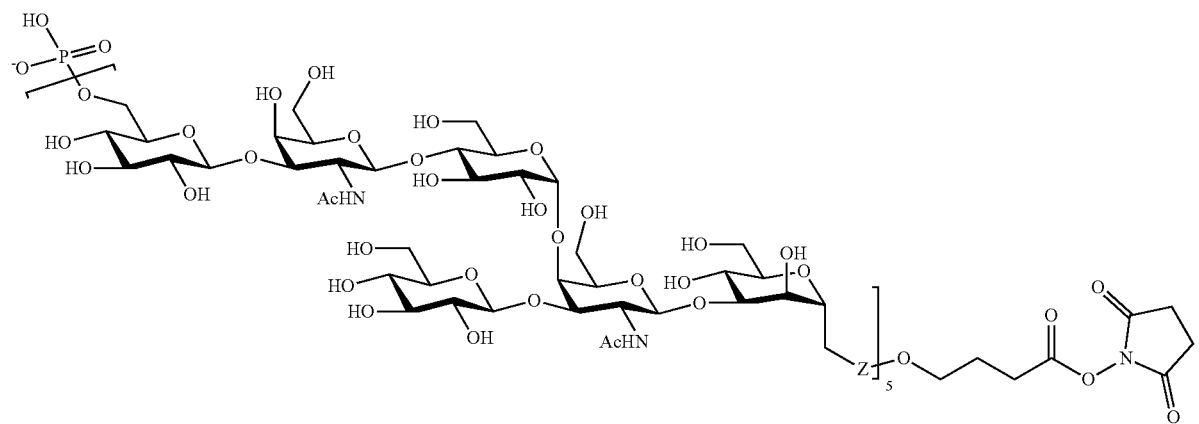

(I'd-12)
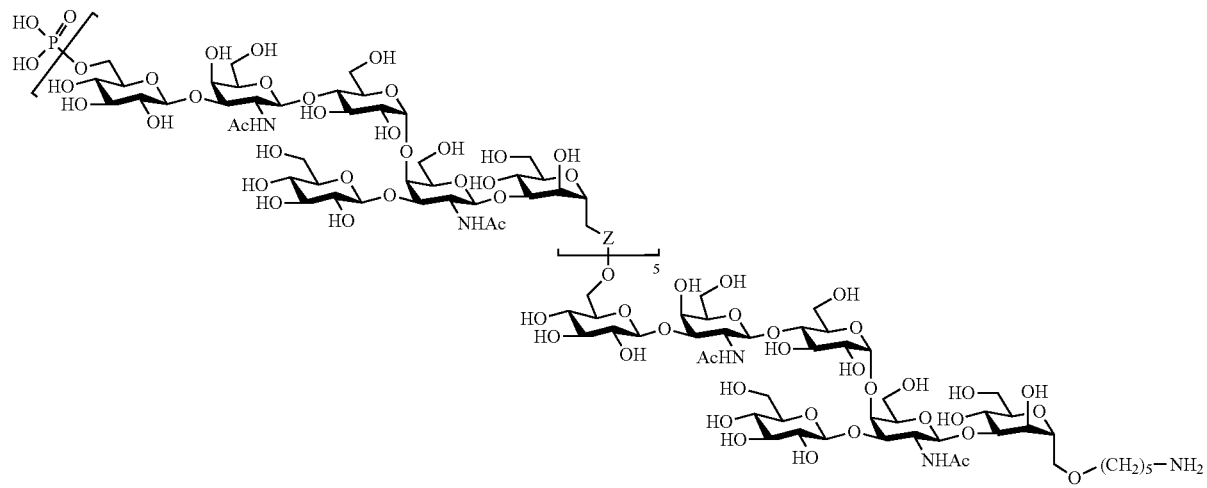
(I'd-13)
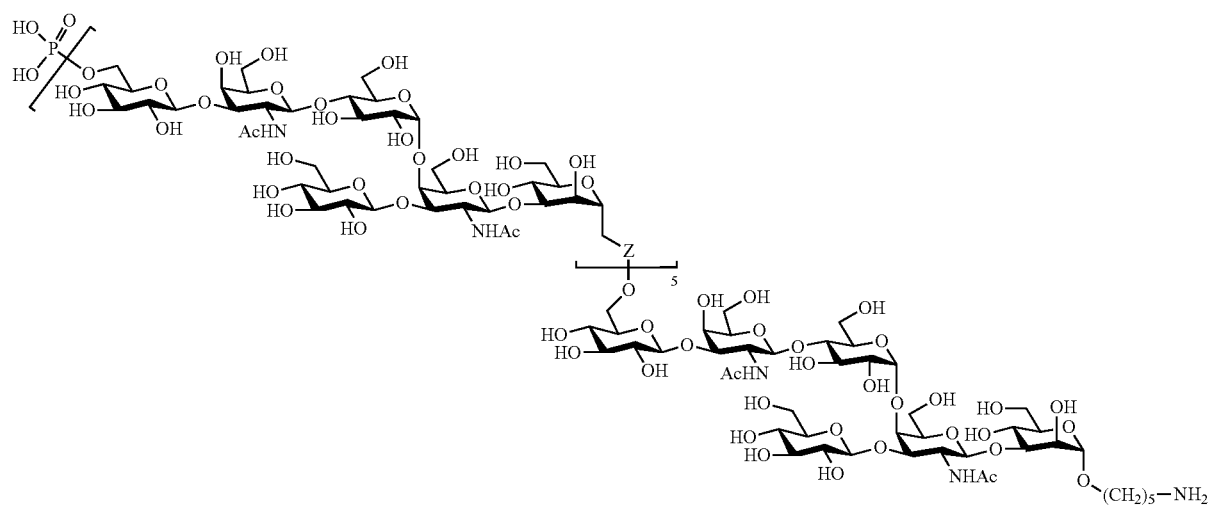
wherein Z is selected from
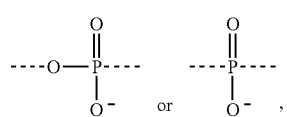
or a pharmaceutically acceptable salt thereof.

5. The saccharide according to claim 4 of formula (I'a-4) or formula (I'b-4),
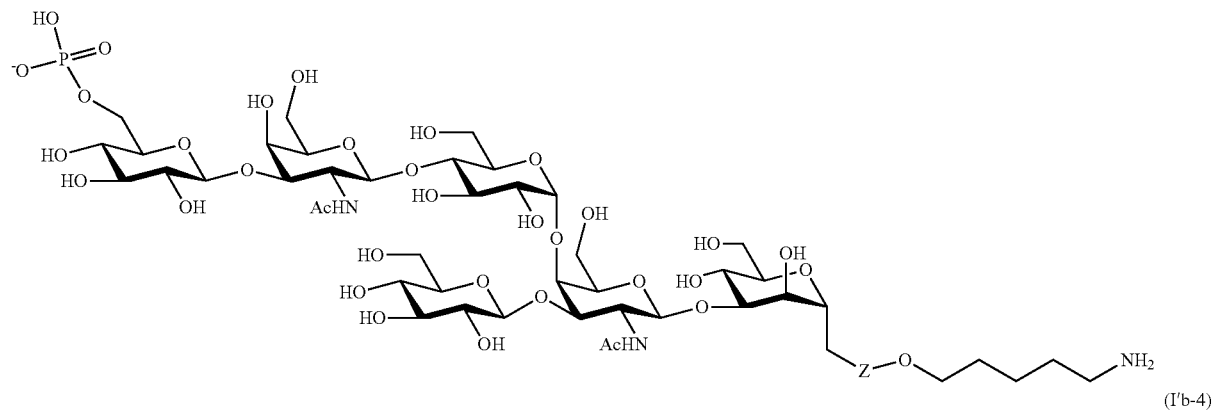
(I'a-4)
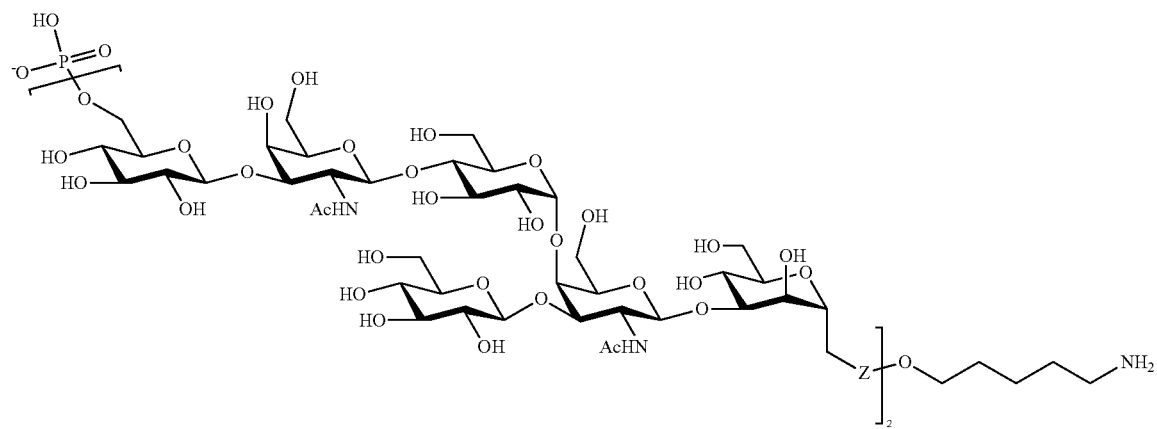
(I'b-4)
wherein Z is
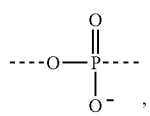
or a pharmaceutically acceptable salt thereof.
6. A conjugate comprising a saccharide of general formula (I)
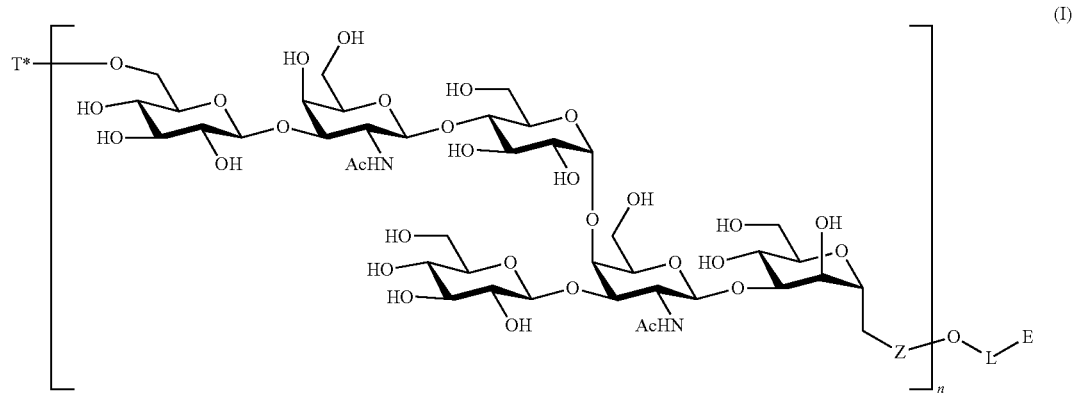
(I)

wherein
n is an integer selected from 1, 2, 3, 4, 5, 6, 7, 8, 9 or 10;
T*- is —P(=O)(OH)$_2$, —P(=O)(O$^-$)(OH) or —PO$_3$$^{2-}$;
Z is selected from

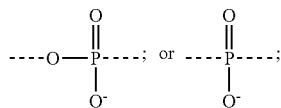

L is a linker;
E is —NH$_2$, —N$_3$, —CN, —O—NH$_2$, —CH=CH$_2$, —C≡CH, —Br, —Cl, —I, —CO$_2$R', —CONH—NH$_2$, —SH, —OH or —SAc; and
R' is —H, —Me, —Et, 4-nitrophenyl, pentafluorophenyl, or N-succinimidyl;
or a diastereoisomer or a pharmaceutically acceptable salt thereof;
covalently linked to an immunogenic carrier through the residue E of the —O-L-E group,
or a pharmaceutically acceptable salt thereof.

7. A conjugate of general formula (IV)

—W— is selected from:

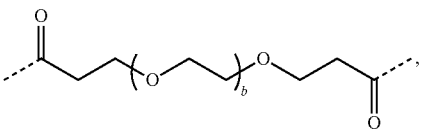

a is an integer selected from 1, 2, 3, 4, 5, 6, 7, 8, 9 or 10,
b is an integer selected from 1, 2, 3 or 4,
CP is a carrier protein;
n is an integer selected from 1, 2, 3, 4, 5, 6, 7, 8, 9 or 10;
T*- is —P(=O)(OH)$_2$, —P(=O)(O$^-$)(OH) or —PO$_3$$^{2-}$;

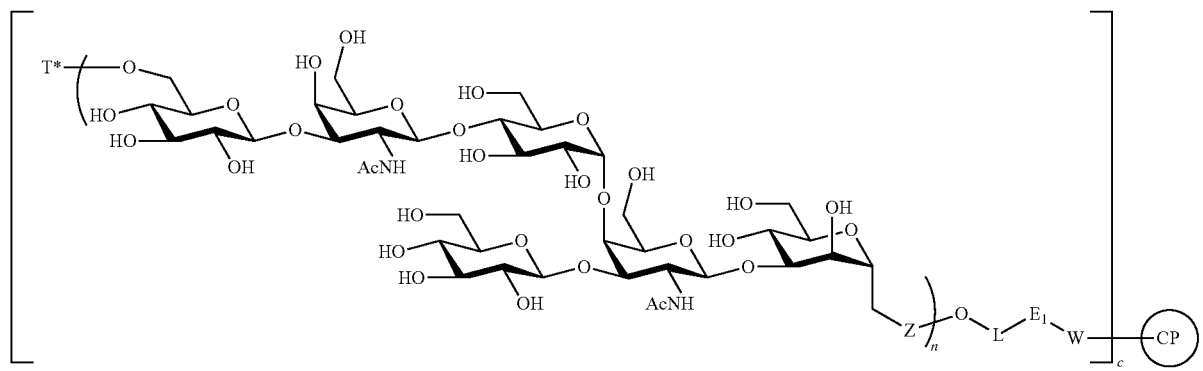

(IV)

wherein
c is between 2 and 18;
-E$_1$- is a covalent bond, —NH—, —O—NH—, —O—, —S—, —CO—, —CH=CH—, —CONH—, —CO—NHNH—,

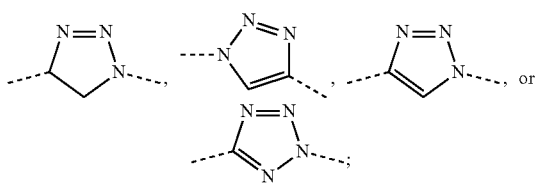

Z is selected from

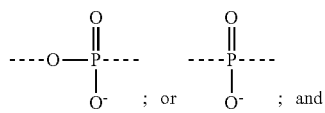

L is a linker,
or a pharmaceutically acceptable salt thereof.

8. The conjugate according to claim 7, wherein the conjugate has any one of the following formulae (IV-2) or (IV-4)

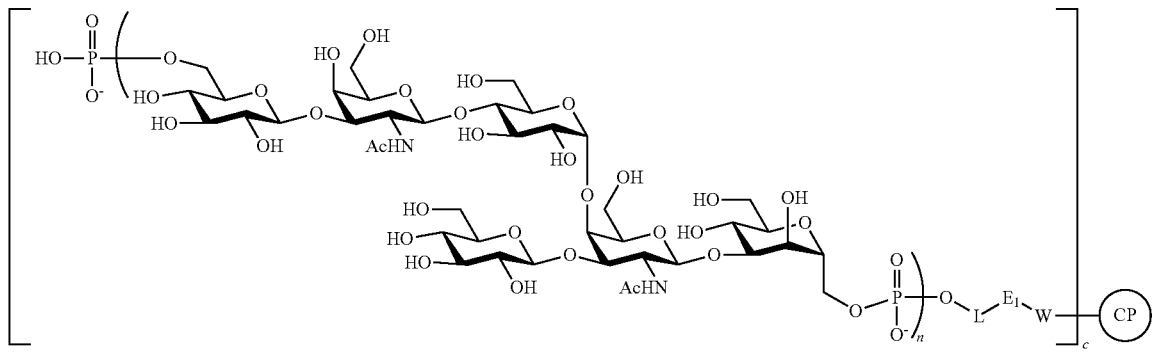
(IV-2)
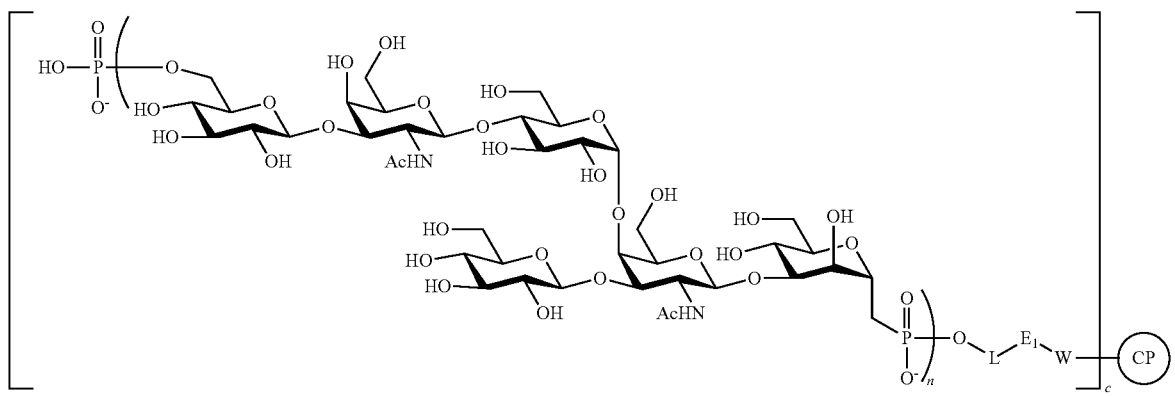
(IV-4)
wherein L, $E_1$, W, c, CP, and n have the same meanings as defined in claim 7,
or a pharmaceutically acceptable salt thereof.
9. The conjugate according to claim 7, wherein the conjugate is of formula (V-2)
wherein L is —$(CH_2)_5$—,
E1 is —NH—,
n is an integer selected from 1 or 2,
c and W have the meaning as defined in claim 8,
or a pharmaceutically acceptable salt thereof.
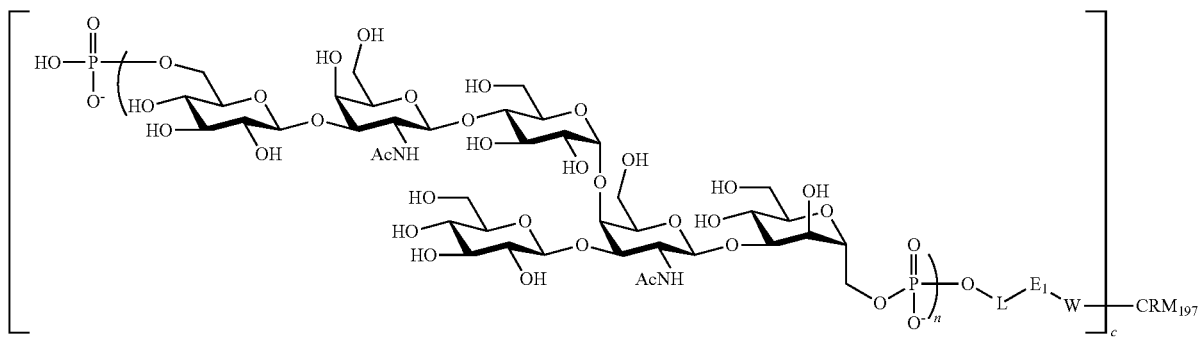
(V-2)

10. The conjugate according to claim 9, wherein —W— is

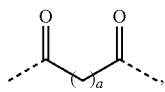

and a is an integer selected from 1, 2, 3, 4, 5, 6, 7, 8, 9 or 10, or a pharmaceutically acceptable salt thereof.

11. A method for detecting antibodies against bacteria containing in their cell-wall polysaccharides one of the following saccharide fragments:

-6)-β-D-Glc-(1, 3)-β-D-GalNAc-(1, 4)-α-D-Glc-(1, 4)-[β-D-Glc-(1, 3)]-β-D-GalNAc-(1, 3)-α-D-Man-(1-;

-3)-α-D-Man-(1, 6)-β-D-Glc-(1, 3)-β-D-GalNAc-(1, 4)-α-D-Glc-(1, 4)-[β-D-Glc-(1, 3)]-β-D-GalNAc-(1;

-4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1;

-4)-α-D-Glc-(1, 4)-[β-D-Glc-(1, 3)]-β-D-GalNAc-(1, 3)-α-D-Man-(1, 6)-β-D-Glc-(1, 3)-β-D-GalNAc-(1; and -3)-β-D-GalNAc-(1, 4)-α-D-Glc-(1, 4)-[β-D-Glc-(1, 3)]-β-D-GalNAc-(1, 3)-α-D-Man-(1, 6)-β-D-Glc-(1, the method comprising contacting a saccharide according to claim 1, or a pharmaceutically acceptable salt thereof, as a binding marker in an immunological assay.

12. A method for raising a protective immune response in a human and/or animal host, the method comprising administering the conjugate according to claim 7, or a pharmaceutically acceptable salt thereof, as a vaccine to the human and/or animal host in need thereof.

13. The method according to claim 12, wherein the conjugate is of formula (V-2)

wherein L is —(CH$_2$)$_5$—,

E$_1$ is —NH—, n is an integer selected from 1 or 2, c is between 2 and 18,

—W— is:

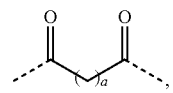

and a is an integer selected from 1, 2, 3, 4, 5, 6, 7, 8, 9 or 10, or a pharmaceutically acceptable salt thereof.

14. A method for the prevention and/or treatment of diseases caused by bacteria containing in their cell-wall polysaccharides one of the following saccharide fragments:

-6)-β-D-Glc-(1, 3)-β-D-GalNAc-(1, 4)-α-D-Glc-(1, 4)-[β-D-Glc-(1, 3)]-β-D-GalNAc-(1, 3)-α-D-Man-(1-;

-3)-α-D-Man-(1, 6)-β-D-Glc-(1, 3)-β-D-GalNAc-(1, 4)-α-D-Glc-(1, 4)-[β-D-Glc-(1, 3)]-β-D-GalNAc-(1;

-4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1;

-4)-α-D-Glc-(1, 4)-[β-D-Glc-(1, 3)]-β-D-GalNAc-(1, 3)-α-D-Man-(1, 6)-β-D-Glc-(1, 3)-β-D-GalNAc-(1; and -3)-β-D-GalNAc-(1, 4)-α-D-Glc-(1, 4)-[β-D-Glc-(1, 3)]-β-D-GalNAc-(1, 3)-α-D-Man-(1, 6)-β-D-Glc-(1, the method comprising administering the conjugate according to claim 7, or a pharmaceutically acceptable salt thereof, as a vaccine to a subject in need thereof.

15. The method according to claim 14, wherein the conjugate is of formula (V-2)

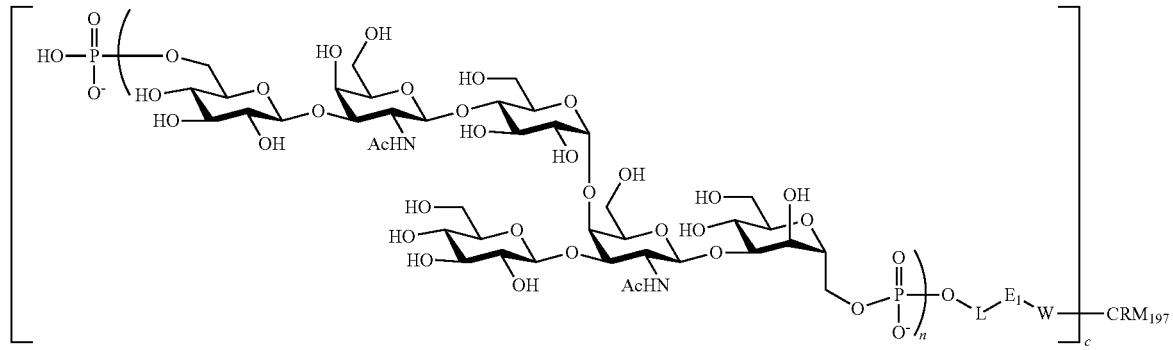

(V-2)

(V-2)

[structure of formula V-2 shown]

wherein L is —(CH$_2$)$_5$—,
E$_1$ is —NH—,
n is an integer selected from 1 or 2,
c is between 2 and 18,
—W— is:

[diketone structure with (—)$_a$]

and
a is an integer selected from 1, 2, 3, 4, 5, 6, 7, 8, 9 or 10,
or a pharmaceutically acceptable salt thereof.

16. The method according to claim 14, wherein the bacterium is *Clostridium difficile*.

17. A pharmaceutical composition comprising the conjugate according to claim 7, or a pharmaceutically acceptable salt thereof, together with at least one pharmaceutically acceptable adjuvant and/or excipient.

18. The pharmaceutical composition according to claim 17, wherein the conjugate is of formula (V-2)

wherein L is —(CH$_2$)$_5$—,
E$_1$ is —NH—,
n is an integer selected from 1 or 2,
c is between 2 and 18,
—W— is:

[diketone structure with (—)$_a$]

and
a is an integer selected from 1, 2, 3, 4, 5, 6, 7, 8, 9 or 10,
or a pharmaceutically acceptable salt thereof.

(V-2)

[structure of formula V-2 shown]

19. A conjugate, wherein the conjugate is of formula (V-2)

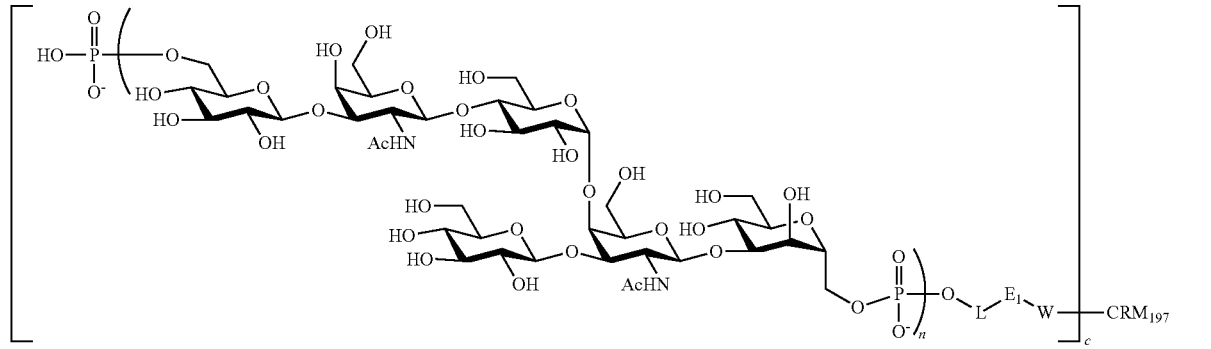

(V-2)

wherein L is —(CH$_2$)$_5$—,
E$_1$ is —NH—,
n is 1,
—W— is

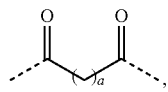

a is 4, and
c is selected from 2 to 18;
or a pharmaceutically acceptable salt thereof.

20. A conjugate having the following, wherein the conjugate is of formula (V-2)

21. A pharmaceutical composition comprising the conjugate according to claim 19, or a pharmaceutically acceptable salt thereof, together with at least one pharmaceutically acceptable adjuvant and/or excipient.

22. A pharmaceutical composition comprising the conjugate according to claim 20, or a pharmaceutically acceptable salt thereof, together with at least one pharmaceutically acceptable adjuvant and/or excipient.

23. A method for raising a protective immune response in a human and/or animal host, the method comprising administering the conjugate according to claim 19, or a pharmaceutically acceptable salt thereof, as a vaccine to the human and/or animal host in need thereof.

24. A method for raising a protective immune response in a human and/or animal host, the method comprising admin-

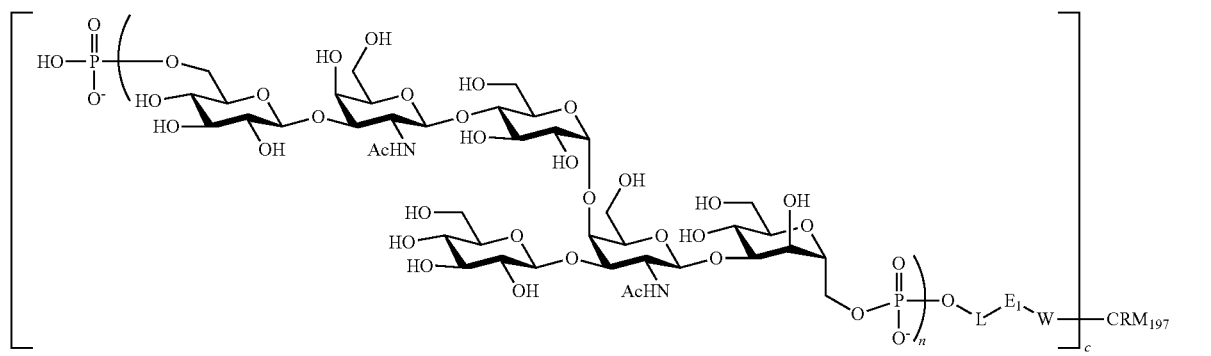

(V-2)

wherein L is —(CH$_2$)$_5$—,
E$_1$ is —NH—,
n is 2,
—W— is

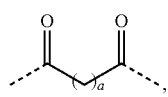

a is 4, and
c is selected from 2 to 18;
or a pharmaceutically acceptable salt thereof.

istering the conjugate according to claim 20, or a pharmaceutically acceptable salt thereof, as a vaccine to the human and/or animal host in need thereof.

25. A method for the prevention and/or treatment of diseases caused by bacteria containing in their cell-wall polysaccharides one of the following saccharide fragments:

-6)-β-D-Glc-(1, 3)-β-D-GalNAc-(1, 4)-α-D-Glc-(1, 4)-[β-D-Glc-(1, 3)]-β-D-GalNAc-(1, 3)-α-D-Man-(1-;

-3)-α-D-Man-(1, 6)-β-D-Glc-(1, 3)-β-D-GalNAc-(1, 4)-α-D-Glc-(1, 4)-[β-D-Glc-(1, 3)]-β-D-GalNAc-(1;

-4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1;

-4)-α-D-Glc-(1, 4)-[β-D-Glc-(1, 3)]-β-D-GalNAc-(1, 3)-α-D-Man-(1, 6)-β-D-Glc-(1, 3)-β-D-GalNAc-(1; and -3)-β-D-GalNAc-(1, 4)-α-D-Glc-(1, 4)-[β-D-Glc-(1, 3)]-β-D-GalNAc-(1, 3)-α-D-Man-(1, 6)-β-D-Glc-(1, the method comprising administering the conjugate according to claim 19, or a pharmaceutically acceptable salt thereof, as a vaccine to a subject in need thereof.

26. The method according to claim 25, wherein the bacterium is *Clostridium difficile*.

27. A method for the prevention and/or treatment of diseases caused by bacteria containing in their cell-wall polysaccharides one of the following saccharide fragments:

-6)-β-D-Glc-(1, 3)-β-D-GalNAc-(1, 4)-α-D-Glc-(1, 4)-[β-D-Glc-(1, 3)]-β-D-GalNAc-(1, 3)-α-D-Man-(1-;

-3)-α-D-Man-(1, 6)-β-D-Glc-(1, 3)-β-D-GalNAc-(1, 4)-α-D-Glc-(1, 4)-[β-D-Glc-(1, 3)]-β-D-GalNAc-(1;

-4)-[β-D-Glc-(1, 3)]-β-D-GalNAc-(1, 3)-α-D-Man-(1, 6)-β-D-Glc-(1, 3)-β-D-GalNAc-(1, 4)-α-D-Glc-(1;

-4)-α-D-Glc-(1, 4)-[β-D-Glc-(1, 3)]-β-D-GalNAc-(1, 3)-α-D-Man-(1, 6)-β-D-Glc-(1, 3)-β-D-GalNAc-(1; and -3)-β-D-GalNAc-(1, 4)-α-D-Glc-(1, 4)-[β-D-Glc-(1, 3)]-β-D-GalNAc-(1, 3)-α-D-Man-(1, 6)-β-D-Glc-(1, the method comprising administering the conjugate according to claim 20, or a pharmaceutically acceptable salt thereof, as a vaccine to a subject in need thereof.

28. The method according to claim 27, wherein the bacterium is *Clostridium difficile*.

29. The conjugate according to claim 7, wherein
n is an integer selected from 1, 2 or 3;
-L- is -$L^a$-, -$L^a$-$L^e$-, -$L^a$-$L^b$-$L^e$-, or -$L^a$-$L^d$-$L^e$-;
-$L^a$- is —$(CH_2)_o$—, —$(CH_2-CH_2-O)_o-C_2H_4$—, or —$(CH_2-CH_2-O)_o-CH_2$;
-$L^b$- is —O—;
-$L^d$- is —$(CH_2)_q$—, —$(CF_2)_q$—, —$(CH_2-CH_2-O)_q-C_2H_4$—, or —$(CH_2-CH_2-O)_q-CH_2$;
-$L^e$- is —$(CH_2)_{p1}$—, —$(CF_2)_{p1}$—, —$C_2H_4-(O-CH_2-CH_2)_{p1}$—, —$CH_2-(O-CH_2-CH_2)_{p1}$— or —$(CH_2)_{p1}-O-(CH_2)_{p2}$—;
o, q, p1 and p2 are independently of each other an integer selected from 1, 2, 3, 4, 5, or 6;

—W— is:

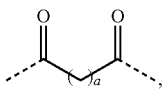

and
a is an integer selected from 2, 3, 4, 5 or 6;
or a pharmaceutically acceptable salt thereof.

30. The conjugate according to claim 8, wherein
n is an integer selected from 1, 2 or 3;
-L- is -$L^a$-, -$L^a$-$L^e$-, -$L^a$-$L^b$-$L^e$-, or -$L^a$-$L^d$-$L^e$-;
-$L^a$- is —$(CH_2)_o$—, —$(CH_2-CH_2-O)_o-C_2H_4$—, or —$(CH_2-CH_2-O)_o-CH_2$;
-$L^b$- is —O—;
-$L^d$- is —$(CH_2)_q$—, —$(CF_2)_q$—, —$(CH_2-CH_2-O)_q-C_2H_4$—, or —$(CH_2-CH_2-O)_q-CH_2$;
-$L^e$- is —$(CH_2)_{p1}$—, —$(CF_2)_{p1}$—, —$C_2H_4-(O-CH_2-CH_2)_{p1}$—, —$CH_2-(O-CH_2-CH_2)_{p1}$— or —$(CH_2)_{p1}-O-(CH_2)_{p2}$—;
o, q, p1 and p2 are independently of each other an integer selected from 1, 2, 3, 4, 5, or 6;

—W— is:

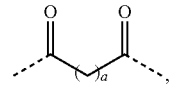

and
a is an integer selected from 2, 3, 4, 5 or 6;
or a pharmaceutically acceptable salt thereof.

31. The conjugate according to claim 29, wherein CP is $CRM_{197}$;
or a pharmaceutically acceptable salt thereof.

32. The conjugate according to claim 30, wherein CP is $CRM_{197}$;
or a pharmaceutically acceptable salt thereof.

33. The conjugate according to claim 10, wherein
a is an integer selected from 2, 3, 4, 5 or 6;
or a pharmaceutically acceptable salt thereof.

* * * * *